(12) United States Patent
Thom

(10) Patent No.: US 9,790,174 B2
(45) Date of Patent: Oct. 17, 2017

(54) KINASE INHIBITORS

(71) Applicants: Respivert Limited, Buckinghamshire (GB); Topivert Pharma Limited, London (GB)

(72) Inventor: Stephen Malcolm Thom, Nottingham (GB)

(73) Assignees: Respivert Limited, Buckinghamsire (GB); Topivert Pharma Limited, London (GB)

( * ) Notice: Subject to any disclaimer, the term of this patent is extended or adjusted under 35 U.S.C. 154(b) by 0 days.

(21) Appl. No.: 15/261,174

(22) Filed: Sep. 9, 2016

(65) Prior Publication Data

US 2016/0376232 A1    Dec. 29, 2016

Related U.S. Application Data

(63) Continuation of application No. 14/242,741, filed on Apr. 1, 2014, now Pat. No. 9,481,648.

(30) Foreign Application Priority Data

Apr. 2, 2013 (GB) .................................. 1305945.6
Dec. 20, 2013 (GB) .................................. 1322678.2
Feb. 14, 2014 (GB) .................................. 1402647.0

(51) Int. Cl.
| | | |
|---|---|---|
| *C07C 317/48* | (2006.01) | |
| *C07C 317/28* | (2006.01) | |
| *C07D 233/90* | (2006.01) | |
| *A61K 31/5377* | (2006.01) | |
| *C07D 239/47* | (2006.01) | |
| *C07D 211/86* | (2006.01) | |
| *A61K 31/44* | (2006.01) | |
| *A61K 31/506* | (2006.01) | |
| *C07D 405/12* | (2006.01) | |
| *C07D 405/14* | (2006.01) | |
| *A61K 31/444* | (2006.01) | |
| *A61K 31/4427* | (2006.01) | |
| *A61K 31/505* | (2006.01) | |
| *A61K 31/541* | (2006.01) | |
| *A61K 31/551* | (2006.01) | |
| *A61K 31/553* | (2006.01) | |
| *C07C 311/08* | (2006.01) | |

(Continued)

(52) U.S. Cl.
CPC ............ *C07C 317/48* (2013.01); *A61K 31/44* (2013.01); *A61K 31/444* (2013.01); *A61K 31/4427* (2013.01); *A61K 31/505* (2013.01); *A61K 31/506* (2013.01); *A61K 31/5377* (2013.01); *A61K 31/541* (2013.01); *A61K 31/551* (2013.01); *A61K 31/553* (2013.01); *C07C 311/08* (2013.01); *C07C 317/28* (2013.01); *C07D 211/86* (2013.01); *C07D 213/74* (2013.01); *C07D 233/90* (2013.01); *C07D 239/47* (2013.01); *C07D 401/12* (2013.01); *C07D 403/12* (2013.01); *C07D 405/12* (2013.01); *C07D 405/14* (2013.01); *C07D 413/12* (2013.01)

(58) Field of Classification Search
CPC .... C07C 317/28; C07C 317/48; C07D 233/90
See application file for complete search history.

(56) References Cited

U.S. PATENT DOCUMENTS

| 6,319,921 B1 | 11/2001 | Cirillo et al. |
|---|---|---|
| 6,492,393 B1 | 12/2002 | Breitfelder et al. |

(Continued)

FOREIGN PATENT DOCUMENTS

| EP | 2 578 582 A1 | 4/2013 |
|---|---|---|
| WO | WO 98/52558 | 11/1998 |

(Continued)

OTHER PUBLICATIONS

U.S. Appl. No. 14/561,290, filed Dec. 5, 2014, Murray.

(Continued)

*Primary Examiner* — Alexander R Pagano
*Assistant Examiner* — Ebenezer O Sackey
(74) *Attorney, Agent, or Firm* — Knobbe, Martens Olson & Bear, LLP

(57) ABSTRACT

There are provided compounds of formula IIb,

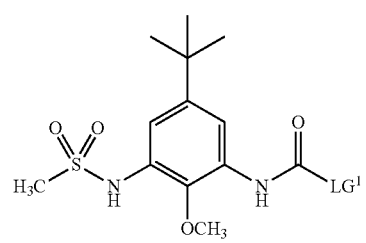

IIb wherein $LG^1$ represents imidazolyl, chloro or aryloxy, which compounds are useful in the preparation of compounds that have antiinflammatory activity (e.g. through inhibition of one or more of members of: the family of p38 mitogen-activated protein kinase enzymes; Syk kinase; and members of the Src family of tyrosine kinases) and have use in therapy, including in pharmaceutical combinations, especially in the treatment of inflammatory diseases, including inflammatory diseases of the lung, eye and intestines.

2 Claims, No Drawings

(51) Int. Cl.
  *C07D 403/12* (2006.01)
  *C07D 213/74* (2006.01)
  *C07D 401/12* (2006.01)
  *C07D 413/12* (2006.01)

(56) References Cited

U.S. PATENT DOCUMENTS

| | | |
|---|---|---|
| 6,492,529 B1 | 12/2002 | Kapadia et al. |
| 6,525,046 B1 | 2/2003 | Cirillo et al. |
| 6,852,717 B2 | 2/2005 | Cirillo et al. |
| 6,872,726 B2 | 3/2005 | Cirillo et al. |
| 6,894,173 B2 | 5/2005 | Zhang et al. |
| 6,916,814 B2 | 7/2005 | Moss et al. |
| 7,241,758 B2 | 7/2007 | Hoa et al. |
| 7,279,475 B2 | 10/2007 | Cirillo et al. |
| 7,652,022 B2 | 1/2010 | Floersheimer et al. |
| 7,838,541 B2 | 11/2010 | Dumas et al. |
| 8,293,748 B2 | 10/2012 | Ito et al. |
| 8,293,771 B2 | 10/2012 | Ito et al. |
| 8,299,073 B2 | 10/2012 | Ito et al. |
| 8,299,074 B2 | 10/2012 | Ito et al. |
| 8,618,140 B2 | 12/2013 | Ito et al. |
| 8,642,773 B2 | 2/2014 | Ito et al. |
| 8,927,563 B2 | 1/2015 | Fyfe et al. |
| 8,933,228 B2 | 1/2015 | Murray et al. |
| 8,975,285 B2 | 3/2015 | Ito et al. |
| 9,024,041 B2 | 5/2015 | King-Underwood |
| 9,079,893 B2 | 7/2015 | Cass |
| 9,108,950 B2 | 8/2015 | Ito et al. |
| 9,126,931 B2 | 9/2015 | Kinoshita et al. |
| 9,249,125 B2 | 2/2016 | Duffy et al. |
| 9,447,076 B2 | 9/2016 | Longshaw et al. |
| 9,475,796 B2 | 10/2016 | Ito et al. |
| 9,481,648 B2 * | 11/2016 | Baker ............... A61K 31/5377 |
| 9,499,486 B2 * | 11/2016 | Fyfe ............... A61K 31/4412 |
| 9,624,196 B2 | 4/2017 | Longshaw et al. |
| 9,701,670 B2 | 7/2017 | Cariou |
| 2001/0011135 A1 | 8/2001 | Riedl et al. |
| 2004/0152725 A1 | 8/2004 | Moss et al. |
| 2005/0014753 A1 | 1/2005 | Ding et al. |
| 2008/0312192 A1 | 12/2008 | Bold et al. |
| 2012/0244120 A1 | 9/2012 | Charron et al. |
| 2013/0029990 A1 | 1/2013 | King-Underwood et al. |
| 2013/0040962 A1 | 2/2013 | King-Underwood et al. |
| 2013/0040995 A1 | 2/2013 | King-Underwood et al. |
| 2013/0102607 A1 | 4/2013 | Cass et al. |
| 2013/0123260 A1 | 5/2013 | Charron et al. |
| 2013/0150343 A1 | 6/2013 | Van Niel et al. |
| 2013/0156826 A1 | 6/2013 | Murray et al. |
| 2014/0057915 A1 | 2/2014 | Cariou et al. |
| 2014/0114061 A1 | 4/2014 | Kugimoto et al. |
| 2014/0228410 A1 | 8/2014 | Ito et al. |
| 2014/0249169 A1 | 9/2014 | Ito et al. |
| 2014/0296208 A1 | 10/2014 | Baker et al. |
| 2014/0296271 A1 | 10/2014 | Fyfe et al. |
| 2015/0203475 A1 | 7/2015 | Duffy et al. |
| 2015/0210722 A1 | 7/2015 | Fyfe et al. |
| 2015/0218137 A1 | 8/2015 | Cariou et al. |
| 2015/0225373 A1 | 8/2015 | Fyfe et al. |
| 2015/0225427 A1 | 8/2015 | Fyfe et al. |
| 2015/0232450 A1 | 8/2015 | Longshaw et al. |
| 2015/0252024 A1 | 9/2015 | Ito et al. |
| 2015/0329523 A1 | 11/2015 | Frickel et al. |
| 2016/0009695 A1 | 1/2016 | Ito et al. |
| 2016/0016934 A1 | 1/2016 | Fyfe et al. |
| 2016/0039797 A1 | 2/2016 | Fyfe |
| 2016/0045482 A1 | 2/2016 | Charron et al. |
| 2016/0045512 A1 | 2/2016 | Charron et al. |
| 2016/0096805 A1 | 4/2016 | Fyfe |
| 2016/0102059 A1 | 4/2016 | Baker et al. |
| 2016/0115152 A1 | 4/2016 | King-Underwood et al. |
| 2016/0318909 A1 | 11/2016 | Fyfe |
| 2016/0318958 A1 | 11/2016 | Fyfe et al. |
| 2016/0340343 A1 | 11/2016 | Fyfe et al. |
| 2016/0340375 A1 | 11/2016 | Fyfe et al. |
| 2016/0368896 A1 | 12/2016 | Longshaw et al. |
| 2017/0007604 A1 | 1/2017 | Ito et al. |
| 2017/0057945 A1 | 3/2017 | Longshaw et al. |

FOREIGN PATENT DOCUMENTS

| | | |
|---|---|---|
| WO | WO 99/23091 | 5/1999 |
| WO | WO 00/41698 | 7/2000 |
| WO | WO 00/42012 | 7/2000 |
| WO | WO 00/43384 | 7/2000 |
| WO | WO 00/55139 | 9/2000 |
| WO | WO 01/04115 | 1/2001 |
| WO | WO 01/36403 | 5/2001 |
| WO | WO 02/083628 | 10/2002 |
| WO | WO 02/083642 | 10/2002 |
| WO | WO 02/092576 | 11/2002 |
| WO | WO 02/096876 | 12/2002 |
| WO | WO 03/005999 | 1/2003 |
| WO | WO 03/068223 | 8/2003 |
| WO | WO 03/068228 | 8/2003 |
| WO | WO 03/072569 | 9/2003 |
| WO | WO 03/099771 | 12/2003 |
| WO | WO 2004/014870 | 2/2004 |
| WO | WO 2005/023761 | 3/2004 |
| WO | WO 2004/089286 | 10/2004 |
| WO | WO 2004/113352 | 12/2004 |
| WO | WO 2005/005396 | 1/2005 |
| WO | WO 2005/018624 | 3/2005 |
| WO | WO 2005/044825 | 5/2005 |
| WO | WO 2005/051366 | 6/2005 |
| WO | WO 2006/015775 | 2/2006 |
| WO | WO 2006/043090 | 4/2006 |
| WO | WO 2007/004749 | 1/2007 |
| WO | WO 2007/053394 | 5/2007 |
| WO | WO 2010/038085 | 4/2010 |
| WO | WO 2010/038086 | 4/2010 |
| WO | WO 2010/067130 | 6/2010 |
| WO | WO 2010/067131 | 6/2010 |
| WO | WO 2010/112936 | 10/2010 |
| WO | WO 2010/143664 A1 | 12/2010 |
| WO | WO 2011/070368 | 6/2011 |
| WO | WO 2011/070369 | 6/2011 |
| WO | WO 2011/121366 | 10/2011 |
| WO | WO 2011/124923 | 10/2011 |
| WO | WO 2011/124930 | 10/2011 |
| WO | WO 2011/154738 | 12/2011 |
| WO | WO 2011/158039 | 12/2011 |
| WO | WO 2011/158042 | 12/2011 |
| WO | WO 2011/158044 | 12/2011 |
| WO | WO 2012/044090 A2 | 4/2012 |
| WO | WO 2013/050756 | 4/2013 |
| WO | WO 2013/050757 | 4/2013 |
| WO | WO 2013/083604 A1 | 6/2013 |
| WO | WO 2014/027209 | 2/2014 |
| WO | WO 2014/033446 | 3/2014 |
| WO | WO 2014/033447 | 3/2014 |
| WO | WO 2014/033448 | 3/2014 |
| WO | WO 2014/033449 | 3/2014 |
| WO | WO 2014/076484 | 5/2014 |
| WO | WO 2014/140582 A1 | 9/2014 |
| WO | WO 2014/162121 A1 | 10/2014 |
| WO | WO 2015/121444 A1 | 8/2015 |
| WO | WO 2015/121660 A1 | 8/2015 |

OTHER PUBLICATIONS

U.S. Appl. No. 15/225,377, filed Aug. 1, 2016, Fyfe et al.
U.S. Appl. No. 15/228,945, filed Aug. 4, 2016, Fyfe et al.
U.S. Appl. No. 15/105,912, filed Jun. 17, 2016, Fyfe et al.
U.S. Appl. No. 15/207,915, filed Jul. 12, 2016, Fyfe et al.
Badrinarayan, et al. 2011 "Sequence, structure, and active site analyses of p38 MAP kinase: Exploiting DFG-out conformation as a strategy to design new type II leads" *Journal of Chemical Information and Modeling* 51; 115-129.
Barnes, et al. 2007 "Trimethylsilylpyrazoles as novel inhibitors of p38 MAP kinase: A new use of silicon bioisosteres in medicinal chemistry" *Bioorganic & Medicinal Chemistry* 17; 354-357.

(56) References Cited

OTHER PUBLICATIONS

Boehm, et al. 2000 "New inhibitors of p38 kinase" *Expert Opinion on Therapeutic Patents* 10(1): 25-37.
CAS Registry No. 1379397-83-7, 2012 American Chemical Society.
CAS Registry No. 1384608-34-7, 2012 American Chemical Society.
Cirillo, et al. 2009 "Discovery and characterization of the N-phenyl-N'-naphthylurea class of p38 kinase inhibitors" *Bioorganic & Medicinal Chemistry* 19; 2386-2391.
Cogan, et al. 2008 "Structure-based design and subsequent optimization of 2-tolyl-(1,2,3-triazol-1-yl-4-carboxamide) inhibitors of p38 MAP kinase" *Bioorganic & Medicinal Chemistry* 18; 3251-3255.
Dietrich, et al. 2010 "The design, synthesis, and evaluation of 8 hybrid DFG-out allosteric kinase inhibitors: A structural analysis of the binding interactions of Gleevec ®, Nexavar®, and BIRB-796" *Bioorganic & Medicinal Chemistry* 18; 5738-5748.
Dodeller, et al. 2006 "The p38 mitogen-activated protein kinase signaling cascade in CD4 T cells" *Arthritis Research & Therapy* 8(2): 1-11.
Dumas, et al. 2004 "Recent developments in the discovery of protein kinase inhibitors from the urea class" *Current Opinion in Drug Discovery & Development* 7(5); 600-616.
Goldberg, et al. 2007 "Discovery and Optimization of p38 Inhibitors via Computer-Assisted Drug Decision" *Journal of Medicinal Chemistry* 50; 4016-4026.
Menard, et al. 2009 "Novel potent BRAF inhibitors: Toward 1 nM compounds through optimization of the Central Phenyl Ring" *Journal of Medicinal Chemistry* 52; 3881-3891.
Montalban, et al. 2010 "KR-003048, a potent, orally active inhibitors of p38 mitogen-activated protein kinase" *European Journal of Pharmacology* 632; 93-102.
Montalban, et al. 2010 "Optimization of α-ketoamide based p38 inhibitors through modifications to the region that binds to the allosteric site" *Bioorganic & Medicinal Chemistry* 20; 4819-4824.
Onions, et al. 2016 "The discovery of narrow spectrum kinase inhibitors: New therapeutic agents for the treatment of COPD and steroid-resistant asthma" *Journal of Medicinal Chemistry*; 1-70.
Patterson, H. et al. 2013 "Protein kinase inhibitors in the treatment of inflammatory and autoimmune diseases" *Clin Exper Immunol* 176: 1-10.
Pettus, et al. 2008 "Small Molecule p38 MAP Kinase Inhibitors for the Treatment of Inflammatory Diseases: Novel Structures and Developments During 2006-2008" *Current Topics in Medicinal Chemistry* 8; 1452-1467.
Robinson, M. 1998 "Medical therapy of inflammatory bowel disease for the 21$^{st}$ century" *Eur J Surg Suppl* 582: 90-98.
Singh, B. et al. 2011 "Immune therapy in inflammatory bowel disease and models of colitis" *Br J Surgery* 88: 1558-1569.
To, et al. 2015 "Potent anti-inflammatory effects of the narrow spectrum kinase inhibitor RV1088 on rheumatoid arthritis synovial membrane cells" *Britch Journal of Pharmacology* 172: 3805-3816.
Zambon, et al. 2010 "Novel hinge binder improves activity and pharmacokinetic properties of BRAF inhibitors" *Journal of Medicinal Chemistry* 53; 5639-5655.
U.S. Appl. No. 15/457,810, filed Mar. 13, 2017, Lonshaw et al.
Australian Examination Report issued in Australian Application No. 2014246870, dated Aug. 23, 2017.

\* cited by examiner

KINASE INHIBITORS

FIELD OF THE INVENTION

This invention relates, inter alia, to compounds which are antiinflammatory agents (e.g. through inhibition of one or more of members of: the family of p38 mitogen-activated protein kinase enzymes (referred to herein as p38 MAP kinase inhibitors), for example the alpha kinase sub-type thereof; Syk kinase; and the Src family of tyrosine kinases). The invention also relates to the use of such compounds in therapy, including in mono- and combination therapies, especially in the treatment of inflammatory diseases, including inflammatory diseases of the lung (such as asthma and chronic obstructive pulmonary disease (COPD)), eye (such as uveitis) and gastrointestinal tract (such as Crohn's disease and ulcerative colitis).

BACKGROUND OF THE INVENTION

The listing or discussion of an apparently prior-published document in this specification should not necessarily be taken as an acknowledgement that the document is part of the state of the art or is common general knowledge.

Four p38 MAPK isoforms (alpha, beta, gamma and delta respectively) have been identified, each displaying different patterns of tissue expression. The p38 MAPK alpha and beta isoforms are found ubiquitously throughout the body, are present in many different cell types and are inhibited by a number of previously described small molecular weight compounds. Early classes of inhibitors were highly toxic due to the broad tissue distribution of these isoforms which resulted in off-target effects of the compounds. Some of the more recently identified inhibitors show improved selectivity for p38 MAPK alpha and beta isoforms and have wider safety margins.

p38 MAP kinase is believed to play a pivotal role in many of the signalling pathways that are involved in initiating and maintaining chronic, persistent inflammation in human disease, for example, in severe asthma, COPD and inflammatory bowel disease (IBD). There is now an abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance, Smith describes the inhibitory effect of p38 MAP kinase inhibitors on TNFα (but not IL-8) release from human PBMCs (Smith, S. J., Br. J. Pharmacol., 2006, 149:393-404).

The use of inhibitors of p38 MAP kinase in the treatment of COPD and IBD has also been proposed. Small molecule inhibitors targeted to p38 MAPKα/β have proved to be effective in reducing various parameters of inflammation in:
- cells and tissues obtained from patients with COPD, who are generally corticosteroid insensitive (Smith, S. J., Br. J. Pharmacol., 2006, 149:393-404);
- biopsies from IBD patients (Docena, G. et al., J. Trans. Immunol., 2010, 162:108-115); and
- in vivo animal models (Underwood, D. C. et al., Am. J. Physiol., 2000, 279:L895-902; Nath, P. et al., Eur. J. Pharmacol., 2006, 544:160-167).

Irusen and colleagues also suggested the possibility of involvement of p38 MAPKα/β on corticosteroid insensitivity via the reduction of binding affinity of the glucocorticoid receptor (GR) in nuclei (Irusen, E. et al., J. Allergy Clin. Immunol., 2002, 109:649-657). Clinical investigations in inflammatory diseases with a range of p38 MAP kinase inhibitors, including AMG548, BIRB 796, VX702, SCIO469 and SCIO323, have been described (Lee, M. R. and Dominguez, C., Current Med. Chem., 2005, 12:2979-2994.). However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specifically mentioned above.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al. (2007; American Thoracic Society Abstract A56) demonstrates that silencing p38 MAPK γ has the potential to restore sensitivity to corticosteroids. Thus, there may be a dual benefit for patients in the use of a p38 MAP kinase inhibitor for the treatment of COPD.

Many patients diagnosed with asthma or with COPD continue to suffer from uncontrolled symptoms and from exacerbations of their medical condition that can result in hospitalisation. This occurs despite the use of the most advanced, currently available treatment regimens, comprising of combination products of an inhaled corticosteroid and a long acting β-agonist. Data accumulated over the last decade indicates that a failure to manage effectively the underlying inflammatory component of the disease in the lung is the most likely reason that exacerbations occur. Given the established efficacy of corticosteroids as anti-inflammatory agents and, in particular, of inhaled corticosteroids in the treatment of asthma, these findings have provoked intense investigation. Resulting studies have identified that some environmental insults invoke corticosteroid-insensitive inflammatory changes in patients' lungs. An example is the response arising from virally-mediated upper respiratory tract infections (URTI), which have particular significance in increasing morbidity associated with asthma and COPD.

It has been disclosed previously that compounds that inhibit the activity of both the c-Src and Syk kinases are effective agents against rhinovirus replication (Charron, C. E. et al., WO 2011/158042) and that compounds that inhibit p59-HCK are effective against influenza virus replication (Charron, C. E. et al., WO 2011/070369). Taken together with inhibition of p38 MAPK, these are particularly attractive properties for compounds to possess that are intended to treat patients with chronic respiratory diseases.

Certain p38 MAPK inhibitors have also been described as inhibitors of replication of respiratory syncytial virus (Cass L. et al., WO 2011/158039).

The precise etiology of IBD is uncertain, but is believed to be governed by genetic and environmental factors that interact to promote an excessive and poorly controlled mucosal inflammatory response directed against components of the luminal microflora. This response is mediated through infiltration of inflammatory neutrophils, dendritic cells and T-cells from the periphery. p38 has become an obvious target for investigation in IBD models as a consequence of its ubiquitous expression in inflammatory cells. Studies investigating the efficacy of p38 inhibitors in animal models of IBD and human biopsies from IBD patients indicated that p38 could be a target for the treatment of IBD (Hove, T. ten et al., *Gut*, 2002, 50:507-512, Docena, G. et al., *J. Trans. Immunol*, 2010, 162:108-115). However, these findings are not completely consistent with other groups reporting no effect with p38 inhibitors (Malamut G. et al., *Dig. Dis. Sci*, 2006, 51:1443-1453). A clinical study in Crohn's patients using the p38 alpha inhibitor BIRB796 demonstrated potential clinical benefit with an improvement in C-reactive protein levels. However this improvement was transient, returning to baseline by week 8 (Schreiber, S. et al., *Clin. Gastro. Hepatology*, 2006, 4:325-334). A small clinical study investigating the efficacy of CNI-1493, a p38 and Jnk inhibitor, in patients with severe Crohn's disease showed significant improvement in clinical score over 8 weeks (Hommes, D. et al. *Gastroenterology*. 2002 122:7-14).

T cells are known to play a key role in mediating inflammation of the gastrointestinal tract. Pioneering work by Powrie and colleagues demonstrated that transfer of naive CD4+ cells into severely compromised immunodeficient (SCID) animals results in the development of colitis which is dependent on the presence of commensal bacteria (Powrie F. et al. *Int Immunol*. 1993 5:1461-71). Furthermore, investigation of mucosal membranes from IBD patients showed an upregulation of CD4+ cells which were either Th1 (IFNg/IL-2) or Th2 (IL5/TGFb) biased depending on whether the patient had Crohn's disease or ulcerative colitis (Fuss I J. et al. *J Immunol*. 1996 157:1261-70.). Similarly, T cells are known to play a key role in inflammatory disorders of the eye with several studies reporting increased levels of T cell associated cytokines (IL-17 and IL-23) in sera of Bechets patients (Chi W. et al. *Invest Ophthalmol Vis Sci*. 2008 49:3058-64). In support of these observations, Direskeneli and colleagues demonstrated that Bechets patients have increased Th17 cells and decreased Treg cells in their peripheral blood (Direskeneli H. et al. *J Allergy Clin Immunol*. 2011 128:665-6).

One approach to inhibit T cell activation is to target kinases which are involved in activation of the T cell receptor signalling complex. Syk and Src family kinases are known to play a key role in this pathway, where Src family kinases, Fyn and Lck, are the first signalling molecules to be activated downstream of the T cell receptor (Barber E K. et al. *PNAS* 1989, 86:3277-81). They initiate the tyrosine phosphorylation of the T cell receptor leading to the recruitment of the Syk family kinase, ZAP-70. Animal studies have shown that ZAP-70 knockout results in a SCID phenotype (Chan A C. et al. *Science*. 1994, 10; 264(5165):1599-601).

A clinical trial in rheumatoid arthritis patients with the Syk inhibitor Fostamatinib demonstrated the potential of Syk as an anti-inflammatory target with patients showing improved clinical outcome and reduced serum levels of IL-6 and MMP-3 (Weinblatt M E. et al. *Arthritis Rheum*. 2008 58:3309-18). Syk kinase is widely expressed in cells of the hematopoietic system, most notably in B cells and mature T cells. Through interaction with immunoreceptor tyrosine-based activation motifs (ITAM), it plays an important role in regulating T cell and B cell expansion as well as mediating immune-receptor signalling in inflammatory cells. Syk activation leads to IL-6 and MMP release—inflammatory mediators commonly found upregulated in inflammatory disorders including IBD and rheumatoid arthritis (Wang Y D. et al *World J Gastroenterol* 2007; 13: 5926-5932, Litinsky I et al. *Cytokine*. 2006 January 33:106-10).

In addition to playing key roles in cell signalling events which control the activity of pro-inflammatory pathways, kinase enzymes are now also recognised to regulate the activity of a range of cellular functions, including the maintenance of DNA integrity (Shilo, Y. *Nature Reviews Cancer*, 2003, 3: 155-168) and co-ordination of the complex processes of cell division. Indeed, certain kinase inhibitors (the so-called "Olaharski kinases") have been found to alter the frequency of micronucleus formation in vitro (Olaharski, A. J. et al., *PLoS Comput. Biol.*, 2009, 5(7), e1000446; doi: 10.1371/journal.pcbi.1000446). Micronucleus formation is implicated in, or associated with, disruption of mitotic processes and is therefore undesirable. Inhibition of glycogen synthase kinase 3α (GSK3α) was found to be a particularly significant factor that increases the likelihood of a kinase inhibitor promoting micronucleus formation. Also, inhibition of the kinase GSK3β with RNAi has been reported to promote micronucleus formation (Tighe, A. et al., *BMC Cell Biology*, 2007, 8:34).

Whilst it may be possible to attenuate the adverse effects of inhibition of Olaharski kinases such as GSK3α by optimisation of the dose and/or by changing the route of administration of a molecule, it would be advantageous to identify further therapeutically useful molecules with low or negligible inhibition of Olaharski kinases, such as GSK 3α and/or have low or negligible disruption of mitotic processes (e.g. as measured in a mitosis assay).

Various compounds, including urea derivatives, are disclosed as inhibiting one or more kinases. Examples of such compounds may be found in WO 99/23091, WO 00/041698, WO 00/043384, WO 00/055139, WO 01/36403, WO 01/4115, WO 02/083628, WO 02/083642, WO 02/092576, WO 02/096876, WO 2003/005999, WO 2003/068223, WO 2003/068228, WO 2003/072569, WO 2004/014870, WO 2004/113352, WO 2005/005396, WO 2005/018624, WO 2005/023761, WO 2005/044825, WO 2006/015775, WO 2006/043090, WO 2007/004749 and WO 2007/053394. Further examples may be found in articles published in:

Curr. Opin. Drug Devel. (2004, 7(5), 600-616);
J. Med. Chem. (2007, 50, 4016-4026; 2009, 52, 3881-3891; and 2010, 53, 5639-5655);
Bioorg. Med. Chem. Lett. (2007, 17, 354-357; 2008, 18, 3251-3255; 2009, 19, 2386-2391; and 2010, 20, 4819-4824);
Curr. Top. Med. Chem. (2008, 8, 1452-1467);
Bioorg. Med. Chem. (2010, 18, 5738-5748);
Eur. J. Pharmacol. (2010, 632, 93-102) and
J. Chem. Inf. Model. (2011, 51, 115-129).

Nevertheless, there remains a need to identify and develop new kinase inhibitors, specifically alternative p38 MAP kinase inhibitors that are suitable for the treatment of inflammation. There is particularly a need for such inhibitors that have improved therapeutic potential over currently available treatments or, in particular, that exhibit a superior therapeutic index (e.g. inhibitors that are at least equally efficacious and, in one or more respects, are less toxic at the relevant therapeutic dose than previous agents).

SUMMARY OF THE INVENTION

We have now discovered, surprisingly, that certain aniline-substituted diarylureas inhibit one or more of p38 MAP kinase, Syk and Src family kinases and therefore possess good anti-inflammatory properties.

Thus, according to a first aspect of the invention, there is provided a compound of formula I,

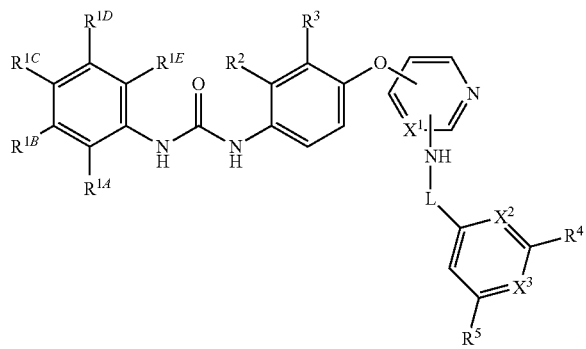

wherein
$R^{1A}$ represents
  H, halo, cyano,
  $C_{1-6}$ alkyl, $C_{2-6}$ alkenyl, $C_{2-6}$ alkynyl, $C_{1-6}$ alkoxy, which latter four groups are optionally substituted by one or more substituents selected from $C_{1-2}$ alkyl, halo, hydroxy, and $C_{1-2}$ alkoxy,
  phenyl or $Het^1$, which latter two groups are optionally substituted with one or more substituents selected from $C_{1-2}$ alkyl and $C_{1-2}$ alkoxy,
or $R^{1A}$ and $R^{1B}$ together represent a structural fragment selected from the following

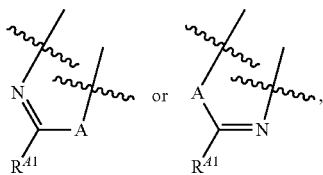

wherein the wavy lines represent the points of attachment to the phenyl ring,
A represents O, S or $N(R^{A2})$,
$R^A$ represents H, $C_{1-4}$ alkyl or hydroxy,
$R^{A2}$ represents H or $C_{1-4}$ alkyl;
$R^{1B}$ represents H, halo, cyano, —$C_{1-4}$ alkylene-CN, —$C_{1-4}$ alkylene-OH, —$NR^X R^{X1}$, —$C(O)OR^X$, —$C(O)NR^X R^Y$, —$S(O)_2 NR^X R^Y$, —$NR^X C(O)R^Y$, —$NR^X S(O)_2 R^{Y1}$, —$NR^{X2}S(O)_2 NR^X R^Y$, —$NR^X P(O)R^{Y1} R^{Y2}$, —$NR^X C(O)OR^{Y1}$ or $Het^1$ optionally substituted with one or more substituents selected from halo, hydroxy, $C_{1-2}$ alkyl and $C_{1-2}$ alkoxy;
$R^X$ and $R^{X1}$ independently represent H or $C_{1-6}$ alkyl, or $R^X$ and $R^{X1}$ together represent $C_{3-6}$ n-alkylene or $C_{4-5}$ n-alkylene interrupted between C2 and C3 by —O— or —$N(R^{X2})$—, or $R^{X1}$ represents $Het^1$ optionally substituted with one or more substituents selected from halo, hydroxy, $C_{1-2}$ alkyl and $C_{1-2}$ alkoxy;
$R^Y$, $R^{Y1}$ and $R^{Y2}$ independently represent $C_{1-6}$ alkyl, $C_{3-7}$ cycloalkyl, phenyl, benzyl, $Het^1$ or $Het^2$, which latter six groups are optionally substituted by one or more substituents selected from $C_{1-2}$ alkyl, halo, hydroxy, $C_{1-2}$ alkoxy, $NH_2$, $N(H)$—$C_{1-4}$ alkyl, $N(C_{1-4}$ alkyl$)_2$, C(O)OH and C(O)O—($C_{1-4}$ alkyl),
or $R^Y$ represents H,
or $R^X$ and $R^Y$ together represent $C_{3-6}$ n-alkylene or $C_{4-5}$ n-alkylene interrupted between C2 and C3 by —O— or —$N(R^{X2})$—;

each $R^{X2}$ independently represents H or $C_{1-4}$ alkyl;
$R^{1C}$ and $R^{1E}$ independently represent H, halo, cyano or methyl;
provided that at least one of $R^{1A}$, $R^{1B}$, $R^{1C}$ and $R^{E1}$ is other than H;
$R^{1D}$ represents trimethylsilyl, $C_{2-7}$ alkyl, $C_{2-7}$ alkenyl, $C_{2-7}$ alkynyl, $C_{3-7}$ cycloalkyl, phenyl, $Het^1$ or $Het^2$, which latter seven groups are optionally substituted by one or more substituents selected from $C_{1-2}$ alkyl, halo, cyano, hydroxy and $C_{1-2}$ alkoxy;
$R^2$ and $R^3$, together with the C-atoms to which they are attached, form a fused phenyl or pyridyl ring, which latter two rings are optionally substituted by one or more substituents selected from $C_{1-3}$ alkyl, $C_{1-3}$ haloalkyl, cyano and halo,
or one of $R^2$ and $R^3$ represents H, halo, cyano, $C_{1-3}$ alkyl or $C_{1-3}$ haloalkyl and the other independently represents halo, cyano, $C_{1-3}$ alkyl or $C_{1-3}$ haloalkyl,
or $R^2$ and $R^3$ together combine to form $C_{3-5}$ alkylene or $C_{3-5}$ alkenylene, which latter two groups are optionally substituted by one or more substituents selected from $C_{1-3}$ alkyl, $C_{1-3}$ haloalkyl, cyano and halo;
$X^1$ represents N or CH;
L represents a direct bond or $C_{1-2}$ alkylene;
$X^2$ and $X^3$ both represent $CR^Z$ or one of $X^2$ and $X^3$ represents N and the other represents $CR^Z$;
$R^Z$ represents hydrogen, halo, cyano, hydroxy, $C_{1-3}$ alkyl or $C_{1-3}$ alkoxy, which latter two groups are optionally substituted by one or more halo atoms;
$R^4$ represents
  -$Q^1$-[—$C(R^{6c})(R^{6d})$—$(CH_2)_{0-1}CH_2$—O]$_{1-12}$—$CH_2(CH_2)_{0-1}CH_2$—$R^{6a}$,
  -$Q^2$-$C(R^{6c})(R^{6d})$—[$C_{1-5}$ alkylene]$R^{6a}$, which $C_{1-5}$ alkylene group is optionally substituted by oxo
  —$S(O)_n R^{6b}$;
  —$COR^{6b}$,
  —$CH_2OH$,
or, when $R^{1B}$ represents either —$C(O)NR^X R^Y$, in which $R^Y$ represents optionally substituted $Het^1$ or optionally substituted $Het^2$, or —$NR^{X2}S(O)_2 NR^X R^Y$ then $R^4$ may alternatively represent H, halo, cyano, hydroxy, $C_{1-3}$ alkyl or $C_{1-3}$ alkoxy, which latter two groups are optionally substituted by one or more halo atoms;
$R^5$ represents $C_{1-3}$ alkoxy or $C_{1-3}$ alkyl, which latter two groups are optionally substituted by one or more halo atoms, or $R^5$ represents H, cyano, —$C(O)NH_2$, hydroxy, halo or $C_{2-3}$ alkynyl;
$R^{6a}$ represents $OR^{7a}$, $N(R^{7b})R^{7c}$ or $CO_2H$;
$R^{6b}$ represents $C_{1-8}$ alkyl, $C_{3-8}$ cycloalkyl, phenyl, $Het^1$ or $Het^2$, which latter five groups are optionally substituted by one or more substituents selected from halo, hydroxyl, $C_{1-3}$ alkyl and $C_{1-3}$ alkoxy;
$R^{6c}$ and $R^{6d}$ independently represent H or methyl;
$R^{7a}$ to $R^{7c}$ independently represent H or $C_{1-4}$ alkyl optionally substituted by one or more halo atoms, or $R^{7b}$ and $R^{7c}$, together with the N-atom to which they are attached, form a 4- to 7-membered heterocyclic group that is fully saturated, partially unsaturated or fully aromatic and which heterocyclic group contains one N atom (the atom to which $R^{7b}$ and $R^{7c}$ are attached) and, optionally, one or more further heteroatoms selected from O, S and N, and which heterocyclic group is optionally substituted by one or more substituents selected from halo, hydroxy, oxo, $C_{1-4}$ alkyl and $C_{1-4}$ alkoxy;
$Q^1$ and $Q^2$ independently represent C(O)NH, O or $S(O)_p$; and
n and p independently represent 0, 1 or 2, Het¹ represents, independently upon each occurrence, a 5- or 6-membered heterocyclic group that is fully aromatic, which group contains one or more heteroatoms selected from N, O and S;

Het² represents, independently upon each occurrence, a 4- to 7-membered heterocyclic group that is fully saturated or partially unsaturated, which group contains one or more heteroatoms selected from N, O and S;

or a pharmaceutically acceptable salt thereof, which compounds may be referred to hereinafter as "the compounds of the invention".

Pharmaceutically acceptable salts that may be mentioned include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of formula I in the form of a salt with another counter-ion, for example using a suitable ion exchange resin.

Examples of pharmaceutically acceptable salts include acid addition salts derived from mineral acids and organic acids, and salts derived from metals.

For the avoidance of doubt, compounds of formula I may contain the stated atoms in any of their natural or non-natural isotopic forms. In this respect, embodiments of the invention that may be mentioned include those in which:
(a) the compound of formula I is not isotopically enriched or labelled with respect to any atoms of the compound; and
(b) the compound of formula I is isotopically enriched or labelled with respect to one or more atoms of the compound.

References herein to an "isotopic derivative" relate to the second of these two embodiments. In particular embodiments of the invention, the compound of formula I is isotopically enriched or labelled (with respect to one or more atoms of the compound) with one or more stable isotopes. Thus, the compounds of the invention that may be mentioned include, for example, compounds of formula I that are isotopically enriched or labelled with one or more atoms such as deuterium or the like.

Compounds of formula I may exhibit tautomerism. All tautomeric forms and mixtures thereof are included within the scope of the invention. For example, the structural fragment containing the substituent $R^{41}$ may exhibit keto-enol tautomerism when the group $R^{41}$ represents OH (giving the fragment —N═C(OH)-A-, which may tautomerise to provide the fragment —NH—C(═O)-A-).

Unless otherwise specified, alkyl groups and alkoxy groups as defined herein may be straight-chain or, when there is a sufficient number (i.e. a minimum of three) of carbon atoms, be branched. Particular alkyl groups that may be mentioned include, for example, methyl, ethyl, n-propyl, iso-propyl, butyl, n-butyl and tert-butyl. Particular alkoxy groups that may be mentioned include, for example, methoxy, ethoxy, propoxy, and butoxy.

Unless otherwise specified, cycloalkyl groups as defined herein may, when there is a sufficient number (i.e. a minimum of four) of carbon atoms, be part cyclic/acyclic.

Unless otherwise specified, alkylene groups as defined herein may be straight-chain or, when there is a sufficient number (i.e. a minimum of two) of carbon atoms, be branched. In particular embodiments of the invention, alkylene refers to straight-chain alkylene.

Unless otherwise stated, the point of attachment of aryl groups may be via any atom of the ring system. However, when aryl groups are bicyclic or tricyclic, they are linked to the rest of the molecule via an aromatic ring. $C_{6-14}$ aryl groups include phenyl, naphthyl and the like. Embodiments of the invention that may be mentioned include those in which aryl is phenyl.

For the avoidance of doubt, oxo substituents that may be present on heterocyclic groups represented by $N(R^{7b})R^{7c}$ may be attached to any appropriate atoms in the heterocyclic ring including, where valencies allow, to C-, N- and/or S-atoms within the ring (thereby forming keto, N-oxide, S(O) and/or S(O)₂ groups).

Values of Het¹ that may be mentioned include oxadiazolyl (e.g. 1,3,4-oxadiazol-2-yl), pyrimidinyl (e.g. pyrimidin-2-yl) and triazolyl (e.g. 1,2,3-triazol-4-yl).

Values of Het² that may be mentioned include morpholinyl (e.g. morpholin-4-yl), oxetanyl (e.g. 3-oxetanyl) and tetrahydropyranyl (e.g. 4-tetrahydropyranyl).

Unless otherwise specified, the term "halo" includes references to fluoro, chloro, bromo or iodo, in particular to fluoro, chloro or bromo, especially fluoro or chloro.

Embodiments of the invention that may be mentioned include those in which the compound of formula I is a compound of formula Ix,

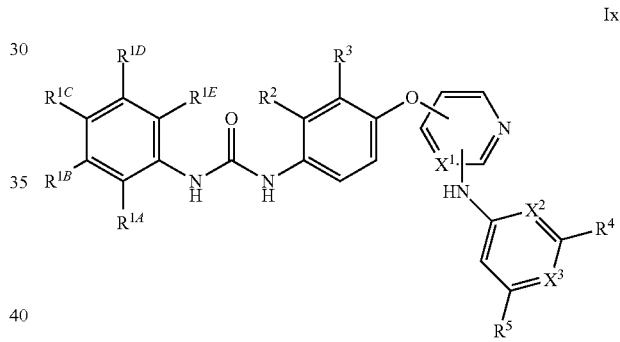

Ix wherein:
$R^{1A}$ represents
  H, halo, cyano,
  $C_{1-6}$ alkyl, $C_{2-6}$ alkenyl, $C_{2-6}$ alkynyl, $C_{1-6}$ alkoxy, which latter four groups are optionally substituted by one or more substituents selected from $C_{1-2}$ alkyl, halo, hydroxy, and $C_{1-2}$ alkoxy,
  phenyl or Het¹, which latter two groups are optionally substituted with one or more substituents selected from $C_{1-2}$ alkyl and $C_{1-2}$ alkoxy;
$R^{1B}$ represents H, halo, cyano, —NR$^X$R$^{X1}$, —C(O)OR$^X$, —C(O)NR$^X$R$^Y$, —S(O)₂NR$^X$R$^Y$, —NR$^X$C(O)R$^Y$, —NR$^X$S(O)₂R$^{Y1}$, —NR$^X$P(O)R$^{Y1}$R$^{Y2}$ or —NR$^X$C(O)OR$^{Y1}$;
$R^X$ and $R^{X1}$ independently represent H or $C_{1-6}$ alkyl, or $R^X$ and $R^{X1}$ together represent $C_{3-6}$ n-alkylene or $C_{4-5}$ n-alkylene interrupted between C2 and C3 by —O— or —N(R$^{X2}$)—;
$R^Y$, $R^{Y1}$ and $R^{Y2}$ independently represent $C_{1-6}$ alkyl, $C_{3-7}$ cycloalkyl, phenyl, Het¹ or Het², which latter five groups are optionally substituted by one or more substituents selected from $C_{1-2}$ alkyl, halo, hydroxy and $C_{1-2}$ alkoxy,
or $R^Y$ represents H,
or $R^X$ and $R^Y$ together represent $C_{3-6}$ n-alkylene or $C_{4-5}$ n-alkylene interrupted between C2 and C3 by —O— or —N(R$^{X2}$)—;

$R^{X2}$ represents H or $C_{1-4}$ alkyl;
$R^4$ represents
 -$Q^1$-[CH$_2$(CH$_2$)$_{0-1}$CH$_2$—O]$_{1-12}$—CH$_2$(CH$_2$)$_{0-1}$CH$_2$—$R^{6a}$,
 -$Q^2$-C($R^{6c}$)($R^{6d}$)—[C$_{1-5}$ alkylene]$R^{6a}$ or
 —S(O)$_n$$R^{6b}$;
$R^{6a}$ represents $OR^{7a}$ or $N(R^{7b})R^{7c}$; and/or Het$^1$ represents 5- or 6-membered heterocyclic group that is fully aromatic, which group contains one or more heteroatoms selected from N, O and S.

Alternative embodiments of the invention that may be mentioned include those in which the compound is of formula I or Ix wherein:
$R^{1A}$ and $R^{1B}$ together represent a structural fragment selected from the following

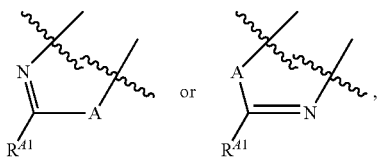

wherein the wavy lines represent the points of attachment to the phenyl ring, A represents O, S or N($R^{A2}$),
$R^A$ represents H, $C_{1-4}$ alkyl or hydroxy,
$R^{A2}$ represents H or $C_{1-4}$ alkyl;
or $R^{1B}$ represents —$C_{1-4}$ alkylene-CN, —$C_{1-4}$ alkylene-OH or, particularly, Het$^1$ optionally substituted with one or more substituents selected from halo, hydroxy, $C_{1-2}$ alkyl and $C_{1-2}$ alkoxy, or —NR$^{X2}$S(O)$_2$NR$^X$R$^Y$;
$R^{X1}$ represents Het$^1$ optionally substituted with one or more substituents selected from halo, hydroxy, $C_{1-2}$ alkyl and $C_{1-2}$ alkoxy;
$R^Y$, $R^{Y1}$ and/or $R^{Y2}$ represents benzyl optionally substituted by one or more substituents selected from $C_{1-2}$ alkyl, halo, hydroxy, $C_{1-2}$ alkoxy, NH$_2$, N(H)—$C_{1-4}$ alkyl, N($C_{1-4}$ alkyl)$_2$, C(O)OH and C(O)O—($C_{1-4}$ alkyl),
or $R^Y$, $R^{Y1}$ and/or $R^{Y2}$ represents $C_{1-6}$ alkyl, $C_{3-7}$ cycloalkyl, phenyl, Het$^1$ or Het$^2$, which latter six groups are substituted by NH$_2$, N(H)—$C_{1-4}$ alkyl, N($C_{1-4}$ alkyl)$_2$, C(O)OH or C(O)O—($C_{1-4}$ alkyl) and optionally further substituted by one or more substituents selected from $C_{1-2}$ alkyl, halo, hydroxy, $C_{1-2}$ alkoxy, NH$_2$, N(H)—$C_{1-4}$ alkyl, N($C_{1-4}$ alkyl)$_2$, C(O)OH and C(O)O—($C_{1-4}$ alkyl);
$R^{1D}$ represents $C_{2-7}$ alkyl, $C_{2-7}$ alkenyl, $C_{2-7}$ alkynyl, $C_{3-7}$ cycloalkyl, phenyl, Het$^1$ or Het$^2$, which latter seven groups are substituted by cyano and optionally further substituted one or more substituents selected from $C_{1-2}$ alkyl, halo, cyano, hydroxy and $C_{1-2}$ alkoxy;
$R^Z$ represents hydroxy;
$R^4$ represents -$Q^2$-C($R^{6c}$)($R^{6d}$)—[C$_{1-5}$ alkylene]-$R^{6a}$, which $C_{1-5}$ alkylene group is substituted by oxo, or, particularly, $R^4$ represents —CH$_2$OH, —COR$^{6b}$ or -$Q^1$-[C($R^{6c}$)($R^{6d}$)—(CH$_2$)$_{0-1}$CH$_2$—O]$_{1-12}$—CH$_2$(CH$_2$)$_{0-1}$CH$_2$—$R^{6a}$ in which $R^{6c}$ and/or $R^{6d}$ represents methyl (e.g. $R^4$ represents —COR$^{6b}$ or -$Q^1$-[C($R^{6c}$)($R^{6d}$)—(CH$_2$)$_{0-1}$CH$_2$—O]$^{1-12}$—CH$_2$(CH$_2$)$_{0-1}$CH$_2$—$R^{6a}$ in which $R^{6c}$ and/or $R^{6d}$ represents methyl);
or, when $R^{1B}$ represents —C(O)NR$^X$R$^Y$, in which $R^Y$ represents optionally substituted Het$^1$ or optionally substituted Het$^2$, or —NR$^{X2}$S(O)$_2$NR$^X$R$^Y$ then $R^4$ may alternatively represent H, halo, cyano, hydroxy, $C_{1-3}$ alkyl or $C_{1-3}$ alkoxy, which latter two groups are optionally substituted by one or more halo atoms;

$R^5$ represents —C(O)NH$_2$ or, particularly, hydroxy; and/or $R^{6a}$ represents CO$_2$H.

Particular alternative embodiments of the invention that may be mentioned include compounds of formula I in which:
$R^{1B}$ represents —$C_{1-4}$ alkylene-CN or —$C_{1-4}$ alkylene-OH;
L represents $C_{1-2}$ alkylene;
$R^4$ represents —CH$_2$OH; and/or
$R^5$ represents —C(O)NH$_2$.

Other alternative embodiments of the invention that may be mentioned include compounds of formula I in which $R^4$ represents -$Q^2$-C($R^{6c}$)($R^{6d}$)—[C$_{1-5}$ alkylene]-$R^{6a}$, which $C_{1-5}$ alkylene group is substituted by oxo.

Embodiments of the invention that may be mentioned include those in which the compound of formula I (or Ix) is a compound of formula Ia,

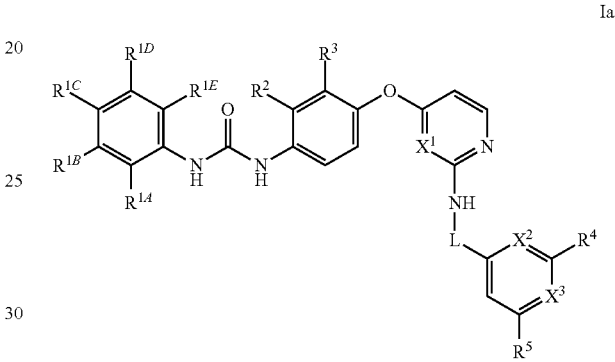

or a pharmaceutically acceptable salt thereof, wherein $R^{1A}$ to $R^{1E}$, $R^2$ to $R^5$, L and $X^1$ to $X^3$ are as hereinbefore defined.

Embodiments of the invention that may be mentioned include those in which one or more of the following definitions apply to the compounds of formula I (or Ix) and Ia:
(a) $R^{1A}$ and $R^{1B}$ together represent a structural fragment selected from the following

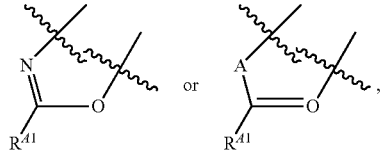

$R^{1A}$ represents phenyl optionally substituted with one or more substituents selected from methyl and methoxy, or, particularly, $R^{1A}$ represents H, halo, $C_{1-4}$ alkyl or $C_{1-4}$ alkoxy, which latter two groups are optionally substituted by one or more fluoro atoms;
(b) $R^A$ represents H, $C_{1-2}$ alkyl or hydroxy,
(c) $R^{1B}$ represents —CH$_2$CN, —CH$_2$OH or, particularly, $R^{1B}$ represents H, halo, cyano, —NR$^X$R$^{X1}$, —C(O)OR$^X$, —C(O)NR$^X$R$^Y$, —S(O)$_2$NR$^X$R$^Y$, —NR$^X$C(O)R$^Y$, —NR$^X$S(O)$_2$R$^{Y1}$, —NR$^X$C(O)OR$^{Y1}$, Het$^1$ or —NR$^{X2}$S(O)$_2$NR$^X$R$^Y$ (e.g. $R^{1B}$ represents H, halo, cyano, —NR$^X$R$^{X1}$, —C(O)OR$^X$, —C(O)NR$^X$R$^Y$, —S(O)$_2$NR$^X$R$^Y$, —NR$^X$C(O)R$^Y$, —NR$^X$S(O)$_2$R$^{Y1}$ or —NR$^X$C(O)OR$^{Y1}$);
(d) $R^{X1}$ represents Het$^1$ or, particularly, $R^X$ and $R^{X1}$ independently represent H or $C_{1-4}$ alkyl, or $R^X$ and $R^{X1}$ together represent $C_{4-5}$ n-alkylene optionally interrupted between C2 and C3 by —O— or —N($R^{X2}$)—;

(e) $R^Y$ represents benzyl, $Het^2$ optionally substituted by one or more substituents selected from methyl, halo, hydroxy and methoxy or, particularly, $R^Y$ and $R^{Y1}$ independently represent $C_{1-4}$ alkyl, $C_{3-6}$ cycloalkyl or phenyl, which latter three groups are optionally substituted by one or more substituents selected from methyl, halo, hydroxy, methoxy, $NH_2$, $N(H)$—$C_{1-2}$ alkyl, $N(C_{1-2}$ alkyl$)_2$, $C(O)OH$ and $C(O)$O—$(C_{1-2}$ alkyl) (e.g. by one or more substituents selected from methyl, halo, hydroxy and methoxy), or $R^Y$ represents H, or $R^X$ and $R^Y$ together represent $C_{4-5}$ n-alkylene optionally interrupted between C2 and C3 by —O— or —N($R^{X2}$)—;

(f) $R^{X2}$ represents H or $C_{1-2}$ alkyl;

(g) $R^{1C}$ and $R^{1E}$ independently represent H or halo;

(h) $R^{1D}$ represents trimethylsilyl, $C_{3-7}$ alkyl, $C(C_{1-2}$ alkyl$)_2$-C≡CH, $C_{3-5}$ cycloalkyl, phenyl or $Het^2$, which latter three groups are optionally substituted by one or more substituents selected from $C_{1-2}$ alkyl, halo and $C_{1-2}$ alkoxy;

(i) $R^2$ and $R^3$, together with the C-atoms to which they are attached, form a fused phenyl ring, or $R^2$ and $R^3$ independently represent halo or $C_{1-2}$ alkyl;

(j) $X^1$ represents N or CH;

(k) L represents $CH_2$ or, particularly, a direct bond;

(l) $X^2$ and $X^3$ both represent CH or one of $X^2$ represents CH and $X^3$ represents N or $CR^Z$; (m) $R^Z$ represents H or halo;

(n) $R^4$ represents
$CH_2OH$ or, particularly,
-$Q^1$-[—C($R^{6c}$)($R^{6d}$)—$CH_2$—O]$_{1-8}$—$CH_2CH_2$—$R^{6a}$,
-$Q^2$-C($R^{6c}$)($R^{6d}$)—[$C_{1-4}$ alkylene]$R^{6a}$ (e.g. -$Q^2$-C($R^{6c}$)($R^{6d}$)—[$C_{1-3}$ alkylene]- or -$Q^2$-C($R^{6c}$)($R^{6d}$)—[$C_{1-2}$ alkylene]$R^{6a}$), which $C_{1-4}$ alkylene group is optionally substituted by oxo
—S(O)$_n$$R^{6b}$;
—$COR^{6b}$, or, when $R^{1B}$ represents either —C(O)NR$^X$R$^Y$, in which $R^Y$ represents optionally substituted $Het^2$, or —NR$^{X2}$S(O)$_2$NR$^X$R$^Y$, then $R^4$ may alternatively represent H, (e.g. $R^4$ represents
-$Q^1$-[$CH_2CH_2$—O]$_{1-8}$—$CH_2CH_2$—$R^{6a}$),
-$Q^2$-$CH_2$[$C_{1-2}$ alkylene]-$R^{6a}$ or
—S(O)$_n$$R^{6b}$);

(o) $R^5$ represents H or, particularly, cyano, chloro, fluoro, $C_{2-3}$ alkynyl, $C_{1-2}$ alkyl or $C_{1-2}$ alkoxy, which latter two groups are optionally substituted by one or more fluoro atoms;

(p) $R^{6a}$ represents $CO_2H$ or, particularly, OH, O—$C_{1-2}$ alkyl or N($R^{7b}$)$R^{7c}$;

(q) $R^{6b}$ represents $C_{1-5}$ alkyl or $C_{3-5}$ cycloalkyl;

(r) $R^{7b}$ and $R^{7c}$ independently represent H or $C_{1-2}$ alkyl (e.g. methyl), or $R^{7b}$ and $R^{7c}$, together with the N-atom to which they are attached, form a 4- to 7-membered heterocyclic group that is fully saturated, which heterocyclic group contains one N atom (the atom to which $R^{7b}$ and $R^{7c}$ are attached) and, optionally, one further heteroatom selected from O, S and N, and which heterocyclic group is optionally substituted by one or more $C_{1-2}$ alkyl groups;

(s) $Q^1$ and $Q^2$ independently represent C(O)NH or O;

(t) n represents 0 or 2;

(u) $Het^1$ represents, independently upon each occurrence, a 5- or 6-membered heterocyclic group that is fully aromatic, which group contains one to three heteroatoms selected from N, O and S;

(v) $Het^2$ represents a 4- to 6-membered (e.g. 5- or 6-membered) heterocyclic group that is fully saturated or partially unsaturated, which group contains one or two heteroatoms selected from N, O and S.

Further embodiments of the invention that may be mentioned include those in which the compound of formula I, Ix or Ia is a compound of formula Ib,

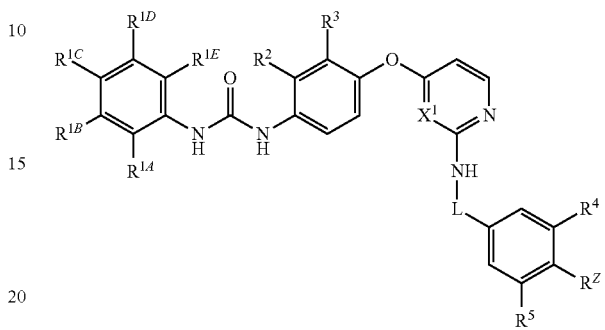

or a pharmaceutically acceptable salt thereof, wherein $R^{1A}$ to $R^{1E}$, $R^2$ to $R^5$, $X^1$ and L are as hereinbefore defined.

Embodiments of the invention that may be mentioned include those in which one or more of the following definitions apply to the compounds of formula I, Ix, Ia and Ib:

(a) $R^{1A}$ represents H or, particularly, fluoro, chloro, methyl or $C_{1-2}$ alkoxy (e.g. methoxy), which latter two groups are optionally substituted by one or more fluoro atoms;

(b) $R^{1B}$ represents H, cyano, —C(O)OR$^X$ or, particularly, fluoro, chloro, $Het^1$, —C(O)NR$^X$R$^Y$, —NR$^X$S(O)$_2$R$^{Y1}$ or —N(H)S(O)$_2$NR$^X$R$^Y$ (e.g. H, cyano, —C(O)OR$^X$ or, particularly, fluoro, chloro, —C(O)NR$^X$R$^Y$ or —NR$^X$S(O)$_2$R$^{Y1}$);

(c) $R^X$ represents H or methyl;

(d) $R^Y$ represents H, $Het^2$, $C_{1-3}$ alkyl or $C_{3-5}$ cycloalkyl, which latter two groups are optionally substituted by fluoro, hydroxy, methoxy, $NH_2$, $N(H)CH_3$, $N(CH_3)_2$, and $C(O)OCH_3$, or $R^X$ and $R^Y$ together represent $C_{4-5}$ n-alkylene optionally interrupted between C2 and C3 by —O— or —N($R^{X2}$)—

(e.g. $R^Y$ represents H or methyl);

(e) $R^{X2}$ represents H or methyl;

(f) $R^{Y1}$ represents $C_{1-4}$ alkyl, $C_{3-6}$ cycloalkyl or phenyl, which latter three groups are optionally substituted by one or more substituents selected from halo, methyl and methoxy;

(g) $R^{1C}$ and $R^{1E}$ independently represent fluoro or, particularly, H;

(h) $R^{1D}$ represents $C_{4-6}$ alkyl, $C(CH_3)_2$—C≡CH, cyclopropyl or morpholinyl (e.g. morpholin-4-yl), which latter two groups are optionally substituted by methyl;

(i) $R^2$ and $R^3$, together with the C-atoms to which they are attached, form a fused phenyl ring, or $R^2$ and $R^3$ both represent methyl or, particularly, chloro;

(j) $X^1$ represents N or CH;

(k) L represents $CH_2$ or, particularly, a direct bond;

(l) $R^Z$ represents chloro or, particularly, H;

(m) $R^4$ represents
-$Q^1$-[C($R^{6c}$)($R^{6d}$)$CH_2$—O]$_{1-6}$—$CH_2CH_2$—$R^{6a}$,
—C(O)NH—C($R^{6c}$)($R^{6d}$)—[$C_{1-3}$ alkylene]-$R^{6a}$ (e.g. —C(O)NH—C($R^{6c}$)($R^{6d}$)—[$C_{1-2}$ alkylene]-$R^{6a}$), which $C_{1-3}$ alkylene group is optionally substituted by oxo, —S(O)$_2$R$^{6b}$,
—COR$^{6b}$;
or, when R$^{1B}$ represents either —C(O)NR$^X$R$^Y$, in which R$^Y$ represents Het$^2$, or —N(H)S(O)$_2$NR$^X$R$^Y$, then R$^4$ may alternatively represent H,
(e.g. R$^4$ represents
-Q$^1$-[CH$_2$CH$_2$—O]$_{1-7}$—CH$_2$CH$_2$—R$^{6a}$,
—C(O)NH—CH$_2$—[C$_{1-2}$ alkylene]-R$^{6a}$ or
—S(O)$_2$R$^{6b}$);
(n) R$^5$ represents H or, particularly, C$_{2-3}$ alkynyl, C$_{1-2}$ alkyl or C$_{1-2}$ alkoxy, which latter two groups are optionally substituted by one or more fluoro atoms (e.g. R$^5$ represents methyl, trifluoromethyl or, particularly, —C≡CH or methoxy, which latter group is optionally substituted by one or more fluoro atoms);
(o) R$^{6a}$ represents OH or, particularly, CO$_2$H, O—CH$_3$ or N(R$^{7b}$)R$^{7c}$ (e.g. O—CH$_3$ or) N(R$^{7b}$)R$^{7c}$;
(p) R$^{6b}$ represents C$_{3-5}$ cycloalkyl (e.g. cyclopropyl);
(q) R$^{7b}$ and R$^{7c}$ both represent methyl, or R$^{7b}$ and R$^{7c}$, together with the N-atom to which they are attached, form a 5- or 6-membered heterocyclic group that is fully saturated, which heterocyclic group contains one N atom (the atom to which R$^{7b}$ and R$^{7c}$ are attached) and, optionally, one further heteroatom selected from O, S and N, and which heterocyclic group is optionally substituted by one or more methyl groups;
(r) Q$^1$ represents C(O)NH or O;
(s) Het$^1$ represents a 5-membered heterocyclic group that is fully aromatic, which group contains one to three heteroatoms selected from N, O and S;
(t) Het$^2$ represents a 4- to 6-membered heterocyclic group that is fully saturated or partially unsaturated, which group contains one or two heteroatoms selected from N, O and S.

Further embodiments of the invention that may be mentioned include those in which the compound of formula I, Ix, Ia or Ib is a compound of formula Ic,

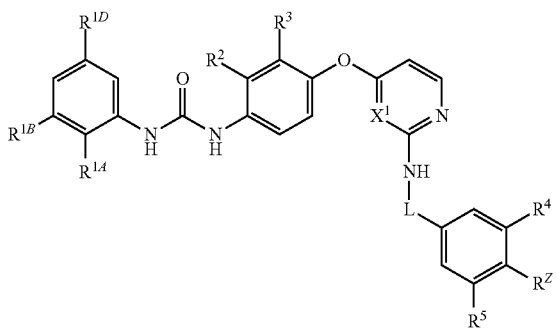

Ic or a pharmaceutically acceptable salt thereof, wherein R$^{1A}$, R$^{1B}$ and R$^{1D}$, R$^2$ to R$^5$, X$^1$, L and R$^Z$ are as hereinbefore defined.

Embodiments of the invention that may be mentioned include those in which one or more of the following definitions apply to the compounds of formula I, Ix, Ia, Ib and Ic:
(a) R$^{1A}$ represents H or, particularly, C$_{1-2}$ alkoxy (e.g. methoxy) optionally substituted by one or more fluoro atoms (e.g. R$^{1A}$ represents methoxy);
(b) R$^{1B}$ represents H, cyano, —C(O)OH, —C(O)N(CH$_3$)$_2$, fluoro, chloro, or, particularly, —C(O)N(H)R$^Y$, —NHS(O)$_2$CH$_3$, —N(H)S(O)$_2$NR$^X$R$^Y$ or Het$^1$
(e.g. H, cyano, —C(O)OH, —C(O)N(CH$_3$)$_2$, fluoro, chloro, or, particularly, —C(O)NH$_2$, —C(O)N(H)CH$_3$ or —NHS(O)$_2$CH$_3$ (e.g. R$^{1B}$ represents H, cyano, —C(O)OH, —C(O)N(CH$_3$)$_2$, fluoro, —C(O)NH$_2$, —C(O)N(H)CH$_3$ or, particularly, —NHS(O)$_2$CH$_3$));
(c) R$^X$ represents H or methyl;
(d) R$^Y$ represents H, Het$^2$, C$_{3-5}$ cycloalkyl or C$_{1-3}$ alkyl, which latter group is optionally substituted by hydroxy, methoxy, NH$_2$, N(H)CH$_3$, N(CH$_3$)$_2$ or C(O)OCH$_3$ (e.g. R$^Y$ represents H or methyl),
or R$^X$ and R$^Y$ together represent C$_{4-5}$ n-alkylene optionally interrupted between C2 and C3 by —O—;
(e) R$^{1D}$ represents morpholinyl, cyclopropyl optionally substituted by methyl or, particularly, branched C$_{4-6}$ alkyl (such as tert-butyl) (e.g. R$^{1D}$ represents morpholin-4-yl or, particularly, tert-butyl);
(f) R$^2$ and R$^3$, together with the C-atoms to which they are attached, form a fused phenyl ring, or R$^2$ and R$^3$ both represent chloro;
(g) X$^1$ represents N or CH;
(h) L represents CH$_2$ or, particularly, a direct bond;
(i) R$^4$ represents
-Q$^1$-[C(H)(R$^{6c}$)CH$_2$—O]$_{1-6}$—CH$_2$CH$_2$—R$^{6a}$,
—C(O)NH—C(H)(R$^{6c}$)—[C$_{1-3}$ alkylene]-R$^{6a}$ (e.g. —C(O)NH—C(H)(R$^{6c}$)—[C$_{1-2}$ alkylene]-R$^{6a}$), which C$_{1-3}$ alkylene group is optionally substituted by oxo,
—S(O)$_2$-cyclopropyl
or, when R$^{1B}$ represents either —C(O)N(H)R$^Y$, in which R$^Y$ represents Het$^2$, or —N(H)S(O)$_2$NR$^X$R$^Y$, then R$^4$ may alternatively represent H,
(e.g. R$^4$ represents
-Q$^1$-[CH$_2$CH$_2$—O]$_{2-6}$—CH$_2$CH$_2$—OCH$_3$,
—C(O)NH—CH$_2$—CH$_2$—N(R$^{7b}$)R$^{7c}$ or
—S(O)$_2$-cyclopropyl;
(j) R$^5$ represents H, —C≡CH, or methoxy, which latter group is optionally substituted by one or more fluoro atoms (for example, R$^5$ represents —C≡CH or, particularly, methoxy, which latter group is optionally substituted by one or more fluoro atoms (e.g. R$^5$ represents —C≡CH or, particularly, OCH$_3$ or OCHF$_2$));
(k) R$^{6a}$ represents OH or, particularly, CO$_2$H, O—CH$_3$ or N(R$^{7b}$)R$^{7c}$ (e.g. O—CH$_3$ or N(R$^{7b}$)R$^{7c}$);
(l) R$^{7b}$ and R$^{7c}$ both represent methyl, or R$^{7b}$ and R$^{7c}$, together with the N-atom to which they are attached, form a piperazinyl group optionally substituted by methyl, a pyrrolidinyl group or a morpholinyl group (e.g. a piperazinyl group optionally substituted by methyl or, particularly, a morpholinyl group); and/or
(m) Q$^1$ represents O or, particularly, C(O)NH.
(n) Het$^1$ represents a 5-membered heterocyclic group that is fully aromatic, which group contains one to three heteroatoms selected from N and O (e.g. Het$^1$ represents oxadiazolyl, such as 1,2,4-oxadiazolyl, or triazolyl, such as 1,2,3-triazolyl);
(o) Het$^2$ represents a 4- to 6-membered heterocyclic group that is fully saturated or partially unsaturated, which group contains one or two heteroatoms selected from N, O and S (e.g. Het$^2$ represents oxetanyl, such as 3-oxetanyl).

Particular embodiments of the invention that may be mentioned include those in which one or more of the following definitions apply to the compounds of formula I, Ix, Ia, Ib and Ic:
(a) R$^{1A}$ represents methoxy or ethoxy;
(b) R$^{1B}$ represents Het$^1$ or, particularly, —C(O)N(H)R$^Y$, —NHS(O)$_2$CH$_3$;

(c) $R^Y$ represents H, $Het^2$, cyclopropyl, $C_1$ alkyl, optionally substituted with $C(O)OCH_3$, or $C_2$ alkyl, which latter group is optionally substituted by hydroxy, methoxy, $NH_2$, $N(H)CH_3$, $N(CH_3)_2$ or $C(O)OCH_3$, (d) $R^{1D}$ represents tert-butyl;

(e) $R^2$ and $R^3$, together with the C-atoms to which they are attached, form a fused phenyl ring;

(f) $X^1$ represents N or CH (e.g. $X^1$ represents N or, particularly, CH);

(g) L represents a direct bond;

(h) $R^4$ represents
  -$Q^1$-[C(H)($R^{6c}$)$CH_2$—O]$_{1-6}$—$CH_2CH_2$—$R^{6a}$,
  —C(O)NH—C(H)($R^{6c}$)—[$C_{1-3}$ alkylene]-$R^{6a}$, which $C_{1-3}$ alkylene group is optionally substituted by oxo (e.g. —C(O)NH—C(H)($CH_3$)$CH_2$—$R^{6a}$, —C(O)NH—$CH_2$C($CH_3$)$_2$—$R^{6a}$, —C(O)NH—$CH_2CH_2CH_2$—$R^{6a}$, —C(O)NH—$CH_2$C(O)—$R^{6a}$ or, particularly, —C(O)NH—$CH_2CH_2$—$R^{6a}$)
  or
  —S(O)$_2$-cyclopropyl
  or, particularly, when $R^{1B}$ represents —C(O)N(H)-$Het^2$, in which $R^Y$ represents $Het^2$, then $R^4$ may alternatively represent H,
  (e.g. $R^{1B}$ represents —C(O)N(H)-$Het^2$ and $R^4$ represents H);

(i) $R^5$ represents —C≡CH or methoxy optionally substituted by one or more fluoro atoms (to give, for example, $OCH_3$ or $OCHF_2$)
  or, particularly, when $R^{1B}$ represents —C(O)N(H)-$Het^2$, in which $R^Y$ represents $Het^2$, then $R^5$ may alternatively represent H.

More particular embodiments of the invention that may be mentioned include those wherein:

(i) when $R^4$ represents —C(O)NH—C(H)($R^{6c}$)—[$C_{1-3}$ alkylene]-$R^{6a}$, which $C_{1-3}$ alkylene group is optionally substituted by oxo (e.g. —C(O)NH—C(H)($CH_3$)$CH_2$—$R^{6a}$, —C(O)NH—$CH_2$C($CH_3$)$_2$—$R^{6a}$, —C(O)NH—$CH_2CH_2CH_2$—$R^{6a}$, —C(O)NH—$CH_2$C(O)—$R^{6a}$ or —C(O)NH—$CH_2CH_2$—$R^{6a}$), then $R^{6a}$ represents N($R^{7b}$)$R^{7c}$; or (ii) when $R^4$ represents -$Q^1$-[C(H)($R^{6c}$)$CH_2$—O]$_{1-6}$—$CH_2CH_2$—$R^{6a}$, then $R^{6a}$ represents OH, $CO_2$H or O—$CH_3$ (e.g. O—$CH_3$).

Other embodiments of the invention that may be mentioned include those in which:
$R^{1B}$ represents —$NR^{X2}S(O)_2NR^XR^Y$ or —C(O)$NR^XR^Y$, in which latter group $R^Y$ represents optionally substituted $Het^1$ or optionally substituted $Het^2$; and
both $R^4$ and $R^5$ represent H.

Still further embodiments of the invention that may be mentioned include those wherein, in the compound of formula I, Ix, Ia, Ib and Ic:
$R^4$ represents
  -$Q^1$-[—C($R^{6c}$)($R^{6d}$)—($CH_2$)$_{0-1}CH_2$—O]$_{1-12}$—$CH_2$($CH_2$)$_{0-1}CH_2$—$R^{6a}$,
  -$Q^2$-C($R^{6c}$)($R^{6d}$)—[$C_{1-5}$ alkylene]$R^{6a}$, which $C_{1-5}$ alkylene group is optionally substituted by oxo,
  —S(O)$_n$$R^{6b}$,
  —$COR^{6b}$,
  —$CH_2OH$,
or, when $R^{1B}$ represents either —C(O)$NR^XR^Y$, in which $R^Y$ represents optionally substituted $Het^1$ or optionally substituted $Het^2$, or —$NR^{X2}S(O)_2NR^XR^Y$, then $R^4$ may alternatively represent H, halo, cyano or $C_{1-3}$ alkyl, which latter group is optionally substituted by one or more halo atoms; $Q^1$ and $Q^2$ independently represent C(O)NH or S(O)$_p$; and n and p independently represent 1 or 2.

Alternatively, embodiments of the invention that may be mentioned include those wherein, in the compound of formula I, Ix, Ia, Ib and Ic:
when $R^4$ represents
  —$SR^{6b}$,
  hydroxy,
  $C_{1-3}$ alkoxy optionally substituted by one or more halo atoms,
  -$Q^1$-[C($R^{6c}$)($R^{6d}$)—($CH_2$)$_{0-1}$—$CH_2$—O]$_{1-12}$—$CH_2$($CH_2$)$_{0-1}CH_2$—$R^{6a}$, wherein $Q^1$ represents O or S
  or
  -$Q^2$-C($R^{6c}$)($R^{6d}$)—[$C_{1-5}$ alkylene]-$R^{6a}$, which $C_{1-5}$ alkylene group is optionally substituted by oxo, wherein $Q^2$ represents O or S,
then $R^5$ represents $C_{1-3}$ alkyl, which latter group is optionally substituted by one or more halo atoms, or $R^5$ represents H, cyano, —C(O)$NH_2$, halo or $C_{2-3}$ alkynyl.

Particular compounds of the invention that may be mentioned include those wherein, in the compound of formula I, Ix, Ia, Ib and Ic, $R^4$ represents:
  —C(O)NH—[C($R^{6c}$)($R^{6d}$)—($CH_2$)$_{0-1}CH_2$—O]$_{1-12}$—$CH_2$($CH_2$)$_{0-1}CH_2$—$R^{6a}$ or
  C(O)NH—C($R^{6c}$)($R^{6d}$)—[$C_{1-5}$ alkylene]-$R^{6a}$, which $C_{1-5}$ alkylene group is optionally substituted by oxo.

Other compounds of formula I, Ix, Ia, Ib or Ic that may be mentioned include the compounds of the examples described hereinafter. Thus, embodiments of the invention that may be mentioned include those in which the compound of formula I, Ix, Ia, Ib or Ic is a compound selected from the list:

3-((4-((4-(3-(5-(tert-butyl)-2-methoxy-3-(methylsulfonamido)phenyl)ureido)naphthalen-1-yl)oxy)pyrimidin-2-yl)amino)-5-ethynyl-N-(2-morpholinoethyl)benzamide;

3-ethynyl-5-((4-((4-(3-(3-fluoro-5-morpholinophenyl)ureido)naphthalen-1-yl)oxy)-pyrimidin-2-yl)amino)-N-(2-morpholinoethyl)benzamide;

3-((4-((4-(3-(5-(tert-butyl)-2-methoxy-3-(methylsulfonamido)phenyl)ureido)naphthalen-1-yl)oxy)pyridin-2-yl)amino)-5-methoxy-N-(2-(2-(2-methoxyethoxy)ethoxy)ethyl)benzamide;

N-(5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)methanesulfonamide;

N-(5-(tert-butyl)-3-(3-(4-((2-((3-(cyclopropylsulfonyl)-5-methoxyphenyl)amino)pyrimidin-4-yl)oxy)naphthalen-1-yl)ureido)-2-methoxyphenyl)methanesulfonamide;

3-((4-((4-(3-(5-(tert-butyl)-2-methoxy-3-(methylsulfonamido)phenyl)ureido)naphthalen-1-yl)oxy)pyrimidin-2-yl)amino)-5-methoxy-N-(2-morpholinoethyl)benzamide;

3-((4-((4-(3-(5-(tert-butyl)-2-methoxy-3-(methylsulfonamido)phenyl)ureido)naphthalen-1-yl)oxy)pyrimidin-2-yl)amino)-5-methoxy-N-(2-(2-(2-methoxyethoxy)ethoxy)ethyl)benzamide;

1-(5-(tert-butyl)-2-methoxyphenyl)-3-(4-((2-((3-methoxy-5-(2-(2-(2-methoxyethoxy)-ethoxy)ethoxy)phenyl)amino)pyrimidin-4-yl)oxy)naphthalen-1-yl)urea;

5-(tert-butyl)-3-(3-(4-((2-((3-ethynyl-5-((2-morpholinoethyl)carbamoyl)phenyl)amino) pyrimidin-4-yl)oxy)naphthalen-1-yl)ureido)-2-methoxy-N-methylbenzamide;

N-(5-(tert-butyl)-3-(3-(2,3-dichloro-4-((2-((3-methoxy-5-(2-(2-(2-methoxyethoxy)ethoxy)-ethoxy)phenyl)amino)pyrimidin-4-yl)oxy)phenyl)ureido)-2-methoxyphenyl)-methanesulfonamide;

N-(5-(tert-butyl)-2-methoxy-3-(3-(4-((2-((3-methoxy-5-(2-(2-(2-methoxyethoxy)ethoxy)-ethoxy)phenyl)amino)pyridin-4-yl)oxy)naphthalen-1-yl)ureido)phenyl)methanesulfonamide;

1-(4-((2-((3-methoxy-5-(2-(2-(2-methoxyethoxy)ethoxy)ethoxy)phenyl)amino)-pyrimidin-4-yl)oxy)naphthalen-1-yl)-3-(2-methoxy-5-morpholinophenyl)urea;

5-(tert-butyl)-2-methoxy-3-(3-(4-((2-((3-methoxy-5-(2-(2-(2-methoxyethoxy)ethoxy)ethoxy)-phenyl)amino)pyrimidin-4-yl)oxy)naphthalen-1-yl)ureido)-N-methylbenzamide;

N-(3-(3-(4-((2-((3-(2,5,8,11,14,17,20-heptaoxadocosan-22-yloxy)-5-methoxyphenyl)amino)-pyrimidin-4-yl)oxy)naphthalen-1-yl)ureido)-5-(tert-butyl)-2-methoxyphenyl)-methanesulfonamide;

N-(5-(tert-butyl)-3-(3-(4-((2-((3-(2-(2-(dimethylamino)ethoxy)ethoxy)ethoxy)-5-methoxyphenyl)amino)pyrimidin-4-yl)oxy)naphthalen-1-yl)ureido)-2-methoxyphenyl)-methanesulfonamide;

3-((4-((4-(3-(5-(tert-butyl)-2-methoxy-3-(methylsulfonamido)phenyl)ureido)naphthalen-1-yl)oxy)pyrimidin-2-yl)amino)-5-ethynyl-N-(2-(2-(2-methoxyethoxy)ethoxy)ethyl)benzamide;

N-(5-(tert-butyl)-3-(3-(4-((2-((3-(difluoromethoxy)-5-(2-(2-(2-methoxyethoxy)ethoxy)ethoxy)-phenyl)amino)pyrimidin-4-yl)oxy)naphthalen-1-yl)ureido)-2-methoxyphenyl)-methanesulfonamide;

N-(5-(tert-butyl)-2-methoxy-3-(3-(4-((2-((3-methoxy-5-(2-(2-(2-morpholinoethoxy)ethoxy)-ethoxy)phenyl)amino)pyrimidin-4-yl)oxy)naphthalen-1-yl)ureido)phenyl)-methanesulfonamide;

5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)-N,N-dimethylbenzamide;

5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)benzamide;

5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)benzoic acid;

1-(5-(tert-butyl)-3-cyano-2-methoxyphenyl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea;

3-(tert-butyl)-5-(3-(4-((2-((3-methoxy-5-(2-(2-(2-methoxyethoxy)ethoxy)ethoxy)phenyl)-amino)pyrimidin-4-yl)oxy)naphthalen-1-yl)ureido)-N-methylbenzamide;

N-(3-(tert-butyl)-5-(3-(4-((2-((3-methoxy-5-(2-(2-(2-methoxyethoxy)ethoxy)ethoxy)-phenyl)amino)pyrimidin-4-yl)oxy)naphthalen-1-yl)ureido)phenyl)methanesulfonamide;

1-(3-amino-5-(tert-butyl)-2-methoxyphenyl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea;

3-(2-(2-(3-((4-((4-(3-(5-(tert-butyl)-2-methoxy-3-(methylsulfonamido)phenyl)ureido)-naphthalen-1-yl)oxy)pyrimidin-2-yl)amino)-5-methoxybenzamido)ethoxy)ethoxy)-propanoic acid;

3-((4-((4-(3-(5-(tert-butyl)-2-methoxy-3-(methylsulfonamido)phenyl)ureido)naphthalen-1-yl)oxy)pyridin-2-yl)amino)-5-methoxy-N-(2-morpholinoethyl)benzamide;

1-(5-(tert-butyl)-2-methoxy-3-(pyrimidin-2-ylamino)phenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea;

5-(tert-butyl)-2-methoxy-3-(3-(4-((2-((3-methoxy-5-(2-(2-(2-methoxyethoxy)ethoxy)-ethoxy)phenyl)amino)pyridin-4-yl)oxy)naphthalen-1-yl)ureido)-N-methylbenzamide;

3-(2-(2-(3-((4-((4-(3-(5-(tert-butyl)-2-methoxy-3-(methylsulfonamido)phenyl)ureido)-naphthalen-1-yl)oxy)pyrimidin-2-yl)amino)-5-methoxyphenoxy)ethoxy)ethoxy)propanoic acid;

3-(2-(3-((4-((4-(3-(5-(tert-butyl)-2-methoxy-3-(methylsulfonamido)phenyl)ureido)naphthalen-1-yl)oxy)pyrimidin-2-yl)amino)-5-methoxyphenoxy)ethoxy)propanoic acid;

2-methoxy-3-(3-(4-((2-((3-methoxy-5-(2-(2-(2-methoxyethoxy)ethoxy)ethoxy)phenyl)-amino)pyrimidin-4-yl)oxy)naphthalen-1-yl)ureido)-N-methyl-5-morpholinobenzamide;

5-(tert-butyl)-N-cyclopropyl-2-methoxy-3-(3-(4-((2-((3-methoxy-5-(2-(2-(2-methoxy-ethoxy)ethoxy)ethoxy)phenyl)amino)pyrimidin-4-yl)oxy)naphthalen-1-yl)ureido)benzamide;

5-(tert-butyl)-2-methoxy-3-(3-(4-((2-((3-methoxy-5-(2-(2-(2-methoxyethoxy)ethoxy)-ethoxy)phenyl)amino)pyridin-4-yl)oxy)naphthalen-1-yl)ureido)benzamide;

5-(tert-butyl)-N-(2-hydroxyethyl)-2-methoxy-3-(3-(4-((2-((3-methoxy-5-(2-(2-(2-methoxy-ethoxy)ethoxy)ethoxy)phenyl)amino)pyrimidin-4-yl)oxy)naphthalen-1-yl)ureido)benzamide;

N-(5-(tert-butyl)-2-methoxy-3-(3-(4-((2-((3-methoxy-5-(2-(2-(2-methoxyethoxy)ethoxy)-phenyl)amino)pyrimidin-4-yl)oxy)naphthalen-1-yl)ureido)phenyl)methanesulfonamide;

methyl 2-(5-(tert-butyl)-2-methoxy-3-(3-(4-((2-((3-methoxy-5-(2-(2-(2-methoxyethoxy)-ethoxy)ethoxy)phenyl)amino)pyrimidin-4-yl)oxy)naphthalen-1-yl)ureido)benzamido)acetate;

N-benzyl-5-(tert-butyl)-2-methoxy-3-(3-(4-((2-((3-methoxy-5-(2-(2-(2-methoxyethoxy)-ethoxy)ethoxy)phenyl)amino)pyrimidin-4-yl)oxy)naphthalen-1-yl)ureido)benzamide;

5-(tert-butyl)-3-(3-(4-((2-((3-ethynyl-5-((2-morpholinoethyl)carbamoyl)phenyl)amino)pyridin-4-yl)oxy)naphthalen-1-yl)ureido)-2-methoxy-N-methylbenzamide;

3-((4-((4-(3-(5-(tert-butyl)-2-methoxy-3-(methylsulfonamido)phenyl)ureido)naphthalen-1-yl)oxy)pyrimidin-2-yl)amino)-N-(2,5,8,11,14,17,20-heptaoxadocosan-22-yl)-5-methoxy-benzamide;

5-(tert-butyl)-N-ethyl-2-methoxy-3-(3-(4-((2-((3-methoxy-5-(2-(2-(2-methoxyethoxy)-ethoxy)ethoxy)phenyl)amino)pyrimidin-4-yl)oxy)naphthalen-1-yl)ureido)benzamide;

5-(tert-butyl)-N-isopropyl-2-methoxy-3-(3-(4-((2-((3-methoxy-5-(2-(2-(2-methoxyethoxy)-ethoxy)ethoxy)phenyl)amino)pyrimidin-4-yl)oxy)naphthalen-1-yl)ureido)benzamide;

5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)-N-(2-methoxyethyl)benzamide;

2-(5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)benzamido)acetic acid;

N-(3-(3-(4-((2-((3-(2,5,8,11,14,17,20-heptaoxadocosan-22-yloxy)-5-methoxyphenyl)-amino)pyridin-4-yl)oxy)naphthalen-1-yl)ureido)-5-(tert-butyl)-2-methoxyphenyl)methanesulfonamide;

5-(tert-butyl)-N-(2-(dimethylamino)ethyl)-2-methoxy-3-(3-(4-((2-((3-methoxy-5-(2-(2-(2-methoxyethoxy)ethoxy)ethoxy)phenyl)amino)pyrimidin-4-yl)oxy)naphthalen-1-yl)ureido)-benzamide;

3-((4-((4-(3-(5-(tert-butyl)-3-carbamoyl-2-methoxyphenyl)ureido)naphthalen-1-yl)oxy)pyridin-2-yl)amino)-5-methoxy-N-(2-morpholinoethyl)benzamide;

3-((4-((4-(3-(5-(tert-butyl)-3-carbamoyl-2-methoxyphenyl)ureido)naphthalen-1-yl)oxy)pyridin-2-yl)amino)-5-ethynyl-N-(2-morpholinoethyl)benzamide;

3-((4-((4-(3-(5-(tert-butyl)-2-methoxy-3-(methylsulfonamido)phenyl)ureido)naphthalen-1-yl)oxy)pyridin-2-yl)amino)-5-ethynyl-N-(2-morpholinoethyl)benzamide;

N-(5-(tert-butyl)-3-(3-(4-((2-((3-(cyclopropanecarbonyl)-5-methoxyphenyl)amino)pyrimidin-4-yl)oxy)naphthalen-1-yl)ureido)-2-methoxyphenyl)methanesulfonamide;

5-(tert-butyl)-2-methoxy-3-(3-(4-((2-((3-methoxy-5-(2-(2-(2-methoxyethoxy)ethoxy)ethoxy)-phenyl)amino)pyrimidin-4-yl)oxy)naphthalen-1-yl)ureido)-N-(oxetan-3-yl)-benzamide;

3-((4-((4-(3-(5-(tert-butyl)-2-methoxy-3-(methylsulfonamido)phenyl)ureido)naphthalen-1-yl)oxy)pyridin-2-yl)amino)-5-ethynyl-N-(2-(2-methoxyethoxy)ethyl)benzamide;

3-((4-((4-(3-(5-(tert-butyl)-3-carbamoyl-2-methoxyphenyl)ureido)naphthalen-1-yl)oxy)pyridin-2-yl)amino)-5-ethynyl-N-(2-(2-(2-methoxyethoxy)ethoxy)ethyl)benzamide;

3-((4-((4-(3-(5-(tert-butyl)-2-methoxy-3-(methylsulfonamido)phenyl)ureido)naphthalen-1-yl)oxy)pyridin-2-yl)amino)-5-ethynyl-N-(2-(2-(2-methoxyethoxy)ethoxy)ethyl)benzamide;

5-(tert-butyl)-2-methoxy-3-(3-(4-((2-((3-methoxy-5-(2-(2-(2-methoxyethoxy)ethoxy)ethoxy)-phenyl)amino)pyrimidin-4-yl)oxy)naphthalen-1-yl)ureido)benzenesulfonamide;

(R)-3-((4-((4-(3-(5-(tert-butyl)-2-methoxy-3-(methylsulfonamido)phenyl)ureido)naphthalen-1-yl)oxy)pyrimidin-2-yl)amino)-5-ethynyl-N-(1-morpholinopropan-2-yl)benzamide;

(S)-3-((4-((4-(3-(5-(tert-butyl)-2-methoxy-3-(methylsulfonamido)phenyl)ureido)naphthalen-1-yl)oxy)pyrimidin-2-yl)amino)-5-ethynyl-N-(1-morpholinopropan-2-yl)benzamide;

N-(5-(tert-butyl)-3-(3-(4-((2-((4-chloro-3-methoxy-5-(2-(2-methoxyethoxy)ethoxy)ethoxy)-phenyl)amino)pyrimidin-4-yl)oxy)naphthalen-1-yl)ureido)-2-methoxyphenyl)-methanesulfonamide;

1-(5-(tert-butyl)-2-methoxy-3-(1,3,4-oxadiazol-2-yl)phenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea;

(S)-5-(tert-butyl)-3-(3-(4-((2-((3-ethynyl-5-((1-morpholinopropan-2-yl)carbamoyl)phenyl)-amino)pyrimidin-4-yl)oxy)naphthalen-1-yl)ureido)-2-methoxy-N-methylbenzamide;

(R)-5-(tert-butyl)-3-(3-(4-((2-((3-ethynyl-5-((1-morpholinopropan-2-yl)carbamoyl)phenyl)-amino)pyrimidin-4-yl)oxy)naphthalen-1-yl)ureido)-2-methoxy-N-methylbenzamide;

3-((4-((4-(3-(3-(tert-butyl)-5-carbamoylphenyl)ureido)naphthalen-1-yl)oxy)pyridin-2-yl)amino)-5-ethynyl-N-(2-(2-(2-methoxyethoxy)ethoxy)ethyl)benzamide;

1-(5-(tert-butyl)-2-oxo-2,3-dihydrobenzo[d]oxazol-7-yl)-3-(4-((2-((3-methoxy-5-(2-(2-(2-methoxyethoxy)ethoxy)ethoxy)phenyl)amino)pyrimidin-4-yl)oxy)naphthalen-1-yl)urea;

1-(5-(tert-butyl)-2-methylbenzo[d]oxazol-7-yl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea;

3-((4-((4-(3-(3-(tert-butyl)-5-(methylsulfonamido)phenyl)ureido)naphthalen-1-yl)oxy)pyridin-2-yl)amino)-5-ethynyl-N-(2-morpholinoethyl)benzamide;

3-((4-((4-(3-(5-(tert-butyl)-2-methoxy-3-(methylsulfonamido)phenyl)ureido)naphthalen-1-yl)oxy)pyridin-2-yl)amino)-5-methoxy-N-(3-morpholinopropyl)benzamide;

(S)-3-((4-((4-(3-(5-(tert-butyl)-2-methoxy-3-(methylsulfonamido)phenyl)ureido)naphthalen-1-yl)oxy)pyridin-2-yl)amino)-5-ethynyl-N-(1-(2-(2-methoxyethoxy)ethoxy)propan-2-yl)benzamide;

(R)-3-((4-((4-(3-(5-(tert-butyl)-2-methoxy-3-(methylsulfonamido)phenyl)ureido)-naphthalen-1-yl)oxy)pyridin-2-yl)amino)-5-ethynyl-N-(1-(2-(2-methoxyethoxy)ethoxy)propan-2-yl)benzamide;

N-(5-(tert-butyl)-2-ethoxy-3-(3-(4-((2-((3-methoxy-5-(2-(2-(2-methoxyethoxy)ethoxy)ethoxy)-phenyl)amino)pyrimidin-4-yl)oxy)naphthalen-1-yl)ureido)phenyl)methanesulfonamide;

1-(5-(tert-butyl)-2-methoxy-3-(1H-1,2,3-triazol-5-yl)phenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea;

N-(5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)-1,1,1-trifluoromethanesulfonamide;

N-(5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)cyclohexanesulfonamide;

N-(5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)piperidine-1-sulfonamide;

N-(5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)dimethylamino-sulfonamide;

5-(tert-butyl)-2-methoxy-N-(oxetan-3-yl)-3-(3-(4-((2-(phenylamino)pyridin-4-yl)oxy)-naphthalen-1-yl)ureido)benzamide;

5-(tert-butyl)-N-(2-(dimethylamino)ethyl)-2-methoxy-3-(3-(4-((2-((3-methoxy-5-(2-(2-(2-methoxyethoxy)ethoxy)ethoxy)phenyl)amino)pyridin-4-yl)oxy)naphthalen-1-yl)ureido)-benzamide;

N-(4-(tert-butyl)-6-(3-(4-((2-((3-methoxy-5-(2-(2-(2-methoxyethoxy)ethoxy)ethoxy)phenyl)-amino)pyrimidin-4-yl)oxy)naphthalen-1-yl)ureido)-[1,1'-biphenyl]-2-yl)methanesulfonamide;

N-(5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)morpholine-4-sulfonamide;

5-(tert-butyl)-2-methoxy-3-(3-(4-((2-((3-methoxy-5-(2-(2-(2-methoxyethoxy)ethoxy)ethoxy)-phenyl)amino)pyridin-4-yl)oxy)naphthalen-1-yl)ureido)-N-(oxetan-3-yl)benzamide;

N-(5-(tert-butyl)-3-(3-(4-((2-((3-(2-(2-(2-hydroxyethoxy)ethoxy)ethoxy)-5-methoxyphenyl)-amino)pyrimidin-4-yl)oxy)naphthalen-1-yl)ureido)-2-methoxyphenyl)methanesulfonamide;

5-(tert-butyl)-2-methoxy-N-(oxetan-3-yl)-3-(3-(4-((2-(phenylamino)pyrimidin-4-yl)oxy)-naphthalen-1-yl)ureido)benzamide;

3-((4-((4-(3-(5-(tert-butyl)-2-methoxy-3-(methylsulfonamido)phenyl)ureido)naphthalen-1-yl)oxy)pyridin-2-yl)amino)-5-methoxy-N-(2-(pyrrolidin-1-yl)ethyl)benzamide;

3-((4-((4-(3-(5-(tert-butyl)-2-methoxy-3-(methylsulfonamido)phenyl)ureido)naphthalen-1-yl)oxy)pyridin-2-yl)amino)-5-methoxy-N-(2-(piperidin-1-yl)ethyl)benzamide;

3-((4-((4-(3-(5-(tert-butyl)-2-methoxy-3-(methylsulfonamido)phenyl)ureido)naphthalen-1-yl)oxy)pyridin-2-yl)amino)-5-methoxy-N-(2-(4-methylpiperazin-1-yl)ethyl)benzamide;

N-(5-(tert-butyl)-2-methoxy-3-(3-(4-((2-(phenylamino)pyridin-4-yl)oxy)naphthalen-1-yl)ureido)phenyl)morpholine-4-sulfonamide;

N-(2-aminoethyl)-5-(tert-butyl)-2-methoxy-3-(3-(4-((2-((3-methoxy-5-(2-(2-(2-methoxyethoxy)-ethoxy)ethoxy)phenyl)amino)pyridin-4-yl)oxy)naphthalen-1-yl)ureido)benzamide;

5-tert-butyl-2-methoxy-N-(oxetan-3-yl)-3-[[4-[[2-(2-pyridylmethylamino)-4-pyridyl]oxy]-1-naphthyl]carbamoylamino]benzamide;

5-tert-butyl-2-methoxy-3-[[4-[[2-(3-methoxyanilino)-4-pyridyl]oxy]-1-naphthyl]-carbamoylamino]N-(oxetan-3-yl)benzamide; 3-[[4-[(2-anilino-4-pyridyl)oxy]-2,3-difluorophenyl]carbamoylamino]-5-tert-butyl-2-methoxy-N-(oxetan-3-yl)benzamide;

3-[[4-[(2-anilino-4-pyridyl)oxy]-1-naphthyl]carbamoylamino]-5-tert-butyl-2-methoxy-N-tetrahydropyran-4-yl-benzamide;

3-[[4-[(2-anilino-4-pyridyl)oxy]-1-naphthyl]carbamoylamino]-5-tert-butyl-2-methoxy-N-(1-methyl-4-piperidyl)benzamide;

3-[[4-[(2-anilino-4-pyridyl)oxy]-1-naphthyl]carbamoylamino]-5-tert-butyl-2-methoxy-N—[(R3)-tetrahydrofuran-3-yl]benzamide;

3-[[4-[(2-anilino-4-pyridyl)oxy]-1-naphthyl]carbamoylamino]-5-tert-butyl-2-methoxy-N-[(3S)-tetrahydrofuran-3-yl]benzamide;

1-[5-tert-butyl-3-(methanesulfonamido)-2-methoxyphenyl]-3-[4-[[2-[3-[2-[2-(2-hydroxyethoxy)ethoxy]ethoxy]-5-methoxy-anilino]-4-pyridyl]oxy]-1-naphthyl]urea;

1-[5-tert-butyl-3-(methanesulfonamido)-2-methoxyphenyl]-3-[4-[[2-[3-(hydroxymethyl)-5-methoxyanilino]-4-pyridyl]oxy]-1-naphthyl]urea;

5-tert-butyl-3-[[4-[[2-[3-(hydroxymethyl)-5-methoxyanilino]-4-pyridyl]oxy]-1-naphthyl]carbamoylamino]-2-methoxybenzamide;

5-tert-butyl-3-[[4-[[2-[3-(hydroxymethyl)-5-methoxyanilino]-4-pyridyl]oxy]-1-naphthyl]carbamoylamino]-2-methoxy-N-methyl-benzamide;

3-[[4-[[4-[[5-tert-Butyl-3-(methanesulfonamido)-2-methoxyphenyl]carbamoylamino]-1-naphthyl]oxy]-2-pyridyl]amino]-5-methoxy-N-(2-morpholino-2-oxoethyl)benzamide;

3-[[4-[[4-[[5-tert-butyl-3-(hydroxymethyl)-2-methoxyphenyl]carbamoylamino]-1-naphthyl]-oxy]-2-pyridyl]amino]-5-ethynyl-N-[2-[2-(2-methoxyethoxy)ethoxy]ethyl]benzamide;

3-[[4-[[4-[[5-tert-butyl-3-(methanesulfonamido)-2-methoxyphenyl]carbamoylamino]-1-naphthyl]oxy]-2-pyridyl]amino]-5-ethynyl-N-[2-(4-methylpiperazin-1-yl)ethyl]benzamide;

3-[[4-[[4-[[5-tert-butyl-3-(methanesulfonamido)-2-methoxyphenyl]carbamoylamino]-1-naphthyl]oxy]-2-pyridyl]amino]-5-ethynyl-N-(3-morpholinopropyl)benzamide;

3-[[4-[[4-[[5-tert-butyl-3-(methanesulfonamido)-2-methoxyphenyl]carbamoylamino]-1-naphthyl]oxy]pyrimidin-2-yl]amino]-5-methoxy-N-[2-(4-methylpiperazin-1-yl)ethyl]benzamide;

3-[[4-[[4-[[5-tert-butyl-3-(methanesulfonamido)-2-methoxyphenyl]carbamoylamino]-1-naphthyl]oxy]pyrimidin-2-yl]amino]-5-methoxy-N-(3-morpholinopropyl)benzamide;

5-tert-butyl-3-[[4-[2-[3-ethynyl-5-(2-morpholinoethylcarbamoyl)anilino]pyrimidin-4-yl]oxy-1-naphthyl]carbamoylamino]-2-methoxy-benzamide;

3-[[4-[[4-[[5-tert-butyl-3-(methanesulfonamido)-2-methoxyphenyl]carbamoylamino]-1-naphthyl]oxy]-2-pyridyl]amino]-5-methoxy-N-(2-methyl-2-morpholinopropyl)benzamide;

3-[[4-[[4-[[5-tert-butyl-3-(methanesulfonamido)-2-methoxyphenyl]carbamoylamino]-1-naphthyl]oxy]-2-pyridyl]amino]-5-methoxy-N-(2-thiomorpholinoethyl)benzamide;

3-[[4-[[4-[[5-tert-butyl-3-(methanesulfonamido)-2-methoxyphenyl]carbamoylamino]-1-naphthyl]oxy]-2-pyridyl]amino]-5-methoxy-N-[2-(1-oxo-1,4-thiazinan-4-yl)ethyl]benzamide;

3-[[4-[[4-[[5-tert-butyl-3-(methanesulfonamido)-2-methoxyphenyl]carbamoylamino]-1-naphthyl]oxy]-2-pyridyl]amino]-N-[2-(1,1-dioxo-1,4-thiazinan-4-yl)ethyl]-5-methoxybenzamide;

3-[[4-[[4-[[5-tert-butyl-3-(methanesulfonamido)-2-methoxyphenyl]carbamoylamino]-1-naphthyl]oxy]-2-pyridyl]amino]-N-[2-(3,3-dimethylmorpholin-4-yl)ethyl]-5-methoxybenzamide;

3-[[4-[[4-[[5-tert-butyl-3-(methanesulfonamido)-2-methoxyphenyl]carbamoylamino]-1-naphthyl]oxy]-2-pyridyl]amino]-N-[2-(2,2-dimethylmorpholin-4-yl)ethyl]-5-methoxybenzamide;

3-[[4-[[4-[[5-tert-butyl-3-(methanesulfonamido)-2-methoxyphenyl]carbamoylamino]-1-naphthyl]oxy]-2-pyridyl]amino]-N-[2-[(2R,6S)-2,6-dimethylmorpholin-4-yl]ethyl]-5-methoxy-benzamide;

3-[[4-[[4-[[5-tert-butyl-3-(methanesulfonamido)-2-methoxyphenyl]carbamoylamino]-1-naphthyl]oxy]-2-pyridyl]amino]-5-methoxy-N-[2-(1,4-oxazepan-4-yl)ethyl]benzamide;

3-[[4-[[4-[[5-tert-butyl-3-(methanesulfonamido)-2-methoxyphenyl]carbamoylamino]-1-naphthyl]oxy]-2-pyridyl]amino]-5-methoxy-N-[2-(4-methyl-1,4-diazepan-1-yl)ethyl]benzamide;

3-[[4-[[4-[[5-tert-butyl-3-(methanesulfonamido)-2-methoxyphenyl]carbamoylamino]-1-naphthyl]oxy]-2-pyridyl]amino]-5-methoxy-N-(2-piperazin-1-ylethyl)benzamide;

3-[[4-[[4-[[5-tert-butyl-3-(methanesulfonamido)-2-methoxyphenyl]carbamoylamino]-1-naphthyl]oxy]-2-pyridyl]amino]-N-[2-[2-(2-hydroxyethoxy)ethoxy]ethyl]-5-methoxybenzamide;

3-[[[4-[[4-[[5-tert-Butyl-3-(methanesulfonamido)-2-methoxyphenyl]carbamoylamino]-1-naphthyl]oxy]pyrimidin-2-yl]amino]methyl]-N-[2-[2-(2-methoxyethoxy)ethoxy]ethyl]benzamide;

3-[[[4-[[4-[[5-tert-butyl-3-(methanesulfonamido)-2-methoxyphenyl]carbamoylamino]-1-naphthyl]oxy]pyrimidin-2-yl]amino]methyl]-N-(2-morpholinoethyl)benzamide;

3-[[4-[[4-[[5-tert-butyl-3-(methanesulfonamido)-2-methoxyphenyl]carbamoylamino]-1-naphthyl]oxy]-2-pyridyl]amino]-5-methoxy-N-[2-(2-methoxyethoxy)ethyl]benzamide;

3-[[4-[[4-[[5-tert-butyl-3-(methanesulfonamido)-2-methoxyphenyl]carbamoylamino]-1-naphthyl]oxy]-2-pyridyl]amino]-5-methoxy-N-[2-[2-[2-(2-methoxyethoxy)ethoxy]ethyl]-benzamide;

3-[[4-[[4-[[5-tert-butyl-3-(methanesulfonamido)-2-methoxyphenyl]carbamoylamino]-1-naphthyl]oxy]-2-pyridyl]amino]-N-[2-(4-hydroxy-1-piperidyl)ethyl]-5-methoxybenzamide;

1-[5-tert-butyl-3-(methanesulfonamido)-2-methoxyphenyl]-3-[4-[2-[3-methoxy-5-[2-[2-(2-methoxyethoxy)ethoxy]ethylsulfinyl]anilino]pyridin-4-yl]oxy-1-naphthyl]urea;

1-[5-tert-Butyl-3-(methanesulfonamido)-2-methoxyphenyl]-3-[4-[2-[3-methoxy-5-[2-[2-(2-methoxyethoxy)ethoxy]ethylsulfonyl]anilino]pyridin-4-yl]oxy-1-naphthyl]urea;

5-tert-butyl-3-[[4-[[2-[3-(hydroxymethyl)-5-methoxyanilino]-4-pyridyl]oxy]-1-naphthyl]-carbamoylamino]-2-methoxy-N-(oxetan-3-yl)benzamide;

3-[[[4-[[4-[[5-tert-butyl-3-(methanesulfonamido)-2-methoxyphenyl]carbamoylamino]-1-naphthyl]oxy]pyrimidin-2-yl]amino]methyl]-5-methoxy-N-[2-[2-(2-methoxyethoxy)ethoxy]-ethyl]benzamide;

3-[[[4-[[4-[[5-tert-butyl-3-(methanesulfonamido)-2-methoxyphenyl]carbamoylamino]-1-naphthyl]oxy]pyrimidin-2-yl]amino]methyl]-5-methoxy-N-(2-morpholinoethyl)benzamide;

1-[5-tert-butyl-3-(cyanomethyl)-2-methoxyphenyl]-3-[4-[[2-[3-methoxy-5-[2-[2-(2-methoxyethoxy)ethoxy]ethyl]anilino]-4-pyridyl]oxy]-1-naphthyl]urea;

3-[[4-[[4-[[5-tert-butyl-3-(cyanomethyl)-2-methoxyphenyl]carbamoylamino]-1-naphthyl]oxy]-2-pyridyl]amino]-5-methoxy-N-(2-morpholinoethyl)benzamide;

3-[[4-[[4-[[5-tert-butyl-3-(cyanomethyl)-2-methoxyphenyl]carbamoylamino]-1-naphthyl]oxy]-2-pyridyl]amino]-5-ethynyl-N-[2-[2-(2-methoxyethoxy)ethoxy]ethyl]benzamide;

5-tert-butyl-3-[[4-[[2-[3-ethynyl-5-(hydroxymethyl)anilino]-4-pyridyl]oxy]-1-naphthyl]carbamoylamino]-2-methoxybenzamide;

3-[[4-[[4-[[5-tert-butyl-3-(methanesulfonamido)-2-methoxyphenyl]carbamoylamino]-1-naphthyl]oxy]-2-pyridyl]amino]-5-methoxy-N-[2-(4-oxo-1-piperidyl)ethyl]benzamide; and 5-tert-butyl-3-[[4-[[2-[3-ethynyl-5-(hydroxymethyl)anilino]-4-pyridyl]oxy]-1-naphthyl]carbamoylamino]-2-methoxy-N-methyl-benzamide, or a pharmaceutically acceptable salt thereof.

In this respect, particular embodiments of the invention that may be mentioned include those in which the compound of formula I, Ix, Ia, Ib or Ic is a compound selected from the list:

3-((4-((4-(3-(5-(tert-butyl)-2-methoxy-3-(methylsulfonamido)phenyl)ureido)naphthalen-1-yl)oxy)pyridin-2-yl)amino)-5-methoxy-N-(2-(2-(2-methoxyethoxy)ethoxy)ethyl)benzamide;

3-((4-((4-(3-(5-(tert-butyl)-2-methoxy-3-(methylsulfonamido)phenyl)ureido)naphthalen-1-yl)oxy)pyrimidin-2-yl)amino)-5-ethynyl-N-(2-(2-(2-methoxyethoxy)ethoxy)ethyl)benzamide;

3-((4-((4-(3-(5-(tert-butyl)-2-methoxy-3-(methylsulfonamido)phenyl)ureido)naphthalen-1-yl)oxy)pyridin-2-yl)amino)-5-methoxy-N-(2-morpholinoethyl)benzamide;

5-(tert-butyl)-2-methoxy-3-(3-(4-((2-((3-methoxy-5-(2-(2-(2-methoxyethoxy)ethoxy)ethoxy)-phenyl)amino)pyridin-4-yl)oxy)naphthalen-1-yl)ureido)-N-methylbenzamide;

5-(tert-butyl)-2-methoxy-3-(3-(4-((2-((3-methoxy-5-(2-(2-(2-methoxyethoxy)ethoxy)ethoxy)-phenyl)amino)pyridin-4-yl)oxy)naphthalen-1-yl)ureido)benzamide;

3-((4-((4-(3-(5-(tert-butyl)-2-methoxy-3-(methylsulfonamido)phenyl)ureido)naphthalen-1-yl)oxy)pyridin-2-yl)amino)-5-methoxy-N-(3-morpholinopropyl)benzamide; and 5-(tert-butyl)-2-methoxy-N-(oxetan-3-yl)-3-(3-(4-((2-(phenylamino)pyridin-4-yl)oxy)-naphthalen-1-yl)ureido)benzamide, or a pharmaceutically acceptable salt thereof.

Other particular embodiments of the invention that may be mentioned include those in which the compound of formula I, Ix, Ia, Ib or Ic is not:

3-((4-((4-(3-(5-(tert-butyl)-2-methoxy-3-(methylsulfonamido)phenyl)ureido)naphthalen-1-yl)oxy)pyridin-2-yl)amino)-5-methoxy-N-(2-(2-(2-methoxyethoxy)ethoxy)ethyl)benzamide;

N-(5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)methanesulfonamide;

3-((4-((4-(3-(5-(tert-butyl)-2-methoxy-3-(methylsulfonamido)phenyl)ureido)naphthalen-1-yl)oxy)pyrimidin-2-yl)amino)-5-ethynyl-N-(2-(2-(2-methoxyethoxy)ethoxy)ethyl)benzamide;

3-((4-((4-(3-(5-(tert-butyl)-2-methoxy-3-(methylsulfonamido)phenyl)ureido)naphthalen-1-yl)oxy)pyridin-2-yl)amino)-5-methoxy-N-(2-morpholinoethyl)benzamide;

5-(tert-butyl)-2-methoxy-3-(3-(4-((2-((3-methoxy-5-(2-(2-(2-methoxyethoxy)ethoxy)ethoxy)-phenyl)amino)pyridin-4-yl)oxy)naphthalen-1-yl)ureido)-N-methylbenzamide;

5-(tert-butyl)-2-methoxy-3-(3-(4-((2-((3-methoxy-5-(2-(2-(2-methoxyethoxy)ethoxy)ethoxy)-phenyl)amino)pyridin-4-yl)oxy)naphthalen-1-yl)ureido)benzamide;

3-((4-((4-(3-(5-(tert-butyl)-2-methoxy-3-(methylsulfonamido)phenyl)ureido)naphthalen-1-yl)oxy)pyridin-2-yl)amino)-5-methoxy-N-(3-morpholinopropyl)benzamide; and/or 5-(tert-butyl)-2-methoxy-N-(oxetan-3-yl)-3-(3-(4-((2-(phenylamino)pyridin-4-yl)oxy)-naphthalen-1-yl)ureido)benzamide, or a pharmaceutically acceptable salt thereof.

Other particular embodiments of the invention that may be mentioned include those in which the compound of formula I, Ix, Ia, Ib or Ic either is or is not 3-((4-((4-(3-(5-(tert-butyl)-2-methoxy-3-(methylsulfonamido)phenyl)ureido)naphthalen-1-yl)oxy)pyrimidin-2-yl)amino)-5-ethynyl-N-(2-(2-(2-methoxyethoxy)ethoxy)ethyl)benzamide or a pharmaceutically acceptable salt thereof.

Examples of salts of compounds of formula I, Ix, Ia, Ib or Ic include all pharmaceutically acceptable salts, such as, without limitation, acid addition salts of strong mineral acids such as HCl and HBr salts and addition salts of strong organic acids such as methanesulfonic acid.

References herein to a compound of the invention (a compound of formula I, Ix, Ia, Ib or Ic) are intended to include references to the compound and to all pharmaceutically acceptable salts, solvates, isotopic derivatives and/or tautomers of said compound, unless the context specifically indicates otherwise. In this respect, solvates that may be mentioned include hydrates.

The compounds of the invention (compounds of formula I, Ix, Ia, Ib or Ic) are p38 MAP kinase inhibitors (especially of the alpha subtype) and are therefore useful in medicine, in particular for the treatment of inflammatory diseases.

Further aspects of the invention that may be mentioned therefore include the following.

(a) A pharmaceutical formulation comprising compound of formula I, Ix, Ia, Ib or Ic, as hereinbefore defined, or pharmaceutically acceptable salt thereof, in admixture with a pharmaceutically acceptable adjuvant, diluent or carrier.

(b) A combination product comprising
  (A) a compound of formula I, Ix, Ia, Ib or Ic, as hereinbefore defined, or pharmaceutically acceptable salt thereof, and
  (B) another therapeutic agent,
  wherein each of components (A) and (B) is formulated in admixture with a pharmaceutically-acceptable adjuvant, diluent or carrier.

In this aspect of the invention, the combination product may be either a single (combination) pharmaceutical formulation or a kit-of-parts.

Thus, this aspect of the invention encompasses a pharmaceutical formulation including a compound of formula I, Ix, Ia, Ib or Ic, as hereinbefore defined, or pharmaceutically acceptable salt thereof, and another therapeutic agent, in admixture with a pharmaceutically acceptable adjuvant, diluent or carrier (which formulation is hereinafter referred to as a "combined preparation").

It also encompasses a kit of parts comprising components:
  (i) a pharmaceutical formulation including a compound of formula I, Ix, Ia, Ib or Ic, as hereinbefore defined, or pharmaceutically acceptable salt thereof, in admixture with a pharmaceutically acceptable adjuvant, diluent or carrier; and
  (ii) a pharmaceutical formulation including another therapeutic agent, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier.

(c) A process for preparing the pharmaceutical formulation of aspect (a) above, said process comprising the step of admixing the compound of formula I, Ix, Ia, Ib or Ic, as hereinbefore defined, or pharmaceutically acceptable salt thereof, with a pharmaceutically acceptable adjuvant, diluent or carrier.

Embodiments of this aspect of the invention that may be mentioned include those in which the pharmaceutically acceptable adjuvant, diluent or carrier is a topically acceptable adjuvant, diluent or carrier (and/or wherein the process is for preparing a topical pharmaceutical formulation, i.e. a pharmaceutical formulation that is adapted for topical administration).

(d) A compound of formula I, Ix, Ia, Ib or Ic, as hereinbefore defined, or pharmaceutically acceptable salt thereof, for use in medicine (or for use as a medicament or as a pharmaceutical).

(e) A compound of formula I, Ix, Ia, Ib or Ic, as hereinbefore defined, or pharmaceutically acceptable salt thereof, or a pharmaceutical formulation or combination product as defined in connection with aspect (a) or (b) of the invention, for use in the treatment or prevention of an inflammatory disease.

(f) The use of
  a compound of formula I, Ix, Ia, Ib or Ic, as hereinbefore defined, or pharmaceutically acceptable salt thereof, or
  a pharmaceutical formulation or combination product as defined in connection with aspect (a) or (b) of the invention,
  for the preparation of a medicament for the treatment or prevention of an inflammatory disease.

(g) A method of treating or preventing an inflammatory disease, said method comprising administering to a subject an effective amount of
  a compound of formula I, Ix, Ia, Ib or Ic, as hereinbefore defined, or pharmaceutically acceptable salt thereof, or
  a pharmaceutical formulation or combination product as defined in connection with aspect (a) or (b) of the invention.

(h) A method of sensitizing a subject to the anti-inflammatory effects of a corticosteroid, said method comprising administering to the subject an effective amount of
  a compound of formula I, Ix, Ia, Ib or Ic, as hereinbefore defined, or pharmaceutically acceptable salt thereof, or
  a pharmaceutical formulation or combination product as defined in connection with aspect (a) or (b) of the invention.

Embodiments of this aspect of the invention that may be mentioned include those in which the subject is one who has become refractory to the anti-inflammatory effects of a corticosteroid.

DETAILED DESCRIPTION OF THE PREFERRED EMBODIMENT

Formulations

In relation to aspects (a) and (b) above, diluents and carriers that may be mentioned include those suitable for parenteral, oral, topical, mucosal and rectal administration.

The pharmaceutical formulations and combination products of aspects (a) and (b) above may be prepared e.g. for parenteral, subcutaneous, intramuscular, intravenous, intra-articular, intravitreous, periocular, retrobulbar, subconjunctival, sub-Tenon, topical ocular or peri-articular administration, particularly in the form of liquid solutions, emulsions or suspensions; for oral administration, particularly in the form of tablets or capsules, and especially involving technologies aimed at furnishing colon-targeted drug release (Patel, M. M. *Expert Opin. Drug Deliv.* 2011, 8 (10), 1247-1258); for topical e.g. pulmonary or intranasal administration, particularly in the form of powders, nasal drops or aerosols and transdermal administration; for topical ocular administration, particularly in the form of solutions, emulsions, suspensions, ointments, implants/inserts, gels, jellies or liposomal microparticle formulations (Ghate, D.; Edelhauser, H. F. *Expert Opin. Drug Deliv.* 2006, 3 (2), 275-287); for ocular administration, particularly in the form of biodegradable and non-biodegradable implants, liposomes and nanoparticles (Thrimawithana, T. R. et al. *Drug Discov. Today* 2011, 16 (5/6), 270-277); for mucosal administration e.g. to buccal, sublingual or vaginal mucosa, and for rectal administration e.g. in the form of a suppository or enema.

The pharmaceutical formulations and combination products of aspects (a) and (b) above may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered sprays. For buccal administration, typical excipients include sugars, calcium stearate, magnesium stearate, pregelatinated starch, and the like.

Pharmaceutical formulations and combination products suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrrolidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules. Such two-piece hard shell capsules may be made from, for example, gelatin or hydroxylpropyl methylcellulose (HPMC).

A dry shell formulation typically comprises of about 40% to 60% w/w concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

A compound of the invention may be administered topically (e.g. to the lung, eye or intestines). Thus, embodiments of aspects (a) and (b) above that may be mentioned include pharmaceutical formulations and combination products that are adapted for topical administration. Such formulations include those in which the excipients (including any adjuvant, diluent and/or carrier) are topically acceptable.

Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoroethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a non-pressurised formulation such as an aqueous solution or suspension. This may be administered by means of a nebuliser e.g. one that can be hand-held and portable or for home or hospital use (i.e. non-portable). The formulation may comprise excipients such as water, buffers, tonicity adjusting agents, pH adjusting agents, surfactants and co-solvents. Suspension liquid and aerosol formulations (whether pressurised or unpressurised) will typically contain the compound of the invention in finely divided form, for example with a $D_{50}$ of 0.5-10 μm e.g. around 1-5 μm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

Topical administration to the lung may also be achieved by use of a dry-powder formulation. A dry powder formulation will contain the compound of the disclosure in finely divided form, typically with a mass mean aerodynamic diameter (MMAD) of 1-10 μm or a $D_{50}$ of 0.5-10 μm e.g. around 1-5 μm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of large particle size e.g. an MMAD of 50 μm or more, e.g. 100 μm or more or a $D_{50}$ of 40-150 μm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Examples of dry powder delivery systems include SPINHALER, DISKHALER, TURBOHALER, DISKUS and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

In one embodiment a compound of the present invention is provided in a micronized dry powder formulation, for example further comprising lactose of a suitable grade optionally together with magnesium stearate, filled into a single dose device such as AEROLISER or filled into a multi dose device such as DISKUS.

The compounds of the present invention may also be administered rectally, for example in the form of suppositories or enemas, which include aqueous or oily solutions as well as suspensions and emulsions. Such compositions are prepared following standard procedures, well known by those skilled in the art. For example, suppositories can be prepared by mixing the active ingredient with a conventional suppository base such as cocoa butter or other glycerides, e.g., Suppocire. In this case, the drug is mixed with a suitable non-irritating excipient which is solid at ordinary temperatures but liquid at the rectal temperature and will therefore melt in the rectum to release the drug. Such materials are cocoa butter and polyethylene glycols.

Generally, for compositions intended to be administered topically to the eye in the form of eye drops or eye ointments, the total amount of the inhibitor will be about 0.0001 to less than 4.0% (w/w).

Preferably, for topical ocular administration, the compositions administered according to the present invention will be formulated as solutions, suspensions, emulsions and other dosage forms. Aqueous solutions are generally preferred, based on ease of formulation, as well as a patient's ability to administer such compositions easily by means of instilling one to two drops of the solutions in the affected eyes. However, the compositions may also be suspensions, viscous or semi-viscous gels, or other types of solid or semi-solid compositions. Suspensions may be preferred for compounds that are sparingly soluble in water.

The compositions administered according to the present invention may also include various other ingredients, including, but not limited to, tonicity agents, buffers, surfactants, stabilizing polymer, preservatives, co-solvents and viscosity building agents. Preferred pharmaceutical compositions of the present invention include the inhibitor with a tonicity agent and a buffer. The pharmaceutical compositions of the present invention may further optionally include a surfactant and/or a palliative agent and/or a stabilizing polymer.

Various tonicity agents may be employed to adjust the tonicity of the composition, preferably to that of natural tears for ophthalmic compositions. For example, sodium chloride, potassium chloride, magnesium chloride, calcium chloride, simple sugars, such as dextrose, fructose, galactose, and/or simply polyols, such as the sugar alcohols mannitol, sorbitol, xylitol, lactitol, isomaltitol, maltitol, and hydrogenated starch hydrolysates may be added to the composition to approximate physiological tonicity. Such an amount of tonicity agent will vary, depending on the particular agent to be added. In general, however, the compositions will have a tonicity agent in an amount sufficient to cause the final composition to have an ophthalmically acceptable osmolality (generally about 150-450 mOsm, preferably 250-350 mOsm and most preferably at approximately 290 mOsm). In general, the tonicity agents of the invention will be present in the range of 2 to 4% w/w. Preferred tonicity agents of the invention include the simple sugars or the sugar alcohols, such as D-mannitol.

An appropriate buffer system (e.g., sodium phosphate, sodium acetate, sodium citrate, sodium borate or boric acid) may be added to the compositions to prevent pH drift under storage conditions. The particular concentration will vary, depending on the agent employed. Preferably however, the buffer will be chosen to maintain a target pH within the range of pH 5 to 8, and more preferably to a target pH of pH 5 to 7.

Surfactants may optionally be employed to deliver higher concentrations of inhibitor. The surfactants function to solubilise the inhibitor and stabilise colloid dispersion, such as micellar solution, microemulsion, emulsion and suspension. Examples of surfactants which may optionally be used include polysorbate, poloxamer, polyoxyl 40 stearate, polyoxyl castor oil, tyloxapol, triton, and sorbitan monolaurate. Preferred surfactants to be employed in the invention have a hydrophile/lipophile/balance "HLB" in the range of 12.4 to 13.2 and are acceptable for ophthalmic use, such as TritonX114 and tyloxapol.

Additional agents that may be added to the ophthalmic compositions of the present invention are demulcents which function as a stabilising polymer. The stabilizing polymer should be an ionic/charged example with precedence for topical ocular use, more specifically, a polymer that carries negative charge on its surface that can exhibit a zeta-potential of (−)10-50 mV for physical stability and capable of making a dispersion in water (i.e. water soluble). A preferred stabilising polymer of the invention would be polyelectrolyte, or polyelectrolytes if more than one, from the family of cross-linked polyacrylates, such as carbomers, polycarbophil and Pemulen®, specifically Carbomer 974p (polyacrylic acid), at 0.1-0.5% w/w.

Other compounds may also be added to the ophthalmic compositions of the present invention to increase the viscosity of the carrier. Examples of viscosity enhancing agents include, but are not limited to: polysaccharides, such as hyaluronic acid and its salts, chondroitin sulfate and its salts, dextrans, various polymers of the cellulose family, vinyl polymers and acrylic acid polymers.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edentate disodium, sorbic acid, polyquarternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

The medical practitioner, or other skilled person, will be able to determine a suitable dosage for the compounds of the invention, and hence the amount of the compound of the invention that should be included in any particular pharmaceutical formulation (whether in unit dosage form or otherwise).

Embodiments of the invention that may be mentioned in connection with the combination products described at (b) above include those in which the other therapeutic agent is one or more therapeutic agents that are known by those skilled in the art to be suitable for treating inflammatory diseases (e.g. the specific diseases mentioned below).

For example, for the treatment of respiratory disorders (such as COPD or asthma), the other therapeutic agent is one or more agents selected from the list comprising:
- steroids (e.g. budesonide, beclomethasone dipropionate, fluticasone propionate, mometasone furoate, fluticasone furoate; a further example is ciclesonide);
- beta agonists, particularly beta2 agonists (e.g. terbutaline, salbutamol, salmeterol, formoterol; further examples are vilanterol, olodaterol, reproterol and fenoterol); and
- xanthines (e.g. theophylline).

For example, for the treatment of respiratory disorders (such as COPD or asthma), the other therapeutic agent is one or more agents selected from the list comprising:
- muscarinic antagonists (e.g. tiotropium, umeclidinium, glycopyrronium, aclidinium and daratropium, any of these for example as the bromide salt); and
- phosphodiesterase inhibitors.

Further, for the treatment of gastrointestinal disorders (such as Crohn's disease or ulcerative colitis), the other therapeutic agent may be, for example, one or more agents selected from the list comprising:
- 5-aminosalicylic acid, or a prodrug thereof (such as sulfasalazine, olsalazine or bisalazide);
- corticosteroids (e.g. prednisolone, methylprednisolone, or budesonide);
- immunosuppressants (e.g. cyclosporin, tacrolimus, methotrexate, azathioprine or 6-mercaptopurine);
- anti-TNFα antibodies (e.g., infliximab, adalimumab, certolizumab pegol or golimumab);
- anti-IL12/IL23 antibodies (e.g., ustekinumab) or small molecule ID 2/IL23 inhibitors (e.g., apilimod);
- Anti-α4β7 antibodies (e.g., vedolizumab);
- MAdCAM-1 blockers (e.g., PF-00547659);
- antibodies against the cell adhesion molecule α4-integrin (e.g., natalizumab);
- antibodies against the IL2 receptor α subunit (e.g., daclizumab or basiliximab); JAK3 inhibitors (e.g., tofacitinib or R348);
- Syk inhibitors and prodrugs thereof (e.g., fostamatinib and R-406);
- Phosphodiesterase-4 inhibitors (e.g., tetomilast);
- HMPL-004;
- probiotics;
- Dersalazine;
- semapimod/CPSI-2364; and
- protein kinase C inhibitors (e.g. AEB-071).

For the treatment of eye disorders (such as uveitis and keratoconjunctivitis sicca (dry eye)), the other therapeutic agent may be, for example, one or more agents selected from the list comprising:
- corticosteroids (e.g. dexamethasone, prednisolone, triamcinolone acetonide, difluprednate or fluocinolone acetonide);
- glucocorticoid agonists (e.g., mapracorat);
- immunosuppressants (e.g. cyclosporin, voclosporin, azathioprine, methotrexate, mycophenolate mofetil or tacrolimus);
- anti-TNFα antibodies (e.g., infliximab, adalimumab, certolizumab pegol, ESBA-105 or golimumab);
- anti-IL-17A antibodies (e.g., secukinumab);
- mTOR inhibitors (e.g., sirolimus);
- VGX-1027;
- adenosine A3 receptor agonists (e.g., CF-101);
- lifitegrast;
- JAK3 inhibitors (e.g., tofacitinib or R348); and
- protein kinase C inhibitors (e.g. AEB-071).

In particular embodiments, for the treatment of eye disorders (such as uveitis and keratoconjunctivitis sicca (dry eye)), the other therapeutic agent may be, for example, one or more agents selected from the list comprising:
- corticosteroids (e.g. dexamethasone, prednisolone, triamcinolone acetonide, difluprednate or fluocinolone acetonide);
- immunosuppressants (e.g. cyclosporin, voclosporin, azathioprine, methotrexate, mycophenolate mofetil or tacrolimus);
- anti-TNFα antibodies (e.g., infliximab, adalimumab, certolizumab pegol, ESBA-105 or golimumab);
- anti-IL-17A antibodies (e.g., secukinumab);
- mTOR inhibitors (e.g., sirolimus);
- VGX-1027;
- JAK3 inhibitors (e.g., tofacitinib or R348); and
- protein kinase C inhibitors (e.g. AEB-071).

Medical Uses

The compounds of the invention may be used as monotherapies for inflammatory diseases, or in combination therapies for such diseases.

Thus, embodiments of aspects (e) to (g) above that may be mentioned include those in which the compound of formula I, Ix, Ia, Ib or Ic (or pharmaceutically acceptable salt thereof) is the sole pharmacologically active ingredient utilised in the treatment.

However, in other embodiments of aspects (e) to (g) above, the compound of formula I, Ix, Ia, Ib or Ic (or pharmaceutically acceptable salt thereof) is administered to a subject who is also administered one or more other therapeutic agents (e.g. wherein the one or more other therapeutic agents are as defined above in connection with combination products).

When used herein, the term "inflammatory disease" specifically includes references to any one or more of the following:
(i) lung diseases or disorders having an inflammatory component, such as cystic fibrosis, pulmonary hypertension, lung sarcoidosis, idiopathic pulmonary fibrosis or, particularly, COPD (including chronic bronchitis and emphysema), asthma or paediatric asthma;
(ii) skin diseases or disorders having an inflammatory component, such as atopic dermatitis, allergic dermatitis, contact dermatitis or psoriasis;
(iii) nasal diseases or disorders having an inflammatory component, such as allergic rhinitis, rhinitis or sinusitis;
(iv) eye diseases or disorders having an inflammatory component, such as conjunctivitis, allergic conjunctivitis, glaucoma, diabetic retinopathy, macular oedema (including diabetic macular oedema), central retinal vein occlusion (CRVO), dry and/or wet age related macular degeneration (AMD), post-operative cataract inflammation, or, particularly, keratoconjunctivitis sicca (dry eye), uveitis (including posterior, anterior and pan uveitis), corneal graft and limbal cell transplant rejection; and
(v) gastrointestinal diseases or disorders having an inflammatory component, such as gluten sensitive enteropathy (coeliac disease), eosinophilic esophagitis, intestinal graft versus host disease or, particularly, Crohn's disease or ulcerative colitis.

References herein to diseases having an inflammatory component include references to diseases that involve inflammation, whether or not there are other (non-inflammatory) symptoms or consequences of the disease.

According to a further aspect of the invention there is provided a process for the preparation of a compound of formula I which process comprises:
(a) reaction of a compound of formula II.

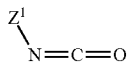

with a compound of formula III,

wherein one of $Z^1$ and $Z^2$ is a structural fragment of formula IV

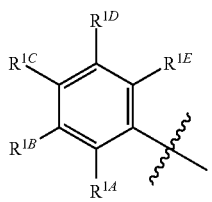

and the other of $Z^1$ and $Z^2$ is a structural fragment of formula V

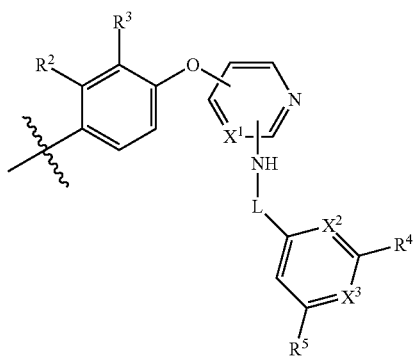

where $R^{1A}$ to $R^{1E}$, $R^2$ to $R^5$, L and $X^1$ to $X^3$ are as hereinbefore defined, for example under conditions known to those skilled in the art, for example at a temperature from ambient (e.g. 15 to 30° C.) to about 110° C. in the presence of a suitable organic solvent (e.g. a polar aprotic solvent such as DMF, THF, 1,4-dioxane, or mixtures thereof);
(b) reaction of a compound of formula IIa,

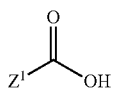

wherein $Z^1$ is as defined above, with a suitable azide-forming agent (i.e. a suitable source of a leaving group and activated azide ion, such as diphenyl phosphorazidate; see, for example, Tetrahedron 1974, 30, 2151-2157) under conditions known to those skilled in the art, such as at sub-ambient to ambient temperature (e.g. from an initial temperature of about −5 to 5° C. to ambient temperature post-reaction) in the presence of an amine base (e.g. triethylamine or a sterically hindered base such as N,N-diisopropylethylamine) and a suitable organic solvent (e.g. a polar aprotic solvent such as DMF, THF, 1,4-dioxane, or mixtures thereof), which reaction is followed, without isolation, by thermal rearrangement (e.g. under heating) of the intermediate acyl azide (of formula $Z^1$—C(O)—N$_3$) e.g. at ambient temperature (such as from 15 to 30° C.) to provide, in situ, a compound of formula II, which compound is then reacted with a compound of formula III, as defined above, to provide the compound of formula I;
(c) reaction of a compound of formula IIb,

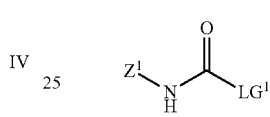

wherein $LG^1$ represents a suitable leaving group (e.g. imidazolyl, chloro, or aryloxy, such as phenoxy) and $Z^1$ is as defined above, with a compound of formula III, as defined above, for example under conditions known to those skilled in the art, such as at ambient temperature (e.g. from ambient to 80° C.), optionally in the presence of an amine base (e.g. triethylamine or a sterically hindered base like N,N-diisopropylethylamine) and a suitable organic solvent (e.g. an aprotic solvent, such as dichloromethane or an ester such as isopropyl acetate);
(d) reaction of a compound of formula VI,

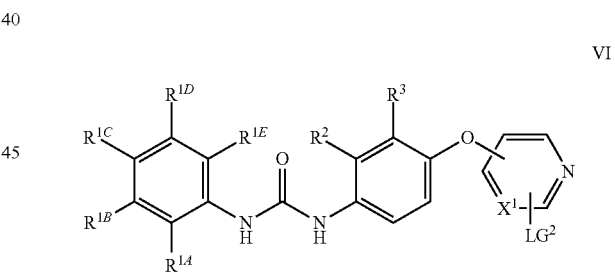

wherein $LG^2$ represents a suitable leaving group (e.g. a halo group such as chloro or bromo) and $R^{1A}$ to $R^{1E}$, $R^2$, $R^3$ and $X^1$ are as hereinbefore defined with a compound of formula VII,

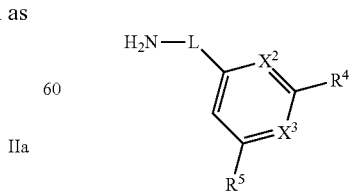

wherein $R^4$, $R^5$, L, $X^2$ and $X^3$ are as hereinbefore defined, for example under conditions known to those skilled in the art (e.g. as described in *J. Am. Chem. Soc.* 2011, 133, 15686-15696), such as at elevated temperature (e.g. from 50 to 110° C.) in the presence of a suitable organic solvent (e.g. a polar aprotic solvent such as DMF, THF, 1,4-dioxane, or mixtures thereof) and, optionally, an acidic catalyst (e.g. a sulfonic acid such as para-toluenesulfonic acid); or (e) for compounds of formula I in which $R^4$ represents —S(O)$_{1-2}$—[C($R^{6c}$)($R^{6d}$)—(CH$_2$)$_{0-1}$—CH$_2$—O]$_{1-12}$—CH$_2$(CH$_2$)$_{0-1}$CH$_2$—$R^{6a}$, —S(O)$_{1-2}$—C($R^{6c}$)($R^{6d}$)—[C$_{1-5}$ alkylene]-$R^{6a}$, —S(O)$_{1-2}R^{6b}$, oxidation of a corresponding compound of formula I in which, respectively, $R^4$ represents —S—[C($R^{6c}$)($R^{6d}$)—(CH$_2$)$_{0-1}$CH$_2$—O]$_{1-12}$—CH$_2$(CH$_2$)$_{0-1}$CH$_2$—$R^{6a}$, —S—C($R^{6c}$)($R^{6d}$)—[C$_{1-5}$ alkylene]-$R^{6a}$, —S—$R^{6b}$, wherein $R^{6a}$ to $R^{6d}$ are as hereinbefore defined, for example under conditions known to those skilled in the art (e.g. at 0 to 25° C. in the presence of a suitable solvent (such as dichloromethane, methanol or a mixture thereof) and a peracid, such as meta-chloroperbenzoic acid);

(f) for compounds of formula I in which $R^4$ represents

—C(O)NH—[C($R^{6c}$)($R^{6d}$)—(CH$_2$)$_{0-1}$CH$_2$—O]$_{1-12}$—CH$_2$(CH$_2$)$_{0-1}$CH$_2$—$R^{6a}$ or

—C(O)NH—C($R^{6c}$)($R^{6d}$)—[C$_{1-5}$ alkylene]-$R^{6a}$, which C$_{1-5}$ alkylene group is optionally substituted by oxo, reaction of a compound of formula VIIa,

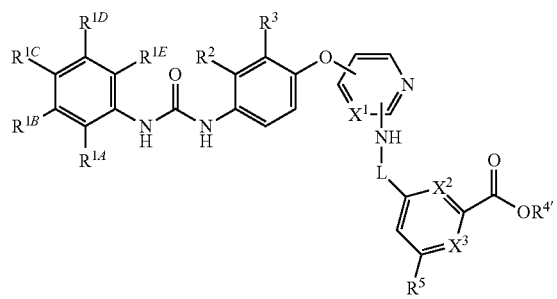

VIIa wherein $R^{4'}$ represents H or a C$_{1-3}$ alkyl group (e.g. methyl) and $R^{1A}$ to $R^{1E}$, $R^2$, $R^3$, $R^5$, L and $X^1$ to $X^3$ are as hereinbefore defined, with a compound of formula VIIb or VIIc, H$_2$N—[C($R^{6c}$)($R^{6d}$)—(CH$_2$)$_{0-1}$CH$_2$—O]$_{1-12}$—CH$_2$(CH$_2$)$_{0-1}$CH$_2$—$R^{6a1}$     VIIb H$_2$N—C($R^{6c}$)($R^{6d}$)—[C$_{1-5}$ alkylene]-$R^{6a1}$ or     VIIc which C$_{1-5}$ alkylene group is optionally substituted by oxo, wherein $R^{6c}$ and $R^{6d}$ are as hereinbefore defined, and $R^{6a1}$ takes the same definition as $R^{6a}$ above, except that CO$_2$H is only present in protected form (e.g. as C(O)O—C$_{1-4}$ alkyl), for example under conditions known to those skilled in the art, such as (i) when $R^{4'}$ represents a C$_{1-3}$ alkyl group, reaction at ambient temperature in the presence of a suitable Lewis acidic catalyst (e.g. a trialkyl aluminium reagent such as trimethylaluminium) and an aprotic organic solvent (e.g. THF) or (ii) when $R^{4'}$ represents H, reaction in the presence of a tertiary amine base (e.g. a trialkylamine such as triethylamine or diisopropylethylamine or a cyclic amine such as N-methylpyrrolidine or N-methylmorpholine), an amide (peptide) coupling reagent (e.g. T3P, HATU, CDI, BOP, PyBOP, HOAt, HOBt or a carbodiimide such as DCC or diisopropylcarbodiimide) and an aprotic organic solvent (e.g. a chlorinated solvent such as DCM, an ester such as ethyl acetate, an amide of dimethylamine such as DMF, or a mixture of any such solvents), followed, if necessary, by deprotection of $R^{6a1}$ when that group represents C(O)O—C$_{1-4}$ alkyl;

(g) for compounds of formula I in which $R^1$ represents —C(O)N$R^X R^Y$, reaction of a compound of formula VIId,

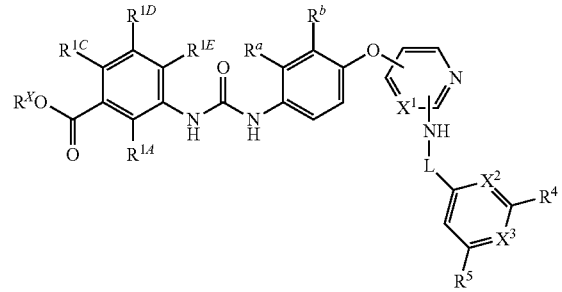

VIId wherein $R^{1A}$, $R^{1C}$, $R^{1D}$, $R^{1E}$, $R^a$, $R^b$, $X^1$ to $X^3$, L, $R^4$ and $R^5$ are as hereinbefore defined and $R^X$ represents H or C$_{1-4}$ alkyl, with a compound of formula VIIe,

VIIe wherein $R^X$ and $R^Y$ are as hereinbefore defined, under conditions known to those skilled in the art, for example when $R^X$ represents H, reaction in the presence of a suitable solvent, a base (e.g. triethylamine or N,N-diisopropylethylamine) and an amide (peptide) coupling reagent, such as HATU, CDI, N,N'-dicyclohexylcarbodiimide, N,N'-diisopropylcarbodiimide BOP or PyBOP, optionally in combination with an activated ester-forming agent such as HOBt or 1-hydroxy-7-azabenzotriazole, when $R^X$ represents H, conversion of the carboxylic acid to an acid halide (e.g. by reaction with a halogenating agent such as thionyl chloride), followed by reaction with the compound of formula (XI) in the presence of a suitable solvent and a base (e.g. triethylamine or N,N-diisopropylethylamine), or when $R^X$ represents C$_{1-4}$ alkyl (e.g. methyl), reaction in the presence of a trialkylaluminium (e.g. trimethylaluminium) and an aprotic solvent (e.g. THF);

(h) deprotection of an protected derivative of a compound of formula I, under conditions known to those skilled in the art, wherein the protected derivative bears a protecting group on an O- or N-atom of the compound of formula I (and, for the avoidance of doubt, a protected derivative of one compound of formula I may or may not represent another compound of formula I).

Compounds of formula II may be prepared according to or by analogy with methods known to those skilled in the art, for example by reaction of a compound of formula IIa, as defined above, with an azide-forming agent, followed by rearrangement of the intermediate acyl azide (as described at (b) above; see, for example, *Tetrahedron* 1974, 30, 2151-2157).

Compounds of formula IIb may be prepared reaction of a compound of formula VIII,

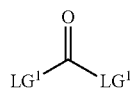

VIII wherein LG$^1$ is as hereinbefore defined, with a compound of formula IX,

IX wherein Z$^1$ is as hereinbefore defined, for example under conditions known to those skilled in the art.

Amines of formula IX may be prepared from carboxylic acids of formula IIa through the route described in (b) above, where the intermediate isocyanate II is hydrolysed with water to give a carbamic acid that loses carbon dioxide to furnish IX. By the same token, the intermediate isocyanate II can be reacted with an alcohol, such as t-butanol, to generate a protected version of IX.

Certain compounds of formula III in which Z$^2$ represents a structural fragment of formula V, or compounds of formula IX in which Z$^1$ represents a structural fragment of formula V, may be synthesised employing the route outlined in Scheme 1 (see, for example: WO 2003/072569; and WO 2008/046216), wherein R$^2$, R$^3$ and X$^1$ to X$^3$ are as hereinbefore defined, LG$^3$ and LG$^4$ represent leaving groups, e.g., halogen or methanesulfonyl, and FG represents a real or latent NH$_2$ group, i.e., a group that is readily transformed into an NH$_2$ group, such as nitro or a protected variant NH-PG$^2$, where PG$^2$ is a typical protecting group (see, for example: Greene, T. W.; Wuts, P. G. M. *Protective Groups in Organic Synthesis*; Wiley, 4th revised edition, 2006; ISBN-10: 0471697540), e.g., a carbamate ester or carboxamide. The sequence starts with the base-mediated S$_N$Ar displacement of LG$^3$ in XI by the aroxides formed when X is treated with base to generate ethers XII. The remaining halogen or methanesulfonyl substituent (LG$^4$) of the ether XII is then displaced i) by an amine of formula VII in a second S$_N$Ar reaction or (ii) via a Buchwald coupling (see, for example, WO 2009/017838) with an amine of formula VII to furnish the desired compound (when FG is NH$_2$), or XIII (when FG is nitro or NH—PG$^2$). When FG is nitro in XIII, the NH$_2$ group may be revealed by a reduction reaction, typically done through hydrogenation employing a suitable catalyst, e.g., palladium on carbon, or employing dissolving metal conditions, such as with iron in glacial acetic acid. Alternatively, when FG is a protecting group, the NH$_2$ group may be revealed by a deprotection reaction. Although only depicted as taking place in the final step of the sequence, it should be noted that the unmasking of the latent NH$_2$ group represented by FG can take place at any stage in the synthetic route shown in Scheme 1.

Scheme 1

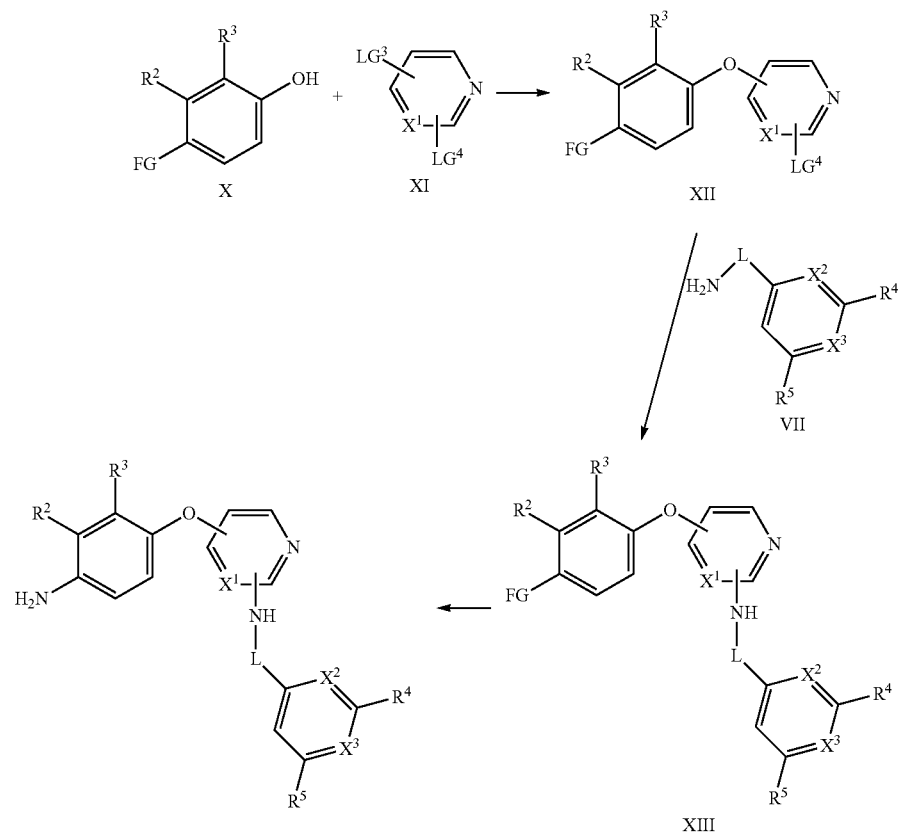

In a similar manner, amines of formula IX in which $Z^1$ represents a structural fragment of formula IV may be synthesised by conversion of a latent to a real $NH_2$ group in a compound of formula XIIIa,

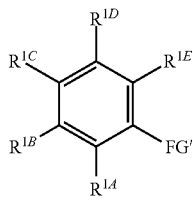

XIIIa wherein FG' is as defined for FG above, except that it does not represent $NH_2$, and $R^{1A}$ to $R^{1E}$ are as hereinbefore defined.

Compounds of formula III in which $Z^2$ represents a structural fragment of formula V, or compounds of formula IX in which $Z^1$ represents a structural fragment of formula V, wherein, in the structural fragment of formula V, $R^4$ represents
—C(O)NH—[C($R^{6c}$)($R^{6d}$)—(CH$_2$)$_{0-1}$CH$_2$—O]$_{1-12}$—CH$_2$(CH$_2$)$_{0-1}$CH$_2$—$R^{6a}$ or
—C(O)NH—C($R^{6c}$)($R^{6d}$)—[C$_{1-5}$ alkylene]-$R^{6a}$,
which C$_{1-5}$ alkylene group is optionally substituted by oxo, may be prepared by analogy with processes described herein for preparing compounds of formula I (see process (f) above) and other compounds of formula III (see, for example, Scheme 1 above), for example by reaction of a compound of XIIIa

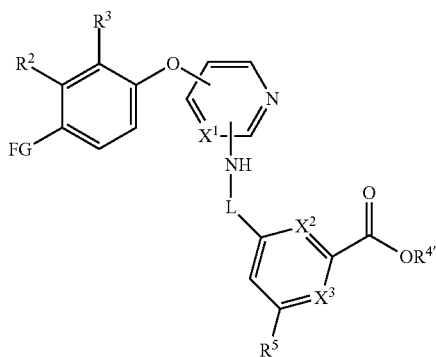

XIIIa wherein FG, $R^2$, $R^3$, $R^{4'}$, $R^5$, L and $X^1$ to $X^3$ are as hereinbefore defined, with a compound of formula VIIb or VIIc, as hereinbefore defined, under conditions known to those skilled in the art (for example the peptide coupling conditions described in respect of process (f) above), followed by conversion (if necessary) of FG to $NH_2$, for example as described above in connection with Scheme 1.

Compounds of formula VI may be synthesised by analogy with the compounds of formula I (see, for example, alternative processes (a) to (c) above). For example, compounds of formula VI can be prepared by reaction of a compound of formula IIx with a compound of formula IIIx, wherein the compounds of formulae IIx and IIIx take the same definitions as the compounds of formulae II and III, with the exception that one of $Z^1$ and $Z^2$ represents a structural fragment of formula IV, as hereinbefore defined, and the other of $Z^1$ and $Z^2$ represents a structural fragment of formula Va,

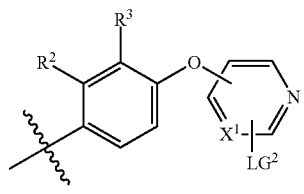

Va

Compounds of formula VII in which L represents a direct bond may be prepared according to or by analogy with procedures known to those skilled in the art, for example as described below.

(i) For compounds of formula VII in which $R^4$ represents
—O—[C($R^{6c}$)($R^{6d}$)—(CH$_2$)$_{0-1}$CH$_2$—O]$_{1-12}$—CH$_2$(CH$_2$)$_{0-1}$CH$_2$—$R^{6a}$ or
—O—C($R^{6c}$)($R^{6d}$)—[C$_{1-5}$ alkylene]-$R^{6a}$,
reaction of a compound of formula XIV,

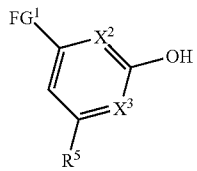

XIV wherein $FG^1$ either represents FG or C(O)O—(C$_{1-6}$ alkyl), and FG, $R^5$, $X^2$ and $X^3$ are as hereinbefore defined, with a compound of formula XVa or XVb LG$^5$-[C($R^{6c}$)($R^{6d}$)—(CH$_2$)$_{0-1}$CH$_2$—O]$_{1-2}$—CH$_2$(CH$_2$)$_{0-1}$CH$_2$—$R^{6a1}$      XVa LG$^5$-C($R^{6c}$)($R^{6d}$)—[C$_{1-5}$ alkylene]-$R^{6a1}$      XVb wherein LG$^5$ represents a suitable leaving group such as halo, (perfluoro)alkane-sulfonate or arylsulfonate (e.g. methanesulfonate or p-toluenesulfonate) and $R^{6a1}$, $R^{6c}$ and $R^{6d}$ are as hereinbefore defined, under conditions known to those skilled in the art (e.g. in the presence of an organic solvent and either a suitable base, followed by when $FG^1$ represents NH-PG$^2$, removal of the PG$^2$ protecting group, when $FG^1$ represents NO$_2$, reduction of NO$_2$ to NH$_2$ or when $FG^1$ represents C(O)O—(C$_{1-6}$ alkyl), saponification to provide the corresponding carboxylic acid and then reaction with a suitable azide-forming agent and thermal rearrangement of the resulting acyl azide (see, for example, process (b) above) and/or by deprotection of $R^{6a1}$ when that group represents C(O)O—C$_{1-4}$ alkyl.

(ii) For compounds of formula VII in which $R^4$ represents
—O—[C($R^{6c}$)($R^{6d}$)—(CH$_2$)$_{0-1}$CH$_2$—O]$_{1-12}$—CH$_2$(CH$_2$)$_{0-1}$CH$_2$—$R^{6a}$ or
—O—C($R^{6c}$)($R^{6d}$)—[C$_{1-5}$ alkylene]-$R^{6a}$
reaction of a compound of formula XIV, as hereinbefore defined, with a compound of formula XVIa or XVIb HO—[C($R^{6c}$)($R^{6d}$)—(CH$_2$)$_{0-1}$CH$_2$—O]$_{1-12}$—CH$_2$(CH$_2$)$_{0-1}$CH$_2$—$R^{6a}$      XVIa HO—C($R^{6c}$)($R^{6d}$)—[C$_{1-5}$ alkylene]-NR$^{6a}$      XVIb wherein $R^{6a1}$, $R^{6c}$ and $R^{6d}$ are as hereinbefore defined, under conditions known to those skilled in the art (e.g.

under Mitsunobu conditions, i.e. in the presence of using triphenylphosphine and an azodicarboxylate, such as diethyl azodicarboxylate or diisopropyl azodicarboxylate), followed by when $FG^1$ represents $NH-PG^2$, removal of the $PG^2$ protecting group, when $FG^1$ represents $NO_2$, reduction of $NO_2$ to $NH_2$ or when $FG^1$ represents $C(O)O-(C_{1-6}$ alkyl), saponification to provide the corresponding carboxylic acid and then reaction with a suitable azide-forming agent and thermal rearrangement of the resulting acyl azide (see, for example, process (b) above) and/or by deprotection of $R^{6a1}$ when that group represents $C(O)O-C_{1-4}$ alkyl.

(iii) For compounds of formula VII in which $R^4$ represents
—S—$[C(R^{6c})(R^{6d})-(CH_2)_{0-1}CH_2-O]_{1-12}-CH_2(CH_2)_{0-1}CH_2-R^{6a}$,
—S—$C(R^{6c})(R^{6d})-[C_{1-5}$ alkylene$]-R^{6a}$ or
—S—$R^{6b}$, reaction of a compound of formula XVII,

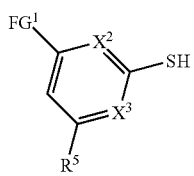

XVII wherein $FG^1$, $R^5$, $X^2$ and $X^3$ are as hereinbefore defined, with a compound of formula XVa or XVb, as hereinbefore defined, or a compound of formula XVIII $LG^5-R^{6b}$     XVIII wherein $LG^5$ and $R^{6b}$ are as hereinbefore defined, under conditions known to those skilled in the art (e.g. in the presence of a suitable base and an organic solvent), followed by when $FG^1$ represents $NH-PG^2$, removal of the $PG^2$ protecting group, when $FG^1$ represents $NO_2$, reduction of $NO_2$ to $NH_2$ or when $FG^1$ represents $C(O)O-(C_{1-6}$ alkyl), saponification to provide the corresponding carboxylic acid and then reaction with a suitable azide-forming agent and thermal rearrangement of the resulting acyl azide (see, for example, process (b) above).

(iv) For compounds of formula VII in which $X^2$ and $X^3$ both represent $CR^Z$ and $R^4$ represents
—S(O)$_{1-2}$—$[C(R^{6c})(R^{6d})-(CH_2)_{0-1}CH_2-O]_{1-12}-CH_2(CH_2)_{0-1}CH_2-R^{6a}$,
—S(O)$_{1-2}$—$C(R^{6c})(R^{6d})-[C_{1-5}$ alkylene$]-R^{6a}$ or
—S(O)$_{1-2}$—$R^{6b}$, oxidation of a compound of formula XIX.

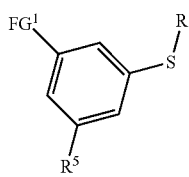

XIX wherein R represents
—$[C(R^{6c})(R^{6d})-(CH_2)_{0-1}CH_2-O]_{1-12}-CH_2(CH_2)_{0-1}CH_2-R^{6a}$,
—$C(R^{6c})(R^{6d})[C_{1-5}$ alkylene$]-R^{6a}$ or
—$R^{6b}$, and $FG^1$ and $R^5$ are as hereinbefore defined, under conditions known to those skilled in the art (e.g. in the presence of a peracid, such as meta-chloroperbenzoic acid), followed by when $FG^1$ represents $NH-PG^2$, removal of the $PG^2$ protecting group, when $FG^1$ represents $NO_2$, reduction of $NO_2$ to $NH_2$ or when $FG^1$ represents $C(O)O-(C_{1-6}$ alkyl), saponification to provide the corresponding carboxylic acid and then reaction with a suitable azide-forming agent and thermal rearrangement of the resulting acyl azide (see, for example, process (b) above).

(v) For compounds of formula VII in which $R^4$ represents —S—$R^{6b}$, coupling of a compound of formula XX

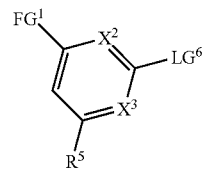

XX wherein $LG^6$ represents a suitable leaving group such as halo or trifluoromethanesulfonate, $FG^1$, $R^5$, $X^2$ and $X^3$ are as hereinbefore defined, with a compound of formula XXI, H—S—$R^{6b}$     XXI wherein $R^{6b}$ is as hereinbefore defined, under conditions known to those skilled in the art (e.g. in the presence of a Pd(0) catalyst, Cu(I) iodide and a suitable base), followed by when $FG^1$ represents $NH-PG^2$, removal of the $PG^2$ protecting group, when $FG^1$ represents $NO_2$, reduction of $NO_2$ to $NH_2$ or when $FG^1$ represents $C(O)O-(C_{1-6}$ alkyl), saponification to provide the corresponding carboxylic acid and then reaction with a suitable azide-forming agent and thermal rearrangement of the resulting acyl azide (see, for example, process (b) above).

(vi) For compounds of formula VII in which $R^4$ represents
-$Q^1$-$[C(R^{6c})(R^{6d})-(CH_2)_{0-1}CH_2-O]_{1-12}-CH_2(CH_2)_{0-1}CH_2-R^{6a}$
wherein $Q^1$ and $R^{6a}$ are as hereinbefore defined, reaction of a compound of formula XXII

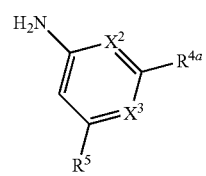

XXII in which $R^{4a}$ represents
-$Q^1$-$[C(R^{6c})(R^{6d})-(CH_2)_{0-1}CH_2-O]_x-CH_2(CH_2)_{0-1}CH_2-OH$ with a compound of formula XXIII,

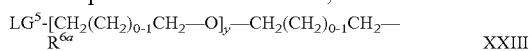

XXIII wherein x and y are integers from 0 to 11, the sum of x and y being from 0 to 11, and $Q^1$, $LG^5$ and $R^{6a}$ are as hereinbefore defined, under conditions known to those skilled in the art (e.g. at ambient temperature in the presence of a base such as sodium hydride and a polar organic solvent such as DMF).

(vii) For compounds of formula VII in which $X^2$ and $X^3$ both represent $CR^Z$ and $R^4$ represents
—S—$C(R^{6c})$—$[C_{1-5}$ alkylene]-$N(R^{7b})R^{7c}$
reaction of a compound of formula XXIV.

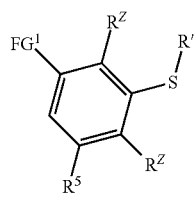

XXIV wherein R' represents
—$C(R^{6c})(R^{6d})$—$[C_{1-5}$ alkylene]-$LG^6$
with a compound of formula $HN(R^{7b})R^{7c}$, wherein $FG^1$, $R^5$, $R^{6b}$, $R^{6c}$, $R^{7b}$, $R^{7c}$, $R^Z$ and $LG^6$ are as hereinbefore defined, under conditions known to those skilled in the art (for example in the presence of a suitable organic solvent (e.g. acetone) and, optionally, catalyst for nucleophilic displacement, such as an iodide sale (e.g. sodium iodide)), followed by
when $FG^1$ represents NH-$PG^2$, removal of the $PG^2$ protecting group,
when $FG^1$ represents $NO_2$, reduction of $NO_2$ to $NH_2$ or
when $FG^1$ represents $C(O)O$—($C_{1-6}$ alkyl), saponification to provide the corresponding carboxylic acid and then reaction with a suitable azide-forming agent and thermal rearrangement of the resulting acyl azide (see, for example, process (b) above).

(viii) For compounds of formula VII in which $R^4$ represents
—$C(O)NH$—$[CH_2(CH_2)_{0-1}CH_2$—$O]_{1-12}$—$CH_2$ $(CH_2)_{0-1}CH_2$—$R^{6a}$ or
—$C(O)NH$—$C(R^{6c})(R^{6d})$—$[C_{1-5}$ alkylene]-$R^{6a}$,
which $C_{1-5}$ alkylene group is optionally substituted by oxo, reaction of a compound of formula XXV,

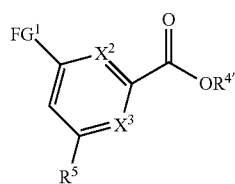

XXV wherein $FG^1$, $R^{4'}$, $R^5$, $R^{6a}$, $R^{6b}$ and $R^{6d}$, $X^2$ and $X^3$ are as hereinbefore defined, with a compound of formula VIIb or VIIc, as hereinbefore defined, under conditions known to those skilled in the art (for example the peptide coupling conditions described in respect of process (f) above), followed by
when $FG^1$ represents NH-$PG^2$, removal of the $PG^2$ protecting group,
when $FG^1$ represents $NO_2$, reduction of $NO_2$ to $NH_2$ or
when $FG^1$ represents $C(O)O$—($C_{1-6}$ alkyl), saponification to provide the corresponding carboxylic acid and then reaction with a suitable azide-forming agent and thermal rearrangement of the resulting acyl azide (see, for example, process (b) above).

(ix) For compounds of formula VII in which $R^4$ represents —$S(O)_2$—$R^{6b}$, coupling of a compound of formula XXVI,

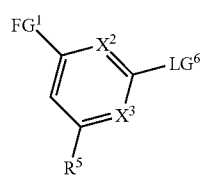

XXVI wherein $R^5$, $X^2$, $X^3$, $FG^1$ and $LG^6$ are as hereinbefore defined, with a compound of formula XXVII,

XXVII wherein $M^{S+}$ is a metal cation, s is 1 or 2 (e.g. s is 1 and M is an alkali metal such as potassium or, particularly, sodium) and Fe' is as hereinbefore defined, under conditions known to those skilled in the art (e.g. at elevated temperature (e.g. 80 to 100° C.) in the presence of: a suitable transition metal catalyst, such as Cu(I) iodide; an aprotic organic solvent, such as DMSO; a suitable base, such as an alkali metal hydroxide (e.g. NaOH); and, optionally, an organic ligand for Cu(I), such as L-proline), followed by
when $FG^1$ represents NH-$PG^2$, removal of the $PG^2$ protecting group,
when $FG^1$ represents $NO_2$, reduction of $NO_2$ to $NH_2$ or
when $FG^1$ represents $C(O)O$—($C_{1-6}$ alkyl), saponification to provide the corresponding carboxylic acid and then reaction with a suitable azide-forming agent and thermal rearrangement of the resulting acyl azide (see, for example, process (b) above).

Compounds of formula VII in which L represents $C_{1-2}$ alkylene may be prepared by analogous procedures.

Similar interconversions of functional groups may also be employed to prepare compounds of formula XIIIa. For example, compounds of formula XIIIa in which $R^{1B}$ represents —$CH_2CN$ may be prepared by reaction of a compound of formula XXVIIa,

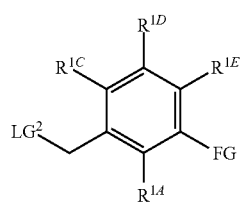

XXVIIa wherein FG, $LG^2$, $R^{1A}$ and $R^{1C}$ to $R^{1E}$ are as hereinbefore defined, with a source of cyanide ion (e.g. NaCN), for example under conditions known to those skilled in the art, such as in the presence of a polar, aprotic organic solvent (e.g. DMSO).

Compounds of formula XXIV in which $LG^6$ represents halo can be prepared according to or by analogy with procedures known to those skilled in the art, for example by reaction of a compound of formula XXVIII,

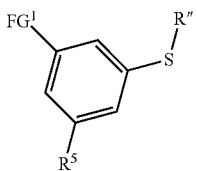

XXVIII wherein R" represents —CH$_2$—[C$_{1-5}$ alkylene]-OH, with a halogenating agent (e.g. a mixture of 2,4,6-trichloro,1,3,5-triazine and dimethylformamide).

Compounds of formula XXVIIa may be prepared according to (or by analogy with) procedures know to those skilled in the art. For example, compounds of formula XXVIIa in which LG$^2$ represents Cl may be prepared by chlorination of a corresponding compound of formula XXVIIb,

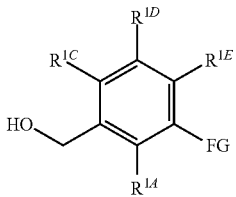

XXVIIb wherein FG, R$^{1A}$ and R$^{1C}$ to R$^{1E}$ are as hereinbefore defined, for example under conditions known to those skilled in the art, such as by reaction with thionyl chloride.

Compounds of formula XXVIIb may, for example, be prepared by reduction of corresponding compounds of formula XXVIIc,

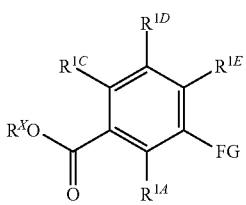

XXVIIc wherein FG, R$^{1A}$ and R$^{1C}$ to R$^{1E}$ are as hereinbefore defined, for example under conditions known to those skilled in the art, such as by reaction with borohydride or aluminium hydride-based reducing agent (e.g. an alkali metal borohydride or aluminium hydride, such as lithium borohydride or lithium aluminium hydride) in the presence of a reaction-inert organic solvent.

It will be understood by persons skilled in the art that compounds represented by formulae II, IIx and IIb are generally reactive intermediates. These intermediates may be formed in situ and reacted directly, without isolation, with compounds of formula III to provide compounds of formula I. Furthermore, it will be understood by those skilled in the art that the use of appropriate protective groups may be required during the processes described above for any of the groups Z$^1$ and Z$^2$ which possess chemically-sensitive functional groups, for example, a hydroxyl group or an amino function.

Many of the compounds illustrated in the Schemes are either commercially available, or can be obtained using the cited procedures, or can be readily prepared by conventional methods by those skilled in the art. See for example Regan, J. et al.; *J. Med. Chem.* 2003, 46, 4676-4686, WO 2000/043384, WO 2007/053346, WO 2007/087448, WO 2007/089512, WO 2009/117080 and WO 2014/027209.

Novel intermediates as described herein form an aspect of the invention. In this respect, a further aspect of the invention relates to a compound of formula IIb as hereinbefore defined (e.g. a compound of formula IIb in which LG$^1$ represents phenoxy). Particular compounds of formula IIb that may be mentioned include those in which:
  Z$^1$ represents a structural fragment of formula IV, in which R$^{1A}$, R$^{1B}$, R$^{1C}$, R$^{1D}$ and R$^{1E}$ are as hereinbefore defined (e.g. in which R$^{1A}$, R$^{1B}$, R$^{1C}$, R$^{1D}$ and R$^{1E}$ take the combinations of definitions illustrated in respect of those groups in any of the compounds of the examples); and
  LG$^1$ is as hereinbefore defined (e.g. LG$^1$ represents phenoxy).

The aspects of the invention described herein (e.g. the above-mentioned compounds, combinations, methods and uses) may have the advantage that, in the treatment of the conditions described herein, they may be more convenient for the physician and/or patient than, be more efficacious than, be less toxic than, have better selectivity over, have a broader range of activity than, be more potent than, produce fewer side effects than, have a better pharmacokinetic and/or pharmacodynamic profile than, have more suitable solid state morphology than, have better long term stability than, or may have other useful pharmacological properties over, similar compounds, combinations, methods (treatments) or uses known in the prior art for use in the treatment of those conditions or otherwise.

The compounds of the invention may additionally (or alternatively):
  exhibit a long duration of action and/or persistence of action (e.g. in comparison to other previously disclosed p38 MAP kinase inhibitors such as, for example, BIRB796);
  not strongly inhibit GSK 3α (e.g. they may have an IC$_{50}$ against GSK 3α of 1,000 nM or greater; such as 1,500, 2,000, 3,000, 4,000, 5,000, 6,000, 7,000, 8,000, 9,000 or 10,000 nM or greater);
  target a smaller portion of the kinome, i.e., with improved selectivity, as illustrated by lowered KinomeScan Selectivity Scores;
  maintain a relatively high local drug concentration between doses (e.g. a high local concentration relative to other previously disclosed p38 MAP kinase inhibitors such as, for example, BIRB796);
  exhibit properties that are particularly suited to topical/local administration (e.g. following topical/local administration, the generation of high target tissue concentrations but low plasma concentrations of the compounds of formula (I) and/or rapid clearance of the compounds of formula (I) from plasma, for example as a result of high renal or hepatic extraction);
  exhibit little or no β-catenin induction and/or inhibition of mitosis in cells;
  not produce increases in binucleated cells containing micronuclei in the human lymphocyte in vitro micronucleus test;
  exhibit little or no time-dependent inhibition of members of the cytochrome P450 superfamily;

show improved chemical stability in the presence of water (e.g. stability to hydrolysis in aqueous mixtures at elevated temperatures) compared to previously disclosed p38 MAP kinase inhibitors such as, for example, BIRB796;

following administration to a patient, give rise to metabolites associated with little or no safety (e.g. toxicity) concerns;

exhibit good solubility and/or cellular permeability;

have a high degree of crystallinity; and/or exhibit little or no hygroscopicity in the solid state.

EXPERIMENTAL METHODS

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated or under a balloon of hydrogen. Microwave reactions were performed in a CEM Discover and Smithcreator microwave reactor, heating to a constant temperature using variable power microwave irradiation.

Normal phase column chromatography was routinely carried out on an automated flash chromatography system such as CombiFlash Companion or CombiFlash RF system using pre-packed silica (230-400 mesh, 40-63 μm) cartridges. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% NH$_3$ in MeOH.

Analytical Methods

Analytical HPLC was carried out using a Waters Xselect CSH C18, 2.5 μm, 4.6×30 mm column eluting with a gradient of 0.1% Formic Acid in MeCN in 0.1% aqueous Formic Acid or a Waters Xbridge BEH C18, 2.5 μm, 4.6×30 mm column eluting with a gradient of MeCN in aqueous 10 mM Ammonium Bicarbonate. UV spectra of the eluted peaks were measured using either a diode array or variable wavelength detector on an Agilent 1100 system.

Analytical LCMS was carried out using a Waters Xselect CSH C18, 2.5 μm, 4.6×30 mm column eluting with a gradient of 0.1% Formic Acid in MeCN in 0.1% aqueous Formic Acid or a Waters Xbridge BEH C18, 2.5 μm, 4.6×30 mm column eluting with a gradient of MeCN in aqueous 10 mM Ammonium Bicarbonate. UV and mass spectra of the eluted peaks were measured using a variable wavelength detector on either an Agilent 1200 or an Agilent Infinity 1260 LCMS with 6120 single quadrupole mass spectrometer with positive and negative ion electrospray.

Preparative HPLC was carried out using a Waters Xselect CSH C18, 5 μm, 19×50 mm column using either a gradient of either 0.1% Formic Acid in MeCN in 0.1% aqueous Formic Acid or a gradient of MeCN in aqueous 10 mM Ammonium Bicarbonate or employing a Waters Xbridge BEH C18, 5 μm, 19×50 mm column using a gradient of MeCN in aqueous 10 mM Ammonium Bicarbonate. Fractions were collected following detection by UV at a single wavelength measured by a variable wavelength detector on a Gilson 215 preparative HPLC or Varian PrepStar preparative HPLC or by mass and UV at a single wavelength measured by a ZQ single quadrupole mass spectrometer, with positive and negative ion electrospray, and a dual wavelength detector on a Waters FractionLynx LCMS.

$^1$H NMR Spectroscopy: $^1$H NMR spectra were acquired on a Bruker Avance III spectrometer at 400 MHz. Either the central peaks of chloroform-d, dimethylsulfoxide-d$_6$ or an internal standard of tetramethylsilane were used as references.

Preparation of Compounds of the Invention

Example 1

3-((4-((4-(3-(5-(tert-Butyl)-2-methoxy-3-(methylsulfonamido)phenyl)ureido)naphthalen-1-yl)oxy)pyrimidin-2-yl)amino)-5-ethynyl-N-(2-morpholinoethyl)benzamide

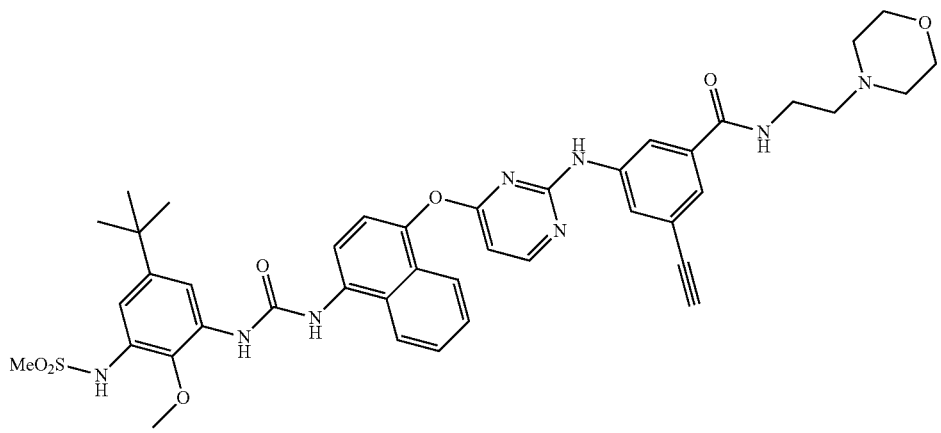 [SMILES: C#Cc1cc(Nc2nccc(Oc3ccc(NC(=O)Nc4cc(C(C)(C)C)cc(NS(C)(=O)=O)c4OC)c4ccccc34)n2)cc(C(=O)NCCN2CCOCC2)c1]

(i)
3-Amino-5-bromo-N-(2-morpholinoethyl)benzamide

T3P (50% w/w in EtOAc, 56.2 mL, 94 mmol), was added carefully to a solution of 3-amino-5-bromobenzoic acid (13.6 g, 63.0 mmol), 2-morpholinoethanamine (16.52 mL, 126 mmol) and Et$_3$N (26.3 mL, 189 mmol) in DCM (200 mL). An ice bath was used sporadically to prevent temperature rising above 35° C. Reaction stirred at room temperature for 1 h. Partitioned with sat. aq. NaHCO$_3$ solution (250 mL). Aqueous separated and partitioned with fresh DCM (250 mL). Organics separated, bulked and partitioned with 20% w/w NaCl solution (250 mL). The organic layer was separated, dried (MgSO$_4$), filtered and solvent evaporated. The crude product was dissolved in DCM (100 mL) and the sub-title compound (13 g) crystallised out on standing as a light tan crystalline solid.

$^1$H NMR (400 MHz, DMSO-d6) δ 8.29 (t, 1H), 7.06 (t, 1H), 6.98 (t, 1H), 6.85 (t, 1H), 5.59 (s, 2H), 3.57 (t, 4H), 3.41-3.26 (m, 2H), 2.48-2.33 (m, 6H).

LCMS m/z 328/330 (M+H)$^+$ (ES$^+$)

(ii) 3-Amino-N-(2-morpholinoethyl)-5-((triisopropylsilyl)ethynyl)benzamide

Pd(PPh$_3$)$_4$ (2.90 g, 2.51 mmol) was added to a degassed suspension of the compound from step (i) above (16.5 g, 50.3 mmol), CuI (0.479 g, 2.51 mmol), and ethynyltriisopropylsilane (16.92 mL, 75 mmol) in Et$_3$N (30 mL) and DMF (150 mL). Reaction heated at 85° C. (block temp.) for 5 h then cooled and filtered (Whatman glass fibre pad GF/C). Solvents evaporated and the residue partitioned between EtOAc (500 mL) and 20% w/w NaCl solution (500 mL). Aqueous layer separated and washed with fresh EtOAc (500 mL). Organic layers bulked, washed with fresh 20% w/w NaCl solution (500 mL), dried (MgSO$_4$), filtered and solvent evaporated to a thick brown oil. The crude product was purified by chromatography on silica gel (220 g column, 2% MeOH:DCM to 10%) to afford the sub-title compound (18.5 g) as a pale yellow glass.

$^1$H NMR (400 MHz, DMSO-d6) δ 8.29 (t, 1H), 7.04 (dd, 1H), 7.02 (t, 1H), 6.79 (dd, 1H), 5.44 (s, 2H), 3.57 (t, 4H), 3.37-3.28 (m, 2H), 2.47-2.36 (m, 6H), 1.11 (s, 21H).

LCMS m/z 430 (M+H)$^+$ (ES$^+$)

(iii) 3-Amino-5-ethynyl-N-(2-morpholinoethyl)benzamide

The compound from step (ii) above (18.5 g, 43.1 mmol) was dissolved in EtOAc (250 mL) and TBAF (1.0 M in THF, 43.1 mL, 43.1 mmol) added. The reaction was stirred for 1 h, then partitioned between water (500 mL) and ethyl acetate (200 mL). Organic layer was separated, washed with 20% w/w NaCl solution (400 mL), dried (MgSO$_4$), filtered and solvents evaporated. The crude product was slurried in Et$_2$O (100 mL) for 30 minutes, filtered and washed with fresh Et$_2$O (20 mL). The solid was oven dried at 45 CC to afford the sub-title compound (9.2 g).

$^1$H NMR (400 MHz, DMSO-d6) δ 8.28 (t, 1H), 7.12-6.97 (m, 2H), 6.76 (t, 1H), 5.45 (s, 2H), 4.08 (s, 1H), 3.57 (t, 4H), 3.41-3.25 (m, 2H), 2.48-2.32 (m, 6H).

LCMS m/z 274 (M+H)$^+$ (ES$^+$)

(iv) tert-Butyl (4-((2-((3-ethynyl-5-((2-morpholinoethyl)carbamoyl)phenyl)amino)pyrimidin-4-yl)oxy) naphthalen-1-yl)carbamate A solution of tert-butyl (4-((2-chloropyrimidin-4-yl)oxy) naphthalen-1-yl)carbamate (see, for example, Ito, K. et al., WO 2010/067130, 17 Jun. 2010; 6.46 g, 17.37 mmol), the compound from step (iii) above (7.12 g, 26.0 mmol) and p-TSA monohydrate (5.62 g, 29.5 mmol) in DMF (60 mL) was heated at 55° C. (internal temperature) for 7 h. The mixture was cooled and added dropwise to sat. aq NaHCO$_3$ (14 Solid filtered and washed with water (50 mL) then isohexane (100 mL). The amorphous solid was stirred in MeOH (200 mL) and product crystallised. Slurried overnight, filtered and the solid washed with MeOH (20 mL) and dried to give the sub-title compound (9 g).

$^1$H NMR (400 MHz, DMSO-d6) δ 9.76 (s, 1H), 9.32 (s, 1H), 8.45 (d, 1H), 8.41-8.33 (m, 1H), 8.16-8.03 (m, 2H), 7.90 (t, 1H), 7.85-7.78 (m, 1H), 7.67-7.51 (m, 3H), 7.48-7.37 (m, 2H), 6.58 (d, 1H), 4.16 (s, 1H), 3.56 (t, 4H), 3.46-3.27 (m, 2H), 2.49-2.30 (m, 6H), 1.52 (s, 9H).

LCMS m/z 609 (M+H)$^+$ (ES$^+$)

(v) 3-((4-((4-Aminonaphthalen-1-yl)oxy)pyrimidin-2-yl)amino)-5-ethynyl-N-(2-morpholinoethyl)benzamide TFA (22 mL, 286 mmol) was added dropwise to a stirred solution of the compound from step (iv) above (9 g, 14.05 mmol) in DCM (50 mL). The reaction was stirred at room temperature for 2 h. The mixture was added dropwise to stirred water (100 mL) and 1.0 M K$_2$CO$_3$ solution (280 mL, 280 mmol) and stirring continued until effervescence ceased. The mixture was extracted with DCM (2×250 mL) then the combined organic phases were dried (MgSO$_4$) and concentrated under reduced pressure. The crude product was purified by chromatography on the Companion (120 g column, 2% MeOH:DCM to 6%) to afford the sub-title compound (6.7 g) as a pale brown foam.

$^1$H NMR (400 MHz, DMSO-d6) δ 9.77 (s, 1H), 8.39 (t, 1H), 8.36 (d, 1H), 8.17-8.10 (m, 1H), 8.06 (s, 1H), 7.94 (dd, 1H), 7.67-7.59 (m, 1H), 7.49-7.38 (m, 3H), 7.15 (d, 1H), 6.70 (d, 1H), 6.37 (d, 1H), 5.79 (s, 2H), 4.20 (s, 1H), 3.56 (t, 4H), 3.41-3.30 (m, 2H), 2.48-2.34 (m, 6H).

LCMS m/z 509 (M+H)$^+$ (ES$^+$)

(vi) Phenyl (5-(tert-butyl)-2-methoxy-3-(methylsulfonamido)phenyl)carbamate

Phenyl chloroformate (0.5 mL, 3.99 mmol) was added to a stirred solution of N-(3-amino-5-(tert-butyl)-2-methoxyphenyl)methanesulfonamide (see, for example, Cirillo, P. F. et al., WO 2002/083628, 24 Oct. 2002; 1 g, 3.67 mmol) and NaHCO$_3$ (620 mg, 7.38 mmol) in THF (10 mL) and DCM (10 mL). The mixture was stirred for 2 h, then water (20 mL) was added. The organic layer was separated, dried (MgSO$_4$), filtered and evaporated to furnish a brown foam, which was stirred in cyclohexane (20 mL) to afford the sub-title compound (1.4 g) as a colourless solid.

$^1$H NMR (400 MHz, DMSO-d6) δ 9.49 (s, 1H), 9.14 (s, 1H), 7.56 (s, 1H), 7.50-7.37 (m, 2H), 7.31-7.13 (m, 4H), 3.77 (s, 3H), 3.06 (s, 3H), 1.25 (s, 9H)

LCMS m/z 393 (M+H)$^+$ (ES$^+$); 391 (M−H)$^−$ (ES$^−$)

(vii) 3-((4-((4-(3-(5-(tert-Butyl)-2-methoxy-3-(methylsulfonamido)phenyl)ureido)-naphthalen-1-yl)oxy) pyrimidin-2-yl)amino)-5-ethynyl-N-(2-morpholinoethyl)benzamide Triethylamine (5 µL, 0.036 mmol) was added to a mixture of the product from step (vi) above (75 mg, 0.191 mmol) and the product from step (v) above (100 mg, 0.197 mmol) in isopropyl acetate (3 mL) and the mixture heated at 50° C. (block temperature) for 6 h. The reaction was cooled to rt and left stirring for 72 h. The resulting solid was filtered and washed with isopropyl acetate (1 mL). The crude product was recrystallised from MeCN (3 mL), washed with MeCN (1 mL), filtered and dried to afford the title compound (100 mg) as a colourless solid.

$^1$H NMR (400 MHz, DMSO-d6) δ 9.76 (s, 1H), 9.32 (s, 1H), 9.13 (s, 1H), 8.90 (s, 1H), 8.44 (d, 1H), 8.35 (t, 1H), 8.27 (d, 1H), 8.18 (d, 1H), 8.13-8.02 (m, 2H), 7.92-7.80 (m, 2H), 7.72-7.64 (m, 1H), 7.63-7.55 (m, 1H), 7.50-7.37 (m, 2H), 7.03 (d, 1H), 6.56 (d, 1H), 4.12 (s, 1H), 3.81 (s, 3H), 3.63-3.48 (m, 4H), 3.40-3.33 (m, 2H), 3.10 (s, 3H), 2.47-2.33 (m, 6H), 1.27 (s, 9H).

LCMS m/z 807 (M+H)$^+$ (ES$^+$)

Example 2

3-Ethynyl-5-((4-((4-(3-(3-fluoro-5-morpholinophenyl)ureido)naphthalen-1-yl)oxy)-pyrimidin-2-yl)amino)-N-(2-morpholinoethyl)benzamide

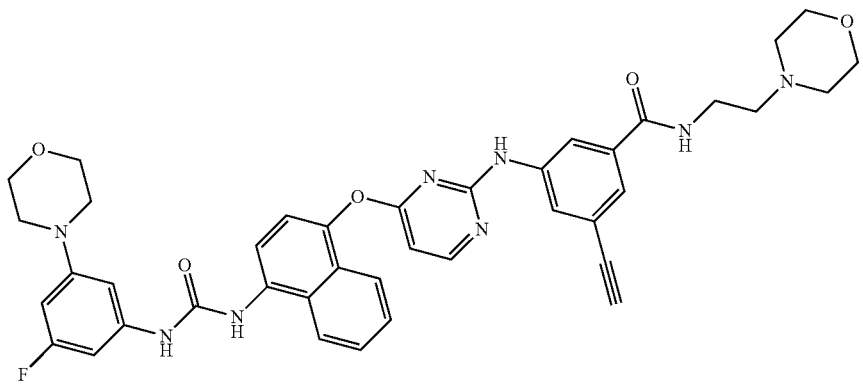 [SMILES: C#Cc1cc(Nc2nccc(Oc3ccc(NC(=O)Nc4cc(F)cc(N5CCOCC5)c4)c4ccccc34)n2)cc(C(=O)NCCN2CCOCC2)c1]

(i) Phenyl (3-fluoro-5-morpholinophenyl)carbamate

A stirred suspension of 3-fluoro-5-morpholinoaniline (1.00 g, 5.10 mmol) and sodium bicarbonate (0.878 g, 10.45 mmol) in DCM (10 mL) and THF (4 mL) was treated dropwise with phenyl chloroformate (0.7 mL, 5.57 mmol). After ~0.1 mL had been added the mixture became very thick and difficult to stir, so it was diluted with more DCM (5 mL) and THF (2 mL) and stirred overnight. The mixture was treated with more sodium bicarbonate (0.086 g, 1.019 mmol) and phenyl chloroformate (0.07 mL, 0.557 mmol) and stirred over the weekend. The mixture was diluted with DCM (30 mL), was washed with water (30 mL) and filtered through a phase-separating cartridge. The filtrate was evaporated and the residue was purified on a 40 g redisep silica cartridge using a gradient of 0 to 50% of ethyl acetate in isohexane as eluent to afford the sub-title compound (1.565 g) as a pink solid.

$^1$H NMR (400 MHz; DMSO-d6) δ 10.27 (s, 1H), 7.45-7.40 (m, 2H), 7.29-7.20 (m, 3H), 6.90 (bs, 1H), 6.82-6.79 (m, 1H), 6.51-6.47 (m, 1H), 3.73-3.70 (m, 4H), 3.10-3.08 (m, 4H). 90% purity LCMS m/z 317 (M+H)$^+$ (ES$^+$)

(ii) tert-Butyl (4-((2-((3-ethynyl-5-((2-morpholinoethyl)carbamoyl)phenyl)amino)pyrimidin-4-yl)oxy)naphthalen-1-yl)carbamate tert-Butyl (4-((2-chloropyrimidin-4-yl)oxy)naphthalen-1-yl)carbamate (see, for example, Ito, K. et al., WO 2010/067130, 17 Jun. 2010; 6.46 g, 17.37 mmol), 3-amino-5-ethynyl-N-(2-morpholinoethyl)benzamide (see Example 1(iii) above; 7.12 g, 26.0 mmol) and p-TSA monohydrate (5.62 g, 29.5 mmol) in DMF (60 mL) was heated at 60° C. (block temperature, 55° C. internal temperature) for 7 h. The mixture was cooled and added dropwise to sat. aq NaHCO$_3$ (1 L). The solid was filtered, washed with water (50 mL) then isohexane (100 mL). The amorphous solid was stirred in MeOH (200 mL) and product crystallised. Slurried overnight, then filtered and solid washed with MeOH (20 mL) and dried to afford the sub-title compound (8 g).

$^1$H NMR (400 MHz, DMSO-d6) δ 9.76 (s, 1H), 9.32 (s, 1H), 8.45 (d, 1H), 8.41-8.33 (m, 1H), 8.16-8.03 (m, 2H), 7.90 (t, 1H), 7.85-7.78 (m, 1H), 7.67-7.51 (m, 3H), 7.48-7.37 (m, 2H), 6.58 (d, 1H), 4.16 (s, 1H), 3.56 (t, 4H), 3.46-3.27 (m, 2H), 2.49-2.30 (m, 6H), 1.52 (s, 9H). 10% w/w de-BOC compound.

LCMS m/z 609 (M+H)$^+$ (ES$^+$)

(iii) 3-((4-((4-Aminonaphthalen-1-yl)oxy)pyrimidin-2-yl)amino)-5-ethynyl-N-(2-morpholinoethyl)benzamide TFA (22 mL, 286 mmol) was added dropwise to a stirred solution of the product from step (ii) above (9 g, 14.05 mmol) in DCM (50 mL). The reaction was stirred at rt for 2 h, then added dropwise to stirred water (100 mL) and 1M potassium carbonate solution (280 mL, 280 mmol) and stirring continued until effervescence ceased. The mixture was extracted with dichloromethane (2×250 mL) then the combined organic phases were dried (MgSO$_4$) and concentrated under reduced pressure. The crude product was purified by chromatography on the Companion (120 g column, 2% MeOH:DCM to 6%) to afford the sub-title compound (6.7 g) as a pale brown foam.

$^1$H NMR (400 MHz, DMSO-d6) δ 9.77 (s, 1H), 8.39 (t, 1H), 8.36 (d, 1H), 8.17-8.10 (m, 1H), 8.06 (s, 1H), 7.94 (dd, 1H), 7.67-7.59 (m, 1H), 7.49-7.38 (m, 3H), 7.15 (d, 1H), 6.70 (d, 1H), 6.37 (d, 1H), 5.79 (s, 2H), 4.20 (s, 1H), 3.56 (t, 4H), 3.41-3.30 (m, 2H), 2.48-2.34 (m, 6H).

LCMS m/z 509 (M+H)$^+$ (ES$^+$)

(iv) 3-Ethynyl-5-((4-((4-(3-(3-fluoro-5-morpholinophenyl)ureido)naphthalen-1-yl)oxy)-pyrimidin-2-yl)amino)-N-(2-morpholinoethyl)benzamide A stirred suspension of the product from step (i) above (100 mg, 0.295 mmol) and the product from step (iii) above (150 mg, 0.295 mmol) in isopropyl acetate (6 mL) was treated with Et$_3$N (10 μL, 0.072 mmol) and stirred at 50° C. (bath) for 1 h (all dissolved) and then at 60° C. for 4 h to give a thick suspension. The mixture was treated with more triethylamine (10 μL, 0.072 mmol) and diluted with isopropyl acetate (6 mL) to aid stirring and stirred at 60° C. overnight. The mixture was allowed to cool then filtered.

The solid was washed with isopropyl acetate (2×2 mL) and digested with boiling acetonitrile (20 mL) for 20 mins. The suspension was allowed to cool then filtered. The solid washed with acetonitrile (2×4 mL) followed by ether (2×4 mL) and dried to afford the title compound (97 mg) as a buff solid.

$^1$H NMR (400 MHz; DMSO-d6) δ 9.76 (s, 1H), 9.13 (s, 1H), 8.82 (s, 1H), 8.45 (d, 1H), 8.35 (t, 1H), 8.17 (d, 1H), 8.06 (s, 1H), 7.99 (d, 1H), 7.86-7.84 (m, 2H), 7.69-7.65 (m, 1H), 7.61-7.57 (m, 1H), 7.45-7.43 (m, 2H), 6.93-6.90 (m, 1H), 6.81 (s, 1H), 6.57 (d, 1H), 6.47-6.43 (m, 1H), 4.12 (s, 1H), 3.76-3.73 (m, 4H), 3.57-3.54 (m, 4H), 3.14-3.12 (m, 4H), 2.46-2.40 (m, 6H). 2H obscured by water.

LCMS m/z 366 (M+2H)$^{2+}$ (ES$^+$)

Example 3

3-((4-((4-(3-(5-(tert-Butyl)-2-methoxy-3-(methylsulfonamido)phenyl)ureido)naphthalen-1-yl)oxy)pyridin-2-yl)amino)-5-methoxy-N-(2-(2-(2-methoxyethoxy)ethoxy)ethyl)benzamide

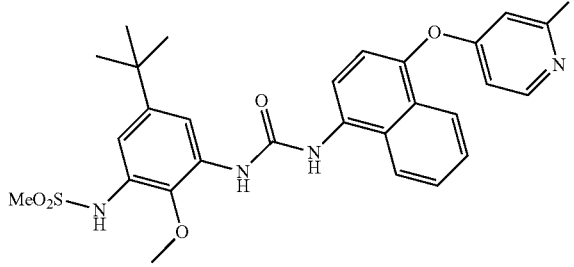

(i) 3-Amino-5-methoxy-N-(2-(2-(2-methoxyethoxy)ethoxy)ethyl)benzamide

3-Amino-5-methoxybenzoic acid (1.0 g, 5.98 mmol) was added to an ice cold suspension of 2-(2-(2-methoxyethoxy)ethoxy)ethanamine (1.2 g, 7.35 mmol), 50% T3P in ethyl acetate (4.50 mL, 7.56 mmol) and TEA (2.5 mL, 17.94 mmol) in ethyl acetate (15 mL). The mixture was allowed to warm to rt and stir overnight. Saturated aq. NaHCO$_3$ solution (20 mL) was added and the mixture was extracted with ethyl acetate (3×10 mL). The combined organic phases were washed with saturated brine (20 mL), dried (MgSO$_4$) and concentrated under reduced pressure to yield a yellow oil. The oil was purified by chromatography on the Companion (40 g column, 0-100% acetone/toluene) to afford a pale yellow oil. The oil was purified by chromatography on the Companion (40 g column, 0-100% THF/DCM) to afford the sub-title compound (843 mg) as a pale yellow oil.

LCMS m/z 313 (M+H)$^+$ (ES$^+$)

(ii) tert-Butyl (4-((2-chloropyridin-4-yl)oxy)naphthalen-1-yl)carbamate

A mixture of 4-((2-chloropyridin-4-yl)oxy)naphthalen-1-amine (see, for example, Ito, K. et al., WO 2010/112936, 7 Oct. 2010; 1000 mg, 3.69 mmol) and di-tert-butyl dicarbonate (750 mg, 3.44 mmol) in t-BuOH (10 mL) was stirred at reflux for 18 h. The mixture was diluted with water (15 mL) and the solid collected by filtration. The solid was triturated in diethyl ether to yield the sub-title compound (1002 mg) as a pale grey solid.

$^1$H NMR (DMSO-d6) 400 MHz, δ: 9.37 (s, 1H), 8.28 (d, 1H), 8.16 (d, 1H), 8.82 (dd, 1H), 7.66 (d, 1H), 7.66-7.54 (m, 2H), 7.40 (d, 1H), 7.03 (d, 1H), 6.91 (dd, 1H), 1.52 (s, 9H).

LCMS m/z 371 (M+H)$^+$ (ES$^+$); 369 (M−H)$^-$ (ES$^-$)

(iii) tert-Butyl (4-((2-((3-methoxy-5-((2-(2-(2-methoxyethoxy)ethoxy)ethyl)carbamoyl)-phenyl)amino)pyridin-4-yl)oxy)naphthalen-1-yl)carbamate Pd$_2$dba$_3$ (22 mg, 0.024 mmol) and BINAP (30 mg, 0.048 mmol) were stirred in 1,4-dioxane (1 mL) for 10 minutes under N$_2$. In a separate vessel, purged with N$_2$, caesium carbonate (455 mg, 1.396 mmol), the product from step (i) above (291 mg, 0.930 mmol) and the product from step (ii) above (345 mg, 0.930 mmol) were stirred in 1,4-dioxane (5 mL). The catalyst solution was added to the main reaction mixture and the whole was heated to 90° C. for 18 h. Upon cooling, the mixture was diluted with water (40 mL) and extracted with ethyl acetate (3×25 mL). The combined organic phases were washed with saturated brine (15 mL), dried (MgSO$_4$) and concentrated under reduced pressure. The crude product was purified by chromatography on the Companion (40 g column, 0-50% acetone/ethyl acetate) to afford the sub-title compound (320 mg) as a sticky orange oil.

$^1$H NMR (DMSO-d6) 400 MHz, δ: 9.37 (s, 1H), 9.09 (s, 1H), 8.35 (t, 1H), 8.17-8.05 (m, 2H), 7.83 (d, 1H), 7.67-7.46 (m, 5H), 7.35 (d, 1H), 6.88 (s, 1H), 6.57 (dd, 1H), 6.09 (d, 1H), 3.74 (s, 3H), 3.58-3.44 (m, 8H), 3.44-3.34 (m, 4H), 3.20 (s, 3H), 1.52 (s, 9H).

LCMS m/z 647 (M+H)$^+$ (ES$^+$); 645 (M−H)$^-$ (ES$^-$)

(iv) 3-((4-((4-Aminonaphthalen-1-yl)oxy)pyridin-2-yl)amino)-5-methoxy-N-(2-(2-(2-methoxyethoxy)ethoxy)ethyl)benzamide A solution of the product from step (iii) above (320 mg, 0.495 mmol) in DCM (1 mL) was treated with TFA (1000 µL, 12.98 mmol) and stirred at rt for 3 h. The mixture was diluted with water (10 mL) and DCM (10 mL). The mixture was neutralised with aq. NaHCO$_3$ solution and passed through a phase separation cartridge. The organic phase was dried (MgSO$_4$) and concentrated to give the sub-title compound (270 mg) as a brown gum.

$^1$H NMR (DMSO-d6) 400 MHz, δ: 9.00 (s, 1H), 8.34 (dd, 1H), 8.20-8.10 (m, 1H), 8.05 (d, 1H), 7.67-7.60 (m, 1H), 7.59-7.55 (m, 1H), 7.52-7.47 (m, 1H), 7.47-7.41 (m, 2H), 7.10 (d, 1H), 6.89-6.84 (m, 1H), 6.71 (d, 1H), 6.51 (dd, 1H), 6.05 (d, 1H), 5.83 (s, 2H), 3.73 (S, 3H), 3.58-3.45 (m, 8H), 3.45-3.35 (m, 4H), 3.21 (s, 3H).

LCMS m/z 547 (M+H)$^+$ (ES$^+$)

(v) 3-((4-((4-(3-(5-(tert-Butyl)-2-methoxy-3-(methylsulfonamido)phenyl)ureido)-naphthalen-1-yl)oxy)pyridin-2-yl)amino)-5-methoxy-N-(2-(2-(2-methoxyethoxy)ethoxy)-ethyl)benzamide Et$_3$N (5.33 μL, 0.038 mmol) was added to a stirred solution of phenyl (5-(tert-butyl)-2-methoxy-3-(methylsulfonamido)phenyl)carbamate (see Example 1(vi) above; 75 mg, 0.191 mmol) and the product from step (iv) above (110 mg, 0.201 mmol) in isopropyl acetate (5 mL) and heated to 50° C. for 8 h. Et$_3$N (5.33 μL, 0.038 mmol) was added and the mixture was heated to 60° C. for a further 3 h. The mixture was concentrated under reduced pressure and the residue was purified by chromatography on the Companion (40 g column, 0-50% acetone/EtOAc) to afford a an off-white solid which was recrystallised in acetonitrile (2 mL) to yield a white solid. The solid was purified by preparative HPLC (Gilson, Acidic (0.1% Formic acid), Waters X-Select Prep-C18, 5 μm, 19×50 mm column, 20-50% MeCN in Water) to afford a white solid which was redissolved in methanol (2 mL) loaded onto an SCX column. The column was washed with methanol (3×3 mL) then eluted with 1% ammonia in methanol to yield the title compound (21 mg) as a white solid.

$^1$H NMR (DMSO-d6) 400 MHz, δ: 9.41 (s, 1H), 9.17 (s, 1H), 9.08 (s, 1H), 8.94 (s, 1H), 8.38 (dd, 1H), 8.30 (d, 1H), 8.19 (d, 1H), 8.12 (d, 1H), 8.11 (d, 1H), 7.87 (d, 1H), 7.74-7.67 (m, 1H), 7.65-7.56 (m, 2H), 7.50 (dd, 1H), 7.39 (d, 1H), 7.02 (d, 1H), 6.91-6.86 (m, 1H), 6.58 (dd, 1H), 6.12 (d, 1H), 3.81 (s, 3H), 3.74 (s, 3H), 3.55-3.46 (m, 8H), 3.42-3.36 (m, 4H), 3.20 (s, 3H), 3.10 (s, 3H), 1.27 (s, 9H).

LCMS m/z 845 (M+H)$^+$ (ES$^+$); 843 (M–H)$^-$ (ES$^-$)

Example 4

N-(5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)methanesulfonamide

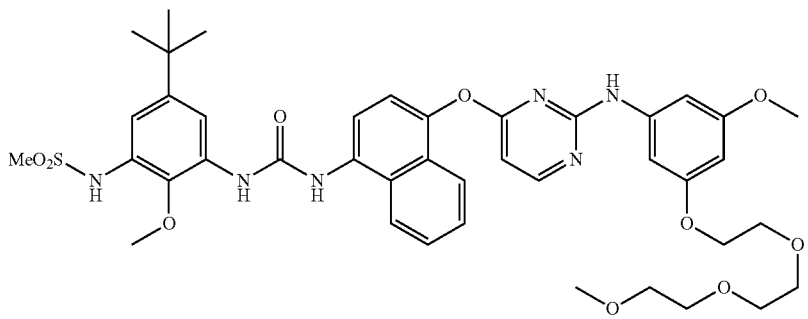 [SMILES: COCCOCCOCCOc1cc(Nc2nccc(Oc3ccc(NC(=O)Nc4cc(C(C)(C)C)cc(NS(C)(=O)=O)c4OC)c4ccccc34)n2)cc(OC)c1]

(i) 3-Methoxy-5-nitrophenol

A mixture of KOH (29.0 g, 517 mmol) and 1-bromo-3-methoxy-5-nitrobenzene (30 g, 129 mmol) in water (70 mL) and dioxane (70 mL) was degassed for 5 minutes prior to the addition of di-tert-butyl(2',4',6'-triisopropyl-[1,1'-biphenyl]-2-yl)phosphine (1.263 g, 2.97 mmol) and Pd$_2$(dba)$_3$ (1.184 g, 1.293 mmol). The resulting mixture was degassed for a further 2 minutes then heated under a nitrogen atmosphere at 100° C. for 2 h. The mixture was cooled, then acidified with 5 M HCl to ~pH 1 and extracted with EtOAc (2×500 mL). The organic layer was washed with saturated brine (200 mL), dried (MgSO$_4$), filtered and concentrated under reduced pressure. The crude product was purified through a pad of silica eluting with 30% EtOAc/isohexane to afford the sub-title compound (20.76 g) as a yellow solid.

$^1$H NMR (400 MHz; DMSO-d6) δ 10.46 (s, 1H), 7.20 (s, 1H), 7.19 (s, 1H), 6.76 (s, 1H), 3.82 (s, 3H).

LCMS m/z 168 (M–H)$^-$ (ES$^-$)

(ii) 1-Methoxy-3-(2-(2-(2-methoxyethoxy)ethoxy)ethoxy)-5-nitrobenzene

To a stirred suspension of the product from step (i) above (8.14 g, 45.7 mmol) and K$_2$CO$_3$ (12.64 g, 91 mmol) in acetone (150 mL) was added 1-bromo-2-(2-(2-methoxyethoxy)-ethoxy)ethane (8.85 mL, 48.0 mmol). The resulting mixture was refluxed overnight, cooled and filtered. The filtrate was evaporated under reduced pressure and the residue purified by chromatography on silica gel (220 g column, 0-60% EtOAc/isohexane) to afford the sub-title compound (13.41 g) as a yellow oil.

$^1$H NMR (DMSO-d6) 400 MHz, δ: 7.34-7.32 (m, 2H), 6.98 (t, 1H), 4.22-4.20 (m, 2H), 3.85 (s, 3H), 3.77-3.74 (m, 2H), 3.60-3.57 (m, 2H), 3.54-3.50 (m, 4H), 3.44-3.40 (m, 2H), 3.23 (s, 3H).

LCMS m/z 316 (M+H)$^+$ (ES$^+$)

(iii) 3-Methoxy-5-(2-(2-(2-methoxyethoxy)ethoxy)ethoxy)aniline

The product from step (ii) above (13.4 g, 42.5 mmol) was dissolved in ethanol (150 mL) and Fe powder (13 g, 233 mmol) was added followed by a solution of NH$_4$Cl (2.3 g, 43.0 mmol) in water (150 mL). The resulting suspension was heated at 80° C. for 3 h. The reaction was cooled to room temperature and filtered through Celite. The filtrate was concentrated in vacuo then partitioned between water (250 mL) and EtOAc (400 mL). The organic layer was separated, dried (MgSO$_4$), filtered and concentrated under reduced pressure. The crude product was purified by chromatography on silica gel (120 g column, 0-4% MeOH/DCM) to afford the sub-title compound (10.95 g) as an oil.

¹H NMR (400 MHz, DMSO-d6) δ 5.76-5.73 (m, 2H), 5.68 (t, 1H), 5.07 (s, 2H), 3.98-3.89 (m, 2H), 3.72-3.65 (m, 2H), 3.63 (s, 3H), 3.60-3.48 (m, 6H), 3.47-3.40 (m, 2H), 3.24 (s, 3H)

LCMS m/z 286 (M+H)⁺ (ES⁺)

(iv) tert-Butyl (4-((2-((3-methoxy-5-(2-(2-(2-methoxyethoxy)ethoxy)ethoxy)phenyl)amino)-pyrimidin-4-yl)oxy)naphthalen-1-yl)carbamate tert-Butyl (4-((2-chloropyrimidin-4-yl)oxy)naphthalen-1-yl)carbamate (see, for example, Ito, K. et al., WO 2010/067130, 17 Jun. 2010; 1 g, 2.69 mmol), the product of step (iii) above (1.15 g, 4.03 mmol) and p-TSA monohydrate (0.100 g, 0.526 mmol) in DMF (10 mL) was heated at 55° C. (internal temperature) for 14 h. The mixture was cooled and added dropwise to sat. aq. NaHCO₃ (100 mL) then partitioned with EtOAc (2×50 mL). Organics were bulked and washed with 20% w/w NaCl solution (50 mL), then dried (MgSO₄), filtered and solvent evaporated. The crude product was purified by chromatography on silica gel (40 g column) to afford the sub-title compound (1.14 g) as a clear brown oil.

¹H NMR (400 MHz, DMSO-d6) δ 9.44 (s, 1H), 9.34 (s, 1H), 8.42 (d, 1H), 8.11 (d, 1H), 7.86-7.76 (m, 1H), 7.66-7.49 (m, 3H), 7.39 (d, 1H), 6.85 (s, 2H), 6.56 (d, 1H), 6.05 (t, 1H), 3.88 (dd, 2H), 3.71-3.63 (m, 2H), 3.59-3.48 (m, 9H), 3.46-3.38 (m, 2H), 3.22 (s, 3H), 1.52 (s, 9H)

LCMS m/z 621 (M+H)⁺ (ES⁺)

(v) 4-((4-Aminonaphthalen-1-yl)oxy)-N-(3-methoxy-5-(2-(2-(2-methoxyethoxy)ethoxy)-ethoxy)phenyl)pyrimidin-2-amine TFA (2.8 mL, 36.3 mmol) was added dropwise to a stirred solution of the product of step (iv) above (1.1 g, 1.772 mmol) in DCM (5 mL). The reaction was stirred at room temperature for 2 h. The mixture was added dropwise to stirred water (10 mL) and 1 M K₂CO₃ solution (35 mL, 35.0 mmol) and stirring continued until effervescence ceased. The mixture was extracted with DCM (2×25 mL) then the combined organic phases were dried (MgSO₄) and concentrated under reduced pressure. The crude product was purified by chromatography on silica gel (40 g column, 2% MeOH:DCM to 5%) to afford a brown gum. Recrystallised from iPrOAc (3 mL) afforded the sub-title compound (0.80 g) as a colourless solid.

¹H NMR (400 MHz, DMSO-d6) δ 9.42 (s, 1H), 8.33 (d, 1H), 8.22-8.03 (m, 1H), 7.69-7.56 (m, 1H), 7.51-7.35 (m, 2H), 7.11 (d, 1H), 6.87 (d, 2H), 6.68 (d, 1H), 6.35 (d, 1H), 6.04 (t, 1H), 5.79 (s, 2H), 3.94-3.78 (m, 2H), 3.74-3.64 (m, 2H), 3.60-3.47 (m, 9H), 3.46-3.38 (m, 2H), 3.22 (s, 3H)

LCMS m/z 521 (M+H)⁺ (ES⁺)

(vi) N-(5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)methanesulfonamide Et₃N (7 μL, 0.050 mmol) was added to a stirred suspension of phenyl (5-(tert-butyl)-2-methoxy-3-(methylsulfonamido)phenyl)carbamate (see Example 1(vi) above; 114 mg, 0.282 mmol) and the product from step (v) above (150 mg, 0.282 mmol) in i-PrOAc (6 mL). The resulting mixture was heated at 70° C. overnight. The reaction was cooled to rt and the solvent removed in vacuo. The crude product was purified by chromatography on silica gel (40 g column, 0-5% MeOH in DCM) to afford an off-white solid at ~90% purity. The crude product was purified by preparative HPLC (Varian, Basic (0.1% Ammonium Bicarbonate), Waters X-Bridge Prep-C18, 5 μm, 19×50 mm column, 20-65% MeCN in Water) to afford a colourless glass, which was triturated with diethyl ether to afford the title compound (21 mg) as a white solid.

¹H NMR (DMSO-d6) 400 MHz, δ: 9.44 (s, 1H), 9.35 (s, 1H), 9.17 (s, 1H), 8.93 (s, 1H), 8.41 (d, 1H), 8.27 (d, 1H), 8.19 (d, 1H), 8.10 (d, 1H), 7.84 (d, 1H), 7.69-7.65 (m, 1H), 7.60-7.56 (m, 1H), 7.41 (d, 1H), 7.02 (d, 1H), 6.83-6.77 (br m, 2H), 6.55 (d, 1H), 6.03-6.02 (m, 1H), 3.89-3.83 (m, 2H), 3.80 (s, 3H), 3.66-3.64 (m, 2H), 3.54-3.47 (m, 9H), 3.40-3.37 (m, 2H), 3.20 (s, 3H), 3.09 (s, 3H), 1.26 (s, 9H).

LCMS m/z 819 (M+H)⁺ (ES⁺); 817 (M−H)⁻ (ES⁻)

Example 5

N-(5-(tert-Butyl)-3-(3-(4-((2-((3-(cyclopropylsulfonyl)-5-methoxyphenyl)amino)pyrimidin-4-yl)oxy)naphthalen-1-yl)ureido)-2-methoxyphenyl)methanesulfonamide

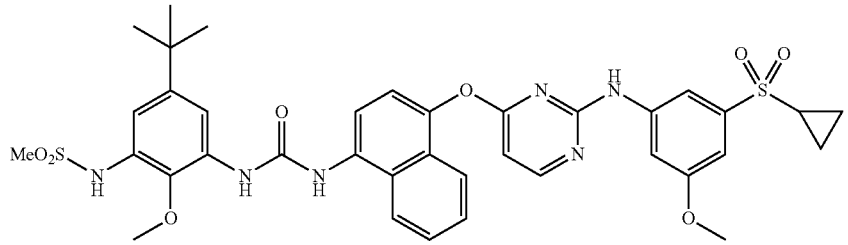 [SMILES: COc1cc(Nc2nccc(Oc3ccc(NC(=O)Nc4cc(C(C)(C)C)cc(NS(C)(=O)=O)c4OC)c4ccccc34)n2)cc(S(=O)(=O)C2CC2)c1]

(i) 1-(Cyclopropylsulfonyl)-3-methoxy-5-nitrobenzene

A mixture of 1-bromo-3-methoxy-5-nitrobenzene (9.05 g, 39.0 mmol), sodium cyclopropanesulfinate (6.5 g, 50.7 mmol), copper(I) iodide (0.743 g, 3.90 mmol), L-proline (0.908 g, 7.88 mmol) and NaOH (0.315 g, 7.88 mmol) in DMSO (50 mL) was heated at 90° C. for 18 h and 100° C. for 12 h. The mixture was partitioned between EtOAc (500 mL) and water (300 mL), the organic layer separated, washed with brine (200 mL), dried (MgSO₄), filtered and evaporated under reduced pressure. The crude product was purified by chromatography on silica gel (120 g column, 0-40% EtOAc/isohexane) to afford the sub-title compound (4.226 g) as a solid.

¹H NMR (400 MHz; DMSO-d6) δ 8.31 (s, 1H), 7.97 (s, 1H), 7.73 (s, 1H), 3.98 (s, 3H), 2.55-2.49 (m, 1H), 1.48-1.36 (m, 2H), 1.15-1.10 (m, 2H).

(ii) 3-(Cyclopropylsulfonyl)-5-methoxyaniline

A mixture of the product from step (i) above (4.22 g, 16.40 mmol), Fe powder (4.3 g, 77 mmol) and NH₄Cl (0.439 g, 8.20 mmol) in EtOH (40 mL) and water (20 mL) was heated under reflux for 1 h. The mixture was cooled, diluted with EtOH (50 mL) and filtered through Celite. The filtrate was evaporated, partitioned between EtOAc (300 mL) and brine (200 mL), the organic layer separated, dried (MgSO₄), filtered, and evaporated under reduced pressure. The residue was triturated with ether and filtered to afford the sub-title compound (3.308 g).
LCMS m/z 228 (M+H)⁺ (ES⁺)

(iii) tert-Butyl (4-((2-((3-(cyclopropylsulfonyl)-5-methoxyphenyl)amino)pyrimidin-4-yl)oxy)-naphthalen-1-yl)carbamate A mixture of tert-butyl (4-((2-chloropyrimidin-4-yl)oxy) naphthalen-1-yl)carbamate (see, for example, Ito, K. et al., WO 2010/067130, 17 Jun. 2010; 2.92 g, 7.86 mmol), the product from step (ii) above (2.5 g, 11.00 mmol) and p-TSA monohydrate (0.3 g, 1.577 mmol) in THF (40 mL) was heated at 55° C. for 4 h. The mixture was cooled, partitioned between EtOAc (150 mL) and water (100 mL), the organic layer separated, washed with brine (50 mL), dried (MgSO₄), filtered and evaporated under reduced pressure. The crude product was purified by chromatography on silica gel (120 g column, 0-50% EtOAc/isohexane) to give a solid which was recrystallised from ether to afford the sub-title compound (3.8 g) as a white solid.
LCMS m/z 563 (M+H)⁺ (ES⁺)

(iv) 4-((4-Aminonaphthalen-1-yl)oxy)-N-(3-(cyclopropylsulfonyl)-5-methoxyphenyl)-pyrimidin-2-amine A mixture of the product from step (iii) above (3.8 g, 6.75 mmol) and TFA (3 mL, 38.9 mmol) in DCM (50 mL) was stirred at room temperature for 18 h. A further 5 mL of TFA was added and stirred for a further 2 h. The solvent was evaporated under reduced pressure and the residue partitioned between DCM (150 mL) and sat. aq. NaHCO₃ solution (150 mL). The organic layer was separated, washed with brine, dried (MgSO₄), filtered and evaporated under reduced pressure. The crude product was purified by chromatography on silica gel (120 g column, 0-2% MeOH/DCM) to afford a foam which was recrystallised from DCM/ether to afford the sub-title compound (2.332 g) as a solid.
¹H NMR (400 MHz; CDCl₃) δ 8.29 (d, 1H), 7.87-7.81 (m, 2H), 7.52-7.45 (m, 4H), 7.22 (s, 1H), 7.11 (d, 1H), 6.97 (s, 1H), 6.78 (d, 1H), 6.38 (d, 1H), 4.18 (s, 2H), 3.68 (s, 3H), 2.42-2.36 (m, 1H), 1.32-1.28 (m, 2H), 1.01-0.96 (m, 2H).
LCMS m/z 463 (M+H)⁺ (ES⁺); 461 (M−H)⁻ (ES⁻)

(v) N-(5-(tert-Butyl)-3-(3-(4-((2-((3-(cyclopropylsulfonyl)-5-methoxyphenyl)amino)-pyrimidin-4-yl)oxy)naphthalen-1-yl)ureido)-2-methoxyphenyl) methanesulfonamide Et₃N (6 μL, 0.043 mmol) was added to a mixture of phenyl (5-(tert-butyl)-2-methoxy-3-(methylsulfonamido)phenyl)carbamate (see Example 1(vi) above; 85 mg, 0.216 mmol) and the product from step (iv) above (100 mg, 0.216 mmol) in isopropyl acetate (3 mL) and the mixture heated at 70° C. (block temperature) for 7 h. The reaction was diluted with DCM and MeOH then concentrated in vacuo onto silica gel. The crude product was purified by chromatography on the Companion (12 g column, 1-5% MeOH DCM) to afford the title compound (94 mg) as a white solid.
¹H NMR (DMSO-d6) 400 MHz, δ: 9.85 (s, 1H), 9.36 (s, 1H), 9.14 (s, 1H), 8.93 (s, 1H), 8.48 (d, 1H), 8.29 (d, 1H), 8.18 (d, 1H), 8.11 (d, 1H), 7.85 (dd, 1H), 7.74 (s, 1H), 7.66-7.70 (m, 1H), 7.57-7.61 (m, 1H), 7.51 (s, 1H), 7.43 (d, 1H), 7.03 (d, 1H), 6.86 (dd, 1H), 6.65 (d, 1H), 3.81 (s, 3H), 3.65 (s, 3H), 3.10 (s, 3H), 2.70-2.76 (m, 1H), 1.27 (s, 9H), 0.99-1.09 (m, 4H).
LCMS m/z 761 (M+H)⁺ (ES⁺)

Example 6

3-((4-((4-(3-(5-(tert-Butyl)-2-methoxy-3-(methylsulfonamido)phenyl)ureido)naphthalen-1-yl)oxy)pyrimidin-2-yl)amino)-5-methoxy-N-(2-morpholinoethyl)benzamide

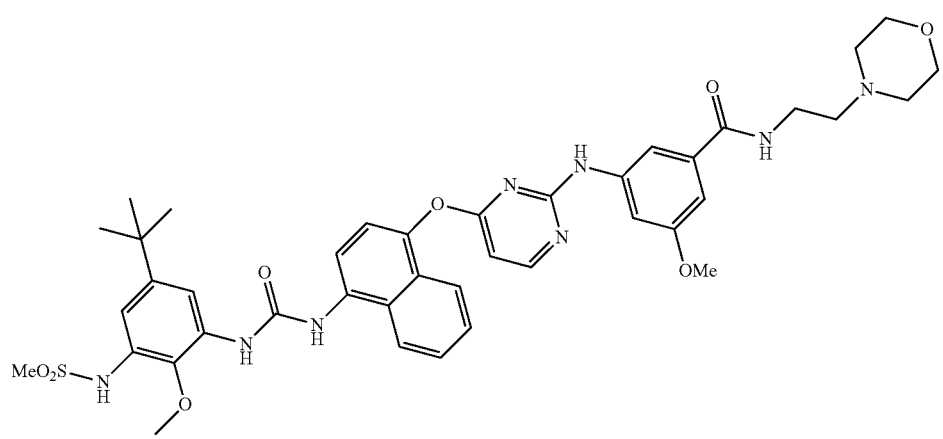 [SMILES: COc1cc(Nc2nccc(Oc3ccc(NC(=O)Nc4cc(C(C)(C)C)cc(NS(C)(=O)=O)c4OC)c4ccccc34)n2)cc(C(=O)NCCN2CCOCC2)c1]

(i) 3-((4-((4-(((tert-Butoxycarbonyl)amino)naphthalen-1-yl)oxy)pyrimidin-2-yl)amino)-5-methoxybenzoic acid N₂ was bubbled through a stirred mixture of tert-butyl (4-((2-chloropyrimidin-4-yl)oxy)naphthalen-1-yl)carbamate (see, for example, Ito, K. et al., WO 2010/067130, 17 Jun. 2010; 10 g, 26.9 mmol), 3-amino-5-methoxybenzoic acid (8.99 g, 53.8 mmol) and p-TSA monohydrate (1.02 g, 5.36 mmol) in THF (150 mL) for 10 min. The mixture was heated under reflux for 20 h, cooled and filtered. The filtrate was evaporated, MeOH (300 mL) added and the solid filtered, washed with MeOH then ether to afford the sub-title compound (10.063 g).

$^1$H NMR (400 MHz; DMSO-d6) δ 12.83 (brs, 1H), 9.68 (s, 1H), 9.32 (s, 1H), 8.44 (d, 1H), 8.11 (d, 1H), 8.13-8.10 (m, 2H), 7.61-7.51 (m, 4H), 7.41 (d, 1H), 6.98 (s, 1H), 6.58 (d, 1H), 3.60 (s, 3H), 1.52 (s, 9H).

LCMS m/z 503 (M+H)⁺ (ES⁺)

(ii) tert-Butyl (4-((2-((3-methoxy-5-((2-morpholinoethyl)carbamoyl)phenyl)amino)-pyrimidin-4-yl)oxy)naphthalen-1-yl)carbamate T3P, 50% w/w in EtOAc (592 µL, 0.995 mmol) was added to a solution of the product from step (i) above (500 mg, 0.995 mmol), 2-morpholinoethanamine (150 µL, 1.143 mmol) and TEA (420 µL, 3.01 mmol) in DMF (10 mL). The mixture was stirred at rt for 1 h. The solvent was evaporated and the residue triturated with water (50 mL) to give the sub-title compound (540 mg).

$^1$H NMR (400 MHz, DMSO-d6) δ 9.61 (s, 1H), 9.34 (s, 1H), 8.42 (dd, 1H), 8.32-8.17 (m, 1H), 8.11 (d, 1H), 7.82 (d, 1H), 7.68-7.48 (m, 4H), 7.48-7.35 (m, 2H), 6.88 (d, 1H), 6.62-6.47 (m, 1H), 3.58 (s, 7H), 3.45-3.25 (m, 2H), 2.43 (s, 6H), 1.52 (s, 9H).

LCMS m/z 615 (M+H)⁺ (ES⁺)

(iii) 3-((4-((4-Aminonaphthalen-1-yl)oxy)pyrimidin-2-yl)amino)-5-methoxy-N-(2-morpholinoethyl)benzamide The product from step (ii) above (570 mg, 0.927 mmol) was suspended in DCM (10 mL) and TFA (1500 µL, 19.47 mmol) added. The reaction mixture was stirred for 2 h. The solvents were evaporated and the residue partitioned between water (20 mL) and DCM (20 mL). The aqueous layer was separated and basified with NaHCO₃ before extraction with DCM (3×20 mL). The organics were bulked, dried (MgSO₄), filtered and evaporated to give a brown solid. The crude product was purified by chromatography on silica gel (40 g column, 5% MeOH:DCM to 10%) to afford the sub-title compound (350 mg) as a colourless solid.

$^1$H NMR (400 MHz, DMSO-d6) δ 9.47 (d, 1H), 8.33 (d, 1H), 8.21-8.11 (m, 1H), 8.07 (s, 1H), 7.72-7.56 (m, 2H), 7.52-7.33 (m, 3H), 7.12 (d, 1H), 6.94-6.80 (m, 1H), 6.71 (d, 1H), 6.33 (d, 1H), 5.69 (s, 2H), 3.61 (s, 3H), 3.58 (t, 4H), 3.36 (q, 2H), 2.47 (t, 2H), 2.42 (t, 4H).

LCMS m/z 515 (M+H)⁺ (ES⁺)

(iv) 3-((4-((4-(3-(5-(tert-Butyl)-2-methoxy-3-(methylsulfonamido)phenyl)ureido)-naphthalen-1-yl)pyrimidin-2-yl)amino)-5-methoxy-N-(2-morpholinoethyl)benzamide Et₃N (6 µL, 0.043 mmol) was added to a mixture of phenyl (5-(tert-butyl)-2-methoxy-3-(methylsulfonamido)phenyl)carbamate (see Example 1(vi) above; 76 mg, 0.194 mmol) and the product from step (iii) above (100 mg, 0.194 mmol) in isopropyl acetate (3 mL) and the mixture heated at 70° C. (block temperature) for 7 h. The reaction was diluted with DCM and MeOH then concentrated in vacuo onto silica gel. The crude product was purified by chromatography on the Companion (12 g column, 1-10% MeOH DCM) to afford the product as a clear oil which was purified further by preparative HPLC (Gilson, Acidic (0.1% Formic acid), Waters X-Select Prep-C18, 5 µm, 19×50 mm column, 20-50% MeCN in Water) to afford the formate salt of the product as a white solid. The material was dissolved in MeOH and loaded onto a pre-conditioned cartridge of SCX resin. The resin was washed with MeOH and the product released with 1% NH₃ in MeOH. The NH₃ solution was concentrated in vacuo to afford the title compound (54 mg) as a white solid.

$^1$H NMR (DMSO-d6) 400 MHz, δ: 9.61 (s, 1H), 9.35 (s, 1H), 9.14 (s, 1H), 8.92 (s, 1H), 8.41 (d, 1H), 8.28 (d, 1H), 8.19 (d, 2H), 8.10 (d, 1H), 7.85 (d, 1H), 7.68 (t, 1H), 7.56-7.61 (m, 2H), 7.43 (d, 1H), 7.34 (s, 1H), 7.03 (d, 1H), 6.86 (s, 1H), 6.55 (d, 1H), 3.81 (s, 3H), 3.59 (s, 3H), 3.49-3.59 (m, 4H), 3.32-3.41 (m, 2H), 3.10 (s, 3H), 2.33-2.50 (m, 6H), 1.27 (s, 9H).

LCMS m/z 407 (M+2H)²⁺ (ES⁺)

Example 7

3-((4-((4-(3-(5-(tert-Butyl)-2-methoxy-3-(methylsulfonamido)phenyl)ureido)naphthalen-1-yl)oxy)pyrimidin-2-yl)amino)-5-methoxy-N-(2-(2-(2-methoxyethoxy)ethoxy)ethyl)-benzamide

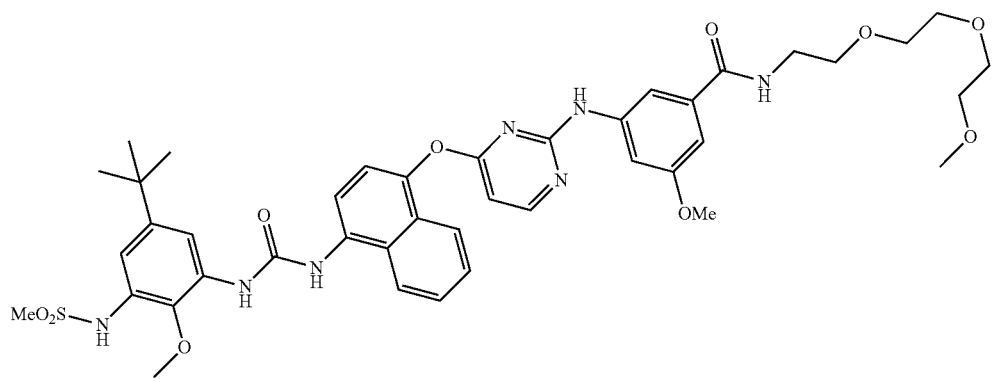 [SMILES: COCCOCCOCCNC(=O)c1cc(Nc2nccc(Oc3ccc(NC(=O)Nc4cc(C(C)(C)C)cc(NS(C)(=O)=O)c4OC)c4ccccc34)n2)cc(OC)c1]

(i) N-(5-(tert-Butyl)-3-(3-(4-((2-chloropyrimidin-4-yl)oxy)naphthalen-1-yl)ureido)-2-methoxyphenyl)methanesulfonamide In a 20 mL vial, a solution of phenyl (5-(tert-butyl)-2-methoxy-3-(methylsulfonamido)-phenyl)carbamate (see Example 1(vi) above; 0.5 g, 1.261 mmol) and 4-((2-chloropyrimidin-4-yl)oxy)naphthalen-1-amine (see, for example, Cirillo, P. F. et al., WO 2002/92576, 21 Nov. 2000; 0.361 g, 1.261 mmol) in isopropyl acetate (13 mL) was treated dropwise with Et₃N (0.035 mL, 0.252 mmol). The resultant brown solution was heated at 70° C. for 72 h and solvent removed in vacuo to afford a brown thick oil. The crude product was purified by chromatography on silica gel (120 g column, 0-60% EtOAc in Hexane) to afford the sub-title compound (0.1584 g) as a clear white solid.

¹H NMR (400 MHz, DMSO-d6) δ 9.40 (s, 1H), 9.13 (s, 1H), 8.92 (s, 1H), 8.66 (d, 1H), 8.30 (d, 1H), 8.17 (d, 1H), 8.10 (d, 1H), 7.81 (d, 1H), 7.70 (ddd, 1H), 7.64-7.55 (m, 1H), 7.44 (d, 1H), 7.27 (d, 1H), 7.02 (d, 1H), 3.80 (s, 3H), 3.09 (s, 3H), 1.26 (s, 9H).

LCMS m/z 570/572 (M+H)⁺ (ES⁺); 568/570 (M−H)⁻ (ES⁻)

(ii) 3-((4-((4-(3-(5-(tert-Butyl)-2-methoxy-3-(methylsulfonamido)phenyl)ureido)naphthalen-1-yl)oxy)pyrimidin-2-yl)amino)-5-methoxy-N-(2-(2-(2-methoxyethoxy)ethoxy)ethyl)-benzamide The product from step (i) above (158 mg, 0.277 mmol), 3-amino-5-methoxy-N-(2-(2-(2-methoxyethoxy)ethoxy)ethyl)benzamide (see Example 3(i) above; 100 mg, 0.320 mmol) and p-TSA monohydrate (13.18 mg, 0.069 mmol) were heated to 65° C. in DMF (3 mL) for 1.5 h. The temperature was increased to 85° C. and the mixture was stirred for a further 3 h. The mixture was diluted with water (10 mL) and saturated aq. NaHCO₃ solution (10 mL), then extracted with ethyl acetate (3×10 mL). The combined organic phases were washed with 20% brine (2×10 mL), saturated brine (10 mL), dried (MgSO₄) and concentrated under reduced pressure. The crude product was purified by chromatography on the Companion (40 g column, 0-100% THF/EtOAc) to afford a pale brown glass. The glass was triturated in diethyl ether to yield a white solid which was purified by preparative HPLC (Gilson, Acidic (0.1% Formic acid), Waters X-Select Prep-C18, 5 µm, 19×50 mm column, 40% isocratic MeCN in Water) to afford the title compound (65 mg) as a white solid.

¹H NMR (DMSO-d6) 400 MHz, δ: 9.60 (s, 1H), 9.36 (s, 1H), 9.14 (br s, 1H), 8.92 (s, 1H), 8.41 (d, 1H), 8.35-8.24 (m, 2H), 8.18 (d, 1H), 8.10 (d, 1H), 7.85 (d, 1H), 7.72-7.64 (m, 1H), 7.63-7.53 (m, 2H), 7.43 (d, 1H), 7.37-7.32 (m, 1H), 7.03 (d, 1H), 6.91-6.86 (m, 1H), 6.54 (d, 1H), 3.81 (s, 3H), 3.59 (s, 3H), 3.55-3.45 (m, 8H), 3.42-3.35 (m, 4H), 3.20 (s, 3H), 3.10 (s, 3H), 1.27 (s, 9H).

LCMS m/z 846 (M+H)⁺ (ES⁺); 844 (M−H)⁻ (ES⁻)

Example 8

1-(5-(tert-Butyl)-2-methoxyphenyl)-3-(4-((2-((3-methoxy-5-(2-(2-(2-methoxyethoxy)ethoxy)-ethoxy)phenyl)amino)pyrimidin-4-yl)oxy)naphthalen-1-yl)urea

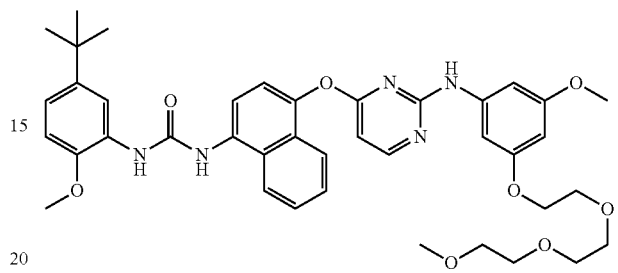

(i) Phenyl (5-(tert-butyl)-2-methoxyphenyl)carbamate

Phenyl chloroformate (1.40 mL, 11.16 mmol) was added to a stirred solution of 5-(tert-butyl)-2-methoxyaniline (2.00 g, 11.16 mmol) and NaHCO₃ (1.90 g, 22.62 mmol) in THF (20 mL) and DCM (20 mL). The mixture was stirred overnight then diluted with water (40 mL) and DCM (20 mL) then passed through a phase-sep cartridge. The resulting filtrate was concentrated in vacuo to afford the sub-title compound (3.53 g) as a red-brown oil.

¹H NMR (DMSO-d6) 400 MHz, δ: 9.04 (s, 1H), 7.68 (s, 1H), 7.40-7.44 (m, 2H), 7.19-7.27 (m, 3H), 7.14 (dd, 1H), 6.98 (d, 1H), 3.82 (s, 3H), 1.25 (s, 9H).

(ii) 1-(5-(tert-Butyl)-2-methoxyphenyl)-3-(4-((2-((3-methoxy-5-(2-(2-(2-methoxyethoxy)-ethoxy)ethoxy)phenyl)amino)pyrimidin-4-yl)oxy)naphthalen-1-yl)urea Et₃N (6 µL, 0.043 mmol) was added to a mixture of the product from step (i) above (58 mg, 0.194 mmol) and 4-((4-aminonaphthalen-1-yl)oxy)-N-(3-methoxy-5-(2-(2-(2-methoxyethoxy)ethoxy)ethoxy)phenyl)pyrimidin-2-amine (see Example 4(v) above; 100 mg, 0.192 mmol) in isopropyl acetate (3 mL) and the mixture heated at 70° C. (block temperature) for 7 days. The reaction was cooled to rt and diluted with MeOH. The solution was concentrated in vacuo onto silica gel. The crude product was purified by chromatography on the Companion (12 g column, 1-5% MeOH in DCM) to afford the title compound (56 mg) as a yellow solid.

¹H NMR (DMSO-d6) 400 MHz, δ: 9.46 (s, 1H), 9.32 (s, 1H), 8.75 (s, 1H), 8.42 (d, 1H), 8.33 (s, 1H), 8.29 (d, 1H), 8.08 (d, 1H), 7.84 (d, 1H), 7.66 (t, 1H), 7.58 (t, 1H), 7.40 (d, 1H), 6.95-6.99 (m, 2H), 6.81 (d, 2H), 6.56 (d, 1H), 6.04 (s, 1H), 3.91 (s, 3H), 3.86-3.88 (m, 2H), 3.65-3.67 (m, 2H), 3.48-3.55 (m, 6H), 3.51 (s, 3H), 3.41 (dd, 2H), 3.22 (s, 3H), 1.27 (s, 9H).

LCMS m/z 726 (M+H)⁺ (ES⁺)

Example 9

5-(tert-Butyl)-3-(3-(4-((2-((3-ethynyl-5-((2-morpholinoethyl)carbamoyl)phenyl)amino)-pyrimidin-4-yl)oxy)naphthalen-1-yl)ureido)-2-methoxy-N-methylbenzamide

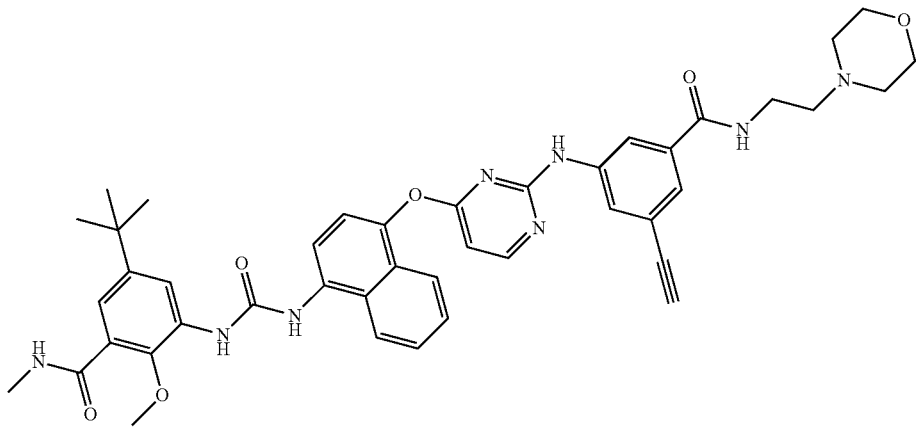 [SMILES: C#Cc1cc(Nc2nccc(Oc3ccc(NC(=O)Nc4cc(C(C)(C)C)cc(C(=O)NC)c4OC)c4ccccc34)n2)cc(C(=O)NCCN2CCOCC2)c1]

(i) Phenyl (5-(tert-butyl)-2-methoxy-3-(methylcarbamoyl)phenyl)carbamate

Phenyl chloroformate (300 μL, 2.391 mmol) was added to a stirred solution of 3-amino-5-(tert-butyl)-2-methoxy-N-methylbenzamide (see, for example, Cirillo, P. F. et al., Bioorg. Med. Chem. Lett. 2009, 19, 2386-2391; 550 mg, 2.327 mmol) and NaHCO$_3$ (300 mg, 3.57 mmol) in THF (5 mL) and DCM (5 mL). The mixture was stirred for 2 h, filtered and the solvent evaporated to give a pale brown oil. Trituration with isohexane (10 mL) gave the sub-title compound (470 mg) as a colourless solid.

$^1$H NMR (400 MHz, DMSO-d6) δ 9.47 (s, 1H), 8.19 (q, 1H), 7.84 (s, 1H), 7.54-7.36 (m, 2H), 7.33-7.14 (m, 4H), 3.75 (s, 3H), 2.80 (d, 3H), 1.27 (s, 9H).

LCMS m/z 357 (M+H)$^+$ (ES$^+$)

(ii) 5-(tert-Butyl)-3-(3-(4-((2-((3-ethynyl-5-((2-morpholinoethyl)carbamoyl)phenyl)amino)-pyrimidin-4-yl)oxy)naphthalen-1-yl)ureido)-2-methoxy-N-methylbenzamide Et$_3$N (5 μL, 0.036 mmol) was added to a mixture of the product from step (i) above (70 mg, 0.196 mmol) and 3-((4-((4-aminonaphthalen-1-yl)oxy)pyrimidin-2-yl) amino)-5-ethynyl-N-(2-morpholinoethyl)benzamide (see Example 2(iii) above; 100 mg, 0.197 mmol) in isopropyl acetate (3 mL) and the mixture heated at 50° C. (block temperature) for 16 h. The reaction mixture was cooled to rt and the solid filtered off. The residue was recrystallised from MeCN (3 mL). The resultant solid was filtered, rinsing with MeCN, and dried in vacuo to afford a tan solid. The crude product was purified by preparative HPLC (Varian, Basic (0.1% Ammonium Bicarbonate), Waters X-Bridge Prep-C18, 5 μm, 19×50 mm column, 35-70% MeCN in Water) to afford the title compound (17 mg) as a colourless solid.

$^1$H NMR (400 MHz, DMSO-d6) δ 9.75 (s, 1H), 9.40 (s, 1H), 8.86 (s, 1H), 8.50-8.38 (m, 2H), 8.34 (t, 1H), 8.26 (d, 1H), 8.17 (q, 1H), 8.10-7.99 (m, 2H), 7.95-7.79 (m, 2H), 7.68 (ddd, 1H), 7.59 (ddd, 1H), 7.50-7.37 (m, 2H), 7.10 (d, 1H), 6.55 (d, 1H), 4.11 (s, 1H), 3.79 (s, 3H), 3.54 (t, 4H), 3.38-3.32 (m, 2H), 2.82 (d, 3H), 2.47-2.33 (m, 6H), 1.28 (s, 9H).

LCMS m/z 771 (M+H)$^+$ (ES$^+$); 769 (M−H)$^−$ (ES$^−$)

Example 10

N-(5-(tert-Butyl)-3-(3-(2,3-dichloro-4-((2-((3-methoxy-5-(2-(2-(2-methoxyethoxy)ethoxy)-ethoxy) phenyl)amino)pyrimidin-4-yl)oxy)phenyl)ureido)-2-methoxyphenyl)-methanesulfonamide

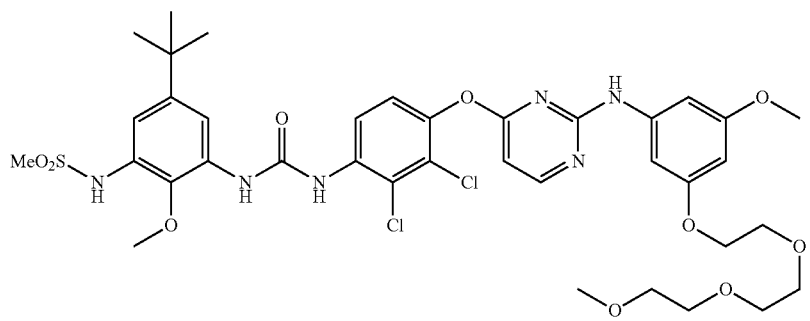 [SMILES: COCCOCCOCCOc1cc(Nc2nccc(Oc3ccc(NC(=O)Nc4cc(C(C)(C)C)cc(NS(C)(=O)=O)c4OC)c(Cl)c3Cl)n2)cc(OC)c1]

(i) 2,3-Dichloro-4-((2-chloropyrimidin-4-yl)oxy)aniline

DBU (11.85 mL, 79 mmol) was added over 5 min to a stirred mixture of 4-amino-2,3-dichlorophenol (10 g, 56.2 mmol) in MeCN (150 mL) at 0-5° C. After stirring for 5 min, 2,4-dichloropyrimidine (8.95 g, 60.1 mmol) was added portionwise over 5 min then the mixture warmed to rt and stirred for 2 h. The solvent was evaporated under reduced pressure and the residue partitioned between ether (200 mL) and water (200 mL). The aqueous layer was extracted with ether (200 mL) then the combined organic layers washed with brine (200 mL), dried (MgSO$_4$), filtered through a pad of silica and evaporated under reduced pressure. The residue was triturated with ether-isohexane, filtered and dried to afford the sub-title compound (14.403 g) as a light brown solid.

$^1$H NMR (CDCl$_3$) 400 MHz, δ: 8.45 (d, 1H), 6.96 (d, 1H), 6.84 (d, 1H), 6.73 (d, 1H), 4.22 (s, 2H).
LCMS m/z 290/2/4 (M+H)$^+$ (ES$^+$)

(ii) N-(5-(tert-Butyl)-3-(3-(2,3-dichloro-4-((2-chloropyrimidin-4-yl)oxy)phenyl)ureido)-2-methoxyphenyl)methanesulfonamide Et$_3$N (11 μL, 0.079 mmol) was added to a stirred solution of phenyl (5-(tert-butyl)-2-methoxy-3-(methylsulfonamido)phenyl)carbamate (see Example 1(vi) above; 200 mg, 0.504 mmol) and the product from step (i) above (154 mg, 0.504 mmol) in i-PrOAc (8 mL). The mixture was stirred at 70° C. for 48 h. The reaction mixture was no longer solubilised and the reaction had stalled. The solvent was removed in vacuo and DMF (5 mL) was added to the resulting residue. A fresh quantity of Et$_3$N (11 μL, 0.079 mmol) was added and the reaction heated at 70° C. for 3 h. A further quantity of phenyl (5-(tert-butyl)-2-methoxy-3-(methylsulfonamido)-phenyl)carbamate (396 mg, 1.009 mmol) was added, followed by Et$_3$N (35.2 μL, 0.252 mmol) and the reaction heated at 70° C. overnight. The reaction was cooled to rt and partitioned between EtOAc (50 mL) and water (40 mL). The organic phase was washed with water (40 mL), brine (40 mL), dried (MgSO$_4$), filtered and concentrated in vacuo to afford a solid (514 mg). The crude product was purified by chromatography on silica gel (40 g column, 0-100% EtOAc in isohexane) to afford the sub-title compound (106 mg) as an off-white semi-solid (85% purity).

$^1$H NMR (DMSO-d6) 400 MHz, δ: 9.22 (s, 1H), 9.15 (s, 1H), 9.12 (s, 1H), 8.71 (d, 1H), 8.22 (d, 1H), 8.08 (d, 1H), 7.46 (d, 1H), 7.35 (d, 1H), 7.04 (d, 1H), 3.74 (s, 3H), 3.07 (s, 3H), 1.25 (s, 9H).
LCMS m/z 588/590 (M+H)$^+$ (ES$^+$); 586/588 (M-H)$^-$ (ES$^-$)

(iii) N-(5-(tert-Butyl)-3-(3-(2,3-dichloro-4-((2-((3-methoxy-5-(2-(2-(2-methoxyethoxy)ethoxy)-ethoxy)phenyl)amino)pyrimidin-4-yl)oxy)phenyl)ureido)-2-methoxyphenyl)-methanesulfonamide To a stirred solution of the product from step (ii) above (100 mg, 0.144 mmol) and 3-methoxy-5-(2-(2-(2-methoxyethoxy)ethoxy)ethoxy)aniline (see Example 4(iii) above; 64 mg, 0.218 mmol) in DMF (4 mL) was added p-TSA monohydrate (14 mg, 0.074 mmol). The resulting solution was stirred at 60° C. for 48 h. The reaction was cooled to rt and partitioned between EtOAc (40 mL) and sat. aq. NaHCO$_3$ (30 mL). The aqueous phase was back-extracted with EtOAc (2×40 mL). The combined organic extracts were washed with water (2×50 mL), brine (50 mL), dried (MgSO$_4$), filtered and concentrated in vacuo to afford a sticky orange oil (150 mg). The crude product was purified by chromatography on silica gel (40 g column, 0-100% EtOAc in isohexane) to give a white semi-solid (57 mg), which was triturated with a diethylether-isohexane mix and filtered to afford an off-white solid (30 mg). The crude product was purified by preparative HPLC (Gilson, Acidic (0.1% Formic acid), Waters X-Select Prep-C18, 5 μm, 19×50 mm column, 40-70% MeCN in Water) to afford the title compound (14 mg) as a white solid.

$^1$H NMR (DMSO-d6) 400 MHz, δ: 9.51 (s, 1H), 9.24 (s, 1H), 9.21-9.10 (br m, 2H), 8.42 (d, 1H), 8.23 (d, 1H), 8.08-8.06 (m, 1H), 7.40 (d, 1H), 7.04 (d, 1H), 6.79 (br s, 1H), 6.75 (br s, 1H), 6.58 (d, 1H), 6.07 (t, 1H), 3.95-3.92 (m, 2H), 3.75 (s, 3H), 3.69-3.67 (m, 2H), 3.60 (s, 3H), 3.56-3.53 (m, 2H), 3.51-3.47 (m, 4H), 3.41-3.39 (m, 2H), 3.21 (s, 3H), 3.07 (s, 3H), 1.25 (s, 9H).
LCMS m/z 837/839 (M+H)$^+$ (ES$^+$); 835/837 (M-H)$^-$ (ES$^-$)

Example 11

N-(5-(tert-Butyl)-2-methoxy-3-(3-(4-((2-((3-methoxy-5-(2-(2-(2-methoxyethoxy)ethoxy)-ethoxy)phenyl)amino)pyridin-4-yl)oxy)naphthalen-1-yl)ureido)phenyl)-methanesulfonamide

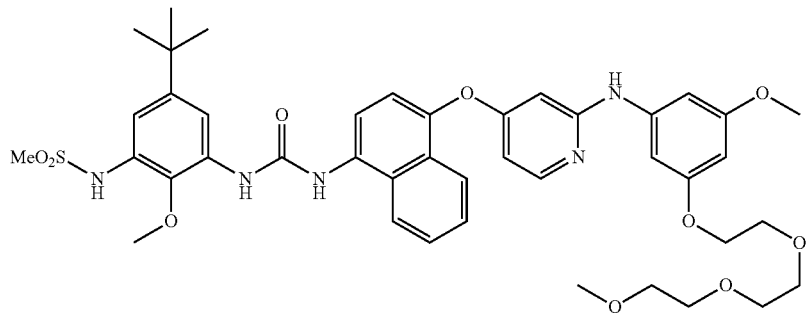 [SMILES: COCCOCCOCCOc1cc(Nc2cc(Oc3ccc(NC(=O)Nc4cc(C(C)(C)C)cc(NS(C)(=O)=O)c4OC)c4ccccc34)ccn2)cc(OC)c1]

(i) tert-Butyl (4-((2-((3-methoxy-5-(2-(2-(2-methoxyethoxy)ethoxy)ethoxy)phenyl)amino)-pyridin-4-yl)oxy)naphthalen-1-yl)carbamate Pd$_2$(dba)$_3$ (22 mg, 0.024 mmol) and BINAP (30 mg, 0.048 mmol) were stirred in 1,4-dioxane (1 mL) for 10 minutes under N$_2$. In a separate vessel, purged with N$_2$, Cs$_2$CO$_3$ (455 mg, 1.396 mmol), 3-methoxy-5-(2-(2-(2-methoxyethoxy)ethoxy)ethoxy)aniline (see Example 4(iii) above; 265 mg, 0.930 mmol) and tert-butyl (4-((2-chloropyridin-4-yl)oxy)-naphthalen-1-yl)carbamate (see Example 3(ii) above; 345 mg, 0.930 mmol) were stirred in 1,4-dioxane (5 mL). The catalyst solution was added to the main reaction mixture and the whole was heated to 90° C. for 48 h. Pd$_2$(dba)$_3$ (22 mg, 0.024 mmol) and BINAP (30 mg, 0.048 mmol) were added and the mixture was stirred for a further 18 h. Water was added (15 mL) and the mixture was extracted with EtOAc (3×15 mL). The combined organic phases were washed with saturated brine (15 mL), dried (MgSO$_4$) and concentrated under reduced pressure. The crude product was purified by chromatography on the Companion (40 g column, 50-100% EtOAc/isohexane) to afford the sub-title compound (194 mg) as a sticky brown oil.

$^1$H NMR (DMSO-d$_6$) 400 MHz, δ: 9.35 (s, 1H), 8.89 (s, 1H), 8.18-8.08 (m, 2H), 7.84 (d, 1H), 7.67-7.52 (m, 3H), 7.35 (d, 1H), 6.91 (s, 1H), 6.79 (s, 1H), 6.58 (dd, 1H), 6.07-6.02 (m, 2H), 4.01-3.95 (m, 2H), 3.74-6.67 (m, 2H), 3.65 (s, 3H), 3.60-3.48 (m, 6H), 3.46-3.39 (m, 2H), 3.23 (s, 3H), 1.52 (s, 9H).

LCMS m/z 620 (M+H)$^+$ (ES$^+$); 618 (M−H)$^−$ (ES$^−$)

(ii) 4-((4-Aminonaphthalen-1-yl)oxy)-N-(3-methoxy-5-(2-(2-(2-methoxyethoxy)ethoxy)-ethoxy)phenyl)pyridin-2-amine A solution of the product from step (i) above (190 mg, 0.307 mmol) in DCM (0.5 mL) was treated with TFA (500 µL, 6.49 mmol) and stirred at rt for 3 h. The mixture was diluted with water (10 mL) and DCM (10 mL). The mixture was neutralised with sat. aq. NaHCO$_3$ and passed through a phase separation cartridge. The organic phase was dried (MgSO$_4$) and concentrated to give the sub-title compound (135 mg) as a brown gum.

$^1$H NMR (DMSO-d$_6$) 400 MHz, δ: 8.08 (s, 1H), 8.20-8.10 (m, 1H), 8.05 (d, 1H), 7.67-7.59 (m, 1H), 7.49-7.39 (m, 2H), 7.09 (d, 1H), 6.89 (s, 1H), 6.76 (s, 1H), 6.71 (d, 1H), 6.52 (dd, 1H), 6.06-5.55 (m, 2H), 5.83 (s, 2H), 4.00-3.90 (m, 2H), 3.74-3.66 (m, 2H), 3.64 (s, 3H), 3.60-3.47 (m, 6H), 3.46-3.38 (m, 2H), 3.23 (s, 3H).

LCMS m/z 520 (M+H)$^+$ (ES$^+$)

(iii) N-(5-(tert-Butyl)-2-methoxy-3-(3-(4-((2-((3-methoxy-5-(2-(2-(2-methoxyethoxy)ethoxy)-ethoxy)phenyl)amino)pyridin-4-yl)oxy)naphthalen-1-yl)ureido)phenyl)methanesulfonamide Et$_3$N (6 µL, 0.043 mmol) was added to a mixture of phenyl (5-(tert-butyl)-2-methoxy-3-(methylsulfonamido)phenyl)carbamate (see Example 1(vi) above; 68.0 mg, 0.173 mmol) and the product from step (ii) above (90 mg, 0.173 mmol) in isopropyl acetate (3 mL) and the mixture heated at 70° C. (block temperature) overnight. The reaction was cooled to rt and diluted with EtOAc. The solution was concentrated in vacuo onto silica gel and purified by chromatography on the Companion (12 g column, 1-5% MeOH in DCM) to afford the product as a pink solid. The solid was triturated with Et$_2$O three times affording the title compound (73 mg) as a pale pink solid.

$^1$H NMR (DMSO-d6) 400 MHz, δ: 9.38 (s, 1H), 9.14 (s, 1H), 8.91 (s, 1H), 8.88 (bs, 1H), 8.29 (d, 1H), 8.19 (d, 1H), 8.12 (d, 1H), 8.10 (s, 1H), 7.87 (d, 1H), 7.69-7.72 (m, 1H), 7.59-7.63 (m, 1H), 7.39 (d, 1H), 7.03 (d, 1H), 6.90 (s, 1H), 6.78 (s, 1H), 6.59 (dd, 1H), 6.09 (d, 1H), 6.04 (t, 1H), 3.97-3.99 (m, 2H), 3.81 (s, 3H), 3.69-3.72 (m, 2H), 3.65 (s, 3H), 3.56-3.58 (m, 2H), 3.50-3.54 (m, 4H), 3.43 (dd, 2H), 3.23 (s, 3H), 3.10 (s, 3H), 1.27 (s, 9H).

LCMS m/z 818 (M+H)$^+$ (ES$^+$)

Example 12

1-(4-((2-((3-Methoxy-5-(2-(2-(2-methoxyethoxy)ethoxy)ethoxy)phenyl)amino)-pyrimidin-4-yl)oxy)naphthalen-1-yl)-3-(2-methoxy-5-morpholinophenyl)urea

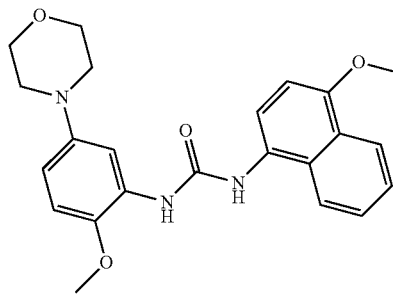

(i) Phenyl (2-methoxy-5-morpholinophenyl)carbamate

Phenyl chloroformate (300 µL, 2.391 mmol) was added to a stirred solution of 2-methoxy-5-morpholinoaniline (500 mg, 2.401 mmol) and NaHCO$_3$ (400 mg, 4.76 mmol) in THF (5 mL) and DCM (5 mL) and the mixture was stirred overnight. The mixture was diluted with water (40 mL) and DCM (20 mL) then the mixture passed through a phase-sep cartridge. The resulting filtrate was concentrated in vacuo to afford the sub-title compound (789 mg) as a yellow oil which solidified on standing.

$^1$H NMR (DMSO-d6) 400 MHz, δ: 9.04-9.31 (m, 1H), 7.23-7.44 (m, 1H), 7.14-7.21 (m, 2H), 6.95-7.01 (m, 1H), 6.69-6.81 (m, 4H), 3.78-3.85 (s, 3H), 3.68-3.73 (m, 4H), 2.96-3.00 (m, 4H).

LCMS m/z 329 (M+H)$^+$ (ES$^+$)

(ii) 1-(4-((2-((3-Methoxy-5-(2-(2-(2-methoxyethoxy)ethoxy)ethoxy)phenyl)amino)-pyrimidin-4-yl)oxy)naphthalen-1-yl)-3-(2-methoxy-5-morpholinophenyl)urea Triethylamine (6 µL, 0.043 mmol) was added to a mixture of the product from step (i) above (58 mg, 0.177 mmol) and 4-((4-aminonaphthalen-1-yl)oxy)-N-(3-methoxy-5-(2-(2-(2-methoxyethoxy)ethoxy)ethoxy)phenyl)pyrimidin-2-amine (see Example 4(v) above; 100 mg, 0.192 mmol) in isopropyl acetate (3 mL) and the mixture heated at 70° C. (block temperature) for 4 days. The reaction was cooled to rt and diluted with MeOH. The solution was concentrated in vacuo onto silica gel. The crude product was purified by chromatography on the Companion (12 g column, 1-5% MeOH in DCM) to afford the product as an off-white solid. The crude product was purified by preparative HPLC (Gilson, Acidic (0.1% Formic acid), Waters X-Select Prep-C18, 5 μm, 19×50 mm column, 25-70% MeCN in Water) to afford the title compound (51 mg) as an off-white solid.

$^1$H NMR (DMSO-d6) 400 MHz, δ: 9.44 (s, 1H), 9.41 (s, 1H), 8.83 (s, 1H), 8.42 (d, 1H), 8.29 (d, 1H), 8.08 (d, 1H), 8.08 (bs, 1H), 7.84 (d, 1H), 7.67 (t, 1H), 7.58 (t, 1H), 7.40 (d, 1H), 7.00 (d, 1H), 6.81 (d, 2H), 6.68 (bs, 1H), 6.55 (d, 1H), 6.04 (t, 1H), 3.90 (s, 3H), 3.85-3.87 (m, 2H), 3.78 (bs, 4H), 3.64-3.66 (m, 2H), 3.48-3.55 (m, 6H), 3.50 (s, 3H), 3.40 (dd, 2H), 3.22 (s, 3H), 3.08 (bs, 4H).

LCMS m/z 378 (M+2H)$^{2+}$ (ES$^+$)

Example 13

5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)-N-methylbenzamide

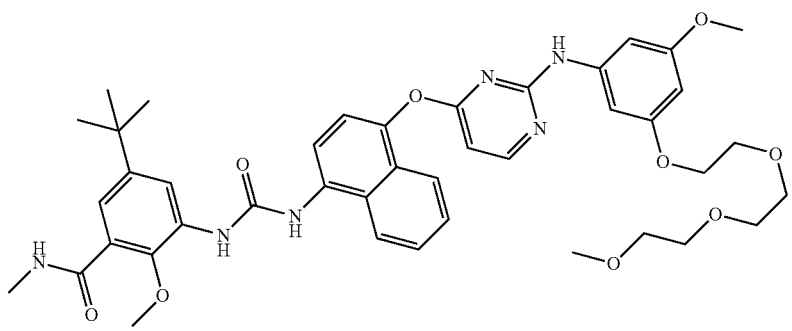 [SMILES: CNC(=O)c1cc(C(C)(C)C)cc(NC(=O)Nc2ccc(Oc3ccnc(Nc4cc(OC)cc(OCCOCCOCCOC)c4)n3)c3ccccc23)c1OC]

Triethylamine (15 μL, 0.108 mmol) was added to a mixture of phenyl (5-(tert-butyl)-2-methoxy-3-(methylcarbamoyl)phenyl)carbamate (see Example 9(i) above; 150 mg, 0.421 mmol) and 4-((4-aminonaphthalen-1-yl)oxy)-N-(3-methoxy-5-(2-(2-(2-methoxyethoxy)-ethoxy)ethoxy)phenyl)pyrimidin-2-amine (see Example 4(v) above; 200 mg, 0.384 mmol) in THF (5 mL) and the mixture heated at 50° C. (block temperature) for 24 h. The solvents were evaporated and the crude product was purified by chromatography on silica gel (40 g column, 2% MeOH:DCM to 5%) to afford a pale brown glass which was triturated with Et$_2$O to afford the title compound (255 mg) as a tan solid.

$^1$H NMR (400 MHz, DMSO-d6) δ 9.43 (s, 2H), 8.89 (s, 1H), 8.45 (d, 1H), 8.42 (d, 1H), 8.28 (d, 1H), 8.17 (q, 1H), 8.08 (d, 1H), 7.89-7.81 (m, 1H), 7.72-7.65 (m, 1H), 7.64-7.56 (m, 1H), 7.42 (d, 1H), 7.11 (d, 1H), 6.87-6.75 (m, 2H), 6.54 (d, 1H), 6.04 (t, 1H), 3.87 (t, 2H), 3.80 (s, 3H), 3.71-3.61 (m, 2H), 3.60-3.46 (m, 9H), 3.44-3.39 (m, 2H), 3.22 (s, 3H), 2.82 (d, 3H), 1.28 (s, 9H).

LCMS m/z 783 (M+H)$^+$ (ES$^+$); 781 (M–H)$^-$ (ES$^-$)

Example 14

N-(3-(3-(4-((2-((3-(2,5,8,11,14,17,20-Heptaoxadocosan-22-yloxy)-5-methoxyphenyl)amino)-pyrimidin-4-yl)oxy)naphthalen-1-yl)ureido)-5-(tert-butyl)-2-methoxyphenyl)-methanesulfonamide

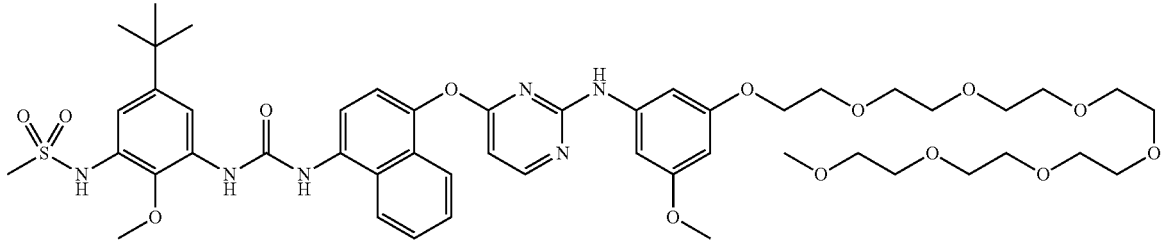 [SMILES: COCCOCCOCCOCCOCCOCCOCCOc1cc(Nc2nccc(Oc3ccc(NC(=O)Nc4cc(C(C)(C)C)cc(NS(C)(=O)=O)c4OC)c4ccccc34)n2)cc(OC)c1]

(i) 22-(3-Methoxy-5-nitrophenoxy)-2,5,8,11,14,17,20-heptaoxadocosane

DIAD (2.76 mL, 14.19 mmol) was added dropwise to a stirred solution of 3-methoxy-5-nitrophenol (2 g, 11.82 mmol), 2,5,8,11,14,17,20-heptaoxadocosan-22-ol (4.03 g, 11.82 mmol) and $PPh_3$ (3.72 g, 14.19 mmol) in THF (15 mL) at 0-5° C. The mixture was warmed to rt, stirred for 18 h then evaporated under reduced pressure. The crude product was purified by chromatography on silica gel (220 g) column, EtOAc then 0-10% EtOH/EtOAc) to afford the sub-title compound (3.905 g, 70% purity) as an oil.

$^1$H NMR (400 MHz; $CDCl_3$) δ 7.38 (s, 1H), 7.36 (s, 1H), 6.78 (s, 1H), 4.19-4.17 (m, 2H), 3.89-3.85 (m, 5H), 3.73-3.62 (m, 22H), 3.56-3.53 (m, 2H), 3.38 (s, 3H).

(ii) 3-(2,5,8,11,14,17,20-Heptaoxadocosan-22-yloxy)-5-methoxyaniline

The product from step (i) above (3.90 g, 5.55 mmol) was dissolved in EtOH (30 mL) and Fe powder (3.10 g, 55.5 mmol) was added followed by a solution of $NH_4Cl$ (2.97 g, 55.5 mmol) in water (15 mL). The resulting suspension was heated at 80° C. for 1 h. The reaction was cooled to rt and filtered. The filtrate was concentrated in vacuo, basified to pH 10 by the addition of sat. aq. $NaHCO_3$ (80 mL), then extracted with EtOAc (3×100 mL). The combined organic extracts were dried ($MgSO_4$), filtered and concentrated in vacuo to afford an orange oil (3.7 g). The crude product was dissolved in the minimum of MeOH and loaded onto SCX. The column was eluted first with MeOH (3 column volumes) and then 1% $NH_3$ in MeOH (3 column volumes). The product containing fraction was concentrated in vacuo to afford the sub-title compound (2.54 g) as a brown oil.

$^1$H NMR (400 MHz, DMSO-d6) δ: 5.75-5.74 (m, 2H), 5.68 (t, 1H), 5.04 (s, 2H), 3.95-3.93 (m, 2H), 3.69-3.67 (m, 2H), 3.62 (s, 3H), 3.58-3.49 (m, 22H), 3.43-3.41 (m, 2H), 3.23 (s, 3H).

LCMS m/z 462 (M+H)$^+$ (ES$^+$)

(iii) tert-Butyl (4-((2-((3-(2,5,8,11,14,17,20-heptaoxadocosan-22-yl)oxy)-5-methoxyphenyl)amino)pyrimidin-4-yl)oxy)naphthalen-1-yl)carbamate To a stirred solution of tert-butyl (4-((2-chloropyrimidin-4-yl)oxy)naphthalen-1-yl)carbamate (see, for example, Ito, K. et al., WO 2010/067130, 17 Jun. 2010; 289 mg, 0.701 mmol) and the product from step (ii) above (500 mg, 1.051 mmol) in DMF (20 mL) was added pTSA monohydrate (67 mg, 0.352 mmol). The resulting solution was heated at 60° C. for 48 h. The reaction was cooled to rt and partitioned between EtOAc (80 mL) and sat. aq. $NaHCO_3$ (50 mL). The aqueous phase was back-extracted with EtOAc (80 mL). The combined organic extracts were washed with water (3×50 mL), brine (50 mL), dried ($MgSO_4$), filtered and concentrated in vacuo to afford an orange oil. The crude product was purified by chromatography on silica gel (40 g column, 0-2% MeOH in EtOAc) to afford the sub-title compound (498 mg) as an orange oil.

$^1$H NMR (400 MHz, DMSO-d6) δ: 9.40 (s, 1H), 9.30 (s, 1H), 8.41 (d, 1H), 8.12-8.09 (m, 1H), 7.82-7.80 (m, 1H), 7.62-7.52 (m, 3H), 7.38 (d, 1H), 6.85 (s, 2H), 6.54 (d, 1H), 6.04 (t, 1H), 3.90-3.84 (m, 2H), 3.69-3.63 (m, 2H), 3.58-3.48 (m, 25H), 3.42-3.40 (m, 2H), 3.22 (s, 3H), 1.52 (s, 9H).

(iv) N-(3-(2,5,8,11,14,17,20-Heptaoxadocosan-22-yloxy)-5-methoxyphenyl)-4-((4-aminonaphthalen-1-yl)oxy)pyrimidin-2-amine To a stirred solution of the product from step (iii) above (452 mg, 0.567 mmol) in DCM (10 mL) was added TFA (2.2 mL, 28.6 mmol). The resulting solution was stirred at rt for 1 h. The reaction mixture was concentrated in vacuo, dissolved in the minimum of MeOH then loaded onto SCX. The column was eluted with MeOH (3 column volumes) then 1% $NH_3$ in MeOH (3 column volumes). The product containing fraction was concentrated in vacuo to afford the sub-title compound (258 mg) as a dark orange oil.

$^1$H NMR (400 MHz, DMSO-d6) δ: 9.30 (s, 1H), 8.32 (d, 1H), 8.14-8.10 (m, 1H), 7.66-7.63 (m, 1H), 7.45-7.39 (m, 2H), 7.10 (d, 1H), 6.87 (s, 2H), 6.70 (d, 1H), 6.34 (d, 1H), 6.04 (t, 1H), 5.68 (s, 2H), 3.89-3.87 (m, 2H), 3.69-3.67 (m, 2H), 3.60-3.47 (m, 25H), 3.45-3.41 (m, 2H), 3.23 (s, 3H).

LCMS m/z 349 (M+2H)$^{2+}$ (ES$^+$)

(v) N-(3-(3-(4-((2-((3-(2,5,8,11,14,17,20-Heptaoxadocosan-22-yloxy)-5-methoxyphenyl)-amino)pyrimidin-4-yl)oxy)naphthalen-1-yl)ureido)-5-(tert-butyl)-2-methoxyphenyl)-methane sulfonamide A mixture of phenyl (5-(tert-butyl)-2-methoxy-3-(methylsulfonamido)phenyl)carbamate (see Example 1(vi) above; 74 mg, 0.187 mmol), the product from step (iv) above (120 mg, 0.170 mmol) and triethylamine (5 µL, 0.036 mmol) in i-PrOAc (2 mL) was heated at 70° C. overnight. The reaction was cooled to rt and concentrated in vacuo. The crude product was purified by chromatography on silica gel (40 g column, 0-10% MeOH in EtOAc) to afford an oil. The oil was dissolved in MeCN and water (4 mL, 1:1) and freeze-dried overnight to afford the title compound (118 mg) as a pale pink solid.

$^1$H NMR (400 MHz, DMSO-d6) δ: 9.41 (s, 1H), 9.34 (s, 1H), 9.13 (s, 1H), 8.91 (s, 1H), 8.41 (d, 1H), 8.27 (d, 1H), 8.19 (d, 1H), 8.10 (d, 1H), 7.85-7.83 (m, 1H), 7.69-7.65 (m, 1H), 7.60-7.56 (m, 1H), 7.41 (d, 1H), 7.02 (d, 1H), 6.82-6.80 (m, 2H), 6.54 (d, 1H), 6.03 (t, 1H), 3.87-3.85 (m, 2H), 3.80 (s, 3H), 3.67-3.64 (m, 2H), 3.55-3.47 (m, 25H), 3.41-3.39 (m, 2H), 3.22 (s, 3H), 3.09 (s, 3H), 1.26 (s, 9H).

LCMS m/z 995 (M+H)$^+$ (ES$^+$)

Example 15

N-(5-(tert-Butyl)-3-(3-(4-((2-((3-(2-(2-(2-(dimethyl-amino)ethoxy)ethoxy)ethoxy)-5-methoxyphenyl)amino)pyrimidin-4-yl)oxy)naphthalen-1-yl)ureido)-2-methoxyphenyl)-methanesulfonamide

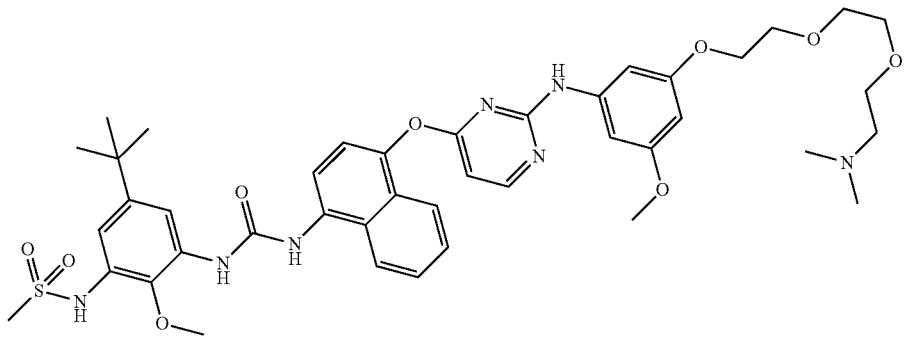 [SMILES: COc1cc(Nc2nccc(Oc3ccc(NC(=O)Nc4cc(C(C)(C)C)cc(NS(C)(=O)=O)c4OC)c4ccccc34)n2)cc(OCCOCCOCCN(C)C)c1]

(i) 2-(2-(2-(3-Methoxy-5-nitrophenoxy)ethoxy)ethoxy)-N,N-dimethylethanamine

DIAD (480 µL, 2.469 mmol) was added dropwise to a stirred solution of 3-methoxy-5-nitrophenol (350 mg, 2.069 mmol), 2-(2-(2-(dimethylamino)ethoxy)ethoxy)ethanol (440 mg, 2.483 mmol) and PPh$_3$ (651 mg, 2.483 mmol) in THF (15 mL) at 0-5° C. The mixture was warmed to rt, stirred for 18 h then the solvent evaporated under reduced pressure. The crude product was loaded onto a column of SCX in MeOH. The column was washed with MeOH and then the product was eluted with 7 M ammonia in MeOH. The resultant mixture was concentrated in vacuo and purified by chromatography on silica gel (40 g column, 0-10% MeOH/DCM) to afford the sub-title compound (428 mg) as a yellow oil.

$^1$H NMR (400 MHz; CDCl$_3$) δ 7.38-7.36 (m, 2H), 6.78 (s, 1H), 4.19-4.17 (m, 2H), 3.89-3.86 (m, 5H), 3.57-3.58 (m, 6H), 2.51 (t, 2H), 2.26 (s, 6H).

LCMS m/z 329 (M+H)$^+$ (ES$^+$)

(ii) 3-(2-(2-(2-(Dimethylamino)ethoxy)ethoxy)ethoxy)-5-methoxyaniline

Pd/C, 10% w/w (50 mg) was added to a solution of the product from step (i) above (420 mg, 1.279 mmol) in EtOH (10 mL) and the mixture stirred under hydrogen (5 bar) for 2 h. The mixture was filtered and the solvent evaporated to give the sub-title compound (380 mg) as a thick yellow oil.

$^1$H NMR (400 MHz, DMSO-d6) δ 5.79-5.72 (m, 2H), 5.68 (t, 1H), 5.06 (s, 2H), 4.01-3.90 (m, 2H), 3.73-3.65 (m, 2H), 3.62 (s, 3H), 3.59-3.54 (m, 2H), 3.54-3.50 (m, 2H), 3.48 (t, 2H), 2.39 (t, 2H), 2.14 (s, 6H).

LCMS m/z 299 (M+H)$^+$ (ES$^+$)

(iii) N-(5-(tert-Butyl)-3-(3-(4-((2-((3-(2-(2-(2-(dimethylamino)ethoxy)ethoxy)ethoxy)-5-methoxyphenyl)amino)pyrimidin-4-yl)oxy)naphthalen-1-yl)ureido)-2-methoxyphenyl)-methanesulfonamide A suspension of N-(5-(tert-butyl)-3-(3-(4-((2-chloropyrimidin-4-yl)oxy)naphthalen-1-yl)ureido)-2-methoxyphenyl)methanesulfonamide (see Example 7(i) above; 73.6 mg, 0.129 mmol), the product from step (ii) above (77 mg, 0.258 mmol) and pTSA monohydrate (54.0 mg, 0.284 mmol) in THF/DMF (6 mL, 1:2) was heated at 60° C. for 24 h. The reaction was cooled to rt and partitioned between EtOAc (40 mL) and sat. aq. NaHCO$_3$ (30 mL). The aqueous layer was extracted with EtOAc (2×40 mL). The combined organic extracts were washed with water (2×50 mL) and brine (2×50 mL), then dried (MgSO$_4$), filtered and concentrated in vacuo. The crude product was purified by chromatography on silica gel (40 g column, 4-10% MeOH) to afford the title compound (51 mg) as a pale pink solid.

$^1$H NMR (400 MHz; DMSO-d6) δ: 9.43 (s, 1H), 9.39 (s, 1H), 9.15 (bs, 1H), 8.94 (s, 1H), 8.42 (d, 1H), 8.29 (d, 1H), 8.19 (d, 1H), 8.10 (d, 1H), 7.85 (d, 1H), 7.68 (t, 1H), 7.59 (t, 1H), 7.41 (d, 1H), 7.03 (d, 1H), 6.83 (s, 1H), 6.81 (s, 1H), 6.55 (d, 1H), 6.03 (t, 1H), 3.86-3.88 (m, 2H), 3.81 (s, 3H), 3.65-3.68 (m, 2H), 3.49-3.60 (m, 6H), 3.51 (s, 3H), 3.10 (s, 3H), 2.51-2.55 (m, 2H), 2.25 (s, 6H), 1.27 (s, 9H).

LCMS m/z 832 (M+H)$^+$ (ES$^+$); 417 (M+2H)$^{2+}$ (ES$^+$)

Example 16

3-((4-((4-(3-(5-(tert-Butyl)-2-methoxy-3-(methylsulfonamido)phenyl)ureido)naphthalen-1-yl)oxy)pyrimidin-2-yl)amino)-5-ethynyl-N-(2-(2-(2-methoxyethoxy)ethoxy)ethyl)benzamide

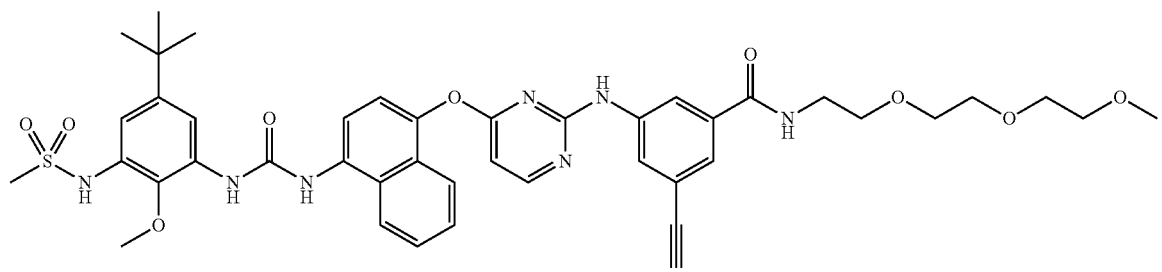

Method 1

(i) 3-Bromo-N-(2-(2-(2-methoxyethoxy)ethyl)-5-nitrobenzamide

T3P, 50 wt % in EtOAc (25 mL, 42.0 mmol) was slowly added to a solution of 3-bromo-5-nitrobenzoic acid (7.05 g, 28.7 mmol), 2-(2-(2-methoxyethoxy)ethoxy)ethanamine (4 g, 24.25 mmol) and Et$_3$N (12 mL, 86 mmol) in EtOAc (50 mL) whilst immersed in an ice-bath. Once the addition was complete, the ice bath was removed and the reaction allowed to stir at rt for 2 h. The mixture was partitioned between sat. aq NaHCO$_3$ solution (100 mL) and EtOAc (100 mL). The organic layer was washed with aq K$_2$CO$_3$ solution (10 g in 100 mL) and brine (100 mL), before being dried (MgSO$_4$), filtered and concentrated in vacuo to afford the sub-title compound (8.23 g) as a brown oil.

$^1$H NMR (400 MHz, DMSO-d6) δ 9.02 (t, 1H), 8.65-8.64 (m, 1H), 8.53 (t, 1H), 8.46 (t, 1H), 3.57-3.43 (m, 10H), 3.41-3.38 (m, 2H), 3.21 (s, 3H).

LCMS m/z 391/393 (M+H)$^+$ (ES$^+$); 389/391 (M−H)$^-$ (ES$^-$)

(ii) 3-Amino-5-bromo-N-(2-(2-(2-methoxyethoxy)ethoxy)ethyl)benzamide

Iron powder (5.90 g, 106 mmol) was added to a solution of the product from step (i) above (8.24 g, 20.43 mmol) and concentrated HCl (2 mL, 23.40 mmol) in EtOH (65 mL) and water (15 mL). The mixture was heat at 75° C. (block temperature) for 1 h. Then, the reaction was cooled to rt, before being diluted with water (30 mL), filtered and concentrated in vacuo. The residue was basified (NaHCO$_3$) then partitioned between EtOAc (350 mL) and water (275 mL). The organic layer was dried (MgSO$_4$), filtered and concentrated in vacuo to afford an orange oil that was purified by chromatography on silica gel (220 g column, 0-5% MeOH in DCM) to afford the sub-title compound (5.25 g) as an orange oil.

$^1$H NMR (400 MHz, DMSO-d6) δ: 8.36 (t, 1H), 7.07 (t, 1H), 7.00-6.99 (m, 1H), 6.84 (t, 1H), 5.57 (s, 2H), 3.52-3.48 (m, 8H), 3.42-3.39 (m, 2H), 3.35 (q, 2H), 3.22 (s, 3H).

LCMS m/z 361/363 (M+H)$^+$ (ES$^+$)

(iii) 3-Amino-N-(2-(2-(2-methoxyethoxy)ethoxy)ethyl)-5-((triisopropylsilyl)ethynyl)-benzamide To a degassed solution of the product from step (ii) above (5.06 g, 13.31 mmol), ethynyltriisopropylsilane (4.5 mL, 20.06 mmol), Cu(I)I (130 mg, 0.683 mmol) and Et$_3$N (8 mL, 57.4 mmol) in DMF (45 mL) was added Pd(PPh$_3$)$_4$ (770 mg, 0.666 mmol). The reaction was heated at 85° C. for 3 h, before being cooled to rt and partitioned between EtOAc (250 mL) and brine (250 mL). The aqueous phase was further extracted with EtOAc (250 mL), then the combined organic extracts were washed with water (3×200 mL) and brine (200 mL), before being dried (MgSO$_4$), filtered and concentrated in vacuo to afford a dark brown oil. The crude product was purified by chromatography on silica gel (220 g column, 0-3% MeOH in DCM) to afford the sub-title compound (5.4 g) as an orange oil.

$^1$H NMR (400 MHz, DMSO-d6) δ: 8.39 (t, 1H), 7.06-7.03 (m, 2H), 6.79-6.78 (m, 1H), 5.43 (s, 2H), 3.54-3.49 (m, 8H), 3.41-3.33 (m, 4H), 3.21 (s, 3H), 1.10 (s, 21H).

LCMS m/z 463 (M+H)$^+$ (ES$^+$)

(iv) 3-Amino-5-ethynyl-N-(2-(2-(2-methoxyethoxy)ethoxy)ethyl)benzamide

To a stirred solution of the product from step (iii) above (5.33 g, 11.40 mmol) in EtOAc (75 mL) was added 1M TBAF in THF (11.40 mL, 11.40 mmol). The reaction was stirred at rt for 1 h, before being partitioned between water (300 mL) and EtOAc (400 mL), the aqueous phase being further extracted with EtOAc (300 mL). The combined organic extracts were washed with brine (400 mL), before being dried (MgSO$_4$), filtered and concentrated to afford an orange oil. The crude product was dissolved in the minimum quantity of MeOH and loaded onto SCX. The column was eluted with MeOH (3 column volumes) followed by 1% NH$_3$ in MeOH (3 column volumes). The product containing fraction was concentrated in vacuo to afford the sub-title compound (3.27 g) as a brown oil.

$^1$H NMR (400 MHz, DMSO-d6) δ: 8.38 (t, 1H), 7.06-7.04 (m, 2H), 6.75-6.74 (m, 1H), 5.46 (s, 2H), 4.09 (s, 1H), 3.53-3.48 (m, 8H), 3.41-3.39 (m, 2H), 3.37-3.33 (m, 2H), 3.21 (s, 3H).

LCMS m/z 307 (M+H)$^+$ (ES$^+$)

(v) tert-Butyl (4-((2-((3-ethynyl-5-((2-(2-(2-methoxyethoxy)ethoxy)ethyl)carbamoyl)-phenyl)amino)pyrimidin-4-yl)oxy)naphthalen-1-yl)carbamate To a stirred solution of the product from step (iv) above (1 g, 3.13 mmol) and tert-butyl (4-((2-chloropyrimidin-4-yl)oxy)naphthalen-1-yl)carbamate (see, for example, Ito, K. et al., WO 2010/067130, 17 Jun. 2010; 777 mg, 2.090 mmol) in DMF (60 mL) was added pTSA monohydrate (200 mg, 1.051 mmol). The resulting solution was stirred at 60° C. for 72 h. The reaction was cooled to rt then partitioned between EtOAc (150 mL) and sat. aq. NaHCO$_3$ (100 mL). The aqueous layer was further extracted with EtOAc (2×150 mL), then the combined organic extracts were washed with water (3×200 mL) and brine (200 mL), before being dried (MgSO$_4$), filtered and concentrated to afford an orange oil (1.17 g). The crude product was purified by chromatography on silica gel (80 g column, 0-5% MeOH in EtOAc) to afford the sub-title compound (552 mg) as a light brown foam.

$^1$H NMR (400 MHz, DMSO-d6) δ: 9.73 (s, 1H), 9.29 (s, 1H), 8.46-8.43 (m, 2H), 8.11-8.09 (m, 2H), 7.92-7.88 (br m, 1H), 7.83-7.80 (m, 1H), 7.62-7.53 (m, 3H), 7.56-7.55 (m, 1H), 7.42 (d, 1H), 6.57 (d, 1H), 4.14 (s, 1H), 3.54-3.48 (m, 8H), 3.40-3.35 (m, 4H), 3.20 (s, 3H), 1.52 (s, 9H).

LCMS m/z 642 (M+H)$^+$ (ES$^+$)

(vi) 3-((4-((4-Aminonaphthalen-1-yl)oxy)pyrimidin-2-yl)amino)-5-ethynyl-N-(2-(2-(2-methoxyethoxy)ethoxy)ethyl)benzamide To a stirred solution of the product from step (v) above (540 mg, 0.825 mmol) in DCM (8 mL) was added TFA (3.2 mL, 41.5 mmol). The reaction was stirred at rt for 1 h. The solution was concentrated in vacuo and the resulting oil dissolved in the minimum of MeOH and loaded onto SCX. The column was eluted with MeOH (3 column volumes), then 1% NH$_3$ in MeOH (3 column volumes). The product-containing portion was concentrated in vacuo to afford the sub-title compound (405 mg) as a light, brown foam.

$^1$H NMR (400 MHz, DMSO-d6) δ: 9.73 (s, 1H), 8.45 (t, 1H), 8.36 (d, 1H), 8.14-8.10 (m, 1H), 8.07-8.05 (br m, 1H), 7.94-7.92 (br m, 1H), 7.65-7.61 (m, 1H), 7.47-7.40 (m, 3H), 7.15 (d, 1H), 6.72 (d, 1H), 6.37 (d, 1H), 5.87 (br s, 2H), 4.17 (s, 1H), 3.54-3.48 (m, 8H), 3.40-3.36 (m, 4H), 3.20 (s, 3H).
LCMS m/z 542 (M+H)+ (ES+)

(vii) 3-((4-((4-(3-(5-(tert-Butyl)-2-methoxy-3-(methylsulfonamido)phenyl)ureido)-naphthalen-1-yl)oxy)pyrimidin-2-yl)amino)-5-ethynyl-N-(2-(2-(2-methoxyethoxy)ethoxy)-ethyl)benzamide A stirred mixture of phenyl (5-(tert-butyl)-2-methoxy-3-(methylsulfonamido)phenyl)-carbamate (see Example 1(vi) above; 95 mg, 0.239 mmol), the product from step (vi) above (120 mg, 0.217 mmol) and Et₃N (6 µL, 0.043 mmol) in i-PrOAc (3 mL) was heated at 70° C. overnight. The reaction was cooled to rt and concentrated in vacuo. The remainder was purified by chromatography on silica gel (40 g column, 0-5% MeOH in EtOAc) to afford an oil, which was triturated with diethyl ether to afford a light beige solid. The crude product was purified by preparative HPLC (Varian, Basic (10 mM Ammonium Bicarbonate), Waters X-Bridge Prep-C18, 5 µm, 19×50 mm column, 35-70% MeCN in Water) to afford the title compound (69 mg) as an off-white solid.

$^1$H NMR (400 MHz, DMSO-d6) δ: 9.74 (s, 1H), 9.32 (s, 1H), 9.13 (s, 1H), 8.89 (s, 1H), 8.46-8.43 (m, 2H), 8.26 (d, 1H), 8.17 (d, 1H), 8.09-8.07 (m, 2H), 7.87-7.83 (m, 2H), 7.69-7.65 (m, 1H), 7.61-7.57 (m, 1H), 7.45-7.43 (m, 2H), 7.02 (d, 1H), 6.55 (d, 1H), 4.11 (s, 1H), 3.80 (s, 3H), 3.53-3.47 (m, 8H), 3.40-3.35 (m, 4H), 3.20 (s, 3H), 3.09 (s, 3H), 1.26 (s, 9H).
LCMS m/z 840 (M+H)+ (ES+); 838 (M–H)− (ES−)

Method 2

(I) 3-Bromo-N-(2-(2-(2-methoxyethoxy)ethoxy)ethyl)-5-nitrobenzamide

To a 10 L flask, equipped with a scrubber under nitrogen, was added 3-bromo-5-nitrobenzoic acid (2686 g, 10.91 mol) and thionyl chloride (5.37 L, 75.8 mol). The reaction was heated to 68° C. [GAS EVOLUTION] and was then stirred at 60° C. overnight, after which LC analysis indicated complete reaction. The reaction was cooled to rt and concentrated in vacuo to furnish 3.2 kg of material, an amount that indicated the presence of thionyl chloride (100% yield=2.88 kg). The mixture was concentrated from toluene (2×3 L) to remove all traces of thionyl chloride. A total of 3370 g of acid chloride was obtained, with toluene accounting for the excess yield.

To a 20 L flask under nitrogen was added 2-(2-(2-methoxyethoxy)ethoxy)ethanamine (890 g, 5.45 mol) and DCM (3.5 L). This was followed by the addition of 8% aq NaHCO₃ (9 L). The acid chloride (1373 g active, 4.89 mol) was then added to the mixture while maintaining the temperature below 25° C. [EXOTHERM and GAS EVOLUTION]. The mixture was stirred for 30 mins, after which LC indicated complete reaction. The organics were separated and washed with 1 M HCl (4.5 L) and 8% aq NaHCO₃ (4.5 L), before being dried, filtered and concentrated in vacuo to give a total of 1956 g of the sub-title compound (95% yield). Analysis by $^1$H NMR indicated a product purity of >95%.

(II) 3-Amino-5-bromo-N-(2-(2-(2-methoxyethoxy)ethoxy)ethyl)benzamide

The product from step (I) above (1 kg, 2.56 mol) was dissolved in THF (3.5 L) and AcOH (500 mL) and hydrogenated at 3 MPa (30 bar) H₂ at up to 60° C. with 5% Pt/C (30 g of JM type 18 MA, 55% water). Analysis after 5 hrs showed a 1:1 ratio of ArNHOH and ArNH₂. The reaction reached completion after being left overnight, with $^1$H NMR analysis showing 3% des-bromo side product. The catalyst was filtered off, then the residue was diluted with ethyl acetate (3 L) and washed with 20% potassium carbonate solution (3.5 L). The organics were then dried, filtered and concentrated in vacuo to provide a residue that was then slurried in 5 volumes of diethyl ether overnight to reduce the level of the des-bromo species (<2% after the slurry). The sub-title compound was obtained in 90% yield with a purity of 86% by LC.

(III) 3-Amino-N-(2-(2-(2-methoxyethoxy)ethoxy)ethyl)-5-((triisopropylsilyl)ethynyl)benzamide To a 10 L flask under nitrogen was added the product from step (II) above (700 g, 1.93 mol) and THF (5.59 L). This was followed by the addition of CuI (19.2 g, 0.1 mol), triethylamine (1.29 L, 9.27 mol) and ethynyltriisopropylsilane (389 g, 2.13 mol). The reaction was degassed and purged with nitrogen three times. Pd(PPh₃)₄ (125.5 g, 0.198 mol) was added and the reaction degassed and purged with nitrogen. The reaction was heated to 65° C. overnight, after which LC indicated 91% product and <1% starting material. The reaction mixture was concentrated in vacuo, then the residue was taken up in ethyl acetate (2 L) and put through a silica plug (2 kg), eluting with additional ethyl acetate (30 L). The product-containing fractions were concentrated in vacuo, then the crude product was dissolved in TBME (5 L) and extracted with 6 N HCl (5 L). The aqueous HCl phase was washed with TBME (2×5 L), before being basified with 6 N NaOH to pH 9-10. The product was then extracted with TBME (2×5 L), the organics were dried, filtered and concentrated in vacuo to give 635 g of the sub-title compound with a purity of >95% by $^1$H NMR (excluding solvents).

(IV) 3-Amino-5-ethynyl-N-(2-(2-(2-methoxyethoxy)ethoxy)ethyl)benzamide

To the product from step (111) above (1200 g, 2.59 mol) in MeCN (8.8 L) was added CsF (433.6 g, 2.85 mol). The reaction was stirred at RT overnight, after which HPLC analysis showed 1.7% product, 97.4% starting material. Additional CsF (420 g, 2.76 mol) was charged and the reaction stirred at RT overnight, whereupon HPLC analysis revealed 91.0% product, 4.4% starting material. The mixture was filtered and the filtrate concentrated in vacuo to give material which was 92.5% product, 0.7% starting material by HPLC. The residue was dissolved in DCM (3 L) and EtOAc (3 L), before being split into two equal portions. Each portion was passed through a silica pad (1.6 kg), eluting with EtOAc (50 L). The filtrates were combined and concentrated in vacuo. The crude material was washed with heptane (2×4 L) to remove silyl impurities. A total of 719 g of sub-title compound was isolated (83% assay by $^1$H NMR, 75% active yield, 597 g active).

(V) tert-Butyl (4-((2-((3-ethynyl-5-((2-(2-(2-methoxyethoxy)ethoxy)ethyl)carbamoyl)phenyl)-amino)pyrimidin-4-yl)oxy)naphthalen-1-yl)carbamate Under N₂ was charged the product from step (IV) above (301.2 g, 250.0 g active, 0.816 mol), tert-butyl (4-((2-chloropyrimidin-4-yl)oxy)naphthalen-1-yl)carbamate (see, for example, Ito, K. et al., WO 2010/067130, 17 Jun. 2010; 252.8 g, 0.680 mol), pTSA.H$_2$O (24.7 g, 0.130 mol) and THF (7600 mL). The dark red solution was heated to reflux for 6 h then cooled to room temperature, after which HPLC analysis indicated 0.25% the product of step (IV), 22.24% the product of step (VI), 8.98% chloropyrimidine starting material and 64.08% the product of step (V). Further product from step (IV) above (27.1 g, 22.5 g active, 73.4 mmol) was charged and the reaction was heated back to reflux and stirred overnight, with HPLC analysis subsequently revealing 0.20% the product of step (IV), 30.23% the product of step (VI), 4.50% starting chloropyrimidine and 58.61% the product of step (V). The reaction was cooled to room temperature and quenched with 20% K$_2$CO$_3$ (735 mL), then the layers were separated, with the organic layer being washed with sat. brine (880 mL). The organic layer was dried over MgSO$_4$, filtered and concentrated to isolate a brown sticky solid. Yield=491.2 g (93.8%). HPLC revealed 30.59% the product of step (VI) and 59.50% the product of step (V), with $^1$H NMR conforming to structure.

(VI) 3-((4-((4-Aminonaphthalen-1-yl)oxy)pyrimidin-2-yl)amino)-5-ethynyl-N-(2-(2-(2-methoxyethoxy)ethoxy)ethyl)benzamide Under N$_2$ was charged the crude product mixture from step (V) above (491.2 g) and DCM (3700 mL). TFA (695 mL, 12.3 equivalents) was added dropwise, while maintaining the temperature below 20° C. The dark brown solution was stirred at room temperature overnight, following which HPLC analysis indicated 86.90% product of step (VI) and 0.94% product of step (V). The mixture was concentrated and the residue taken up in EtOAc (3700 mL), before being washed with sat. aq. NaHCO$_3$ (2×2000 mL) until a pH of 7-8 was achieved. The organic layer was dried over MgSO$_4$, filtered and concentrated to isolate a purple solid. Yield=360.8 g. HPLC purity 78.58%.

(VII) 5-tert-Butyl-2-methoxy-3-nitroaniline

Under N$_2$ was charged 4-tert-butyl-2,6-dinitroanisole (620 g, 2.439 mol), IMS (4774 mL) and 10% Pd/C (31.8 g). The reaction mixture was heated to reflux (78° C.) and 4-methyl-1-cyclohexene (500 mL, 4.159 mol) was added dropwise over 4.5 h. The reaction was stirred at reflux overnight, whereupon HPLC analysis indicated 72.13% product and 27.17% starting material. Further 4-methyl-1-cyclohexene (160 mL, 1.331 mol) was added dropwise over 3 h and the reaction was stirred at reflux for 72 h. HPLC analysis indicated 92.72% product and 0% starting material. The reaction was cooled to room temperature and the catalyst was removed via vacuum filtration and washed with IMS (500 mL). The solvents were concentrated to ca. 1200 mL to give a ratio of 1:4.45 product:ethanol (target 1:5). 2 M HCl (124 mL) was charged dropwise to the remainder while maintaining the temperature below 23° C. Water (3100 mL) was charged and the resulting suspension was stirred at room temperature for 1.5 h. The solid was collected via vacuum filtration and washed with water (2×1000 mL). The resulting orange needles were dried, under vacuum, at 40° C. overnight.

Yield=475.2 g (86.9%). Purity >97% by $^1$H NMR. HPLC purity 98.8%. KF 0.36%.

(VIII) N-(5-tert-Butyl-2-methoxy-3-nitrophenyl)methanesulfonamide

Under N$_2$ was charged the product of step (VII) (471 g, 2.099 mol), toluene (1880 mL) and pyridine (471 mL), then methanesulfonyl chloride (179 mL) was added dropwise over 1 h while maintaining the temperature below 35° C. The reaction was stirred at 30-35° C. overnight, before being cooled to below 20° C., then water (1880 mL) and 2 M HCl (1880 mL) were charged (pH 3 achieved). The layers were separated and the organic phase was washed with 2.5% brine (1880 mL). Heptane (3760 mL) was then charged to the organic layer over 0.5 h to isolate a precipitate. The mixture was cooled to 0° C. and stirred for 1 h. The solid was collected via vacuum filtration and washed with heptane (1880 mL), before being dried, under vacuum, at 40° C. overnight. Yield=551 g (87%). HPLC purity 98.5%. Purity >97% by $^1$H NMR.

(IX) N-(3-Amino-5-tert-butyl-2-methoxyphenyl)methanesulfonamide

To a 5 L hydrogenator was charged the product from step (VIII) above (209.4 g, 0.693 mol), methanol (1675 mL, 8 volumes) and 10% Pd/C (10.2 g). The vessel was purged with 3×N$_2$ and 3×H$_2$ and then stirred under 0.3447 MPa (50 psi) H$_2$ until no further exotherm was observed, with HPLC indicating 96.35% product and 1.10% starting material. The reaction was diluted with THF (314 mL) and the catalyst was removed via vacuum filtration (Cuno filter), before being washed with THF (1000 mL). The solvents were concentrated to isolate a light brown solid, which was dried under vacuum at 40 CC overnight. Yield=167.0 g (88.5%). HPLC purity 96.7%. Purity >95% by $^1$H NMR.

(X) Phenyl N-[5-tert-butyl-3-(methanesulfonamido)-2-methoxyphenyl]carbamate

Under N$_2$ was charged the product of step (IX) above (167.0 g, 613 mmol), NaHCO$_3$ (77.3 g, 920 mmol), THF (870 mL) and DCM (1440 mL). Phenyl chloroformate (82.6 mL, 659 mmol) was added dropwise, while maintaining the temperature below 20° C., and the reaction was stirred at room temperature for 4 h. HPLC analysis of the reaction mixture indicated 98.6% product and 0.03% starting material. The reaction mixture was filtered and the cake was washed with THF (~50 mL). The filtrate was concentrated to ~900 mL and cyclohexane (2400 mL) was added, then the mixture was left to stir overnight. The resulting solid was collected via vacuum filtration and washed with cyclohexane (500 mL). The pale pink solid produced was dried, under vacuum, at 40° C. for 4 h. Yield=232.6 g (96.7%). HPLC purity 94.5%. $^1$H NMR purity >95%.

(XI) 3-((4-((4-(3-(5-(tert-Butyl)-2-methoxy-3-(methylsulfonamido)phenyl)ureido)naphthalen-1-yl)oxy)pyrimidin-2-yl)amino)-5-ethynyl-N-(2-(2-(2-methoxyethoxy)ethoxy)ethyl)benzamide Under N$_2$ was charged the product of step (vi) above (175.5 g, 0.324 mol), the product of step (X) above (145.0 g, 0.369 mmol) and iPrOAc (8800 mL). The resulting solution was heated to 60° C. and NEt$_3$ (9.3 mL) was charged in one portion, then the mixture was left to stir at 60° C. overnight, following which HPLC analysis indicated 25.77% product of step (VI), 3.60% product of step (X) and 57.85% product of step (XI). Further product of step (X) (36.0 g, 0.092 mol) was charged, then the reaction was left to stir at 60° C. overnight, whereupon HPLC analysis indicated 5.47% product of step (VI), 3.72% product of step (X) and 73.33% product of step (XI). The reaction mixture was cooled to room temperature, before being concentrated to isolate a dark purple solid (522.9 g). This solid was recrystallised from acetonitrile (2615 mL, 5 volumes), before being collected via vacuum filtration and washed with iPrOAc (2×500 mL). The pink solid obtained was dried, under vacuum, at 40° C. overnight, yielding 181.1 g (66.5%) of the title compound with HPLC purity 99.27%. $^1$H NMR conformed to structure.

Example 17

N-(5-(tert-Butyl)-3-(3-(4-((2-((3-(difluoromethoxy)-5-(2-(2-(2-methoxyethoxy)ethoxy)-ethoxy)phenyl)amino)pyrimidin-4-yl)oxy)naphthalen-1-yl)ureido)-2-methoxyphenyl)-methanesulfonamide

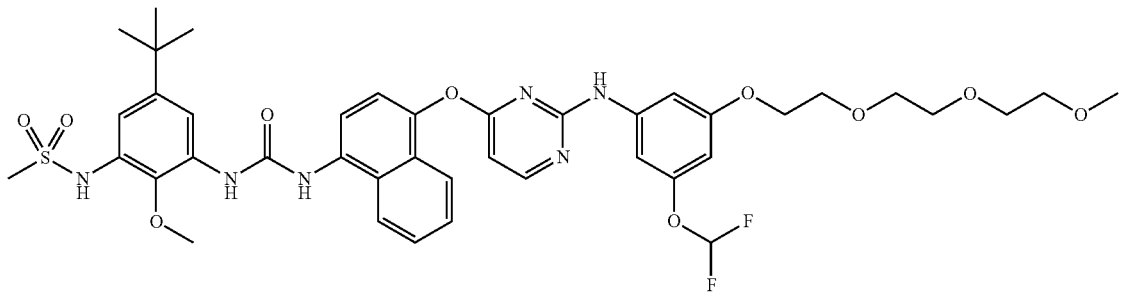

(i) 1-Bromo-3-(2-(2-(2-methoxyethoxy)ethoxy)ethoxy)-5-nitrobenzene

A mixture of 3-bromo-5-nitrophenol (1.5 g, 6.88 mmol), 1-bromo-2-(2-(2-methoxyethoxy)-ethoxy)ethane (1.72 g, 7.57 mmol), sodium iodide (0.103 g, 0.688 mmol) and K$_2$CO$_3$ (2.85 g, 20.64 mmol) in MeCN (30 mL) was heated at 60° C. for 18 h. The mixture was cooled and partitioned between EtOAc (150 mL) and water (150 mL). The organic layer was separated, dried (MgSO$_4$), filtered and evaporated under reduced pressure. The crude product was purified by chromatography on silica gel (40 g column, 0-50% EtOAc/isohexane) to afford the sub-title compound (2.5 g) as an oil.
$^1$H NMR (400 MHz; DMSO-d6) δ 7.97 (s, 1H), 7.72 (s, 1H), 7.41 (s, 1H), 4.22-4.19 (m, 2H), 3.90-3.87 (m, 2H), 3.74-3.54 (m, 8H), 3.38 (s, 3H).

(ii) 3-(2-(2-(2-Methoxyethoxy)ethoxy)ethoxy)-5-nitrophenol

A mixture of KOH (1.54 g, 27.4 mmol) and the product from step (i) above (2.5 g, 5.83 mmol) in water (10 mL) and dioxane (10 mL) was degassed for 5 minutes prior to the addition of di-tert-butyl(2',4',6'-triisopropyl-[1,1'-biphenyl]-2-yl)phosphine (0.067 g, 0.158 mmol) and Pd$_2$(dba)$_3$ (0.063 g, 0.069 mmol). The resulting mixture was degassed for a further 2 minutes and then heated under a nitrogen atmosphere at 100° C. for 2 h. The mixture was cooled then partitioned between ether (100 mL) and water (100 mL). The aqueous layer was acidified with aq. 1 M HCl to ~pH 1 and extracted with ethyl acetate (2×200 mL). The organic layer was washed with saturated brine (200 mL), dried over MgSO$_4$, filtered, and concentrated under reduced pressure. The crude product was purified by chromatography on silica gel (40 g column, 0-80% EtOAc/isohexane) to afford an oil which was triturated with ether/isohexane to give a solid. The solid was filtered and dried to afford the sub-title compound (1.46 g).

$^1$H NMR (400 MHz; CDCl$_3$) δ 7.61 (s, 1H), 7.27 (s, 1H), 7.19 (s, 1H), 6.76 (s, 1H), 4.13-4.11 (m, 2H), 3.85-3.83 (m, 2H), 3.76-3.67 (m, 6H), 3.61-3.59 (m, 2H), 3.39 (s, 3H).
LCMS m/z 302 (M+H)$^+$ (ES$^+$); 300 (M−H)$^−$ (ES$^−$)

(iii) 1-(Difluoromethoxy)-3-(2-(2-(2-methoxyethoxy)ethoxy)ethoxy)-5-nitrobenzene A mixture of the product from step (ii) above (1.4 g, 4.65 mmol), sodium 2-chloro-2,2-difluoroacetate (1.771 g, 11.62 mmol) and Cs$_2$CO$_3$ (3.03 g, 9.29 mmol) in DMF (15 mL) was heated at 100° C. for 1 h. The mixture was partitioned between EtOAc (100 mL) and water (100 mL), the organic layer washed with water (100 mL), dried (MgSO$_4$), filtered and evaporated under reduced pressure. The crude product was purified by chromatography on silica gel (40 g column, 0-80% EtOAc/isohexane) to afford the sub-title compound (900 mg) as an oil.
$^1$H NMR (400 MHz, CDCl$_3$) δ 7.64 (s, 1H), 7.59 (s, 1H), 7.04 (s, 1H), 6.58 (t, 1H), 4.23-4.20 (m, 2H), 3.90-3.88 (m, 2H), 3.75-3.64 (m, 6H), 3.56-3.54 (m, 2H), 3.38 (s, 3H).
LCMS m/z 352 (M+H)$^+$ (ES$^+$)

(iv) 3-(Difluoromethoxy)-5-(2-(2-(2-methoxyethoxy)ethoxy)ethoxy)aniline

A mixture of the product from step (iii) above (890 mg, 2.53 mmol), Fe powder (890 mg, 15.94 mmol) and NH$_4$Cl (50 mg, 0.935 mmol) in EtOH (12 mL) and water (4 mL) was heated under reflux for 1 h. The mixture was cooled, filtered and the MeOH removed under reduced pressure. The residue was partitioned between EtOAc (100 mL) and aq sat NaHCO$_3$ soln (100 mL), the organic layer washed with brine (100 mL), dried (MgSO$_4$), filtered and evaporated under reduced pressure to afford the sub-title compound (749 mg).
$^1$H NMR (400 MHz, CDCl$_3$) δ 6.45 (t, 1H), 6.09 (s, 1H), 6.08 (s, 1H), 6.03 (s, 1H), 4.07 (m, 2H), 3.83-3.81 (m, 2H), 3.77 (s, 2H), 3.74-3.71 (m, 2H), 3.69-3.64 (m, 4H), 3.56-3.54 (m, 2H), 3.38 (s, 3H).
LCMS m/z 322 (M+H)$^+$ (ES$^+$)

(v) N-(5-(tert-Butyl)-3-(3-(4-((2-((3-(difluoromethoxy)-5-(2-(2-(2-methoxyethoxy)ethoxy)-ethoxy)phenyl)amino)pyrimidin-4-yl)oxy)naphthalen-1-yl)ureido)-2-methoxyphenyl)-methanesulfonamide To a stirred solution of N-(5-(tert-butyl)-3-(3-(4-((2-chloropyrimidin-4-yl)oxy)naphthalen-1-yl)ureido)-2-methoxyphenyl)methanesulfonamide (see Example 7(i) above; 150 mg, 0.250 mmol) and the product from step (iv) above (104 mg, 0.317 mmol) in DMF (7 mL) was added pTSA monohydrate (24 mg, 0.126 mmol). The reaction was heated at 60° C. for 48 h. The reaction was cooled to rt then partitioned between EtOAc (40 mL) and sat aq. NaHCO₃ (40 mL). The aqueous phase was back-extracted with EtOAc (2×40 mL). The combined organic extracts were washed with water (3×50 mL), brine (50 mL), dried (MgSO₄), filtered and concentrated in vacuo to afford an oil (212 mg). The crude product was purified by chromatography on silica gel (40 g column, 100% EtOAc) to afford a foam, which was triturated with diethyl ether to afford the title compound (90 mg) as an off-white solid.

$^1$H NMR (400 MHz, DMSO-d6) δ: 9.63 (s, 1H), 9.34 (s, 1H), 9.13 (s, 1H), 8.90 (s, 1H), 8.44 (d, 1H), 8.27 (d, 1H), 8.18 (d, 1H), 8.10 (d, 1H), 7.85-7.83 (m, 1H), 7.69-7.65 (m, 1H), 7.60-7.56 (m, 1H), 7.42 (d, 1H), 7.23-6.86 (m, 4H), 6.58 (d, 1H), 6.28 (t, 1H), 3.92-3.89 (m, 2H), 3.80 (s, 3H), 3.68-3.66 (m, 2H), 3.55-3.53 (m, 2H), 3.50-3.47 (m, 4H), 3.40-3.38 (m, 2H), 3.20 (s, 3H), 3.09 (s, 3H), 1.26 (s, 9H).

LCMS m/z 855 (M+H)⁺ (ES⁺)

Example 18

N-(5-(tert-Butyl)-2-methoxy-3-(3-(4-((2-((3-methoxy-5-(2-(2-(2-morpholinoethoxy)ethoxy)-ethoxy)phenyl)amino)pyrimidin-4-yl)oxy)naphthalen-1-yl)ureido)phenyl)methanesulfonamide

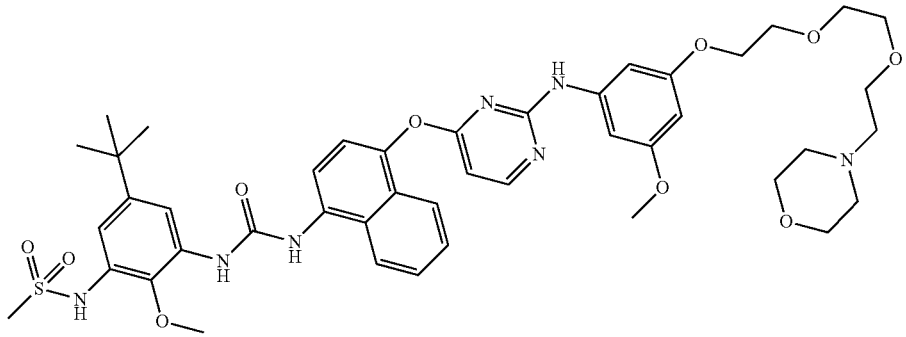 [SMILES: COc1cc(Nc2nccc(Oc3ccc(NC(=O)Nc4cc(C(C)(C)C)cc(NS(C)(=O)=O)c4OC)c4ccccc34)n2)cc(OCCOCCOCCN2CCOCC2)c1]

(i) 4-(2-(2-(2-(3-Methoxy-5-nitrophenoxy)ethoxy)ethoxy)ethyl)morpholine

DIAD (530 μL, 2.73 mmol) was added dropwise to a stirred solution of 3-methoxy-5-nitrophenol (386 mg, 2.280 mmol), 2-(2-(2-morpholinoethoxy)ethoxy)ethanol (600 mg, 2.74 mmol) and PPh₃ (718 mg, 2.74 mmol) in THF (15 mL) at 0-5° C. The mixture was warmed to rt, stirred for 18 h then the solvent evaporated under reduced pressure. The crude product was loaded onto a column of SCX in MeOH. The column was washed with MeOH and then the product was eluted with 7 M ammonia in MeOH. The resultant mixture was concentrated in vacuo and purified by chromatography on silica gel (40 g column, 0-5% MeOH/DCM) to afford the sub-title compound (728 mg) as a yellow oil.

$^1$H NMR (400 MHz; CDCl₃) δ 7.40-7.36 (m, 2H), 6.78 (s, 1H), 4.18 (t, 2H), 3.89-3.96 (m, 5H), 3.73-3.62 (m, 10H), 2.59 (t, 2H), 2.50 (br s, 4H).

LCMS m/z 371 (M+H)⁺ (ES⁺)

(ii) 3-Methoxy-5-(2-(2-(2-morpholinoethoxy)ethoxy)ethoxy)aniline

Pd/C, 10% w/w (100 mg) was added to a solution of the product from step (i) above (720 mg, 1.944 mmol) in EtOH (10 mL) and the mixture stirred under hydrogen (5 bar) for 2 h. The mixture was filtered and the solvent evaporated to give the sub-title compound (650 mg) as a thick yellow oil.

$^1$H NMR (400 MHz, DMSO-d6) δ 5.79-5.71 (m, 2H), 5.68 (t, 1H), 5.06 (s, 2H), 3.98-3.90 (m, 2H), 3.73-3.65 (m, 2H), 3.62 (s, 3H), 3.59-3.48 (m, 10H), 2.45 (t, 2H), 2.42-2.33 (m, 4H).

LCMS m/z 341 (M+H)⁺ (ES⁺)

(iii) N-(5-(tert-Butyl)-2-methoxy-3-(3-(4-((2-((3-methoxy-5-(2-(2-(2-morpholinoethoxy)-ethoxy)ethoxy)phenyl)amino)pyrimidin-4-yl)oxy)naphthalen-1-yl)ureido)phenyl)methanesulfonamide A suspension of N-(5-(tert-butyl)-3-(3-(4-((2-chloropyrimidin-4-yl)oxy)naphthalen-1-yl)ureido)-2-methoxyphenyl)methanesulfonamide (see Example 7(i) above; 84 mg, 0.147 mmol), the product from step (ii) above (100 mg, 0.294 mmol) and pTSA monohydrate (62 mg, 0.326 mmol) in THF/DMF (6 mL, 1:2) was heated at 60° C. for 24 h. The reaction was cooled to rt and partitioned between EtOAc (40 mL) and sat. aq. NaHCO₃ (30 mL). The aqueous layer was extracted with EtOAc (2×40 mL). The combined organic extracts were washed with water (2×50 mL), brine (2×50 mL), dried (MgSO₄), filtered and concentrated in vacuo. The crude product was purified by chromatography on silica gel (40 g column, 0-5% MeOH) and the product triturated with Et₂O to afford a pale pink solid. The crude product was purified by preparative HPLC (Varian, Basic (0.1% Ammonium Bicarbonate), Waters X-Bridge Prep-C18, 5 μm, 19×50 mm column, 35-70% MeCN in Water) to afford the title compound (52 mg) as a white solid.

$^1$H NMR (400 MHz; DMSO-d6) δ: 9.43 (s, 1H), 9.35 (s, 1H), 9.13 (s, 1H), 8.92 (s, 1H), 8.42 (d, 1H), 8.28 (d, 1H), 8.19 (d, 1H), 8.10 (d, 1H), 7.85 (d, 1H), 7.68 (t, 1H), 7.59 (t, 1H), 7.42 (d, 1H), 7.03 (d, 1H), 6.83 (s, 1H), 6.80 (s, 1H), 6.55 (s, 1H), 6.03 (t, 1H), 3.86-3.88 (m, 2H), 3.81 (s, 3H), 3.65-3.67 (m, 2H), 3.49-3.58 (m, 10H), 3.52 (s, 3H), 3.10 (s, 3H), 2.30-2.46 (m, 6H), 1.27 (s, 9H).

LCMS m/z 438 (M+2H)²⁺ (ES⁺)

Example 19

5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)-N,N-dimethylbenzamide

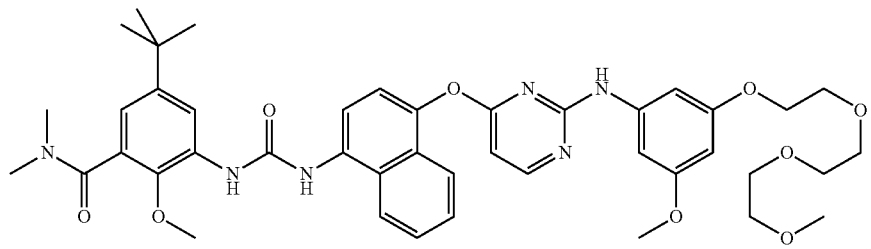 [SMILES: COCCOCCOCCOc1cc(Nc2nccc(Oc3ccc(NC(=O)Nc4cc(C(C)(C)C)cc(C(=O)N(C)C)c4OC)c4ccccc34)n2)cc(OC)c1]

(i) Phenyl (4-((2-((3-methoxy-5-(2-(2-(2-methoxy-ethoxy)ethoxy)ethoxy)phenyl)amino)-pyrimidin-4-yl)oxy)naphthalen-1-yl)carbamate Phenyl chloroformate (125 μL, 0.996 mmol) was added to a stirred solution of 4-((4-aminonaphthalen-1-yl)oxy)-N-(3-methoxy-5-(2-(2-(2-methoxyethoxy)ethoxy)ethoxy)-phenyl)pyrimidin-2-amine (see Example 4(v) above; 500 mg, 0.960 mmol) and NaHCO$_3$ (125 mg, 1.488 mmol) in THF (5 mL) and DCM (5 mL) and the mixture was stirred for 2 h. The mixture was filtered and the solvent evaporated from the filtrate to give a pale brown oil which was stirred in isohexane (20 mL) overnight. The resultant solid was filtered off and dried to afford the sub-title compound (600 mg).

$^1$H NMR (400 MHz, CDCl$_3$) δ 8.30 (d, 1H), 8.12 (d, 1H), 8.03-7.79 (m, 3H), 7.70-7.57 (m, 1H), 7.57-7.48 (m, 1H), 7.48-7.35 (m, 2H), 7.35-7.16 (m, 4H), 7.04 (s, 1H), 6.69-6.54 (m, 1H), 6.47 (d, 1H), 6.41 (s, 1H), 6.05 (t, 1H), 3.79-3.70 (m, 6H), 3.70-3.65 (m, 4H), 3.63 (s, 3H), 3.60-3.52 (m, 2H), 3.35 (s, 3H).

LCMS m/z 641 (M+H)$^+$ (ES$^+$)

(ii) 5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)-N,N-dimethylbenzamide TEA (10 μL, 0.072 mmol) was added to a solution of the product from step (i) above (100 mg, 0.156 mmol) and 3-amino-5-(tert-butyl)-2-methoxy-N,N-dimethylbenzamide (40 mg, 0.160 mmol) in THF (5 mL) and the reaction heated at 50° C. (block temperature) for 16 h. The solvent was evaporated and the crude product was purified by chromatography on silica gel (40 g column, 2% MeOH:DCM to 8%) to afford the title compound (124 mg) as a tan solid.

$^1$H NMR (400 MHz, DMSO-d6) δ 9.41 (d, 2H), 8.89 (s, 1H), 8.51-8.36 (m, 2H), 8.28 (d, 1H), 8.08 (d, 1H), 7.85 (d, 1H), 7.74-7.63 (m, 1H), 7.65-7.52 (m, 1H), 7.42 (d, 1H), 6.94-6.68 (m, 3H), 6.55 (d, 1H), 6.04 (t, 1H), 3.87 (t, 2H), 3.77 (s, 3H), 3.72-3.60 (m, 2H), 3.60-3.45 (m, 9H), 3.45-3.36 (m, 2H), 3.22 (s, 3H), 3.04 (s, 3H), 2.85 (s, 3H), 1.28 (s, 9H).

LCMS m/z 797 (M+H)$^+$ (ES$^+$); 795 (M−H)$^-$ (ES$^-$)

Example 20

5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)benzamide

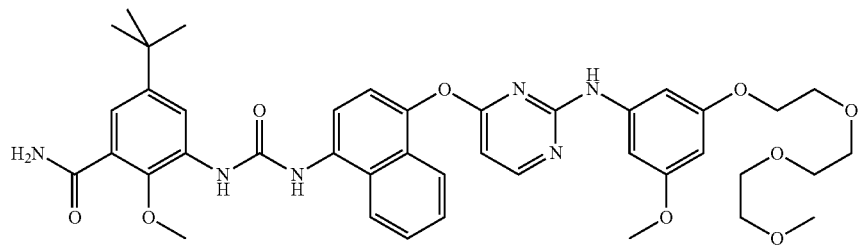 [SMILES: COCCOCCOCCOc1cc(Nc2nccc(Oc3ccc(NC(=O)Nc4cc(C(C)(C)C)cc(C(N)=O)c4OC)c4ccccc34)n2)cc(OC)c1]

TEA (10 μL, 0.072 mmol) was added to a solution of phenyl (4-((2-((3-methoxy-5-(2-(2-(2-methoxyethoxy)ethoxy)ethoxy)phenyl)amino)pyrimidin-4-yl)oxy)naphthalen-1-yl)carbamate (see Example 19(i) above; 100 mg, 0.156 mmol) and 3-amino-5-(tert-butyl)-2-methoxybenzamide (35 mg, 0.157 mmol) in THF (5 mL) and the reaction heated at 50° C. (block temperature) for 16 h. The solvent was evaporated and the crude product was purified by chromatography on silica gel (40 g column, 2% MeOH:DCM to 8%) to afford the title compound (110 mg) as a pale tan solid.

$^1$H NMR (400 MHz, DMSO-d6) δ 9.43 (s, 2H), 8.92 (s, 1H), 8.46 (d, 1H), 8.42 (d, 1H), 8.28 (d, 1H), 8.09 (d, 1H), 7.85 (d, 1H), 7.76-7.64 (m, 2H), 7.64-7.53 (m, 2H), 7.42 (d,

1H), 7.22 (d, 1H), 6.89-6.70 (m, 2H), 6.55 (d, 1H), 6.04 (t, 1H), 3.87 (t, 2H), 3.83 (s, 3H), 3.73-3.62 (m, 2H), 3.61-3.44 (m, 9H), 3.44-3.37 (m, 2H), 3.22 (s, 3H), 1.29 (s, 9H).

LCMS m/z 769 (M+H)⁺ (ES⁺); 767 (M−H)⁻ (ES⁻)

Example 21

5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)benzoic acid

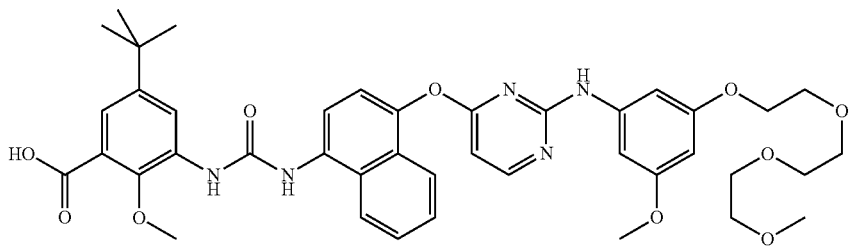 [SMILES: COCCOCCOCCOc1cc(Nc2nccc(Oc3ccc(NC(=O)Nc4cc(C(C)(C)C)cc(C(=O)O)c4OC)c4ccccc34)n2)cc(OC)c1]

(i) 3-Amino-5-(tert-butyl)-2-methoxybenzoic acid

5% Pd—C (50 mg) was added to a solution of 5-(tert-butyl)-2-methoxy-3-nitrobenzoic acid (450 mg, 1.777 mmol) in EtOH (3 mL) and acetic acid (2 drops). The reaction was stirred under hydrogen (5 bar) for 2 h. The catalyst was filtered off and the solvent evaporated to give the sub-title compound (380 mg) as a dark brown foam.

LCMS m/z 224 (M+H)⁺ (ES⁺)

(ii) 5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)benzoic acid TEA (30 µL, 0.215 mmol) was added to a solution of phenyl (4-((2-((3-methoxy-5-(2-(2-(2-methoxyethoxy)ethoxy)ethoxy)phenyl)amino)pyrimidin-4-yl)oxy)naphthalen-1-yl)carbamate (see Example 19(i) above; 100 mg, 0.156 mmol) and the product from step (i) above (50 mg, 0.168 mmol) in THF (5 mL) and the reaction heated at 50° C. (block temperature) for 16 h. The solvent was evaporated and the crude product was purified by chromatography on silica gel (40 g column, 5% MeOH:DCM to 10%). This product was purified by preparative HPLC (Varian, Basic (0.1% Ammonium Bicarbonate), Waters X-Bridge Prep-C18, 5 µm, 19×50 mm column, 25-55% MeCN in Water) to afford the title compound (25 mg) as a pale yellow solid.

¹H NMR (400 MHz, DMSO-d6) δ 9.52 (s, 1H), 9.42 (s, 1H), 8.97 (s, 1H), 8.48 (d, 1H), 8.41 (d, 1H), 8.30 (d, 1H), 8.08 (d, 1H), 7.85 (d, 1H), 7.72-7.63 (m, 1H), 7.63-7.51 (m, 1H), 7.42 (d, 1H), 7.26 (d, 1H), 6.92-6.70 (m, 2H), 6.55 (d, 1H), 6.04 (t, 1H), 3.86 (s, 5H), 3.72-3.62 (m, 2H), 3.57-3.45 (m, 9H), 3.44-3.35 (m, 2H), 3.21 (s, 3H), 1.28 (s, 9H).

LCMS m/z 770 (M+H)⁺ (ES⁺)

Example 22

1-(5-(tert-Butyl)-3-cyano-2-methoxyphenyl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea

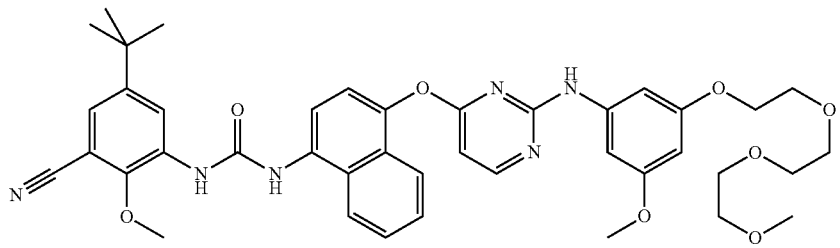 [SMILES: COCCOCCOCCOc1cc(Nc2nccc(Oc3ccc(NC(=O)Nc4cc(C(C)(C)C)cc(C#N)c4OC)c4ccccc34)n2)cc(OC)c1]

TEA (10 µL, 0.072 mmol) was added to a solution of phenyl (4-((2-((3-methoxy-5-(2-(2-(2-methoxyethoxy)ethoxy)ethoxy)phenyl)amino)pyrimidin-4-yl)oxy)naphthalen-1-yl)carbamate (see Example 19(i) above; 100 mg, 0.156 mmol) and 3-amino-5-(tert-butyl)-2-methoxybenzonitrile (35 mg, 0.171 mmol) in THF (5 mL) and the reaction heated at 50° C. (block temperature) for 16 h. The solvent was evaporated and the crude product was purified by chromatography on silica gel (40 g column, 2% MeOH:DCM to 8%). This product was purified by preparative HPLC (Varian, Basic (0.1% Ammonium Bicarbonate), Waters X-Bridge Prep-C18, 5 µm, 19×50 mm column, 35-70% MeCN in Water) to afford the title compound (40 mg) as a pale yellow solid.

¹H NMR (400 MHz, DMSO-d6) δ 9.60-9.29 (m, 2H), 9.08 (s, 1H), 8.71 (d, 1H), 8.42 (d, 1H), 8.27 (d, 1H), 8.07 (d, 1H), 7.86 (d, 1H), 7.76-7.65 (m, 1H), 7.65-7.52 (m, 1H), 7.52-7.30 (m, 2H), 6.93-6.69 (m, 2H), 6.55 (d, 1H), 6.04 (t, 1H), 4.03 (s, 3H), 3.94-3.79 (m, 2H), 3.78-3.60 (m, 2H), 3.60-3.45 (m, 9H), 3.45-3.37 (m, 2H), 3.22 (s, 3H), 1.29 (s, 9H).
LCMS m/z 751 (M+H)⁺ (ES⁺); 749 (M−H)⁻ (ES⁻)

Example 23

3-(tert-Butyl)-5-(3-(4-((2-((3-methoxy-5-(2-(2-(2-methoxyethoxy)ethoxy)ethoxy)phenyl)-amino)pyrimidin-4-yl)oxy)naphthalen-1-yl)ureido)-N-methylbenzamide

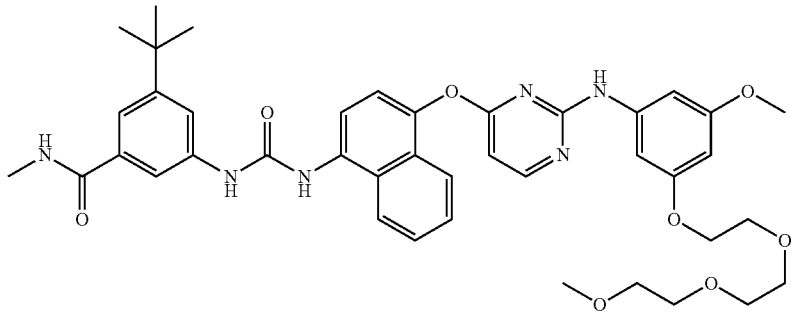 [SMILES: CNC(=O)c1cc(NC(=O)Nc2ccc(Oc3ccnc(Nc4cc(OC)cc(OCCOCCOCCOC)c4)n3)c3ccccc23)cc(C(C)(C)C)c1]

(i) Methyl 3-((tert-butoxycarbonyl)amino)-5-(tert-butyl)benzoate

To a stirred solution of 3-(tert-butyl)-5-(methoxycarbonyl)benzoic acid (2.3 g, 9.73 mmol) and triethylamine (1.628 mL, 11.68 mmol) in dioxane (15 mL) and tBuOH (10 mL, 105 mmol) under N₂ at 0° C. was added DPPA (2.52 mL, 11.68 mmol). The mixture was stirred at rt for 10 minutes then heated to 80° C. for 4 h. The reaction was cooled to rt and diluted with EtOAc (100 mL). The organic phase was washed with 1M HCl aq. (50 mL), water (50 mL), sat. NaHCO₃ aq. (50 mL) and brine (50 mL), then dried (MgSO₄), filtered and concentrated in vacuo onto silica gel. The crude product was purified by chromatography on the Companion (80 g column, 0-25% EtOAc in hexane) to afford the sub-title compound (1.80 g) as a white solid.

¹H NMR (DMSO-d6) 400 MHz, δ: 9.49 (s, 1H), 8.03 (s, 1H), 7.73 (t, 1H), 7.58 (t, 1H), 3.84 (s, 3H), 1.49 (s, 9H), 1.28 (s, 9H).
LCMS m/z 252 (M+H-tBu)⁺ (ES⁺)

(ii) 3-((tert-Butoxycarbonyl)amino)-5-(tert-butyl)benzoic acid

To a stirred solution of the product from step (i) above (1.80 g, 5.09 mmol) in THF (50 mL) and MeOH (10 mL) was added NaOH (2.0 M aq.) (7.6 mL, 15.20 mmol) and the reaction stirred at rt overnight. Additional NaOH (4 mL) was added and stirring continued for 5 h. The organic solvent was removed in vacuo and the resulting aqueous phase washed with Et₂O. The aqueous phase was acidified with 1M HCl and extracted with EtOAc (2×50 mL). The combined organic phases were dried (MgSO₄), filtered and concentrated in vacuo affording a greasy, pale yellow solid. The solid was triturated with hexane and then collected by filtration, washing with more hexane to afford the sub-title compound (1.21 g) as a free-flowing white solid.

¹H NMR (400 MHz; DMSO-d6) δ: 12.84 (s, 1H), 9.44 (s, 1H), 7.98 (s, 1H), 7.72 (s, 1H), 7.58 (s, 1H), 1.49 (s, 9H), 1.28 (s, 9H).
LCMS m/z 238 (M+H-tBu)⁺ (ES⁺); 292 (M−H)⁻ (ES⁻)

(iii) tert-Butyl (3-(tert-butyl)-5-(methylcarbamoyl)phenyl)carbamate

To a stirred solution of methanamine (2.0M in THF) (520 µL, 1.040 mmol), the product from step (ii) above (300 mg, 1.023 mmol) and HATU (514 mg, 1.352 mmol) in DMF (5 mL) was added Hünig's base (725 µL, 4.16 mmol) and the reaction was stirred for 3 h. The reaction was diluted with water (100 mL) and the aqueous phase extracted with EtOAc (2×50 mL). The combined organic phases were washed with water (100 mL) and brine (50 mL) then dried (MgSO₄), filtered and concentrated in vacuo onto silica gel. The crude product was purified by chromatography on the Companion (40 g column, 0-50% EtOAc in hexane) to afford the sub-title compound (220 mg) as a colourless oil.

¹H NMR (DMSO-d6) 400 MHz, δ: 9.35 (s, 1H), 8.32 (q, 1H), 7.78 (s, 1H), 7.58 (s, 1H), 7.43 (s, 1H), 2.77 (d, 3H), 1.48 (s, 9H), 1.28 (s, 9H).
LCMS m/z 307 (M+H)⁺ (ES⁺); 251 (M+H-tBu)⁺ (ES⁺)

(iv) 3-Amino-5-(tert-butyl)-N-methylbenzamide

To a stirred solution of the product from step (iii) above (220 mg, 0.718 mmol) in DCM (15 mL) was added TFA (2 mL, 26.0 mmol) and the reaction stirred at rt for 3 h. The reaction was concentrated in vacuo and the residue re-dissolved in MeOH (1 mL) and loaded onto a pre-conditioned cartridge of SCX resin. The resin was washed with MeOH then the product released in 1% NH₃ in MeOH. The NH₃ solution was concentrated in vacuo affording the sub-title compound (110 mg) as an off-white foam.
LCMS m/z 207 (M+H)⁺ (ES⁺)

(v) 3-(tert-Butyl)-5-(3-(4-((2-((3-methoxy-5-(2-(2-(2-methoxyethoxy)ethoxy)ethoxy)-phenyl)amino)pyrimidin-4-yl)oxy)naphthalen-1-yl)ureido)-N-methylbenzamide Triethylamine (9.0 µL, 0.065 mmol) was added to a mixture of phenyl (4-((2-((3-methoxy-5-(2-(2-(2-methoxyethoxy)ethoxy)ethoxy)phenyl)amino)pyrimidin-4-yl)oxy)naphthalen-1-yl)carbamate above (see Example 19(i) above; 64.4 mg, 0.312 mmol) and the product from step (iv) above (200 mg, 0.312 mmol) in isopropyl acetate (3 mL) and the mixture heated at 60° C. (block temperature) for 1 h. The reaction was diluted with MeOH and concentrated in vacuo onto silica gel. The material was purified by column chromatography on the Companion (12 g column, 1-5% MeOH in DCM) to afford the title compound (97 mg) as an off-white solid.

¹H NMR (400 MHz, DMSO-d6) δ: 9.43 (s, 1H), 9.17 (s, 1H), 8.80 (s, 1H), 8.39-8.42 (m, 2H), 8.20 (d, 1H), 8.05 (d, 1H), 7.85 (d, 1H), 7.80 (s, 1H), 7.66-7.70 (m, 2H), 7.59 (t, 1H), 7.50 (s, 1H), 7.42 (d, 1H), 6.82 (d, 2H), 6.55 (d, 1H), 6.04 (t, 1H), 3.86-3.88 (m, 2H), 3.65-3.67 (m, 2H), 3.48-3.55 (m, 6H), 3.51 (s, 3H), 3.41 (dd, 2H), 3.22 (s, 3H), 2.80 (d, 3H), 1.33 (s, 9H).

LCMS m/z 377 (M+2H)²⁺ (ES⁺)

Example 24

N-(3-(tert-Butyl)-5-(3-(4-((2-((3-methoxy-5-(2-(2-(2-methoxyethoxy)ethoxy)ethoxy)-phenyl)amino)pyrimidin-4-yl)oxy)naphthalen-1-yl)ureido)phenyl)methanesulfonamide

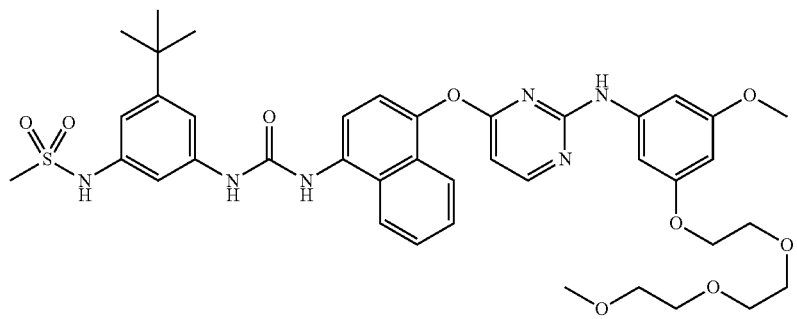 [SMILES: COCCOCCOCCOc1cc(Nc2nccc(Oc3ccc(NC(=O)Nc4cc(NS(C)(=O)=O)cc(C(C)(C)C)c4)c4ccccc34)n2)cc(OC)c1]

(i) Di-tert-butyl (5-(tert-butyl)-1,3-phenylene)dicarbamate

To a stirred solution of 5-(tert-butyl)isophthalic acid (1.0 g, 4.50 mmol) and triethylamine (1.380 mL, 9.90 mmol) in dioxane (15 mL) and tBuOH (10 mL, 105 mmol) under N₂ at 0° C. was added DPPA (2.15 mL, 9.98 mmol). The mixture was stirred at rt for 10 min then heated to 80° C. for 4 h. The reaction was cooled to rt and diluted with EtOAc (100 mL). The organic phase was washed with 1M HCl aq. (50 mL), water (50 mL), sat. NaHCO₃ aq. (50 mL) and brine (50 mL), then dried (MgSO₄), filtered and concentrated in vacuo onto silica gel. The crude product was purified by chromatography on the Companion (40 g column, 0-15% EtOAc in hexane) to afford the sub-title compound (1.01 g) as a white solid.

¹H NMR (400 MHz, DMSO-d6) δ: 9.14 (s, 2H), 7.54 (s, 1H), 7.08 (d, 2H), 1.47 (s, 18H), 1.21 (s, 9H).

LCMS m/z 253 (M+H− 2×tBu)⁺ (ES⁺)

(ii) 5-(tert-Butyl)benzene-1,3-diamine

To a stirred solution of the product from step (i) above (1.01 g, 2.217 mmol) in DCM (40 mL) was added TFA (5 mL, 64.9 mmol) and the reaction stirred at rt overnight. The reaction was concentrated in vacuo and the residue re-dissolved in MeOH (5 ml) and loaded onto a pre-conditioned cartridge of SCX resin. The resin was washed with MeOH then the product released in 1% NH₃ in MeOH. The NH₃ solution was concentrated in vacuo affording the sub-title compound (269 mg) as an off-white foam.

¹H NMR (400 MHz, DMSO-d6) δ: 5.85 (d, 2H), 5.66 (t, 1H), 4.62 (bs, 4H), 1.16 (s, 9H).

LCMS m/z 165 (M+H)⁺ (ES⁺)

(iii) N-(3-Amino-5-(tert-butyl)phenyl)methanesulfonamide

Methanesulfonyl chloride (125 μL, 1.604 mmol) was added dropwise to a stirred solution of the product from step (ii) above (269 mg, 1.638 mmol) and triethylamine (320 μL, 2.293 mmol) in DCM (15 mL) at 0-5° C. The mixture was stirred for 30 minutes, warmed to rt and stirred for an additional 20 h. More triethylamine (0.1 mL) and methanesulfonyl chloride (0.02 mL) were added and stirring continued for 1 h. The mixture was washed with 10% brine (10 mL), dried (MgSO₄), filtered and evaporated under reduced pressure. The crude product was purified by chromatography on silica gel (12 g column, 0-50% EtOAc in hexane) to afford the sub-title compound (258 mg) as a pale brown gum.

LCMS m/z 243 (M+H)⁺ (ES⁺)

(iv) N-(3-(tert-Butyl)-5-(3-(4-((2-((3-methoxy-5-(2-(2-(2-methoxyethoxy)ethoxy)ethoxy)-phenyl)amino)pyrimidin-4-yl)oxy)naphthalen-1-yl)ureido)phenyl)methanesulfonamide Triethylamine (24 μL, 0.172 mmol) was added to a mixture of the product from step (iii) above (258 mg, 0.852 mmol) and phenyl (4-((2-((3-methoxy-5-(2-(2-(2-methoxyethoxy)-ethoxy)ethoxy)phenyl)amino)pyrimidin-4-yl)oxy)naphthalen-1-yl)carbamate (see Example 19(i) above; 545 mg, 0.851 mmol) in isopropyl acetate (6 mL) and the mixture heated at 60° C. (block temperature) for 1 h. The reaction was diluted with THF and concentrated in vacuo onto silica gel. The material was purified by column chromatography on the Companion (40 g column, 1-4% MeOH in DCM) to afford the title compound (372 mg) as a pale orange solid.

¹H NMR (400 MHz, DMSO-d6) δ: 9.66 (s, 1H), 9.42 (s, 1H), 9.14 (s, 1H), 8.75 (s, 1H), 8.42 (d, 1H), 8.19 (d, 1H), 8.06 (d, 1H), 7.85 (d, 1H), 7.67 (t, 1H), 7.59 (t, 1H), 7.41 (d, 1H), 7.37 (s, 1H), 7.29 (s, 1H), 6.90 (s, 1H), 6.82 (d, 2H), 6.55 (d, 1H), 6.04 (t, 1H), 3.86-3.88 (m, 2H), 3.65-3.67 (m, 2H), 3.48-3.56 (m, 6H), 3.52 (s, 3H), 3.41 (dd, 2H), 3.22 (s, 3H), 3.01 (s, 3H), 1.28 (s, 9H).

LCMS m/z 789 (M+H)⁺ (ES⁺); 395 (M+2H)²⁺ (ES⁺)

Example 25

1-(3-Amino-5-(tert-butyl)-2-methoxyphenyl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea

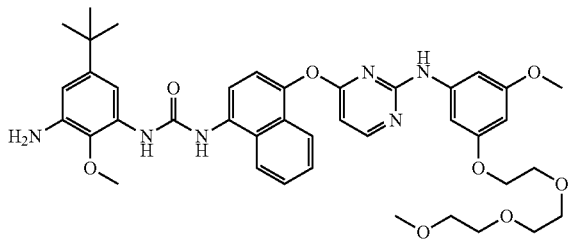 [SMILES: COCCOCCOCCOc1cc(Nc2nccc(Oc3ccc(NC(=O)Nc4cc(C(C)(C)C)cc(N)c4OC)c4ccccc34)n2)cc(OC)c1]

Triethylamine (25 μL, 0.179 mmol) was added to a mixture of 5-(tert-butyl)-2-methoxybenzene-1,3-diamine (150 mg, 0.772 mmol) and phenyl (4-((2-((3-methoxy-5-(2-(2-(2-methoxyethoxy)ethoxy)ethoxy)phenyl)amino)pyrimidin-4-yl)oxy)naphthalen-1-yl)carbamate (see Example 19(i) above; 495 mg, 0.772 mmol) in isopropyl acetate (6 mL) and the mixture heated at 60° C. (block temperature) for 1 h. The reaction was diluted with Et$_2$O and stirred for 15 minutes resulting in the precipitation of a pale solid which was removed by filtration. The filtrate was concentrated in vacuo onto silica gel. The material was purified by column chromatography on the Companion (12 g column, 1-5% MeOH in DCM) to afford the title compound (220 mg) as a pink foam.

$^1$H NMR (400 MHz, DMSO-d6) δ: 9.42 (s, 1H), 9.32 (s, 1H), 8.67 (s, 1H), 8.41 (d, 1H), 8.29 (d, 1H), 8.08 (d, 1H), 7.84 (d, 1H), 7.67 (t, 1H), 7.56-7.60 (m, 2H), 7.40 (d, 1H), 6.82 (d, 2H), 6.54 (d, 1H), 6.43 (d, 1H), 6.04 (t, 1H), 4.81 (s, 2H), 3.86-3.88 (m, 2H), 3.71 (s, 3H), 3.65-3.67 (m, 2H), 3.48-3.56 (m, 6H), 3.52 (s, 3H), 3.41 (dd, 2H), 3.22 (s, 3H), 1.22 (s, 9H).

LCMS m/z 371 (M+2H)$^{2+}$ (ES$^+$)

Example 26

3-(2-(2-(3-((4-((4-(3-(5-(tert-Butyl)-2-methoxy-3-(methylsulfonamido)phenyl)ureido)-naphthalen-1-yl)oxy)pyrimidin-2-yl)amino)-5-methoxybenzamido)ethoxy)ethoxy)-propanoic acid

(i) tert-Butyl 3-(2-(2-(3-amino-5-methoxybenzamido)ethoxy)ethoxy)propanoate

A stirred mixture of 3-amino-5-methoxybenzoic acid (178 mg, 1.066 mmol), tert-butyl 3-(2-(2-aminoethoxy)ethoxy)propanoate (500 mg, 2.132 mmol) and triethylamine (450 μL, 3.23 mmol) in DCM (4 mL) was cooled in an ice-bath. 50 wt % T3P in EtOAc (950 μL, 1.596 mmol) was added, the ice-bath was removed and the reaction mixture allowed to warm to rt and stirred at this temperature for 2 h. The reaction mixture was partitioned between sat. aq. NaHCO$_3$ (20 mL) and DCM (20 mL). The aqueous phase was back extracted with fresh DCM (20 mL). The combined organic extracts were washed with water (40 mL), brine (40 mL), dried (MgSO$_4$), filtered and concentrated in vacuo to afford an oil (496 mg). The crude product was purified by chromatography on silica gel (40 g column, 0-100% EtOAc in isohexane) to afford the sub-title compound (295 mg) as an oil.

$^1$H NMR (400 MHz, DMSO-d6) δ: 8.19 (t, 1H), 6.62 (t, 1H), 6.53-6.52 (m, 1H), 6.25 (t, 1H), 5.22 (s, 2H), 3.69 (s, 3H), 3.58 (t, 2H), 3.53-3.47 (m, 6H), 3.34 (q, 2H), 2.40 (t, 2H), 1.39 (s, 9H).

LCMS m/z 383 (M+H)$^+$ (ES$^+$)

(ii) tert-Butyl 3-(2-(2-(3-((4-((4-(3-(5-(tert-butyl)-2-methoxy-3-(methylsulfonamido)phenyl)-ureido)naphthalen-1-yl)oxy)pyrimidin-2-yl)amino)-5-methoxybenzamido)ethoxy)ethoxy)-propanoate To a stirred solution of N-(5-(tert-butyl)-3-(3-(4-((2-chloropyrimidin-4-yl)oxy)naphthalen-1-yl)ureido)-2-methoxyphenyl)methanesulfonamide (see Example 7(i) above; 200 mg, 0.333 mmol) and the product from step (i) above (191 mg, 0.500 mmol) in DMF (9 mL) was added pTSA (32 mg, 0.168 mmol). The resulting mixture was heated at 60° C. overnight. The reaction was cooled to rt and partitioned between sat. aq. NaHCO$_3$ (40 mL) and EtOAc (50 mL). A white solid crashed out in the aqueous layer. Water (50 mL) was added and the layers separated. The aqueous layer was back extracted with EtOAc (50 mL). The combined organic extracts were washed with water (50 mL), brine (50 mL), dried (MgSO$_4$), filtered and concentrated in vacuo to afford an oil. The crude product was purified by chromatography on silica gel (40 g column, 0-5% MeOH in EtOAc) to afford the sub-title compound (185 mg) as an oil.

$^1$H NMR (400 MHz, DMSO-d6) δ: 9.59 (s, 1H), 9.34 (s, 1H), 9.12 (s, 1H), 8.91 (s, 1H), 8.41 (d, 1H), 8.29-8.26 (m, 2H), 8.20-8.17 (m, 1H), 8.09 (d, 1H), 7.85-7.83 (m, 1H), 7.69-7.65 (m, 1H), 7.60-7.56 (m, 2H), 7.42 (d, 1H), 7.34 (s, 1H), 7.02 (d, 1H), 6.88-6.87 (m, 1H), 6.54-6.52 (m, 1H), 3.80 (s, 3H), 3.60-3.54 (m, 5H), 3.53-3.46 (m, 6H), 3.38-3.33 (m, 2H), 3.09 (s, 3H), 2.38 (t, 2H), 1.36 (s, 9H), 1.26 (s, 9H).

LCMS m/z 459 (M+2H)$^{2+}$ (ES$^+$)

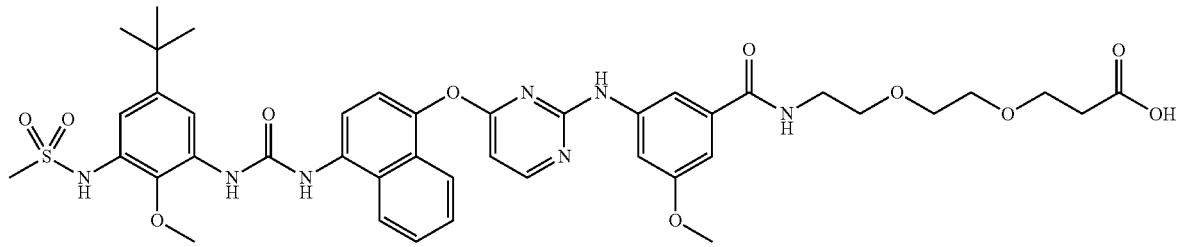 [SMILES: COc1cc(Nc2nccc(Oc3ccc(NC(=O)Nc4cc(C(C)(C)C)cc(NS(C)(=O)=O)c4OC)c4ccccc34)n2)cc(C(=O)NCCOCCOCCC(=O)O)c1]

(iii) 3-(2-(2-(3-((4-((4-(3-(5-(tert-Butyl)-2-methoxy-3-(methylsulfonamido)phenyl)ureido)-naphthalen-1-yl)oxy)pyrimidin-2-yl)amino)-5-methoxybenzamido)ethoxy)ethoxy)-propanoic acid TFA (600 µL, 7.79 mmol) was added to a stirred solution of the product from step (ii) above (179 mg, 0.156 mmol) in DCM (2 mL). The reaction mixture was stirred at rt for 1 h. The solvent was removed in vacuo and the resulting oil dissolved in the minimum of MeOH and loaded onto a SCX column. The column was eluted with MeOH then 1% $NH_3$ in MeOH. The product containing fraction was concentrated in vacuo, then purified by chromatography on silica gel (40 g column, 0-10% MeOH in DCM) to afford a colourless glass. The glass was triturated with diethyl ether, filtered and dried to afford the title compound (31 mg) as a white solid.

$^1$H NMR (400 MHz, DMSO-d6) δ: 12.13 (s, 1H), 9.59 (s, 1H), 9.35 (s, 1H), 9.12 (s, 1H), 8.91 (s, 1H), 8.41 (d, 1H), 8.31-8.26 (m, 2H), 8.18 (d, 1H), 8.09 (d, 1H), 7.84 (d, 1H), 7.69-7.65 (m, 1H), 7.60-7.56 (m, 2H), 7.42 (d, 1H), 7.34 (s, 1H), 7.02 (d, 1H), 6.88 (s, 1H), 6.53 (d, 1H), 3.80 (s, 3H), 3.59-3.56 (m, 5H), 3.52-3.46 (m, 6H), 3.38-3.34 (m, 2H), 3.09 (s, 3H), 2.41 (t, 2H), 1.26 (s, 9H).

LCMS m/z 860 (M+H)$^+$ (ES$^+$); 858 (M–H)$^-$ (ES$^-$)

Example 27

3-((4-((4-(3-(5-(tert-Butyl)-2-methoxy-3-(methylsulfonamido)phenyl)ureido)naphthalen-1-yl)oxy)pyridin-2-yl)amino)-5-methoxy-N-(2-morpholinoethyl)benzamide

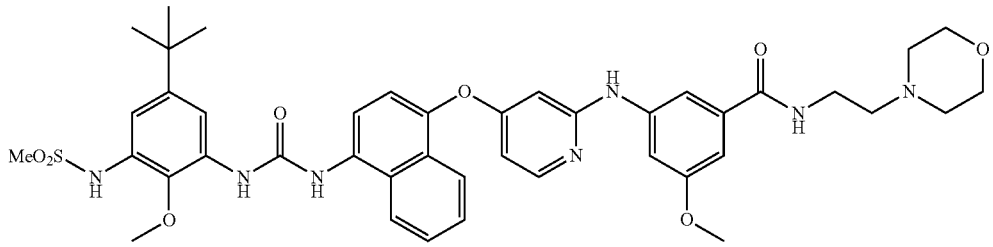 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCCN2CCOCC2)c1]

(i)
3-Amino-5-methoxy-N-(2-morpholinoethyl)benzamide

To a stirred mixture of 3-amino-5-methoxybenzoic acid (5.20 g, 31.1 mmol), Et$_3$N (4.50 mL, 32.3 mmol) and 2-morpholinoethanamine (4.23 mL, 32.3 mmol) in THF (150 mL) and DMF (4 mL) was added HATU (14.72 g, 38.7 mmol) and the reaction stirred at ambient temperature overnight. After this time the mixture was taken up in ethyl acetate (300 mL) and washed with sat NaHCO$_3$ (aq) (2×100 mL). The aqueous was back extracted with further ethyl acetate (4×50 mL) and organics combined, dried over MgSO$_4$, filtered and concentrated under reduced pressure. Trituration with isohexanes (100 mL) afforded a pale orange gum (15 g). The crude product was purified by chromatography on the Companion (220 g column, 0-60% IPA in DCM). Fractions were combined as two separate batches to afford the sub-title compound as two separate batches (2.48 g and 2.87 g) as orange solids.

$^1$H NMR (400 MHz; CDCl$_3$) δ: 6.69-6.64 (m, 3H), 6.35 (t, 1H), 3.81 (br.s, 2H), 3.81 (s, 3H), 3.73 (m, 4H), 3.53 (dd, 2H), 2.62-2.57 (m, 2H), 2.53-2.49 (m, 4H).

LCMS m/z 280 (M+H)$^+$ (ES$^+$)

The first batch (2.0 g) was recrystallised in acetonitrile (18 mL) to yield the sub-title compound (1.70 g) as a white solid which was used in the next step.

(ii) tert-Butyl (4-((2-((3-methoxy-5-((2-morpholinoethyl)carbamoyl)phenyl)amino)pyridin-4-yl)oxy)naphthalen-1-yl)carbamate Pd$_2$dba$_3$ (123 mg, 0.135 mmol) and BINAP (168 mg, 0.270 mmol) were stirred in 1,4-dioxane (5 mL) for 10 min under N$_2$. In a separate vessel, purged with N$_2$, caesium carbonate (1318 mg, 4.04 mmol), the product from step (i) above (753 mg, 2.70 mmol) and tert-butyl (4-((2-chloropyridin-4-yl)oxy)naphthalen-1-yl)carbamate (see Example 3(ii) above; 1000 mg, 2.70 mmol) were stirred in 1,4-dioxane (10 mL). The catalyst solution was added to the main reaction mixture and the whole was heated to 90° C. for 18 h. Upon cooling, the mixture was diluted with water (80 mL) and extracted with ethyl acetate (3×75 mL). The combined organic phases were washed with saturated brine (75 mL), dried (MgSO$_4$) and concentrated under reduced pressure. The crude product was purified by chromatography on the Companion (80 g column, 0-10% MeOH(10% NH$_3$)/DCM) to afford the sub-title compound (750 mg) as a tan glass.

LCMS m/z 614 (M+H)$^+$ (ES$^+$); 612 (M–H)$^-$ (ES$^-$)

(iii) 3-((4-((4-Aminonaphthalen-1-yl)oxy)pyridin-2-yl)amino)-5-methoxy-N-(2-morpholinoethyl)benzamide A solution of the product from step (ii) above (750 mg, 1.222 mmol) in isopropanol (2 mL) was added to a 4 M HCl solution (10 mL) at rt and stirred for 1 h. The mixture was basified with saturated Na$_2$CO$_3$ solution (30 mL) and extracted with ethyl acetate (3×50 mL). The combined organic phases were washed with saturated brine (50 mL), dried (MgSO$_4$) and concentrated under reduced pressure. The resulting brown oil was triturated in diethyl ether (25 mL) and collected by filtration to yield the sub-title compound (490 mg) as a cream solid.

LCMS m/z 514 (M+H)$^+$ (ES$^+$)

(iv) 3-((4-((4-(3-(5-(tert-Butyl)-2-methoxy-3-(methylsulfonamido)phenyl)ureido)-naphthalen-1-yl)oxy)pyridin-2-yl)amino)-5-methoxy-N-(2-morpholinoethyl)benzamide Triethylamine (5 µL, 0.036 mmol) was added to a mixture of phenyl (5-(tert-butyl)-2-methoxy-3-(methylsulfonamido)phenyl)carbamate (see Example 1(vi) above; 75 mg, 0.191 mmol) and the product from step (iii) above (82 mg, 0.159 mmol) in isopropyl acetate (5 mL) and the mixture heated at 50° C. (block temperature) for 48 h. The mixture was concentrated under reduced pressure onto loose silica gel.

The silicate was purified by chromatography on silica gel (80 g column, EtOAc) to afford a colourless glass. The glass was purified by preparative HPLC (Gilson, Acidic (0.1% Formic acid), Acidic, Waters X-Select Prep-C18, 5 μm, 19×50 mm column, 10-60% MeCN in Water) to afford a colourless glass. The glass was redissolved in EtOAc (40 mL) and washed with NaHCO$_3$ solution (40 mL), saturated brine (40 mL), dried (MgSO$_4$) and concentrated under reduced pressure to yield the title compound (55 mg) as a tan glass.

$^1$H NMR (400 MHz, DMSO-d6) δ: 9.38 (s, 1H), 9.14 (s, 1H), 9.05 (s, 1H), 8.91 (s, 1H), 8.33-8.27 (d, 1H), 8.26-8.20 (m, 1H), 8.19 (d, 1H), 8.14-8.08 (m, 2H), 7.91-7.81 (m, 1H), 7.74-7.67 (m, 1H), 7.67-7.58 (m, 1H), 7.56 (dd, 1H), 7.51 (dd, 1H), 7.39 (d, 1H), 7.02 (d, 1H), 6.85 (dd, 1H), 6.58 (dd, 1H), 6.13 (d, 1H), 3.81 (s, 3H), 3.75 (s, 3H), 3.60-3.53 (m, 4H), 3.39-3.32 (m, 2H), 3.10 (s, 3H), 2.48-2.35 (m, 6H), 1.27 (s, 9H).

LCMS m/z 812 (M+H)$^+$ (ES$^+$); 810 (M−H)$^-$ (ES$^-$)

Example 28

1-(5-(tert-Butyl)-2-methoxy-3-(pyrimidin-2-ylamino)phenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea

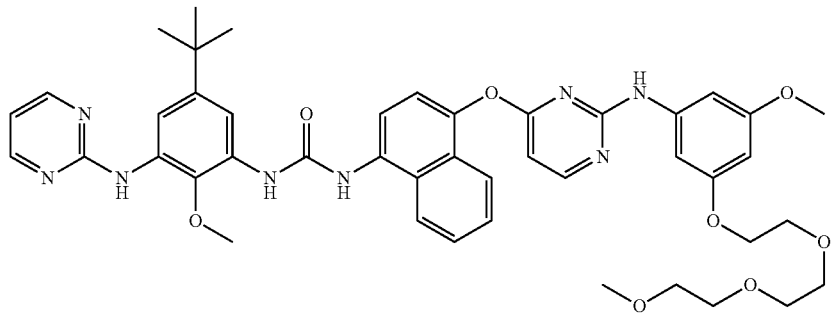 [SMILES: COCCOCCOCCOc1cc(Nc2nccc(Oc3ccc(NC(=O)Nc4cc(C(C)(C)C)cc(Nc5ncccn5)c4OC)c4ccccc34)n2)cc(OC)c1]

A suspension of 1-(3-amino-5-(tert-butyl)-2-methoxyphenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea (see Example 25 above; 100 mg, 0.135 mmol), 2-chloropyrimidine (16 mg, 0.140 mmol) and p-TSA monohydrate (52 mg, 0.273 mmol) in THF/DMF (3 mL, 1:2) was heated at 70° C. for overnight, then at 60° C. for 4 days. The reaction was cooled to rt and combined with a similar 50 mg reaction. The combined mixture was partitioned between EtOAc (40 mL) and sat. aq. NaHCO$_3$ (30 mL). The aqueous layer was extracted with EtOAc (2×40 mL). The combined organic extracts were washed with water (2×50 mL), brine (2×50 mL), dried (MgSO$_4$), filtered and concentrated in vacuo. The crude product was purified by chromatography on silica gel (40 g column, 1-5% MeOH/DCM) to afford a pink solid. The crude product was further purified by chromatography on the silica gel (40 g column, 100% EtOAc) to afford the title compound (38 mg) as a pink solid.

$^1$H NMR (400 MHz; DMSO-d6) δ: 9.43 (s, 1H), 9.34 (s, 1H), 8.89 (s, 1H), 8.49 (s, 1H), 8.46 (d, 2H), 8.42 (d, 1H), 8.29 (d, 1H), 8.11-8.13 (m, 2H), 7.85 (d, 1H), 7.68 (t, 1H), 7.57-7.61 (m, 2H), 7.42 (d, 1H), 6.81-6.84 (m, 3H), 6.55 (d, 1H), 6.04 (t, 1H), 3.86-3.88 (m, 2H), 3.75 (s, 3H), 3.65-3.67 (m, 2H), 3.48-3.56 (m, 6H), 3.52 (s, 3H), 3.41 (dd, 2H), 3.21 (s, 3H), 1.29 (s, 9H).

LCMS m/z 410 (M+2H)$^{2+}$ (ES$^+$)

Example 29

5-(tert-Butyl)-2-methoxy-3-(3-(4-((2-((3-methoxy-5-(2-(2-(2-methoxyethoxy)ethoxy)-ethoxy)phenyl)amino)pyridin-4-yl)oxy)naphthalen-1-yl)ureido)-N-methylbenzamide

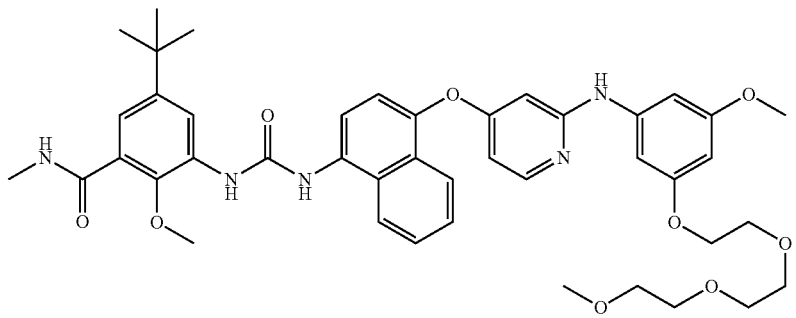 [SMILES: CNC(=O)c1cc(C(C)(C)C)cc(NC(=O)Nc2ccc(Oc3ccnc(Nc4cc(OC)cc(OCCOCCOCCOC)c4)c3)c3ccccc23)c1OC]

Phenyl (5-(tert-butyl)-2-methoxy-3-(methylcarbamoyl)phenyl)carbamate (see Example 9(i) above; 107 mg, 0.301 mmol), 4-((4-aminonaphthalen-1-yl)oxy)-N-(3-methoxy-5-

(2-(2-(2-methoxyethoxy)ethoxy)ethoxy)phenyl)pyridin-2-amine (see Example 11(ii) above; 125 mg, 0.241 mmol) and Et₃N (33.5 μL, 0.241 mmol) were heated to 50° C. in THF (5 mL) overnight. The mixture was concentrated under reduced pressure and purified by chromatography on the Companion (40 g column, 1-5% MeOH/DCM) to afford a white foam. The foam was further purified by preparative HPLC (Gilson, Acidic (0.1% Formic acid), Acidic, Waters X-Select Prep-C18, 5 μm, 19×50 mm column, 25-80 MeCN in Water). Fractions were combined, concentrated to remove acetonitrile, and diluted with saturated NaHCO₃ solution (50 mL). The product was extracted with ethyl acetate (3×50 mL) and the organic phases were washed with saturated brine (50 mL), dried (MgSO₄) and concentrated under reduced pressure to afford the title compound (100 mg) as a tan glass.

¹H NMR (400 MHz, DMSO-d6) δ: 9.47 (s, 1H), 8.89 (s, 2H), 8.44 (d, 1H), 8.30 (d, 1H), 8.18 (q, 1H), 8.11 (d, 1H), 8.09 (d, 1H), 7.87 (d, 1H), 7.71 (ddd, 1H), 7.61 (ddd, 1H), 7.39 (d, 1H), 7.11 (d, 1H), 6.91 (dd, 1H), 6.79 (dd, 1H), 6.57 (dd, 1H), 6.09 (d, 1H), 6.04 (dd, 1H), 4.01-3.94 (m, 2H), 3.80 (s, 3H), 3.74-3.68 (m, 2H), 3.66 (s, 3H), 3.60-3.55 (m, 2H), 3.55-3.48 (m, 4H), 3.45-3.39 (m, 2H), 3.23 (s, 3H), 2.82 (d, 3H), 1.29 (s, 9H).

LCMS m/z 782 (M+H)⁺ (ES⁺); 780 (M−H)⁻ (ES⁻)

Example 30

3-(2-(2-(3-((4-((4-(3-(5-(tert-Butyl)-2-methoxy-3-(methylsulfonamido)phenyl)ureido)-naphthalen-1-yl)oxy)pyrimidin-2-yl)amino)-5-methoxyphenoxy)ethoxy)ethoxy)propanoic acid mmol) was added, followed by a solution of NH₄Cl (855 mg, 15.98 mmol) in water (7 mL). The resulting suspension was heated at 80° C. for 1 h. The reaction was cooled to rt and filtered. The filtrate was concentrated in vacuo, diluted with water (40 mL) then partitioned between sat. aq. NaHCO₃ (40 mL) and EtOAc (60 mL). The aqueous phase was back extracted with EtOAc (50 mL). The combined organic extracts were washed with water (50 mL), brine (50 mL), dried (MgSO₄), filtered and concentrated in vacuo to afford an orange oil. The crude product was dissolved in the minimum of MeOH and loaded onto SCX. The column was eluted with MeOH (3 column volumes) followed by 1% NH₃ in MeOH (3 column volumes). The product containing portion was concentrated in vacuo to afford the sub-title compound (422 mg) as a brown oil.

¹H NMR (400 MHz, DMSO-d6) δ: 5.75-5.73 (m, 2H), 5.67 (t, 1H), 5.04 (s, 2H), 3.94-3.91 (m, 2H), 3.68-3.66 (m, 2H), 3.62-3.58 (m, 5H), 3.57-3.54 (m, 2H), 3.52-3.49 (m, 2H), 2.42 (t, 2H), 1.39 (t, 9H).

LCMS m/z 356 (M+H)⁺ (ES⁺)

(iii) tert-Butyl 3-(2-(2-(3-((4-((4-(3-(5-(tert-butyl)-2-methoxy-3-(methylsulfonamido)phenyl)-ureido)naphthalen-1-yl)oxy)pyrimidin-2-yl)amino)-5-methoxyphenoxy)ethoxy)ethoxy)-propanoate To a stirred solution of N-(5-(tert-butyl)-3-(3-(4-((2-chloropyrimidin-4-yl)oxy)naphthalen-1-yl)ureido)-2-methoxy-

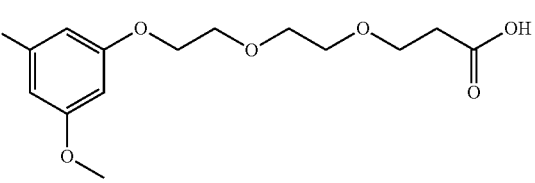

(i) tert-Butyl 3-(2-(2-(3-Methoxy-5-nitrophenoxy)ethoxy)ethoxy)propanoate

DIAD (730 μL, 3.60 mmol) was added dropwise to a stirred solution of 3-methoxy-5-nitrophenol (510 mg, 2.99 mmol), tert-butyl 3-(2-(2-hydroxyethoxy)ethoxy)propanoate (700 mg, 2.99 mmol) and triphenylphosphine (950 mg, 3.59 mmol) in THF (4 mL) at 0-5° C. The reaction was allowed to warm to rt and stirred at this temperature overnight. The reaction mixture was concentrated in vacuo. The crude product was purified by chromatography on silica gel (80 g column, 0-100% EtOAc in isohexane) to afford the sub-title compound (1.13 g) as a yellow oil, which solidified on standing. The product was used in the next without further purification.

¹H NMR (400 MHz, DMSO-d6) δ: 7.34-7.32 (m, 2H), 6.98 (t, 1H), 4.21-4.19 (m, 2H), 3.85 (s, 3H), 3.76-3.74 (m, 2H), 3.60-3.56 (m, 4H), 3.52-3.50 (m, 2H), 2.40 (t, 2H), 1.38 (s, 9H). 42 wt % Hydrazine by-product present (ii) tert-Butyl 3-(2-(2-(3-amino-5-methoxyphenoxy)ethoxy)ethoxy)propanoate The product from step (i) above (1.10 g, 1.598 mmol) was dissolved in EtOH (15 mL) and Fe powder (895 mg, 16.03 phenyl)methanesulfonamide (see Example 7(i) above; 204 mg, 0.340 mmol) and the product from step (ii) above (185 mg, 0.510 mmol) in DMF (9 mL) was added p-TSA monohydrate (32 mg, 0.168 mmol). The reaction mixture was stirred at 60° C. for 48 h. The reaction was cooled to rt, diluted with water (40 mL), then partitioned between sat. aq. NaHCO₃ (40 mL) and EtOAc (50 mL). The organic phase was washed with water (2×50 mL), brine (50 mL), dried (MgSO₄), filtered and concentrated in vacuo to afford a foam. The crude product was purified by chromatography on silica gel (40 g column, 0-100% EtOAc in isohexane) to afford the sub-title compound (180 mg) as a beige foam.

¹H NMR (400 MHz, DMSO-d6) δ: 9.41 (s, 1H), 9.34 (s, 1H), 9.13 (s, 1H), 8.91 (s, 1H), 8.41 (d, 1H), 8.27 (d, 1H), 8.19 (d, 1H), 8.10 (d, 1H), 7.85-7.83 (m, 1H), 7.69-7.65 (m, 1H), 7.60-7.56 (m, 1H), 7.41 (d, 1H), 7.02 (d, 1H), 6.83-6.78 (br m, 2H), 6.54 (d, 1H), 6.02 (t, 1H), 3.87-3.84 (m, 2H), 3.80 (s, 3H), 3.66-3.64 (m, 2H), 3.56 (t, 2H), 3.54-3.45 (m, 7H), 3.09 (s, 3H), 2.39 (t, 2H), 1.36 (s, 9H), 1.26 (s, 9H).

(iv) 3-(2-(2-(3-((4-((4-(3-(5-(tert-Butyl)-2-methoxy-3-(methylsulfonamido)phenyl)ureido)-naphthalen-1-yl)oxy)pyrimidin-2-yl)amino)-5-methoxyphenoxy)ethoxy)ethoxy)propanoic acid TFA (698 μL, 9.06 mmol) was added to a stirred solution of the product from step (iii) above (179 mg, 0.181 mmol) in DCM (2 mL). The reaction mixture was stirred at rt for 1 h. The solvent was removed in vacuo and the resulting oil dissolved in the minimum of MeOH and loaded onto an SCX column. The column was eluted with MeOH (3 column volumes), then 1% $NH_3$ in MeOH (3 column volumes). Formation of some of the methyl ester occurred. The crude product was dissolved in THF (5 mL) and water (1 mL), 2M NaOH (0.5 mL) added and stirred for 4 h. The mixture was acidified to pH 2 with 1M HCl then extracted with EtOAc (40 mL). The organic layer was washed with water (10 mL), dried ($MgSO_4$), filtered and evaporated under reduced pressure. The crude product was purified by chromatography on silica gel (12 g column, 0-10% MeOH/DCM) to give a solid that was triturated with 5% MeOH/DCM (5 mL), the solid filtered, washed with MeCN (5 mL) and DCM (5 mL) to afford the title compound (47 mg) as an off white solid.

$^1$H NMR (DMSO-d6) 400 MHz, δ: 12.08 (s, 1H), 9.35 (s, 1H), 9.28 (s, 1H), 9.07 (brs, 1H), 8.85 (s, 1H), 8.34 (d, 1H), 8.20 (d, 1H), 8.11 (s, 1H), 8.03 (d, 1H), 7.77 (d, 1H), 7.62-7.58 (m, 1H), 7.53-7.50 (m, 1H), 7.34 (d, 1H), 6.96 (s, 1H), 6.74 (s, 2H), 6.47 (d, 1H), 5.96 (s, 1H), 3.80-3.78 (m, 2H), 3.74 (s, 3H), 3.59-3.57 (m, 2H), 3.51 (t, 2H), 3.47-3.40 (m, 7H), 3.03 (s, 3H), 2.35 (t, 2H), 1.20 (s, 9H).

LCMS m/z 833 (M+H)$^+$ (ES$^+$); 831 (M−H)$^−$ (ES$^−$)

Example 31

3-(2-(3-((4-((4-(3-(5-(tert-Butyl)-2-methoxy-3-(methylsulfonamido)phenyl)ureido)-naphthalen-1-yl)oxy)pyrimidin-2-yl)amino)-5-methoxyphenoxy)ethoxy)propanoic acid

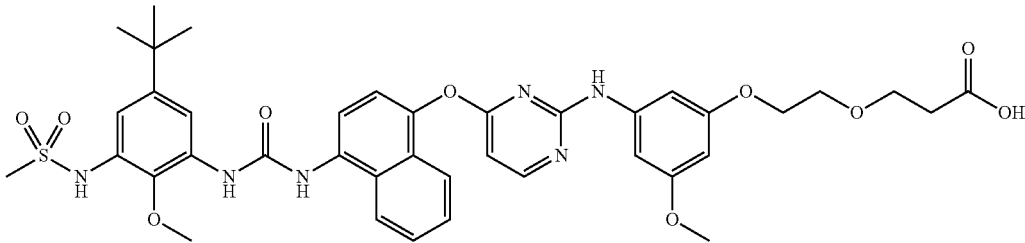 [SMILES: COc1cc(Nc2nccc(Oc3ccc(NC(=O)Nc4cc(C(C)(C)C)cc(NS(C)(=O)=O)c4OC)c4ccccc34)n2)cc(OCCOCCC(=O)O)c1]

The title compound was prepared using the method of Example 30 above to afford the product (53 mg) as an off white solid.

$^1$H NMR (DMSO-d6) 400 MHz, δ: 9.36 (s, 1H), 9.29 (s, 1H), 9.06 (s, 1H), 8.85 (s, 1H), 8.34 (d, 1H), 8.21 (d, 1H), 8.11 (s, 1H), 8.03 (d, 1H), 7.78 (d, 1H), 7.62-7.58 (m, 1H), 7.54-7.50 (m, 1H), 7.34 (d, 1H), 6.96 (s, 1H), 6.74 (s, 2H), 6.48 (d, 1H), 5.96 (s, 1H), 3.80-3.77 (m, 2H), 3.74 (s, 3H), 3.58-3.55 (m, 4H), 3.44 (s, 3H), 3.03 (s, 3H), 2.37 (t, 2H), 1.20 (s, 9H).

LCMS m/z 789 (M+H)$^+$ (ES$^+$); 787 (M−H)$^−$ (ES$^−$)

Example 32

2-Methoxy-3-(3-(4-((2-((3-methoxy-5-(2-(2-(2-methoxyethoxy)ethoxy)ethoxy)phenyl)-amino)pyrimidin-4-yl)oxy)naphthalen-1-yl)ureido)-N-methyl-5-morpholinobenzamide

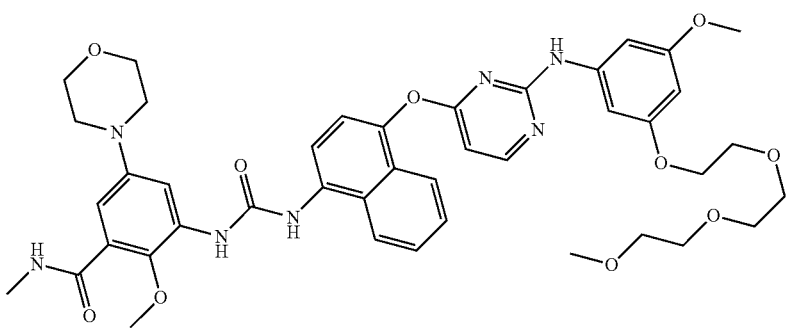 [SMILES: CNC(=O)c1cc(N2CCOCC2)cc(NC(=O)Nc2ccc(Oc3ccnc(Nc4cc(OC)cc(OCCOCCOCCOC)c4)n3)c3ccccc23)c1OC]

(i) Methyl 2-methoxy-5-morpholino-3-nitrobenzoate

A degassed solution of Pd$_2$(dba)$_3$ (170 mg, 0.186 mmol) and BINAP (240 mg, 0.385 mmol) was added to a degassed suspension of methyl 5-bromo-2-methoxy-3-nitrobenzoate (1680 mg, 3.82 mmol), morpholine (500 μL, 5.73 mmol) and Cs$_2$CO$_3$ (1900 mg, 5.83 mmol) and heated to 90° C. for 48 h. The mixture was diluted with water (100 mL) and extracted with ethyl acetate (3×100 mL). The combined organic phases were washed with saturated brine (100 mL), dried (MgSO$_4$) and concentrated under reduced pressure. The crude product was purified by chromatography on the Companion (80 g column, 0-50% EtOAc/isohexanes) to afford a waxy yellow solid. Diethyl ether (50 mL) was added and the resulting solid was removed by filtration. The filtrate was concentrated under reduced pressure to yield the sub-title compound (389 mg) as a yellow solid.

LCMS m/z 297 (M+H)$^+$ (ES$^+$)

(ii) 2-Methoxy-N-methyl-5-morpholino-3-nitrobenzamide

The product from step (i) above (340 mg, 1.148 mmol) and 40% aqueous methanamine solution (5 mL, 64.4 mmol) were heated to 50° C. in ethanol in a sealed tube overnight. The mixture was co-evaporated with toluene (150 mL) and the residue was absorbed onto silica gel. The silicate was purified by chromatography on the Companion (4 g column, 0-50% EtOAc/isohexanes) to afford the sub-title compound (210 mg) as a yellow solid.

$^1$H NMR (400 MHz, DMSO-d6) δ: 8.40-8.27 (m, 1H), 7.44 (d, 1H), 7.27 (d, 1H), 3.75 (s, 3H), 3.75-3.67 (m, 4H), 3.21-3.13 (m, 4H), 2.78 (d, 3H).
LCMS m/z 296 (M+H)$^+$ (ES$^+$)

(iii) 3-Amino-2-methoxy-N-methyl-5-morpholinobenzamide

A suspension of the product from step (ii) above (100 mg, 0.339 mmol) and Pd/C (36.0 mg) in ethanol (2 mL) was stirred at rt under a balloon of hydrogen for 18 h. Repeated in duplicate. The combined reaction suspensions were filtered and the filtrate was concentrated under reduced pressure. The crude product was purified by chromatography on the Companion (12 g column, 0-5% MeOH/DCM) to afford the sub-title compound (159 mg) as a brown oil.

LCMS m/z 266 (M+H)$^+$ (ES$^+$)

(iv) 2-Methoxy-3-(3-(4-((2-((3-methoxy-5-(2-(2-(2-methoxyethoxy)ethoxy)ethoxy)phenyl)-amino)pyrimidin-4-yl)oxy)naphthalen-1-yl)ureido)-N-methyl-5-morpholinobenzamide Triethylamine (10 μL, 0.072 mmol) was added to a mixture of the product from step (iii) above (70 mg, 0.264 mmol) and phenyl (4-((2-((3-methoxy-5-(2-(2-(2-methoxy-ethoxy)-ethoxy)ethoxy)phenyl)amino)pyrimidin-4-yl)oxy)naphthalen-1-yl)carbamate (see Example 19(i) above; 125 mg, 0.195 mmol) in isopropyl acetate (3 mL) and the mixture heated at 60° C. (block temperature) for 18 h. The mixture was diluted with ethyl acetate (30 mL) and washed with water (10 mL), saturated NaHCO$_3$ solution (10 mL), saturated brine (10 mL), dried (MgSO$_4$) and concentrated under reduced pressure. The residue was purified by preparative HPLC (Gilson, Acidic (0.1% Formic acid), Acidic, Waters X-Select Prep-C18, 5 μm, 19×50 mm column, 30-70 MeCN in Water) to afford the title compound (61 mg) as a tan glass.

$^1$H NMR (400 MHz, DMSO-d6) δ: 9.47 (s, 1H), 9.45 (s, 1H), 8.89 (s, 1H), 8.41 (d, 1H), 8.28 (d, 1H), 8.17 (q, 1H), 8.08 (d, 1H), 8.07 (s, 1H), 7.85 (d, 1H), 7.68 (ddd, 1H), 7.59 (ddd, 1H), 7.42 (d, 1H), 6.86-6.74 (m, 2H), 6.67 (d, 1H), 6.54 (d, 1H), 6.03 (dd, 1H), 3.90-3.81 (m, 2H), 3.80-3.70 (m, 4H), 3.76 (s, 3H), 3.69-3.61 (m, 2H), 3.58-3.45 (m, 6H), 3.50 (s, 3H), 3.44-0.3.38 (m, 2H), 3.22 (s, 3H), 3.09-2.99 (m, 4H), 2.81 (d, 3H).
LCMS m/z 812 (M+H)$^+$ (ES$^+$); 810 (M–H)$^-$ (ES$^-$)

Example 33

5-(tert-Butyl)-N-cyclopropyl-2-methoxy-3-(3-(4-((2-((3-methoxy-5-(2-(2-(2-methoxy-ethoxy)ethoxy)ethoxy)phenyl)amino)pyrimidin-4-yl)oxy)naphthalen-1-yl)ureido)-benzamide

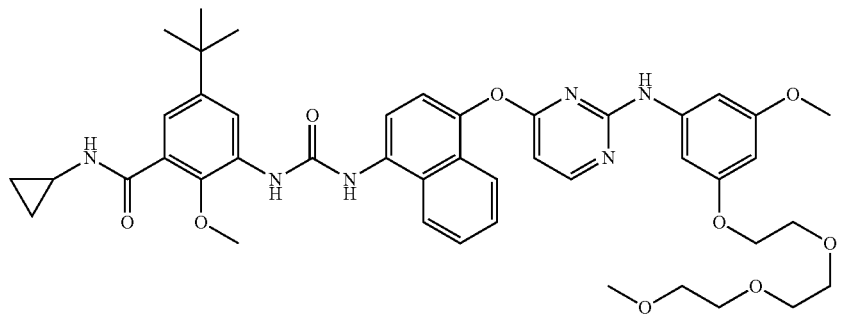 [SMILES: COCCOCCOCCOc1cc(Nc2nccc(Oc3ccc(NC(=O)Nc4cc(C(C)(C)C)cc(C(=O)NC5CC5)c4OC)c4ccccc34)n2)cc(OC)c1]

(i) Methyl 5-(tert-butyl)-2-methoxy-3-(3-(4-((2-((3-methoxy-5-(2-(2-(2-methoxyethoxy)-ethoxy)ethoxy)phenyl)amino)pyrimidin-4-yl)oxy)naphthalen-1-yl)ureido)benzoate Triethylamine (45 μL, 0.323 mmol) was added to a mixture of methyl 3-amino-5-(tert-butyl)-2-methoxybenzoate (370 mg, 1.561 mmol) and phenyl (4-((2-((3-methoxy-5-(2-(2-(2-methoxyethoxy)ethoxy)ethoxy)phenyl)amino) pyrimidin-4-yl)oxy)naphthalen-1-yl)carbamate (see Example 19(i) above; 1000 mg, 1.561 mmol) in isopropyl acetate (12 mL) and the mixture heated at 60° C. (block temperature) for 1 h. The reaction was concentrated in vacuo onto silica gel and the crude product purified by chromatography on the Companion (40 g column, 1-3% MeOH in DCM) to afford the sub-title compound (1.02 g) as a white foam.

¹H NMR (400 MHz, DMSO-d6) δ: 9.45 (s, 1H), 9.43 (s, 1H), 8.98 (s, 1H), 8.62 (d, 1H), 8.42 (d, 1H), 8.28 (d, 1H), 8.08 (d, 1H), 7.86 (d, 1H), 7.69 (t, 1H), 7.60 (t, 1H), 7.43 (d, 1H), 7.35 (d, 1H), 6.81 (d, 2H), 6.55 (d, 1H), 6.04 (t, 1H), 3.85-3.88 (m, 2H), 3.88 (s, 3H), 3.85 (s, 3H), 3.65-3.67 (m, 2H), 3.48-3.55 (m, 6H), 3.52 (s, 3H), 3.41 (dd, 2H), 3.21 (s, 3H), 1.29 (s, 9H).
LCMS m/z 393 (M+2H)²⁺ (ES⁺)

(ii) 5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)benzoic acid To a stirred solution of the product from step (i) above (1.02 g, 1.301 mmol) in THF (40 mL) and water (10 mL) was added NaOH (2M aq.) (3.90 mL, 7.81 mmol) and the reaction vigorously stirred for 3 h. MeOH (10 mL) was added and stirring continued over the weekend. The reaction was concentrated in vacuo affording a pale purple solid. The material was suspended in water and acidified with 1M HCl causing a solid to precipitate. The solid was collected by filtration, washed with water and the solid dried at 40° C. under vacuum affording the sub-title compound (877 mg) as a beige solid.
¹H NMR (400 MHz, DMSO-d6) δ: 9.54 (s, 1H), 9.52 (s, 1H), 9.02 (s, 1H), 8.58 (d, 1H), 8.42 (d, 1H), 8.31 (d, 1H), 8.08 (d, 1H), 7.85 (d, 1H), 7.68 (t, 1H), 7.59 (t, 1H), 7.42 (d, 1H), 7.35 (d, 1H), 6.80 (d, 2H), 6.58 (d, 1H), 6.05 (t, 1H), 5.59 (bs, 1H), 3.85-3.88 (m, 2H), 3.85 (s, 3H), 3.65-3.67 (m, 2H), 3.47-3.55 (m, 6H), 3.52 (s, 3H), 3.40 (dd, 2H), 3.21 (s, 3H), 1.29 (s, 9H).
LCMS m/z 385 (M+2H)²⁺ (ES⁺)

(iii) 5-(tert-Butyl)-N-cyclopropyl-2-methoxy-3-(3-(4-((2-((3-methoxy-5-(2-(2-(2-methoxy-ethoxy)ethoxy)ethoxy)phenyl)amino)pyrimidin-4-yl)oxy)naphthalen-1-yl)ureido)-benzamide A stirred mixture of the product from step (ii) above (70 mg, 0.091 mmol), cyclopropanamine (13.0 µL, 0.188 mmol) and triethylamine (38.0 µL, 0.273 mmol) in DCM (4 mL) was cooled in an ice-bath. 50 wt % T3P in EtOAc (80 µL, 0.134 mmol) was added, the ice-bath was removed and the reaction mixture allowed to warm to rt and stirred at this temperature for 2 h. The reaction mixture was partitioned between sat. aq. NaHCO₃ (10 mL) and DCM (10 mL). The aqueous phase was back extracted with fresh DCM (10 mL). The combined organic extracts were washed with water (20 mL), brine (20 mL), dried (MgSO₄), filtered and concentrated in vacuo onto silica gel. The crude product was purified by chromatography on the Companion (12 g column, 1-4% MeOH in DCM) to afford the title compound (51 mg) as a white solid.

¹H NMR (400 MHz, DMSO-d6) δ: 9.44 (s, 1H), 9.42 (s, 1H), 8.90 (s, 1H), 8.44 (d, 1H), 8.42 (d, 1H), 8.29 (d, 1H), 8.26 (s, 1H), 8.08 (d, 1H), 7.85 (d, 1H), 7.68 (t, 1H), 7.59 (t, 1H), 7.42 (d, 1H), 7.02 (d, 1H), 6.81 (d, 2H), 6.55 (d, 1H), 6.03 (t, 1H), 3.86-3.88 (m, 2H), 3.78 (s, 3H), 3.65-3.67 (m, 2H), 3.48-3.55 (m, 6H), 3.51 (s, 3H), 3.41 (dd, 2H), 3.21 (s, 3H), 2.85-2.90 (m, 1H), 1.28 (s, 9H), 0.70-0.75 (m, 2H), 0.55-0.59 (m, 2H).
LCMS m/z 405 (M+2H)²⁺ (ES⁺)

Example 34

5-(tert-Butyl)-2-methoxy-3-(3-(4-((2-((3-methoxy-5-(2-(2-(2-methoxyethoxy)ethoxy) ethoxy)phenyl)amino)pyridin-4-yl)oxy)naphthalen-1-yl)ureido) benzamide

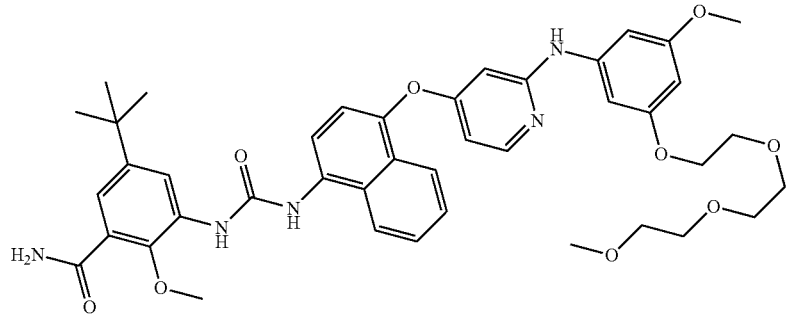 [SMILES: COCCOCCOCCOc1cc(Nc2cc(Oc3ccc(NC(=O)Nc4cc(C(C)(C)C)cc(C(N)=O)c4OC)c4ccccc34)ccn2)cc(OC)c1]

(i) Phenyl (4-((2-((3-methoxy-5-(2-(2-(2-methoxyethoxy)ethoxy)ethoxy)phenyl)amino)-pyridin-4-yl)oxy)naphthalen-1-yl)carbamate Phenyl chloroformate (37 µL, 0.295 mmol) was added to a stirred solution of 4-((4-aminonaphthalen-1-yl)oxy)-N-(3-methoxy-5-(2-(2-(2-methoxyethoxy)ethoxy)ethoxy)-phenyl)pyridin-2-amine (see Example 19(i) above; 150 mg, 0.289 mmol) and NaHCO₃ (50 mg, 0.595 mmol) in THF (1.5 mL) and DCM (5 mL). The mixture was stirred over the weekend. The mixture was diluted with water (5 mL) and DCM (5 mL) and the mixture passed through a phase-sep cartridge. The resulting filtrate was concentrated in vacuo giving the product as a pink gum. The material was stirred vigorously in hexane for 1 h then concentrated in vacuo affording the sub-title compound (183 mg) as a pink solid.
LCMS m/z 640 (M+H)⁺ (ES⁺)

(ii) 5-(tert-Butyl)-2-methoxy-3-(3-(4-((2-((3-methoxy-5-(2-(2-(2-methoxyethoxy)ethoxy)-ethoxy)phenyl)amino)pyridin-4-yl)oxy)naphthalen-1-yl)ureido)benzamide Triethylamine (7 µL, 0.050 mmol) was added to a mixture of 3-amino-5-(tert-butyl)-2-methoxybenzamide (51 mg, 0.229 mmol) and the product from step (i) above (183 mg, 0.229 mmol) in isopropyl acetate (3 mL) and the mixture heated at 60 CC (block temperature) for 1 h. The reaction was concentrated in vacuo onto silica gel and the crude product purified by chromatography on the Companion (40 g column, 1-5% MeOH in DCM) to afford the product as a pink foam. The material was dissolved in MeOH and loaded onto a pre-conditioned cartridge of SCX resin. The resin was washed with MeOH then the product released with 1% NH₃ in MeOH. The ammonia solution was concentrated in vacuo and the residue purified further by prep-HPLC (Varian, XS Basic, 40-80% MeCN, 10 min) affording the title compound (24 mg) as a beige solid.
¹H NMR (400 MHz, DMSO-d6) δ: 9.47 (s, 1H), 8.93 (s, 1H), 8.88 (s, 1H), 8.46 (d, 1H), 8.30 (d, 1H), 8.12 (d, 1H), 8.10 (d, 1H), 7.87 (d, 1H), 7.69-7.73 (m, 2H), 7.58-7.63 (m, 2H), 7.39 (d, 1H), 7.22 (d, 1H), 6.91 (t, 1H), 6.78 (t, 1H), 6.58 (dd, 1H), 6.08 (d, 1H), 6.04 (t, 1H), 3.97-3.99 (m, 2H), 3.83 (s, 3H), 3.69-3.72 (m, 2H), 3.65 (s, 3H), 3.50-3.58 (m, 6H), 3.42 (dd, 2H), 3.23 (s, 3H), 1.29 (s, 9H).

LCMS m/z 385 (M+2H)$^{2+}$ (ES$^+$)

Example 35

5-(tert-Butyl)-N-(2-hydroxyethyl)-2-methoxy-3-(3-(4-((2-((3-methoxy-5-(2-(2-(2-methoxy-ethoxy)ethoxy)ethoxy)phenyl)amino)pyrimidin-4-yl)oxy)naphthalen-1-yl)ureido)-benzamide

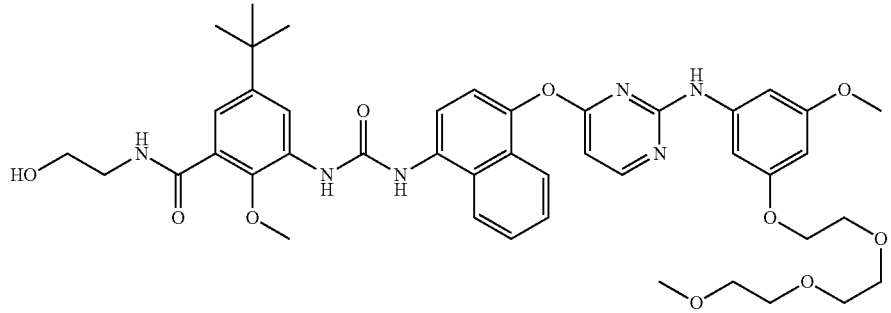 [SMILES: COCCOCCOCCOc1cc(Nc2nccc(Oc3ccc(NC(=O)Nc4cc(C(C)(C)C)cc(C(=O)NCCO)c4OC)c4ccccc34)n2)cc(OC)c1]

A stirred mixture of 5-(tert-butyl)-2-methoxy-3-(3-(4-((2-((3-methoxy-5-(2-(2-(2-methoxy-ethoxy)ethoxy)ethoxy)phenyl)amino)pyrimidin-4-yl)oxy)naphthalen-1-yl)ureido)benzoic acid (see Example 21 above; 70 mg, 0.091 mmol), 2-aminoethanol (11 μL, 0.182 mmol) and triethylamine (38.0 μL, 0.273 mmol) in DCM (4 mL) was cooled in an ice-bath. 50 wt % T3P in EtOAc (80 μL, 0.134 mmol) was added, the ice-bath was removed and the reaction mixture allowed to warm to rt and stirred at this temperature for 2 h. A further equivalent of 2-aminoethanol was added and stirring was continued overnight. The reaction mixture was partitioned between sat. aq. NaHCO$_3$ (10 mL) and DCM (10 mL). The aqueous phase was back extracted with fresh DCM (10 mL). The combined organic extracts were washed with water (20 mL), brine (20 mL), dried (MgSO$_4$), filtered and concentrated in vacuo onto silica gel. The crude product was purified by chromatography on the Companion (12 g column, 1-5% MeOH in DCM) to afford the title compound (26 mg) as a pale pink solid.

$^1$H NMR (400 MHz, DMSO-d6) δ: 9.44 (s, 1H), 9.42 (s, 1H), 8.93 (s, 1H), 8.47 (d, 1H), 8.42 (d, 1H), 8.24-8.29 (m, 2H), 8.09 (d, 1H), 7.85 (d, 1H), 7.69 (t, 1H), 7.59 (t, 1H), 7.42 (d, 1H), 7.21 (d, 1H), 6.81 (d, 2H), 6.55 (d, 1H), 6.04 (t, 1H), 4.80 (t, 1H), 3.86-3.88 (m, 2H), 3.81 (s, 3H), 3.65-3.67 (m, 2H), 3.48-3.59 (m, 8H), 3.51 (s, 3H), 3.36-3.41 (m, 4H), 3.21 (s, 3H), 1.29 (s, 9H).

LCMS m/z 407 (M+2H)$^{2+}$ (ES$^+$)

Example 36

N-(5-(tert-Butyl)-2-methoxy-3-(3-(4-((2-((3-methoxy-5-(2-(2-methoxyethoxy)ethoxy)-phenyl)amino)pyrimidin-4-yl)oxy)naphthalen-1-yl)ureido)phenyl)methanesulfonamide

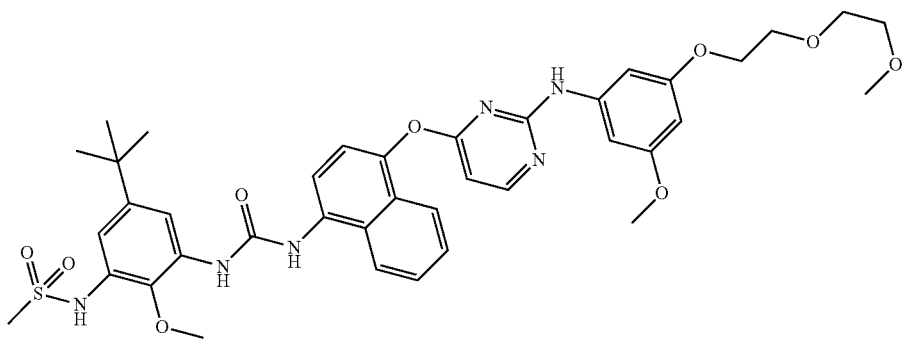 [SMILES: COCCOCCOc1cc(Nc2nccc(Oc3ccc(NC(=O)Nc4cc(C(C)(C)C)cc(NS(C)(=O)=O)c4OC)c4ccccc34)n2)cc(OC)c1]

(i) 1-Methoxy-3-(2-(2-methoxyethoxy)ethoxy)-5-nitrobenzene

A mixture of 3-methoxy-5-nitrophenol (2 g, 11.82 mmol), 1-bromo-2-(2-methoxyethoxy)-ethane (2.4 g, 13.11 mmol) and K$_2$CO$_3$ (4.90 g, 35.5 mmol) in acetone (40 mL) was heated at reflux for 30 h. The mixture was partitioned between EtOAc (200 mL) and water (100 mL), the organic layer separated, washed with brine (100 mL), dried (MgSO$_4$), filtered and evaporated under reduced pressure. The crude product was purified by chromatography on silica gel (120 g column, 0-40% EtOAc/isohexane) to afford the sub-title compound (2.762 g) as an oil.

$^1$H NMR (CDCl$_3$) 400 MHz, δ: 7.39 (s, 1H), 7.36 (s, 1H), 6.78 (s, 1H), 4.19 (t, 2H), 3.88 (t, 2H), 3.85 (s, 3H), 3.73-3.71 (m, 2H), 3.60-3.57 (m, 2H), 3.39 (s, 3H).

(ii) 3-Methoxy-5-(2-(2-methoxyethoxy)ethoxy)aniline

A mixture of the product from step (i) above (2.75 g, 10.14 mmol), 5% Pd—C (500 mg) in EtOH (30 mL) was hydrogenated at 4 Bar for 18 h. The mixture was filtered through Celite and the filtrate evaporated under reduced pressure to afford the sub-title compound (2.294 g) as a brown oil.

$^1$H NMR (CDCl$_3$) 400 MHz, δ: 5.93 (t, 1H), 5.88 (t, 1H), 5.86 (t, 1H), 4.08 (t, 2H), 3.82 (t, 2H), 3.73 (s, 3H), 3.72-3.69 (m, 2H), 3.64 (s, 2H), 3.58-3.55 (m, 2H), 3.39 (s, 3H).
LCMS m/z 242 (M+H)$^+$ (ES$^+$)

(iii) N-(5-(tert-Butyl)-2-methoxy-3-(3-(4-((2-((3-methoxy-5-(2-(2-methoxyethoxy)ethoxy) phenyl)amino)pyrimidin-4-yl)oxy)naphthalen-1-yl)ureido) phenyl)methanesulfonamide A mixture of N-(5-(tert-butyl)-3-(3-(4-((2-chloropyrimidin-4-yl)oxy)naphthalen-1-yl)ureido)-2-methoxyphenyl) methanesulfonamide (see Example 7(i) above; 150 mg, 0.263 mmol), the product from step (ii) above (127 mg, 0.526 mmol) and p-TSA monohydrate (15 mg, 0.079 mmol) in THF (6 mL) was heated at 60° C. for 18 h. The mixture was partitioned between EtOAc (50 mL) and sat aq NaHCO$_3$ (50 mL), the organic layer separated, washed with brine (50 mL), dried (MgSO$_4$), filtered and evaporated under reduced pressure. The crude product was purified by chromatography on silica gel (40 g column, 0-50% EtOAc/isohexane) to give a solid that was triturated with ether/EtOAc, then filtered and dried to afford the title compound (83 mg) as a white solid.

$^1$H NMR (DMSO-d6) 400 MHz, δ: 9.45 (s, 1H), 9.36 (s, 1H), 9.15 (s, 1H), 8.93 (s, 1H), 8.42 (d, 1H), 8.28 (d, 1H), 8.19 (s, 1H), 8.11 (d, 1H), 7.85 (d, 1H), 7.70-7.66 (m, 1H), 7.61-7.57 (m, 1H), 7.42 (d, 1H), 7.02 (s, 1H), 6.81 (brd, 2H), 6.56 (d, 1H), 6.04 (s, 1H), 3.87-3.85 (m, 2H), 3.81 (s, 3H), 3.66-3.64 (m, 2H), 3.55-3.51 (m, 5H), 3.43-3.41 (m, 2H), 3.22 (s, 3H), 3.10 (s, 3H), 1.27 (s, 9H).
LCMS m/z 775 (M+H)$^+$ (ES$^+$); 773 (M−H)$^−$ (ES$^−$)

Example 37

Methyl 2-(5-(tert-butyl)-2-methoxy-3-(3-(4-((2-((3-methoxy-5-(2-(2-(2-methoxyethoxy)-ethoxy)ethoxy) phenyl)amino)pyrimidin-4-yl)oxy)naphthalen-1-yl) ureido)benzamido)-acetate

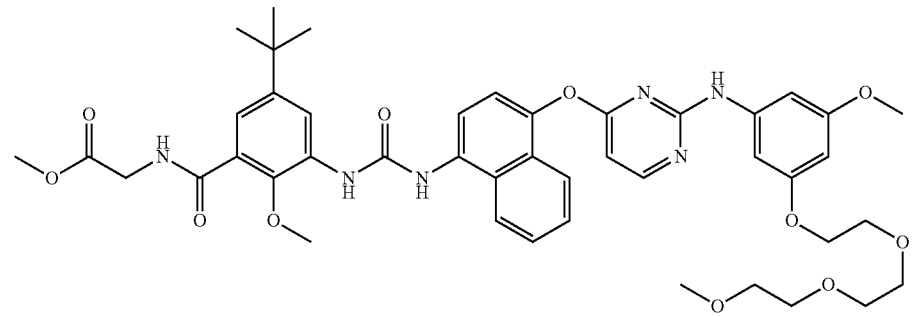 [SMILES: COCCOCCOCCOc1cc(Nc2nccc(Oc3ccc(NC(=O)Nc4cc(C(C)(C)C)cc(C(=O)NCC(=O)OC)c4OC)c4ccccc34)n2)cc(OC)c1]

A stirred mixture of 5-(tert-butyl)-2-methoxy-3-(3-(4-((2-((3-methoxy-5-(2-(2-(2-methoxy ethoxy)ethoxy)ethoxy) phenyl)amino)pyrimidin-4-yl)oxy)naphthalen-1-yl)ureido) benzoic acid (see Example 21 above; 60 mg, 0.078 mmol), methyl 2-aminoacetate, HCl (20 mg, 0.159 mmol) and triethylamine (35 μL, 0.251 mmol) in DCM (4 mL) was cooled in an ice-bath. 50 wt % T3P in EtOAc (70 μL, 0.118 mmol) was added, the ice-bath was removed and the reaction mixture allowed to warm to rt and stirred at this temperature for 2 h. The reaction mixture was partitioned between sat. aq. NaHCO$_3$ (10 mL) and DCM (10 mL). The aqueous phase was back extracted with fresh DCM (10 mL). The combined organic extracts were washed with water (20 mL), brine (20 mL), dried (MgSO$_4$), filtered and concentrated in vacuo onto silica gel. The crude product was purified by chromatography on the Companion (12 g column, 1-5% MeOH in DCM) to afford the title compound (35 mg) as an off-white solid.

$^1$H NMR (400 MHz, DMSO-d6) δ: 9.44 (s, 1H), 9.43 (s, 1H), 8.94 (s, 1H), 8.67 (t, 1H), 8.51 (d, 1H), 8.42 (d, 1H), 8.28 (d, 1H), 8.09 (d, 1H), 7.86 (d, 1H), 7.69 (t, 1H), 7.60 (t, 1H), 7.43 (d, 1H), 7.25 (d, 1H), 6.82 (d, 2H), 6.55 (d, 1H), 6.04 (t, 1H), 4.10 (d, 2H), 3.86-3.88 (m, 2H), 3.86 (s, 3H), 3.71 (s, 3H), 3.65-3.67 (m, 2H), 3.48-3.55 (m, 6H), 3.52 (s, 3H), 3.40 (dd, 2H), 3.22 (s, 3H), 1.29 (s, 9H).

LCMS m/z 421 (M+2H)$^{2+}$ (ES$^+$)

Example 38

N-Benzyl-5-(tert-butyl)-2-methoxy-3-(3-(4-((2-((3-methoxy-5-(2-(2-(2-methoxyethoxy)-ethoxy)ethoxy)phenyl)amino)pyrimidin-4-yl)oxy)naphthalen-1-yl)ureido)benzamide

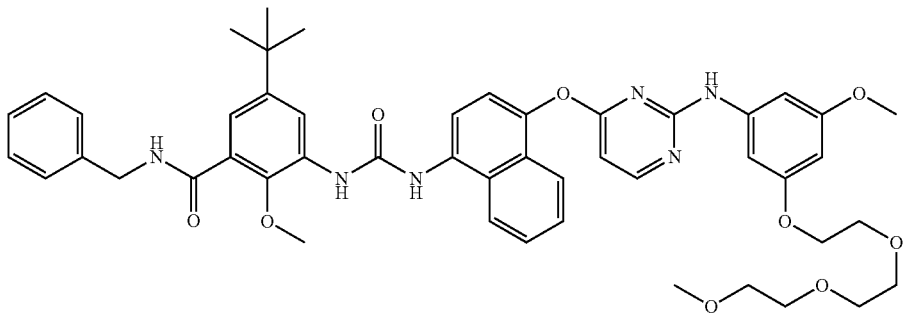 [SMILES: COCCOCCOCCOc1cc(Nc2nccc(Oc3ccc(NC(=O)Nc4cc(C(C)(C)C)cc(C(=O)NCc5ccccc5)c4OC)c4ccccc34)n2)cc(OC)c1]

A stirred mixture of 5-(tert-butyl)-2-methoxy-3-(3-(4-((2-((3-methoxy-5-(2-(2-(2-methoxy ethoxy)ethoxy)ethoxy)phenyl)amino)pyrimidin-4-yl)oxy)naphthalen-1-yl)ureido) benzoic acid (see Example 21 above; 60 mg, 0.078 mmol), phenylmethanamine (17 µL, 0.156 mmol) and triethylamine (35 µL, 0.251 mmol) in DCM (4 mL) was cooled in an ice-bath. 50 wt % T3P in EtOAc (70 µL, 0.118 mmol) was added, the ice-bath was removed and the reaction mixture allowed to warm to rt and stirred at this temperature for 2 h. The reaction mixture was partitioned between sat. aq. NaHCO$_3$ (10 mL) and DCM (10 mL). The aqueous phase was back extracted with fresh DCM (10 mL). The combined organic extracts were washed with water (20 mL), brine (20 mL), dried (MgSO$_4$), filtered and concentrated in vacuo onto silica gel. The crude product was purified by chromatography on the Companion (12 g column, 1-5% MeOH in DCM) to afford the title compound (38 mg) as an off-white solid.

$^1$H NMR (400 MHz, DMSO-d6) δ: 9.43 (s, 1H), 9.41 (s, 1H), 8.93 (s, 1H), 8.78 (t, 1H), 8.47 (d, 1H), 8.42 (d, 1H), 8.27 (d, 1H), 8.09 (d, 1H), 7.85 (d, 1H), 7.68 (t, 1H), 7.59 (t, 1H), 7.36-7.43 (m, 5H), 7.26-7.30 (m, 1H), 7.15 (d, 1H), 6.81 (d, 2H), 6.55 (d, 1H), 6.04 (t, 1H), 4.52 (d, 2H), 3.86-3.88 (m, 2H), 3.74 (s, 3H), 3.65-3.67 (m, 2H), 3.48-3.55 (m, 6H), 3.51 (s, 3H), 3.41 (dd, 2H), 3.21 (s, 3H), 1.29 (s, 9H).

LCMS m/z 430 (M+2H)$^{2+}$ (ES$^+$)

Example 39

5-(tert-Butyl)-3-(3-(4-((2-((3-ethynyl-5-((2-morpholinoethyl)carbamoyl)phenyl)amino)-pyridin-4-yl)oxy)naphthalen-1-yl)ureido)-2-methoxy-N-methylbenzamide (i) tert-Butyl (4-((2-((3-((2-morpholinoethyl)carbamoyl)-5-(((triisopropylsilyl)ethynyl)phenyl)amino)pyridin-4-yl)oxy)naphthalen-1-yl)carbamate Pd$_2$(dba)$_3$ (0.125 g, 0.137 mmol) was added to a degassed suspension of tert-butyl (4-((2-chloropyridin-4-yl)oxy)naphthalen-1-yl)carbamate (see Example 3(ii) above; 1 g, 2.70 mmol), 3-amino-N-(2-morpholinoethyl)-5-(((triisopropylsilyl)ethynyl)benzamide (see Example 1(ii) above; 1.26 g, 2.93 mmol), BINAP (0.17 g, 0.273 mmol), and Cs$_2$CO$_3$ (2.7 g, 8.29 mmol) in 1,4-dioxane (12 mL) under nitrogen. The mixture was stirred under nitrogen at 90° C. (block temperature) for 18 h. The reaction mixture was filtered and partitioned between water (20 mL) and EtOAc (20 mL). The aqueous was separated and washed again with EtOAc (20 mL). The organics were bulked, dried (MgSO$_4$), filtered and evaporated to a brown gum. The crude product was purified by chromatography on silica gel (80 g column, 2% MeOH:DCM to 8%) to afford the sub-title compound (1.8 g) as a tan solid.

$^1$H NMR (400 MHz, DMSO-d6) δ 9.37 (s, 1H), 9.21 (s, 1H), 8.41 (t, 1H), 8.19-8.10 (m, 2H), 8.10-8.07 (m, 1H), 7.96-7.89 (m, 1H), 7.88-7.79 (m, 1H), 7.68-7.53 (m, 3H), 7.42-7.32 (m, 2H), 6.61 (dd, 1H), 6.10 (d, 1H), 3.66-3.51 (m, 4H), 3.41-3.33 (m, 2H), 2.49-2.34 (m, 6H), 1.53 (s, 9H), 1.11 (s, 21H).

LCMS m/z 764 (M+H)$^+$ (ES$^+$); 762 (M−H)$^-$ (ES$^-$)

(ii) 3-((4-((4-Aminonaphthalen-1-yl)oxy)pyridin-2-yl)amino)-N-(2-morpholinoethyl)-5-((triisopropylsilyl)ethynyl)benzamide The product from step (i) above (1.8 g, 2.356 mmol) was dissolved in DCM (20 mL) and TFA (2 mL, 26.0 mmol) added. The reaction was stirred at rt for 16 h. The solvents were evaporated and the residue partitioned between DCM (20 mL) and sat. NaHCO$_3$ soln (20 mL). The aqueous was

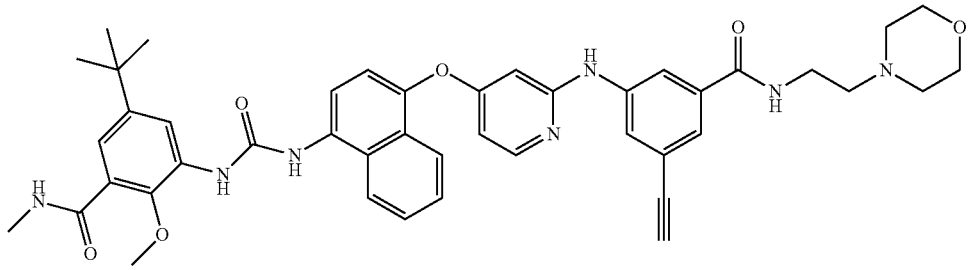 [SMILES: C#Cc1cc(Nc2cc(Oc3ccc(NC(=O)Nc4cc(C(C)(C)C)cc(C(=O)NC)c4OC)c4ccccc34)ccn2)cc(C(=O)NCCN2CCOCC2)c1]

separated and washed with fresh DCM (20 mL). The organics were separated, bulked, dried (MgSO$_4$), filtered and evaporated to give the sub-title compound (1.3 g) as a brown foam.

$^1$H NMR (400 MHz, DMSO-d6) δ 9.11 (s, 1H), 8.40 (t, 1H), 8.23-8.11 (m, 1H), 8.11-8.00 (m, 2H), 7.96-7.85 (m, 1H), 7.70-7.56 (m, 1H), 7.50-7.39 (m, 2H), 7.34 (t, 1H), 7.10 (d, 1H), 6.72 (d, 1H), 6.55 (dd, 1H), 6.05 (d, 1H), 5.83 (s, 2H), 3.69-3.48 (m, 4H), 3.43-3.34 (m, 2H), 2.49-2.27 (m, 6H), 1.10 (s, 21H).

LCMS m/z 664 (M+H)$^+$ (ES$^+$)

(iii) 5-(tert-Butyl)-2-methoxy-N-methyl-3-(3-(4-((2-((3-((2-morpholinoethyl)carbamoyl)-5-((triisopropylsilyl)ethynyl)phenyl)amino)pyridin-4-yl)oxy)naphthalen-1-yl)ureido)-benzamide Triethylamine (10 μL, 0.072 mmol) was added to a solution of phenyl (5-(tert-butyl)-2-methoxy-3-(methylcarbamoyl)phenyl)carbamate (see Example 9(i) above; 64 mg, 0.180 mmol) and the product from step (ii) above (120 mg, 0.181 mmol) in THF (2 mL) and the reaction stirred at 50° C. for 24 h. The solvent was evaporated and the crude product was purified by chromatography on silica gel (40 g column, 4% MeOH:DCM to 10%) to afford the sub-title compound (120 mg) as a pale pink solid.

LCMS m/z 927 (M+H)$^+$ (ES$^+$)

(iv) 5-(tert-Butyl)-3-(3-(4-((2-((3-ethynyl-5-((2-morpholinoethyl)carbamoyl)phenyl)amino)-pyridin-4-yl)oxy)naphthalen-1-yl)ureido)-2-methoxy-N-methyl-benzamide The product from step (iii) above (120 mg, 0.130 mmol) was dissolved in THF (3 mL) and TBAF, 1M in THF (150 μL, 0.150 mmol) added. The mixture was stirred for 1 h then partitioned between water (10 mL) and DCM (10 mL). The organic layer was separated and washed with 20% w/w NaCl soln. (10 mL). The organics were separated, dried (MgSO$_4$) filtered and solvents evaporated to give a tan solid. The crude product was purified by chromatography on silica gel (40 g column, 4% MeOH:DCM to 10%) to afford the title compound (60 mg) as a colourless solid.

$^1$H NMR (400 MHz, DMSO-d6) δ 9.48 (s, 1H), 9.22 (s, 1H), 8.89 (s, 1H), 8.44 (d, 1H), 8.38 (t, 1H), 8.30 (d, 1H), 8.21-8.12 (m, 2H), 8.12-8.03 (m, 2H), 7.93 (t, 1H), 7.88 (d, 1H), 7.77-7.67 (m, 1H), 7.66-7.55 (m, 1H), 7.47-7.34 (m, 2H), 7.12 (d, 1H), 6.62 (dd, 1H), 6.14 (d, 1H), 4.19 (s, 1H), 3.80 (s, 3H), 3.56 (t, 4H), 3.50-3.37 (m, 2H), 2.82 (d, 3H), 2.49-2.30 (m, 6H), 1.28 (s, 9H).

LCMS m/z 770 (M+H)$^+$ (ES$^+$); 768 (M−H)$^-$ (ES$^-$)

Example 40

3-((4-((4-(3-(5-(tert-Butyl)-2-methoxy-3-(methylsulfonamido)phenyl)ureido)naphthalen-1-yl)oxy)pyrimidin-2-yl)amino)-N-(2,5,8,11,14,17,20-heptaoxadocosan-22-yl)-5-methoxy-benzamide

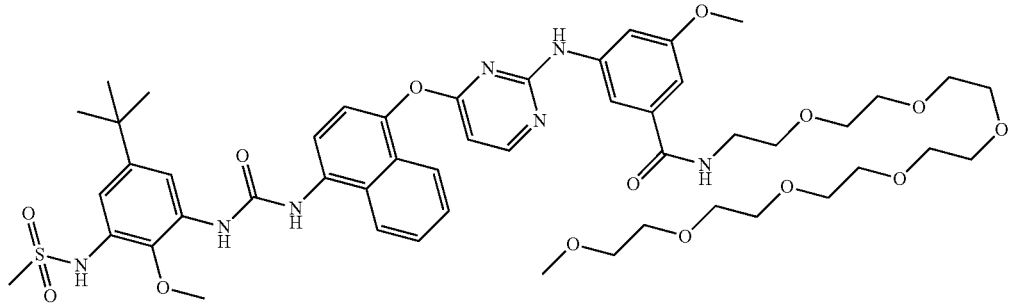 [SMILES: COCCOCCOCCOCCOCCOCCOCCNC(=O)c1cc(Nc2nccc(Oc3ccc(NC(=O)Nc4cc(C(C)(C)C)cc(NS(C)(=O)=O)c4OC)c4ccccc34)n2)cc(OC)c1]

(i) tert-Butyl (4-((2-((3-(2,5,8,11,14,17,20-heptaoxadocosan-22-ylcarbamoyl)-5-methoxyphenyl)amino)pyrimidin-4-yl)oxy)naphthalen-1-yl)carbamate A stirred mixture of 3-((4-((4-((tert-butoxycarbonyl)amino)naphthalen-1-yl)oxy)pyrimidin-2-yl)amino)-5-methoxybenzoic acid (see Example 6(i) above; 800 mg, 1.592 mmol), 2,5,8,11,14,17,20-heptaoxadocosan-22-amine (513 mg, 1.512 mmol) and triethylamine (666 μL, 4.78 mmol) in DCM (60 mL) was cooled in an ice-bath. 50 wt % T3P in EtOAc (1422 μL, 2.388 mmol) was added, the ice-bath was removed and the reaction mixture allowed to warm to rt and stirred at this temperature for overnight. The reaction mixture was partitioned between sat. aq. NaHCO$_3$ (100 mL) and DCM (100 mL). The aqueous phase was back extracted with fresh DCM (50 mL). The combined organic extracts were washed with water (50 mL), brine (50 mL), dried (MgSO$_4$), filtered and concentrated in vacuo onto silica gel. The crude product was purified by chromatography on the Companion (80 g column, 2-5% MeOH in DCM) to afford the sub-title compound (1.01 g) as a white solid.

$^1$H NMR (400 MHz, DMSO-d6) δ: 9.60 (s, 1H), 9.33 (s, 1H), 8.42 (d, 1H), 8.32 (t, 1H), 8.11 (d, 1H), 7.82 (d, 1H), 7.54-7.63 (m, 4H), 7.39-7.42 (m, 2H), 6.91 (s, 1H), 6.55 (d, 1H), 3.58 (s, 3H), 3.48-3.52 (m, 24H), 3.37-3.43 (m, 4H), 3.23 (s, 3H), 1.52 (s, 9H).

LCMS m/z 385 (M-tBu+2H)2+ (ES$^+$)

(ii) 3-((4-((4-Aminonaphthalen-1-yl)oxy)pyrimidin-2-yl)amino)-N-(2,5,8,11,14,17,20-heptaoxadocosan-22-yl)-5-methoxybenzamide TFA (1.0 mL, 12.98 mmol) was added to a stirred solution of the product from step (i) above (1.01 g, 1.226 mmol) in DCM (50 mL) at rt then stirred overnight. More TFA (5 mL) was added and stirring continued for 4 h. The reaction mixture was concentrated in vacuo then the residue partitioned between DCM and NaHCO$_3$ aq. solution. The organic phase was dried (MgSO$_4$), filtered and concentrated in vacuo affording the sub-title compound (816 mg) as a pale yellow gum.

LCMS m/z 363 (M+2H)$^{2+}$ (ES$^+$)

(iii) 3-((4-((4-(3-(5-(tert-Butyl)-2-methoxy-3-(methylsulfonamido)phenyl)ureido)-naphthalen-1-yl)oxy)pyrimidin-2-yl)amino)-N-(2,5,8,11,14,17,20-heptaoxadocosan-22-yl)-5-methoxybenzamide Triethylamine (7.0 μL, 0.050 mmol) was added to a mixture of phenyl (5-(tert-butyl)-2-methoxy-3-(methylsulfonamido)phenyl)carbamate (see Example 1(vi) above; 100 mg, 0.255 mmol) and the product from step (ii) above (172 mg, 0.238 mmol) in isopropyl acetate (5 mL) and the mixture heated at 50° C. (block temperature) for 65 h. The mixture was cooled to rt and concentrated in vacuo onto silica gel. The crude material was purified by chromatography on silica gel (12 g column, 1-5% MeOH in DCM) to afford a colourless glass. The material was dissolved in DCM and washed with 1M HCl. The organic phase was dried (MgSO₄), filtered and concentrated in vacuo affording the title compound (131 mg) as a pale yellow solid.

¹H NMR (400 MHz, DMSO-d6) δ: 9.65 (s, 1H), 9.42 (s, 1H), 9.13 (s, 1H), 8.96 (s, 1H), 8.42 (d, 1H), 8.29-8.33 (m, 2H), 8.19 (d, 1H), 8.10 (d, 1H), 7.85 (d, 1H), 7.67 (t, 1H), 7.57-7.61 (m, 2H), 7.43 (d, 1H), 7.34 (s, 1H), 7.03 (d, 1H), 6.90 (s, 1H), 6.56 (d, 1H), 3.81 (s, 3H), 3.60 (s, 3H), 3.47-3.51 (m, 24H), 3.35-3.42 (m, 4H), 3.23 (s, 3H), 3.10 (s, 3H), 1.27 (s, 9H).

LCMS m/z 512 (M+2H)²⁺ (ES⁺)

Example 41

5-(tert-Butyl)-N-ethyl-2-methoxy-3-(3-(4-((2-((3-methoxy-5-(2-(2-(2-methoxyethoxy)-ethoxy)ethoxy)phenyl)amino)pyrimidin-4-yl)oxy)naphthalen-1-yl)ureido)benzamide

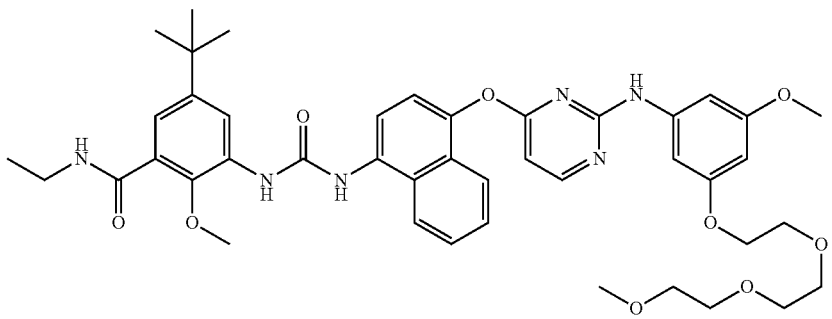 [SMILES: CCNC(=O)c1cc(C(C)(C)C)cc(NC(=O)Nc2ccc(Oc3ccnc(Nc4cc(OC)cc(OCCOCCOCCOC)c4)n3)c3ccccc23)c1OC]

A stirred mixture of 5-(tert-butyl)-2-methoxy-3-(3-(4-((2-((3-methoxy-5-(2-(2-(2-methoxy ethoxy)ethoxy)ethoxy)phenyl)amino)pyrimidin-4-yl)oxy)naphthalen-1-yl)ureido)benzoic acid (see Example 21 above; 60 mg, 0.078 mmol), ethanamine (13 μL, 0.161 mmol) and triethylamine (35 μL, 0.251 mmol) in DCM (4 mL) was cooled in an ice-bath. 50 wt % T3P in EtOAc (70 μL, 0.118 mmol) was added, the ice-bath was removed and the reaction mixture allowed to warm to rt and stirred at this temperature overnight. The reaction mixture was partitioned between sat. aq. NaHCO₃ (10 mL) and DCM (10 mL). The aqueous phase was back extracted with fresh DCM (10 mL). The combined organic extracts were washed with water (20 mL), brine (20 mL), dried (MgSO₄), filtered and concentrated in vacuo onto silica gel. The crude product was purified by chromatography on the Companion (12 g column, 1-5% MeOH in DCM) to afford the title compound (22 mg) as an off-white solid.

¹H NMR (400 MHz, DMSO-d6) δ: 9.42 (s, 2H), 8.99 (s, 1H), 8.45 (d, 1H), 8.42 (d, 1H), 8.28 (d, 1H), 8.23 (t, 1H), 8.08 (d, 1H), 7.85 (d, 1H), 7.68 (t, 1H), 7.59 (t, 1H), 7.42 (d, 1H), 7.10 (d, 1H), 6.82 (d, 2H), 6.55 (d, 1H), 6.04 (t, 1H), 3.86-3.88 (m, 2H), 3.81 (s, 3H), 365-3.67 (m, 2H), 3.48-3.55 (m, 6H), 3.51 (s, 3H), 3.41 (dd, 2H), 3.28-3.55 (m, 2H under H2O peak), 3.22 (s, 3H), 1.29 (s, 9H), 1.16 (t, 3H).

LCMS m/z 797 (M+H)⁺ (ES⁺); 795 (M−H)⁻ (ES⁻)

Example 42

5-(tert-Butyl)-N-isopropyl-2-methoxy-3-(3-(4-((2-((3-methoxy-5-(2-(2-(2-methoxyethoxy)-ethoxy)ethoxy)phenyl)amino)pyrimidin-4-yl)oxy)naphthalen-1-yl)ureido)benzamide

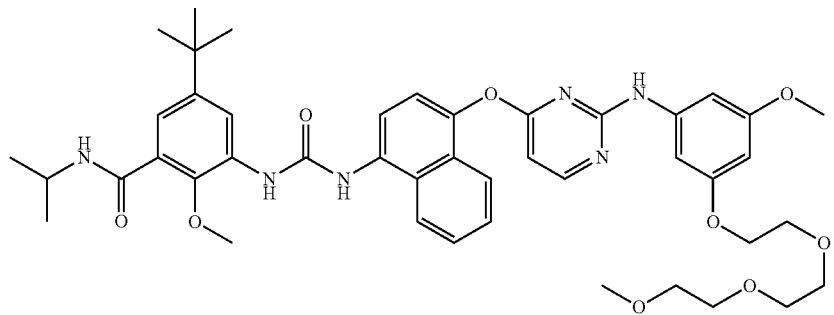 [SMILES: COCCOCCOCCOc1cc(Nc2nccc(Oc3ccc(NC(=O)Nc4cc(C(C)(C)C)cc(C(=O)NC(C)C)c4OC)c4ccccc34)n2)cc(OC)c1]

A stirred mixture of 5-(tert-butyl)-2-methoxy-3-(3-(4-((2-((3-methoxy-5-(2-(2-(2-methoxy ethoxy)ethoxy)ethoxy)phenyl)amino)pyrimidin-4-yl)oxy)naphthalen-1-yl)ureido) benzoic acid (see Example 21 above; 60 mg, 0.078 mmol), propan-2-amine (14 µL, 0.163 mmol) and triethylamine (35 µL, 0.251 mmol) in DCM (4 mL) was cooled in an ice-bath. 50 wt % T3P in EtOAc (70 µL, 0.118 mmol) was added, the ice-bath was removed and the reaction mixture allowed to warm to rt and stirred at this temperature overnight. The reaction mixture was partitioned between sat. aq. NaHCO$_3$ (10 mL) and DCM (10 mL). The aqueous phase was back extracted with fresh DCM (10 mL). The combined organic extracts were washed with water (20 mL), brine (20 mL), dried (MgSO$_4$), filtered and concentrated in vacuo onto silica gel. The crude product was purified by chromatography on the Companion (12 g column, 1-5% MeOH in DCM) to afford the title compound (21 mg) as an off-white solid.

$^1$H NMR (400 MHz, DMSO-d6) δ: 9.43 (s, 1H), 9.41 (s, 1H), 8.91 (s, 1H), 8.44 (d, 1H), 8.42 (d, 1H), 8.28 (d, 1H), 8.08 (t, 2H), 7.85 (d, 1H), 7.68 (t, 1H), 7.59 (t, 1H), 7.42 (d, 1H), 7.07 (d, 1H), 6.82 (d, 2H), 6.55 (d, 1H), 6.04 (t, 1H), 4.06-4.15 (m, 1H), 3.86-3.88 (m, 2H), 3.81 (s, 3H), 3.65-3.67 (m, 2H), 3.48-3.55 (m, 6H), 3.51 (s, 3H), 3.40 (dd, 2H), 3.22 (s, 3H), 1.29 (s, 9H), 1.20 (d, 6H).

LCMS m/z 811 (M+H)$^+$ (ES$^+$); 809 (M−H)$^−$ (ES$^−$)

Example 43

5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)-N-(2-methoxyethyl)-benzamide

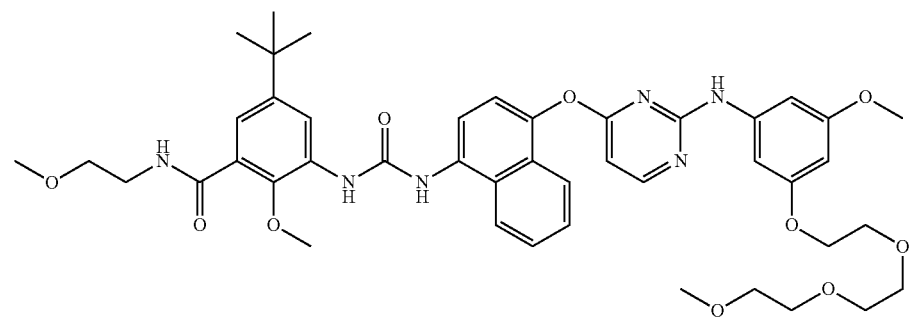 [SMILES: COCCNC(=O)c1cc(C(C)(C)C)cc(NC(=O)Nc2ccc(Oc3ccnc(Nc4cc(OC)cc(OCCOCCOCCOC)c4)n3)c3ccccc23)c1OC]

A stirred mixture of 5-(tert-butyl)-2-methoxy-3-(3-(4-((2-((3-methoxy-5-(2-(2-(2-methoxy ethoxy)ethoxy)ethoxy)phenyl)amino)pyrimidin-4-yl)oxy)naphthalen-1-yl)ureido)benzoic acid (see Example 21 above; 60 mg, 0.078 mmol), 2-methoxyethanamine (14 µL, 0.161 mmol) and triethylamine (33 µL, 0.237 mmol) in DCM (4 mL) was cooled in an ice-bath. 50 wt % T3P in EtOAc (70 µL, 0.118 mmol) was added, the ice-bath was removed and the reaction mixture allowed to warm to rt and stirred at this temperature for 2 h. The reaction mixture was partitioned between sat. aq. NaHCO$_3$ (10 mL) and DCM (10 mL). The aqueous phase was back extracted with fresh DCM (10 mL). The combined organic extracts were washed with water (20 mL), brine (20 mL), dried (MgSO$_4$), filtered and concentrated in vacuo onto silica gel. The crude product was purified by chromatography on the Companion (12 g column, 1-5% MeOH in DCM) to afford the title compound (33 mg) as an off-white solid.

$^1$H NMR (400 MHz, DMSO-d6) δ: 9.43 (s, 1H), 9.41 (s, 1H), 8.94 (s, 1H), 8.47 (d, 1H), 8.42 (d, 1H), 8.27-8.30 (m, 2H), 8.09 (d, 1H), 7.85 (d, 1H), 7.68 (t, 1H), 7.57 (t, 1H), 7.42 (d, 1H), 7.20 (d, 1H), 6.81 (d, 2H), 6.55 (d, 1H), 6.04 (t, 1H), 3.86-3.88 (m, 2H), 3.81 (s, 3H), 3.65-3.67 (m, 2H), 3.47-3.55 (m, 10H), 3.51 (s, 3H), 3.40 (dd, 2H), 3.33 (s, 3H), 3.22 (s, 3H), 1.29 (s, 9H).

LCMS m/z 827 (M+H)$^+$ (ES$^+$); 414 (M+2H)$^{2+}$ (ES$^+$)

Example 44

2-(5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)benzamido)acetic acid

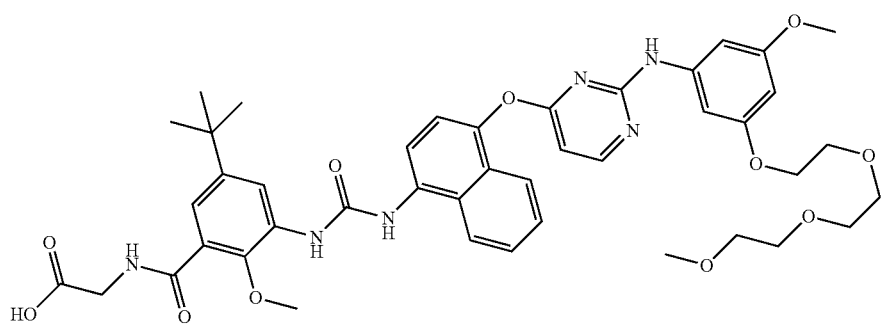 [SMILES: COCCOCCOCCOc1cc(Nc2nccc(Oc3ccc(NC(=O)Nc4cc(C(C)(C)C)cc(C(=O)NCC(=O)O)c4OC)c4ccccc34)n2)cc(OC)c1]

To a stirred solution of methyl 2-(5-(tert-butyl)-2-methoxy-3-(3-(4-((2-((3-methoxy-5-(2-(2-(2-methoxyethoxy)ethoxy)ethoxy)phenyl)amino)pyrimidin-4-yl)oxy)naphthalen-1-yl)ureido)-benzamido)acetate (see Example 37 above; 29 mg, 0.034 mmol) in THF (3 mL) and water (0.5 mL) was added NaOH (2M aq.) (100 µL, 0.200 mmol) and the reaction vigorously stirred for 4 h. The THF was removed in vacuo affording a pale purple solution. The solution was acidified with 1M HCl causing a solid to precipitate. This solid was solubilised in a 3:1 mix of DCM/EtOAc and the organic phase dried by passage through a phase sep cartridge. The organic phase was concentrated in vacuo affording the title compound (23 mg) as a pale yellow solid.

$^1$H NMR (400 MHz, DMSO-d6) δ: 9.45 (s, 1H), 9.44 (s, 1H), 8.96 (s, 1H), 8.57 (t, 1H), 8.50 (d, 1H), 8.42 (d, 1H), 8.29 (d, 1H), 8.09 (d, 1H), 7.85 (d, 1H), 7.69 (t, 1H), 7.60 (t, 1H), 7.42 (d, 1H), 7.29 (d, 1H), 6.81 (d, 2H), 6.55 (d, 1H), 6.04 (t, 1H), 4.02 (d, 2H), 3.85-3.88 (m, 2H), 3.85 (s, 3H), 3.65-3.67 (m, 2H), 3.48-3.55 (m, 6H), 3.52 (s, 3H), 3.41 (dd, 2H), 3.21 (s, 3H), 1.29 (s, 9H).

LCMS m/z 827 (M+H)$^+$ (ES$^+$); 414 (M+2H)$^{2+}$ (ES$^+$)

Example 45

N-(3-(3-(4-((2-((3-(2,5,8,11,14,17,20-Heptaoxadocosan-22-yloxy)-5-methoxyphenyl)-amino)pyridin-4-yl)oxy)naphthalen-1-yl)ureido)-5-(tert-butyl)-2-methoxyphenyl)methanesulfonamide

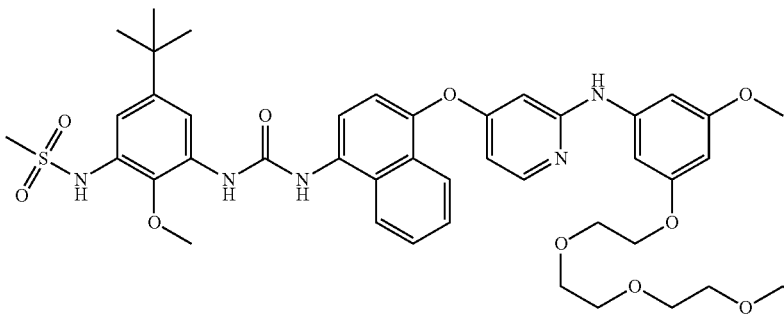
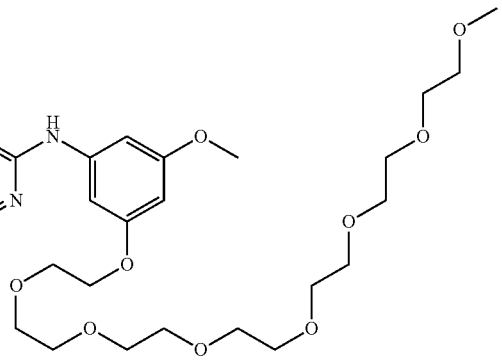

(i) 22-Chloro-2,5,8,11,14,17,20-heptaoxadocosane

SOCl$_2$ (900 µL, 12.33 mmol) was added over 5 min to a solution of 2,5,8,11,14,17,20-heptaoxadocosan-22-ol (3.2 g, 9.40 mmol) and pyridine (760 µL, 9.40 mmol) in CHCl$_3$ (20 mL) at rt. The mixture was heated under reflux for 3 h, cooled and evaporated under reduced pressure. The residue was partitioned between EtOAc (200 mL) and water (100 mL), the organic layer washed with sat. aq NaHCO$_3$ (100 mL), dried (MgSO$_4$), filtered and evaporated under reduced pressure to afford the sub-title compound (1.616 g) as an oil.

$^1$H NMR (CDCl$_3$) 400 MHz, δ: 3.77-3.74 (m, 2H), 3.68-3.62 (m, 24H), 3.56-3.54 (m, 2H), 3.38 (s, 3H).

(ii) 22-(3-Methoxy-5-nitrophenoxy)-2,5,8,11,14,17,20-heptaoxadocosane

A mixture of 3-methoxy-5-nitrophenol (0.830 g, 4.90 mmol), the product from step (i) above (1.6 g, 4.46 mmol), KI (0.370 g, 2.229 mmol) and K$_2$CO$_3$ (1.3 g, 9.41 mmol) in MeCN (20 mL) was heated at 60° C. for 30 h. The mixture was partitioned between EtOAc (150 mL) and water (100 mL), the organic layer separated, dried (MgSO$_4$) and evaporated under reduced pressure. The crude product was purified by chromatography on silica gel (80 g column, 0-5% MeOH/DCM) to afford the sub-title compound (1.958 g) as an oil.

$^1$H NMR (CDCl$_3$) 400 MHz, δ: 7.38 (t, 1H), 7.37 (t, 1H), 6.78 (t, 1H), 4.19-4.17 (m, 2H), 3.89-3.87 (m, 2H), 3.86 (s, 3H), 3.74-3.63 (m, 22H), 3.56-3.53 (m, 2H), 3.38 (s, 3H).

LCMS m/z 492 (M+H)$^+$ (ES$^+$)

(iii) 3-(2,5,8,11,14,17,20-Heptaoxadocosan-22-yloxy)-5-methoxyaniline

A mixture of the product from step (ii) above (1.95 g, 3.97 mmol) and 10% Pd/C (300 mg) in EtOH (30 mL) was hydrogenated under a balloon of hydrogen for 5 h then filtered through Celite. The filtrate was evaporated under reduced pressure to afford the sub-title compound (1.51 g) as an oil.

$^1$H NMR (CDCl$_3$) 400 MHz, δ: 5.93 (t, 1H), 5.88 (t, 1H), 5.86 (t, 1H), 4.08-4.05 (m, 2H), 3.83-3.80 (m, 2H), 3.73 (s, 3H), 3.71-3.63 (m, 22H), 3.56-3.53 (m, 2H), 3.38 (s, 3H).

(iv) tert-Butyl (4-((2-((3-(2,5,8,11,14,17,20-heptaoxadocosan-22-yloxy)-5-methoxyphenyl) amino)pyridin-4-yl)oxy)naphthalen-1-yl)carbamate N$_2$ was bubbled through a mixture of the product from step (iii) above (1.5 g, 3.25 mmol), tert-butyl (4-((2-chloropyridin-4-yl)oxy)naphthalen-1-yl)carbamate (see Example 3(ii) above; 900 mg, 2.427 mmol), BINAP (0.079 g, 0.126 mmol), Pd$_2$(dba)$_3$ (0.058 g, 0.063 mmol) and Cs$_2$CO$_3$ (1.2 g, 3.68 mmol) in dioxane (20 mL) for 5 min then the mixture heated at 100° C. for 20 h. The mixture was cooled, partitioned between EtOAc (150 mL) and water (100 mL), the organic layer washed with brine (100 mL), dried (MgSO$_4$), filtered and evaporated under reduced pressure. The crude product was purified by chromatography on silica gel (120 g column, 0-5% MeOH/DCM) to afford the sub-title compound (785 mg, 50% purity) as an oil.

LCMS m/z 796 (M+H)$^+$ (ES$^+$); 794 (M−H)$^-$ (ES$^-$)

(v) N-(3-(2,5,8,11,14,17,20-Heptaoxadocosan-22-yloxy)-5-methoxyphenyl)-4-((4-aminonaphthalen-1-yl)oxy)pyridin-2-amine TFA (1 mL, 12.98 mmol) was added to a solution of the product from step (iv) above (780 mg, 0.490 mmol) in DCM (10 mL) and the mixture stirred at rt for 6 h. The solvent was evaporated and the residue partitioned between DCM (80 mL) and aq NaHCO$_3$ (50 mL). The organic phase was separated. washed with brine (50 mL), dried (MgSO$_4$), filtered and evaporated under reduced pressure. The crude product was purified by chromatography on silica gel (80 g column, 0-5% MeOH/DCM) to afford the sub-title compound (252 mg) as a brown oil.

$^1$H NMR (CDCl$_3$) 400 MHz, δ: 7.98 (d, 1H), 7.89 (d, 1H), 7.81 (d, 1H), 7.52-7.44 (m, 2H), 7.04 (d, 1H), 6.75 (d, 1H), 6.46 (d, 1H), 6.36 (s, 1H), 6.34 (s, 1H), 6.26 (s, 1H), 6.12 (s, 1H), 3.84-3.76 (m, 4H), 3.74-3.60 (m, 25H), 3.53-3.51 (m, 2H), 3.36 (s, 3H).

LCMS m/z 696 (M+H)$^+$ (ES$^+$)

(vi) N-(3-(3-(4-((2-((3-(2,5,8,11,14,17,20-Heptaoxadocosan-22-yloxy)-5-methoxyphenyl)-amino)pyridin-4-yl)oxy)naphthalen-1-yl)ureido)-5-(tert-butyl)-2-methoxyphenyl) methanesulfonamide A mixture of phenyl (5-(tert-butyl)-2-methoxy-3-(methylsulfonamido)phenyl)carbamate (see Example 1(vi) above; 176 mg, 0.448 mmol), the product from step (v) above (240 mg, 0.345 mmol) and Et₃N (20 µL, 0.143 mmol) in iPrOAc (3 mL) was heated at 60° C. for 4 h. The solvent was evaporated and the residue purified by chromatography on silica gel (40 g column, 0-5% MeOH/DCM) then purified by preparative HPLC (Gilson, Acidic (0.1% Formic acid), 20-80% MeCN in Water) to give a gum that was loaded onto a column of SCX in MeOH. The column was washed with MeOH and then the product was eluted with 0.7 M ammonia in MeOH. The resultant mixture was concentrated in vacuo to give a red gum which was purified by chromatography on silica gel (12 g column, 0-20% MeCN/EtOAc) to afford the title compound (53 mg) as a pink foam.

¹H NMR (DMSO-d6) 400 MHz, δ: 9.39 (s, 1H), 9.15 (s, 1H), 8.92 (s, 1H), 8.88 (s, 1H), 8.30 (d, 1H), 8.19 (d, 1H), 8.12 (d, 1H), 8.10 (s, 1H), 7.87 (d, 1H), 7.73-7.69 (m, 1H), 7.63-7.59 (m, 1H), 7.39 (d, 1H), 7.02 (d, 1H), 6.92 (s, 1H), 7.78 (s, 1H), 6.59-6.57 (m, 1H), 6.08 (d, 1H), 6.04 (s, 1H), 3.99-3.97 (m, 2H), 3.81 (s, 3H), 3.72-3.70 (m, 2H), 3.65 (s, 3H), 3.59-3.46 (m, 22H), 3.42-3.40 (m, 2H), 3.23 (s, 3H), 3.10 (s, 3H), 1.27 (s, 9H).

LCMS m/z 994 (M+H)⁺ (ES⁺); 992 (M−H)⁻ (ES⁻)

Example 46

5-(tert-Butyl)-N-(2-(dimethylamino)ethyl)-2-methoxy-3-(3-(4-((2-((3-methoxy-5-(2-(2-(2-methoxyethoxy)ethoxy)ethoxy)phenyl)amino)pyrimidin-4-yl)oxy)naphthalen-1-yl)ureido)-benzamide

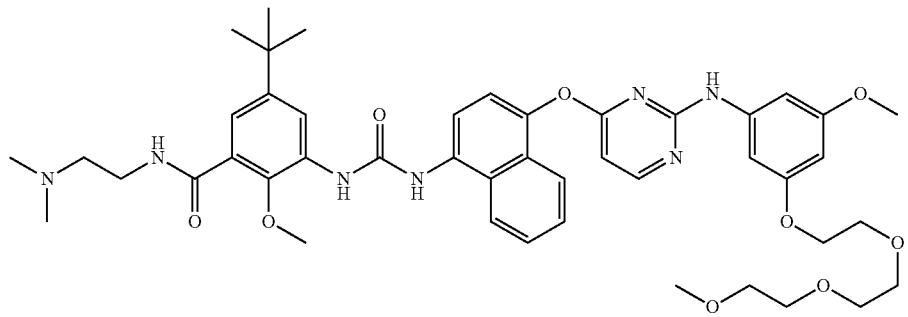 [SMILES: COCCOCCOCCOc1cc(Nc2nccc(Oc3ccc(NC(=O)Nc4cc(C(C)(C)C)cc(C(=O)NCCN(C)C)c4OC)c4ccccc34)n2)cc(OC)c1]

A stirred mixture of 5-(tert-butyl)-2-methoxy-3-(3-(4-((2-((3-methoxy-5-(2-(2-(2-methoxy ethoxy)ethoxy)ethoxy)phenyl)amino)pyrimidin-4-yl)oxy)naphthalen-1-yl)ureido) benzoic acid (see Example 21 above; 60 mg, 0.078 mmol), N1,N1-dimethylethane-1,2-diamine (17.03 µL, 0.156 mmol) and triethylamine (32.6 µL, 0.234 mmol) in DCM (4 mL) was cooled in an ice-bath. 50 wt % T3P in EtOAc (69.6 µL, 0.117 mmol) was added, the ice-bath was removed and the reaction mixture allowed to warm to rt and stirred at this temperature for 2 h. The reaction mixture was partitioned between sat. aq. NaHCO₃ (10 mL) and DCM (10 mL). The aqueous phase was back extracted with fresh DCM (10 mL). The combined organic extracts were washed with water (20 mL), brine (20 mL), dried (MgSO₄), filtered and concentrated in vacuo onto silica gel. The crude product was purified by chromatography on the Companion (12 g column, 5-10% MeOH in DCM) to afford the product as a white solid. The crude product was purified by preparative HPLC (Gilson, Basic (0.1% Ammonium Bicarbonate), Basic, Waters X-Bridge Prep-C18, 5 µm, 19×50 mm column) to afford the title compound (22 mg) as a pale brown solid.

¹H NMR (400 MHz, DMSO-d6) δ: 9.44 (s, 1H), 9.41 (s, 1H), 8.99 (s, 1H), 8.49 (d, 1H), 8.42 (d, 1H), 8.32 (t, 1H), 8.8 (d, 1H), 8.10 (d, 1H), 7.85 (d, 1H), 7.69 (t, 1H), 7.60 (t, 1H), 7.42 (d, 1H), 7.29 (d, 1H), 6.81 (d, 2H), 6.55 (d, 1H), 6.03 (t, 1H), 3.85-3.88 (m, 2H), 3.81 (s, 3H), 3.65-3.67 (m, 2H), 3.48-3.55 (m, 6H), 3.51 (s, 3H), 3.39-3.41 (m, 4H), 3.31-3.34 (m, 2H), 3.21 (s, 3H), 2.27 (bs, 6H), 1.29 (s, 9H).

LCMS m/z 840 (M+H)⁺ (ES⁺); 420 (M+2H)²⁺ (ES⁺)

Example 47

3-((4-((4-(3-(5-(tert-Butyl)-3-carbamoyl-2-methoxy-phenyl)ureido)naphthalen-1-yl)oxy)pyridin-2-yl)amino)-5-methoxy-N-(2-morpholinoethyl)benz-amide

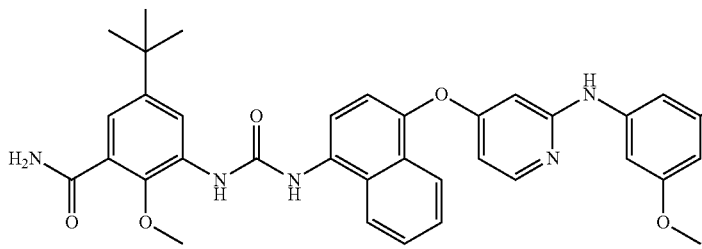

(i) Phenyl (4-((2-((3-methoxy-5-((2-morpholino-ethyl)carbamoyl)phenyl)amino)pyridin-4-yl)oxy)naphthalen-1-yl)carbamate To a stirred mixture of 3-((4-((4-aminonaphthalen-1-yl)oxy)pyridin-2-yl)amino)-5-methoxy-N-(2-morpholino-ethyl)benzamide (see Example 27(iii) above; 372 mg, 0.703 mmol) and NaHCO$_3$ (117 mg, 1.398 mmol) in DCM (1.4 mL) and THF (0.6 mL) was added phenyl chloroformate (93 μL, 0.734 mmol). The resulting mixture was stirred at rt overnight. The reaction mixture was partitioned between water (10 mL) and DCM (10 mL), then passed through a phase sep cartridge. The filtrate was concentrated in vacuo to afford a light beige foam which was triturated with a mixture of diethyl ether and isohexane, filtered and dried to afford the sub-title compound (272 mg, 77% purity) as a sand coloured solid.

LCMS m/z 634 (M+H)$^+$ (ES$^+$)

(ii) 3-((4-((4-(3-(5-(tert-Butyl)-3-carbamoyl-2-methoxyphenyl)ureido)naphthalen-1-yl)oxy)pyridin-2-yl)amino)-5-methoxy-N-(2-morpholinoethyl)benz-amide Triethylamine (23 μL, 0.165 mmol) was added to a stirred mixture of 3-amino-5-(tert-butyl)-2-methoxybenzamide (75 mg, 0.334 mmol) and the product from step (i) above (275 mg, 0.334 mmol) in i-PrOAc (4.5 mL). The resulting mixture was heated at 60° C. for 1 h. DMF (2 mL) was added and stirring continued at 60° C. overnight. The reaction was cooled then partitioned between water (20 mL) and EtOAc (20 mL). The organic phase was washed with water (2×20 mL), brine (20 mL), dried (MgSO$_4$), filtered and concentrated in vacuo to afford a brown residue. The crude product was purified by chromatography on silica gel (40 g column, 0-10% (1% NH$_3$ in MeOH) in DCM) to afford a glass, which was triturated with diethyl ether, filtered and dried to afford an off-white solid. The product was purified by chromatography on silica gel (12 g column, 0-10% MeOH in DCM) to afford the title compound (19 mg) as a white solid.

$^1$H NMR (400 MHz, DMSO-d6) δ: 9.47 (s, 1H), 9.07 (s, 1H), 8.92 (s, 1H), 8.45 (d, 1H), 8.30 (d, 1H), 8.23 (t, 1H), 8.11-8.08 (m, 2H), 7.87 (d, 1H), 7.73-7.68 (m, 2H), 7.62-7.55 (m, 3H), 7.51-7.48 (m, 1H), 7.38 (d, 1H), 7.21 (d, 1H), 6.87-6.84 (m, 1H), 6.58-6.56 (m, 1H), 6.13 (d, 1H), 3.82 (s, 3H), 3.74 (s, 3H), 3.57-3.54 (m, 4H), 2H under H2O peak at 3.33 ppm, 2.45-2.36 (m, 6H), 1.28 (s, 9H).

LCMS m/z 762 (M+H)$^+$ (ES$^+$); 760 (M−H)$^−$ (ES$^−$)

Example 48

3-((4-((4-(3-(5-(tert-Butyl)-3-carbamoyl-2-methoxy-phenyl)ureido)naphthalen-1-yl)oxy)pyridin-2-yl)amino)-5-ethynyl-N-(2-morpholinoethyl)benzamide

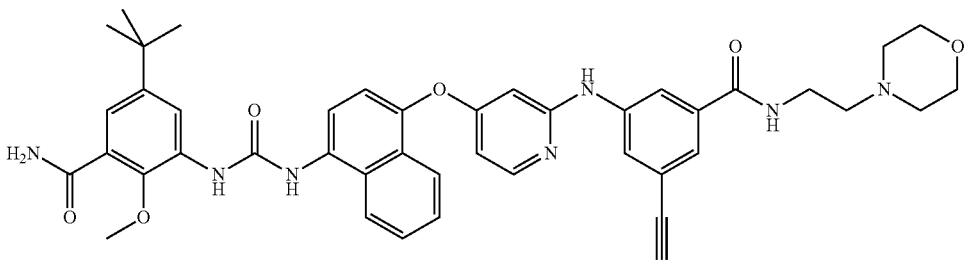 [SMILES: C#Cc1cc(Nc2cc(Oc3ccc(NC(=O)Nc4cc(C(C)(C)C)cc(C(N)=O)c4OC)c4ccccc34)ccn2)cc(C(=O)NCCN2CCOCC2)c1]

(i) Phenyl (5-(tert-butyl)-3-carbamoyl-2-methoxy-phenyl)carbamate

Phenyl chloroformate (300 μL, 2.391 mmol) was added to a stirred solution of 3-amino-5-(tert-butyl)-2-methoxybenz-amide (390 mg, 1.755 mmol) and NaHCO$_3$ (450 mg, 5.36 mmol) in THF (10 mL) and DCM (10 mL). The mixture was stirred for 2 h then filtered and the solvent evaporated from the filtrate to give a pale brown oil which was stirred in cyclohexane (20 mL) overnight. The resultant solid was filtered off and dried to give the sub-title compound (500 mg) as a tan crystalline solid.

¹H NMR (400 MHz, CDCl₃) δ 8.40 (s, 1H), 7.77 (d, 1H), 7.51 (s, 1H), 7.48-7.39 (m, 2H), 7.38-7.31 (m, 1H), 7.31-7.24 (m, 1H), 7.24-7.18 (m, 2H), 5.95 (s, 1H), 3.90 (s, 3H), 1.32 (s, 9H).

LCMS m/z 343 (M+H)⁺ (ES⁺)

(ii) 3-((4-((4-(3-(5-(tert-Butyl)-3-carbamoyl-2-methoxyphenyl)ureido)naphthalen-1-yl)oxy)pyridin-2-yl)amino)-N-(2-morpholinoethyl)-5-((triisopropylsilyl)ethynyl)benzamide TEA (10 μL, 0.072 mmol) was added to a solution of 3-((4-((4-aminonaphthalen-1-yl)oxy)-pyridin-2-yl)amino)-N-(2-morpholinoethyl)-5-((triisopropylsilyl)ethynyl)benz-

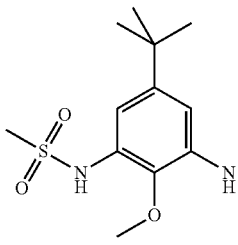

amide (see Example 39(ii) above; 260 mg, 0.392 mmol) and the product from step (i) above (150 mg, 0.438 mmol) in THF (2 mL). The reaction mixture was stirred at 60° C. for 16 h. The temperature was increased to 65° C. and stirring continued for a further 24 h. The solvents were evaporated and the crude product was purified by chromatography on silica gel (40 g column, 5% MeOH:DCM to 8%) to give a tan glass. This material was stirred in MeCN (8 mL) at 65° C. for 1 h then cooled, filtered and washed with MeCN (2 mL) to afford the sub-title compound (168 mg) as a colourless solid.

LCMS m/z 913 (M+H)⁺ (ES⁺)

(iii) 3-((4-((4-(3-(5-(tert-Butyl)-3-carbamoyl-2-methoxyphenyl)ureido)naphthalen-1-yl)oxy)pyridin-2-yl)amino)-5-ethynyl-N-(2-morpholinoethyl)benzamide The product from step (ii) above (168 mg, 0.184 mmol) was dissolved in THF (2 mL) and TBAF, 1M in THF (250 μL, 0.250 mmol) added. The reaction mixture was stirred at rt for 2 h. The solvents were evaporated and the residue stirred in diethyl ether (8 mL) for 72 h. The resulting precipitate was filtered off and washed with diethyl ether (3 mL) to give a colourless solid. The crude product was purified by preparative HPLC (Varian, Basic (0.1% Ammonium Bicarbonate), Basic, Waters X-Bridge Prep-C18, 5 μm, 19×50 mm column, 40%-80% MeCN in Water) to afford the title compound (75 mg) as a colourless solid.

¹H NMR (400 MHz, DMSO-d6) δ 9.49 (s, 1H), 9.23 (s, 1H), 8.94 (s, 1H), 8.46 (d, 1H), 8.39 (t, 1H), 8.31 (d, 1H), 8.15 (d, 1H), 8.13-8.07 (m, 2H), 7.93 (t, 1H), 7.91-7.83 (m, 1H), 7.80-7.67 (m, 2H), 7.67-7.53 (m, 2H), 7.47-7.32 (m, 2H), 7.22 (d, 1H), 6.63 (dd, 1H), 6.12 (d, 1H), 4.21 (s, 1H), 3.83 (s, 3H), 3.65-3.48 (m, 4H), 3.41-3.34 (m, 2H), 2.48-2.33 (m, 6H), 1.29 (s, 9H).

LCMS m/z 756 (M+H)⁺ (ES⁺); 754 (M−H)⁻ (ES⁻)

Example 49

3-((4-((4-(3-(5-(tert-Butyl)-2-methoxy-3-(methylsulfonamido)phenyl)ureido)naphthalen-1-yl)oxy)pyridin-2-yl)amino)-5-ethynyl-N-(2-morpholinoethyl)benzamide

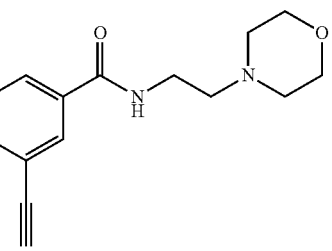

TEA (10 μL, 0.072 mmol) was added to a solution of 3-((4-((4-aminonaphthalen-1-yl)oxy)pyridin-2-yl)amino)-N-(2-morpholinoethyl)-5-((triisopropylsilyl)ethynyl)benzamide (see Example 39(ii) above; 120 mg, 0.181 mmol) and phenyl (5-(tert-butyl)-2-methoxy-3-(methylsulfonamido)phenyl)carbamate (see Example 1(vi) above; 75 mg, 0.191 mmol) in iPrOAc. The reaction mixture was stirred at 60° C. for 16 h then the temperature was increased to 65° C. and stirring continued for a further 24 h. The solvents were evaporated and the crude product was purified by chromatography on silica gel (40 g column, 2% MeOH:DCM to 8%) to give a beige glass (143 mg) which was dissolved in THF (2 mL) and TBAF, 1M in THF (200 μL, 0.200 mmol) added. The reaction mixture was stirred at rt for 2 h. The solvents were evaporated and the residue stirred in diethyl ether (8 mL) for 72 h. The resulting precipitate was filtered off and washed with diethyl ether (3 mL) to give a colourless solid. The crude product was purified by preparative HPLC (Varian, Basic (0.1% Ammonium Bicarbonate), Basic, Waters X-Bridge Prep-C18, 5 μm, 19×50 mm column, 40%-80% MeCN in Water) to afford the title compound (25 mg) as a colourless solid.

¹H NMR (400 MHz, DMSO-d6) δ 9.40 (s, 1H), 9.22 (s, 1H), 9.14 (s, 1H), 8.92 (s, 1H), 8.39 (t, 1H), 8.30 (d, 1H), 8.22-8.06 (m, 4H), 7.97-7.90 (m, 1H), 7.90-7.84 (m, 1H), 7.75-7.67 (m, 1H), 7.66-7.57 (m, 1H), 7.46-7.32 (m, 2H), 7.02 (d, 1H), 6.63 (dd, 1H), 6.12 (d, 1H), 4.20 (s, 1H), 3.81 (s, 3H), 3.56 (t, 4H), 3.09 (s, 3H), 2.47-2.35 (m, 6H), 1.27 (s, 9H). 2H under the water peak at 3.32 ppm.

LCMS m/z 806 (M+H)⁺ (ES⁺); 804 (M−H)⁻ (ES⁻)

Example 50

N-(5-(tert-Butyl)-3-(3-(4-((2-((3-(cyclopropanecarbonyl)-5-methoxyphenyl)amino)-pyrimidin-4-yl)oxy)naphthalen-1-yl)ureido)-2-methoxyphenyl)methanesulfonamide

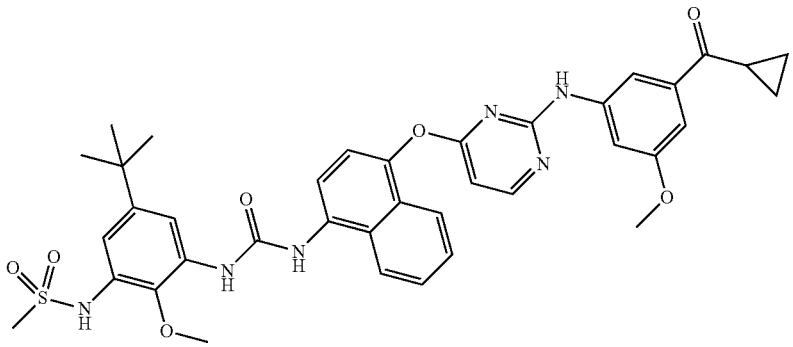 [SMILES: COc1cc(Nc2nccc(Oc3ccc(NC(=O)Nc4cc(C(C)(C)C)cc(NS(C)(=O)=O)c4OC)c4ccccc34)n2)cc(C(=O)C2CC2)c1]

(i) (3-Amino-5-methoxyphenyl)(cyclopropyl)methanone

Cyclopropylmagnesium bromide (1M in 2-Me THF, 20 mL, 20.00 mmol) was added to a mixture of 3-amino-5-methoxybenzonitrile (1 g, 6.75 mmol) and copper(I) bromide (20 mg, 0.139 mmol) in THF (10 mL) at rt under $N_2$. The mixture was stirred for 1 h at rt then heated under reflux for 2 h. The mixture was cooled and aq. 1M HCl (20 mL) added and stirred for 1 h. The mixture was partitioned between EtOAc (100 mL) and aq NaHCO₃ (50 mL), the organic layer separated, dried (MgSO₄), filtered and evaporated under reduced pressure. The crude product was purified by chromatography on silica gel (40 g column, 0-40% EtOAc/isohexane) to afford the sub-title compound (71 mg) as an orange oil.

¹H NMR (CDCl₃) 400 MHz, δ: 6.95-6.93 (m, 2H), 6.42 (t, 1H), 3.82 (s, 3H), 3.80 (s, 2H), 2.62-2.56 (m, 1H), 1.23-1.19 (m, 2H), 1.03-0.99 (m, 2H).
LCMS m/z 192 (M+H)⁺ (ES⁺)

(ii) N-(5-(tert-Butyl)-3-(3-(4-((2-((3-(cyclopropanecarbonyl)-5-methoxyphenyl)amino)-pyrimidin-4-yl)oxy)naphthalen-1-yl)ureido)-2-methoxyphenyl)methanesulfonamide A mixture of N-(5-(tert-butyl)-3-(3-(4-((2-chloropyrimidin-4-yl)oxy)naphthalen-1-yl)ureido)-2-methoxyphenyl)methanesulfonamide (see Example 7(i) above; 194 mg, 0.340 mmol), the product from step (i) above (65 mg, 0.340 mmol) and p-TSA monohydrate (20 mg, 0.105 mmol) in THF (3 mL) was heated at 60° C. for 20 h. The mixture was partitioned between EtOAc (50 mL) and sat aq NaHCO₃ (50 mL), the organic layer separated, washed with water, dried (MgSO₄), filtered and evaporated under reduced pressure. The crude product was purified by chromatography on silica gel (40 g column, 0-5% MeOH/DCM) and the product triturated with MeCN to give a solid (110 mg). The solid was purified by preparative HPLC (Varian, Basic (0.1% Ammonium Bicarbonate), Basic, Waters X-Bridge Prep-C18, 5 μm, 19×50 mm column, 50-95% MeCN in Water) to afford the title compound (5 mg) as a solid.

¹H NMR (DMSO-d6) 400 MHz, δ: 9.68 (s, 1H), 9.35 (s, 1H), 9.13 (s, 1H), 8.92 (s, 1H), 8.45 (d, 1H), 8.28 (d, 1H), 8.18 (d, 1H), 8.11 (d, 1H), 7.87-7.83 (m, 2H), 7.70-7.66 (m, 1H), 7.61-7.57 (m, 1H), 7.50 (s, 1H), 7.43 (d, 1H), 7.11-6.96 (m, 2H), 6.60 (d, 1H), 3.81 (s, 3H), 3.63 (s, 3H), 3.09 (s, 3H), 2.69-2.62 (m, 1H), 1.27 (s, 9H), 0.98 (d, 4H).
LCMS m/z 725 (M+H)⁺ (ES⁺); 723 (M−H)⁻ (ES⁻)

Example 51

5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)-N-(oxetan-3-yl)-benzamide

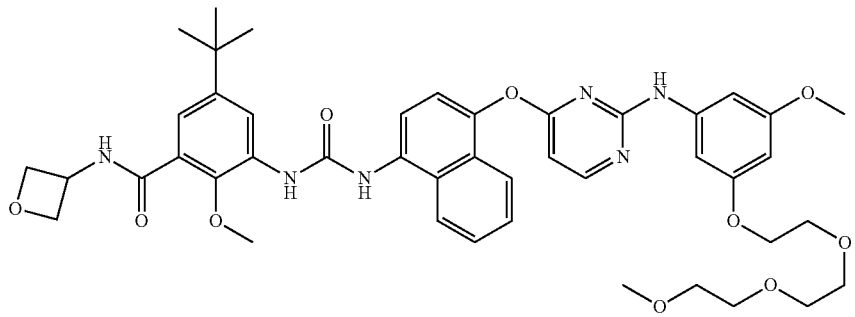 [SMILES: COCCOCCOCCOc1cc(Nc2nccc(Oc3ccc(NC(=O)Nc4cc(C(C)(C)C)cc(C(=O)NC5COC5)c4OC)c4ccccc34)n2)cc(OC)c1]

A stirred mixture of 5-(tert-butyl)-2-methoxy-3-(3-(4-((2-((3-methoxy-5-(2-(2-(2-methoxyethoxy)ethoxy)ethoxy)phenyl)amino)pyrimidin-4-yl)oxy)naphthalen-1-yl)ureido)benzoic acid (see Example 21 above; 60 mg, 0.078 mmol), oxetan-3-amine (10.85 µL, 0.156 mmol) and triethylamine (35 µL, 0.251 mmol) in DCM (4 mL) was cooled in an ice-bath. 50 wt % T3P in EtOAc (70 µL, 0.118 mmol) was added, the ice-bath was removed and the reaction mixture allowed to warm to rt and stirred for 2 h. The reaction mixture was partitioned between sat. aq. NaHCO$_3$ (10 mL) and DCM (10 mL). The aqueous phase was back extracted with fresh DCM (10 mL). The combined organic extracts were washed with water (20 mL), brine (20 mL), dried (MgSO$_4$), filtered and concentrated in vacuo onto silica gel. The crude product was purified by chromatography on the Companion (12 g column, 1-5% MeOH in DCM) to afford the title compound (38 mg) as a white solid.

$^1$H NMR (400 MHz, DMSO-d6) δ: 9.43 (s, 2H), 8.98 (d, 1H), 8.91 (s, 1H), 8.47 (d, 1H), 8.42 (d, 1H), 8.28 (d, 1H), 8.09 (d, 1H), 7.86 (d, 1H), 7.69 (t, 1H), 7.60 (t, 1H), 7.42 (d, 1H), 7.07 (d, 1H), 6.82 (d, 2H), 6.55 (d, 1H), 6.04 (t, 1H), 4.99-5.08 (m, 1H), 4.81 (t, 2H), 4.60 (t, 2H), 3.86-3.88 (m, 2H), 3.81 (s, 3H), 3.65-3.67 (m, 2H), 3.48-3.56 (m, 6H), 3.51 (s, 3H), 3.41 (dd, 2H), 3.22 (s, 3H), 1.29 (s, 9H).

LCMS m/z 825 (M+H)$^+$ (ES$^+$); 413 (M+2H)$^{2+}$ (ES$^+$)

Example 52

3-((4-((4-(3-(5-(tert-Butyl)-2-methoxy-3-(methylsulfonamido)phenyl)ureido)naphthalen-1-yl)oxy)pyridin-2-yl)amino)-5-ethynyl-N-(2-(2-methoxyethoxy)ethyl)benzamide

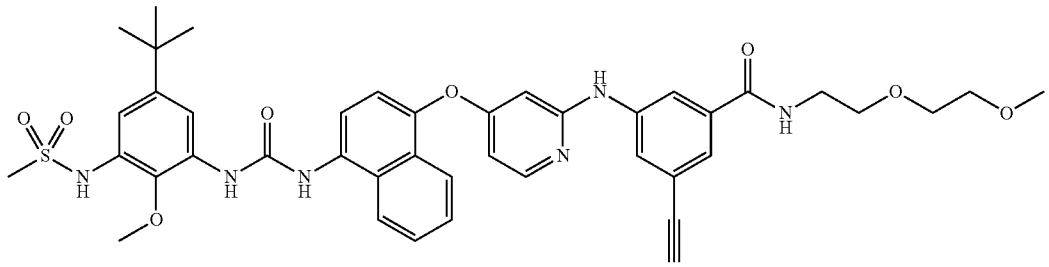

(i) 3-Amino-5-((triisopropylsilyl)ethynyl)benzoic acid

Pd(PPh$_3$)$_4$ (9.36 g, 8.10 mmol) was added to a degassed suspension of 3-amino-5-bromobenzoic acid (50 g, 231 mmol), CuI (1.499 g, 7.87 mmol), and ethynyltriisopropylsilane (80 mL, 356 mmol) in Et$_3$N (300 mL) and DMF (300 mL). The mixture was heated to 90° C. for 2 h. The mixture was cooled and carefully poured into ice-cold HCl (2.0M aq.) (1100 mL, 2200 mmol) and diluted with diethyl ether (500 mL). The biphasic mixture was filtered to remove palladium residues. The layers of the filtrate were separated and the aqueous phase was extracted with a further portion of diethyl ether (300 mL). The organic phases were combined and washed with 20% brine (2×300 mL), 40% brine (300 mL), dried (MgSO$_4$) and concentrated in vacuo affording a pale orange solid. The solid was recrystallised in acetonitrile (250 mL) and collected by filtration, washing with fresh acetonitrile (2×30 mL) affording the product as a yellow solid. The solid was slurried in hexane (250 mL) for 5 h then filtered, washing with more hexane to afford the sub-title compound (45.5 g) as a pale yellow solid.

$^1$H NMR (400 MHz, DMSO-d6) δ: 12.87 (bs, 1H), 7.18 (t, 1H), 7.10 (t, 1H), 6.86 (t, 1H), 5.54 (bs, 2H), 1.10 (s, 21H).

LCMS m/z 318 (M+H)$^+$ (ES$^+$); 316 (M−H)$^−$ (ES$^−$)

(ii) 3-((4-((4-((tert-Butoxycarbonyl)amino)naphthalen-1-yl)oxy)pyridin-2-yl)amino)-5-((triisopropylsilyl)ethynyl)benzoic acid N$_2$ was bubbled through a mixture of tert-butyl (4-((2-chloropyridin-4-yl)oxy)naphthalen-1-yl)carbamate (see Example 3(ii) above; 0.5 g, 1.348 mmol), the product from step (i) (0.490 g, 1.544 mmol), Cs$_2$CO$_3$ (0.966 g, 2.97 mmol), BINAP (0.078 g, 0.125 mmol) and Pd$_2$dba$_3$ (0.056 g, 0.061 mmol) in dioxane (15 mL) for 10 min then heated at 90 C for 4 h. The mixture was partitioned between ether (100 mL) and 1M HCl (50 mL), the organic layer separated, washed with water, dried (MgSO$_4$), filtered and evaporated under reduced pressure. The residue was triturated with ether/isohexane, filtered and dried to afford the crude sub-title compound (760 mg).

(iii) 3-((4-((4-((tert-Butoxycarbonyl)amino)naphthalen-1-yl)oxy)pyridin-2-yl)amino)-5-ethynylbenzoic acid 1.0 M TBAF in THF (2.5 mL, 2.500 mmol) was added to a stirred solution of the crude product from step (ii) above (760 mg) in THF (15 mL). The mixture was stirred for 2 h then water (10 mL) added and acidified to pH-4 with 1M HCl. The mixture was partitioned between EtOAc (70 mL) and water (40 mL), the organic phase washed with sat brine (50 mL), dried (MgSO$_4$), filtered and evaporated under reduced pressure. The crude product was purified by chromatography on silica gel (40 g column, 0-100% EtOAc/isohexane) to afford the sub-title compound (344 mg) as a foam.

$^1$H NMR (DMSO-d6) 400 MHz, δ: 13.07 (s, 1H), 9.39 (s, 1H), 9.29 (s, 1H), 8.18-8.13 (m, 4H), 7.84 (d, 1H), 7.66-7.56 (m, 3H), 7.44 (s, 1H), 7.38 (d, 1H), 6.66 (dd, 1H), 6.07 (d, 1H), 4.22 (s, 1H), 1.53 (s, 9H).

LCMS m/z 496 (M+H)$^+$ (ES$^+$)

(iv) tert-Butyl (4-((2-((3-ethynyl-5-((2-(2-methoxyethoxy)ethyl)carbamoyl)phenyl)amino)-pyridin-4-yl)oxy)naphthalen-1-yl)carbamate HATU (422 mg, 1.110 mmol) was added to a stirred solution of the product from step (iii) (500 mg, 1.009 mmol), 2-(2-methoxyethoxy)ethanamine (180 mg, 1.514 mmol) and Hünig's Base (529 µL, 3.03 mmol) in DMF (10 mL) at rt. The mixture was stirred for 3 h then partitioned between EtOAc (100 mL) and aq sat NaHCO$_3$ soln (50 mL). The organic layer was washed with brine (50 mL), dried (MgSO₄), filtered and evaporated under reduced pressure. The residue was purified by chromatography on silica gel (40 g column, 20-100% EtOAc/isohexane) to afford the sub-title compound (530 mg) as a foam.

¹H NMR (CDCl₃) 400 MHz, δ: 8.06 (d, 1H), 7.96-7.93 (m, 2H), 7.80-7.76 (m, 2H), 7.70 (s, 1H), 7.60-7.48 (m, 2H), 7.41 (s, 1H), 7.18 (d, 1H), 6.89 (s, 1H), 6.83-6.76 (m, 2H), 6.42 (dd, 1H), 6.20 (d, 1H), 3.67-3.53 (m, 8H), 3.36 (s, 3H), 3.07 (s, 1H), 1.57 (s, 9H).

LCMS m/z 597 (M+H)⁺ (ES⁺); 595 (M−H)⁻ (ES⁻)

8.18 (d, 1H), 8.15 (d, 1H), 8.13-8.09 (m, 2H), 7.93 (t, 1H), 7.88 (d, 1H), 7.78-7.67 (m, 1H), 7.66-7.57 (m, 1H), 7.42 (t, 1H), 7.40 (d, 1H), 7.03 (d, 1H), 6.63 (dd, 1H), 6.13 (d, 1H), 4.19 (s, 1H), 3.81 (s, 3H), 3.58-3.47 (m, 4H), 3.47-3.41 (m, 2H), 3.41-3.35 (m, 2H), 3.23 (s, 3H), 3.10 (s, 3H), 1.27 (s, 9H).

LCMS m/z 795 (M+H)⁺ (ES⁺); 793 (M−H)⁻ (ES⁻)

Example 53

3-((4-((4-(3-(5-(tert-Butyl)-3-carbamoyl-2-methoxyphenyl)ureido)naphthalen-1-yl)oxy)pyridin-2-yl)amino)-5-ethynyl-N-(2-(2-(2-methoxyethoxy)ethoxy)ethyl)benzamide

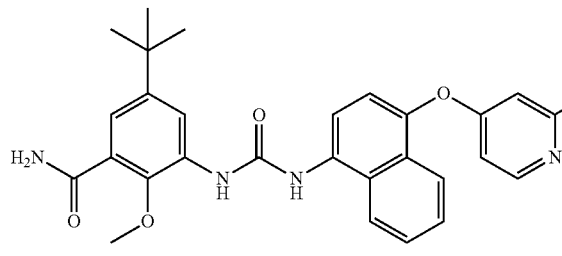
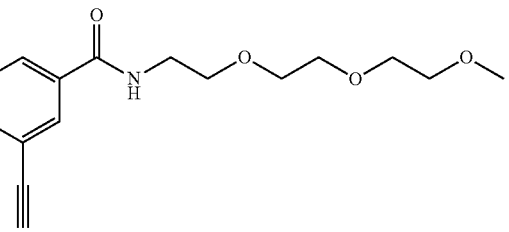

(v) 3-((4-((4-Aminonaphthalen-1-yl)oxy)pyridin-2-yl)amino)-5-ethynyl-N-(2-(2-methoxy-ethoxy)ethyl)benzamide TFA (1 mL, 12.98 mmol) was added dropwise to a stirred solution of the product from step (iv) above (520 mg, 0.871 mmol) in DCM (10 mL). The reaction was stirred at rt for 16 h. The solvents were evaporated and the residue partitioned between DCM (20 mL) and sat. NaHCO₃ soln (20 mL), the aqueous was separated and washed with DCM (20 mL). The organics were bulked, dried, filtered and evaporated to afford the title compound (430 mg) as a brown glass.

¹H NMR (400 MHz, DMSO-d6) δ 9.14 (s, 1H), 8.46 (t, 1H), 8.23-8.13 (m, 1H), 8.13-8.02 (m, 2H), 7.92 (t, 1H), 7.69-7.57 (m, 1H), 7.50-7.42 (m, 2H), 7.41 (t, 1H), 7.11 (d, 1H), 6.72 (d, 1H), 6.57 (dd, 1H), 6.06 (d, 1H), 5.85 (s, 2H), 4.18 (s, 1H), 3.58-3.47 (m, 4H), 3.47-3.42 (m, 2H), 3.40-3.35 (m, 2H), 3.23 (s, 3H).

LCMS m/z 497 (M+H)⁺ (ES⁺)

(vi) 3-((4-((4-(3-(5-(tert-Butyl)-2-methoxy-3-(methylsulfonamido)phenyl)ureido)-naphthalen-1-yl)oxy)pyridin-2-yl)amino)-5-ethynyl-N-(2-(2-methoxy-ethoxy)ethyl)-benzamide Et₃N (10 µL, 0.072 mmol) was added to a solution of phenyl (5-(tert-butyl)-2-methoxy-3-(methylsulfonamido)phenyl)carbamate (see Example 1(vi) above; 100 mg, 0.252 mmol) and the product from step (v) above (100 mg, 0.201 mmol) in iPrOAc (3 mL) at 60° C. (block temperature) and the mixture stirred for 16 h. The solvent was evaporated and the crude product was purified by chromatography on silica gel (40 g column, 1% MeOH:DCM to 6%) to give 120 mg as a brown glass The crude product was purified by preparative HPLC (Varian, Basic (0.1% Ammonium Bicarbonate), Basic, Waters X-Bridge Prep-C18, 5 µm, 19×50 mm column, 35-70% MeCN in Water) to afford the title compound (65 mg) as a colourless solid.

¹H NMR (400 MHz, DMSO-d6) δ 9.39 (s, 1H), 9.21 (s, 1H), 9.14 (s, 1H), 8.91 (s, 1H), 8.47 (t, 1H), 8.30 (d, 1H), (i) tert-Butyl (4-((2-((3-ethynyl-5-((2-(2-(2-methoxyethoxy)ethoxy)ethyl)carbamoyl)-phenyl)amino)pyridin-4-yl)oxy)naphthalen-1-yl)carbamate HATU (500 mg, 1.315 mmol) was added to a stirred solution of 3-((4-((4-(((tert-butoxycarbonyl)amino)naphthalen-1-yl)oxy)pyridin-2-yl)amino)-5-ethynylbenzoic acid (see Example 52(iii) above; 500 mg, 1.009 mmol), 2-(2-(2-methoxyethoxy)ethoxy)-ethanamine (277 mg, 1.695 mmol) and triethylamine (250 µL, 1.796 mmol) in N,N-dimethylformamide (10 mL). The mixture was stirred at rt for 18 h. The mixture was diluted with EtOAc (50 mL) and washed with water (50 mL), 20% brine (3×50 mL) and saturated brine (50 mL). The organic phase was dried (MgSO₄), filtered and concentrated under reduced pressure. The crude product was purified by chromatography on the Companion (40 g column, EtOAc) to afford the sub-title compound (580 mg) as a tan foam.

LCMS m/z 641 (M+H)⁺ (ES⁺); 639 (M−H)⁻ (ES⁻)

(ii) 3-((4-((4-Aminonaphthalen-1-yl)oxy)pyridin-2-yl)amino)-5-ethynyl-N-(2-(2-(2-methoxy-ethoxy)ethoxy)ethyl)benzamide TFA (1 mL, 12.98 mmol) was added to a solution of the product from step (i) above (580 mg, 0.905 mmol) in DCM (5 mL) at rt and stirred overnight. The volatiles were removed under reduced pressure and the residue was redissolved in DCM (20 mL). The organic phase was washed with saturated NaHCO₃ solution (20 mL), dried (MgSO₄) and concentrated under reduced pressure to yield the sub-title compound (475 mg).

LCMS m/z 541 (M+H)⁺ (ES⁺); 539 (M−H)⁻ (ES⁻)

(iii) 3-((4-((4-(3-(5-(tert-Butyl)-3-carbamoyl-2-methoxyphenyl)ureido)naphthalen-1-yl)oxy)pyridin-2-yl)amino)-5-ethynyl-N-(2-(2-(2-methoxyethoxy)ethoxy)ethyl)benzamide To a stirred mixture of phenyl (5-(tert-butyl)-3-carbamoyl-2-methoxyphenyl)carbamate (see Example 48(i) above;

127 mg, 0.366 mmol) and the product from step (ii) above (200 mg, 0.366 mmol) in i-PrOAc (6 mL) was added Et₃N (11 μL, 0.079 mmol). The reaction mixture was heated at 60° C. overnight. The solvent was removed in vacuo and the crude product was purified by chromatography on silica gel (40 g column, 0-5% MeOH in DCM) to afford a foam, which was triturated with diethyl ether, filtered and dried to afford the title compound (187 mg) as a light beige solid.

¹H NMR (400 MHz, DMSO-d6) δ: 9.47 (s, 1H), 9.21 (s, 1H), 8.92 (s, 1H), 8.48-8.44 (m, 2H), 8.30 (d, 1H), 8.15 (d, 1H), 8.11-8.09 (m, 2H), 7.93 (t, 1H), 7.87 (d, 1H), 7.73-7.69 (m, 2H), 7.63-7.59 (m, 1H), 7.56 (s, 1H), 7.42-7.38 (m, 2H), 7.22 (d, 1H), 6.62 (dd, 1H), 6.13 (d, 1H), 4.18 (s, 1H), 3.83 (s, 3H), 3.53-3.48 (m, 8H), 3.40-3.35 (m, 4H), 3.20 (s, 3H), 1.28 (s, 9H).

LCMS m/z 789 (M+H)⁺ (ES⁺)

Example 54

3-((4-((4-(3-(5-(tert-Butyl)-2-methoxy-3-(methylsulfonamido)phenyl)ureido)naphthalen-1-yl)oxy)pyridin-2-yl)amino)-5-ethynyl-N-(2-(2-(2-methoxyethoxy)ethoxy)ethyl)benzamide

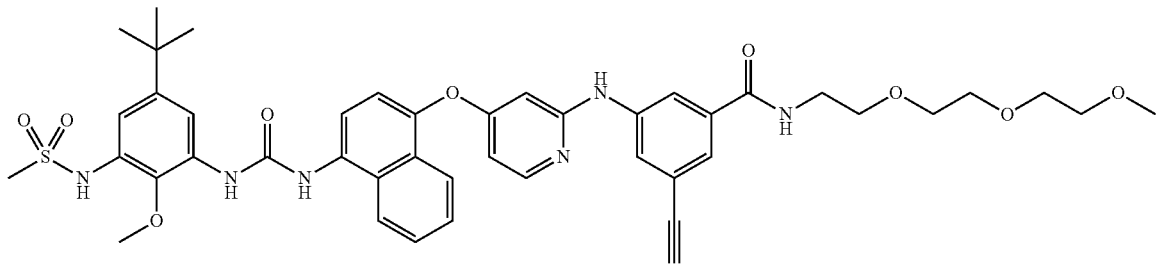

To a stirred mixture of phenyl (5-(tert-butyl)-2-methoxy-3-(methylsulfonamido)-phenyl)carbamate (see Example 1(vi) above; 144 mg, 0.363 mmol) and 3-((4-((4-aminonaphthalen-1-yl)oxy)pyridin-2-yl)amino)-5-ethynyl-N-(2-(2-(2-methoxyethoxy)ethoxy)-ethyl)benzamide (see Example 53(ii) above; 198 mg, 0.363 mmol) in i-PrOAc (6 mL) was added Et₃N (11 μL, 0.079 mmol). The reaction mixture was heated at 60° C. overnight. The solvent was removed in vacuo. The crude product was purified by chromatography on silica gel (40 g column, 0-5% MeOH in DCM) to afford an orange foam at ~85% purity. The crude product was purified by preparative HPLC (Varian, Basic (0.1% Ammonium Bicarbonate), Basic, Waters X-Bridge Prep-C18, 5 μm, 19×50 mm column, 35-70% MeCN in Water) to afford the title compound (89 mg) as an off-white solid.

¹H NMR (400 MHz, DMSO-d6) δ: 9.40 (s, 1H), 9.25 (s, 1H), 9.13 (s, 1H), 8.91 (s, 1H), 8.47 (t, 1H), 8.30 (d, 1H), 8.18 (d, 1H), 8.15-8.08 (m, 3H), 7.92 (t, 1H), 7.88-7.86 (m, 1H), 7.72-7.68 (m, 1H), 7.63-7.59 (m, 1H), 7.43 (s, 1H), 7.39 (d, 1H), 7.02 (d, 1H), 6.63 (dd, 1H), 6.13 (d, 1H), 4.19 (s, 1H), 3.80 (s, 3H), 3.52-3.48 (m, 8H), 3.40-3.37 (m, 4H), 3.20 (s, 3H), 3.09 (s, 3H), 1.26 (s, 9H).

LCMS m/z 839 (M+H)⁺ (ES⁺)

Example 55

5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)benzenesulfonamide

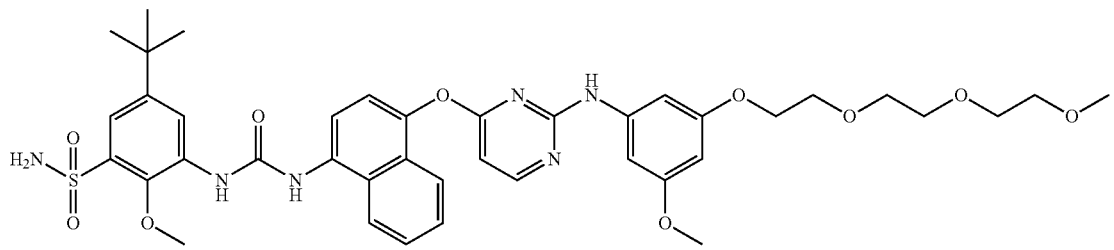 [SMILES: COCCOCCOCCOc1cc(Nc2nccc(Oc3ccc(NC(=O)Nc4cc(C(C)(C)C)cc(S(N)(=O)=O)c4OC)c4ccccc34)n2)cc(OC)c1]

(i) 5-(tert-Butyl)-2-methoxy-3-nitrobenzenesulfonamide

To an ice-cooled solution of 5-(tert-butyl)-2-methoxy-3-nitrobenzene-1-sulfonyl chloride (1.5 g, 4.87 mmol) in acetone (8 mL) was added NH$_4$OH (20 mL, 502 mmol). The resulting mixture was stirred at rt for 1 h. The mixture was diluted with water (50 mL) and concentrated under reduced pressure remove excess ammonia and acetone. The aqueous precipitate was collected by filtration to yield the sub-title compound (990 mg) as an off white solid.

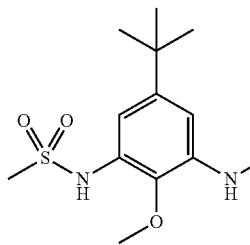

$^1$H NMR (400 MHz, DMSO-d6) δ 8.15 (d, 1H), 8.07 (d, 1H), 7.61 (br s, 2H), 3.90 (s, 3H), 1.33 (s, 9H).
LCMS m/z 306 (M+NH$_4$)+(ES$^+$); 287 (M−H)$^−$ (ES$^−$)

(ii) 3-Amino-5-(tert-butyl)-2-methoxybenzenesulfonamide

5% Platinum on carbon was added to a solution of the product from step (i) above (440 mg, 1.526 mmol) in ethanol (8 mL) and ethyl acetate (2 mL) and stirred under a balloon of hydrogen at rt for 2 h. Repeated in duplicate. The combined reactions were filtered to remove the catalyst and the filtrate was concentrated under reduced pressure. The crude product was purified by chromatography on the Companion (12 g column, Et$_2$O) to afford the sub-title compound (870 mg) as a white solid.
$^1$H NMR (400 MHz, DMSO-d6) δ 6.98 (s, 2H), 6.97 (d, 1H), 6.95 (d, 1H), 5.18 (br s, 2H), 3.73 (s, 3H), 1.23 (s, 9H).
LCMS m/z 259 (M+H)$^+$ (ES$^+$); 257 (M−H)$^−$ (ES$^−$)

(iii) 5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)benzenesulfonamide The product from step (ii) above (65.0 mg, 0.251 mmol), phenyl (4-((2-((3-methoxy-5-(2-(2-(2-methoxyethoxy)ethoxy)ethoxy)phenyl)amino)pyrimidin-4-yl)oxy)naphthalen-1-yl) carbamate (see Example 19(i) above; 100 mg, 0.156 mmol) and Et$_3$N (5.00 µL, 0.036 mmol) in iPrOAc were heated to 50° C. (block temperature) overnight. The temperature was increased to 63° C. and the mixture was stirred for a further 18 h. The mixture was concentrated under reduced pressure and the residue was purified by chromatography on the Companion (40 g column, 50-100% EtOAc/isohexane) to afford the title compound (55 mg) as a white powder.
$^1$H NMR (400 MHz, DMSO-d6) δ 9.46-9.40 (m, 2H), 8.99 (s, 1H), 8.55 (d, 1H), 8.41 (d, 1H), 8.27 (d, 1H), 8.10 (d, 1H), 7.86 (d, 1H), 7.69 (ddd, 1H), 7.60 (ddd, 1H), 7.44 (s, 1H), 7.43 (d, 1H), 7.33 (s, 2H), 6.86-6.74 (m, 2H), 6.55 (d, 1H), 6.04 (dd, 1H), 3.92 (s, 3H), 3.90-3.82 (m, 2H), 3.70-3.63 (m, 2H), 3.58-3.45 (m, 6H), 3.51 (s, 3H), 3.43-3.38 (m, 2H), 3.22 (s, 3H), 1.30 (s, 9H).
LCMS m/z 805 (M+H)$^+$ (ES$^+$); 803 (M−H)$^−$ (ES$^−$)

Example 56

(R)-3-((4-((4-(3-(5-(tert-Butyl)-2-methoxy-3-(methylsulfonamido)phenyl)ureido)-naphthalen-1-yl)oxy)pyrimidin-2-yl)amino)-5-ethynyl-N-(1-morpholinopropan-2-yl)-benzamide

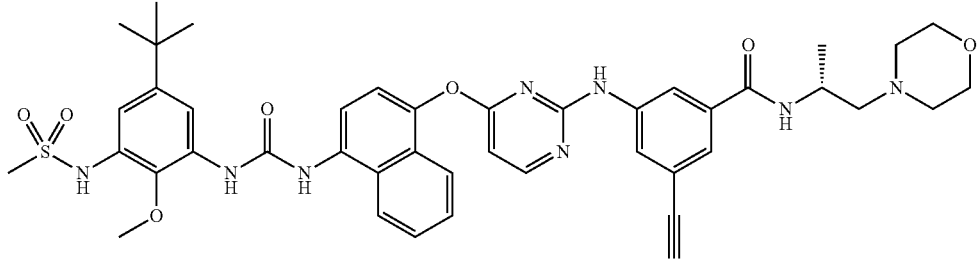 [SMILES: C#Cc1cc(Nc2nccc(Oc3ccc(NC(=O)Nc4cc(C(C)(C)C)cc(NS(C)(=O)=O)c4OC)c4ccccc34)n2)cc(C(=O)N[C@H](C)CN2CCOCC2)c1]

(i) 3-((4-((4-((tert-Butoxycarbonyl)amino)naphthalen-1-yl)oxy)pyrimidin-2-yl)amino)-5-((triisopropylsilyl)ethynyl)benzoic acid A suspension of tert-butyl (4-((2-chloropyrimidin-4-yl)oxy)naphthalen-1-yl)carbamate (see, for example, Ito, K. et al., WO 2010/067130, 17 Jun. 2010; 42.6 g, 115 mmol), 3-amino-5-((triisopropylsilyl)ethynyl)benzoic acid (see Example 52(i) above; 40.00 g, 126 mmol), BINAP (6.42 g, 10.31 mmol) and caesium carbonate (74.6 g, 229 mmol) in 1,4-dioxane (500 mL) was degassed with nitrogen for 10 minutes. Pd$_2$(dba)$_3$ (4.20 g, 4.58 mmol) was added and the mixture was heated to 90° C. for 2.5 h. The mixture was diluted with diethyl ether (600 mL) then washed with water (600 mL), followed by 0.5 M HCl solution (500 mL) and saturated brine (500 mL). The organic phase was dried (MgSO$_4$), filtered and concentrated in vacuo affording the sub-title compound (96 g) as a red foam which was used in the next step without further purification.

(ii) 3-((4-((4-((tert-butoxycarbonyl)amino)naphthalen-1-yl)oxy)pyrimidin-2-yl)amino)-5-ethynylbenzoic acid The compound from step (i) above (96 g) was dissolved in THF (60 mL) and diluted with MeCN (400 mL). 1.0 M TBAF in THF (235 mL, 235 mmol) was added and the reaction stirred at rt overnight. The reaction was diluted with MeCN (300 mL) and water (600 mL), then 1M HCl solution (100 mL, 1 eq.) was added and stirring continued resulting in the precipitation of a pink solid which was collected by filtration. The pink solid was triturated in MeCN at 80° C., collected by filtration and dried at 40° C. under vacuum for 2 h. The solid was re-suspended in (9:1) EtOAc/THF (400 mL) and heated to 60° C. for 90 mins then cooled to rt and stirred overnight. The suspended solid was collected by filtration, washing with EtOAc affording the sub-title compound (47 g) as a pale yellow/beige solid.

¹H NMR (400 MHz, DMSO-d6) δ: 13.12 (bs, 1H), 9.83 (s, 1H), 9.32 (s, 1H), 8.46 (d, 1H), 8.28 (s, 1H), 8.10 (d, 1H), 8.01 (s, 1H), 7.82 (d, 1H), 7.54-7.63 (m, 3H), 7.49 (s, 1H), 7.42 (d, 1H), 6.61 (d, 1H), 4.17 (s, 1H), 1.52 (s, 9H).
LCMS m/z 497 (M+H)⁺ (ES⁺); 495 (M–H)⁻ (ES⁻)

(iii) (R)-tert-Butyl (4-((2-((3-ethynyl-5-((1-morpholinopropan-2-yl)carbamoyl)phenyl)-amino)pyrimidin-4-yl)oxy)naphthalen-1-yl)carbamate To a stirred solution of (R)-1-morpholinopropan-2-amine, HCl (0.364 g, 2.014 mmol), the product from step (ii) above (1.0 g, 2.014 mmol) and HATU (0.996 g, 2.62 mmol) in DMF (15 mL) was added Hünig's base (1.403 mL, 8.06 mmol) and the reaction was stirred overnight. The reaction was diluted with water resulting in the precipitation of a beige solid. The suspension was stirred for an additional 20 minutes then the solid collected by filtration washing with water. The crude product was purified by chromatography on the Companion (80 g column, 1-5% MeOH in DCM) to afford the sub-title compound (752 mg) as a pale brown solid.
LCMS m/z 623 (M+H)⁺ (ES⁺); 312 (M+2H)²⁺ (ES⁺)

(iv) (R)-3-((4-((4-aminonaphthalen-1-yl)oxy)pyrimidin-2-yl)amino)-5-ethynyl-N-(1-morpholinopropan-2-yl)benzamide To a stirred solution of the product from step (iii) above (752 mg, 1.208 mmol) in DCM (80 mL) was added TFA (2000 µL, 26.0 mmol) and the reaction stirred at rt overnight. The mixture was concentrated in vacuo and the residue re-dissolved in DCM (100 mL). The solution was washed with sat. NaHCO₃ solution (100 mL) and the organic phase dried (MgSO₄), filtered and concentrated in vacuo affording the sub-title compound (667 mg) as a pale brown glassy solid.
¹H NMR (400 MHz, DMSO-d6) δ: 9.74 (s, 1H), 8.35 (d, 1H), 8.12-8.15 (m, 2H), 8.05 (s, 1H), 7.95 (s, 1H), 7.62-7.64 (m, 1H), 7.41-7.46 (m, 3H), 7.14 (d, 1H), 6.70 (d, 1H), 6.36 (d, 1H), 5.76 (s, 2H), 4.13-4.20 (m, 1H), 4.18 (s, 1H), 3.54 (t, 4H), 2.39-2.45 (m, 5H), 2.26 (dd, 1H), 1.13 (d, 3H).
LCMS m/z 523 (M+H)⁺ (ES⁺); 262 (M+2H)²⁺ (ES⁺)

(v) (R)-3-((4-((4-(3-(5-(tert-Butyl)-2-methoxy-3-(methylsulfonamido)phenyl)ureido)-naphthalen-1-yl)oxy)pyrimidin-2-yl)amino)-5-ethynyl-N-(1-morpholinopropan-2-yl)-benzamide To a stirred solution of phenyl (5-(tert-butyl)-2-methoxy-3-(methylsulfonamido)phenyl)-carbamate (see Example 1(vi) above; 90 mg, 0.227 mmol) and the product from step (iv) above (100 mg, 0.191 mmol) in iPrOAc (3 mL) was added triethylamine (10 µL, 0.072 mmol). The reaction was heated to 60° C. (block temperature) for 18 h during which time a gel formed. The reaction was diluted with THF and concentrated in vacuo onto silica gel. The residue was purified by chromatography on the Companion (12 g column, 3% MeOH:DCM to 5%) affording an orange solid. The solid was triturated in iPrOAc and the solid collected by filtration, washing with further iPrOAc affording a cream-coloured solid. The solid was dissolved in MeOH and reconcentrated twice affording the title compound (72 mg) as a cream-coloured solid.
¹H NMR (DMSO-d6) 400 MHz, δ: 9.75 (s, 1H), 9.33 (s, 1H), 9.14 (s, 1H), 8.90 (s, 1H), 8.44 (d, 1H), 8.27 (d, 1H), 8.18 (d, 1H), 8.13 (d, 1H), 8.09 (d, 1H), 8.05 (d, 1H), 7.89 (s, 1H), 7.85 (d, 1H), 7.68 (t, 1H), 7.60 (t, 1H), 7.44-7.46 (m, 2H), 7.03 (d, 1H), 6.55 (d, 1H), 4.12-4.20 (m, 1H), 4.12 (s, 1H), 3.81 (s, 3H), 3.53 (t, 4H), 3.10 (s, 3H), 2.34-2.44 (m, 5H), 2.26 (dd, 1H), 1.27 (s, 9H), 1.12 (d, 3H).
LCMS m/z 821 (M+H)⁺ (ES⁺); 411 (M+2H)²⁺ (ES⁺)

Example 57

(S)-3-((4-((4-(3-(5-(tert-butyl)-2-methoxy-3-(methylsulfonamido)phenyl)ureido)-naphthalen-1-yl)oxy)pyrimidin-2-yl)amino)-5-ethynyl-N-(1-morpholinopropan-2-yl)benzamide

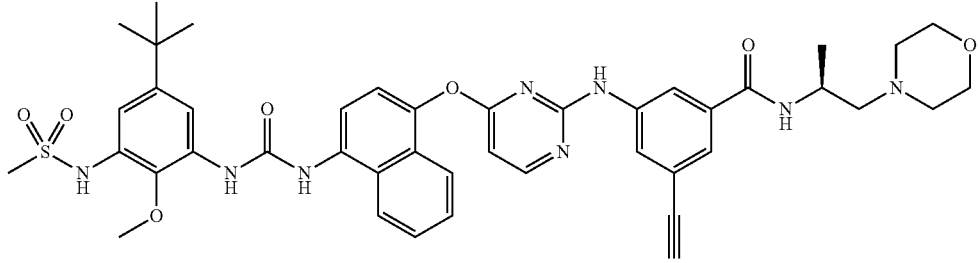 [SMILES: C#Cc1cc(Nc2nccc(Oc3ccc(NC(=O)Nc4cc(C(C)(C)C)cc(NS(C)(=O)=O)c4OC)c4ccccc34)n2)cc(C(=O)N[C@@H](C)CN2CCOCC2)c1]

(i) (S)-tert-Butyl (4-((2-((3-ethynyl-5-((1-morpholinopropan-2-yl)carbamoyl)phenyl)amino)pyrimidin-4-yl)oxy)naphthalen-1-yl)carbamate To a stirred solution of (S)-1-morpholinopropan-2-amine, HCl (0.364 g, 2.014 mmol), 3-((4-((4-((tert-butoxycarbonyl)amino)naphthalen-1-yl)oxy)pyrimidin-2-yl)amino)-5-ethynyl-benzoic acid (see Example 56(ii) above; 1.0 g, 2.014 mmol) and HATU (0.996 g, 2.62 mmol) in DMF (15 mL) was added Hünig's base (1.403 mL, 8.06 mmol) and the reaction was stirred overnight. The reaction was diluted with water resulting in the precipitation of a beige solid. The suspension was stirred for an additional 20 minutes then the solid collected by filtration washing with water. The crude product was purified by chromatography on the Companion (80 g column, 1-5% MeOH in DCM) to afford the sub-title compound (920 mg) as a pale brown solid.
LCMS m/z 623 (M+H)⁺ (ES⁺); 312 (M+2H)²⁺ (ES⁺)

(ii) (S)-3-((4-((4-Aminonaphthalen-1-yl)oxy)pyrimidin-2-yl)amino)-5-ethynyl-N-(1-morpholinopropan-2-yl)benzamide To a stirred solution of the product from step (i) above (920 mg, 1.477 mmol) in DCM (80 mL) was added TFA (2000 μL, 26.0 mmol) and the reaction stirred at rt overnight. The mixture was concentrated in vacuo and the residue re-dissolved in DCM (100 mL). The solution was washed with sat. NaHCO$_3$ solution (100 mL) and the organic phase dried (MgSO$_4$), filtered and concentrated in vacuo affording the sub-title compound (728 mg) as a pale brown solid.

$^1$H NMR (400 MHz, DMSO-d6) δ: 9.74 (s, 1H), 8.35 (d, 1H), 8.11-8.15 (m, 2H), 8.05 (s, 1H), 7.95 (s, 1H), 7.62-7.65 (m, 1H), 7.41-7.47 (m, 3H), 7.14 (d, 1H), 6.71 (d, 1H), 6.36 (d, 1H), 5.76 (s, 2H), 4.13-4.20 (m, 1H), 4.18 (s, 1H), 3.54 (t, 4H), 2.39-2.45 (m, 5H), 2.26 (dd, 1H), 1.13 (d, 3H).

LCMS m/z 523 (M+H)$^+$ (ES$^+$); 262 (M+2H)$^{2+}$ (ES$^+$)

(iii) (S)-3-((4-((4-(3-(5-(tert-butyl)-2-methoxy-3-(methylsulfonamido)phenyl)ureido)-naphthalen-1-yl)oxy)pyrimidin-2-yl)amino)-5-ethynyl-N-(1-morpholinopropan-2-yl)-benzamide To a stirred solution of phenyl (5-(tert-butyl)-2-methoxy-3-(methylsulfonamido)phenyl)-carbamate (see Example 1(vi) above; 91 mg, 0.230 mmol) and the product from step (ii) above (100 mg, 0.191 mmol) in iPrOAc (3 mL) was added triethylamine (10 μL, 0.072 mmol).

The reaction was heated to 60° C. (block temperature) for 18 h during which time a gel formed. The reaction was diluted with THF and concentrated in vacuo onto silica gel. The residue was purified by chromatography on the Companion (12 g column, 3% MeOH:DCM to 5%) affording an orange solid. The solid was triturated in iPrOAc and the solid collected by filtration, washing with further iPrOAc affording a cream coloured solid. The material was dissolved in MeOH and re-concentrated twice affording the title compound (64 mg) as a cream-coloured solid.

$^1$H NMR (DMSO-d6) 400 MHz, δ: 9.75 (s, 1H), 9.33 (s, 1H), 9.13 (s, 1H), 8.90 (s, 1H), 8.44 (d, 1H), 8.27 (d, 1H), 8.18 (d, 1H), 8.13 (d, 1H), 8.09 (d, 1H), 8.05 (d, 1H), 7.89 (s, 1H), 7.85 (d, 1H), 7.68 (t, 1H), 7.60 (t, 1H), 7.44-7.46 (m, 2H), 7.03 (d, 1H), 6.55 (d, 1H), 4.12-4.20 (m, 1H), 4.12 (s, 1H), 3.81 (s, 3H), 3.53 (t, 4H), 3.10 (s, 3H), 2.34-2.44 (m, 5H), 2.26 (dd, 1H), 1.27 (s, 9H), 1.12 (d, 3H).

LCMS m/z 821 (M+H)$^+$ (ES$^+$); 411 (M+2H)$^{2+}$ (ES$^+$)

Example 58

N-(5-(tert-Butyl)-3-(3-(4-((2-((4-chloro-3-methoxy-5-(2-(2-(2-methoxyethoxy)ethoxy)ethoxy)-phenyl) amino)pyrimidin-4-yl)oxy)naphthalen-1-yl)ureido)-2-methoxyphenyl)-methanesulfonamide (i) 5-Amino-2-chloro-3-methoxyphenol BBr$_3$ (1.1 mL, 11.64 mmol) was added dropwise to a solution of 4-chloro-3,5-dimethoxyaniline (2.19 g, 11.67 mmol) in DCM at rt. (ppte formed). The mixture was stirred for 18 h then heated under reflux for 6 h. A further 1 ml of BBr$_3$ was added and the mixture stirred for 24 h then quenched carefully with MeOH (10 mL). Water (100 mL) was added and the aqueous layer separated then basified with sat aq Na$_2$CO$_3$ to pH 6. The mixture was extracted with DCM (2×100 mL), the organic layers combined, dried (MgSO$_4$), filtered and evaporated under reduced pressure. The residue was triturated with ether/isohexane to afford the sub-title compound (640 mg).

$^1$H NMR (400 MHz; DMSO-d6) δ 9.44 (s, 1H), 5.84 (s, 1H), 5.82 (s, 1H), 5.09 (s, 2H), 3.69 (s, 3H).

LCMS m/z 174/6 (M+H)$^+$ (ES$^+$)

(ii) 4-Chloro-3-methoxy-5-(2-(2-(2-methoxyethoxy) ethoxy)ethoxy)aniline

A mixture of 5-amino-2-chloro-3-methoxyphenol (630 mg, 3.23 mmol), 1-bromo-2-(2-(2-methoxyethoxy)ethoxy) ethane (907 mg, 3.99 mmol), sodium iodide (54 mg, 0.360 mmol) and K$_2$CO$_3$ (1.5 g, 10.85 mmol) in MeCN (20 mL) was heated at 60° C. for 18 h. The mixture was cooled and partitioned between EtOAc (150 mL) and water (150 mL). The organic layer was separated, dried (MgSO$_4$), filtered and evaporated under reduced pressure. The crude product was purified by chromatography on silica gel (40 g column, 0-100% EtOAc/isohexane) to afford the sub-title compound (860 mg) as an oil.

$^1$H NMR (400 MHz; CDCl$_3$) δ 5.98 (s, 1H), 5.96 (s, 1H), 4.13 (t, 2H), 3.88 (t, 2H), 3.84 (s, 3H), 3.80-3.78 (m, 2H), 3.69-3.66 (m, 4H), 3.57-3.55 (m, 2H), 3.38 (s, 3H).

LCMS m/z 320/2 (M+H)$^+$ (ES$^+$)

(iii) N-(5-(tert-Butyl)-3-(3-(4-((2-((4-chloro-3-methoxy-5-(2-(2-(2-methoxyethoxy)ethoxy)-ethoxy) phenyl)amino)pyrimidin-4-yl)oxy)naphthalen-1-yl) ureido)-2-methoxyphenyl) methanesulfonamide A suspension of N-(5-(tert-butyl)-3-(3-(4-((2-chloropyrimidin-4-yl)oxy)naphthalen-1-yl)ureido)-2-methoxyphenyl)methanesulfonamide (see Example 7(i) above; 100 mg, 0.175 mmol), the product from step (ii) above (112 mg, 0.351 mmol) and p-TSA monohydrate (10 mg, 0.053 mmol) in THF/DMF (6 mL, 1:2) was heated at 60° C. for 24 h. The reaction was cooled to rt and partitioned between EtOAc (40 mL) and sat. aq. NaHCO$_3$ (30 mL). The aqueous layer was extracted with EtOAc (2×40 mL). The combined organic

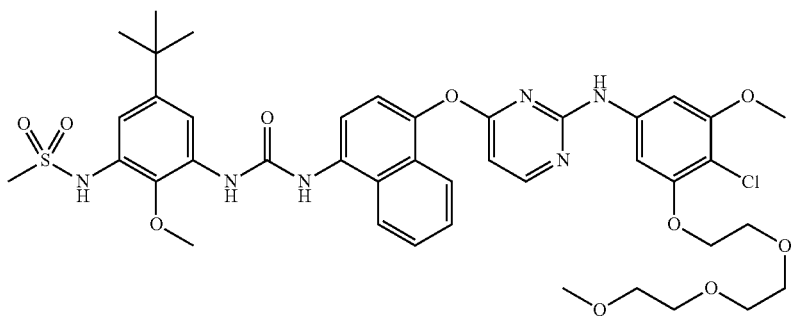 [SMILES: COCCOCCOCCOc1cc(Nc2nccc(Oc3ccc(NC(=O)Nc4cc(C(C)(C)C)cc(NS(C)(=O)=O)c4OC)c4ccccc34)n2)cc(OC)c1Cl]

extracts were washed with water (2×50 mL), brine (2×50 mL), dried (MgSO$_4$), filtered and concentrated in vacuo onto silica gel. The crude product was purified by chromatography on silica gel (40 g column, 1-3% MeOH) affording the title compound (53 mg) as an off-white solid.

$^1$H NMR (400 MHz; DMSO-d6) δ: 9.15 (s, 1H), 9.36 (s, 1H), 9.14 (s, 1H), 8.90 (s, 1H), 8.46 (d, 1H), 8.27 (d, 1H), 8.19 (d, 1H), 8.08 (d, 1H), 7.86 (d, 1H), 7.69 (t, 1H), 7.60 (t, 1H), 7.42 (d, 1H), 7.07 (d, 2H), 7.03 (d, 1H), 6.64 (d, 1H), 3.82 (s, 5H), 3.66-3.68 (m, 2H), 3.57 (dd, 2H), 3.46-3.50 (m, 7H), 3.39 (dd, 2H), 3.21 (s, 3H), 3.10 (s, 3H), 1.27 (s, 9H).

LCMS m/z 427 (M+2H)$^{2+}$ (ES$^+$)

Example 59

1-(5-(tert-Butyl)-2-methoxy-3-(1,3,4-oxadiazol-2-yl) phenyl)-3-(4-((2-((3-methoxy-5-(2-(2-(2-methoxy-ethoxy)ethoxy)ethoxy)phenyl)amino)pyrimidin-4-yl) oxy)naphthalen-1-yl)urea

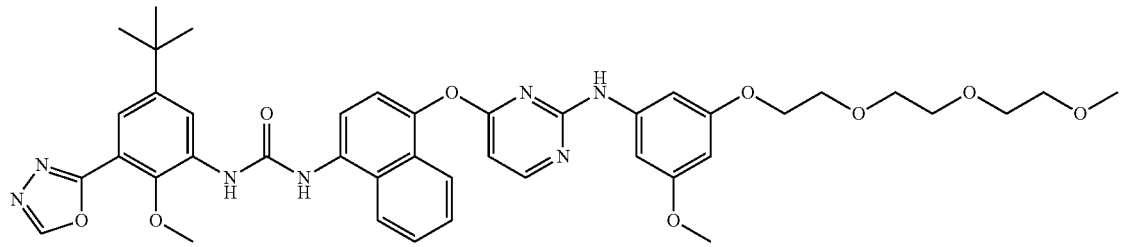 [SMILES: COCCOCCOCCOc1cc(Nc2nccc(Oc3ccc(NC(=O)Nc4cc(C(C)(C)C)cc(-c5nnco5)c4OC)c4ccccc34)n2)cc(OC)c1]

(i) tert-Butyl 2-(5-(tert-butyl)-2-methoxy-3-nitrobenzoyl)hydrazinecarboxylate

To a solution of 5-(tert-butyl)-2-methoxy-3-nitrobenzoic acid (500 mg, 1.974 mmol), tert-butyl hydrazinecarboxylate (313 mg, 2.369 mmol) and Hünig's Base (1034 μL, 5.92 mmol) in dry DMF (5 mL) was added HATU (901 mg, 2.369 mmol) and the mixture stirred for 2 hours at rt. The reaction mixture was poured onto water (50 mL) and extracted into ethyl acetate (2×20 mL). The combined organic phase was dried (MgSO$_4$), filtered and concentrated in vacuo. The crude product was purified by chromatography on the Companion (40 g column, 0-50% ethyl acetate:isohexane) to afford the sub-title compound (607 mg) as a colourless oil which turned yellow on standing and slowly began to crystallise.

$^1$H NMR (400 MHz, DMSO-d6) δ: 10.17 (s, 1H), 9.06 (s, 1H), 7.99 (d, 1H), 7.62 (s, 1H), 3.88 (s, 3H), 1.44 (s, 9H), 1.31 (s, 9H).

LCMS m/z 312 (M+H-tBu)$^+$ (ES$^+$); 366 (M-H)$^-$ (ES$^-$)

(ii) 5-(tert-Butyl)-2-methoxy-3-nitrobenzohydrazide

To a solution of the product from step (i) above (607 mg, 1.487 mmol) in DCM (15 mL) was added TFA (5728 μL, 74.3 mmol) and the mixture allowed to stand for 1 hour. The reaction was concentrated in vacuo and the residue was loaded onto a pre-conditioned cartridge of SCX resin. The resin was washed with MeOH and the product released with 1% NH$_3$ in MeOH affording the sub-title compound (302 mg) as a yellow oil.

$^1$H NMR (400 MHz, DMSO-d6) δ: 9.63 (s, 1H), 7.92 (d, 1H), 7.63 (d, 1H), 4.58 (bs, 2H), 3.83 (s, 3H), 1.30 (s, 9H).

LCMS m/z 268 (M+H)$^+$ (ES$^+$)

(iii) 2-(5-(tert-Butyl)-2-methoxy-3-nitrophenyl)-1,3,4-oxadiazole

The product from step (ii) above (302 mg, 1.130 mmol) was dissolved in triethyl orthoformate (8.0 mL, 48.1 mmol) and p-TSA monohydrate (21.49 mg, 0.113 mmol) added. The mixture heated to 130° C. with stirring overnight then cooled to rt. The reaction was concentrated in vacuo and the crude product purified by chromatography on the Companion (12 g column, 1-3% MeOH in DCM) to afford the sub-title compound (350 mg, 90% purity) as a yellow oil.

$^1$H NMR (400 MHz, DMSO-d6) δ: 9.47 (s, 1H), 8.20 (d, 1H), 8.19 (d, 1H), 3.87 (s, 3H), 1.35 (s, 9H).

LCMS m/z 278 (M+H)$^+$ (ES$^+$)

(iv) 5-(tert-Butyl)-2-methoxy-3-(1,3,4-oxadiazol-2-yl)aniline

The product from step (iii) above (350 mg, 1.136 mmol) was dissolved in ethanol (7 mL) and Fe powder (630 mg, 11.28 mmol) was added followed by a solution of NH$_4$Cl (600 mg, 11.22 mmol) in water (3.5 mL). The resulting suspension was heated at 80° C. for 2 h. The reaction was cooled to rt and filtered. The filtrate was concentrated in vacuo then partitioned between water (50 mL) and EtOAc (50 mL). The aqueous phase was extracted with EtOAc (25 mL). The combined organic extracts were washed with brine (30 mL), dried (MgSO$_4$), filtered and concentrated in vacuo onto silica gel. The crude product was purified by chromatography on silica gel (40 g column, 1-5% MeOH in DCM) to afford the sub-title compound (160 mg) as a colourless oil.

$^1$H NMR (DMSO-d6) 400 MHz, δ: 9.31 (s, 1H), 7.04 (d, 1H), 7.07 (d, 1H), 5.20 (s, 2H), 3.68 (s, 3H), 1.26 (s, 9H).

LCMS m/z 248 (M+H)$^+$ (ES$^+$)

(v) 1-(5-(tert-Butyl)-2-methoxy-3-(1,3,4-oxadiazol-2-yl)phenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea Triethylamine (8 μL, 0.057 mmol) was added to a mixture of the product from step (iv) above (80 mg, 0.259 mmol) and phenyl (4-((2-((3-methoxy-5-(2-(2-(2-methoxyethoxy)ethoxy)-ethoxy)phenyl)amino)pyrimidin-4-yl)oxy)naphthalen-1-yl)carbamate (see Example 19(i) above; 166 mg, 0.259 mmol) in isopropyl acetate (3 mL) and the mixture heated at 60° C. (block temperature) for 5 h during which time reaction became turbid. The mixture was diluted with THF and concentrated in vacuo onto silica gel. The crude product was purified by chromatography on the Companion (40 g column, 1-5% MeOH in DCM) to afford the title compound (164 mg) as a pale pink solid.

¹H NMR (400 MHz, DMSO-d6) δ: 9.49 (s, 1H), 9.45 (s, 1H), 9.42 (s, 1H), 9.10 (s, 1H), 8.67 (d, 1H), 8.43 (d, 1H), 8.29 (d, 1H), 8.10 (d, 1H), 7.86 (d, 1H), 7.70 (t, 1H), 7.60 (t, 1H), 7.53 (d, 1H), 7.44 (d, 1H), 6.81 (d, 2H), 6.56 (d, 1H), 6.04 (t, 1H), 3.86-3.91 (m, 2H), 3.86 (s, 3H), 3.65-3.67 (m, 2H), 3.47-3.54 (m, 6H), 3.52 (s, 3H), 3.40 (dd, 2H), 3.21 (s, 3H), 1.33 (s, 9H).

LCMS m/z 794 (M+H)⁺ (ES⁺), 398 (M+2H)²⁺ (ES⁺)

Example 60

(S)-5-(tert-Butyl)-3-(3-(4-((2-((3-ethynyl-5-((1-morpholinopropan-2-yl)carbamoyl) phenyl)amino)pyrimidin-4-yl)oxy)naphthalen-1-yl)ureido)-2-methoxy-N-methylbenzamide

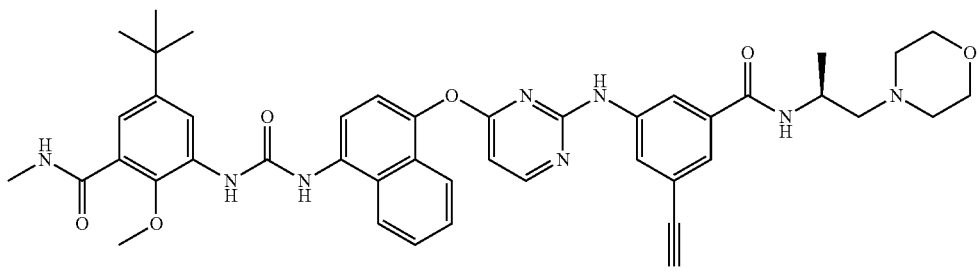 [SMILES: C#Cc1cc(Nc2nccc(Oc3ccc(NC(=O)Nc4cc(C(C)(C)C)cc(C(=O)NC)c4OC)c4ccccc34)n2)cc(C(=O)N[C@@H](C)CN2CCOCC2)c1]

To a stirred solution of phenyl (5-(tert-butyl)-2-methoxy-3-(methylcarbamoyl)phenyl)-carbamate (see Example 9(i) above; 123 mg, 0.344 mmol) and (S)-3-((4-((4-aminonaphthalen-1-yl)oxy)pyrimidin-2-yl)amino)-5-ethynyl-N-(1-morpholinopropan-2-yl)benzamide (see Example 57(ii) above; 150 mg, 0.287 mmol) in iPrOAc (3 mL) was added triethylamine (15 µL, 0.108 mmol). The reaction was heated to 60° C. (block temperature) for 24 h then evaporated under reduced pressure. The crude product was purified by chromatography on silica gel (40 g column, 0-10% EtOH/EtOAc) then triturated with EtOAc/ether to afford a solid that was purified by preparative HPLC (Gilson, Acidic (0.1% Formic acid), Waters X-Select Prep-C18, 5 µm, 19×50 mm column, 20-95% MeCN in Water). The fractions containing product were evaporated, partitioned between EtOAc (50 mL) and sat aq NaHCO₃ soln (20 mL), the organic layer was washed with water (20 mL), dried (MgSO₄), filtered and evaporated under reduced pressure. The solid was triturated with ether, then filtered to a give a solid that was dissolved in MeCN/DCM. The solvent was evaporated to afford the title compound (41 mg) as a solid.

¹H NMR (DMSO-d6) 400 MHz, δ: 9.75 (s, 1H), 9.44 (s, 1H), 8.88 (s, 1H), 8.45-8.43 (m, 2H), 8.28 (d, 1H), 8.19-8.05 (m, 4H), 7.90 (s, 1H), 7.86 (d, 1H), 7.71-7.58 (m, 2H), 7.46-7.44 (m, 2H), 7.12 (s, 1H), 6.56-6.53 (m, 1H), 4.21-4.13 (m, 2H), 3.80 (s, 3H), 3.53 (s, 4H), 2.82 (d, 3H), 2.44-2.22 (m, 6H), 1.28 (s, 9H), 1.12 (d, 3H).

LCMS m/z 785 (M+H)⁺ (ES⁺); 783 (M−H)⁻ (ES⁻)

Example 61

(R)-5-(tert-Butyl)-3-(3-(4-((2-((3-ethynyl-5-((1-morpholinopropan-2-yl)carbamoyl)phenyl) amino)pyrimidin-4-yl)oxy)naphthalen-1-yl)ureido)-2-methoxy-N-methylbenzamide

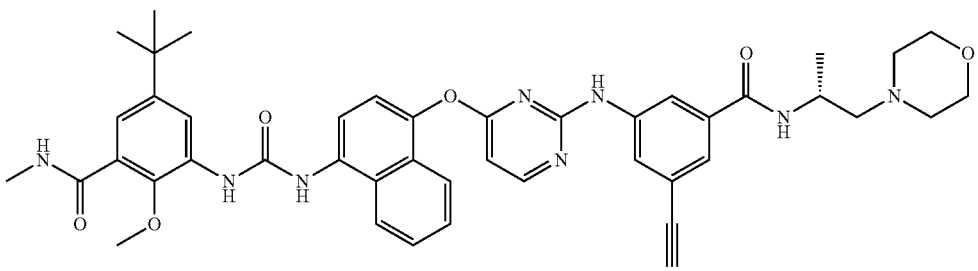 [SMILES: C#Cc1cc(Nc2nccc(Oc3ccc(NC(=O)Nc4cc(C(C)(C)C)cc(C(=O)NC)c4OC)c4ccccc34)n2)cc(C(=O)N[C@H](C)CN2CCOCC2)c1]

To a stirred solution of phenyl (5-(tert-butyl)-2-methoxy-3-(methylcarbamoyl)phenyl)-carbamate (see Example 9(i) above; 123 mg, 0.344 mmol) and (R)-3-((4-((4-aminonaphthalen-1-yl)oxy)pyrimidin-2-yl)amino)-5-ethynyl-N-(1-morpholinopropan-2-yl)benzamide (see Example 56(iv) above; 150 mg, 0.287 mmol) in iPrOAc (3 mL) was added triethylamine (15 µL, 0.108 mmol). The reaction was heated to 60° C. (block temperature) for 24 h then evaporated under reduced pressure. The crude product was purified by chromatography on silica gel (40 g column, 0-10% EtOH/EtOAc) then triturated with EtOAc/ether to afford a solid that was purified by preparative HPLC (Gilson, Acidic (0.1% Formic acid), Waters X-Select Prep-C18, 5 µm, 19×50 mm column, 20-95% MeCN in Water). The fractions containing product were evaporated, partitioned between EtOAc (50 mL) and sat aq NaHCO₃ soln (20 mL), the organic layer was washed with water (20 mL), dried (MgSO₄), filtered and evaporated under reduced pressure. The solid was triturated with ether, then filtered to a give a solid that was dissolved in MeCN/DCM. The solvent was evaporated to afford the title compound (47 mg).

¹H NMR (DMSO-d6) 400 MHz, δ: 9.75 (s, 1H), 9.44 (s, 1H), 8.89 (s, 1H), 8.45-8.43 (m, 2H), 8.28 (d, 1H), 8.19-8.05 (m, 4H), 7.90 (s, 1H), 7.86 (d, 1H), 7.71-7.58 (m, 2H), 7.46-7.44 (m, 2H), 7.12 (s, 1H), 6.56-6.53 (m, 1H), 4.22-4.13 (m, 2H), 3.80 (s, 3H), 3.53 (s, 4H), 2.82 (d, 3H), 2.44-2.23 (m, 6H), 1.28 (s, 9H), 1.12 (d, 3H).

LCMS m/z 785 (M+H)⁺ (ES⁺); 783 (M−H)⁻ (ES⁻)

Example 62

3-((4-((4-(3-(3-(tert-Butyl)-5-carbamoylphenyl)ureido)naphthalen-1-yl)oxy)pyridin-2-yl)amino)-5-ethynyl-N-(2-(2-(2-methoxyethoxy)ethoxy)ethyl)benzamide (i) Phenyl (3-(tert-butyl)-5-carbamoylphenyl)carbamate Phenyl chloroformate (99 μL, 0.779 mmol) was added to a stirred solution of 3-amino-5-(tert-butyl)benzamide (128 mg, 0.599 mmol) and NaHCO₃ (151 mg, 1.798 mmol) in THF (3 mL) and DCM (3 mL). The mixture was stirred at rt overnight. The mixture was diluted with water (15 mL) and DCM (15 mL) and passed through a phase sep cartridge. The organic layer was concentrated in vacuo to afford the sub-title compound (209 mg) as a sticky oil.

LCMS m/z 313 (M+H)⁺ (ES⁺), 75% purity (ii) 3-((4-((4-(3-(3-(tert-Butyl)-5-carbamoylphenyl)ureido)naphthalen-1-yl)oxy)pyridin-2-yl)amino)-5-ethynyl-N-(2-(2-(2-methoxyethoxy)ethoxy)ethyl)benzamide To a stirred solution of the product from step (i) above (204 mg, 0.490 mmol) and 3-((4-((4-aminonaphthalen-1-yl)oxy)pyridin-2-yl)amino)-5-ethynyl-N-(2-(2-(2-methoxy-ethoxy)-ethoxy)ethyl)benzamide (see Example 53(ii) above; 188 mg, 0.344 mmol) in i-PrOAc (5 mL) was added Et₃N (25 μL, 0.179 mmol). The resulting mixture was stirred at 60° C. overnight. The solvent was removed in vacuo to afford a brown oil. The crude product was purified by chromatography on silica gel (40 g column, 0-6% MeOH in EtOAc) to afford a glass, which was triturated with a diethyl ether/isohexane mix to afford a solid (137 mg). The crude product was purified by preparative HPLC (Gilson, Basic (0.1% Ammonium Bicarbonate), Basic, Waters X-Bridge Prep-C18, 5 μm, 19×50 mm column, 35-70% MeCN in Water) to afford the title compound (98 mg) as a colourless solid.

¹H NMR (400 MHz, DMSO-d6) δ 9.22 (s, 1H), 9.18 (s, 1H), 8.89 (s, 1H), 8.47 (t, 1H), 8.23 (d, 1H), 8.15 (d, 1H),

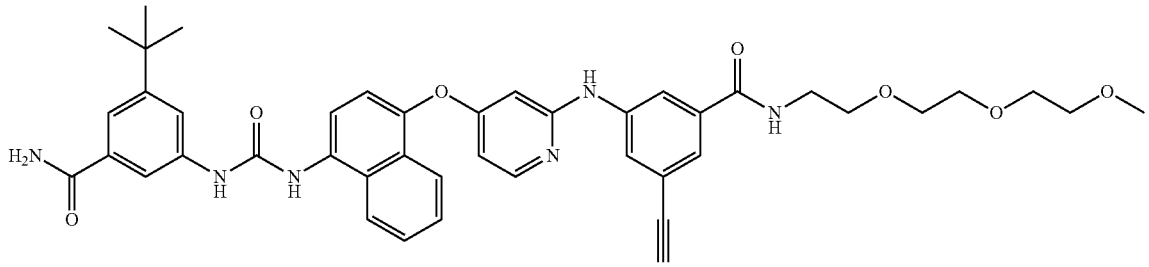 [SMILES: C#Cc1cc(Nc2cc(Oc3ccc(NC(=O)Nc4cc(C(N)=O)cc(C(C)(C)C)c4)c4ccccc34)ccn2)cc(C(=O)NCCOCCOCCOC)c1]

8.11 (dd, 1H), 8.07 (d, 1H), 7.98 (s, 1H), 7.94 (t, 1H), 7.88 (d, 1H), 7.80 (t, 1H), 7.75-7.67 (m, 2H), 7.66-7.58 (m, 1H), 7.55 (t, 1H), 7.42 (t, 1H), 7.40 (d, 1H), 7.31 (s, 1H), 6.63 (dd, 1H), 6.13 (d, 1H), 4.19 (s, 1H), 3.55-3.47 (m, 8H), 3.43-3.37 (m, 4H), 3.21 (s, 3H), 1.33 (s, 9H).

LCMS m/z 759 (M+H)⁺ (ES⁺); 757 (M−H)⁻ (ES⁻)

Example 63

1-(5-(tert-Butyl)-2-oxo-2,3-dihydrobenzo[d]oxazol-7-yl)-3-(4-((2-((3-methoxy-5-(2-(2-(2-methoxyethoxy)ethoxy)ethoxy)phenyl)amino)pyrimidin-4-yl)oxy)naphthalen-1-yl)urea

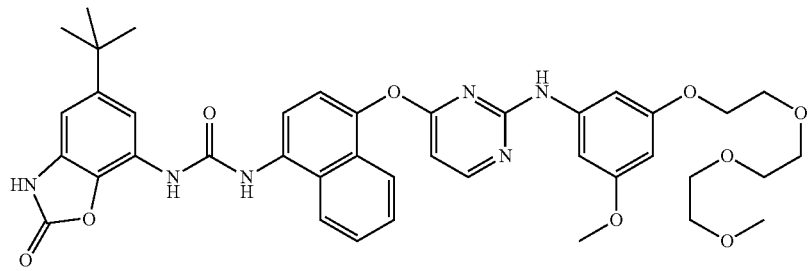 [SMILES: COCCOCCOCCOc1cc(Nc2nccc(Oc3ccc(NC(=O)Nc4cc(C(C)(C)C)cc5[nH]c(=O)oc45)c4ccccc34)n2)cc(OC)c1]

(i) 2-Amino-4-(tert-butyl)-6-nitrophenol

10% Pd—C (J&M type 39 50% w/w H₂O, 1 g) was added to a solution of 4-(tert-butyl)-2,6-dinitrophenol (1 g, 4.16 mmol) and ammonium formate (1.5 g, 23.79 mmol) in MeCN (10 mL) and the mixture heated at reflux for 90 min then left stirring overnight. The mixture was filtered on glass fibre filter pad and the solid washed with EtOAc (10 mL) The filtrate was evaporated and the resulting solid filtered through silica (10 g) eluting with DCM to afford the sub-title compound (300 mg) as a dark red crystalline solid.

¹H NMR (400 MHz, DMSO-d6) δ 7.11 (d, 1H), 7.06 (d, 1H), 1.24 (s, 9H).

LCMS m/z 211 (M+H)⁺ (ES⁺)

(ii) 5-(tert-Butyl)-7-nitrobenzo[d]oxazol-2(3H)-one

Pyridine (200 μL, 2.473 mmol) was added to a solution of 4-nitrophenyl carbonochloridate (200 mg, 0.992 mmol) and the product from step (i) above (210 mg, 0.999 mmol) in DCM (10 mL). The reaction mixture was stirred for 72 h and then partitioned between DCM (10 mL) and sat. NaHCO₃ soln. (20 mL). The organics were separated, dried (MgSO₄), filtered and the solvent evaporated to a brown solid. The crude product was purified by chromatography on silica gel (40 g column, 10% EtOAc:isohexane to 60%) to afford the sub-title compound (150 mg) as a colourless solid.

¹H NMR (400 MHz, DMSO-d6) δ 12.24 (s, 1H), 7.76 (d, 1H), 7.48 (d, 1H), 1.34 (s, 9H).

LCMS m/z 259 (M+Na)+(ES⁺); 235 (M−H)⁻ (ES⁻)

(iii) 7-Amino-5-(tert-butyl)benzo[d]oxazol-2(3H)-one

10% Pd—C (J&M type 39 50% w/w H₂O, 50 mg) was added to a solution of the product from step (ii) above (150 mg, 0.635 mmol) and cyclohexene (4 mL, 39.5 mmol) in EtOH (10 mL) and the mixture heated at reflux for 3 h. The reaction mixture was allowed to cool to rt and stirred overnight. The mixture was filtered (Whatmans glass fibre GF/A) and the solvent evaporated to give a brown gum, used crude in next step.

¹H NMR (400 MHz, DMSO-d6) δ 11.18 (s, 1H), 6.53-6.39 (m, 1H), 6.34-6.19 (m, 1H), 5.21 (s, 2H), 1.23 (s, 9H)

LCMS m/z 207 (M+H)⁺ (ES⁺)

(iv) 1-(5-(tert-Butyl)-2-oxo-2,3-dihydrobenzo[d]oxazol-7-yl)-3-(4-((2-((3-methoxy-5-(2-(2-(2-methoxyethoxy)ethoxy)ethoxy)phenyl)amino)pyrimidin-4-yl)oxy)naphthalen-1-yl)urea TEA (20 μL, 0.143 mmol) was added to a solution of phenyl (4-((2-((3-methoxy-5-(2-(2-(2-methoxyethoxy)ethoxy)ethoxy)phenyl)amino)pyrimidin-4-yl)oxy)naphthalen-1-yl)carbamate (see Example 19(i) above; 250 mg, 0.390 mmol) and the product from step (iii) above (90 mg, 0.436 mmol) in THF (3 mL) and the reaction heated at 60° C. (block temperature) for 16 h then stirred at rt for 48 h. The solvent was evaporated and the crude product was purified by chromatography on silica gel (40 g column, 50% EtOAc:isohexane to 100%) to afford the title compound (200 mg) as a colourless glass.

¹H NMR (400 MHz, DMSO-d6) δ 11.61 (s, 1H), 9.44 (s, 1H), 9.27 (s, 1H), 9.14 (s, 1H), 8.42 (d, 1H), 8.24 (d, 1H), 8.14 (d, 1H), 8.00 (d, 1H), 7.85 (d, 1H), 7.74-7.63 (m, 1H), 7.65-7.55 (m, 1H), 7.42 (d, 1H), 6.88-6.76 (m, 2H), 6.74 (d, 1H), 6.56 (d, 1H), 6.03 (t, 1H), 3.86 (t, 2H), 3.73-3.60 (m, 2H), 3.58-3.45 (m, 9H), 3.44-3.37 (m, 2H), 3.21 (s, 3H), 1.30 (s, 9H).

LCMS m/z 753 (M+H)⁺ (ES⁺); 751 (M−H)⁻ (ES⁻)

Example 64

1-(5-(tert-Butyl)-2-methylbenzo[d]oxazol-7-yl)-3-(4-((2-((3-methoxy-5-(2-(2-(2-methoxy-ethoxy)ethoxy)ethoxy)phenyl)amino)pyrimidin-4-yl)oxy)naphthalen-1-yl)urea

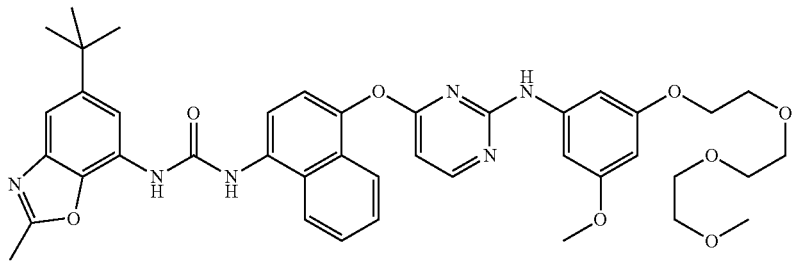 [SMILES: COCCOCCOCCOc1cc(Nc2nccc(Oc3ccc(NC(=O)Nc4cc(C(C)(C)C)cc5nc(C)oc45)c4ccccc34)n2)cc(OC)c1]

(i) 5-(tert-Butyl)-2-methyl-7-nitrobenzo[d]oxazole

2-Amino-4-(tert-butyl)-6-nitrophenol (200 mg, 0.951 mmol) was dissolved in triethyl orthoacetate (5 mL, 27.3 mmol) and the reaction mixture heated at 100° C. (block temperature) for 16 h. The solvent was evaporated and the crude product was purified by chromatography on silica gel (12 g column, 10% EtOAc:isohexane to 40%) to afford the sub-title compound (150 mg) as a waxy yellow solid.

¹H NMR (400 MHz, DMSO-d6) δ 8.19 (d, 1H), 8.10 (d, 1H), 2.72 (s, 3H), 1.39 (s, 9H).

LCMS m/z 235 (M+H)⁺ (ES⁺)

(ii) 5-(tert-Butyl)-2-methylbenzo[d]oxazol-7-amine

5% Pd—C (J &M type 87L 50% paste in H₂O, 30 mg) was added to a solution of the product from step (i) above (150 mg, 0.640 mmol) in ethanol (3 mL) and the reaction stirred under hydrogen for 16 h. The reaction was filtered through Celite and the solvent evaporated to afford the sub-title compound (125 mg).

¹H NMR (400 MHz, DMSO-d6) δ 6.80 (d, 1H), 6.66 (d, 1H), 5.32 (s, 2H), 2.54 (s, 3H), 1.27 (s, 9H).

LCMS m/z 205 (M+H)⁺ (ES⁺)

(iii) 1-(5-(tert-Butyl)-2-methylbenzo[d]oxazol-7-yl)-3-(4-((2-((3-methoxy-5-(2-(2-(2-methoxyethoxy)ethoxy)ethoxy)phenyl)amino)pyrimidin-4-yl)oxy)naphthalen-1-yl)urea TEA (20 µL, 0.143 mmol) was added to a solution of phenyl (4-((2-((3-methoxy-5-(2-(2-(2-methoxyethoxy)ethoxy)ethoxy)phenyl)amino)pyrimidin-4-yl)oxy)naphthalen-1-yl)carbamate (see Example 19(i) above; 350 mg, 0.546 mmol) and the product from step (ii) above (125 mg, 0.612 mmol) in THF (3 mL) and the reaction heated at 60° C. (block temperature) for 16 h then stirred at rt for 48 h. The solvent was evaporated and the crude product was purified by chromatography on silica gel (40 g column, 50% EtOAc:isohexane to 100%) to afford the title compound (300 mg) as a pale yellow glass.

$^1$H NMR (400 MHz, DMSO-d6) δ 9.44 (s, 1H), 9.40 (s, 1H), 9.19 (s, 1H), 8.42 (d, 1H), 8.27 (d, 1H), 8.18 (d, 1H), 8.14 (d, 1H), 7.86 (d, 1H), 7.73-7.65 (m, 1H), 7.65-7.57 (m, 1H), 7.43 (d, 1H), 7.30 (d, 1H), 6.88-6.73 (m, 2H), 6.56 (d, 1H), 6.04 (t, 1H), 3.91-3.81 (m, 2H), 3.70-3.61 (m, 2H), 3.58-3.44 (m, 9H), 3.43-3.36 (m, 2H), 3.21 (s, 3H), 2.67 (s, 3H), 1.35 (s, 9H).

LCMS m/z 751 (M+H)$^+$ (ES$^+$)

Example 65

3-((4-((4-(3-(3-(tert-Butyl)-5-(methylsulfonamido)phenyl)ureido)naphthalen-1-yl)oxy)-pyridin-2-yl)amino)-5-ethynyl-N-(2-morpholinoethyl)benzamide

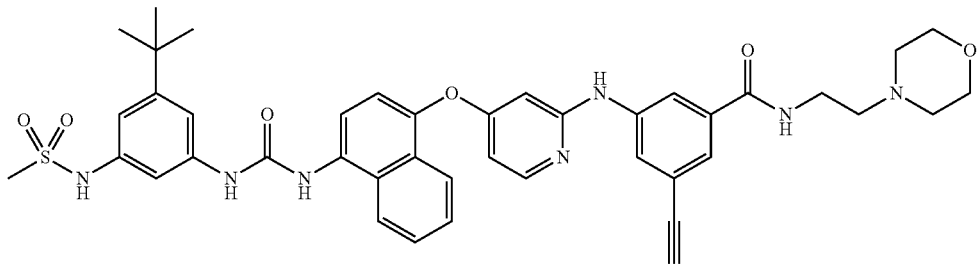 [SMILES: C#Cc1cc(Nc2cc(Oc3ccc(NC(=O)Nc4cc(NS(C)(=O)=O)cc(C(C)(C)C)c4)c4ccccc34)ccn2)cc(C(=O)NCCN2CCOCC2)c1]

(i) Phenyl (3-(tert-butyl)-5-(methylsulfonamido)phenyl)carbamate

Phenyl chloroformate (45 µL, 0.359 mmol) was added to a stirred solution of N-(3-amino-5-(tert-butyl)phenyl)methanesulfonamide (80 mg, 0.330 mmol) and NaHCO$_3$ (70 mg, 0.833 mmol) in THF (1 mL) and DCM (1 mL). The reaction mixture was stirred for 1 h then filtered and the filtrate evaporated to a brown gum which was stirred in cyclohexane for 16 h. The liquid was decanted off to give the sub-title compound (63 mg).

LCMS m/z 363 (M+H)$^+$ (ES$^+$); 361 (M-H)$^-$ (ES$^-$)

(ii) 3-((4-((4-(3-(3-(tert-Butyl)-5-(methylsulfonamido)phenyl)ureido)naphthalen-1-yl)oxy)-pyridin-2-yl)amino)-N-(2-morpholinoethyl)-5-((triisopropylsilyl)ethynyl)benzamide Et$_3$N (10 µL, 0.072 mmol) was added to a solution of the product from step (i) above (63 mg, 0.174 mmol) and 3-((4-((4-aminonaphthalen-1-yl)oxy)pyridin-2-yl)amino)-N-(2-morpholinoethyl)-5-((triisopropylsilyl)ethynyl)benzamide (see Example 39(ii) above; 100 mg, 0.151 mmol) in iPrOAc (1 mL) at 60° C. (block temperature) and the mixture stirred for 16 h. The solvent was evaporated and the residue was purified by chromatography on silica gel (12 g column, 2% MeOH:DCM to 8%) to give a brown gum. The crude product was purified by preparative HPLC (Gilson, Basic (0.1% Ammonium Bicarbonate), Basic, Waters X-Bridge Prep-C18, 5 µm, 19×50 mm column, 50-95% MeCN in Water) to afford the sub-title compound (80 mg) as a colourless solid.

$^1$H NMR (400 MHz, DMSO-d6) δ 9.66 (s, 1H), 9.19 (s, 1H), 9.15 (s, 1H), 8.79 (s, 1H), 8.41 (t, 1H), 8.21 (d, 1H), 8.12 (d, 1H), 8.10-8.05 (m, 2H), 7.91 (dd, 1H), 7.87 (d, 1H), 7.76-7.66 (m, 1H), 7.66-7.54 (m, 1H), 7.39 (d, 1H), 7.36 (dt, 2H), 7.29 (t, 1H), 6.89 (t, 1H), 6.61 (dd, 1H), 6.12 (d, 1H), 3.57 (t, 4H), 3.01 (s, 3H), 2.48-2.34 (m, 6H), 1.28 (s, 9H), 1.11 (s, 21H). CH$_2$ under water peak at 3.32 ppm.

(iii) 3-((4-((4-(3-(3-(tert-Butyl)-5-(methylsulfonamido)phenyl)ureido)naphthalen-1-yl)oxy)pyridin-2-yl)amino)-5-ethynyl-N-(2-morpholinoethyl)benzamide The product from step (ii) above (80 mg, 0.086 mmol) was dissolved in THF (2 mL) and TBAF, 1M in THF (100 µL, 0.100 mmol) added. The reaction mixture was stirred at rt for 16 h. The solvents were evaporated and the crude product was purified by preparative HPLC (Gilson, Basic (0.1% Ammonium Bicarbonate), Basic, Waters X-Bridge Prep-C18, 5 µm, 19×50 mm column, 35-75% MeCN in Water) to afford the title compound (12 mg) as a colourless solid.

$^1$H NMR (400 MHz, DMSO-d6) δ 9.69 (s, 1H), 9.30 (s, 1H), 9.24 (s, 1H), 8.95 (s, 1H), 8.40 (t, 1H), 8.23 (d, 1H), 8.15 (d, 1H), 8.09 (t, 1H), 8.06 (d, 1H), 7.93 (t, 1H), 7.86 (d, 1H), 7.74-7.65 (m, 1H), 7.65-7.57 (m, 1H), 7.42-7.38 (m, 2H), 7.36 (t, 1H), 7.30 (t, 1H), 6.88 (t, 1H), 6.64 (dd, 1H), 6.10 (d, 1H), 4.21 (s, 1H), 3.56 (t, 4H), 3.01 (s, 3H), 2.48-2.32 (m, 6H), 1.28 (s, 9H). CH$_2$ under the water peak at 3.32 ppm.

LCMS m/z 776 (M+H)$^+$ (ES$^+$)

Example 66

3-((4-((4-(3-(5-(tert-Butyl)-2-methoxy-3-(methylsulfonamido)phenyl)ureido)naphthalen-1-yl)oxy)pyridin-2-yl)amino)-5-methoxy-N-(3-morpholinopropyl)benzamide

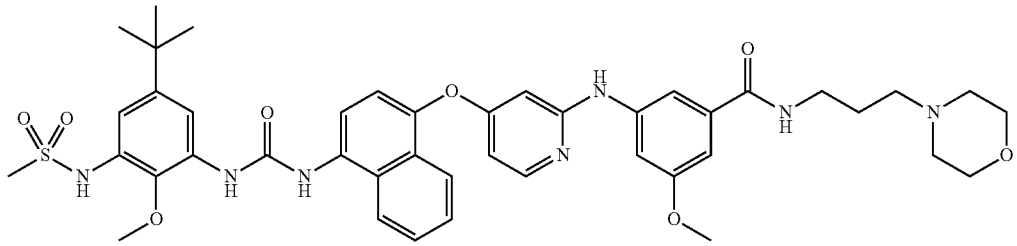 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCCCN2CCOCC2)c1]

(i) 3-((4-((4-(((tert-Butoxycarbonyl)amino)naphthalen-1-yl)oxy)pyridin-2-yl)amino)-5-methoxybenzoic acid In a 100 mL flask, a suspension of tert-butyl (4-((2-chloropyridin-4-yl)oxy)naphthalen-1-yl)carbamate (see Example 3(ii) above; 2.2673 g, 6.11 mmol), 3-amino-5-methoxybenzoic acid (1.226 g, 7.34 mmol), $Cs_2CO_3$ (5.98 g, 18.34 mmol), 2,2'-bis(diphenylphosphino)-1,1'-binaphthalene (0.358 g, 0.575 mmol) and $Pd_2(dba)_3$ (0.258 g, 0.281 mmol) in dioxane (45 mL) was de-gassed by bubbling $N_2$ through for 10 min. The resultant brown suspension was heated at 90° C. for 15 h. The mixture was partitioned between EtOAc (400 mL) and aq 1M HCl (200 mL), the organic layer was washed with 10% brine soln (2×240 mL), dried ($MgSO_4$), filtered and evaporated under reduced pressure. The crude product was purified by chromatography on silica gel (220 g column, 0.5-5% MeOH in DCM) to afford the sub-title compound (1.19 g) as an off-white solid.

$^1$H NMR (400 MHz, DMSO-d6) δ 12.86 (s, 1H), 9.37 (s, 1H), 9.14 (s, 1H), 8.14 (m, 1H), 8.13 (m, 1H), 7.84 (m, 1H), 7.74 (m, 1H), 7.67-7.54 (m, 4H), 7.36 (d, 1H), 6.96 (dd, 1H), 6.61 (dd, 1H), 6.09 (d, 1H), 3.74 (s, 3H), 1.53 (s, 9H).
LCMS m/z 502 (M+H)$^+$ (ES$^+$); 500 (M−H)$^-$ (ES$^-$)

(ii) tert-Butyl (4-((2-((3-methoxy-5-((3-morpholinopropyl)carbamoyl)phenyl)amino)pyridin-4-yl)oxy)naphthalen-1-yl)carbamate In a 20 mL vial, a solution of the product from step (i) above (84 mg, 0.151 mmol), 3-morpholinopropan-1-amine (32.6 mg, 0.226 mmol) and Hünig's Base (79 µL, 0.452 mmol) in DMF (2.9 mL) was treated with HATU (63.0 mg, 0.166 mmol). The resultant yellow solution was stirred at rt for 3 h. The solution was then partitioned between 10% aq brine (50 mL) and EtOAc (50 mL). The organic layer was washed with sat aq $NaHCO_3$ soln (20 mL), 0.5M HCl (20 mL). Acidic aqueous phase was basified with $NaHCO_3$ soln (100 mL), extracted with EtOAc (3×100 mL), the organic phase washed with 10% aq. brine (50 mL), dried ($Na_2SO_4$), filtered and evaporated under reduced pressure to afford the sub-title compound (69 mg, 80% purity) as pink solid.
LCMS m/z 314 (M+2H)$^{2+}$ (ES$^+$)

(iii) 3-((4-((4-Aminonaphthalen-1-yl)oxy)pyridin-2-yl)amino)-5-methoxy-N-(3-morpholinopropyl)benzamide In a 20 mL vial, a solution of the product from step (ii) above (68 mg, 0.108 mmol) in DCM (1 mL) was treated dropwise with TFA (334 µL, 4.33 mmol). The resultant brown solution was stirred at rt for 3 h. The solution was diluted with toluene (200 mL) and concentrated in vacuo to afford a brown solid which was dissolved in EtOAc (100 mL). The EtOAc phase was washed with saturated $NaHCO_3$ solution (3×20 mL), water (3×20 mL) and brine (1×20 mL). The solvent was evaporated off in vacuo to afford the sub-title compound (47 mg) as a brown foam.

$^1$H NMR (400 MHz, DMSO-d6) δ 8.97 (s, 1H), 8.30 (t, 1H), 8.20-8.10 (m, 1H), 8.05 (d, 1H), 7.68-7.58 (m, 1H), 7.53 (t, 1H), 7.47 (t, 1H), 7.46-7.41 (m, 2H), 7.09 (d, 1H), 6.83 (dd, 1H), 6.70 (d, 1H), 6.51 (dd, 1H), 6.05 (d, 1H), 5.81 (s, 2H), 3.72 (s, 3H), 3.55 (t, 4H), 3.24 (m, 2H), 2.40-2.19 (m, 6H), 1.65 (m, 2H)
LCMS m/z 528 (M+H)$^+$ (ES$^+$)

(iv) 3-((4-((4-(3-(5-(tert-Butyl)-2-methoxy-3-(methylsulfonamido)phenyl)ureido)naphthalen-1-yl)oxy)pyridin-2-yl)amino)-5-methoxy-N-(3-morpholinopropyl)benzamide In a 20 mL vial, a solution of phenyl (5-(tert-butyl)-2-methoxy-3-(methylsulfonamido)-phenyl)carbamate (see Example 1(vi) above; 35.9 mg, 0.091 mmol), the product from step (iii) above (42 mg, 0.080 mmol) in isopropyl acetate (1.5 mL) was treated with triethylamine (4.6 µL, 0.033 mmol). The resultant brown solution was heated at 50° C. for 17 h then evaporated to dryness in vacuo. The crude product was purified by chromatography on silica gel (12 g column, 1-10% MeOH in 1% MeOH in DCM) to give crude material that was purified by preparative HPLC (Gilson, Acidic (0.1% Formic acid), Acidic, Waters X-Select Prep-C18, 5 µm, 19×50 mm column, 25-70% MeCN in Water) to afford the title compound (9 mg) as a clear white solid.

$^1$H NMR (400 MHz, DMSO-d6) δ 9.37 (s, 1H), 9.13 (s, 1H), 9.04 (s, 1H), 8.90 (s, 1H), 8.36-8.24 (m, 2H), 8.18 (d, 1H), 8.11 (s, 1H), 8.09 (d, 1H), 7.92-7.81 (m, 1H), 7.76-7.66 (m, 1H), 7.65-7.57 (m, 1H), 7.55 (t, 1H), 7.49 (t, 1H), 7.38 (d, 1H), 7.02 (d, 1H), 6.85 (dd, 1H), 6.57 (dd, 1H), 6.13 (d, 1H), 3.80 (s, 3H), 3.74 (s, 3H), 3.60-3.49 (m, 4H), 3.28-3.21 (m, 2H), 3.09 (s, 3H), 2.32 (d, 6H), 1.72-1.58 (m, 2H), 1.26 (s, 9H)
LCMS m/z 826 (M+H)$^+$ (ES$^+$); 824 (M−H)$^-$ (ES$^-$)

Example 67

(S)-3-((4-((4-(3-(5-(tert-Butyl)-2-methoxy-3-(methylsulfonamido)phenyl)ureido)-naphthalen-1-yl)oxy)pyridin-2-yl)amino)-5-ethynyl-N-(1-(2-(2-methoxyethoxy)ethoxy)-propan-2-yl)benzamide

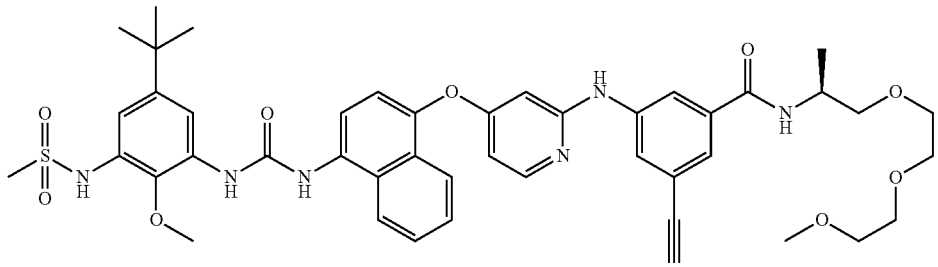 [SMILES: C#Cc1cc(Nc2cc(Oc3ccc(NC(=O)Nc4cc(C(C)(C)C)cc(NS(C)(=O)=O)c4OC)c4ccccc34)ccn2)cc(C(=O)N[C@@H](C)COCCOCCOC)c1]

(i) (S)—N,N-Dibenzyl-1-(2-(2-methoxyethoxy)ethoxy)propan-2-amine

NaH (0.188 g, 4.70 mmol) was added to a stirred solution of (S)-2-(dibenzylamino)propan-1-ol (1 g, 3.92 mmol) in DMF (10 mL) at 0-5° C. The mixture was stirred for 20 min then 1-bromo-2-(2-methoxyethoxy)ethane (0.860 g, 4.70 mmol) in DMF (2 mL) was added and the mixture warmed to rt. Tetrabutylammonium iodide (0.579 g, 1.566 mmol) was added and stirred for 4 h. A further portion of NaH (0.188 g, 4.70 mmol) then 1-bromo-2-(2-methoxyethoxy)ethane (0.5 g) was added and stirred for 18 h. The mixture was quenched with water (20 mL) and extracted with EtOAc (80 mL). The organic layer was washed with brine (20 mL), dried (MgSO$_4$), filtered and evaporated under reduced pressure. The crude product was purified by chromatography on silica gel (40 g column, 0-20% EtOAc/isohexane) to afford the sub-title compound (695 mg) as an oil.

$^1$H NMR (CDCl$_3$) 400 MHz, δ: 7.38 (d, 4H), 7.29-7.25 (m, 4H), 7.21-7.17 (m, 2H), 3.72 (d, 2H), 3.65-3.61 (m, 5H), 3.58 (d, 2H), 3.55-3.52 (m, 4H), 3.40 (dd, 1H), 3.37 (s, 3H), 3.06-2.98 (m, 1H), 1.07 (d, 3H).

LCMS m/z 358 (M+H)$^+$ (ES$^+$)

(ii) (S)-1-(2-(2-Methoxyethoxy)ethoxy)propan-2-amine

A mixture of the product from step (i) above (685 mg, 1.916 mmol) and 10% Pd/C (120 mg, JM type 39) in EtOH (15 mL) was hydrogenated under a balloon of hydrogen for 20 h. The mixture was filtered through Celite, washing with EtOH (50 mL). The filtrate was evaporated and the crude product was loaded onto a column of SCX in MeOH. The column was washed with MeOH and then the product was eluted with 0.7 M ammonia in MeOH. The resultant mixture was concentrated in vacuo to afford the sub-title compound (305 mg) as a colourless oil.

$^1$H NMR (CDCl$_3$) 400 MHz, δ: 3.68-3.54 (m, 8H), 3.43-3.40 (m, 1H), 3.39 (s, 3H), 3.19-3.10 (m, 2H), 1.72 (s, 2H, under water), 1.03 (d, 3H).

(iii) (5)-tert-Butyl (4-((2-((3-ethynyl-5-((1-(2-(2-methoxyethoxy)ethoxy)propan-2-yl)carbamoyl)phenyl)amino)pyridin-4-yl)oxy)naphthalen-1-yl)carbamate HATU (422 mg, 1.110 mmol) was added to a stirred solution of 3-((4-((4-(((tert-butoxy-carbonyl)amino)naphthalen-1-yl)oxy)pyridin-2-yl)amino)-5-ethynylbenzoic acid (see Example 52(iii) above; 500 mg, 1.009 mmol), the product from step (ii) above (268 mg, 1.514 mmol) and Hünig's Base (530 μL, 3.03 mmol) in DMF (10 mL) at rt. The mixture was stirred for 5 h then partitioned between EtOAc (150 mL) and water (100 mL). The organic layer was washed with sat aq NaHCO$_3$ soln (100 mL), water (100 mL), dried (MgSO$_4$), filtered and evaporated under reduced pressure. The crude product was purified by chromatography on silica gel (40 g column, 0-100% EtOAc/isohexane) to afford the sub-title compound (536 mg) as a foam.

LCMS m/z 655 (M+H)$^+$ (ES$^+$)

(iv) (S)-3-((4-((4-Aminonaphthalen-1-yl)oxy)pyridin-2-yl)amino)-5-ethynyl-N-(1-(2-(2-methoxyethoxy)ethoxy)propan-2-yl)benzamide TFA (625 μL, 8.11 mmol) was added to a stirred solution of the product from step (iii) above (531 mg, 0.811 mmol) in DCM (5 mL) and stirred at rt for 18 h. The mixture was concentrated under reduced pressure, the residue was redissolved in ethyl acetate (50 mL) and washed with saturated NaHCO$_3$ solution (50 mL). The organic phase was dried (MgSO$_4$), filtered and concentrated under reduced pressure to the sub-title compound (455 mg) as a brown foam.

LCMS m/z 555 (M+H)$^+$ (ES$^+$); 599 (M$_+$HCO2)– (ES$^−$)

(v) (S)-3-((4-((4-(3-(5-(tert-Butyl)-2-methoxy-3-(methylsulfonamido)phenyl)ureido)-naphthalen-1-yl)oxy)pyridin-2-yl)amino)-5-ethynyl-N-(1-(2-(2-methoxyethoxy)ethoxy)-propan-2-yl) benzamide A stirred solution of the product from step (iv) above (160 mg, 0.288 mmol), phenyl (5-(tert-butyl)-2-methoxy-3-(methylsulfonamido)phenyl)carbamate (see Example 1(vi) above; 130 mg, 0.331 mmol) and Et$_3$N (20 μL, 0.143 mmol) in isopropyl acetate (5 mL) was heated to 50° C. (block temp) over a weekend. The mixture was concentrated under reduced pressure, the residue was purified by preparative HPLC (Gilson, Acidic (0.1% Formic acid), Acidic, Waters X-Select Prep-C18, 5 μm, 19×50 mm column, 20-95% MeCN in Water). Fractions were concentrated to remove acetonitrile, basified with NaHCO$_3$ (150 mL) and extracted with ethyl acetate (100 mL). The organic phase was washed with saturated brine (100 mL), dried (MgSO$_4$) and concentrated under reduced pressure to afford a pink foam. The foam was triturated in diethyl ether (20 mL) to afford the title compound (107 mg) as a pink solid.

$^1$H NMR (400 MHz, DMSO-d6) δ: 9.39 (s, 1H), 9.21 (s, 1H), 9.14 (br s, 1H), 8.91 (s, 1H), 8.30 (d, 1H), 8.24-8.08 (m, 5H), 7.91-7.84 (m, 2H), 7.77-7.65 (ddd, 1H), 7.65-7.57 (ddd, 1H), 7.43 (dd, 1H), 7.40 (d, 1H), 7.02 (d, 1H), 6.62 (dd, 1H), 6.13 (d, 1H), 4.19 (s, 1H), 4.14 (ddq, 1H), 3.81 (s, 3H), 3.57-3.33 (m, 10H), 3.20 (s, 3H), 3.10 (s, 3H), 1.27 (s, 9H), 1.11 (d, 3H).

LCMS m/z 853 (M+H)$^+$ (ES$^+$); 851 (M−H)$^−$ (ES$^−$)

Example 68

(R)-3-((4-((4-(3-(5-(tert-Butyl)-2-methoxy-3-(methylsulfonamido)phenyl)ureido)-naphthalen-1-yl)oxy)pyridin-2-yl)amino)-5-ethynyl-N-(1-(2-(2-methoxyethoxy)ethoxy)-propan-2-yl)benzamide

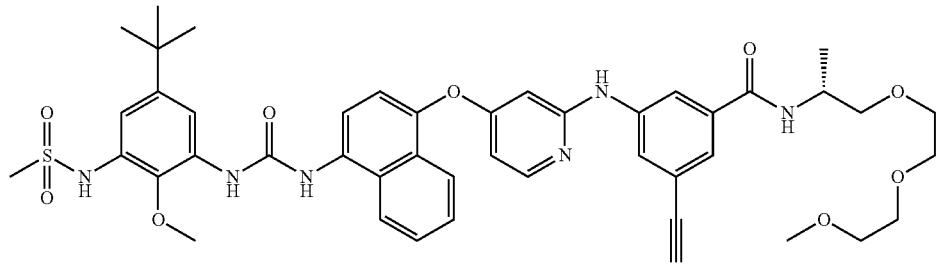 [SMILES: C#Cc1cc(Nc2cc(Oc3ccc(NC(=O)Nc4cc(C(C)(C)C)cc(NS(C)(=O)=O)c4OC)c4ccccc34)ccn2)cc(C(=O)N[C@H](C)COCCOCCOC)c1]

The title compound was prepared using the method of Example 67 above to afford the product (112 mg) as a white solid.

$^1$H NMR (400 MHz, DMSO-d6) δ: 9.39 (s, 1H), 9.21 (s, 1H), 9.14 (br s, 1H), 8.91 (s, 1H), 8.30 (d, 1H), 8.24-8.08 (m, 5H), 7.91-7.84 (m, 2H), 7.77-7.65 (ddd, 1H), 7.65-7.57 (ddd, 1H), 7.43 (dd, 1H), 7.40 (d, 1H), 7.02 (d, 1H), 6.62 (dd, 1H), 6.13 (d, 1H), 4.19 (s, 1H), 4.14 (ddq, 1H), 3.81 (s, 3H), 3.57-3.33 (m, 10H), 3.20 (s, 3H), 3.10 (s, 3H), 1.27 (s, 9H), 1.11 (d, 3H).

LCMS m/z 853 (M+H)$^+$ (ES$^+$); 851 (M–H)$^-$ (ES$^-$)

Example 69

N-(5-(tert-butyl)-2-ethoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)methanesulfonamide

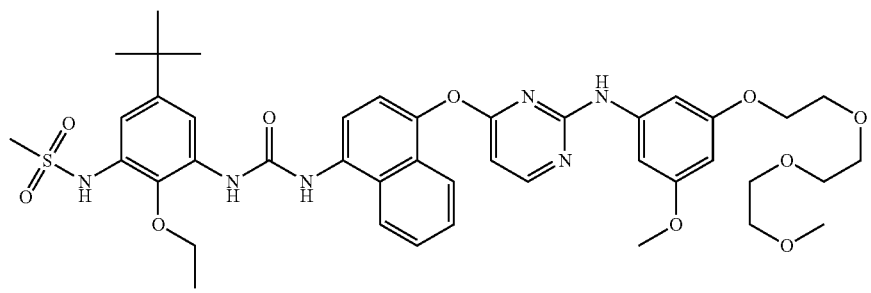 [SMILES: CCOc1c(NC(=O)Nc2ccc(Oc3ccnc(Nc4cc(OC)cc(OCCOCCOCCOC)c4)n3)c3ccccc23)cc(C(C)(C)C)cc1NS(C)(=O)=O]

TEA (10 µL, 0.072 mmol) was added to a solution of phenyl (4-((2-((3-methoxy-5-(2-(2-(2-methoxyethoxy)ethoxy)ethoxy)phenyl)amino)pyrimidin-4-yl)oxy)naphthalen-1-yl)carbamate (see Example 19(i) above; 170 mg, 0.265 mmol) and N-(3-amino-5-(tert-butyl)-2-ethoxyphenyl)methanesulfonamide (see, for example, Wagner, H. et al., WO 2010/026095, 11 Mar. 2010; 80 mg, 0.279 mmol) in THF (3 mL) and the reaction heated at 60° C. (block temperature) for 16 h. The solvent was evaporated and the crude product was purified by chromatography on silica gel (40 g column, 50% EtOAc:isohexane to 100%) to afford the title compound (183 mg) as a colourless glass.

$^1$H NMR (400 MHz, DMSO-d6) δ 9.43 (s, 1H), 9.37 (s, 1H), 9.03 (s, 1H), 8.73 (s, 1H), 8.41 (d, 1H), 8.26 (d, 1H), 8.12 (d, 1H), 8.07 (d, 1H), 7.85 (d, 1H), 7.73-7.63 (m, 1H), 7.63-7.52 (m, 1H), 7.42 (d, 1H), 7.02 (d, 1H), 6.91-6.72 (m, 2H), 6.55 (d, 1H), 6.04 (t, 1H), 4.02 (q, 2H), 3.93-3.78 (m, 2H), 3.73-3.59 (m, 2H), 3.59-3.45 (m, 9H), 3.45-3.37 (m, 2H), 3.21 (s, 3H), 3.10 (s, 3H), 1.43 (t, 3H), 1.27 (s, 9H)

LCMS m/z 833 (M+H)$^+$ (ES$^+$); 831 (M–H)$^-$ (ES$^-$)

Example 70

1-(5-(tert-Butyl)-2-methoxy-3-(1H-1,2,3-triazol-5-yl)phenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea

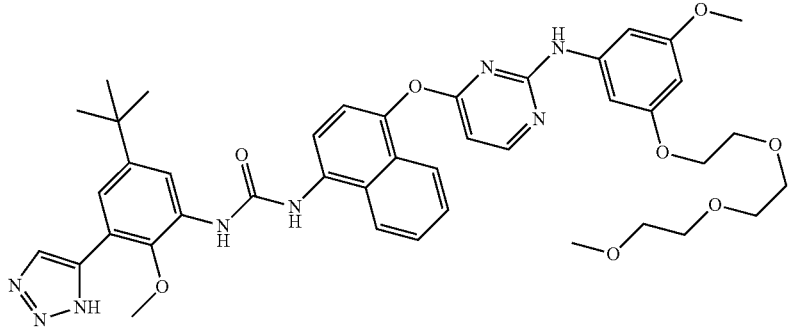 [SMILES: COCCOCCOCCOc1cc(Nc2nccc(Oc3ccc(NC(=O)Nc4cc(C(C)(C)C)cc(-c5cnn[nH]5)c4OC)c4ccccc34)n2)cc(OC)c1]

(i) ((5-(tert-Butyl)-2-methoxy-3-nitrophenyl)ethynyl)trimethylsilane

To a stirred solution of 1-bromo-5-(tert-butyl)-2-methoxy-3-nitrobenzene (500 mg, 1.735 mmol) and triethylamine (1200 μL, 8.61 mmol) in dioxane (7 mL) was added ethynyltrimethylsilane (720 μL, 5.21 mmol), PdCl$_2$(PPh$_3$)$_2$ (180 mg, 0.256 mmol) and copper(I) iodide (100 mg, 0.525 mmol). The reaction was heated to 60° C. (block temp) overnight. The reaction was cooled to rt and diluted with Et$_2$O (20 mL). The mixture was filtered through Celite and the filtrate washed with 0.1M HCl (20 mL) then NaHCO$_3$ solution (2×20 mL) and brine. The organic phase was dried (MgSO$_4$), filtered and concentrated in vacuo giving a brown semi-solid. The crude product was purified by chromatography on the Companion (40 g column, 20% DCM in hexane) to afford the sub-title compound (466 mg) as a yellow oil.

$^1$H NMR (400 MHz; CDCl$_3$) δ: 7.70 (d, 1H), 7.63 (d, 1H), 4.07 (s, 3H), 1.32 (s, 9H), 0.29 (s, 9H).

(ii) 5-(tert-Butyl)-1-ethynyl-2-methoxy-3-nitrobenzene

A mixture of the product from step (i) above (400 mg, 1.310 mmol) and potassium carbonate (800 mg, 5.79 mmol) in MeOH (15 mL) and water (6 mL) was stirred at rt for 30 minutes. The mixture was diluted with EtOAc (100 mL) and water (100 mL). The aqueous phase was extracted with further EtOAc (2×50 mL). Brine (20 mL) was added to the aqueous phase and one further extraction in EtOAc (50 mL) performed. The combined organic phase was dried (MgSO$_4$), filtered and concentrated in vacuo affording a dark yellow/orange oil. The crude product was purified by chromatography on the Companion (12 g column, 0-10% EtOAc in hexane) to afford the sub-title compound (290 mg) as a pale yellow oil.

$^1$H NMR (CDCl$_3$) 400 MHz, δ: 7.75 (d, 1H), 7.68 (d, 1H), 4.08 (s, 3H), 3.39 (s, 1H), 1.33 (s, 9H).
LCMS m/z 234 (M+H)$^+$ (ES$^+$)

(iii) 5-(5-(tert-Butyl)-2-methoxy-3-nitrophenyl)-1H-1,2,3-triazole

To a stirred solution of the product from step (ii) above (290 mg, 1.243 mmol) in a 9:1 solution of DMF/MeOH (3 mL) was added copper(I) iodide (12 mg, 0.063 mmol) and azidotrimethylsilane (250 μL, 1.884 mmol). The reaction was heated to 100° C. and stirred for 7 h. The reaction was cooled to rt and diluted with EtOAc (50 mL). The organic phase was washed with water (50 mL) and brine (2×30 mL), then dried (MgSO$_4$), filtered and concentrated in vacuo. The mL) was added copper(I) iodide (12 mg, 0.063 mmol) and crude product was purified by chromatography on the Companion (12 g column, 10-30% EtOAc in hexane) to afford the sub-title compound (156 mg) as a pale yellow oil.

$^1$H NMR (DMSO-d6) 400 MHz, δ: 8.34 (s, 1H), 8.26 (s, 1H), 7.89 (d, 1H), 3.72 (s, 3H), 1.34 (s, 9H).
LCMS m/z 277 (M+H)$^+$ (ES$^+$); 275 (M−H)$^−$ (ES$^−$)

(iv) 5-(tert-Butyl)-2-methoxy-3-(1H-1,2,3-triazol-5-yl)aniline

The product from step (iii) above (156 mg, 0.565 mmol) was dissolved in ethanol (5 mL) and Fe powder (315 mg, 5.65 mmol) was added followed by a solution of NH$_4$Cl (300 mg, 5.61 mmol) in water (2 mL). The resulting suspension was heated at 80° C. for 2 h. The reaction was cooled to rt and filtered. The filtrate was concentrated in vacuo then partitioned between water (50 mL) and EtOAc (50 mL). The aqueous phase was extracted with EtOAc (25 mL). The combined organic extracts were washed with brine (30 mL), dried (MgSO$_4$), filtered and concentrated in vacuo onto silica gel. The crude product was purified by chromatography on silica gel (12 g column, 1-10% MeOH in DCM) to afford the sub-title compound (8 mg) as a colourless oil.
LCMS m/z 247 (M+H)$^+$ (ES$^+$)

(v) 1-(5-(tert-Butyl)-2-methoxy-3-(1H-1,2,3-triazol-5-yl)phenyl)-3-(4-((2-((3-methoxy-5-(2-(2-(2-methoxyethoxy)ethoxy)ethoxy)phenyl)amino)pyrimidin-4-yl)oxy)naphthalen-1-yl)urea Triethylamine (1 μL, 7.17 μmol) was added to a mixture of the product from step (iv) above (8 mg, 0.032 mmol) and phenyl (4-((2-((3-methoxy-5-(2-(2-(2-methoxyethoxy)ethoxy)ethoxy)phenyl)amino)pyrimidin-4-yl)oxy)naphthalen-1-yl)carbamate (see Example 19(i) above; 21 mg, 0.033 mmol) in isopropyl acetate (1.5 mL) and the mixture heated at 60° C. (block temperature) for 5 h during which time reaction became turbid. Reaction left standing for 6 days during which time a suspension formed. The solid was collected by filtration, washing with further iPrOAc to afford the title compound (21 mg) as a pale pink solid.

$^1$H NMR (400 MHz, DMSO-d6) δ: 15.05-15.42 (bm, 1H), 9.43 (s, 2H), 8.98 (bs, 1H), 8.42 (d, 1H), 8.30 (d, 1H), 8.19-8.40 (bm, 2H), 8.11 (d, 1H), 7.86 (d, 1H), 7.69 (t, 1H), 7.60 (t, 1H), 7.44-7.84 (bm, 1H), 7.43 (d, 1H), 6.82 (d, 2H), 6.56 (d, 1H), 6.04 (t, 1H), 3.86-3.88 (m, 2H), 3.71 (s, 3H), 3.65-3.67 (m, 2H), 3.47-3.56 (m, 6H), 3.52 (s, 3H), 3.40 (dd, 2H), 3.21 (s, 3H), 1.33 (s, 9H).
LCMS m/z 793 (M+H)2+(ES$^+$), 397 (M+2H)$^{2+}$ (ES$^+$)

Example 71

N-(5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)-1,1,1-trifluoromethanesulfonamide

(i) N-(5-(tert-Butyl)-2-methoxy-3-nitrophenyl)-1,1,1-trifluoromethanesulfonamide To a stirred solution of 5-(tert-butyl)-2-methoxy-3-nitroaniline (100 mg, 0.441 mmol) in chloroform (2.5 mL) at 0-5° C., was added triethylamine (80 μL, 0.574 mmol) then trifluoromethanesulfonic anhydride (75 μL, 0.444 mmol). The mixture was heated at reflux for 2 h. The reaction mixture was quenched with sat. aq. NaHCO₃ solution (10 mL) and the layers separated. The aqueous layer was back-extracted with DCM (2×10 mL). The combined organic extracts were dried (MgSO₄), filtered and concentrated in vacuo to afford a brown oil. The crude product was purified by chromatography on silica gel (12 g column, 1-10% MeOH in DCM) to afford a dark yellow oil (70 mg).

LCMS m/z 355 (M−H)⁻ (ES⁻)

(ii) N-(3-Amino-5-(tert-butyl)-2-methoxyphenyl)-1,1,1-trifluoromethanesulfonamide The product from step (i) above (70 mg, 0.196 mmol) was dissolved in ethanol (3 mL) and Fe powder (110 mg, 1.965 mmol) was added followed by a solution of NH₄Cl (105 mg, 1.965 mmol) in water (1 mL). The resulting suspension was heated at 80° C. for 2 h. The reaction was cooled to rt and filtered. The filtrate was concentrated in vacuo then partitioned between water (10 mL) and EtOAc (10 mL). The aqueous phase was extracted with EtOAc (10 mL). The combined organic extracts were washed with brine (15 mL), dried (MgSO₄), filtered and concentrated in vacuo onto silica gel. The crude product was purified by chromatography on silica gel (12 g column, 1-5% MeOH in DCM) to afford the sub-title compound (55 mg) as a white solid.

LCMS m/z 327 (M+H)⁺ (ES⁺); 325 (M−H)⁻ (ES⁻)

(iii) N-(5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)-1,1,1-trifluoromethanesulfonamide Triethylamine (5 μL, 0.036 mmol) was added to a mixture of the product from step (ii) above (55 mg, 0.169 mmol) and phenyl (4-((2-((3-methoxy-5-(2-(2-(2-methoxyethoxy)ethoxy)-ethoxy)phenyl)amino)pyrimidin-4-yl)oxy)naphthalen-1-yl)carbamate (see Example 19(i) above; 108 mg, 0.169 mmol) in isopropyl acetate (3 mL) and the mixture heated at 60° C. (block temperature) for 5 h. The reaction was cooled to rt and concentrated in vacuo onto silica gel. The crude product was purified by chromatography on the Companion (12 g column, 1-5% MeOH in DCM) to afford the title compound (112 mg) as a pale pink solid.

¹H NMR (400 MHz, DMSO-d6) δ: 11.51 (bs, 1H), 9.43 (s, 1H), 9.35 (s, 1H), 9.00 (s, 1H), 8.42 (d, 1H), 8.36 (s, 1H), 8.28 (d, 1H), 8.11 (d, 1H), 7.85 (d, 1H), 7.68 (t, 1H), 7.59 (t, 1H), 7.42 (d, 1H), 6.91 (d, 1H), 6.81 (d, 2H), 6.55 (d, 1H), 6.04 (t, 1H), 3.85-3.88 (m, 2H), 3.88 (s, 3H), 3.65-3.67 (m, 2H), 3.48-3.55 (m, 6H), 3.52 (s, 3H), 3.40 (dd, 2H), 3.22 (s, 3H), 1.27 (s, 9H).

LCMS m/z 873 (M+H)⁺ (ES⁺)

Example 72

N-(5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)cyclohexanesulfonamide

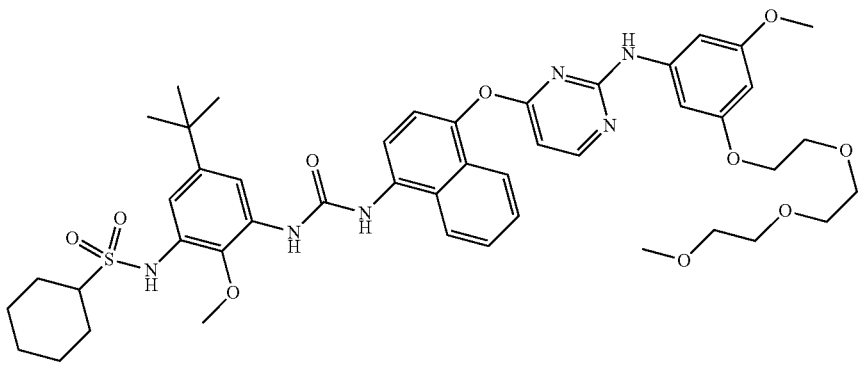 [SMILES: COCCOCCOCCOc1cc(Nc2nccc(Oc3ccc(NC(=O)Nc4cc(C(C)(C)C)cc(NS(=O)(=O)C5CCCCC5)c4OC)c4ccccc34)n2)cc(OC)c1]

(i) N-(3-Amino-5-(tert-butyl)-2-methoxyphenyl) cyclohexanesulfonamide

To a stirred solution of 5-(tert-butyl)-2-methoxybenzene-1,3-diamine (100 mg, 0.515 mmol) in DCM (3 mL) at 0-5° C., was added pyridine (290 μL, 3.59 mmol) then cyclohexanesulfonyl chloride (90 μL, 0.618 mmol). The mixture was warmed to rt and stirred for 7 days. The reaction was concentrated in vacuo and the residue azeotroped with toluene (2×10 mL). The residue was dissolved in a mixture of DCM and MeOH and concentrated in vacuo onto silica gel. The crude product was purified by chromatography on the Companion (12 g column, 5-40% EtOAc in hexane) to afford the sub-title compound (69 mg, 90% purity) as a sticky pink gum.

$^1$H NMR (400 MHz, DMSO-d6) δ: 8.61 (s, 1H), 6.58 (d, 1H), 6.56 (d, 1H), 4.88 (s, 2H), 3.63 (s, 3H), 2.96-3.01 (m, 1H), 2.09-2.12 (m, 2H), 1.78-1.81 (m, 2H), 1.60-1.63 (m, 1H), 1.29-1.37 (m, 2H), 1.13-1.29 (m, 3H), 1.19 (s, 9H).

(ii) N-(5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)-cyclohexanesulfonamide Triethylamine (5 μL, 0.036 mmol) was added to a mixture of the product from step (i) above (69 mg, 0.182 mmol) and phenyl (4-((2-((3-methoxy-5-(2-(2-(2-methoxyethoxy)ethoxy)-ethoxy)phenyl)amino)pyrimidin-4-yl)oxy)naphthalen-1-yl)carbamate (see Example 19(i) above; 120 mg, 0.187 mmol) in isopropyl acetate (3 mL) and the mixture heated at 60° C. (block temperature) for 4 h. The reaction was cooled to rt and concentrated in vacuo onto silica gel. The crude product was purified by chromatography on the Companion (12 g column, 1-4% MeOH in DCM) to afford the product as a pale pink solid. The material was solubilised in DCM (10 mL) and washed with 1M HCl solution (10 mL). The organic phase was filtered through a hydrophobic frit and concentrated in vacuo affording the title compound (88 mg) as a pale yellow solid.

$^1$H NMR (400 MHz, DMSO-d6) δ: 9.50 (s, 1H), 9.40 (s, 1H), 9.04 (s, 1H), 8.95 (s, 1H), 8.42 (d, 1H), 8.30 (d, 1H), 8.16 (s, 1H), 8.11 (d, 1H), 7.85 (d, 1H), 7.67 (t, 1H), 7.59 (t, 1H), 7.42 (d, 1H), 7.02 (d, 1H), 6.80 (d, 2H), 6.57 (d, 1H), 6.05 (t, 1H), 3.86-3.88 (m, 2H), 3.81 (s, 3H), 3.65-3.67 (m, 2H), 3.48-3.55 (m, 6H), 3.52 (s, 3H), 3.40 (dd, 2H), 3.22 (s, 3H), 3.02-3.08 (m, 1H), 2.17 (bd, 2H), 1.84 (bd, 2H), 1.65 (bd, 1H), 1.42-1.51 (m, 2H), 1.16-1.32 (m, 3H), 1.26 (s, 9H).

LCMS m/z 887 (M+H)$^+$ (ES$^+$)

Example 73

N-(5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)piperidine-1-sulfonamide

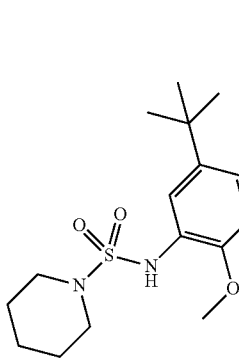
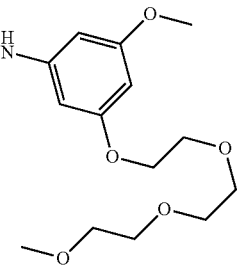

(i) N-(3-Amino-5-(tert-butyl)-2-methoxyphenyl) piperidine-1-sulfonamide

To a stirred solution of 5-(tert-butyl)-2-methoxybenzene-1,3-diamine (150 mg, 0.772 mmol) in DCM (4 mL) at 0-5° C., was added pyridine (440 μL, 5.44 mmol) then piperidine-1-sulfonyl chloride (108 μL, 0.772 mmol). The mixture was warmed to rt and stirred for 6 days. The reaction was concentrated in vacuo and the residue azeotroped with toluene (2×10 mL). The residue was dissolved in a mixture of DCM and MeOH and concentrated in vacuo onto silica gel. The crude product was purified by chromatography on the Companion (40 g column, 1-2% MeOH in DCM, detecting at 225 nm) to afford a yellow solid. The material was re-purified by chromatography on the Companion (12 g column, 1-5% THF in DCM, detecting at 225 nm) to afford the sub-title compound (135 mg) as a pale yellow solid.

LCMS m/z 342 (M+H)$^+$ (ES$^+$); 340 (M−H)$^-$ (ES$^-$)

(ii) N-(5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)piperidine-1-sulfonamide Triethylamine (5 μL, 0.036 mmol) was added to a mixture of the product from step (i) above (60 mg, 0.176 mmol) and phenyl (4-((2-((3-methoxy-5-(2-(2-(2-methoxyethoxy)ethoxy)ethoxy)phenyl)amino)pyrimidin-4-yl)oxy)naphthalen-1-yl)carbamate (see Example 19(i) above; 115 mg, 0.179 mmol) in isopropyl acetate (3 mL) and the mixture heated at 60° C. (block temperature) overnight. The reaction was cooled to rt and concentrated in vacuo onto silica gel. The crude product was purified by chromatography on the Companion (12 g column, 1-4% MeOH in DCM) to afford a solid. The material was solubilised in DCM (10 mL) and washed with 1M HCl solution (10 mL). The organic phase was filtered through a hydrophobic frit and concentrated in vacuo affording the title compound (121 mg) as a pale yellow solid.

¹H NMR (400 MHz, DMSO-d6) δ: 9.55 (s, 1H), 9.44 (s, 1H), 9.13 (s, 1H), 8.95 (s, 1H), 8.42 (d, 1H), 8.31 (d, 1H), 8.11 (s, 1H), 8.10 (d, 1H), 7.85 (d, 1H), 7.67 (t, 1H), 7.59 (t, 1H), 7.42 (d, 1H), 7.11 (d, 1H), 6.79 (d, 2H), 6.58 (d, 1H), 6.06 (t, 1H), 3.86-3.88 (m, 2H), 3.80 (s, 3H), 3.65-3.67 (m, 2H), 3.48-3.55 (m, 6H), 3.52 (s, 3H), 3.40 (dd, 2H), 3.22 (s, 3H), 3.16-3.17 (m, 4H), 1.45-1.57 (m, 6H), 1.26 (s, 9H).

LCMS m/z 888 (M+H)⁺ (ES⁺); 886 (M−H)⁻ (ES⁻)

Example 74

N-(5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)dimethylamino-sulfonamide (ii) N-(5-(tert-Butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)-dimethylamino-sulfonamide Triethylamine (5 μL, 0.036 mmol) was added to a mixture of the product from step (i) above (55 mg, 0.182 mmol) and phenyl (4-((2-((3-methoxy-5-(2-(2-(2-methoxyethoxy)ethoxy)-ethoxy)phenyl)amino)pyrimidin-4-yl)oxy)naphthalen-1-yl)carbamate (see Example 19(i) above; 117 mg, 0.182 mmol) in isopropyl acetate (3 mL) and the mixture heated at 60° C. (block temperature) overnight. The reaction was cooled to rt and concentrated in vacuo onto silica gel. The crude product was purified by chromatography on the Companion (12 g column, 1-4% MeOH in DCM) to a

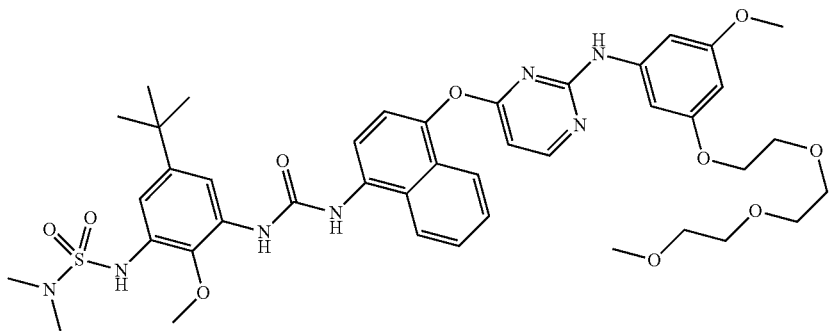 [SMILES: COCCOCCOCCOc1cc(Nc2nccc(Oc3ccc(NC(=O)Nc4cc(C(C)(C)C)cc(NS(=O)(=O)N(C)C)c4OC)c4ccccc34)n2)cc(OC)c1]

(i) N-(3-Amino-5-(tert-butyl)-2-methoxyphenyl)dimethylamino-sulfonamide

To a stirred solution of 5-(tert-butyl)-2-methoxybenzene-1,3-diamine (200 mg, 1.029 mmol) in DCM (4 mL) at 0-5° C., was added pyridine (580 μL, 7.17 mmol) then dimethylsulfamoyl chloride (110 μL, 1.024 mmol). The mixture was warmed to rt and stirred overnight. The reaction was concentrated in vacuo and the residue azeotroped with toluene (2×10 mL). The residue was dissolved in a mixture of DCM and MeOH and concentrated in vacuo onto silica gel. The crude product was purified by chromatography on the Companion (40 g column, 1-2% MeOH in DCM, detecting at 225 nm) to afford a yellow solid. The material was re-purified by chromatography on the Companion (12 g column, 1-5% THF in DCM, detecting at 225 nm) to afford the sub-title compound (164 mg) as a pale yellow solid.

LCMS m/z 302 (M+H)⁺ (ES⁺); 300 (M−H)⁻ (ES⁻)

colourless solid. The material was solubilised in DCM (10 mL) and washed with 1M HCl solution (10 mL). The organic phase was filtered through a hydrophobic frit and concentrated in vacuo affording the title compound (104 mg) as a pale yellow solid.

¹H NMR (400 MHz, DMSO-d6) δ: 9.58 (s, 1H), 9.46 (s, 1H), 9.10 (s, 1H), 8.96 (s, 1H), 8.42 (d, 1H), 8.32 (d, 1H), 8.13 (d, 1H), 8.10 (d, 1H), 7.85 (d, 1H), 7.67 (t, 1H), 7.59 (t, 1H), 7.42 (d, 1H), 7.08 (d, 1H), 6.78 (d, 2H), 6.59 (d, 1H), 6.06 (t, 1H), 3.86-3.88 (m, 2H), 3.82 (s, 3H), 3.65-3.67 (m, 2H), 3.48-3.55 (m, 6H), 3.52 (s, 3H), 3.41 (dd, 2H), 3.22 (s, 3H), 2.78 (s, 6H), 1.26 (s, 9H).

LCMS m/z 848 (M+H)⁺ (ES⁺); 846 (M−H)⁻ (ES⁻)

Example 75

5-(tert-Butyl)-2-methoxy-N-(oxetan-3-yl)-3-(3-(4-((2-(phenylamino)pyridin-4-yl)oxy)-naphthalen-1-yl)ureido)benzamide

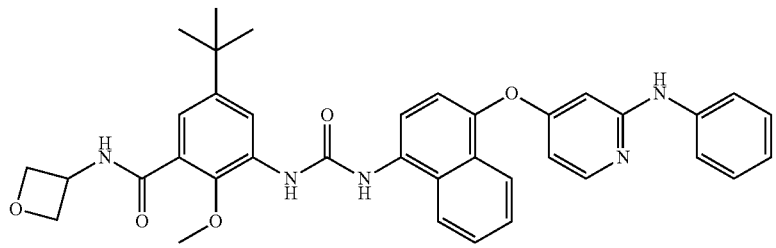 [SMILES: COc1c(NC(=O)Nc2ccc(Oc3ccnc(Nc4ccccc4)c3)c3ccccc23)cc(C(C)(C)C)cc1C(=O)NC1COC1]

(i) tert-Butyl (4-((2-(phenylamino)pyridin-4-yl)oxy) naphthalen-1-yl)carbamate Nitrogen was bubbled through a mixture of aniline (1.1 g, 11.81 mmol), tert-butyl (4-((2-chloropyridin-4-yl)oxy)naphthalen-1-yl)carbamate (see Example 3(ii) above; 4 g, 10.79 mmol), 2,2'-bis(diphenylphosphino)-1,1'-binaphthalene (0.441 g, 0.709 mmol), Pd$_2$dba$_3$ (0.324 g, 0.354 mmol) and caesium carbonate (6.16 g, 18.90 mmol) in dioxane (50 mL) for 5 min then the mixture heated at 100° C. for 3 h. The mixture was diluted with EtOAc (200 mL), filtered and the solvent evaporated under reduced pressure. Ether (20 mL) was added and the white solid filtered off, washed with ether (5 mL) and dried to afford the product (3.33 g) as a white solid. The filtrate was purified by chromatography on silica gel (220 g column, 0-50% EtOAc/isohexane) to give a solid that was triturated with ether, filtered and dried to afford additional product (608 mg) as a white solid. Materials were combined to afford the sub-title compound (3.938 g) as a white solid.

$^1$H NMR (400 MHz, CDCl$_3$) δ: 8.02 (d, 1H), 7.97 (dd, 2H), 7.87 (brd, 1H), 7.63-7.51 (m, 2H), 7.21 (d, 1H), 7.07-7.02 (m, 1H), 6.86 (brs, 2H), 6.41 (d, 1H), 6.34 (dd, 1H), 1.59 (s, 9H). Peaks under CHCl$_3$ LCMS m/z 428 (M+H)$^+$ (ES$^+$); 426 (M–H)$^-$ (ES$^-$)

(ii) 4-((4-Aminonaphthalen-1-yl)oxy)-N-phenylpyridin-2-amine

TFA (10 mL, 130 mmol) was added to a solution of the product from step (i) above (3.9 g, 9.12 mmol) in DCM (50 mL) and stirred at rt for 1 h. The volatiles were removed under reduced pressure and the residue was redissolved in DCM (75 mL). The solution was washed with saturated NaHCO$_3$ solution (50 mL) followed by saturated brine (50 mL) and dried (MgSO$_4$). The drying agent was removed by filtration and the filtrate was concentrated under reduced pressure to yield a pale pink solid. The solid was recrystallised in iPrOAc (60 mL) to yield the sub-title compound (1.1 g) as a white solid. The filtrate was concentrated under reduced pressure and redissolved in refluxing iPrOAc (60 mL). Isohexane (60 mL) was added and the mixture was allowed to cool whilst stirring. The 2nd crop was collected by filtration to yield the sub-title compound (1.2 g) as a pale pink solid. Combined yield of 2.3 g.

$^1$H NMR (400 MHz, DMSO-d6) δ: 8.82 (s, 1H), 8.20-8.11 (m, 1H), 8.02 (d, 1H), 7.69-7.61 (m, 1H), 7.61-7.54 (m, 2H), 7.49-7.40 (m, 2H), 7.22-7.14 (m, 2H), 7.10 (d, 1H), 6.82 (ddd, 1H), 6.71 (d, 1H), 6.49 (dd, 1H), 6.02 (d, 1H), 5.81 (br s, 2H).

LCMS m/z 328 (M+H)$^+$ (ES$^+$)

(iii) Methyl 5-(tert-butyl)-2-methoxy-3-((phenoxycarbonyl)amino)benzoate

Phenyl chloroformate (264 µL, 2.107 mmol) was added to a stirred mixture of methyl 3-amino-5-(tert-butyl)-2-methoxybenzoate (500 mg, 2.107 mmol) and NaHCO$_3$ (354 mg, 4.21 mmol) in DCM (20 mL) and THF (5 mL) at rt. The mixture was stirred overnight then partitioned between DCM (20 mL) and water (20 mL). The organic layer was separated and dried via a hydrophobic frit, affording the sub-title compound (812 mg) as a pale yellow oil which solidified on standing.

LCMS m/z 358 (M+H)$^+$ (ES$^+$)

(iv) Methyl 5-(tert-butyl)-2-methoxy-3-(3-(4-((2-(phenylamino)pyridin-4-yl)oxy)-naphthalen-1-yl) ureido)benzoate Triethylamine (48 µL, 0.344 mmol) was added to a mixture of the product from step (iii) above (610 mg, 1.707 mmol) and the product from step (ii) above (560 mg, 1.711 mmol) in iPrOAc (20 mL) and the mixture heated at 70 CC (block temperature) overnight. The reaction mixture was diluted with THF and concentrated in vacuo onto silica gel. The crude product was purified by chromatography on the Companion (40 g column, 0.5-3% MeOH in DCM) to afford the sub-title compound (688 mg) as a light brown foam.

LCMS m/z 591 (M+H)$^+$ (ES$^+$); 589 (M–H)$^-$ (ES$^-$)

(v) 5-(tert-Butyl)-2-methoxy-3-(3-(4-((2-(phenylamino)pyridin-4-yl)oxy)naphthalen-1-yl)-ureido) benzoic acid, HCl To a stirred solution of the product from step (iv) above (688 mg, 1.165 mmol) in THF (25 mL) and water (5 mL) was added NaOH (2M aq.) (3500 µL, 7.00 mmol). MeOH (2 mL) was added and stirring continued for 48 h. Additional NaOH was added (1 mL) and stirring continued over a weekend. The reaction was concentrated in vacuo affording a brown gum. The material was suspended in water and acidified with 1M HCl causing a solid to precipitate. The solid was collected by filtration, washing with water and the solid dried at 40° C. under vacuum affording the sub-title compound (590 mg) as a pink solid.

LCMS m/z 577 (M+H)$^+$ (ES$^+$); 575 (M–H)$^-$ (ES$^-$)

(vi) 5-(tert-Butyl)-2-methoxy-N-(oxetan-3-yl)-3-(3-(4-((2-(phenylamino)pyridin-4-yl)oxy)-naphthalen-1-yl)ureido)benzamide A stirred mixture of the product from step (v) above (80 mg, 0.130 mmol), oxetan-3-amine (13.63 µL, 0.196 mmol) and Et$_3$N (54.6 µL, 0.391 mmol) in DCM (4 mL) was cooled in an ice-bath. T3P (50 wt % in EtOAc) (78 µL, 0.130 mmol) was added, the ice-bath was removed and the reaction mixture allowed to warm to rt and stirred overnight. Further portions of amine (10 µL), Et$_3$N (25 µL) and T3P (20 µL) were added and stirring continued overnight. The reaction mixture was partitioned between sat. aq. NaHCO$_3$ (10 mL) and DCM (10 mL). The aqueous phase was back extracted with fresh DCM (10 mL). The combined organic extracts were washed with water (20 mL), brine (20 mL), dried (MgSO$_4$), filtered and concentrated in vacuo onto silica gel. The crude product was purified by chromatography on the Companion (12 g column, 1-4% MeOH in DCM) to afford the title compound (63 mg) as a pink/brown solid.

$^1$H NMR (400 MHz, DMSO-d6) δ: 9.46 (s, 1H), 8.98 (d, 1H), 8.90 (s, 2H), 8.47 (d, 1H), 8.30 (d, 1H), 8.09 (d, 2H), 7.89 (d, 1H), 7.72 (t, 1H), 7.58-7.64 (m, 3H), 7.39 (d, 1H), 7.20 (t, 2H), 7.08 (d, 1H), 6.84 (t, 1H), 6.55 (dd, 1H), 6.11 (d, 1H), 4.99-5.08 (m, 1H), 4.81 (t, 2H), 4.60 (t, 2H), 3.82 (s, 3H), 1.29 (s, 9H).

LCMS m/z 632 (M+H)$^+$ (ES$^+$); 630 (M−H)− (ES$^-$)

Example 76

5-(tert-Butyl)-N-(2-(dimethylamino)ethyl)-2-methoxy-3-(3-(4-((2-((3-methoxy-5-(2-(2-(2-methoxyethoxy)ethoxy)ethoxy)phenyl)amino)pyridin-4-yl)oxy)naphthalen-1-yl)ureido)-benzamide

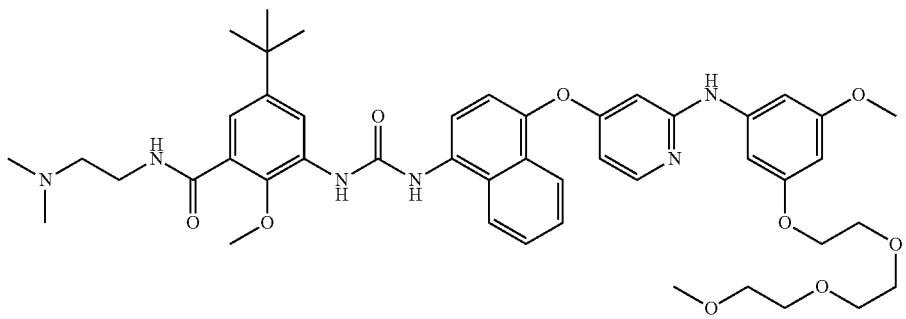

(i) Methyl 5-(tert-butyl)-2-methoxy-3-(3-(4-((2-((3-methoxy-5-(2-(2-(2-methoxyethoxy)-ethoxy)ethoxy)phenyl)amino)pyridin-4-yl)oxy)naphthalen-1-yl)ureido)benzoate Triethylamine (16.10 µL, 0.115 mmol) was added to a mixture of methyl 5-(tert-butyl)-2-methoxy-3-((phenoxycarbonyl)amino)benzoate (see Example 75(iii) above; 206 mg, 0.577 mmol) and 4-((4-aminonaphthalen-1-yl)oxy)-N-(3-methoxy-5-(2-(2-(2-methoxyethoxy)-ethoxy)ethoxy)phenyl)pyridin-2-amine (see Example 11(ii) above; 300 mg, 0.577 mmol) in iPrOAc (8 mL) and the mixture heated at 70° C. (block temperature) overnight. The reaction was cooled to rt and concentrated in vacuo onto silica gel. The crude product was purified by chromatography on the Companion (40 g column, 1-5% MeOH in DCM) to afford the sub-title compound (363 mg) as an off-white foam.

LCMS m/z 783 (M+H)$^+$ (ES$^+$)

(ii) 5-(tert-butyl)-2-methoxy-3-(3-(4-((2-((3-methoxy-5-(2-(2-(2-methoxyethoxy)ethoxy)-ethoxy)phenyl)amino)pyridin-4-yl)oxy)naphthalen-1-yl)ureido)benzoic acid, HCl To a stirred solution of the product from step (i) above (363 mg, 0.417 mmol) in THF (10 mL) and water (2 mL) was added NaOH (2M aq.) (1252 µL, 2.504 mmol). MeOH (1 mL) was added and stirring continued for 48 h. The reaction was concentrated in vacuo affording a yellow/brown gum. The material was suspended in water and acidified with 1M HCl causing a pale solid to precipitate. The solid was collected by filtration, washing with water and the solid dried at 40° C. under vacuum affording the sub-title compound (315 mg) as a pale pink solid.

LCMS m/z 769 (M+H)$^+$ (ES$^+$); 767 (M−H)$^-$ (ES$^-$)

(iii) 5-(tert-Butyl)-N-(2-(dimethylamino)ethyl)-2-methoxy-3-(3-(4-((2-((3-methoxy-5-(2-(2-(2-methoxyethoxy)ethoxy)ethoxy)phenyl)amino)pyridin-4-yl)oxy)naphthalen-1-yl)ureido)-benzamide A stirred mixture of the product from step (ii) above (100 mg, 0.124 mmol), N1,N1-dimethylethane-1,2-diamine (27 µL, 0.247 mmol) and Et$_3$N (69 µL, 0.495 mmol) in DCM (4 mL) was cooled in an ice-bath. T3P (50 wt % in EtOAc) (89 µL, 0.149 mmol) was added, the ice-bath was removed and the reaction mixture allowed to warm to rt and stirred over the weekend. The reaction mixture was partitioned between sat. aq. NaHCO$_3$ (10 mL) and DCM (10 mL). The aqueous phase was back extracted with fresh DCM (10 mL). The combined organic extracts were washed with water (20 mL), brine (20 mL), dried (MgSO$_4$), filtered and concentrated in vacuo onto silica gel. The crude product was purified by chromatography on the Companion (12 g column, 1-5% MeOH in DCM) to afford a pale pink foam. The crude product was purified by preparative HPLC (Varian, Basic (0.1% Ammonium Bicarbonate), Basic, Waters X-Bridge Prep-C18, 5 µm, 19×50 mm column, 25-70% MeCN in Water) to afford the title compound (44 mg) as a white solid.

$^1$H NMR (400 MHz, DMSO-d6) δ: 9.47 (s, 1H), 8.99 (s, 1H), 8.89 (s, 1H), 8.48 (d, 1H), 8.35 (t, 1H), 8.30 (d, 1H), 8.10-8.12 (m, 2H), 7.87 (d, 1H), 7.71 (t, 1H), 7.61 (t, 1H), 7.39 (d, 1H), 7.28 (d, 1H), 6.91 (s, 1H), 6.78 (s, 1H), 6.58 (dd, 1H), 6.08 (d, 1H), 6.04 (t, 1H), 3.97-3.99 (m, 2H), 3.81 (s, 3H), 3.69-3.71 (m, 2H), 3.65 (s, 3H), 3.56-3.58 (m, 2H), 3.50-3.54 (m, 4H), 3.41-3.45 (m, 4H), 3.22 (s, 3H), 2H under DMSO, 2.33 (bs, 6H), 1.29 (s, 9H).

LCMS m/z 839 (M+H)$^+$ (ES$^+$); 837 (M−H)− (ES$^-$)

Example 77

5-(tert-Butyl)-2-methoxy-3-(3-(4-((2-(3-methoxy-5-(2-(2-(2-methoxyethoxy)ethoxy)ethoxy)-phenyl)amino)pyridin-4-yl)oxy)naphthalen-1-yl)ureido)-N-(oxetan-3-yl)benzamide

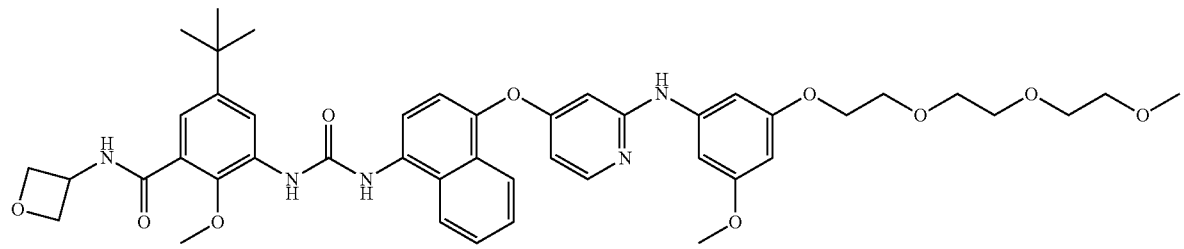 [SMILES: COCCOCCOCCOc1cc(Nc2cc(Oc3ccc(NC(=O)Nc4cc(C(C)(C)C)cc(C(=O)NC5COC5)c4OC)c4ccccc34)ccn2)cc(OC)c1]

A stirred mixture of 5-(tert-butyl)-2-methoxy-3-(3-(4-((2-((3-methoxy-5-(2-(2-(2-methoxy-ethoxy)ethoxy)ethoxy)phenyl)amino)pyridin-4-yl)oxy)naphthalen-1-yl)ureido)benzoic acid, HCl (see Example 76(ii) above; 137 mg, 0.170 mmol), oxetan-3-amine (24 µL, 0.345 mmol) and triethylamine (100 µL, 0.717 mmol) in DCM (5 mL) was cooled in an ice-bath. 50 wt % T3P in EtOAc (150 µL, 0.252 mmol) was added, the ice-bath was removed and the reaction mixture allowed to warm to rt and stirred for 2 h. The reaction mixture was partitioned between sat. aq. NaHCO$_3$ (10 mL) and DCM (10 mL). The aqueous phase was back extracted with fresh DCM (10 mL). The combined organic extracts were washed with water (20 mL), brine (20 mL), dried (MgSO$_4$), filtered and concentrated in vacuo onto silica gel. The crude product was purified by chromatography on the Companion (12 g column, 1-5% MeOH in DCM) to afford the title compound (117 mg) as a white solid.

$^1$H NMR (400 MHz, DMSO-d6) δ: 9.46 (s, 1H), 8.98 (d, 1H), 8.91 (s, 1H), 8.88 (s, 1H), 8.47 (d, 1H), 8.30 (d, 1H), 8.08-8.12 (m, 2H), 7.88 (d, 1H), 7.72 (t, 1H), 7.61 (t, 1H), 7.39 (d, 1H), 7.08 (d, 1H), 6.91 (s, 1H), 6.79 (s, 1H), 6.58 (dd, 1H), 6.10 (d, 1H), 6.04 (t, 1H), 4.99-5.08 (m, 1H), 4.81 (t, 2H), 4.60 (t, 2H), 3.97-3.99 (m, 2H), 3.81 (s, 3H), 3.70-3.72 (m, 2H), 3.66 (s, 3H), 3.50-3.58 (m, 6H), 3.43 (dd, 2H), 3.23 (s, 3H), 1.29 (s, 9H).

LCMS m/z 824 (M+H)$^+$ (ES$^+$); 412 (M+2H)$^{2+}$ (ES$^+$)

Example 78

5-(tert-Butyl)-2-methoxy-N-(oxetan-3-yl)-3-(3-(4-((2-(phenylamino)pyrimidin-4-yl)oxy)-naphthalen-1-yl)ureido)benzamide

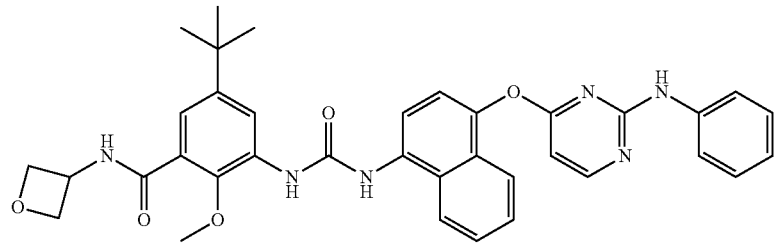 [SMILES: COc1c(NC(=O)Nc2ccc(Oc3ccnc(Nc4ccccc4)n3)c3ccccc23)cc(C(C)(C)C)cc1C(=O)NC1COC1]

(i) Methyl 5-(tert-butyl)-2-methoxy-3-(3-(4-((2-(phenylamino)pyrimidin-4-yl)oxy)naphthalen-1-yl)ureido)benzoate Triethylamine (25 µL, 0.179 mmol) was added to a mixture of methyl 5-(tert-butyl)-2-methoxy-3-((phenoxycarbonyl)amino)benzoate (see Example 75(iii) above; 320 mg, 0.895 mmol) and 4-((4-aminonaphthalen-1-yl)oxy)-N-phenylpyrimidin-2-amine (see, for example, Ito, K. et al., WO 2013/050756, 294 mg, 0.895 mmol) in isopropyl acetate (10 mL) and the mixture heated at 60° C. (block temperature) overnight, during which time a solid precipitated from solution. The solid was collected by filtration, washing with additional iPrOAc afforded the sub-title compound (275 mg) as a white solid.

LCMS m/z 592 (M+H)$^+$ (ES$^+$)

(ii) 5-(tert-Butyl)-2-methoxy-3-(3-(4-((2-(phenylamino)pyrimidin-4-yl)oxy)naphthalen-1-yl)ureido)benzoic acid To a stirred solution of the product from step (i) above (275 mg, 0.465 mmol) in THF (10 mL) and water (2 mL) was added NaOH (2M aq.) (1000 µL, 2.000 mmol). MeOH (1 mL) was added and stirring continued overnight. Further portions of NaOH (0.5 mL), water (0.5 mL) and MeOH (0.5 mL) were added and stirring continued overnight. The reaction was concentrated in vacuo affording a pale pink solid. The material was suspended in water and acidified with 1M HCl causing a solid to precipitate. The mixture was sonicated for 2 mins then the solid collected by filtration, washing with water. The solid was dried at 40° C. under vacuum affording the sub-title compound (233 mg) as a yellow solid.

LCMS m/z 578 (M+H)$^+$ (ES$^+$); 576 (M−H)$^−$ (ES$^−$)

(iii) 5-(tert-Butyl)-2-methoxy-N-(oxetan-3-yl)-3-(3-(4-((2-(phenylamino)pyrimidin-4-yl)oxy)naphthalen-1-yl)ureido)benzamide A stirred mixture of the product from step (ii) above (60 mg, 0.104 mmol), oxetan-3-amine (11 µL, 0.158 mmol) and triethylamine (45 µL, 0.323 mmol) in DCM (4 mL) was cooled in an ice-bath. 50 wt % T3P in EtOAc (62 µL, 0.104 mmol) was added, the ice-bath was removed and the reaction mixture allowed to warm to rt and stirred over the weekend. The reaction mixture was partitioned between sat. aq. NaHCO$_3$ (10 mL) and DCM (10 mL). The aqueous phase was back extracted with fresh DCM (10 mL). The combined organic extracts were washed with water (20 mL), brine (20 mL), dried (MgSO$_4$), filtered and concentrated in vacuo onto silica gel. The crude product was purified by chromatography on the Companion (12 g column, 1-5% MeOH in DCM) to afford the title compound (41 mg) as a white solid.

$^1$H NMR (400 MHz, DMSO-d6) δ: 9.53 (s, 1H), 9.49 (s, 1H), 9.00 (d, 1H), 8.90 (s, 1H), 8.49 (d, 1H), 8.41 (d, 1H), 8.29 (d, 1H), 8.06 (d, 1H), 7.84 (d, 1H), 7.69 (t, 1H), 7.59 (t, 1H), 7.43 (d, 1H), 7.29 (bd, 2H), 7.07 (d, 1H), 6.99 (t, 2H), 6.77 (t, 1H), 6.60 (d, 1H), 4.99-5.08 (m, 1H), 4.81 (t, 2H), 4.60 (t, 2H), 3.82 (s, 3H), 1.29 (s, 9H).

LCMS m/z 633 (M+H)$^+$ (ES$^+$); 631 (M−H)$^−$ (ES$^−$)

Example 79

3-((4-((4-(3-(5-(tert-Butyl)-2-methoxy-3-(methylsulfonamido)phenyl)ureido)naphthalen-1-yl)oxy)pyridin-2-yl)amino)-5-methoxy-N-(2-(4-methylpiperazin-1-yl)ethyl)benzamide

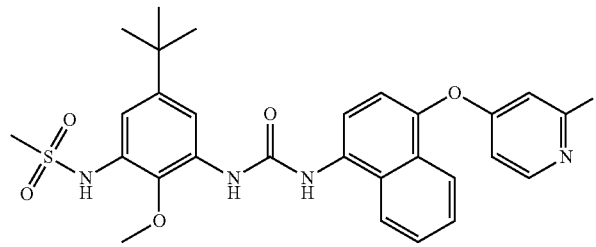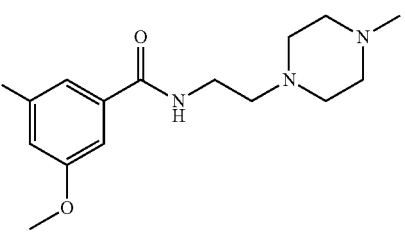

(i) tert-Butyl (4-((2-((3-methoxy-5-((2-(4-methylpiperazin-1-yl)ethyl)carbamoyl)phenyl)amino) pyridin-4-yl)oxy)naphthalen-1-yl)carbamate In a 20 mL vial, a solution of 3-((4-((4-(((tert-butoxycarbonyl)amino)naphthalen-1-yl)oxy)-pyridin-2-yl)amino)-5-methoxybenzoic acid (see Example 66(i) above; 250 mg, 0.476 mmol), 2-(4-methylpiperazin-1-yl)ethanamine (102 mg, 0.713 mmol) and Hünig's Base (249 µL, 1.427 mmol) in DMF (9 mL) was treated with HATU (199 mg, 0.523 mmol). The solution was then partitioned between 10% aq brine (150 mL) and EtOAc (150 mL). The organic layer was washed with sat aq NaHCO$_3$ soln (60 mL), 10% aq. brine (50 mL), dried (Na$_2$SO$_4$), filtered and evaporated under reduced pressure to afford the sub-title compound (300 mg) as beige solid.

LCMS m/z 627 (M+H)$^+$ (ES$^+$); 625 (M−H)$^−$ (ES$^−$)

(ii) 3-((4-((4-Aminonaphthalen-1-yl)oxy)pyridin-2-yl)amino)-5-methoxy-N-(2-(4-methylpiperazin-1-yl)ethyl)benzamide In a 20 mL vial, a solution of the product from step (i) above (300 mg, 0.479 mmol) in DCM (5 mL) was treated dropwise with TFA (1475 µL, 19.15 mmol). The resultant brown solution was stirred at RT for 3 h. The solution was diluted with toluene (400 mL) and concentrated in vacuo to afford a brown solid which was dissolved in EtOAc (300 mL). The EtOAc phase was washed with saturated NaHCO$_3$ solution (3×100 mL), water (3×100 mL) and brine (1×100 mL). The solvent was evaporated in vacuo to afford the sub-title compound (200 mg) as a brown foam.

LCMS m/z 527 (M+H)$^+$ (ES$^+$)

(iii) 3-((4-((4-(3-(5-(tert-Butyl)-2-methoxy-3-(methylsulfonamido)phenyl)ureido)-naphthalen-1-yl)oxy)pyridin-2-yl)amino)-5-methoxy-N-(2-(4-methylpiperazin-1-yl)ethyl)-benzamide In a 20 mL vial, a solution of phenyl (5-(tert-butyl)-2-methoxy-3-(methylsulfonamido)-phenyl)carbamate (see Example 1(vi) above; 74.5 mg, 0.190 mmol), the product from step (ii) above (100 mg, 0.190 mmol) in isopropyl acetate was treated with TEA (5.29 µL, 0.038 mmol). The resultant brown suspension was heated at 60° C. for 18 h then evaporated to dryness in vacuo. The crude product was purified by preparative HPLC (Gilson, Acidic (0.1% Formic acid), Acidic, Waters X-Select Prep-C18, 5 µm, 19×50 mm column, 25-70% MeCN in Water). The residue was partitioned between 20 mL sat. NaHCO$_3$ and EtOAc (20 mL), organic phase was washed with brine (20 mL), dried over sodium sulfate and the solvent removed in vacuo to afford the title compound (48 mg) as an off-white solid.

$^1$H NMR (400 MHz, DMSO-d6) δ 9.40 (s, 1H), 9.16 (s, 1H), 9.07 (s, 1H), 8.93 (s, 1H), 8.30 (d, 1H), 8.22 (t, 1H), 8.19 (d, 1H), 8.13 (d, 1H), 8.11 (s, 1H), 7.90-7.84 (m, 1H), 7.71 (m, 1H), 7.61 (m, 1H), 7.56 (t, 1H), 7.50 (m, 1H), 7.39 (d, 1H), 7.02 (d, 1H), 6.85 (m, 1H), 6.58 (dd, 1H), 6.13 (d, 1H), 3.81 (s, 3H), 3.74 (s, 3H), 3.10 (s, 3H), 2.48-2.20 (m, 8H), 2.14 (s, 3H), 1.27 (s, 9H). (Four Protons overlapping the water peak)

LCMS m/z 825 (M+H)$^+$ (ES$^+$); 823 (M−H)$^−$ (ES$^−$)

Example 80

5-(tert-Butyl)-2-methoxy-N-(oxetan-3-yl)-3-(3-(4-((2-((pyridin-2-ylmethyl)amino)pyridin-4-yl)oxy)naphthalen-1-yl)ureido)benzamide

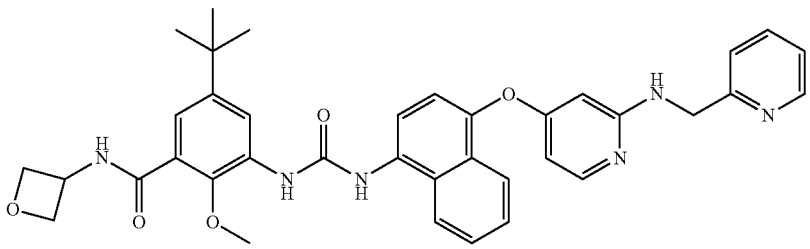 [SMILES: COc1c(NC(=O)Nc2ccc(Oc3ccnc(NCc4ccccn4)c3)c3ccccc23)cc(C(C)(C)C)cc1C(=O)NC1COC1]

(i) tert-Butyl (4-((2-((pyridin-2-ylmethyl)amino)pyridin-4-yl)oxy)naphthalen-1-yl)carbamate A mixture of tert-butyl (4-((2-chloropyridin-4-yl)oxy)naphthalen-1-yl)carbamate (see Example 3(ii) above; 1.0 g, 2.70 mmol), pyridin-2-ylmethanamine (0.350 g, 3.24 mmol), $Pd_2(dba)_3$ (0.150 g, 0.164 mmol), $Cs_2CO_3$ (1.5 g, 4.60 mmol) and BINAP (0.200 g, 0.321 mmol) in 1,4-dioxane (15 mL) was purged with nitrogen for 10 minutes. The mixture was then heated to 90° C. for 18 h then diluted with DCM (50 mL) and filtered. The filtrate was concentrated under reduced pressure and purified by chromatography on the Companion (80 g column, 50-100% EtOAc/isohexane) to afford the sub-title compound (390 mg) as an orange glass.

LCMS m/z 443 (M+H)$^+$ (ES$^+$); 441 (M−H)$^-$ (ES$^-$)

(ii) 4-((4-Aminonaphthalen-1-yl)oxy)-N-(pyridin-2-ylmethyl)pyridin-2-amine

The product from step (i) above (390 mg, 0.749 mmol) and TFA (1.0 mL, 12.98 mmol) were stirred in DCM (5 mL) at rt for 1 h. The mixture was co-evaporated in toluene (40 mL) then redissolved in DCM (15 mL). The solution was washed with saturated $NaHCO_3$ solution (15 mL) then loaded directly onto the Companion (40 g column, 50-100% EtOAc/isohexane) to afford the sub-title compound (235 mg) as a brown foam.

LCMS m/z 343 (M+H)$^+$ (ES$^+$); 341 (M−H)$^-$ (ES$^-$). 90% purity

(iii) Methyl 5-(tert-butyl)-2-methoxy-3-(3-(4-((2-((pyridin-2-ylmethyl)amino)pyridin-4-yl)oxy)naphthalen-1-yl)ureido)benzoate Methyl 5-(tert-butyl)-2-methoxy-3-((phenoxycarbonyl)amino)benzoate (see Example 75(iii) above; 175 mg, 0.447 mmol), the product from step (ii) above (200 mg, 0.432 mmol) and $Et_3N$ (20 μL, 0.143 mmol) were heated to 70° C. in isopropyl acetate (5 mL) for 18 h. The volatiles were removed under reduced pressure and the residue was purified by chromatography on the Companion (40 g column, 0-5% MeOH/EtOAc) to afford the sub-title compound (200 mg) as a brown solid.

LCMS m/z 606 (M+H)$^+$ (ES$^+$)

(iv) 5-(tert-Butyl)-2-methoxy-3-(3-(4-((2-((pyridin-2-ylmethyl)amino)pyridin-4-yl)oxy)naphthalen-1-yl)ureido)benzoic acid The product from step (iii) above (200 mg, 0.330 mmol) and LiOH monohydrate (20 mg, 0.477 mmol) were stirred in water (1 mL), methanol (0.5 mL) and THF (1 mL) at rt for 18 h. The mixture was diluted with water (10 mL) and washed with diethyl ether (10 mL). The aqueous layer was acidified with 1 M citric acid solution (1 mL) and extracted with ethyl acetate (10 mL). A solid formed in the separating funnel which was identified as product. This was combined with the ethyl acetate layer and dissolved fully by adding methanol (10 mL). This combined solution was concentrated onto loose silica and the silicate was purified by chromatography on the Companion (12 g column, 0-20% MeOH(1% $NH_3$)/DCM) to afford the sub-title compound (130 mg) as a tan glass.

LCMS m/z 592 (M+H)$^+$ (ES$^+$); 590 (M−H)$^-$ (ES$^-$)

(v) 5-(tert-Butyl)-2-methoxy-N-(oxetan-3-yl)-3-(3-(4-((2-((pyridin-2-ylmethyl)amino)-pyridin-4-yl)oxy)naphthalen-1-yl)ureido)benzamide HATU (104 mg, 0.275 mmol) was added to a stirred solution of the product from step (iv) above (130 mg, 0.220 mmol), $Et_3N$ (50 μL, 0.359 mmol) and oxetan-3-amine (50 mg, 0.684 mmol) in DMF (3 mL). The mixture was stirred at rt over a weekend. The mixture was diluted with ethyl acetate (10 mL) then washed with water (10 mL), 20% brine (2×10 mL) and saturated brine (10 mL). The organic phase was dried (MgSO$_4$), filtered and concentrated under reduced pressure to yield a brown foam. The crude product was purified by chromatography on the Companion (12 g column, 0-5% MeOH/DCM) to afford the title compound (114 mg) as a beige solid.

$^1$H NMR (DMSO-d6) 400 MHz, δ: 9.42 (s, 1H), 8.96 (d, 1H), 8.88 (s, 1H), 8.45 (d, 1H), 8.45-8.42 (m, 1H), 8.27 (d, 1H), 8.04 (d, 1H), 7.89-7.83 (m, 2H), 7.73-7.65 (m, 2H), 7.59 (ddd, 1H), 7.30 (d, 1H), 7.24 (d, 1H), 7.20 (ddd, 1H), 7.10 (dd, 1H), 7.06 (d, 1H), 6.24 (dd, 1H), 5.93 (d, 1H), 5.08-4.96 (m, 1H), 4.80 (dd, 2H), 4.59 (dd, 2H), 4.49 (d, 2H), 3.80 (s, 3H), 1.28 (s, 9H).

LCMS m/z 647 (M+H)$^+$ (ES$^+$); 645 (M−H)$^-$ (ES$^-$)

Example 81

5-(tert-Butyl)-2-methoxy-3-(3-(4-((2-((3-methoxyphenyl)amino)pyridin-4-yl)oxy)naphthalen-1-yl)ureido)-N-(oxetan-3-yl)benzamide

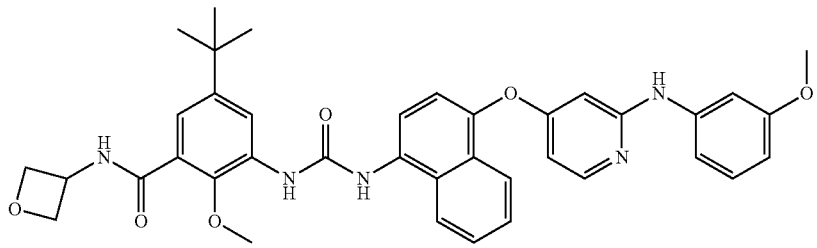 [SMILES: COc1cccc(Nc2cc(Oc3ccc(NC(=O)Nc4cc(C(C)(C)C)cc(C(=O)NC5COC5)c4OC)c4ccccc34)ccn2)c1]

(i) tert-Butyl (4-((2-((3-methoxyphenyl)amino)pyridin-4-yl)oxy)naphthalen-1-yl)carbamate Pd$_2$(dba)$_3$ (120 mg, 0.131 mmol) was added to a degassed suspension of tert-butyl (4-((2-chloropyridin-4-yl)oxy)naphthalen-1-yl)carbamate (see Example 3(ii) above; 1 g, 2.70 mmol), 3-methoxyaniline (0.32 mL, 2.85 mmol), xantphos (150 mg, 0.259 mmol) and Cs$_2$CO$_3$ (1.4 g, 4.30 mmol) in 1,4-dioxane (10 mL) and the reaction heated under nitrogen at 85° C. for 4 h. The reaction mixture was diluted with DCM (100 mL) and filtered. The filtrate was washed with 1M citric acid solution (100 mL), dried (MgSO$_4$) and the solvent evaporated. The crude product was purified by chromatography on silica gel (40 g column, 20-40% EtOAc/isohexane) to afford a pink foam. The foam was stirred in isopropyl acetate (20 mL) overnight and the solid removed by filtration. The filtrate was concentrated under reduced pressure to yield the sub-title compound (560 mg) as a pink gum.

LCMS m/z 458 (M+H)$^+$ (ES$^+$)

(ii) 4-((4-Aminonaphthalen-1-yl)oxy)-N-(3-methoxyphenyl)pyridin-2-amine

TFA (1.0 mL, 12.98 mmol) was added to a solution of the product from step (i) above (560 mg, 1.224 mmol) in DCM (3 mL) and the reaction left stirring overnight. The solvents were evaporated and the residue partitioned between sat NaHCO$_3$ soln. (10 mL) and DCM (10 mL). The organics were separated, dried (MgSO$_4$), filtered and the solvent evaporated to give a pink foam. The foam was purified by chromatography on the Companion (40 g column, 50-100% EtOAc/isohexane) to afford the sub-title compound (375 mg) as a purple solid.

$^1$H NMR (400 MHz, DMSO-d6) δ 8.90 (s, 1H), 8.21-8.10 (m, 1H), 8.03 (d, 1H), 7.69-7.57 (m, 1H), 7.52-7.39 (m, 2H), 7.35-7.28 (m, 1H), 7.14-7.00 (m, 3H), 6.71 (d, 1H), 6.53 (dd, 1H), 6.43 (dt, 1H), 6.02 (d, 1H), 5.91 (s, 2H), 3.67 (s, 3H).

LCMS m/z 358 (M+H)$^+$ (ES$^+$)

(iii) Methyl 5-(tert-butyl)-2-methoxy-3-(3-(4-((2-((3-methoxyphenyl)amino)pyridin-4-yl)oxy)naphthalen-1-yl)ureido)benzoate Methyl 5-(tert-butyl)-2-methoxy-3-((phenoxycarbonyl)amino)benzoate (see Example 75(iii) above; 175 mg, 0.447 mmol), the product from step (ii) above (150 mg, 0.420 mmol) and Et$_3$N (20 μL, 0.143 mmol) were heated to 70° C. in isopropyl acetate (5 mL) for 18 h. The volatiles were removed under reduced pressure and the residue was purified by chromatography on the Companion (40 g column, 20-80% EtOAc/isohexane) to afford the sub-title compound (130 mg) as a purple solid.

LCMS m/z 621 (M+H)$^+$ (ES$^+$), 85% purity

(iv) 5-(tert-Butyl)-2-methoxy-3-(3-(4-((2-((3-methoxyphenyl)amino)pyridin-4-yl)oxy)naphthalen-1-yl)ureido)benzoic acid The product from step (iii) above (130 mg, 0.209 mmol) and LiOH monohydrate (12 mg, 0.286 mmol) were stirred in water (1 mL), methanol (0.5 mL) and THF (1 mL) at rt for 18 h. The mixture was diluted with water (10 mL) and washed with diethyl ether (10 mL). The aqueous layer was acidified with 1 M citric acid solution (1 mL) and extracted with ethyl acetate (10 mL). The organic phase was dried (MgSO$_4$), filtered and concentrated under reduced pressure. The crude product was purified by chromatography on the Companion (12 g column, 0-20% MeOH(1% NH3)/DCM) to afford the sub-title compound (90 mg) as a tan glass.

LCMS m/z 607 (M+H)$^+$ (ES$^+$); 605 (M–H)$^-$ (ES$^-$)

(v) 5-(tert-Butyl)-2-methoxy-3-(3-(4-((2-((3-methoxyphenyl)amino)pyridin-4-yl)oxy)naphthalen-1-yl)ureido)-N-(oxetan-3-yl)benzamide HATU (70 mg, 0.184 mmol) was added to a stirred solution of the product from step (iv) above (90 mg, 0.148 mmol), Et$_3$N (40 μL, 0.287 mmol) and oxetan-3-amine (30 mg, 0.410 mmol) in DMF (3 mL). The mixture was stirred at rt over a weekend. The mixture was diluted with ethyl acetate (10 mL) then washed with water (10 mL), 20% brine (2×10 mL) and saturated brine (10 mL). The organic phase was dried (MgSO$_4$), filtered and concentrated under reduced pressure to yield a brown foam. The crude product was purified by chromatography on the Companion (12 g column, 0-5% MeOH/DCM) to afford the title compound (74 mg) as a white solid.

$^1$H NMR (DMSO-d6) 400 MHz, δ: 9.46 (s, 1H), 8.97 (d, 1H), 8.93-8.87 (m. 2H), 8.46 (d, 1H), 8.29 (d, 1H), 8.10 (d, 1H), 8.09 (d, 1H), 7.88 (d, 1H), 7.72 (ddd, 1H), 7.62 (ddd, 1H), 7.39 (d, 1H), 7.36-7.31 (m, 1H), 7.13-7.04 (m, 3H), 6.56 (dd, 1H), 6.47-6.39 (m, 1H), 6.10 (d, 1H), 5.09-4.97 (m, 1H), 4.81 (dd, 2H), 4.60 (dd, 2H), 3.81 (s, 3H), 3.68 (s, 3H), 1.29 (s, 9H).

LCMS m/z 662 (M+H)$^+$ (ES$^+$); 660 (M–H)$^-$ (ES$^-$)

Example 82

5-(tert-Butyl)-3-(3-(2,3-difluoro-4-((2-(phenylamino)pyridin-4-yl)oxy)phenyl)ureido)-2-methoxy-N-(oxetan-3-yl)benzamide

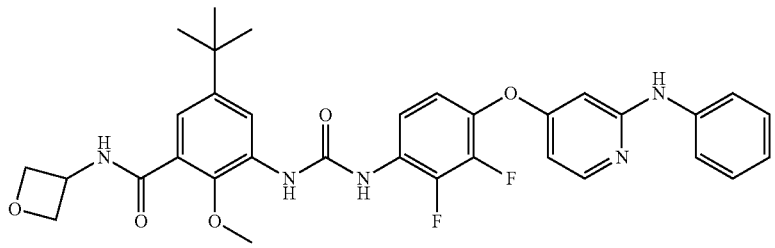 [SMILES: COc1c(NC(=O)Nc2ccc(Oc3ccnc(Nc4ccccc4)c3)c(F)c2F)cc(C(C)(C)C)cc1C(=O)NC1COC1]

(i) tert-Butyl (4-((2-chloropyridin-4-yl)oxy)-2,3-difluorophenyl)carbamate 4-((2-Chloropyridin-4-yl)oxy)-2,3-difluoroaniline (see, for example, Flynn, D. L., et al., WO 2013/036232, 4.33 g, 14.51 mmol) and di-tert-butyl dicarbonate (3.5 g, 16.04 mmol) were heated to reflux in tert-butanol (60 mL) for 18 h. Di-tert-butyl dicarbonate (3.5 g, 16.04 mmol) was added and the mixture was heated to reflux for a further 3 days. The mixture was diluted with ethyl acetate (300 mL) and washed with water (3×200 mL) followed by saturated brine (200 mL). The organic phase was dried (MgSO$_4$), filtered then concentrated under reduced pressure. The crude product was purified by chromatography on the Companion (120 g column, 10-50% EtOAc/isohexane) then purified again on the Companion (80 g column, DCM) to afford the sub-title compound (3.11 g) as a yellow oil.

$^1$H NMR (400 MHz, CDCl3) δ 8.19 (d, 1H), 7.89 (dd, 1H), 6.88 (ddd, 1H), 6.78-6.71 (m, 2H), 6.69-6.61 (m, 1H), 1.48 (s, 9H).

LCMS m/z 357, 359 (M+H)$^+$ (ES$^+$)

(ii) tert-Butyl (2,3-difluoro-4-((2-(phenylamino)pyridin-4-yl)oxy)phenyl)carbamate A mixture of BINAP (300 mg, 0.482 mmol), Pd$_2$(dba)$_3$ (210 mg, 0.229 mmol), the product from step (i) above (1.5 g, 4.20 mmol) and Cs$_2$CO$_3$ (2.1 g, 6.45 mmol) in dioxane (25 mL) was degassed for 5 min. Aniline (400 μL, 4.39 mmol) was added and the mixture heated at 70° C. for 3 h then 85° C. for 8 h. The mixture was diluted with DCM (150 mL) and filtered. The filtrate was concentrated under reduced pressure then purified by chromatography on the Companion (80 g column, 20-40% EtOAc/isohexane) to afford the sub-title compound (1.2 g) as an orange foam.

LCMS m/z 414 (M+H)$^+$ (ES"); 412 (M−H)$^-$ (ES$^-$)

(iii) 4-(4-Amino-2,3-difluorophenoxy)-N-phenylpyridin-2-amine, 1.0 TFA

TFA (4.0 ml, 51.9 mmol) was added to a solution of the product from step (ii) above (1.35 g, 3.27 mmol) in DCM (10 mL) and stirred at rt for 1 h. The mixture was concentrated under reduced pressure then co-evaporated with toluene (50 mL). The TFA salt was purified by chromatography on the Companion (40 g column, 30-70% EtOAc/isohexane) to afford the sub-title compound (1.36 g) as a tan solid.

LCMS m/z 314 (M+H)$^+$ (ES$^+$)

(iv) Methyl 5-(tert-butyl)-3-(3-(2,3-difluoro-4-((2-(phenylamino)pyridin-4-yl)oxy)phenyl)ureido)-2-methoxybenzoate The product from step (iii) above (200 mg, 0.468 mmol) was dissolved in isopropyl acetate (5 mL) and washed with NaHCO$_3$ solution (2×5 mL) followed by saturated brine (5 mL). The organic phase was dried (MgSO$_4$) then heated to 70° C. with methyl 5-(tert-butyl)-2-methoxy-3-((phenoxycarbonyl)amino)benzoate (see Example 75(iii) above; 175 mg, 0.447 mmol) and Et$_3$N (20 μL, 0.143 mmol) for 48 h. Upon cooling, a solid was removed by filtration and the filtrate was concentrated under reduced pressure then purified by chromatography on the Companion (40 g column, 1-2% MeOH/DCM) to afford the sub-title compound (219 mg) as a light brown gum.

LCMS m/z 577 (M+H)$^+$ (ES$^+$)

(v) 5-(tert-Butyl)-3-(3-(2,3-difluoro-4-((2-(phenylamino)pyridin-4-yl)oxy)phenyl)ureido)-2-methoxybenzoic acid The product from step (iv) above (220 mg, 0.382 mmol) and LiOH monohydrate (10 mg, 0.238 mmol) were stirred in water (1 mL), methanol (0.5 mL) and THF (1 mL) at rt for 18 h. The mixture was diluted with water (15 mL) and the resulting solid was removed by filtration. The filtrate was acidified with 1 M citric acid solution (1 mL) and extracted with ethyl acetate (20 mL). The organic phase was dried (MgSO$_4$), filtered and concentrated under reduced pressure. The crude product was purified by chromatography on the Companion (12 g column, 0-20% MeOH(1% NH$_3$)/DCM) to afford the sub-title compound (50 mg) as a tan glass.

LCMS m/z 563 (M+H)$^+$ (ES$^+$); 561 (M−H)$^-$ (ES$^-$)

(vi) 5-(tert-Butyl)-3-(3-(2,3-difluoro-4-((2-(phenylamino)pyridin-4-yl)oxy)phenyl)ureido)-2-methoxy-N-(oxetan-3-yl)benzamide HATU (50 mg, 0.131 mmol) was added to a stirred solution of the product from step (v) above (50 mg, 0.089 mmol), Et$_3$N (30 μl, 0.215 mmol) and oxetan-3-amine (20 mg, 0.274 mmol) in DMF (3 mL). The mixture was stirred at rt over a weekend. Water (10 mL) was added dropwise and the resulting precipitate was collected by filtration. The solid was purified by chromatography on the Companion (12 g column, 0-5% MeOH/DCM) to afford the title compound (35 mg) as a white solid.

¹H NMR (DMSO-d6) 400 MHz, δ: 9.55 (s, 1H), 9.00 (s, 1H), 8.96 (d, 1H), 8.93 (s, 1H), 8.40 (d, 1H), 8.14-8.06 (m, 2H), 7.67-7.60 (m, 2H), 7.28-7.18 (m, 3H), 7.08 (d, 1H), 6.88 (ddd, 1H), 6.50 (dd, 1H), 6.25 (d, 1H), 5.08-4.95 (m, 1H), 4.80 (dd, 2H), 4.58 (dd, 2H), 3.76 (s, 3H), 1.29 (s, 9H).
LCMS m/z 618 (M+H)⁺ (ES⁺); 616 (M−H)⁻ (ES⁻)

Example 83

The following compounds were prepared by methods analogous to those described above. Where chemical shifts from ¹H NMR spectra are reported, these were obtained at 400 MHz and ambient temperature, unless otherwise specified.

(a) N-(4-(tert-butyl)-6-(3-(4-((2-((3-methoxy-5-(2-(2-(2-methoxyethoxy)ethoxy)ethoxy)phenyl)-amino)pyrimidin-4-yl)oxy)naphthalen-1-yl)ureido)-[1,1'-biphenyl]-2-yl)methanesulfonamide

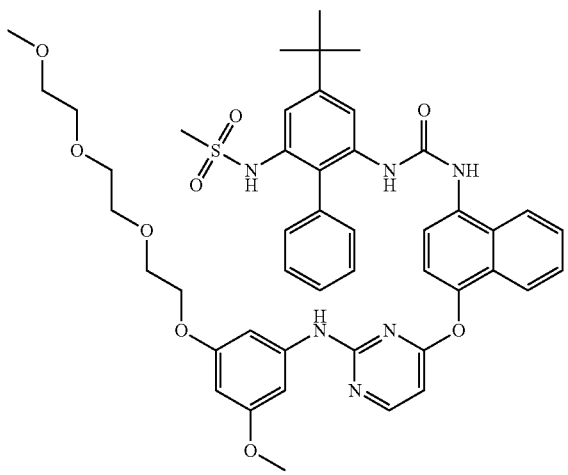 [SMILES: COCCOCCOCCOc1cc(Nc2nccc(Oc3ccc(NC(=O)Nc4cc(C(C)(C)C)cc(NS(C)(=O)=O)c4-c4ccccc4)c4ccccc34)n2)cc(OC)c1]

δ: 9.41 (s, 1H), 9.00 (s, 1H), 8.47 (s, 1H), 8.40 (d, 1H), 8.00 (d, 1H), 7.92 (s, 1H), 7.88 (d, 1H), 7.81 (d, 1H), 7.68 (s, 1H), 7.62-7.45 (m, 5H), 7.38-7.36 (m, 3H), 7.18 (s, 1H), 6.80 (brd, 2H), 6.53 (d, 1H), 6.04 (s, 1H), 3.88 (t, 2H), 3.66 (t, 2H), 3.56-3.49 (m, 9H), 3.42-3.40 (m, 2H), 3.22 (s, 3H), 2.60 (s, 3H), 1.33 (s, 9H).
LCMS m/z 865 (M+H)⁺ (ES⁺)

(b) N-(5-(tert-butyl)-2-methoxy-3-(3-(4-((2-((3-methoxy-5-(2-(2-(2-methoxyethoxy)ethoxy)-ethoxy)phenyl)amino)pyrimidin-4-yl)oxy)naphthalen-1-yl)ureido)phenyl)morpholine-4-sulfonamide

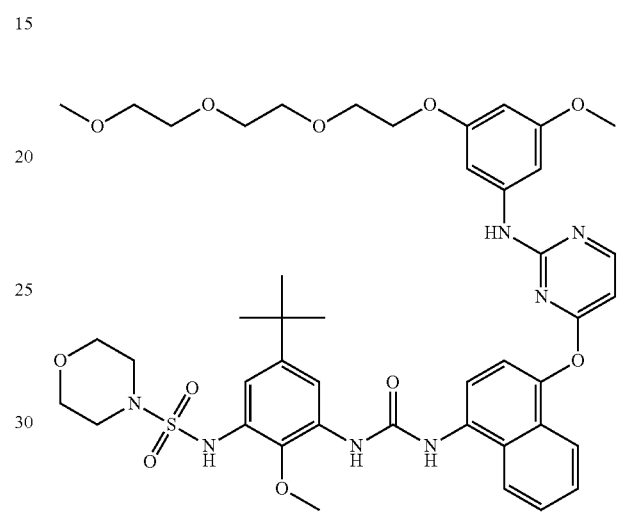

δ: 9.44 (s, 1H), 9.35 (s, 1H), 9.32 (s, 1H), 8.92 (s, 1H), 8.42 (d, 1H), 8.28 (d, 1H), 8.17 (d, 1H), 8.11 (d, 1H), 7.85 (d, 1H), 7.68 (t, 1H), 7.59 (t, 1H), 7.42 (d, 1H), 7.10 (d, 1H), 6.81 (d, 2H), 6.55 (d, 1H), 6.04 (t, 1H), 3.86-3.88 (m, 2H), 3.82 (s, 3H), 3.65-3.67 (m, 2H), 3.60-3.63 (m, 4H), 3.48-3.54 (m, 6H), 3.51 (s, 3H), 3.40 (dd, 2H), 3.22 (s, 3H), 3.14-3.16 (m, 4H), 1.27 (s, 9H).
LCMS m/z 890 (M+H)⁺ (ES⁺)

(c) N-(5-(tert-butyl)-3-(3-(4-((2-((3-(2-(2-(2-hydroxyethoxy)ethoxy)ethoxy)-5-methoxyphenyl)-amino)pyrimidin-4-yl)oxy)naphthalen-1-yl)ureido)-2-methoxyphenyl)methanesulfonamide

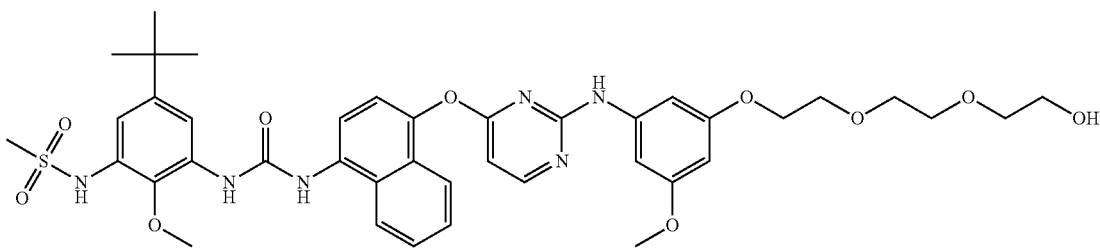 [SMILES: COc1cc(Nc2nccc(Oc3ccc(NC(=O)Nc4cc(C(C)(C)C)cc(NS(C)(=O)=O)c4OC)c4ccccc34)n2)cc(OCCOCCOCCO)c1]

δ: 9.44 (s, 1H), 9.36 (s, 1H), 9.16 (s, 1H), 8.93 (s, 1H), 8.42 (d, 1H), 8.27 (d, 1H), 8.19 (s, 1H), 8.11 (d, 1H), 7.85 (d, 1H), 7.68 (dd, 1H), 7.59 (dd, 1H), 7.42 (d, 1H), 7.02 (s, 1H), 6.81 (brs, 2H), 6.55 (d, 1H), 6.04 (s, 1H), 4.58 (t, 1H), 3.89-3.85 (m, 2H), 3.81 (s, 3H), 3.68-3.64 (m, 2H), 3.55-3.45 (m, 9H), 3.42-3.37 (m, 2H), 3.10 (s, 3H), 1.27 (s, 9H).

LCMS m/z 805 (M+H)$^+$ (ES$^+$)

(d) 3-((4-((4-(3-(5-(tert-butyl)-2-methoxy-3-(methyl-sulfonamido)phenyl)ureido)naphthalen-1-yl)oxy)pyridin-2-yl)amino)-5-methoxy-N-(2-(pyrrolidin-1-yl)ethyl)benzamide

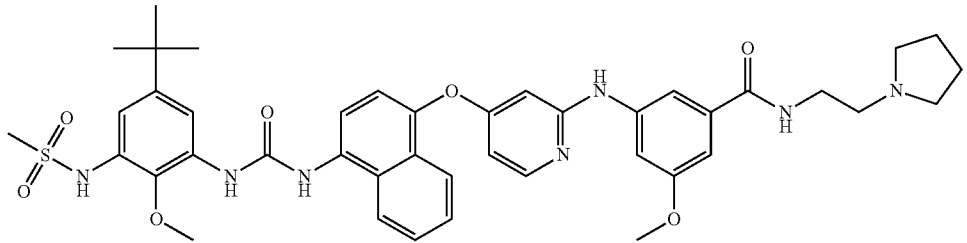 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCCN2CCCC2)c1]

δ 9.39 (s, 1H), 9.11 (d, 2H), 8.92 (s, 1H), 8.39-8.23 (m, 2H), 8.18 (d, 1H), 8.14-8.06 (m, 2H), 7.91-7.80 (m, 1H), 7.69 (m, 1H), 7.60 (m, 1H), 7.56 (t, 1H), 7.49 (t, 1H), 7.38 (d, 1H), 7.01 (d, 1H), 6.86 (m, 1H), 6.57 (dd, 1H), 6.11 (d, 1H), 3.80 (s, 3H), 3.73 (s, 3H), 3.09 (s, 3H), 2.65-2.52 (m, 4H), 1.67 (m, 4H), 1.26 (s, 9H). 4 Protons overlapping the water peak LCMS m/z 796 (M+H)$^+$ (ES$^+$)

(e) 3-((4-((4-(3-(5-(tert-butyl)-2-methoxy-3-(methyl-sulfonamido)phenyl)ureido)naphthalen-1-yl)oxy)pyridin-2-yl)amino)-5-methoxy-N-(2-(piperidin-1-yl)ethyl)benzamide

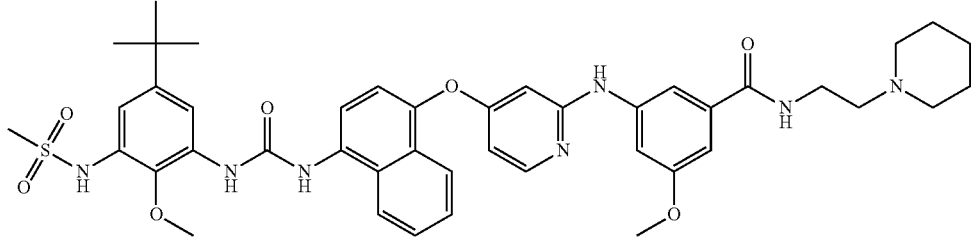 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCCN2CCCCC2)c1]

δ 9.40 (s, 1H), 9.16 (s, 1H), 9.07 (s, 1H), 8.93 (s, 1H), 8.30 (d, 1H), 8.26-8.17 (m, 2H), 8.12 (d, 1H), 8.11 (s, 1H), 7.91-7.84 (m, 1H), 7.71 (m, 1H), 7.61 (m, 1H), 7.56 (t, 1H), 7.50 (m, 1H), 7.39 (d, 1H), 7.02 (d, 1H), 6.86 (m, 1H), 6.58 (dd, 1H), 6.13 (d, 1H), 3.81 (s, 3H), 3.74 (s, 3H), 3.10 (s, 3H), 2.39 (s, 6H), 1.55-1.44 (m, 4H), 1.38 (s, 2H), 1.27 (s, 9H). 2 Protons overlapping the water peak LCMS m/z 810 (M+H)$^+$ (ES$^+$)

187

(f) N-(5-(tert-butyl)-2-methoxy-3-(3-(4-((2-(phenylamino)pyridin-4-yl)oxy)naphthalen-1-yl)ureido)phenyl)morpholine-4-sulfonamide

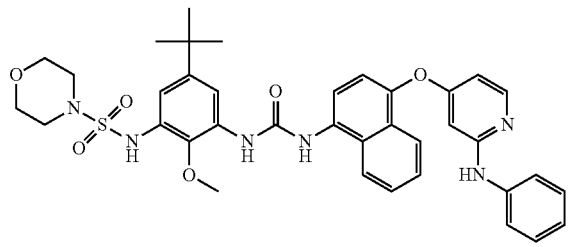 [SMILES: COc1c(NC(=O)Nc2ccc(Oc3ccnc(Nc4ccccc4)c3)c3ccccc23)cc(C(C)(C)C)cc1NS(=O)(=O)N1CCOCC1]

δ: 9.39 (s, 1H), 9.34 (s, 1H), 8.92 (d, 2H), 8.30 (d, 1H), 8.17 (d, 1H), 8.08-8.12 (m, 2H), 7.88 (d, 1H), 7.71 (t, 1H), 7.58-7.63 (m, 3H), 7.39 (d, 1H), 7.20 (t, 2H), 7.10 (d, 1H), 6.84 (t, 1H), 6.55 (dd, 1H), 6.09 (d, 1H), 3.82 (s, 3H), 3.60-3.62 (m, 4H), 3.13-3.15 (m, 4H), 1.27 (s, 9H).

LCMS m/z 697 (M+H)⁺ (ES⁺)

(g) N-(2-aminoethyl)-5-(tert-butyl)-2-methoxy-3-(3-(4-((2-((3-methoxy-5-(2-(2-(2-methoxy-ethoxy)ethoxy)ethoxy)phenyl)amino)pyridin-4-yl)oxy)naphthalen-1-yl)ureido)benzamide

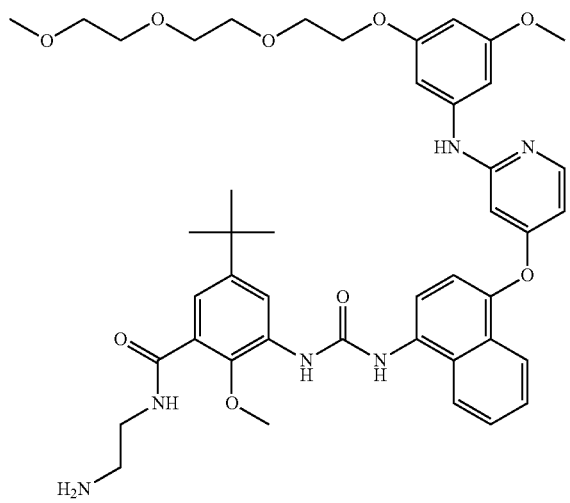

δ: 9.48 (s, 1H), 8.94 (s, 1H), 8.90 (s, 1H), 8.45 (d, 1H), 8.34 (t, 1H), 8.30 (d, 1H), 8.09-8.12 (m, 2H), 7.87 (d, 1H), 7.71 (t, 1H), 7.61 (t, 1H), 7.39 (d, 1H), 7.18 (d, 1H), 6.91 (s, 1H), 6.78 (s, 1H), 6.58 (dd, 1H), 6.08 (d, 1H), 6.04 (t, 1H), 3.97-3.99 (m, 2H), 3.81 (s, 3H), 3.69-3.71 (m, 2H), 3.65 (s, 3H), 3.56-3.58 (m, 2H), 3.50-3.54 (m, 4H), 3.42 (dd, 2H), 4H under H₂O, 3.23 (s, 3H), 2.78 (t, 2H), 1.29 (s, 9H).

LCMS m/z 811 (M+H)⁺ (ES⁺)

Example 84

The following compounds were prepared by methods analogous to those described above. Where chemical shifts from ¹H NMR spectra are reported, these were obtained at 400 MHz and ambient temperature, unless otherwise specified.

188

(a) 3-[[4-[(2-Anilino-4-pyridyl)oxy]-1-naphthyl]carbamoylamino]-5-tert-butyl-2-methoxy-N-tetrahydropyran-4-yl-benzamide

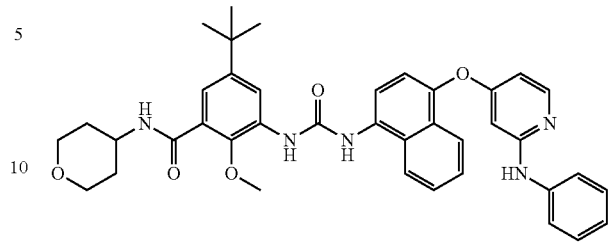

¹H NMR (400 MHz, DMSO-d6) δ: 9.44 (s, 1H), 8.90 (d, 2H), 8.43 (d, 1H), 8.29 (d, 1H), 8.21 (d, 1H), 8.08 (d, 1H), 8.07 (s, 1H), 7.88 (d, 1H), 7.73-7.68 (m, 1H), 7.63-7.57 (m, 3H), 7.38 (d, 1H), 7.19 (dd, 2H), 7.06 (d, 1H), 6.85-6.82 (m, 1H), 6.55 (dd, 1H), 6.10 (d, 1H), 4.04-4.00 (m, 1H), 3.89-3.87 (m, 2H), 3.80 (s, 3H)

LCMS m/z 660 (M+H)⁺ (ES⁺); 658 (M−H)⁻ (ES⁻)

(b) 3-[[4-[(2-Anilino-4-pyridyl)oxy]-1-naphthyl]carbamoylamino]-5-tert-butyl-2-methoxy-N-(1-methyl-4-piperidyl)benzamide

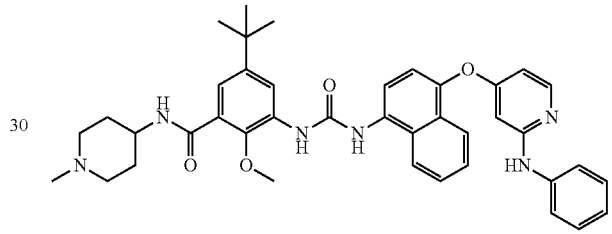

¹H NMR (400 MHz, DMSO-d6) δ: 9.46 (s, 1H), 8.90 (d, 2H), 8.43 (d, 1H), 8.29 (d, 1H), 8.18 (d, 1H), 8.07-8.07 (m, 2H), 7.88 (d, 1H), 7.70 (t, 1H), 7.63-7.57 (m, 3H), 7.38 (d, 1H), 7.19 (t, 2H), 7.05 (d, 1H), 6.84 (t, 1H), 6.53 (dd, 1H), 6.10 (d, 1H), 3.82-3.79 (m, 4H), 2.91-2.87 (m, 2H), 2.33 (bs, 3H), 1.91-1.88 (m, 2H), 1.64-1.60 (m, 2H), 1.28 (s, 9H).

LCMS m/z 673 (M+H)⁺ (ES⁺); 671 (M−H)⁻ (ES⁻)

(c) 3-[[4-[(2-Anilino-4-pyridyl)oxy]-1-naphthyl]carbamoylamino]-5-tert-butyl-2-methoxy-N-[(3R)-tetrahydrofuran-3-yl]benzamide

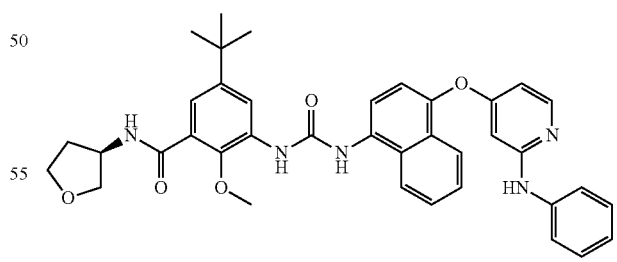 [SMILES: COc1c(NC(=O)Nc2ccc(Oc3ccnc(Nc4ccccc4)c3)c3ccccc23)cc(C(C)(C)C)cc1C(=O)NC1CCN(C)CC1]

¹H NMR (400 MHz, DMSO-d6) δ: 9.45 (s, 1H), 8.94 (bs, 1H), 8.91 (s, 1H), 8.44-8.42 (m, 2H), 8.29 (d, 1H), 8.09-8.07 (m, 2H), 7.88 (d, 1H), 7.69 (t, 1H), 7.61-7.57 (m, 3H), 7.38 (d, 1H), 7.20 (t, 2H), 7.06 (d, 1H), 6.85 (t, 1H), 6.55 (dd, 1H), 6.10 (s, 1H), 4.50-4.45 (m, 1H), 3.87-3.73 (m, 6H), 3.63 (dd, 1H), 2.20-2.15 (m, 1H), 1.93-1.90 (m, 1H), 1.28 (s, 9H).

LCMS m/z 646 (M+H)⁺ (ES⁺); 644 (M−H)⁻ (ES⁻)

(d) 3-[[4-[(2-Anilino-4-pyridyl)oxy]-1-naphthyl]
carbamoylamino]-5-tert-butyl-2-methoxy-N-[(3S)-
tetrahydrofuran-3-yl]benzamide

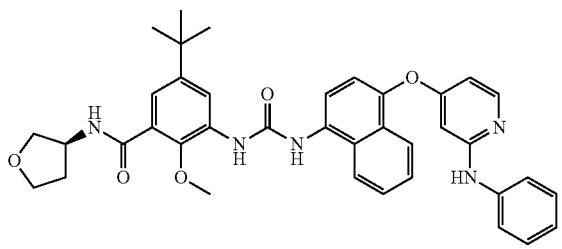 [SMILES: COc1c(NC(=O)Nc2ccc(Oc3ccnc(Nc4ccccc4)c3)c3ccccc23)cc(C(C)(C)C)cc1C(=O)N[C@H]1CCOC1]

$^1$H NMR (400 MHz, DMSO-d6) δ: 9.44 (s, 1H), 8.90 (d, 2H), 8.44-8.42 (m, 2H), 8.29 (d, 1H), 8.09 (d, 1H), 8.07 (s, 1H), 7.88 (d, 1H), 7.71 (t, 1H), 7.63-7.57 (m, 3H), 7.38 (d, 1H), 7.19 (t, 2H), 7.06 (d, 1H), 6.84 (t, 1H), 6.55 (dd, 1H), 6.10 (d, 1H), 4.50-4.45 (m, 1H), 3.90-3.73 (m, 6H), 3.64 (dd, 1H), 2.22-2.13 (m, 1H), 1.95-1.87 (m, 1H), 1.28 (s, 9H).

LCMS m/z 646 (M+H)$^+$ (ES$^+$); 644 (M−H)$^−$ (ES$^−$)

(e) 1-[5-tert-Butyl-3-(methanesulfonamido)-2-
methoxy-phenyl]-3-[4-[[2-[3-[2-[2-(2-hydroxy-
ethoxy)ethoxy]ethoxy]-5-methoxy-anilino]-4-
pyridyl]oxy]-1-naphthyl]urea

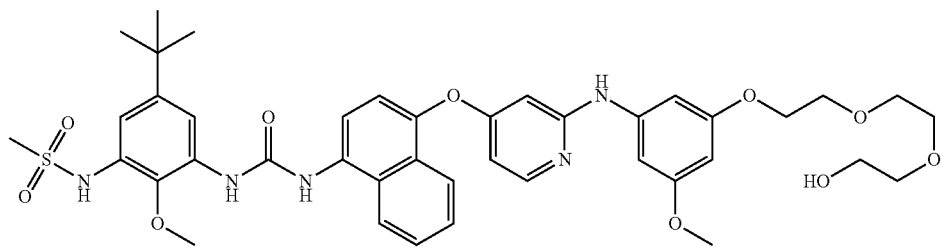 [SMILES: COc1cc(Nc2cc(Oc3ccc(NC(=O)Nc4cc(C(C)(C)C)cc(NS(C)(=O)=O)c4OC)c4ccccc34)ccn2)cc(OCCOCCOCCO)c1]

$^1$H NMR (400 MHz, DMSO-d6) δ 9.38 (s, 1H), 9.13 (s, 1H), 9.13 (s, 1H), 8.90 (s, 1H), 8.30 (d, 1H), 8.18 (d, 1H), 8.11 (dd, 2H), 7.87 (d, 1H), 7.75-7.66 (m, 1H), 7.67-7.56 (m, 1H), 7.39 (d, 1H), 7.03 (d, 1H), 6.91 (t, 1H), 6.79 (t, 1H), 6.58 (dd, 1H), 6.08 (d, 1H), 6.04 (t, 1H), 4.57 (t, 1H), 4.03-3.92 (m, 2H), 3.81 (s, 3H), 3.77-3.69 (m, 2H), 3.66 (s, 3H), 3.63-3.52 (m, 4H), 3.52-3.45 (m, 2H), 3.45-3.39 (m, 2H), 3.09 (s, 3H), 1.27 (s, 9H).

LCMS m/z 804 (M+H)$^+$ (ES$^+$)

(f) 1-[5-tert-Butyl-3-(methanesulfonamido)-2-
methoxyphenyl]-3-[4-[[2[3-(hydroxymethyl)-5-
methoxyanilino]-4-pyridyl]oxy]-1-naphthyl]urea

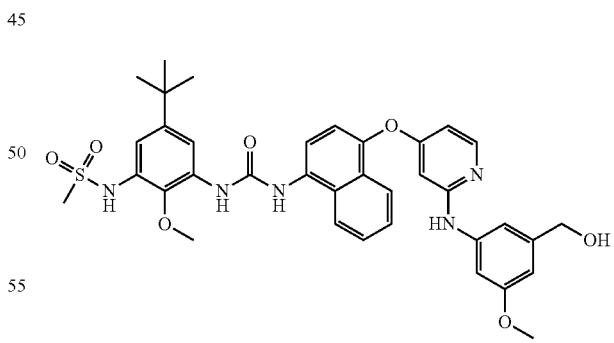

$^1$H NMR (400 MHz, DMSO-d6) δ 9.39 (s, 1H), 9.14 (s, 1H), 8.91 (s, 1H), 8.89 (s, 1H), 8.30 (d, 1H), 8.18 (d, 1H), 8.14-8.06 (m, 2H), 7.88 (d, 1H), 7.74-7.67 (m, 1H), 7.65-7.58 (m, 1H), 7.38 (d, 1H), 7.24 (t, 1H), 7.07-6.98 (m, 2H), 6.54 (dd, 1H), 6.43-6.38 (m, 1H), 6.12 (d, 1H), 5.10 (t, 1H), 4.38 (d, 2H), 3.81 (s, 3H), 3.67 (s, 3H), 3.09 (s, 3H), 1.27 (s, 9H).

LCMS m/z 686 (M+H)$^+$ (ES$^+$)

(g) 5-tert-Butyl-3-[[4-[[2-[3-(hydroxymethyl)-5-methoxyanilino]-4-pyridyl]oxy]-1-naphthyl]carbamoylamino]-2-methoxybenzamide

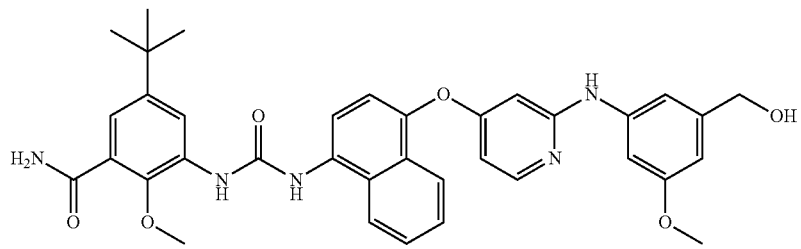 [SMILES: COc1cc(CO)cc(Nc2cc(Oc3ccc(NC(=O)Nc4cc(C(C)(C)C)cc(C(N)=O)c4OC)c4ccccc34)ccn2)c1]

¹H NMR (400 MHz, DMSO-d6) δ 9.47 (s, 1H), 8.93 (s, 1H), 8.89 (s, 1H), 8.46 (d, 1H), 8.30 (d, 1H), 8.16-8.05 (m, 2H), 7.88 (d, 1H), 7.77-7.67 (m, 2H), 7.66-7.59 (m, 1H), 7.57 (s, 1H), 7.38 (d, 1H), 7.24 (t, 1H), 7.22 (d, 1H), 7.07-6.97 (m, 1H), 6.54 (dd, 1H), 6.45-6.37 (m, 1H), 6.12 (d, 1H), 5.10 (s, 1H), 4.38 (s, 2H), 3.83 (s, 3H), 3.67 (s, 3H), 1.29 (s, 9H).
LCMS m/z 636 (M+H)⁺ (ES⁺)

(h) 5-tert-Butyl-3-[[4-[[2-[3-(hydroxymethyl)-5-methoxyanilino]-4-pyridyl]oxy]-1-naphthyl]carbamoylamino]-2-methoxy-N-methyl-benzamide

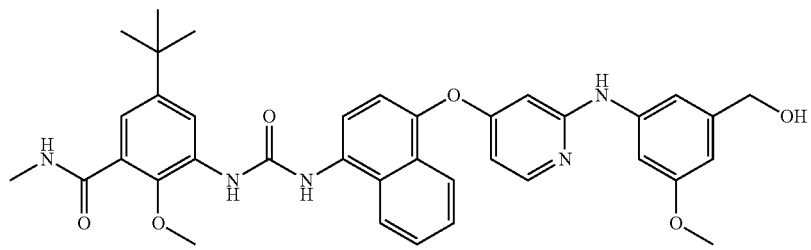 [SMILES: CNC(=O)c1cc(C(C)(C)C)cc(NC(=O)Nc2ccc(Oc3ccnc(Nc4cc(CO)cc(OC)c4)c3)c3ccccc23)c1OC]

¹H NMR (400 MHz, DMSO-d6) δ 9.48 (s, 1H), 8.89 (s, 2H), 8.44 (d, 1H), 8.30 (d, 1H), 8.18 (q, 1H), 8.10 (d, 1H), 8.08 (d, 1H), 7.88 (d, 1H), 7.78-7.67 (m, 1H), 7.67-7.56 (m, 1H), 7.38 (d, 1H), 7.24 (t, 1H), 7.11 (d, 1H), 7.08-6.96 (m, 1H), 6.54 (dd, 1H), 6.46-6.35 (m, 1H), 6.13 (d, 1H), 5.10 (s, 1H), 4.38 (s, 2H), 3.80 (s, 3H), 3.67 (s, 3H), 2.82 (d, 3H), 1.28 (s, 9H).
LCMS m/z 650 (M+H)⁺ (ES⁺)

Example 85

Unless otherwise specified, the following compounds were prepared by methods analogous to those described above. Where chemical shifts from ¹H NMR spectra are reported, these were obtained at 400 MHz and ambient temperature, unless otherwise specified.

Example 85(a)

3-[[4-[[4-[[5-tert-Butyl-3-(methanesulfonamido)-2-methoxyphenyl]-carbamoylamino]-1-naphthyl]oxy]-2-pyridyl]amino]-5-methoxy-N-(2-morpholino-2-oxo-ethyl)benzamide

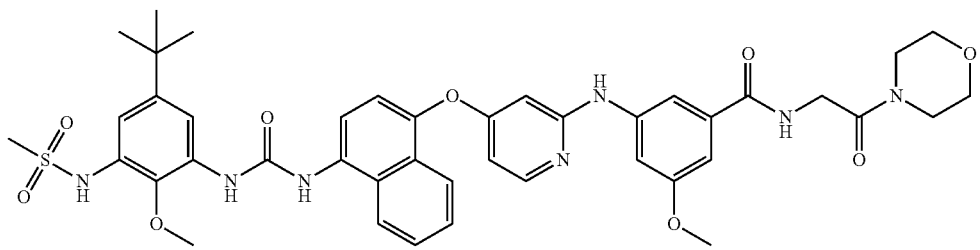 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCC(=O)N2CCOCC2)c1]

¹H NMR (400 MHz, DMSO-d6) δ 9.39 (s, 1H), 9.13 (br s, 1H), 9.09 (s, 1H), 8.91 (s, 1H), 8.37 (dd, 1H), 8.30 (d, 1H), 8.19 (d, 1H), 8.13 (s, 1H), 8.10 (d, 1H), 7.88 (d, 1H), 7.71 (ddd, 1H), 7.63-7.60 (m, 1H), 7.61 (ddd, 1H), 7.54 (dd, 1H), 7.39 (d, 1H), 8.03 (d, 1H), 6.92 (dd, 1H), 6.58 (dd, 1H), 6.14 (d, 1H), 4.09 (d, 2H), 3.81 (s, 3H), 3.76 (s, 3H), 3.64-3.53 (m, 4H), 3.53-3.40 (m, 4H), 3.10 (s, 3H), 1.27 (s, 9H).

LCMS m/z 826 (M+H)⁺ (ES⁺); 824 (M−H)⁻ (ES⁻)

Example 85(b)

3-[[4-[[4-[[5-tert-Butyl-3-(hydroxymethyl)-2-methoxyphenyl]-carbamoylamino]-1-naphthyl]oxy]-2-pyridyl]amino]-5-ethynyl-N-[2-[2-(2-methoxyethoxy)ethoxy]ethyl]benzamide

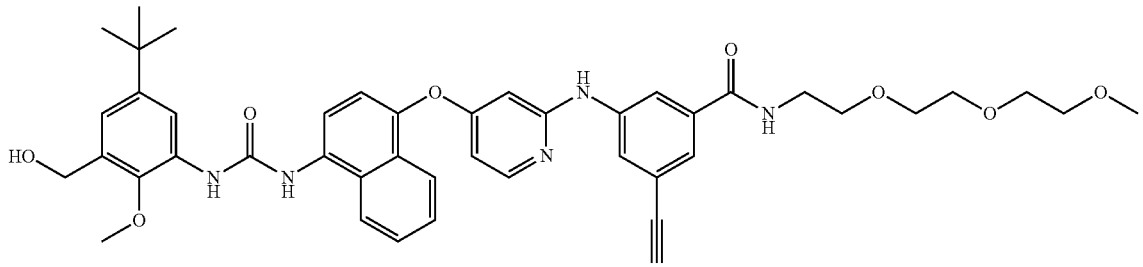 [SMILES: C#Cc1cc(Nc2cc(Oc3ccc(NC(=O)Nc4cc(C(C)(C)C)cc(CO)c4OC)c4ccccc34)ccn2)cc(C(=O)NCCOCCOCCOC)c1]

This compound was prepared by the following method.

(i) Phenyl (5-(tert-butyl)-3-(hydroxymethyl)-2-methoxyphenyl)carbamate

Phenyl chloroformate (0.278 ml, 2.222 mmol) was added to a stirred mixture of (3-amino-5-(tert-butyl)-2-methoxyphenyl)methanol (Kaneko, H et al., WO 2011/040509, 0.5 g, 2.222 mmol) and NaHCO₃ (0.373 g, 4.44 mmol) in DCM (20 ml) and THF (2 mL) at rt. The reaction mixture was stirred for 17 hours then partitioned with DCM (2 mL) and water (10 mL). The aqueous layer was extracted with DCM (5 mL). The combined organic layers were dried over MgSO₄, filtered and concentrated in vacuo to afford the sub-title compound (895 mg, 74% purity).

LCMS m/z 312 (M+H−H₂O)⁺ (ES⁺)

(ii) 3-((4-((4-(3-(5-(tert-Butyl)-3-(hydroxymethyl)-2-methoxyphenyl)ureido)naphthalen-1-yl)oxy)pyridin-2-yl)amino)-5-ethynyl-N-(2-(2-(2-methoxyethoxy)ethoxy)ethyl)benzamide Triethylamine (2.60 µL, 0.019 mmol) was added to a mixture of the product from step (i) above (30.5 mg, 0.092 mmol) and 3-((4-((4-aminonaphthalen-1-yl)oxy)pyridin-2-yl)amino)-5-ethynyl-N-(2-(2-(2-methoxyethoxy)ethoxy)ethyl)benzamide (see Example 53(ii) above; 50 mg, 0.092 mmol) in isopropyl acetate (4 mL) and the mixture heated at 70° C. (block temperature) overnight (17 hours). A solution of the product from step (i) above (70 mg) in isopropyl acetate (1 mL) was added to the reaction mixture, and the reaction mixture was heated at 70° C. overnight. The reaction mixture was diluted with THF and concentrated in vacuo to afford a pale pink gum. The crude product was purified by preparative HPLC (Gilson, Acidic (0.1% Formic acid), Acidic, Waters X-Select Prep-C18, 5 µm, 19×50 mm column, 25-70% MeCN in Water) to afford the title compound (10 mg) as a colourless solid.

¹H NMR (400 MHz, DMSO-d6) δ: 9.42 (s, 1H), 9.21 (s, 1H), 8.80 (s, 1H), 8.47 (t, 1H), 8.30 (d, 1H), 8.24 (d, 1H), 8.14 (d, 1H), 8.11-8.09 (m, 2H), 7.92 (t, 1H), 7.86 (d, 1H), 7.72-7.68 (m, 1H), 7.62-7.58 (m, 1H), 7.41-7.38 (m, 2H), 7.10 (d, 1H), 6.61 (dd, 1H), 6.12 (d, 1H), 5.11 (t, 1H), 4.56 (d, 2H), 4.18 (s, 1H), 3.77 (s, 3H), 3.52-3.48 (m, 8H), 3.40-3.38 (m, 4H), 3.20 (s, 3H), 1.28 (s, 9H).

LCMS m/z 776 (M+H)⁺ (ES⁺)

Example 85(c)

3-[[4-[[4-[[5-tert-Butyl-3-(methanesulfonamido)-2-methoxyphenyl]-carbamoylamino]-1-naphthyl]oxy]-2-pyridyl]amino]-5-ethynyl-N-[2-(4-methylpiperazin-1-yl)ethyl]benzamide

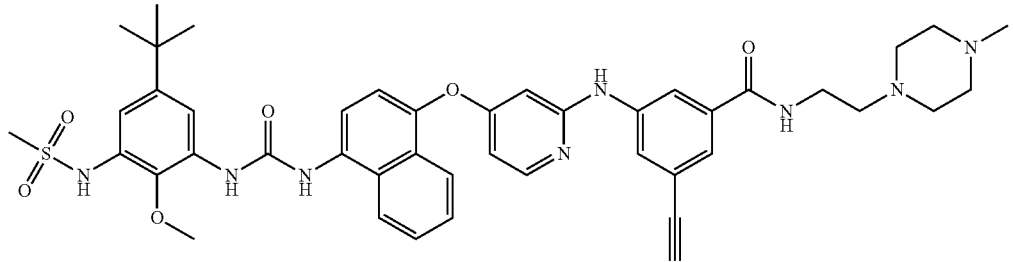

¹H NMR (400 MHz, DMSO-d6) δ 9.40 (s, 1H), 9.21 (s, 1H), 9.14 (br s, 1H), 8.91 (s, 1H), 8.35 (dd, 1H), 8.30 (d, 1H), 8.18 (d, 1H), 8.15 (d, 1H), 8.13 (d, 1H), 8.09 (dd, 1H), 7.93 (dd, 1H), 7.87 (d, 1H), 7.71 (ddd, 1H), 7.61 (ddd, 1H), 7.42-7.37 (m, 2H), 7.02 (d, 1H), 6.62 (dd, 1H), 6.12 (d, 1H), 4.19 (s, 1H), 3.81 (s, 3H), 3.38-3.28 (m, 2H), 3.10 (s, 3H), 2.40-2.25 (m, 10H), 2.14 (s, 3H), 1.27 (s, 9H).

LCMS m/z 819 (M+H)⁺ (ES⁺); 817 (M−H)⁻ (ES⁻)

Example 85(d)

3-[[4-[[4-[[5-tert-Butyl-3-(methanesulfonamido)-2-methoxyphenyl]-carbamoylamino]-1-naphthyl]oxy]-2-pyridyl]amino]-5-ethynyl-N-(3-morpholinopropyl)-benzamide

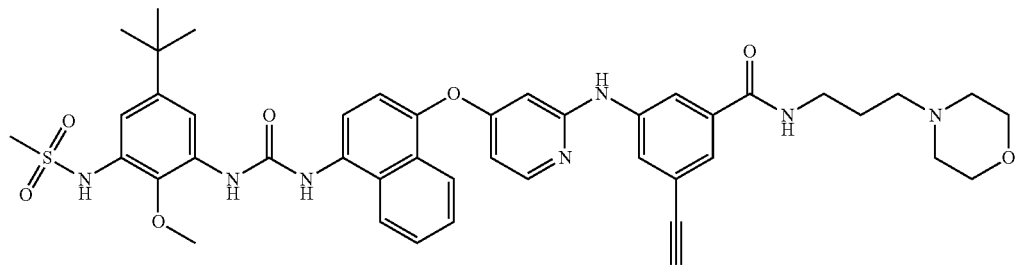 [SMILES: C#Cc1cc(Nc2cc(Oc3ccc(NC(=O)Nc4cc(C(C)(C)C)cc(NS(C)(=O)=O)c4OC)c4ccccc34)ccn2)cc(C(=O)NCCCN2CCOCC2)c1]

$^1$H NMR (400 MHz, DMSO-d6) δ 9.40 (s, 1H), 9.21 (s, 1H), 9.14 (br s, 1H), 8.91 (s, 1H), 8.46 (dd, 1H), 8.30 (d, 1H), 8.18 (d, 1H), 8.15 (d, 1H), 8.12 (d, 1H), 8.09 (dd, 1H), 7.92 (dd, 1H), 7.87 (d, 1H), 7.71 (ddd, 1H), 7.61 (ddd, 1H), 7.40 (d, 1H), 7.39 (d, 1H), 7.02 (d, 1H), 6.62 (dd, 1H), 6.12 (d, 1H), 4.19 (s, 1H), 3.81 (s, 3H), 3.59-3.50 (m, 4H), 3.30-3.21 (m, 2H), 3.10 (s, 3H), 2.40-2.25 (m, 6H), 1.71-1.60 (m, 2H), 1.27 (s, 9H).
LCMS m/z 820 (M+H)$^+$ (ES$^+$); 818 (M−H)$^-$ (ES$^-$)

Example 85(e)

3-[[4-[[4-[[5-tert-Butyl-3-(methanesulfonamido)-2-methoxyphenyl]-carbamoylamino]-1-naphthyl]oxy]pyrimidin-2-yl]amino]-5-methoxy-N-[2-(4-methylpiperazin-1-yl)ethyl]benzamide

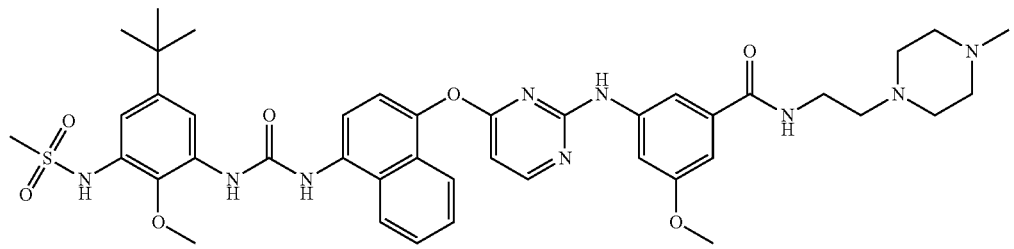

$^1$H NMR (400 MHz, DMSO-d6) δ 9.61 (s, 1H), 9.36 (s, 1H), 9.14 (s, 1H), 8.93 (s, 1H), 8.42 (d, 1H), 8.28 (d, 1H), 8.19 (d, 1H), 8.17 (dd, 1H), 8.10 (d, 1H), 7.85 (d, 1H), 7.68 (ddd, 1H), 7.59 (ddd, 1H), 7.56 (s, 1H), 7.43 (d, 1H), 7.36-7.30 (m, 1H), 7.02 (d, 1H), 6.85 (dd, 1H), 6.55 (d, 1H), 3.81 (s, 3H), 3.59 (s, 3H), 3.37-3.26 (m, 4H), 3.10 (s, 3H), 2.47-2.19 (m, 8H), 2.14 (s, 3H), 1.27 (s, 9H).
LCMS m/z 826 (M+H)$^+$ (ES$^+$); 824 (M−H)$^-$ (ES$^-$)

Example 85(f)

3-[[4-[[4-[[5-tert-Butyl-3-(methanesulfonamido)-2-methoxyphenyl]-carbamoylamino]-1-naphthyl]oxy]pyrimidin-2-yl]amino]5-methoxy-N-(3-morpholinopropyl)-benzamide

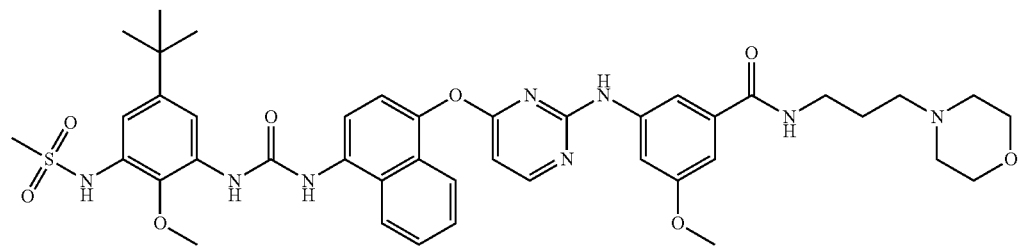 [SMILES: COc1cc(Nc2nccc(Oc3ccc(NC(=O)Nc4cc(C(C)(C)C)cc(NS(C)(=O)=O)c4OC)c4ccccc34)n2)cc(C(=O)NCCCN2CCOCC2)c1]

¹H NMR (400 MHz, DMSO-d6) δ 9.60 (s, 1H), 9.36 (s, 1H), 9.14 (s, 1H), 8.93 (s, 1H), 8.41 (d, 1H), 8.34-8.24 (m, 2H), 8.19 (d, 1H), 8.10 (d, 1H), 7.85 (d, 1H), 7.68 (ddd, 1H), 7.59 (ddd, 1H), 7.56 (s, 1H), 7.43 (d, 1H), 7.36-7.30 (m, 1H), 7.02 (d, 1H), 6.86 (dd, 1H), 6.54 (d, 1H), 3.81 (s, 3H), 3.59 (s, 3H), 3.57-3.51 (m, 4H), 3.29-3.20 (m, 2H), 3.10 (s, 3H), 2.41-2.23 (m, 6H), 1.70-1.58 (m, 2H), 1.27 (s, 9H).

LCMS m/z 827 (M+H)⁺ (ES⁺); 825 (M–H)⁻ (ES⁻)

Example 85(g)

5-tert-Butyl-3-[[4-[2-[3-ethynyl-5-(2-morpholinoethylcarbamoyl)anilino]-pyrimidin-4-yl]oxy-1-naphthyl]carbamoylamino]-2-methoxy-benzamide

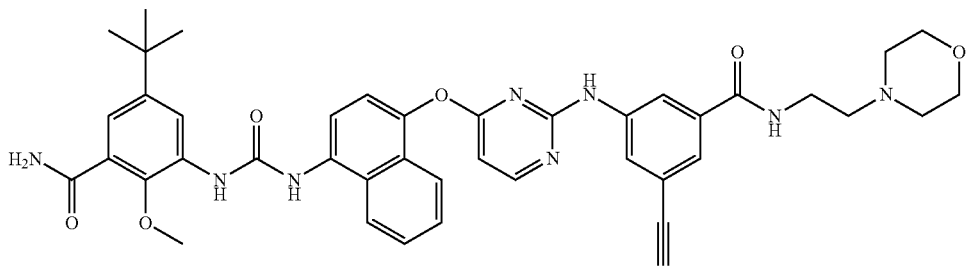 [SMILES: C#Cc1cc(Nc2nccc(Oc3ccc(NC(=O)Nc4cc(C(C)(C)C)cc(C(N)=O)c4OC)c4ccccc34)n2)cc(C(=O)NCCN2CCOCC2)c1]

¹H NMR (400 MHz, DMSO-d6) δ 9.76 (s, 1H), 9.43 (s, 1H), 8.92 (s, 1H), 8.49-8.41 (m, 2H), 8.36 (dd, 1H), 8.27 (d, 1H), 8.11-8.02 (m, 2H), 7.91-7.80 (m, 2H), 7.76-7.64 (m, 2H), 7.64-7.51 (m, 2H), 7.49-7.40 (m, 2H), 7.22 (d, 1H), 6.56 (d, 1H), 4.13 (s, 1H), 3.83 (s, 3H), 3.62-3.48 (m, 4H), 2H under water peak, 2.50-2.30 (m, 6H), 1.29 (s, 9H).

LCMS m/z 757 (M+H)⁺ (ES⁺); 755 (M–H)⁻ (ES⁻)

Example 85(h)

3-[[4-[[4-[[5-tert-Butyl-3-(methanesulfonamido)-2-methoxyphenyl]-carbamoylamino]-1-naphthyl]oxy]-2-pyridyl]amino]-5-methoxy-N-(2-methyl-2-morpholinopropyl)benzamide

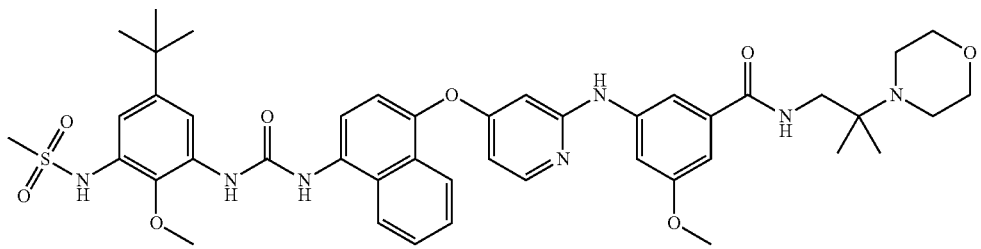 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCC(C)(C)N2CCOCC2)c1]

¹H NMR (400 MHz, DMSO-d6) δ 9.39 (s, 1H), 9.14 (br s, 1H), 9.08 (s, 1H), 8.91 (s, 1H), 8.30 (d, 1H), 8.19 (d, 1H), 8.13-8.09 (m, 2H), 7.88 (d, 1H), 7.71 (ddd, 1H), 7.63-7.60 (m, 1H), 7.61 (ddd, 1H), 7.57 (dd, 1H), 7.51 (dd, 1H), 7.39 (d, 1H), 7.03 (d, 1H), 6.82 (dd, 1H), 6.60 (dd, 1H), 6.13 (d, 1H), 3.81 (s, 3H), 3.75 (s, 3H), 3.60-3.53 (m, 4H), 3.25 (d, 2H), 3.10 (s, 3H), 2.56-2.47 (m, 4H), 1.27 (s, 9H) 0.99 (s, 6H).

LCMS m/z 840 (M+H)⁺ (ES⁺); 838 (M–H)⁻ (ES⁻)

Example 85(i)

3-[[4-[[4-[[5-tert-Butyl-3-(methanesulfonamido)-2-methoxyphenyl]-carbamoylamino]-1-naphthyl]oxy]-2-pyridyl]amino]-5-methoxy-N-(2-thiomorpholino-ethyl)-benzamide

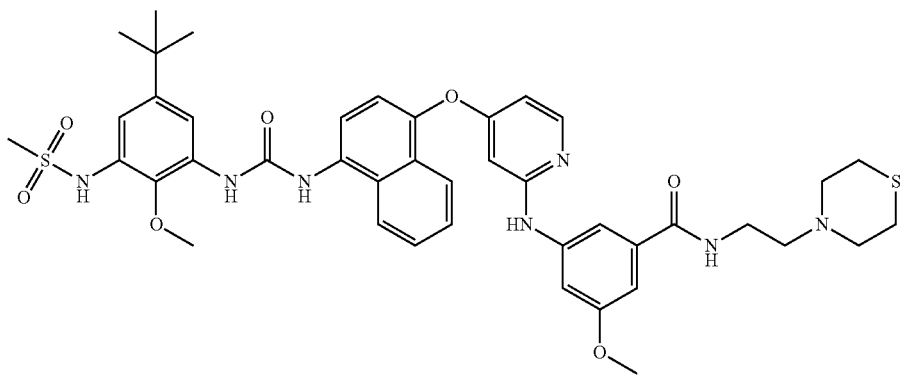 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCCN2CCSCC2)c1]

$^1$H NMR (400 MHz, DMSO-d6) δ 9.38 (s, 1H), 9.14 (br s, 1H), 9.06 (s, 1H), 8.91 (s, 1H), 8.30 (d, 1H), 8.20 (dd, 1H), 8.19 (d, 1H), 8.12 (s, 1H), 8.10 (d, 1H), 7.88 (d, 1H), 7.71 (ddd, 1H), 7.61 (ddd, 1H), 7.55 (dd, 1H), 7.51 (dd, 1H), 7.39 (d, 1H), 7.02 (d, 1H), 6.85 (dd, 1H), 6.58 (dd, 1H), 6.13 (d, 1H), 3.81 (s, 3H), 3.74 (s, 3H), 3.38-3.26 (m, 2H), 3.10 (s, 3H), 2.73-2.66 (m, 4H), 2.62-2.55 (m, 4H), 2.48 (t, 2H), 1.27 (s, 9H).

LCMS m/z 828 (M+H)$^+$ (ES$^+$); 826 (M−H)$^−$ (ES$^−$).

Example 85(i)

3-[[4-[[4-[[5-tert-Butyl-3-(methanesulfonamido)-2-methoxyphenyl]-carbamoylamino]-1-naphthyl]oxy]-2-pyridyl]amino]-5-methoxy-N-[2-(1-oxo-1,4-thiazi-nan-4-yl)ethyl]benzamide

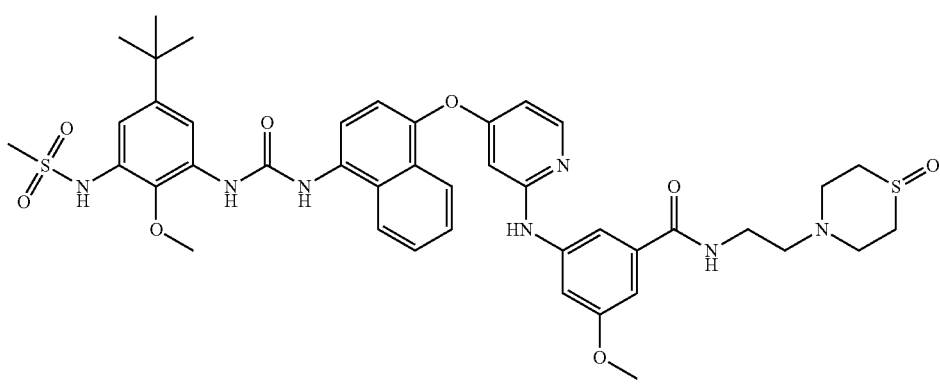

$^1$H NMR (400 MHz, DMSO-d6) δ: 9.40 (s, 1H), 9.17 (s, 1H), 9.08 (s, 1H), 8.93 (s, 1H), 8.31-8.25 (m, 2H), 8.19 (d, 1H), 8.12 (d, 1H), 8.11 (s, 1H), 7.87 (d, 1H), 7.73-7.69 (m, 1H), 7.63-7.59 (m, 1H), 7.56 (s, 1H), 7.51 (s, 1H), 7.39 (d, 1H), 7.02 (d, 1H), 6.86 (s, 1H), 6.58 (dd, 1H), 6.12 (d, 1H), 3.81 (s, 3H), 3.87 (s, 3H), 3.10 (s, 3H), 2.96-2.82 (m, 4H), 2.73-2.66 (m, 4H), 1.27 (s, 9H). (2×CH2 under water and DMSO peaks)

LCMS m/z 844 (M+H)$^+$ (ES$^+$); 842 (M−H)$^−$ (ES$^−$).

Example 85(k)

3-[[4-[[4-[[5-tert-Butyl-3-(methanesulfonamido)-2-methoxyphenyl]-carbamoylamino]-1-naphthyl]oxy]-2-pyridyl]amino]-N-[2-(1,1-dioxo-1,4-thiazinan-4-yl)ethyl]-5-methoxybenzamide

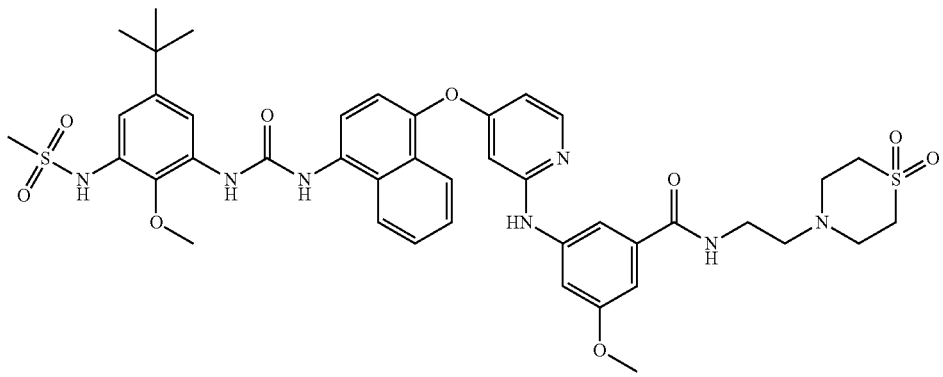 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCCN2CCS(=O)(=O)CC2)c1]

$^1$H NMR (400 MHz, DMSO-d6) δ: 9.38 (s, 1H), 9.13 (s, 1H), 9.05 (s, 1H), 8.90 (s, 1H), 8.29 (d, 1H), 8.24 (t, 1H), 8.18 (d, 1H), 8.12 (s, 1H), 8.10 (d, 1H), 7.87 (d, 1H), 7.72-7.68 (m, 1H), 7.60-7.58 (m, 1H), 7.54 (t, 1H), 7.50 (t, 1H), 7.38 (d, 1H), 7.02 (d, 1H), 6.85-6.84 (m, 1H), 6.57 (dd, 1H), 6.12 (d, 1H), 3.80 (s, 3H), 3.74 (s, 3H), 3.09 (s, 3H), 3.07-3.05 (m, 4H), 2.67-2.94 (m, 4H), 2.64 (t, 2H), 1.26 (s, 9H). (2 protons under the water signal)

LCMS m/z 430 (M+2H)$^{2+}$ (ES$^+$).

Example 85(l)

3-[[4-[[4-[[5-tert-Butyl-3-(methanesulfonamido)-2-methoxyphenyl]-carbamoylamino]-1-naphthyl]oxy]-2-pyridyl]amino]-N-[2-(3,3-dimethylmorpholin-4-yl)ethyl]-5-methoxybenzamide

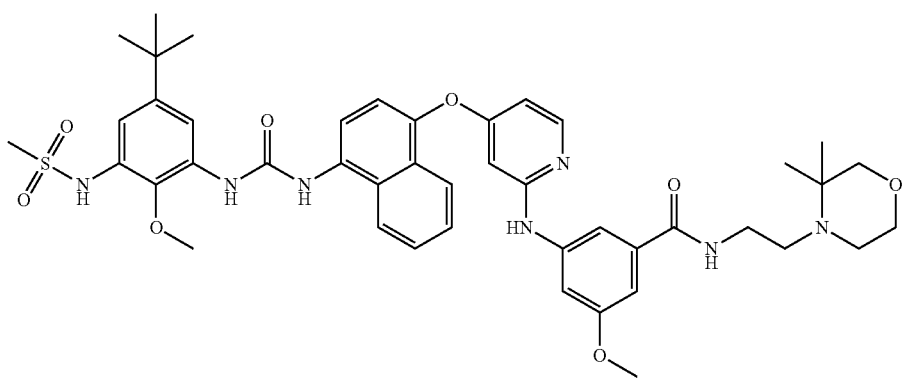 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCCN2CCOCC2(C)C)c1]

$^1$H NMR (400 MHz, DMSO-d6) δ: 9.39 (s, 1H), 9.16 (s, 1H), 9.06 (s, 1H), 8.89 (s, 1H), 8.29 (d, 1H), 8.19 (d, 2H), 8.11 (d, 1H), 8.10 (d, 1H), 7.86 (d, 1H), 7.70 (dd, 1H), 7.59 (dd, 1H), 7.52-7.50 (m, 2H), 7.38 (d, 1H), 7.01 (d, 1H), 6.85 (t, 1H), 6.58 (dd, 1H), 6.11 (d, 1H), 3.80 (s, 3H), 3.73 (s, 3H), 3.58 (t, 2H), 3.23-3.18 (m, 4H), 3.09 (s, 3H), 2.45-2.41 (m, 2H), 1.26 (s, 9H), 0.91 (s, 6H). (2H under the DMSO peak)

LCMS m/z 840 (M+H)$^+$ (ES$^+$); 838 (M–H)$^-$ (ES$^-$).

Example 85(m)

3-[[4-[[4-[[5-tert-Butyl-3-(methanesulfonamido)-2-methoxyphenyl]-carbamoylamino]-1-naphthyl]oxy]-2-pyridyl]amino]-N-[2-(2,2-dimethylmorpholin-4-yl)ethyl]-5-methoxybenzamide

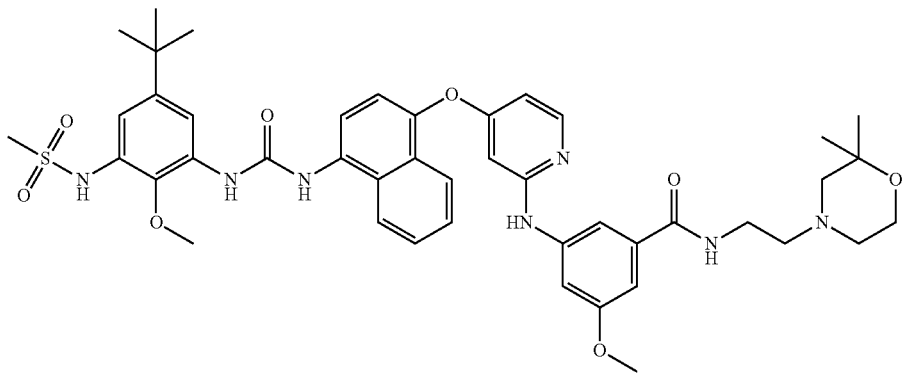 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCCN2CCOC(C)(C)C2)c1]

¹H NMR (400 MHz, DMSO-d6) δ 9.39 (s, 1H), 9.14 (br s, 1H), 9.06 (s, 1H), 8.91 (s, 1H), 8.30 (d, 1H), 8.18 (d, 1H), 8.17 (dd, 1H), 8.12 (d, 1H), 8.10 (s, 1H), 7.87 (d, 1H), 7.71 (ddd, 1H), 7.61 (ddd, 1H), 7.55 (dd, 1H), 7.51 (dd, 1H), 7.39 (d, 1H), 7.02 (d, 1H), 6.84 (dd, 1H), 6.57 (dd, 1H), 6.13 (d, 1H), 3.81 (s, 3H), 3.74 (s, 3H), 3.61-3.54 (m, 2H), 3.39-3.31 (m, 2H), 3.10 (s, 3H), 2.39 (t, 2H), 2.36-2.28 (m, 2H), 2.20 (s, 2H), 1.27 (s, 9H), 1.14 (s, 6H).
LCMS m/z 840 (M+H)⁺ (ES⁺); 838 (M−H)⁻ (ES⁻).

Example 85(n)

3-[[4-[[4-[[5-tert-Butyl-3-(methanesulfonamido)-2-methoxyphenyl]-carbamoylamino]-1-naphthyl]oxy]-2-pyridyl]amino]-N-[2-[(2R,6S)-2,6-dimethylmorpholin-4-yl]ethyl]-5-methoxybenzamide

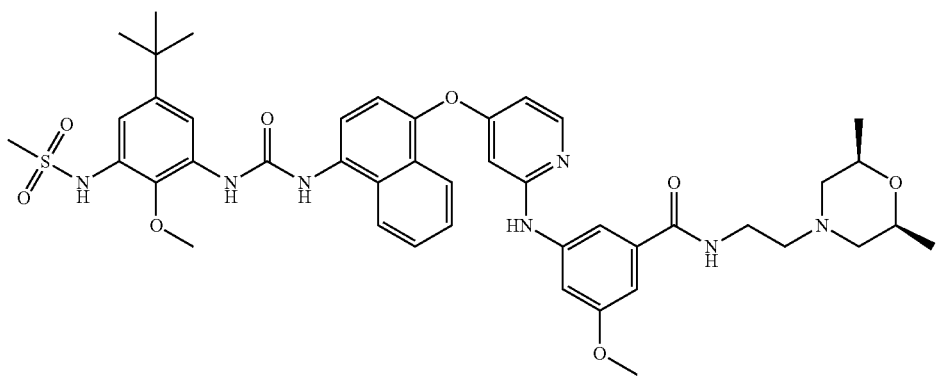

¹H NMR (400 MHz, DMSO-d6) δ 9.42 (s, 1H), 9.14 (br s, 1H), 9.06 (s, 1H), 8.93 (s, 1H), 8.31 (d, 1H), 8.22 (dd, 1H), 8.18 (d, 1H), 8.12 (s, 1H), 8.10 (d, 1H), 7.87 (d, 1H), 7.70 (ddd, 1H), 7.61 (ddd, 1H), 7.56 (dd, 1H), 7.50 (dd, 1H), 7.39 (d, 1H), 7.02 (d, 1H), 6.85 (dd, 1H), 6.58 (dd, 1H), 6.13 (d, 1H), 3.81 (s, 3H), 3.74 (s, 3H), 3.60-3.47 (m, 2H), 3.39-3.31 (m, 2H), 3.10 (s, 3H), 2.77 (d, 2H), 2.42 (t, 2H), 1.64 (t, 2H), 1.27 (s, 9H), 1.03 (d, 6H).
LCMS m/z 840 (M+H)⁺ (ES⁺); 838 (M−H)⁻ (ES⁻).

Example 85(o)

5-tert-Butyl-3-[[4-[[2-[3-ethynyl-5-(hydroxymethyl) anilino]-4-pyridyl]oxy]-1-naphthyl]carbamoylamino]-2-methoxy-benzamide

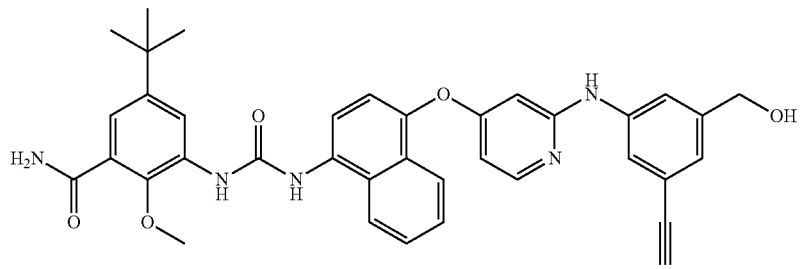 [SMILES: C#Cc1cc(CO)cc(Nc2cc(Oc3ccc(NC(=O)Nc4cc(C(C)(C)C)cc(C(N)=O)c4OC)c4ccccc34)ccn2)c1]

$^1$H NMR (400 MHz, DMSO-d6) δ: 9.47 (s, 1H), 9.02 (s, 1H), 8.91 (s, 1H), 8.45 (d, 1H), 8.29 (d, 1H), 8.12 (d, 1H), 8.09 (d, 1H), 7.87 (d, 1H), 7.80 (t, 1H), 7.73-7.69 (m, 2H), 7.63-7.59 (m, 2H), 7.45 (bs, 1H), 7.39 (d, 1H), 7.22 (d, 1H), 6.89 (s, 1H), 6.58 (dd, 1H), 6.10 (d, 1H), 5.18 (t, 1H), 4.39 (d, 2H), 4.05 (s, 1H), 3.82 (s, 3H), 1.28 (s, 9H).
LCMS m/z 630 (M+H)$^+$ (ES$^+$); 628 (M−H)$^−$ (ES$^−$)

Example 85(p)

3-[[4-[[4-[[5-tert-Butyl-3-(methanesulfonamido)-2-methoxyphenyl]-carbamoylamino]-1-naphthyl]oxy]-2-pyridyl]amino]-5-methoxy-N-[2-(4-methyl-1,4-diazepan-1-yl)ethyl]benzamide

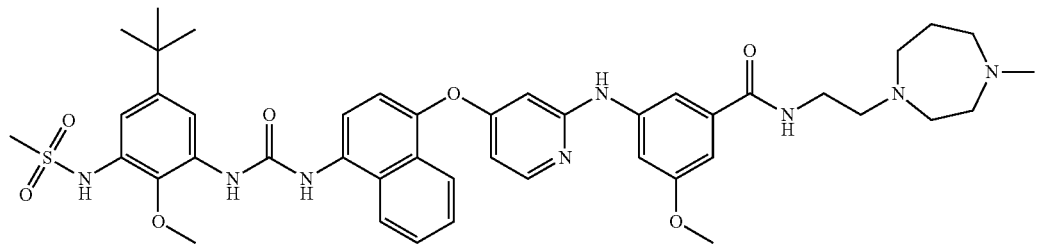

$^1$H NMR (400 MHz, DMSO-d6) δ 9.45 (s, 1H), 9.15 (br s, 1H), 9.07 (s, 1H), 8.94 (s, 1H), 8.32 (d, 1H), 8.20 (dd, 1H), 8.18 (d, 1H), 8.12 (s, 1H), 8.10 (d, 1H), 7.87 (d, 1H), 7.70 (ddd, 1H), 7.61 (ddd, 1H), 7.55 (dd, 1H), 7.52 (dd, 1H), 7.38 (d, 1H), 7.03 (d, 1H), 6.86 (dd, 1H), 6.60 (dd, 1H), 6.13 (d, 1H), 3.81 (s, 3H), 3.75 (s, 3H), 3.36-3.24 (m, 2H), 3.10 (s, 3H), 2.77-2.57 (d, 10H), 2.34 (s, 3H), 1.79-1.68 (m, 2H), 1.27 (s, 9H).
LCMS m/z 839 (M+H)$^+$ (ES$^+$); 837 (M−H)$^−$ (ES$^−$)

Example 85(q)

3-[[4-[[4-[[5-tert-Butyl-3-(methanesulfonamido)-2-methoxyphenyl]-carbamoylamino]-1-naphthyl]oxy]-2-pyridyl]amino]-5-methoxy-N-(2-piperazin-1-yl)ethyl)benzamide

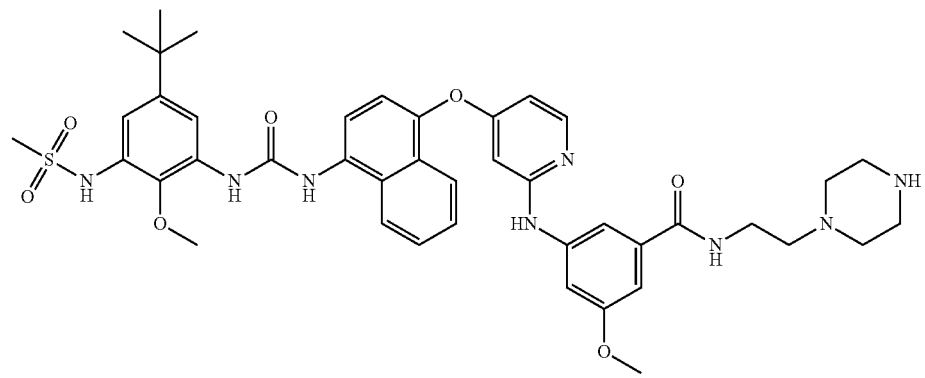 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCCN2CCNCC2)c1]

$^1$H NMR (400 MHz, DMSO-d6) δ 9.39 (s, 1H), 9.06 (s, 1H), 8.91 (s, 1H), 8.30 (d, 1H), 8.24-8.14 (m, 2H), 8.12 (s, 1H), 8.10 (d, 1H), 7.87 (d, 1H), 7.76-7.67 (m, 1H), 7.66-7.57 (m, 1H), 7.55 (t, 1H), 7.51 (t, 1H), 7.39 (d, 1H), 7.03 (d, 1H), 6.86 (dd, 1H), 6.58 (dd, 1H), 6.13 (d, 1H), 3.81 (s, 3H), 3.74 (s, 3H), 3.09 (s, 3H), 2.69 (t, 4H), 2.41 (t, 2H), 2.38-2.26 (m, 4H), 1.27 (s, 9H). CH2 under water peak 3.32 ppm, one exchangeable proton not visible.

LCMS m/z 811 (M+H)$^+$ (ES$^+$); 809 (M−H)$^−$ (ES$^−$)

Example 85(r)

3-[[4-[[5-tert-Butyl-3-(methanesulfonamido)-2-methoxyphenyl]-carbamoylamino]-1-naphthyl]oxy]-2-pyridyl]amino]-N-[2-[2-(2-hydroxyethoxy)ethoxy]-ethyl]-5-methoxy-benzamide

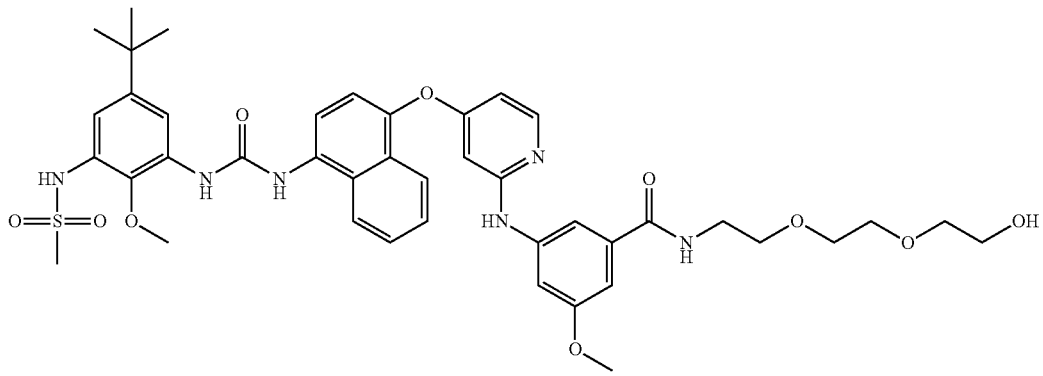 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCCOCCOCCO)c1]

$^1$H NMR (400 MHz, DMSO-d6) δ 9.39 (s, 1H), 9.14 (s, 1H), 9.06 (s, 1H), 8.91 (s, 1H), 8.35 (t, 1H), 8.30 (d, 1H), 8.19 (d, 1H), 8.12 (s, 1H), 8.10 (d, 1H), 7.88 (d, 1H), 7.75-7.67 (m, 1H), 7.65-7.59 (m, 1H), 7.58 (t, 1H), 7.51 (t, 1H), 7.39 (d, 1H), 7.03 (d, 1H), 6.89 (dd, 1H), 6.57 (dd, 1H), 6.14 (d, 1H), 4.57 (t, 1H), 3.81 (s, 3H), 3.75 (s, 3H), 3.59-3.49 (m, 6H), 3.49-3.44 (m, 2H), 3.44-3.35 (m, 4H), 3.10 (s, 3H), 1.27 (s, 9H).

LCMS m/z 831 (M+H)$^+$ (ES$^+$); 829 (M−H)$^−$ (ES$^−$).

Example 85(s)

3-[[[4-[[4-[[5-tert-Butyl-3-(methanesulfonamido)-2-methoxyphenyl]-carbamoylamino]-1-naphthyl]oxy]pyrimidin-2-yl]amino]methyl]-N-[2-[2-(2-methoxyethoxy)ethoxy]ethyl]benzamide

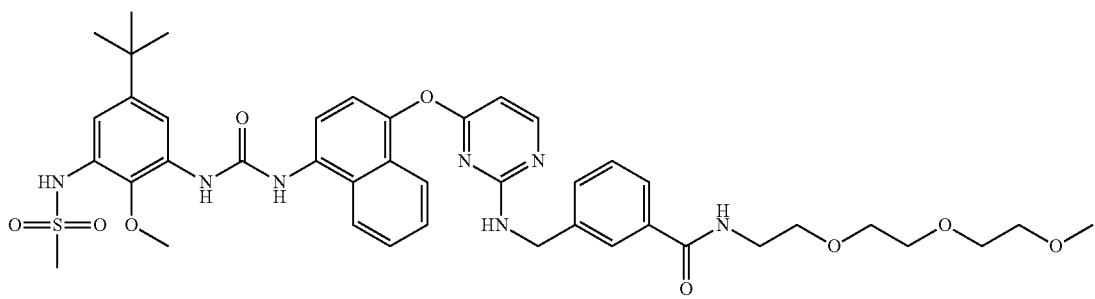 [SMILES: COCCOCCOCCNC(=O)c1cccc(CNc2nccc(Oc3ccc(NC(=O)Nc4cc(C(C)(C)C)cc(NS(C)(=O)=O)c4OC)c4ccccc34)n2)c1]

¹H NMR (400 MHz, DMSO-d6, 100° C.) δ: 9.08 (s, 1H), 6.82 (s, 1H), 8.55 (s, 1H), 8.23 (d, 1H), 8.18 (d, 1H), 8.10 (d, 1H), 7.96-7.94 (m, 2H), 7.85 (d, 1H), 7.71 (s, 1H), 7.63-7.60 (m, 2H), 7.55-7.53 (m, 1H), 7.31-7.19 (m, 4H), 7.06 (d, 1H), 6.22 (d, 1H), 4.36 (d, 2H), 3.84 (s, 3H), 3.56-3.52 (m, 8H), 3.43-3.41 (m, 4H), 3.24 (s, 3H), 3.08 (s, 3H), 1.29 (s, 9H).

LCMS m/z 830 (M+H)+415 (M+2H)$^{2+}$ (ES$^+$); 828 (M−H)$^−$ (ES$^−$).

Example 85(t)

3-[[[4-[[4-[[5-tert-Butyl-3-(methanesulfonamido)-2-methoxyphenyl]-carbamoylamino]-1-naphthyl]oxy]pyrimidin-2-yl]amino]methyl]-N-(2-morpholino-ethyl)-benzamide

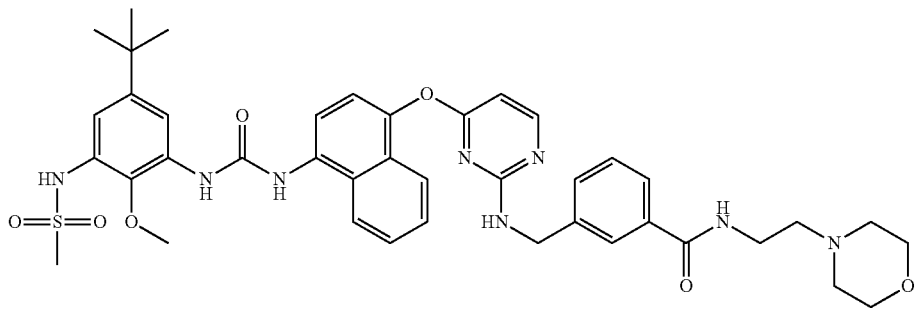 [SMILES: COc1c(NC(=O)Nc2ccc(Oc3ccnc(NCc4cccc(C(=O)NCCN5CCOCC5)c4)n3)c3ccccc23)cc(C(C)(C)C)cc1NS(C)(=O)=O]

The product was analysed by LCMS (Agilent, X-Select, Waters X-Select UPLC C18, 1.7 μm, 2.1×30 mm, Basic (0.1% Ammonium Bicarbonate) 4 min method, 5-95% MeCN/water): m/z 797 (M+H)$^+$ (ES$^+$); 795 (M−H)$^−$ (ES$^−$), at 2.23 min, 99% purity @ 254 nm.

Example 85(u)

3-[[4-[[4-[[5-tert-Butyl-3-(methanesulfonamido)-2-methoxyphenyl]-carbamoylamino]-1-naphthyl]oxy]-2-pyridyl]amino]-5-methoxy-N-[2-(2-methoxy-ethoxy)-ethyl]benzamide

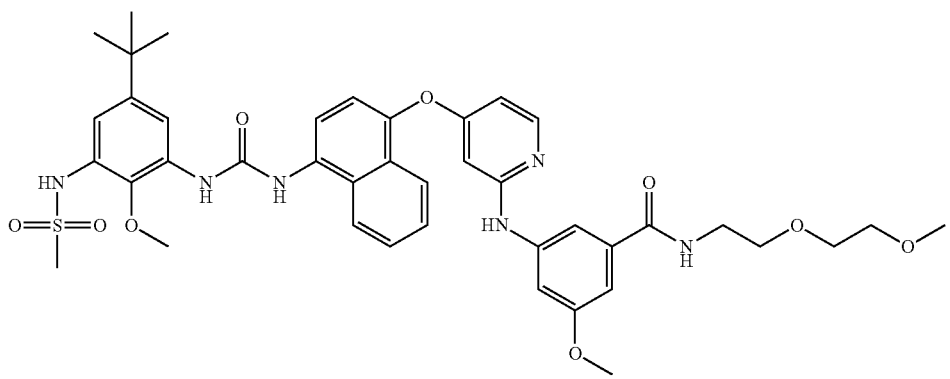 [SMILES: COCCOCCNC(=O)c1cc(Nc2cc(Oc3ccc(NC(=O)Nc4cc(C(C)(C)C)cc(NS(C)(=O)=O)c4OC)c4ccccc34)ccn2)cc(OC)c1]

$^1$H NMR (400 MHz, DMSO-d6) δ 9.40 (s, 1H), 9.14 (br s, 1H), 9.06 (s, 1H), 8.92 (s, 1H), 8.34 (dd, 1H), 8.30 (d, 1H), 8.18 (d, 1H), 8.12 (s, 1H), 8.10 (d, 1H), 7.87 (d, 1H), 7.71 (ddd, 1H), 7.61 (ddd, 1H), 7.58 (dd, 1H), 7.51 (dd, 1H), 7.39 (d, 1H), 7.02 (d, 1H), 6.89 (dd, 1H), 6.58 (dd, 1H), 6.13 (d, 1H), 3.81 (s, 3H), 3.75 (s, 3H), 3.56-3.47 (m, 4H), 3.46-3.42 (m, 2H), 3.41-3.34 (m, 2H), 3.23 (s, 3H), 3.10 (s, 3H), 1.27 (s, 9H).

LCMS m/z 801 (M+H)$^+$ (ES$^+$); 799 (M−H)$^-$ (ES$^-$).

Example 85(v)

3-[[4-[[4-[[5-tert-Butyl-3-(methanesulfonamido)-2-methoxyphenyl]-carbamoylamino]-1-naphthyl]oxy]-2-pyridyl]amino]-5-methoxy-N-[2-[2-[2-(2-methoxyethoxy)ethoxy]ethoxy]-ethyl]benzamide

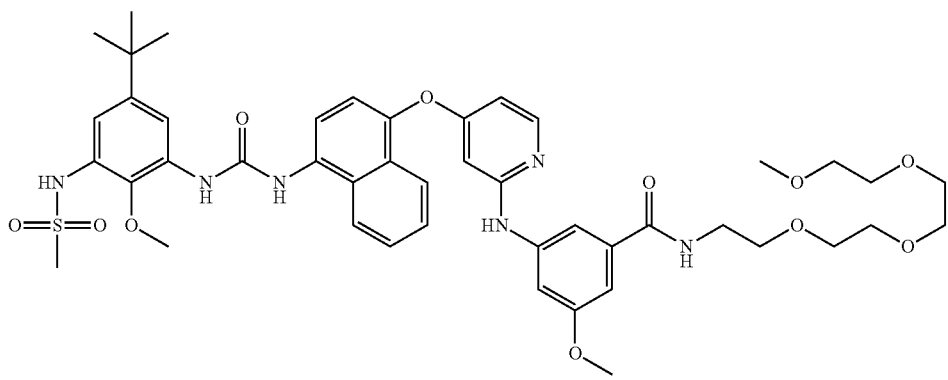 [SMILES: COCCOCCOCCOCCNC(=O)c1cc(Nc2cc(Oc3ccc(NC(=O)Nc4cc(C(C)(C)C)cc(NS(C)(=O)=O)c4OC)c4ccccc34)ccn2)cc(OC)c1]

$^1$H NMR (400 MHz, DMSO-d6) δ 9.40 (s, 1H), 9.17 (s, 1H), 9.08 (s, 1H), 8.94 (s, 1H), 8.37 (t, 1H), 8.30 (d, 1H), 8.19 (d, 1H), 8.13 (d, 1H), 8.11 (d, 1H), 7.87 (d, 1H), 7.75-7.67 (m, 1H), 7.65-7.59 (m, 1H), 7.58 (t, 1H), 7.51 (t, 1H), 7.39 (d, 1H), 7.02 (d, 1H), 6.89 (dd, 1H), 6.58 (dd, 1H), 6.13 (d, 1H), 3.81 (s, 3H), 3.75 (s, 3H), 3.54-3.44 (m, 12H), 3.42-3.36 (m, 4H), 3.21 (s, 3H), 3.10 (s, 3H), 1.27 (s, 9H).

LCMS m/z 889 (M+H)$^+$ (ES$^+$).

Example 85(w)

3-[[4-[[4-[[5-tert-Butyl-3-(methanesulfonamido)-2-methoxyphenyl]-carbamoylamino]-1-naphthyl]oxy]-2-pyridyl]amino]-N-[2-(4-hydroxy-1-piperidyl)ethyl]-5-methoxybenzamide

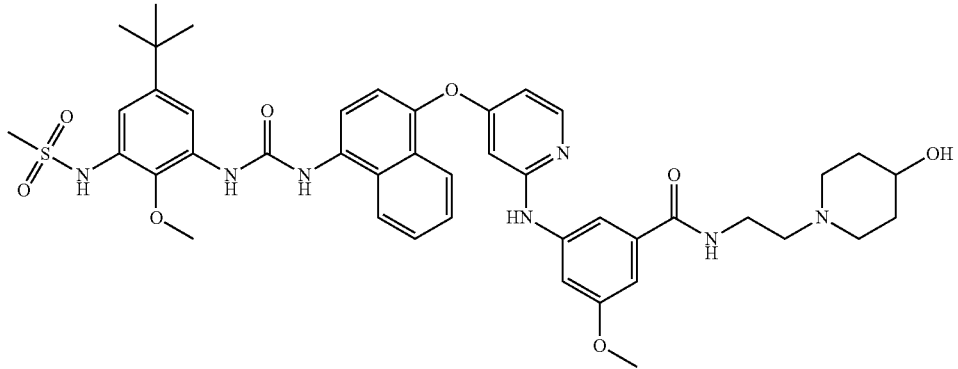 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCCN2CCC(O)CC2)c1]

¹H NMR (400 MHz, DMSO-d6) δ 9.39 (s, 1H), 9.14 (br s, 1H), 9.06 (s, 1H), 8.91 (s, 1H), 8.30 (d, 1H), 8.23-8.19 (m, 1H), 8.19 (d, 1H), 8.12 (s, 1H), 8.10 (d, 1H), 7.87 (d, 1H), 7.71 (ddd, 1H), 7.61 (ddd, 1H), 7.55 (dd, 1H), 7.51 (dd, 1H), 7.39 (d, 1H), 7.02 (d, 1H), 6.85 (dd, 1H), 6.57 (dd, 1H), 6.13 (d, 1H), 4.52 (d, 1H), 3.81 (s, 3H), 3.74 (s, 3H), 3.48-3.36 (m, 1H), 3.36-3.26 (m, 2H), 3.10 (s, 3H), 2.79-2.66 (m, 2H), 2.42 (t, 2H), 2.06 (t, 2H), 1.75-1.63 (m, 2H), 1.44-1.31 (m, 2H), 1.27 (s, 9H).

LCMS m/z 826 (M+H)⁺ (ES⁺); 824 (M−H)⁻ (ES⁻)

Example 85(x)

1-[5-tert-Butyl-3-(methanesulfonamido)-2-methoxyphenyl]-3[4-[2-[3-methoxy-5-[2-[2-(2-methoxyethoxy)ethoxy]ethylsulfinyl]anilino]pyridin-4-yl]oxy-1-naphthyl]urea

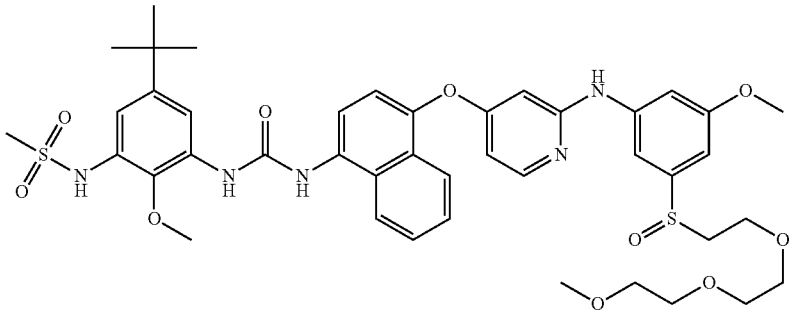 [SMILES: COCCOCCOCCS(=O)c1cc(Nc2cc(Oc3ccc(NC(=O)Nc4cc(C(C)(C)C)cc(NS(C)(=O)=O)c4OC)c4ccccc34)ccn2)cc(OC)c1]

This compound was prepared by the following method.

(i) N-(5-(tert-Butyl)-3-(3-(4-((2-chloropyridin-4-yl)oxy)naphthalen-1-yl)ureido)-2-methoxyphenyl)methanesulfonamide 4-((2-Chloropyridin-4-yl)oxy)naphthalen-1-amine (see, for example, Ito, K. et al., WO 2010/112936, 7 Oct. 2010; 1.75 g, 6.46 mmol) was added to a solution of phenyl (5-(tert-butyl)-2-methoxy-3-(methylsulfonamido)phenyl) carbamate (see Example 1(vi) above; 2.3 g, 5.86 mmol) and TEA (0.2 mL, 1.435 mmol) in 2-Me-THF (25 mL) and heated at 65° C. (block temperature) for 20 h. Phenyl (5-(tert-butyl)-2-methoxy-3-(methylsulfonamido)phenyl)-carbamate (0.5 g, 1.274 mmol) and TEA (0.1 mL, 0.717 mmol) were added and heating continued for a further 5 h. Further quantities of phenyl (5-(tert-butyl)-2-methoxy-3-(methylsulfonamido)phenyl)carbamate (0.5 g, 1.274 mmol) and TEA (0.1 mL, 0.717 mmol) were added and heating continued for a further 16 h. The resultant solid was filtered off and washed with 2-Me-THF (5 mL) to afford the sub-title compound (2.5 g).

¹H NMR (400 MHz, DMSO-d6) δ 9.41 (s, 1H), 9.13 (s, 1H), 8.94 (s, 1H), 8.32 (d, 1H), 8.29 (d, 1H), 8.18 (d, 1H), 8.14 (d, 1H), 7.85 (d, 1H), 7.76-7.68 (m, 1H), 7.66-7.59 (m, 1H), 7.42 (d, 1H), 7.06-7.01 (m, 2H), 6.94 (dd, 1H), 3.81 (s, 3H), 3.10 (s, 3H), 1.27 (s, 9H).

LCMS m/z 569/571 (M+H)⁺ (ES⁺); 567/569 (M−H)⁻ (ES⁻)

(ii) 2-((3-Methoxy-5-nitrophenyl)thio)ethanol

1-Bromo-3-methoxy-5-nitrobenzene (2.36 g, 10.17 mmol), Pd₂(dba)₃ (0.4 g, 0.437 mmol) and xantphos (0.5 g, 0.864 mmol) were added to a degassed solution of DIPEA (5.5 mL, 31.5 mmol) and 2-mercaptoethanol (0.75 mL, 10.70 mmol) in 1,4-dioxane (20 mL). The mixture was heated under nitrogen at 100° C. (block temperature) for 16 h then filtered through Celite and the solvents were evaporated. The residue was dissolved in DCM (~10 mL) and then isohexane added (~10 mL). The resultant solid was filtered off to give 1.5 g of the desired product. The filtrate was purified by chromatography on the Companion (80 g column, 10% EtOAc:isohexane to 30%) to afford 750 mg of the subtitle compound as a pale yellow solid. Combined yield of subtitle compound was 2.25 g.

¹H NMR (400 MHz, DMSO-d6) δ 7.69 (t, 1H), 7.50 (t, 1H), 7.33 (dd, 1H), 5.05 (t, 1H), 3.88 (s, 3H), 3.63 (q, 2H), 3.18 (t, 2H).

LCMS m/z 212 (M+H−H₂O)⁺ (ES⁺)

(iii) (3-Methoxy-5-nitrophenyl)(2-(2-(2-methoxyethoxy)ethoxy)ethyl)sulfane

The product from step (ii) above (1 g, 4.36 mmol) was dissolved in dry DMF (10 mL) under nitrogen and NaH (0.2 g, 5.00 mmol) added. Stirred for 10 minutes, then 1-bromo-2-(2-methoxyethoxy)ethane (0.75 ml, 5.57 mmol) and NaI (0.065 g, 0.436 mmol) added and stirred at rt for 2.5 h. The mixture was charged again with NaH (0.2 g, 5.00 mmol) and 1-bromo-2-(2-methoxyethoxy)ethane (0.75 ml, 5.57 mmol), stirred for a further 1 h then partitioned between NH₄Cl solution (200 mL) and ethyl acetate (100 mL). The organic layer was separated and washed with 20% NaCl soln. (200 mL). The organic layer was separated, dried (MgSO₄), filtered and solvent evaporated. The crude product was purified by chromatography on silica gel (80 g column, 30% EtOAc:isohexane to 50%) to afford the sub-title compound (1 g) as a clear yellow oil.

¹H NMR (400 MHz, CDCl₃) δ 7.80 (t, 1H), 7.53 (t, 1H), 7.18 (dd, 1H), 3.89 (s, 3H), 3.75 (t, 2H), 3.71-3.63 (m, 6H), 3.59-3.53 (m, 2H), 3.40 (s, 3H), 3.22 (t, 2H).

(iv) 1-Methoxy-34(2-(2-(2-methoxyethoxy)ethoxy)ethyl)sulfinyl)-5-nitrobenzene mCPBA (350 mg, 1.562 mmol) was added slowly to an ice cold solution of the product from step (iii) above (600 mg, 1.811 mmol) in ice cold DCM (5 mL). The reaction was stirred at 0° C. for 1 h then mCPBA (35 mg, 0.156 mmol) added and stirring at 0° C. continued for a further 10 minutes. The reaction mixture was filtered cold and the filtrate immediately partitioned with sodium bisulphite 20% w/w (20 mL). The organic layer was separated, washed with sat. NaHCO₃ soln. (20 mL), dried (MgSO₄), filtered and the solvent evaporated to a yellow oil. The crude product was purified by chromatography on silica gel (12 g column, 0% MeOH:EtOAc to 5%) to afford the sub-title compound (570 mg) as a yellow oil.

$^1$H NMR (400 MHz, CDCl$_3$) δ 8.04 (dd, 1H), 7.83 (t, 1H), 7.59 (dd, 1H), 4.04-3.98 (m, 1H), 3.98 (s, 3H), 3.83 (dt, 1H), 3.73-3.61 (m, 6H), 3.61-3.53 (m, 2H), 3.40 (s, 3H), 3.20-3.09 (m, 1H), 3.09-2.99 (m, 1H).

LCMS m/z 348 (M+H)$^+$ (ES$^+$)

(v) 3-Methoxy-5-((2-(2-(2-methoxyethoxy)ethoxy)ethyl)sulfinyl)aniline

A suspension of the product from step (iv) above (570 mg, 1.641 mmol) and 5% palladium on carbon (50% paste with water) (100 mg, 0.023 mmol) in ethanol (5 mL) was stirred under hydrogen (5 bar) for 2 h. The catalyst was removed by filtration and the filtrate was concentrated under reduced pressure to yield a pale yellow oil. The material was redissolved in EtOH (5 ml) and 5% palladium on carbon (50% paste with water) (100 mg, 0.023 mmol) added and the reaction stirred under hydrogen (5 bar) for 72 h. The catalyst was removed by filtration and the filtrate was concentrated under reduced pressure to give a yellow oil. The crude product was purified by chromatography on silica gel (12 g column, 2% MeOH:DCM to 8%) to afford the sub-title compound (250 mg) as a pale yellow oil.

$^1$H NMR (400 MHz, DMSO-d6) δ 6.45 (t, 1H), 6.32 (dd, 1H), 6.22 (t, 1H), 5.50 (s, 2H), 3.77 (ddd, 1H), 3.71 (s, 3H), 3.62 (dt, 1H), 3.57-3.49 (m, 6H), 3.48-3.39 (m, 2H), 3.25 (s, 3H), 3.04 (ddd, 1H), 2.89 (dt, 1H).

LCMS m/z 318 (M+H)$^+$ (ES$^+$)

(vi) 1-[5-tert-Butyl-3-(methanesulfonamido)-2-methoxyphenyl]-3-[4-[2-[3-methoxy-5-[2-[2-(2-methoxyethoxy)ethoxy]ethylsulfinyl]anilino]pyridin-4-yl]oxy-1-naphthyl]urea A mixture of the product from step (i) above (100 mg, 0.176 mmol), the product from step (v) above (75 mg, 0.236 mmol), K$_2$CO$_3$ (50 mg, 0.362 mmol), BrettPhos G1 precatalyst (5 mg, 6.26 μmol) and tBuBrettPhos (3 mg, 6.19 μmol) were degassed under vacuum, back filling with nitrogen 3 times. NMP (1 mL) was added and the suspension degassed under vacuum, back filling with nitrogen 3 times. The reaction was then heated under nitrogen at 75° C. (block temperature) for 1 h. The reaction mixture was cooled and partitioned between 20% w/w NaCl soln. (20 mL) and DCM (10 mL), the organics were separated, dried (MgSO$_4$), filtered and the solvent evaporated to give a brown oil. The crude product was preabsorbed onto silica (4 g) and purified by chromatography on silica gel (12 g column, 2% MeOH:DCM to 8%) to give a brown gum which was further purified by preparative HPLC (Varian, Basic (0.1% Ammonium Bicarbonate), Basic, Waters X-Bridge Prep-C18, 5 μm, 19×50 mm column, 25-80% MeCN in Water) to afford the title compound (70 mg) as a colourless solid.

$^1$H NMR (400 MHz, DMSO-d6) δ 9.39 (s, 1H), 9.22 (s, 1H), 9.12 (s, 1H), 8.91 (s, 1H), 8.30 (d, 1H), 8.18 (d, 1H), 8.14 (d, 1H), 8.12 (d, 1H), 7.87 (d, 1H), 7.76-7.67 (m, 1H), 7.66-7.56 (m, 1H), 7.52-7.47 (m, 1H), 7.46 (t, 1H), 7.39 (d, 1H), 7.03 (d, 1H), 6.70 (dd, 1H), 6.62 (dd, 1H), 6.13 (d, 1H), 3.81 (s, 3H), 3.80-3.76 (m, 1H), 3.76 (s, 3H), 3.62 (dt, 1H), 3.56-3.47 (m, 6H), 3.45-3.39 (m, 2H), 3.23 (s, 3H), 3.10 (s, 3H), 3.09-3.03 (m, 1H), 2.92 (dt, 1H), 1.27 (s, 9H).

LCMS m/z 425 (M+2H)$^{2+}$ (ES$^+$)

Example 85(y)

1-[5-tert-Butyl-3-(methanesulfonamido)-2-methoxyphenyl]-3-[4-[2-[3-methoxy-5-[2-[2-(2-methoxyethoxy)ethoxy]ethylsulfonyl]anilino]pyridin-4-yl]oxy-1-naphthyl]urea

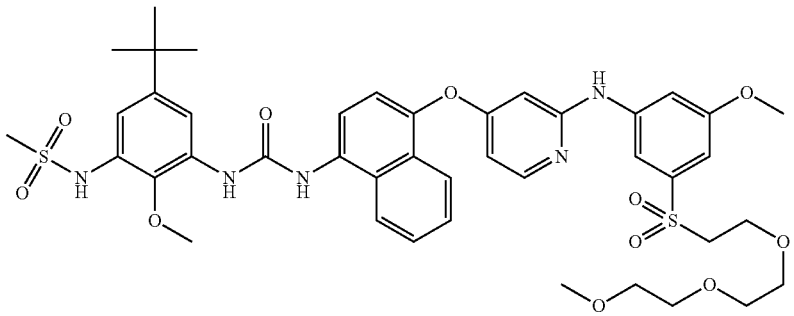 [SMILES: COCCOCCOCCS(=O)(=O)c1cc(Nc2cc(Oc3ccc(NC(=O)Nc4cc(C(C)(C)C)cc(NS(C)(=O)=O)c4OC)c4ccccc34)ccn2)cc(OC)c1]

This compound was prepared by the following method.

(i) 1-Methoxy-3-((2-(2-(2-methoxyethoxy)ethoxy)ethyl)sulfonyl)-5-nitrobenzene mCPBA (750 mg, 3.35 mmol) was added slowly to an ice cold solution of (3-methoxy-5-nitrophenyl)(2-(2-(2-methoxyethoxy)ethoxy)ethyl)sulfane (see Example 85(y) (iii) above; 450 mg, 1.358 mmol) in ice cold DCM (5 mL). The reaction was stirred at 0° C. for 30 min then allowed to warm to rt and stirred for 1 h. The reaction mixture was filtered and the filtrate immediately partitioned with sodium bisulphite solution 20% w/w (20 mL). The organic layer was separated, washed with sat. NaHCO$_3$ soln. (20 mL), dried (MgSO$_4$), filtered and the solvent evaporated to a yellow oil. The crude product was purified by chromatography on silica gel (12 g column, 50% EtOAc:isohexane to 100%) to afford the sub-title compound (470 mg)

$^1$H NMR (400 MHz, CDCl$_3$) δ 8.37 (dd, 1H), 7.98 (t, 1H), 7.78 (dd, 1H), 4.00 (s, 3H), 3.92 (t, 2H), 3.59-3.44 (m, 10H), 3.37 (s, 3H).

LCMS m/z 364 (M+H)$^+$ (ES$^+$)

(ii) 3-Methoxy-5-((2-(2-(2-methoxyethoxy)ethoxy)ethyl)sulfonyl)aniline

A suspension of the product from step (i) above (470 mg, 1.293 mmol) and 5% palladium on carbon (50% paste with water) (100 mg, 0.023 mmol) in ethanol (5 mL) was stirred under hydrogen (5 bar) for 2 h. The catalyst was removed by filtration and the filtrate was concentrated under reduced pressure to afford the sub-title compound (400 mg).

$^1$H NMR (400 MHz, DMSO-d6) δ 6.68 (t, 1H), 6.52 (dd, 1H), 6.39 (t, 1H), 5.67 (s, 2H), 3.74 (s, 3H), 3.67 (t, 2H), 3.54-3.37 (m, 10H), 3.23 (s, 3H).

LCMS m/z 334 (M+H)$^+$ (ES$^+$)

(iii) 1-[5-tert-Butyl-3-(methanesulfonamido)-2-methoxyphenyl]-3-[4-[2-[3-methoxy-5-[2-[2-(2-methoxyethoxy)ethoxy]ethylsulfonyl]anilino]pyridin-4-yl]oxy-1-naphthyl]urea A mixture of N-(5-(tert-butyl)-3-(3-(4-((2-chloropyridin-4-yl)oxy)naphthalen-1-yl)ureido)-2-methoxyphenyl)methanesulfonamide (see Example 85(y)(i) above; 100 mg, 0.176 mmol), the product from step (ii) above (75 mg, 0.225 mmol), K$_2$CO$_3$ (50 mg, 0.362 mmol), BrettPhos G1 precatalyst (5 mg, 6.26 μmol) and tBuBrettPhos (3 mg, 6.19 μmol) were degassed under vacuum, back filling with nitrogen 3 times. NMP (1 mL) was added and the suspension degassed under vacuum, back filling with nitrogen 3 times. The reaction was then heated under nitrogen at 75° C. (block temperature) for 1 h. The reaction mixture was cooled and partitioned between 20% w/w NaCl soln. (20 mL) and DCM (10 mL), the organics were separated, dried (MgSO$_4$), filtered and the solvent evaporated to give a brown oil. The crude product was preabsorbed onto silica (4 g) and purified by chromatography on silica gel (12 g column, 2% MeOH:DCM to 10%) to give a brown gum which was further purified by preparative HPLC (Varian, Basic (0.1% Ammonium Bicarbonate), Basic, Waters X-Bridge Prep-C18, 5 μm, 19×50 mm column, 25-80% MeCN in Water) to afford the title compound (85 mg).

$^1$H NMR (400 MHz, DMSO-d6) δ 9.39 (s, 1H), 9.33 (s, 1H), 9.12 (s, 1H), 8.91 (s, 1H), 8.31 (d, 1H), 8.18 (d, 1H), 8.16 (d, 1H), 8.12 (d, 1H), 7.87 (d, 1H), 7.78-7.67 (m, 3H), 7.67-7.55 (m, 1H), 7.40 (d, 1H), 7.03 (d, 1H), 6.88 (t, 1H), 6.65 (dd, 1H), 6.13 (d, 1H), 3.82 (s, 3H), 3.79 (s, 3H), 3.68 (t, 2H), 3.54 (t, 2H), 3.42-3.36 (m, 4H), 3.18 (s, 3H), 3.10 (s, 3H), 1.27 (s, 9H). 2×CH2 obscured by H2O at 3.33 ppm.

LCMS m/z 433 (M+2H)$^{2+}$ (ES$^+$)

Example 86

The following compounds are prepared by methods analogous to those described above.

(a) 5-tert-Butyl-3-[[4-[[2-[3-(hydroxymethyl)-5-methoxyanilino]-4-pyridyl]oxy]-1-naphthyl]carbamoylamino]-2-methoxy-N-(oxetan-3-yl)benzamide

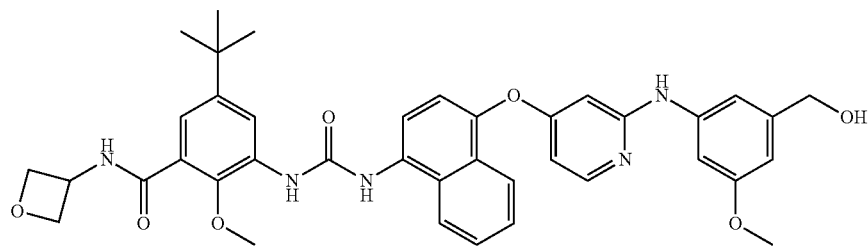 [SMILES: COc1cc(CO)cc(Nc2cc(Oc3ccc(NC(=O)Nc4cc(C(C)(C)C)cc(C(=O)NC5COC5)c4OC)c4ccccc34)ccn2)c1]

(b) 3-[[[4-[[4-[[5-tert-Butyl-3-(methanesulfonamido)-2-methoxy-phenyl]carbamoylamino]-1-naphthyl]oxy]pyrimidin-2-yl]amino]methyl]-5-methoxy-N-[2-[2-(2-methoxyethoxy)ethoxy]-ethyl]benzamide

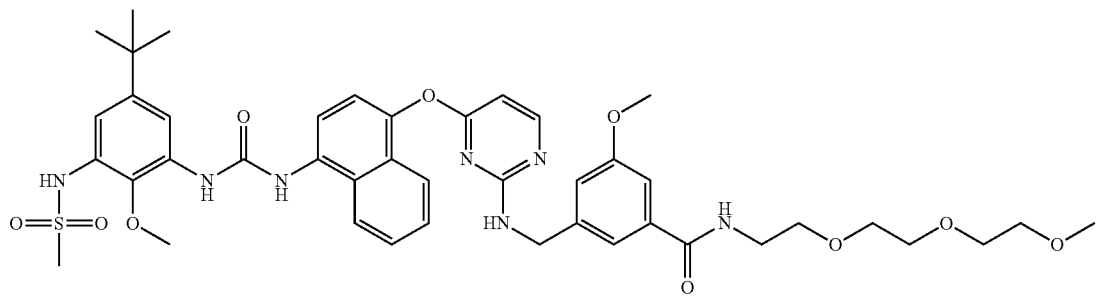 [SMILES: COCCOCCOCCNC(=O)c1cc(CNc2nccc(Oc3ccc(NC(=O)Nc4cc(C(C)(C)C)cc(NS(C)(=O)=O)c4OC)c4ccccc34)n2)cc(OC)c1]

(c) 3-[[[4-[[4-[[5-tert-Butyl-3-(methanesulfonamido)-2-methoxy-phenyl]carbamoylamino]-1-naphthyl]oxy]pyrimidin-2-yl]amino]methyl]-5-methoxy-N-(2-morpholinoethyl)benzamide

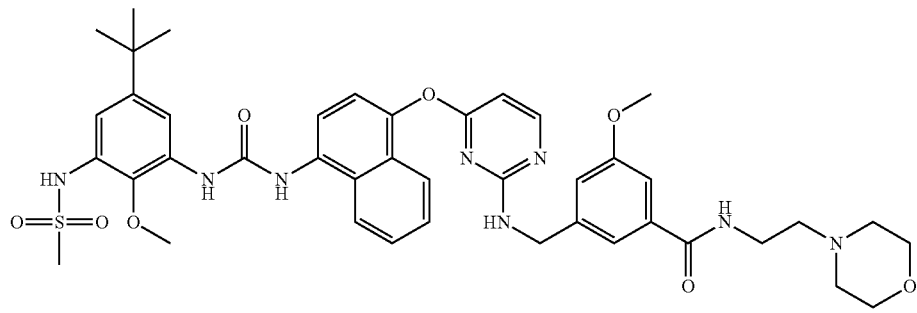 [SMILES: COc1cc(CNc2nccc(Oc3ccc(NC(=O)Nc4cc(C(C)(C)C)cc(NS(C)(=O)=O)c4OC)c4ccccc34)n2)cc(C(=O)NCCN2CCOCC2)c1]

(d) 1-[5-tert-Butyl-3-(cyanomethyl)-2-methoxyphenyl]-3-[4-[[2-[3-methoxy-5-[2-[2-(2-methoxyethoxy)ethoxy]ethoxy]anilino]-4-pyridyl]oxy]-1-naphthyl]urea

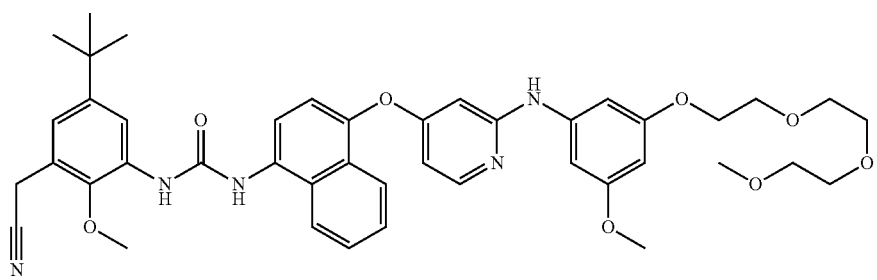 [SMILES: COCCOCCOCCOc1cc(Nc2cc(Oc3ccc(NC(=O)Nc4cc(C(C)(C)C)cc(CC#N)c4OC)c4ccccc34)ccn2)cc(OC)c1]

(e) 3-[[4-[[4-[[5-tert-Butyl-3-(cyanomethyl)-2-methoxy-phenyl]carbamoylamino]-1-naphthyl]oxy]-2-pyridyl]amino]-5-methoxy-N-(2-morpholinoethyl)benzamide

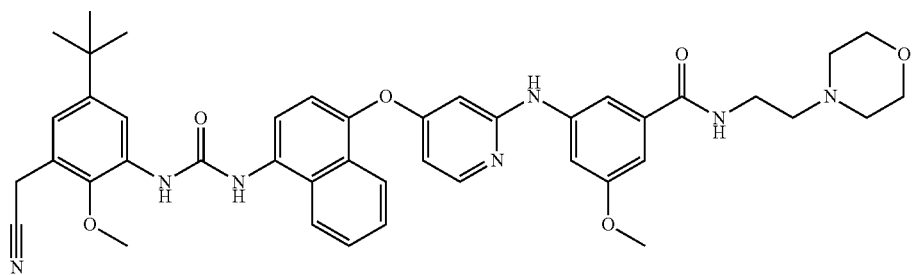 [SMILES: COc1cc(Nc2cc(Oc3ccc(NC(=O)Nc4cc(C(C)(C)C)cc(CC#N)c4OC)c4ccccc34)ccn2)cc(C(=O)NCCN2CCOCC2)c1]

(f) 3-[[4-[[4-[[5-tert-Butyl-3-(cyanomethyl)-2-methoxy-phenyl]carbamoylamino]-1-naphthyl]oxy]-2-pyridyl]amino]-5-ethynyl-N-[2-[2-(2-methoxy-ethoxy)ethoxy]ethyl]benzamide

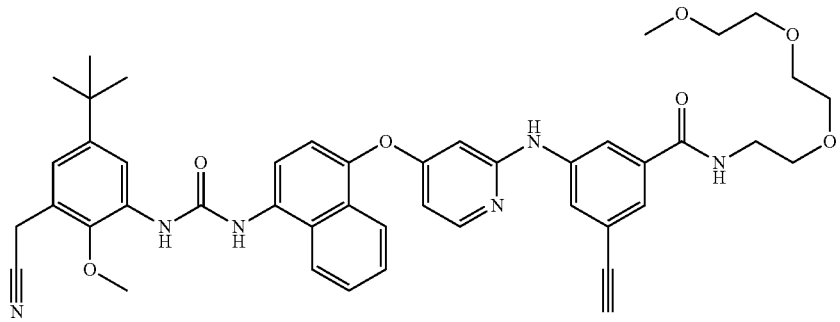 [SMILES: C#Cc1cc(Nc2cc(Oc3ccc(NC(=O)Nc4cc(C(C)(C)C)cc(CC#N)c4OC)c4ccccc34)ccn2)cc(C(=O)NCCOCCOCCOC)c1]

(g) 3-[[4-[[4-[[5-tert-Butyl-3-(methanesulfonamido)-2-methoxyphenyl]-carbamoylamino]-1-naphthyl]oxy]-2-pyridyl]amino]-5-methoxy-N-[2-(1,4-oxazepan-4-yl)ethyl]benzamide

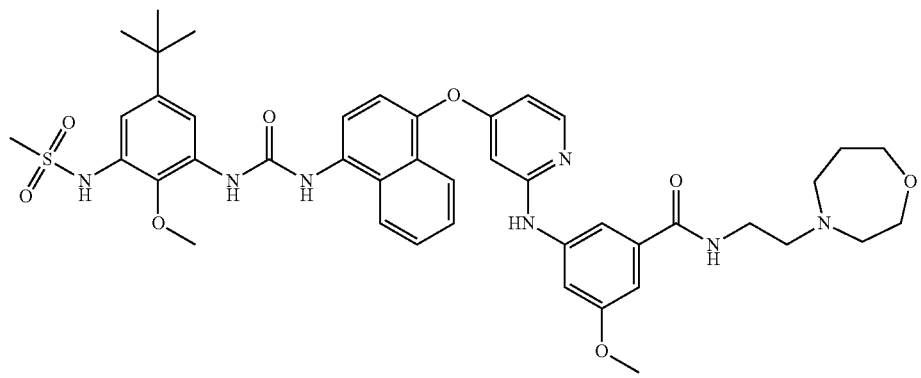 [SMILES: COc1cc(Nc2cc(Oc3ccc(NC(=O)Nc4cc(C(C)(C)C)cc(NS(C)(=O)=O)c4OC)c4ccccc34)ccn2)cc(C(=O)NCCN2CCCOCC2)c1]

(h) 3-[[4-[[4-[[5-tert-Butyl-3-(methanesulfonamido)-2-methoxyphenyl]-carbamoylamino]-1-naphthyl]oxy]-2-pyridyl]amino]-5-methoxy-N-[2-(4-oxo-1-piperidyl)ethyl]benzamide

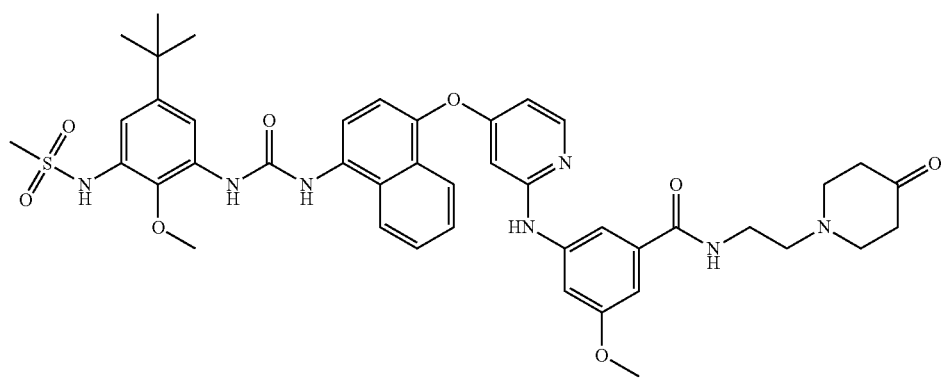

(i) 5-tert-Butyl-3-[[4-[[2-[3-ethynyl-5-(hydroxymethyl)anilino]-4-pyridyl]oxy]-1-naphthyl]carbamoylamino]-2-methoxy-N-methyl-benzamide

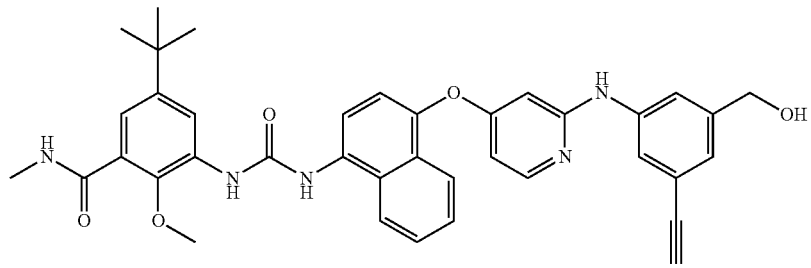 [SMILES: C#Cc1cc(CO)cc(Nc2cc(Oc3ccc(NC(=O)Nc4cc(C(C)(C)C)cc(C(=O)NC)c4OC)c4ccccc34)ccn2)c1]

Biological Testing: Experimental Methods
Enzyme Binding Assays (Kinomescan)
Kinase enzyme binding activities of compounds disclosed herein may be determined using a proprietary assay which measures active site-directed competition binding to an immobilized ligand (Fabian, M. A. et al., *Nature Biotechnol.*, 2005, 23:329-336). These assays may be conducted by DiscoverX (formerly Ambit; San Diego, Calif.). The percentage inhibition produced by incubation with a test compound may be calculated relative to the non-inhibited control.

Enzyme Inhibition Assays
The enzyme inhibitory activities of compounds disclosed herein are determined by FRET using synthetic peptides labelled with both donor and acceptor fluorophores (Z-LYTE, Invitrogen Ltd., Paisley, UK).

p38 MAPKα Enzyme Inhibition
The following two assay variants can be used for determination of p38 MAPKα inhibition.

Method 1
The inhibitory activities of test compounds against the p38 MAPKα isoform (MAPK14: Invitrogen) are evaluated indirectly by determining the level of activation/phosphorylation of the down-stream molecule, MAPKAP-K2. The p38 MAPKα protein (80 ng/mL, 2.5 μL) is mixed with the test compound (2.5 μL of either 4 μg/mL, 0.4 μg/mL, 0.04 μg/mL or 0.004 μg/mL) for 2 hr at RT. The mix solution (2.5 μL) of the p38α inactive target MAPKAP-K2 (Invitrogen, 600 ng/mL) and FRET peptide (8 μM; a phosphorylation target for MAPKAP-K2) is then added, then the kinase reaction is initiated by adding ATP (40 μM, 2.5 μL). The mixture is incubated for 1 hr at RT. Development reagent (protease, 5 μL) is added for 1 hr prior to detection in a fluorescence microplate reader (Varioskan® Flash, Thermo-Fisher Scientific).

Method 2
This method follows the same steps as Method 1 above, but utilises a higher concentration of the p38 MAPKα protein (2.5 μL of 200 ng/mL protein instead of 2.5 μL of 80 ng/mL protein) for mixing with the test compound (tested at either 1 μg/mL, 0.1 μg/mL, 0.01 μg/mL or 0.001 μg/mL).

p38 MAPKγ Enzyme Inhibition
The inhibitory activities of compounds of the invention against p38MAPKγ (MAPK12: Invitrogen), are evaluated in a similar fashion to that described hereinabove. The enzyme (800 ng/mL, 2.5 μL) is incubated with the test compound (2.5 μL of either 4 μg/mL, 0.4 μg/mL, 0.04 μg/mL, or 0.004 μg/mL) for 2 hr at RT. The FRET peptides (8 μM, 2.5 μL), and appropriate ATP solution (2.5 μL, 400 μM) are then added to the enzymes/compound mixtures and the whole is incubated for 1 hr. Development reagent (protease, 5 μL) is added for 1 hr prior to detection in a fluorescence microplate reader (Varioskan® Flash, Thermo Scientific).

c-Src and Syk Enzyme Inhibition
The inhibitory activities of compounds of the invention against c-Src and Syk enzymes (Invitrogen), are evaluated in a similar fashion to that described hereinabove. The relevant enzyme (3000 ng/mL or 2000 ng/mL respectively, 2.5 μL) is incubated with the test compound (either 1 μg/mL, 0.1 μg/mL, 0.01 μg/mL, or 0.001 μg/mL, 2.5 μL each) for 2 hr at RT. The FRET peptides (8 μM 2.5 μL), and appropriate ATP solutions (2.5 μL, 800 μM for c-Src, and 60 μM ATP for Syk) are then added to the enzymes/compound mixtures and the mixture incubated for 1 hr. Development reagent (protease, 5 μL) is added for 1 hr prior to detection in a fluorescence microplate reader (Varioskan® Flash, ThermoFisher Scientific).

GSK 3α Enzyme Inhibition
The following two assay variants can be used for determination of GSK 3α inhibition.

Method 1
The inhibitory activities of compounds of the invention against the GSK 3α enzyme isoform (Invitrogen), are evaluated by determining the level of activation/phosphorylation of the target peptide. The GSK3-α protein (500 ng/mL, 2.5 μL) is mixed with the test compound (2.5 μL at either 4 μg/mL, 0.4 μg/mL, 0.04 μg/mL, or 0.004 μg/mL) for 2 hr at RT. The FRET peptide (8 μM, 2.5 μL), which is a phosphorylation target for GSK3α, and ATP (40 μM, 2.5 μL) are then added to the enzyme/compound mixture and the resulting mixture incubated for 1 hr. Development reagent (protease, 5 μL) is added for 1 hr prior to detection in a fluorescence microplate reader (Varioskan® Flash, ThermoFisher Scientific).

In all cases, the site-specific protease cleaves non-phosphorylated peptide only and eliminates the FRET signal. Phosphorylation levels of each reaction are calculated using the ratio of coumarin emission (donor) over fluorescein emission (acceptor), for which high ratios indicate high phosphorylation and low ratios indicate low phosphorylation levels. The percentage inhibition of each reaction is calculated relative to non-inhibited control and the 50% inhibitory concentration ($IC_{50}$ value) is then calculated from the concentration-response curve.

Method 2
This method follows the same steps as Method 1 above, but utilises a shorter period of mixing of the test compound (105 minutes instead of 2 hours) with the GSK3-α protein. In addition, the concentrations of test compound employed are either 10 μg/mL, 1 μg/mL, 0.1 μg/mL, or 0.01 μg/mL Cellular Assays
The compounds of the invention were studied using one or more of the following assays.

(a) Inhibition of p38 MAPKα and Lck in Jurkat Cells

Jurkat T cells were cultured in starve medium (RPMI 1640+5% FBS) for 24 h prior to the experiment. Cells were harvested and resuspended at $10\times10^6$ cells/mL in starve medium and then plated into round-bottomed 96 well plates at $1\times10^6$ cells/well. Serial dilutions of test compound were added (1% final DMSO concentration) for 2 h prior to stimulation. Following pre-incubation with compound, cells were stimulated with $H_2O_2$ (0.05% final) for 5 min. The reaction was stopped by centrifugation at 2000 rpm (3 min, 4° C.), then the supernatant was removed and 100 μL of cold fix/perm solution (BD Fix/Perm kit #554714) added. Plates were incubated for 20 min at 4° C. before centrifugation and washing with supplied 1× wash medium (BD Fix/Perm kit #554714). Cells were stained for either phospho-p38α (T180/182), supplied by Cell Signalling Technology (9211s), or phospho-Lck (Y394), supplied by R&D (MAB7500). Antibodies were diluted to 5 μg/mL (R&D) or 1:200 (Cell Signalling Technology) in wash medium, before being incubated 1 h at 4° C. in the dark. Following 3 repeat washes with ice cold wash buffer, secondary antibody (anti-rabbit-FITC #F1362 or anti-mouse-FITC #F2883, both from Sigma) was added at a dilution of 1:1000 and incubated for 1 h at 4° C. in the dark. Cells were washed 3× times in cold wash buffer then, following a final wash in cold PBS, were resuspended in 150 μL cold PBS. Cells were analysed by flow cytometry using BD Accuri C6.

(aa) LPS-Induced TNFα/IL-8 Release in d-U937 Cells

U937 cells, a human monocytic cell line, are differentiated to macrophage-type cells by incubation with phorbol myristate acetate (PMA; 100 ng/mL) for 48 to 72 hr. Cells are pre-incubated with final concentrations of test compound for 2 hr and are then stimulated with 0.1 μg/mL of LPS (from *E. Coli*: 0111:B4, Sigma) for 4 hr. The supernatant is collected for determination of TNFα and IL-8 concentrations by sandwich ELISA (Duo-set, R&D systems). The inhibition of TNFα production is calculated as a percentage of that achieved by 10 μg/mL of BIRB796 at each concentration of test compound by comparison against vehicle control. The relative 50% effective concentration ($REC_{50}$) is determined from the resultant concentration-response curve. The inhibition of IL-8 production is calculated at each concentration of test compound by comparison with vehicle control. The 50% inhibitory concentration ($IC_{50}$) is determined from the resultant concentration-response curve.

(b) LPS-Induced TNFα/IL-8 Release in PBMC Cells

Peripheral blood mononuclear cells (PBMCs) from healthy subjects are separated from whole blood using a density gradient (Lymphoprep, Axis-Shield Healthcare). The PBMCs are seeded in 96 well plates and treated with compounds at the desired concentration for 2 hours before addition of 1 ng/mL LPS (*Escherichia Coli* 0111:B4 from Sigma Aldrich) for 24 hours under normal tissue culture conditions (37° C., 5% $CO_2$). The supernatant is harvested for determination of IL-8 and TNFα concentrations by sandwich ELISA (Duo-set, R&D systems) and read on the fluorescence microplate reader (Varioskan® Flash, Thermo-Fisher Scientific). The concentration at 50% inhibition ($IC_{50}$) of IL-8 and TNFα production is calculated from the dose response curve.

(c) IL-2 and IFN Gamma Release in CD3/CD28 Stimulated PBMC Cells

PBMCs from healthy subjects are separated from whole blood using a density gradient (Lymphoprep, Axis-Shield Healthcare). Cells are added to a 96 well plate pre-coated with a mixture of CD3/CD28 monoclonal antibodies (0.3 μg/mL eBioscience and 3 μg/mL BD Pharmingen respectively). Compound at the desired concentration is then added to the wells and the plate left for 3 days under normal tissue culture conditions. Supernatants are harvested and IL-2 and IFN gamma release determined by Sandwich ELISA (Duo-set, R&D System). The $IC_{50}$ is determined from the dose response curve.

(d) IL-1β-Induced IL-8 Release in HT29 Cells

HT29 cells, a human colon adenocarcinoma cell line, are plated in a 96 well plate (24 hr) and pre-treated with compounds at the desired concentration for 2 hours before addition of 5 ng/mL of IL-1β (Abcam) for 24 hours. Supernatants are harvested for IL-8 quantification by Sandwich ELISA (Duo-set, R&D System). The $IC_{50}$ is determined from the dose response curve.

(e) LPS-Induced IL-8 and TNFα Release in Primary Macrophages

PBMCs from healthy subjects are separated from whole blood using a density gradient (Lymphoprep, Axis-Shield Healthcare). Cells are incubated for 2 hrs and non-adherent cells removed by washing. To differentiate the cells to macrophages, they are incubated with 5 ng/mL of GM-CSF (Peprotech) for 7 days under normal tissue culture conditions. Compounds are then added to the cells at the desired concentration for a 2 hour pre-treatment before stimulation with 10 ng/mL LPS for 24 hours. Supernatants are harvested and IL-8 and TNFα release determined by Sandwich ELISA (Duo-set, R&D System). The $IC_{50}$ is determined from the dose response curve.

(f) Poly I:C-Induced ICAM-1 Expression in BEAS2B Cells

Poly I:C is used in these studies as a simple, RNA virus mimic. Poly I:C-Oligofectamine mixture (1 μg/mL Poly I:C, ±2% Oligofectamine, 25 μL; Invivogen Ltd., San Diego, Calif., and Invitrogen, Carlsbad, Calif., respectively) is transfected into BEAS2B cells (human bronchial epithelial cells, ATCC). Cells are pre-incubated with final concentrations of test compounds for 2 hr and the level of ICAM1 expression on the cell surface is determined by cell-based ELISA. At a time point 18 hr after poly I:C transfection, cells are fixed with 4% formaldehyde in PBS and then endogenous peroxidase is quenched by the addition of washing buffer (100 μL, 0.05% Tween in PBS: PBS-Tween) containing 0.1% sodium azide and 1% hydrogen peroxide. Cells are washed with wash-buffer (3×200 μL) and after blocking the wells with 5% milk in PBS-Tween (100 μL) for 1 hr, the cells are incubated with anti-human ICAM-1 antibody (50 μL; Cell Signalling Technology, Danvers, Mass.) in 1% BSA PBS overnight at 4° C.

The cells are washed with PBS-Tween (3×200 μL) and incubated with the secondary antibody (100 μL; HRP-conjugated anti-rabbit IgG, Dako Ltd., Glostrup, Denmark). The cells are then incubated with substrate (50 μL) for 2-20 min, followed by the addition of stop solution (50 μL, 1N $H_2SO_4$). The ICAM-1 signal is detected by reading the absorbance at 450 nm against a reference wavelength of 655 nm using a spectrophotometer. The cells are then washed with PBS-Tween (3×200 μL) and total cell numbers in each well are determined by reading absorbance at 595 nm after Crystal Violet staining (50 μL of a 2% solution in PBS) and elution by 1% SDS solution (100 μL) in distilled water. The measured OD 450-655 readings are corrected for cell number by dividing with the OD595 reading in each well. The inhibition of ICAM-1 expression is calculated at each concentration of test compound by comparison with vehicle control. The 50% inhibitory concentration ($IC_{50}$) is determined from the resultant concentration-response curve.

(g) Cell Mitosis Assay

Peripheral blood mononucleocytes (PBMCs) from healthy subjects are separated from whole blood (Quintiles, London, UK) using a density gradient (Histopaque®-1077, Sigma-Aldrich, Poole, UK). The PBMCs (3 million cells per sample) are subsequently treated with 2% PHA (phytohaemagglutinin, Sigma-Aldrich, Poole, UK) for 48 hr, followed by a 20 hr exposure to varying concentrations of test compounds. At 2 hr before collection, PBMCs are treated with demecolcine (0.1 µg/mL; Invitrogen, Paisley, UK) to arrest cells in metaphase. To observe mitotic cells, PBMCs are permeabilised and fixed by adding Intraprep (50 µL; Beckman Coulter, France), and stained with anti-phosphohistone 3 (0.26 ng/L; #9701; Cell Signalling, Danvers, Mass.) and propidium iodide (1 mg/mL; Sigma-Aldrich, Poole, UK) as previously described (Muehlbauer P. A. and Schuler M. J., *Mutation Research,* 2003, 537:117-130). Fluorescence is observed using an ATTUNE flow cytometer (Invitrogen, Paisley, UK), gating for lymphocytes. The percentage inhibition of mitosis is calculated for each treatment relative to vehicle (0.5% DMSO) treatment.

(h) Rhinovirus-Induced IL-8 Release and ICAM-1 Expression

Human rhinovirus RV16 is obtained from the American Type Culture Collection (Manassas, Va.). Viral stocks are generated by infecting HeLa cells with HRV until 80% of the cells are cytopathic.

BEAS2B cells are infected with HRV at an MOI of 5 and incubated for 2 hr at 33° C. with gentle shaking to promote absorption. The cells are then washed with PBS, fresh media added and the cells are incubated for a further 72 hr. The supernatant is collected for assay of IL-8 concentrations using a Duoset ELISA development kit (R&D systems, Minneapolis, Minn.).

The level of ICAM-1 expressing cell surface is determined by cell-based ELISA. At 72 hr after infection, cells are fixed with 4% formaldehyde in PBS. After quenching endogenous peroxidase by adding 0.1% sodium azide and 1% hydrogen peroxide, wells are washed with wash-buffer (0.05% Tween in PBS: PBS-Tween). After blocking well with 5% milk in PBS-Tween for 1 hr, the cells are incubated with anti-human ICAM-1 antibody in 5% BSA PBS-Tween (1:500) overnight. Wells are washed with PBS-Tween and incubated with the secondary antibody (HRP-conjugated anti-rabbit IgG, Dako Ltd.). The ICAM-1 signal is detected by adding substrate and reading at 450 nm with a reference wavelength of 655 nm using a spectrophotometer. The wells are then washed with PBS-Tween and total cell numbers in each well are determined by reading absorbance at 595 nm after Crystal Violet staining and elution with 1% SDS solution. The measured $OD_{450-655}$ readings are corrected for cell number by dividing with the $OD_{595}$ reading in each well. Compounds are added 2 hr before HRV infection and 2 hr after infection when non-infected HRV is washed out.

(i) Assessment of HRV16 Induced Cytopathic Effect (CPE) in MRC5 Cells

MRC5 cells are infected with HRV16 at an MOI of 1 in DMEM containing 5% FCS and 1.5 mM $MgCl_2$, followed by incubation for 1 hr at 33° C. to promote adsorption. The supernatants are aspirated, and then fresh media added followed by incubation for 4 days. Where appropriate, cells are pre-incubated with compound or DMSO for 2 hr, and the compounds and DMSO added again after washout of the virus.

Supernatants are aspirated and incubated with methylene blue solution (100 µL, 2% formaldehyde, 10% methanol and 0.175% Methylene Blue) for 2 hr at RT. After washing, 1% SDS in distilled water (100 µL) is added to each well, and the plates are shaken lightly for 1-2 hr prior to reading the absorbance at 660 nm. The percentage inhibition for each well is calculated. The $IC_{50}$ value is calculated from the concentration-response curve generated by the serial dilutions of the test compounds.

(j) In Vitro RSV Virus Load in Primary Bronchial Epithelial Cells

Normal human bronchial epithelial cells (NHBEC) grown in 96 well plates are infected with RSV A2 (Strain A2, HPA, Salisbury, UK) at a MOI of 0.001 in the LHC8 Media: RPMI-1640 (50:50) containing 15 mM magnesium chloride and incubated for 1 hr at 37° C. for adsorption. The cells are washed with PBS (3×200 µL), then fresh media (200 µL) is added and incubation continued for 4 days. Where appropriate, cells are pre-incubated with the compound or DMSO for 2 hr, and then added again after washout of the virus.

The cells are fixed with 4% formaldehyde in PBS solution (50 µL) for 20 min, washed with WB (3×200 µL) (washing buffer, PBS including 0.5% BSA and 0.05% Tween-20) and incubated with blocking solution (5% condensed milk in PBS) for 1 hr. Cells are then washed with WB (3×200 µL) and incubated for 1 hr at RT with anti-RSV (2F7) F-fusion protein antibody (40 µL; mouse monoclonal, lot 798760, Cat. No.ab43812, Abcam) in 5% BSA in PBS-tween. After washing, cells are incubated with an HRP-conjugated secondary antibody solution (50 µL) in 5% BSA in PBS-Tween (lot 00053170, Cat. No. PO447, Dako) and then TMB substrate added (50 µL; substrate reagent pack, lot 269472, Cat. No. DY999, R&D Systems, Inc.). This reaction is stopped by the addition of 2N $H_2SO_4$ (50 µL) and the resultant signal is determined colourimetrically (OD: 450 nm with a reference wavelength of 655 nm) in a microplate reader (Varioskan® Flash, ThermoFisher Scientific).

Cells are then washed and a 2.5% crystal violet solution (50 µL; lot 8656, Cat. No. PL7000, Pro-Lab Diagnostics) is applied for 30 min. After washing with WB, 1% SDS in distilled water (100 µL) is added to each well, and plates are shaken lightly on the shaker for 1 hr prior to reading the absorbance at 595 nm. The measured $OD_{450-655}$ readings are corrected to the cell number by dividing the $OD_{450-655}$ by the $OD_{595}$ readings. The percentage inhibition for each well is calculated and the $IC_{50}$ value is calculated from the concentration-response curve generated from the serial dilutions of compound.

(k) Cell Viability Assay: MTT Assay

Differentiated U937 cells are pre-incubated with each test compound (final concentration 1 µg/mL or 10 µg/mL in 200 µL media indicated below) under two protocols: the first for 4 hr in 5% FCS RPMI1640 media and the second in 10% FCS RPMI1640 media for 24 h. The supernatant is replaced with new media (200 µL) and MTT stock solution (10 µL, 5 mg/mL) is added to each well. After incubation for 1 hr the media are removed, DMSO (200 µL) is added to each well and the plates are shaken lightly for 1 hr prior to reading the absorbance at 550 nm. The percentage loss of cell viability is calculated for each well relative to vehicle (0.5% DMSO) treatment. Consequently an apparent increase in cell viability for drug treatment relative to vehicle is tabulated as a negative percentage.

(l) Human Biopsy Assay

Intestinal mucosa biopsies are obtained from the inflamed regions of the colons of IBD patients. The biopsy material is cut into small pieces (2-3 mm) and placed on steel grids in an organ culture chamber at 37° C. in a 5% $CO_2$/95% $O_2$ atmosphere in serum-free media. DMSO control or test compounds at the desired concentration are added to the tissue and incubated for 24 hr in the organ culture chamber. The supernatant is harvested for determination of IL-6, IL-8, IL-1β and TNFα levels by R&D ELISA. Percentage inhibition of cytokine release by the test compounds is calculated relative to the cytokine release determined for the DMSO control (100%).

(m) Accumulation of β Catenin in d-U937 Cells

U937 cells, a human monocytic cell line, are differentiated into macrophage-type cells by incubation with PMA (100 ng/mL) for between 48 to 72 hr. The cells are then incubated with either final concentrations of test compound or vehicle for 18 hr. The induction of β-catenin by the test compounds is stopped by replacing the media with 4% formaldehyde solution. Endogenous peroxide activity is neutralised by incubating with quenching buffer (100 μL, 0.1% sodium azide, 1% $H_2O_2$ in PBS with 0.05% Tween-20) for 20 min. The cells are washed with washing buffer (200 pt; PBS containing 0.05% Tween-20) and incubated with blocking solution (200 pt; 5% milk in PBS) for 1 hr, re-washed with washing buffer (200 pt) and then incubated overnight with anti-β-catenin antibody solution (50 μL) in 1% BSA/PBS (BD, Oxford, UK).

After washing with washing buffer (3×200 pt; PBS containing 0.05% Tween-20), cells are incubated with a HRP-conjugated secondary antibody solution (100 μL) in 1% BSA/PBS (Dako, Cambridge, UK) and the resultant signal is determined colourimetrically (OD: 450 nm with a reference wavelength of 655 nm) using TMB substrate (50 μL; R&D Systems, Abingdon, UK). This reaction is stopped by addition of 1N $H_2SO_4$ solution (50 μL). Cells are then washed with washing buffer and 2% crystal violet solution (50 μL) is applied for 30 min. After washing with washing buffer (3×200 μL), 1% SDS (100 μL) is added to each well and the plates are shaken lightly for 1 hr prior to measuring the absorbance at 595 nm (Varioskan® Flash, Thermo-Fisher Scientific).

The measured $OD_{450-655}$ readings are corrected for cell number by dividing the $OD_{450-655}$ by the $OD_{595}$ readings. The percentage induction for each well is calculated relative to vehicle, and the ratio of induction normalised in comparison with the induction produced by a standard control comprising the Reference compound N-(4-(4-(3-(3-tert-butyl-1-p-tolyl-1H-pyrazol-5-yl)ureido)naphthalen-1-yloxy)pyridin-2-yl)-2-methoxyacetamide (1 μg/mL), which is defined as unity.

(n) T Cell Proliferation

PBMCs from healthy subjects are separated from whole blood using a density gradient (Lymphoprep, Axis-Shield Healthcare). The lymphocyte fraction is first enriched for CD4+ T cells by negative magnetic cell sorting as per the manufacturer's instructions (Miltenyi Biotec 130-091-155). Naïve CD4+ T cells are then separated using positive magnetic selection of CD45RA+ cells using microbeads as per the manufacturer's instructions (130-045-901). Cells are plated at $2×10^5$ cells per well in 100 μL RPMI/10% FBS on 96 well flat bottomed plate (Corning Costar). 25 μL of test compound are diluted to the appropriate concentration (8× final concentration) in normal medium and added to duplicate wells on the plate to achieve a dose response range of 0.03 ng/mL 250 ng/mL. DMSO is added as a negative control. Plates are allowed to pre-incubate for 2 hours before stimulation with 1 μg/mL anti-CD3 (OKT3; eBioscience). After 72 h, the medium in each well is replaced with 150 μL of fresh medium containing 10 μM BrdU (Roche). After 16 h, the supernatant is removed, the plate is dried and the cells fixed by adding 100 μL of fix/denature solution to each well for 20 min as per the manufacturer's instructions (Roche). Plates are washed once with PBS before addition of the anti-BrdU detection antibody and incubated for 90 mins at room temperature. Plates are then washed gently 3× with the wash buffer supplied and developed by addition of 100 μL of substrate solution. The reaction is stopped by addition of 50 μL of 1 M $H_2SO_4$ and read for absorbance at 450 nm on a plate reader (Varioskan® Flash, ThermoFisher Scientific). The $IC_{50}$ is determined from the dose response curve.

(o) IL-2 and IFNγ Release in CD3/CD28 Stimulated LPMC Cells from IBD Patients

Lamina propria mononuclear cells (LPMCs) are isolated and purified from inflamed IBD mucosa of surgical specimens or from normal mucosa of surgical specimens as follows: The mucosa is removed from the deeper layers of the surgical specimens with a scalpel and cut in fragments of size 3-4 mm. The epithelium is removed by washing the tissue fragments three times with 1 mM EDTA (Sigma-Aldrich, Poole, UK) in HBSS (Sigma-Aldrich) with agitation using a magnetic stirrer, discarding the supernatant after each wash. The sample is subsequently treated with type 1A collagenase (1 mg/mL; Sigma-Aldrich) for 1 h with stirring at 37° C. The resulting cell suspension is then filtered using a 100 μm cell strainer, washed twice, resuspended in RPMI-1640 medium (Sigma-Aldrich) containing 10% fetal calf serum, 100 U/mL penicillin and 100 μg/mL streptomycin, and used for cell culture.

Freshly isolated LPMCs ($2×10^5$ cells/well) are stimulated with 1 μg/mL α-CD3/α-CD28 for 48 h in the presence of either DMSO control or appropriate concentrations of compound. After 48 h, the supernatant is removed and assayed for the presence of TNFα and IFNγ by R&D ELISA. Percentage inhibition of cytokine release by the test compounds is calculated relative to the cytokine release determined for the DMSO control (100%).

(p) Inhibition of Cytokine Release from Myofibroblasts Isolated from IBD Patients Myofibroblasts from inflamed IBD mucosa are isolated as follows: The mucosa is dissected and discarded and 1 mm-sized mucosal samples are cultured at 37° C. in a humidified $CO_2$ incubator in Dulbecco's modified Eagle's medium (DMEM, Sigma-Aldrich) supplemented with 20% FBS, 1% non-essential amino acids (Invitrogen, Paisley, UK), 100 U/mL penicillin, 100 μg/mL streptomycin, 50 μg/mL gentamycin, and 1 μg/mL amphotericin (Sigma-Aldrich). Established colonies of myofibroblasts are seeded into 25-cm$^2$ culture flasks and cultured in DMEM supplemented with 20% FBS and antibiotics to at least passage 4 to provide a sufficient quantity for use in stimulation experiments.

Subconfluent monolayers of myofibroblasts, seeded in 12-well plates at $3×10^5$ cells per well, are starved in serum-free medium for 24 h at 37° C., 5% $CO_2$, before being cultured for 24 h in the presence of either DMSO control or appropriate concentrations of compound. After 24 h, the supernatant is removed and assayed for the presence of IL-8 and IL-6 by R&D ELISA. Percentage inhibition of cytokine release by the test compounds is calculated relative to the cytokine release determined for the DMSO control (100%).

(q) Human Neutrophil Degranulation

Neutrophils are Isolated from Human Peripheral Blood as Follows:

Blood is collected by venepuncture and anti-coagulated by addition of 1:1 EDTA:sterile phosphate buffered saline (PBS, no Ca+/Mg+). Dextran (3% w/v) is added (1 part dextran solution to 4 parts blood) and the blood allowed to stand for approximately 20 minutes at rt. The supernatant is carefully layered on a density gradient (Lymphoprep, Axis- Shield Healthcare) and centrifuged (15 mins, 2000 rpm, no brake). The supernatant is aspirated off and the cell pellet is re-suspended in sterile saline (0.2%) for no longer than 60 seconds (to lyse contaminating red blood cells). 10 times volume of PBS is then added and the cells centrifuged (5 mins, 1200 rpm). Cells are re-suspended in HBSS+ (Hanks buffered salt solution (without phenol red) containing cytochalasin B (5 μg/mL) and 1 mM $CaCl_2$) to achieve $5\times10^6$ cells/mL.

$5\times10^4$ cells are added to each well of a V-bottom 96 well plate and are incubated (30 mins, 37° C.) with the appropriate concentration of test compound (0.3-1000 ng/mL) or vehicle (DMSO, 0.5% final conc). Degranulation is stimulated by addition of fMLP (final concentration 1 μM). After a further incubation (30 mins, 37° C.), the cells are removed by centrifugation (5 mins, 1500 rpm) and the supernatants transferred to a flat bottom 96 well plate. An equal volume of tetramethylbenzidine (TMB) is added and, after 10 mins, the reaction terminated by addition of an equal volume of sulphuric acid (0.5 M) and absorbance read at 450 nm (background at 655 nm subtracted). The 50% inhibitory concentration ($IC_{50}$) is determined from the resultant concentration-response curve.

(r) Cell Cytotoxicity Assay $5\times10^4$ TK6 cells (lymphoblastic T cell line) are added to the appropriate number of wells of a 96 well plate in 195 μL of media (RPMI supplemented with 10% foetal bovine serum). 5 μL of DMSO control (final concentration 0.5% v/v) or test compound (final concentration either 5 or 1 μg/mL) is added to the wells and incubated at 37° C., 5% $CO_2$. After 24 hours, the plate is centrifuged at 1300 rpm for 3 minutes and the supernatant discarded. Cells are then resuspended in 7.5 μg/mL propidium iodide (PI) in PBS. After 15 minutes, cells are analysed by flow cytometry (BD accuri). The % viability is calculated as the % of cells that are PI negative in the test wells normalised to the DMSO control.

In Vivo Screening: Pharmacodynamics and Anti-Inflammatory Activity (i) LPS-Induced Neutrophil Accumulation in Mice Non-fasted Balb/c mice are dosed by the intra tracheal route with either vehicle, or the test substance at the indicated times (within the range 2-8 hr) before stimulation of the inflammatory response by application of an LPS challenge. At T=0, mice are placed into an exposure chamber and exposed to LPS (7.0 mL, 0.5 mg/mL solution in PBS) for 30 min. After a further 8 hr, the animals are anesthetized, their tracheas cannulated and BALF extracted by infusing and then withdrawing from their lungs 1.0 mL of PBS via the tracheal catheter. Total and differential white cell counts in the BALF samples are measured using a Neubaur haemocytometer. Cytospin smears of the BALF samples are prepared by centrifugation at 200 rpm for 5 min at RT and stained using a DiffQuik stain system (Dade Behring). Cells are counted using oil immersion microscopy. Data for neutrophil numbers in BAL are represented as mean±S.E.M. (standard error of the mean). The percentage inhibition of neutrophil accumulation is calculated for each treatment relative to vehicle treatment.

(ii) Cigarette Smoke Model

A/J mice (males, 5 weeks old) are exposed to cigarette smoke (4% cigarette smoke, diluted with air) for 30 min/day for 11 days using a Tobacco Smoke Inhalation Experiment System for small animals (Model SIS-CS; Sibata Scientific Technology, Tokyo, Japan). Test substances are administered intra-nasally (35 μL of solution in 50% DMSO/PBS) once daily for 3 days after the final cigarette smoke exposure. At 12 hr after the last dosing, each of the animals is anesthetized, the trachea cannulated and bronchioalveolar lavage fluid (BALF) is collected. The numbers of alveolar macrophages and neutrophils are determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil).

(iii) DSS-Induced Colitis in Mice

Non-fasted, 10-12 week old, male BDF1 mice are dosed by oral gavage twice daily with either vehicle, reference item (5-ASA) or test compound one day before (Day −1) stimulation of the inflammatory response by treatment with dextran sodium sulphate (DSS). On Day 0 of the study, DSS (5% w/v) is administered in the drinking water followed by BID dosing of the vehicle (5 mL/kg), reference (100 mg/kg) or test compound (5 mg/kg) for 7 days. The drinking water with DSS is replenished every 3 days. During the study, animals are weighed every day and stool observations are made and recorded as a score, based on stool consistency. At the time of sacrifice on Day +6, the large intestine is removed and the length and weight are recorded. Sections of the colon are taken for either MPO analysis, to determine neutrophil infiltration, or for histopathology scoring to determine disease severity.

(iv) TNBS-Induced Colitis in Mice

Non-fasted, 10-12 week old, male BDF1 mice are dosed by oral gavage twice daily with either vehicle (5 mL/kg), reference item (Budesonide 2.5 mg/kg) or test compound (1 or 5 mg/kg) one day before (Day −1) stimulation of the inflammatory response by treatment with 2,4,6-trinitrobenzenesulphonic acid (TNBS) (15 mg/mL in 50% ethanol/50% saline). On Day 0 of the study TNBS (200 μL) is administered intra-colonically via a plastic catheter with BID dosing of the vehicle, reference or test compound continuing for 2 or 4 days. During the study, animals are weighed every day and stool observations are made and recorded as a score, based on stool consistency. At the time of sacrifice on Day 2 (or Day 4), the large intestine is removed and the length and weight recorded. Sections of the colon are taken for histopathology scoring to determine disease severity.

(v) Adoptive Transfer in Mice

On Study day 0, female Balb/C mice are terminated and spleens obtained for $CD45RB^{high}$ cell isolation (Using SCID IBD cell Separation protocol). Approximately $4\times10^5$ cells/mL $CD45RB^{high}$ cells are then injected intraperitoneally (100 μL/mouse) into female SCID animals. On study day 14, mice are weighed and randomized into treatment groups based on body weight. On Day 14, compounds are administered BID, via oral gavage, in a peanut oil vehicle at the dose levels outlined below in Tables 6a and 6b and a dose volume of 5 mL/kg. Treatment continues until study day 42, at which point the animals are necropsied 4 hours after the morning administration. The colon length and weight are recorded and used as a secondary endpoint in the study as a measurement of colon oedema. The colon is then divided into six cross-sections, four of which are used for histopathology scoring (primary endpoint) and two are homogenised for cytokine analysis. Data shown is the % inhibition of the induction window between nave animals and vehicle animals, where higher inhibition implies closer to the non-diseased, nave, phenotype.

(vi) Endotoxin-Induced Uveitis in Rats

Male, Lewis rats (6-8 weeks old, Charles River UK Limited) are housed in cages of 3 at 19-21° C. with a 12 h light/dark cycle (07:00/19:00) and fed a standard diet of rodent chow and water ad libitum. Non-fasted rats are weighed, individually identified on the tail with a permanent marker, and receive a single intravitreal administration into the right vitreous humor (5 µL dose volume) of 100 ng/animal of LPS (*Escherichia coli* 0111:B4 prepared in PBS, Sigma Aldrich, UK) using a 32-gauge needle. Untreated rats are injected with PBS. Test compound, dexamethasone (Dex) or vehicle (20% hydroxypropyl-β-cyclodextrin, 0.1% HPMC, 0.01% Benzalkonium chloride, 0.05% EDTA, 0.7% NaCl in deionised water) are administered by the topical route onto the right eye (10 µL) of animals 30 minutes prior to LPS, at the time of LPS administration, and 1, 2 and 4 hours post LPS administration. Before administration, the solution or suspension to be administered is agitated for 5 minutes to ensure a uniform suspension. 6 hours after LPS dosing, animals are euthanized by overdose with pentobarbitone (i.v.). Following euthanasia, the right eye of each animal is enucleated and dissected into front (anterior) and back (posterior) sections around the lens. Each section is weighed and homogenised in 500 µL of sterile phosphate buffered saline followed by 20 minutes centrifugation at 12000 rpm at 4° C. The resulting supernatant is divided into 3 aliquots and stored at −80° C. until subsequent cytokine analysis by R&D DuoSet ELISA.

Summary of In Vitro and In Vivo Screening Results

TABLE 1a

Dissociation constants for selected kinases determined by LeadHunter Discover Services (DiscoveRx Corporation, Fremont, CA), using the KINOMEscan™ technology.

| Test Compound Example No. | Dissociation Constant (nM) | | |
|---|---|---|---|
| | Lck | p38 MAPKα | Syk |
| Example 3 | 2.3 | 6.9 | 10 |
| Example 4 | 3.0 | 19 | 14 |
| Example 16 | 4.1 | 9 | 21 |
| Example 27 | 4.3 | 29 | 27 |
| Example 75 | 2.5 | 14 | 8.8 |

Studies conducted by LeadHunter Discover Services (DiscoveRx Corporation, Fremont, Calif.) using the KINOMEscan™ technology determined that compounds of Example 3, 4, 16, 27 and 75 did not have any significant effect on the binding of the kinases B-Raf and B-Raf (V600E) to their standard ligands. Moreover, these compounds showed substantially improved selectivities compared to the Reference Compound N-(4-(4-(3-(3-tert-butyl-1-p-tolyl-1H-pyrazol-5-yl)ureido)naphthalen-1-yloxy)pyridin-2-yl)-2-methoxyacetamide (WO 2010/112936), as evidenced by lower selectivity scores (Table 1b).

TABLE 1b

KinomeScan Selectivity score data at 50 and 500 nM; S(35) = (number of non-mutant kinases with % Ctrl <35)/(number of non-mutant kinases tested); S(10) = (number of non-mutant kinases with % Ctrl <10)/(number of non-mutant kinases tested); S(1) = (number of non-mutant kinases with % Ctrl <1)/(number of non-mutant kinases tested)

| | KinomeScan Selectivity Scores/number of individual kinase hits | | | | | |
|---|---|---|---|---|---|---|
| | 50 nM | | | 500 nM | | |
| Compound | S(35) | S(10) | S(1) | S(35) | S(10) | S(1) |
| Reference Compound | 0.174/67 | 0.083/32 | 0.018/7 | 0.370/143 | 0.272/105 | 0.117/45 |
| Ex. 3 | 0.091/36 | 0.023/9 | 0.000/0 | 0.235/93 | 0.149/59 | 0.046/18 |
| Ex. 4 | 0.091/36 | 0.020/8 | 0.000/0 | 0.253/100 | 0.149/59 | 0.053/21 |
| Ex. 16 | 0.068/27 | 0.023/9 | 0.000/0 | 0.197/78 | 0.129/51 | 0.038/15 |
| Ex. 27 | 0.066/26 | 0.023/9 | 0.000/0 | 0.238/94 | 0.154/61 | 0.046/18 |
| Ex. 75 | 0.099/39 | 0.035/14 | 0.005/2 | 0.230/91 | 0.139/55 | 0.038/15 |

TABLE 1c

Results from in vitro p38 MAPKα (Method 2), c-Src, Syk and GSK3α (Method 2) inhibition assays

| Test Compound Example No. | IC50 Values for Enzyme Inhibition (nM) | | | |
|---|---|---|---|---|
| | p38 MAPKα | c-Src | Syk | GSK3α |
| 1 | 118 | 12 | 51 | 657 |
| 2 | 37 | 45 | 1368 | 12720 |
| 3 | 87 | 20 | 692 | 4318 |
| 4 | 91 | 14 | 86 | 2657 |
| 5 | 271 | 48 | 1169 | 2866 |
| 6 | 34 | 11 | 421 | 541 |
| 7 | 39 | 9 | 554 | 516 |
| 8 | — | — | — | 9944 |
| 9 | — | 8 | 27 | 1630 |
| 10 | 551 | 18 | 63 | 1309 |
| 11 | 124 | 21 | 193 | 12226 |
| 12 | — | — | — | 11255 |
| 13 | 28 | 9 | 35 | 824 |
| 14 | 49 | 11 | 106 | 1013 |
| 15 | 28 | 28 | 237 | 905 |
| 16 | 224 | 24 | 591 | 411 |
| 17 | 179 | 40 | 149 | 5462 |
| 18 | 52 | 10 | 76 | 3115 |
| 19 | — | — | — | 4429 |
| 20 | 33 | 6 | 29 | 748 |
| 21 | — | — | — | 1633 |
| 22 | — | — | — | 2136 |
| 23 | 11 | 11 | 147 | 733 |
| 24 | 30 | 14 | 549 | 680 |
| 25 | — | — | — | 1892 |
| 26 | — | — | — | 51 |
| 27 | 41 | 26 | 443 | 4502 |
| 28 | — | — | — | 3211 |
| 29 | 26 | 19 | 96 | 6321 |
| 30 | — | — | — | 150 |
| 31 | — | — | — | 135 |
| 32 | — | — | — | 629 |
| 33 | — | 11 | 28 | 828 |
| 34 | 25 | 19 | 85 | 9330 |
| 35 | 120 | 13 | 48 | 597 |
| 36 | 69 | 16 | 67 | 2086 |
| 37 | — | 12 | 43 | 1515 |
| 38 | — | — | — | 10688 |
| 39 | 140 | 29 | 571 | 1596 |
| 40 | — | — | — | 379 |
| 41 | — | — | — | 446 |
| 42 | — | — | — | 705 |
| 43 | — | — | — | 520 |

TABLE 1c-continued

Results from in vitro p38 MAPKα (Method 2), c-Src, Syk and GSK3α (Method 2) inhibition assays

| Test Compound Example No. | IC50 Values for Enzyme Inhibition (nM) | | | |
|---|---|---|---|---|
| | p38 MAPKα | c-Src | Syk | GSK3α |
| 44 | — | — | — | 80 |
| 45 | 145 | 39 | 455 | 2156 |
| 46 | 110 | 15 | 20 | 636 |
| 47 | 92 | 15 | 169 | 1599 |
| 48 | 229 | 45 | 490 | 5033 |
| 49 | 258 | 56 | 1224 | 8355 |
| 50 | — | — | — | 13796 |
| 51 | 170 | 15 | 49 | 977 |
| 52 | 277 | 100 | 1258 | 12580 |
| 53 | 132 | 46 | 1268 | 8784 |
| 54 | 140 | 42 | 1192 | 11919 |
| 55 | 157 | 22 | 131 | 2365 |
| 56 | 335 | 45 | 631 | 763 |
| 57 | 286 | 48 | 706 | 1125 |
| 58 | 181 | 48 | 461 | 4345 |
| 59 | 132 | 28 | 128 | 978 |
| 60 | — | — | — | 539 |
| 61 | — | — | — | 372 |
| 62 | 32 | 44 | 1318 | 10645 |
| 63 | — | — | — | 829 |
| 64 | — | — | — | 1457 |
| 65 | 326 | 85 | 1289 | 7396 |
| 66 | 140 | 23 | 330 | 2427 |
| 67 | 245 | 56 | 1172 | 11723 |
| 68 | 209 | 70 | 1172 | 11723 |
| 69 | 147 | 13 | 121 | 1526 |
| 70 | 332 | 67 | 86 | 3968 |
| 71 | — | — | — | 2622 |
| 72 | — | — | — | 11273 |
| 73 | — | — | — | 11261 |
| 74 | — | — | — | 9679 |
| 75 | 123 | 97 | 214 | 6033 |
| 76 | 159 | 31 | 35 | 4790 |
| 77 | 216 | 23 | 39 | 3545 |
| 78 | — | — | — | 896 |
| 79 | 56 | 35 | 339 | 4329 |
| 80 | 18 | 968 | 1546 | 1247 |
| 81 | 173 | 58 | 121 | 4930 |
| 82 | — | — | — | 182 |
| 83(a) | 142 | 22 | 1156 | 8328 |
| 83(b) | 246 | 48 | 802 | 9150 |
| 83(c) | — | — | — | 738 |
| 83(d) | — | — | — | 1018 |
| 83(e) | — | — | — | 1589 |
| 83(f) | — | — | — | 14351 |
| 83(g) | — | — | — | 2205 |
| 84(a) | 275 | — | — | 12639 |
| 84(b) | — | — | — | 4509 |
| 84(c) | — | — | — | 4952 |
| 84(d) | — | — | — | 6285 |
| 84(e) | 77 | 36 | 125 | 4468 |
| 84(f) | — | — | — | 3402 |
| 84(g) | 86 | 28 | 137 | 2275 |
| 84(h) | 79 | 21 | 130 | 1649 |
| 85(a) | 38 | 29 | 656 | 6743 |
| 85(b) | 90 | 54 | 1289 | 6996 |
| 85(c) | — | — | — | 3565 |
| 85(d) | 158 | 120 | 1220 | 6913 |
| 85(e) | — | — | — | 300 |
| 85(f) | — | — | — | 390 |
| 85(g) | — | — | — | 437 |
| 85(h) | 67 | 110 | 1190 | 11905 |
| 85(i) | — | 51 | 397 | 8140 |
| 85(j) | — | — | — | 736 |
| 85(k) | — | 49 | 264 | 4725 |
| 85(l) | — | — | — | 10247 |
| 85(m) | — | 72 | 1190 | 10284 |
| 85(n) | — | 45 | 427 | 7127 |
| 85(o) | — | — | — | — |
| 85(p) | — | — | — | 1160 |
| 85(q) | — | — | — | 249 |
| 85(r) | — | — | — | 2242 |
| 85(s) | — | — | — | — |
| 85(t) | — | — | — | — |
| 85(u) | — | 40 | 1249 | 5944 |
| 85(v) | — | — | — | 2516 |
| 85(w) | — | — | — | 769 |
| 85(x) | — | — | — | 878 |
| 85(y) | — | 206 | 1155 | 2627 |

TABLE 1d

Data from phosphoflow assays evaluating cellular p38 MAPKα and Lck inhibition with the compound of Example 16.

| Test Article | IC$_{50}$ Values (ng/mL) | |
|---|---|---|
| | phospho-p38 MAPKα | phospho-Lck |
| Example 16 | 20 | 6 |

TABLE 2

Inhibition of cytokine release in stimulated cells (assays (aa), (b), (c) and (d) above).

| Test Compound Example No. | IC$_{50}$ Values for Inhibition of Cytokine Release (nM) | | | | | | |
|---|---|---|---|---|---|---|---|
| | dU937 cells | | PBMCs | | | | HT29 cells |
| | IL-8 | TNFα | IL-8 | TNFα | IL-2 | IFNγ | IL-8 |
| 1 | — | — | 1.4 | — | 112.1 | 10.4 | — |
| 2 | — | — | 142.0 | — | 1368.4 | 35.7 | — |
| 3 | 1.3 | 0.4 | 1.2 | — | 190.2 | 9.6 | 8.1 |
| 4 | 0.8 | 1.0 | 1.4 | 0.7 | 40.5 | 4.2 | 4.9 |
| 5 | 1.4 | 0.5 | 2.4 | — | 151.3 | 10.3 | 6.8 |
| 6 | — | — | 0.8 | — | 89.9 | 9.3 | — |
| 7 | — | — | 1.1 | — | — | — | — |
| 8 | — | — | 28.1 | — | — | — | — |
| 9 | — | — | 1.2 | — | — | — | — |
| 10 | 0.8 | 0.3 | 2.3 | — | 9.0 | 4.4 | 4.6 |
| 11 | 1.4 | 1.2 | 2.6 | — | 73.6 | 17.7 | 9.3 |
| 12 | — | — | 107.0 | — | — | — | 1324.8 |
| 13 | — | — | 1.3 | — | 57.4 | 4.6 | — |
| 14 | 0.6 | 0.5 | 1.7 | — | 182.2 | 19.7 | 3.0 |
| 15 | — | — | 0.9 | — | — | — | — |
| 16 | — | — | 1.5 | — | 74.0 | 7.3 | 8.0 |
| 17 | 1.4 | — | 1.8 | — | 65.6 | 8.2 | 5.1 |
| 18 | — | — | 1.0 | — | — | — | — |
| 19 | — | — | 8.7 | — | — | — | — |
| 20 | — | — | 1.1 | — | 84.3 | 9.0 | — |
| 21 | — | — | 34.4 | — | — | — | — |
| 22 | — | — | 16.9 | — | — | — | — |
| 23 | — | — | 2.6 | — | 17.1 | 9.1 | 4.7 |
| 24 | — | — | 1.9 | — | 24.9 | 10.7 | — |
| 25 | — | — | 7.0 | — | — | — | — |
| 26 | — | — | 21.7 | — | — | — | — |
| 27 | — | — | 1.9 | — | 46.3 | 11.0 | 8.3 |
| 28 | — | — | 11.9 | — | — | — | — |
| 29 | — | — | 2.3 | — | 51.2 | 3.5 | 0.6 |
| 30 | — | — | 5.7 | — | — | — | — |
| 31 | — | — | 7.2 | — | — | — | — |
| 32 | — | — | 7.7 | — | — | — | — |
| 33 | — | — | 4.2 | — | — | — | — |
| 34 | — | — | 3.0 | — | 62.5 | 7.6 | 2.1 |
| 35 | — | — | 1.4 | — | 51.0 | 3.5 | — |
| 36 | — | — | 1.8 | — | 65.3 | 5.7 | 0.8 |

TABLE 2-continued

Inhibition of cytokine release in stimulated cells (assays (aa), (b), (c) and (d) above).

IC$_{50}$ Values for Inhibition of Cytokine Release (nM)

| Test Compound Example No. | dU937 cells IL-8 | TNFα | PBMCs IL-8 | TNFα | IL-2 | IFNγ | HT29 cells IL-8 |
|---|---|---|---|---|---|---|---|
| 37 | — | — | 2.2 | — | — | — | — |
| 38 | — | — | 6.3 | — | — | — | — |
| 39 | — | — | 2.5 | — | 132.3 | 9.6 | 5.3 |
| 40 | — | — | 3.1 | — | — | — | — |
| 41 | — | — | 4.5 | — | — | — | — |
| 42 | — | — | 6.6 | — | — | — | — |
| 43 | — | — | 2.0 | — | — | — | — |
| 44 | — | — | 86.8 | — | — | — | — |
| 45 | — | — | 1.4 | — | 182.2 | 7.8 | 2.1 |
| 46 | — | — | 0.9 | — | — | 2.0 | — |
| 47 | — | — | 1.6 | — | 102.5 | 7.3 | — |
| 48 | — | — | 3.4 | — | 144.5 | 17.2 | 10.2 |
| 49 | — | — | 2.5 | — | 226.9 | 11.0 | 8.6 |
| 50 | — | — | 12.1 | — | — | — | — |
| 51 | — | — | 1.6 | — | 46.3 | 1.8 | 1.7 |
| 52 | — | — | 2.4 | — | 204.9 | 39.0 | 17.3 |
| 53 | — | — | 1.6 | — | 181.0 | 14.9 | 6.4 |
| 54 | — | — | 1.6 | — | 354.0 | 33.3 | — |
| 55 | — | — | 2.2 | — | 35.2 | 12.0 | 4.5 |
| 56 | — | — | 1.8 | — | 35.2 | 12.2 | 8.6 |
| 57 | — | — | 3.6 | — | 140.3 | 74.5 | 21.2 |
| 58 | — | — | 2.6 | — | 136.6 | 17.1 | 10.6 |
| 59 | — | — | 3.3 | — | 58.6 | 7.6 | — |
| 60 | — | — | 2.0 | — | — | — | — |
| 61 | — | — | 2.1 | — | — | — | — |
| 62 | — | — | 4.6 | — | 48.7 | 32.2 | — |
| 63 | — | — | 17.3 | — | — | — | — |
| 64 | — | — | 10.5 | — | — | — | — |
| 65 | — | — | 4.0 | — | 130.8 | 34.4 | 145.4 |
| 66 | — | — | 1.9 | — | 49.2 | 20.2 | 16.4 |
| 67 | — | — | 2.7 | — | 200.2 | 39.5 | — |
| 68 | — | — | 2.8 | — | 219.7 | 68.8 | — |
| 69 | — | — | 1.6 | — | — | 2.2 | — |
| 70 | — | — | 4.9 | — | — | 7.4 | 4.1 |
| 71 | — | — | 114.3 | — | — | — | 1145.6 |
| 72 | — | — | 11.8 | — | — | — | 19.2 |
| 73 | — | — | 19.0 | — | — | — | 31.6 |
| 74 | — | — | 6.6 | — | — | — | 11.7 |
| 75 | — | — | 5.0 | — | 56.8 | 14.9 | — |
| 76 | — | — | 1.9 | — | — | — | — |
| 77 | — | — | 2.0 | — | — | — | — |
| 78 | — | — | 14.0 | — | — | — | — |
| 79 | — | — | 3.4 | — | 284.1 | 5.9 | 13.1 |
| 80 | — | — | 4.3 | — | 1546.2 | 23.8 | — |
| 81 | — | — | 2.7 | — | 98.8 | 4.0 | — |
| 82 | — | — | 6.6 | — | — | — | — |
| 83(a) | — | — | 39.0 | — | — | — | 62.5 |
| 83(b) | — | — | 3.7 | — | 109.2 | — | — |
| 83(c) | — | — | 1.8 | — | — | — | — |
| 83(d) | — | — | 12.1 | — | — | — | — |
| 83(e) | — | — | 8.0 | — | — | — | — |
| 83(f) | — | — | 13.1 | — | — | — | — |
| 83(g) | — | — | 7.3 | — | — | — | — |
| 84(a) | — | — | 12.4 | — | — | — | — |
| 84(b) | — | — | 9.1 | — | — | — | — |
| 84(c) | — | — | 21.8 | — | — | — | — |
| 84(d) | — | — | 11.5 | — | — | — | — |
| 84(e) | — | — | 1.3 | — | — | — | — |
| 84(f) | — | — | 13.5 | — | — | — | — |
| 84(g) | — | — | 0.7 | — | 43.5 | 1.3 | — |
| 84(h) | — | — | 0.7 | — | 51.3 | 1.7 | — |
| 85(a) | — | — | 0.8 | — | 53.8 | 11.8 | — |
| 85(b) | — | — | 1.5 | — | 123.3 | 16.2 | — |
| 85(c) | — | — | 4.6 | — | — | — | — |
| 85(d) | — | — | 2.1 | — | 94.3 | 15.4 | — |
| 85(e) | — | — | 1.7 | — | — | — | — |
| 85(f) | — | — | 0.7 | — | — | — | — |
| 85(g) | — | — | 1.0 | — | — | — | — |
| 85(h) | — | — | 2.2 | — | 150.2 | 23.0 | — |
| 85(i) | — | — | 1.5 | — | — | — | — |
| 85(j) | — | — | 2.1 | — | — | — | — |
| 85(k) | — | — | 1.7 | — | 57.1 | 9.3 | — |
| 85(l) | — | — | 2.8 | — | — | — | — |
| 85(m) | — | — | 1.8 | — | — | — | — |
| 85(n) | — | — | 1.9 | — | — | — | — |
| 85(o) | — | — | — | — | — | — | — |
| 85(p) | — | — | 7.1 | — | — | — | — |
| 85(q) | — | — | 6.1 | — | — | — | — |
| 85(r) | — | — | 0.6 | — | — | — | — |
| 85(s) | — | — | — | — | — | — | — |
| 85(t) | — | — | — | — | — | — | — |
| 85(u) | — | — | 1.4 | — | — | — | — |
| 85(v) | — | — | 0.4 | — | — | — | — |
| 85(w) | — | — | 2.9 | — | — | — | — |
| 85(x) | — | — | 0.9 | — | — | — | — |
| 85(y) | — | — | 1.7 | — | — | — | — |

As illustrated in Table 3 below, the compounds of Examples 4, 16 and 27 were also screened in cellular assay (I), i.e., the ex-vivo human biopsy model described above, where they demonstrated significant anti-inflammatory effects in biopsies from ulcerative colitis (UC) patients. In contrast to healthy volunteers, intestinal mucosal biopsies from UC patients have been shown to spontaneously release pro-inflammatory cytokines in vitro (Onken, J. E. et al., *J Clin Immunol*, 2008, 126(3): 345-352). Thus, the compounds of Examples 4, 16 and 27 significantly inhibited cytokine (IL-1β, IL-6 and IL-8) release compared to the DMSO control when incubated, at 1 μg/mL, for 24 hours with biopsies from ulcerative colitis patients.

TABLE 3

Summary of results from assays using intestinal mucosa biopsies from the inflamed regions of the colon of various patients suffering from ulcerative colitis (a form of IBD).

| | Cytokine release from biopsies of UC patients | | | | | |
|---|---|---|---|---|---|---|
| Treatment group | n | IL-1β release | n | IL-6 release | n | IL-8 release |
| DMSO control | | 100% | | 100% | | 100% |
| Example 4 (1 μg/mL) | 2 | 17 ± 21 | 3 | 5 ± 1 | 3 | 2 ± 1 |
| Example 16 (1 μg/mL) | 4 | 5 ± 8 | 4 | 17 ± 23 | 2 | 9 ± 15 |
| Example 27 (1 μg/mL) | 1 | 11 ± 54 | 2 | 48 ± 26 | 2 | 60 ± 15 |

As illustrated in Table 4a below, compounds of the examples of the present invention are, for the most part, markedly less active than the Reference Compound (N-(4-(4-(3-(3-tert-butyl-1-p-tolyl-1H-pyrazol-5-yl)ureido)naphthalen-1-yloxy)pyridin-2-yl)-2-methoxyacetamide; WO 2010/112936) in assay (g) above, which measures impact on cell division (mitosis) in PBMCs.

TABLE 4a

Effect of compounds of the examples on cell division in PBMCs (NT = not tested)

| Test compound | % Inhibition of mitosis at 5 µg/mL |
|---|---|
| Reference compound | 87.8[a] |
| 1 | 22.1 |
| 2 | 4.0 |
| 3 | 31.7 |
| 4 | 43.0 |
| 5 | 44.9 |
| 6 | 41.7 |
| 7 | NT |
| 8 | NT |
| 9 | NT |
| 10 | 70.2 |
| 11 | 33.5 |
| 12 | NT |
| 13 | 46.1 |
| 14 | 49.8 |
| 15 | 97.5 |
| 16 | 20.5 |
| 17 | 37.0 |
| 18 | 92.7 |
| 19 | NT |
| 20 | 44.3 |
| 21 | NT |
| 22 | NT |
| 23 | 25.4 |
| 24 | 22.5 |
| 25 | NT |
| 26 | NT |
| 27 | 49.8 |
| 28 | NT |
| 29 | 34.6 |
| 30 | NT |
| 31 | NT |
| 32 | NT |
| 33 | NT |
| 34 | 40.4 |
| 35 | 41.1 |
| 36 | 45.0 |
| 37 | 45.9 |
| 38 | NT |
| 39 | 34.7 |
| 40 | NT |
| 41 | NT |
| 42 | NT |
| 43 | NT |
| 44 | NT |
| 45 | 45.0 |
| 46 | 67.1 |
| 47 | 59.1 |
| 48 | 44.2 |
| 49 | 40.1 |
| 50 | NT |
| 51 | 44.3 |
| 52 | 31.0 |
| 53 | 30.3 |
| 54 | 37.8 |
| 55 | 54.3 |
| 56 | 46.4 |
| 57 | 42.1 |
| 58 | 41.7 |
| 59 | 55.3 |
| 60 | NT |
| 61 | NT |
| 62 | NT |
| 63 | NT |
| 64 | NT |
| 65 | 51.1 |
| 66 | 66.6 |
| 67 | 35.6 |
| 68 | NT |
| 69 | NT |
| 70 | NT |
| 71 | NT |
| 72 | NT |
| 73 | NT |
| 74 | NT |
| 75 | 42.6 |
| 76 | 91.3 |
| 77 | NT |
| 78 | NT |
| 79 | 54.4 |
| 80 | 70.4 |
| 81 | 58.1 |
| 82 | NT |
| 83(a) | NT |
| 83(b) | NT |
| 83(c) | 57.1 |
| 83(d) | NT |
| 83(e) | NT |
| 83(f) | NT |
| 83(g) | NT |
| 84(a) | NT |
| 84(b) | NT |
| 84(c) | NT |
| 84(d) | NT |
| 84(e) | NT |
| 84(f) | NT |
| 84(g) | 84.6 |
| 84(h) | 87.0 |
| 85(a) | 46.3 |
| 85(b) | 25.3 |
| 85(c) | NT |
| 85(d) | 33.2 |
| 85(e) | NT |
| 85(f) | NT |
| 85(g) | NT |
| 85(h) | 27.5 |
| 85(i) | NT |
| 85(j) | NT |
| 85(k) | 41.0 |
| 85(l) | NT |
| 85(m) | 26.4 |
| 85(n) | 26.6 |
| 85(o) | NT |
| 85(p) | NT |
| 85(q) | NT |
| 85(r) | NT |
| 85(s) | NT |
| 85(t) | NT |
| 85(u) | 38.4 |
| 85(v) | NT |
| 85(w) | NT |
| 85(x) | NT |
| 85(y) | 20.1 |

[a]See, for example, the value reported in WO 2013/050757.

As illustrated in Table 4b below, compounds of the examples of the present invention did not elicit any substantial β-catenin induction when studied in assay (m) above. Thus, the potential of those compounds tested to increase cellular concentrations of β-catenin was found to be negative in that their inductive effect at various test concentrations was substantially less than the effect produced by the Reference Compound at 1 µg/mL.

TABLE 4b

Effect of compounds of the examples on β-catenin induction (NT = not tested)

| Test compound | % β-catenin induction Concentration of test compound | | |
|---|---|---|---|
| | 1 µg/mL | 5 µg/mL | 10 µg/mL |
| Reference compound | 100 | NT | NT |
| 1 | 18 | 17 | NT |
| 2 | −6 | −4 | NT |
| 3 | 0 | 4 | 4 |
| 4 | 3 | 20 | 20 |
| 5 | 10 | 27 | 19 |
| 6 | 7 | 20 | 11 |
| 7 | 13 | 29 | 29 |
| 8 | NT | NT | NT |
| 9 | 32 | 48 | 67 |
| 10 | 12 | 42 | 39 |
| 11 | −8 | −5 | −2 |
| 12 | NT | NT | NT |
| 13 | 7 | 34 | 26 |
| 14 | 0 | 16 | 14 |
| 15 | −2 | −6 | −17 |
| 16 | 21 | 14 | 26 |
| 17 | 5 | 23 | 23 |
| 18 | 1 | 9 | 17 |
| 19 | NT | NT | NT |
| 20 | 4 | 31 | 29 |
| 21 | NT | NT | NT |
| 22 | NT | NT | NT |
| 23 | −4 | 10 | 9 |
| 24 | −3 | 27 | 25 |
| 25 | NT | NT | NT |
| 26 | NT | NT | NT |
| 27 | −12 | −7 | −1 |
| 28 | NT | NT | NT |
| 29 | 4 | 7 | −4 |
| 30 | NT | NT | NT |
| 31 | NT | NT | NT |
| 32 | NT | NT | NT |
| 33 | NT | NT | NT |
| 34 | 1 | 7 | −9 |
| 35 | NT | NT | NT |
| 36 | −4 | 28 | 18 |
| 37 | 4 | 38 | 46 |
| 38 | NT | NT | NT |
| 39 | −11 | −12 | −18 |
| 40 | NT | NT | NT |
| 41 | NT | NT | NT |
| 42 | NT | NT | NT |
| 43 | NT | NT | NT |
| 44 | NT | NT | NT |
| 45 | −4 | −7 | −14 |
| 46 | −2 | 2 | −29 |
| 47 | −5 | 4 | 8 |
| 48 | −2 | −4 | −3 |
| 49 | −1 | −2 | −5 |
| 50 | NT | NT | NT |
| 51 | 3 | 33 | 29 |
| 52 | 2 | 9 | 1 |
| 53 | −1 | 1 | 2 |
| 54 | 5 | 5 | −2 |
| 55 | 11 | 23 | 45 |
| 56 | 3 | 13 | 14 |
| 57 | 4 | 6 | 11 |
| 58 | 5 | 2 | 10 |
| 59 | 14 | 33 | 28 |
| 60 | NT | NT | NT |
| 61 | NT | NT | NT |
| 62 | NT | NT | NT |
| 63 | NT | NT | NT |
| 64 | NT | NT | NT |
| 65 | 5 | 2 | 6 |
| 66 | 0 | 6 | 3 |
| 67 | 3 | 2 | −2 |
| 68 | 2 | 2 | −1 |
| 69 | 10 | 17 | 25 |
| 70 | NT | NT | NT |
| 71 | NT | NT | NT |
| 72 | NT | NT | NT |
| 73 | NT | NT | NT |
| 74 | NT | NT | NT |
| 75 | 3 | 25 | 30 |
| 76 | 2 | −1 | −13 |
| 77 | −4 | −1 | −1 |
| 78 | NT | NT | NT |
| 79 | −4 | 1 | 5 |
| 80 | 5 | 38 | 47 |
| 81 | 4 | 14 | 13 |
| 82 | NT | NT | NT |
| 83(a) | NT | NT | NT |
| 83(b) | −6 | −9 | −6 |
| 83(c) | 4 | 31 | 33 |
| 83(d) | NT | NT | NT |
| 83(e) | NT | NT | NT |
| 83(f) | NT | NT | NT |
| 83(g) | NT | NT | NT |
| 84(a) | NT | NT | NT |
| 84(b) | NT | NT | NT |
| 84(c) | NT | NT | NT |
| 84(d) | NT | NT | NT |
| 84(e) | −1 | 5 | 7 |
| 84(f) | NT | NT | NT |
| 84(g) | 1 | 8 | 7 |
| 84(h) | −1 | 11 | 10 |
| 85(a) | NT | NT | NT |
| 85(b) | NT | NT | NT |
| 85(c) | NT | NT | NT |
| 85(d) | NT | NT | NT |
| 85(e) | NT | NT | NT |
| 85(f) | NT | NT | NT |
| 85(g) | NT | NT | NT |
| 85(h) | NT | NT | NT |
| 85(i) | NT | NT | NT |
| 85(j) | NT | NT | NT |
| 85(k) | NT | NT | NT |
| 85(l) | NT | NT | NT |
| 85(m) | NT | NT | NT |
| 85(n) | NT | NT | NT |
| 85(o) | NT | NT | NT |
| 85(p) | NT | NT | NT |
| 85(q) | NT | NT | NT |
| 85(r) | NT | NT | NT |
| 85(s) | NT | NT | NT |
| 85(t) | NT | NT | NT |
| 85(u) | NT | NT | NT |
| 85(v) | NT | NT | NT |
| 85(w) | NT | NT | NT |
| 85(x) | NT | NT | NT |
| 85(y) | NT | NT | NT |

As illustrated in Table 5 below, the compounds of Examples 3, 4, 16, 27, 34, 75 and 79 were also screened in in vivo assay (iv) above, as conducted over 2 days and employing a vehicle comprising a defined mixture of corn oil (32.5%), transcutol (20%), maisine (12.5%) and cremophor ELP (35%). Histopathology analysis revealed that the compounds of Examples 3, 4, 16, 27, 34, 75 and 79 displayed substantial activity in this in vivo model of colonic inflammation. In particular, these compounds, when dosed orally at 5 mg/kg, demonstrated marked improvements in ulcer grade and epithelial repair compared to the vehicle control. Furthermore, they produced a marked reduction in inflammatory cell infiltrate in the reticular and laminar propria zones.

TABLE 5

Effect of compounds of the examples on TNBS-induced colitis in mice.

| Experiment no. | Treatment group | n | TNBS Ulcer grade | LP inflammation |
|---|---|---|---|---|
| 1 | Non-diseased | 6 | 0.2 ± 0.2 | 0.3 ± 0.2 |
| 1 | TNBS + Vehicle | 24 | 4.7 ± 0.2 | 4.3 ± 0.2 |
| 1 | TNBS + Example 4 (1 mg/kg) | 12 | 3.6 ± 0.4 | 2.6 ± 0.3 |
| 2 | Non-diseased | 6 | 0.2 ± 0.2 | 0.3 ± 0.2 |
| 2 | TNBS + Vehicle | 24 | 4.3 ± 0.2 | 4.6 ± 0.1 |
| 2 | TNBS + Example 27 (5 mg/kg) | 12 | 3.3 ± 0.5 | 3.2 ± 0.4 |
| 3 | Non-diseased | 6 | 0.0 ± 0.0 | 0.2 ± 0.2 |
| 3 | TNBS + Vehicle | 24 | 4.4 ± 0.2 | 4.5 ± 0.2 |
| 3 | TNBS + Example 75 (5 mg/kg) | 12 | 3.0 ± 0.4 | 2.3 ± 0.4 |
| 4 | Non-diseased | 6 | 0.0 ± 0.0 | 0.2 ± 0.2 |
| 4 | TNBS + Vehicle | 24 | 4.4 ± 0.2 | 4.5 ± 0.4 |
| 4 | TNBS + Example 34 (5 mg/kg) | 12 | 3.6 ± 0.2 | 2.6 ± 0.3 |
| 4 | TNBS + Example 79 (5 mg/kg) | 11 | 3.4 ± 0.6 | 3.5 ± 0.5 |
| 5 | Non-diseased | 6 | 0.0 ± 0.0 | 0.2 ± 0.2 |
| 5 | TNBS + Vehicle | 24 | 4.4 ± 0.4 | 4.8 ± 0.4 |
| 5 | TNBS + Example 16 | 12 | 3.6 ± 0.5 | 3.8 ± 0.4 |
| 5 | TNBS + Example 3 | 12 | 3.7 ± 0.4 | 3.8 ± 0.5 |

As illustrated in Tables 6a and 6b below, the compounds of Examples 3, 4, 16 and 27 were also screened in the in vivo (adoptive transfer) assay (v) above. Analysis of the relative ratios of colon weight to length in nave, control and treated animals at the end of the study revealed that the compounds of Examples 3, 4, 16 and 27 displayed significant activity in this T cell driven in vivo model of colonic inflammation.

TABLE 6a

Summary of results from adoptive transfer mouse model.

| Treatment group | Dose | Colon weight:length | % Inhibition |
|---|---|---|---|
| Naïve | N/A | 0.022 ± 0.001 | 100 |
| Cyclosporin A | 75 mg/kg | 0.029 ± 0.001 | 64 |
| Vehicle control | N/A | 0.042 ± 0.005 | 0 |
| Example 4 | 0.3 mg/kg | 0.030 ± 0.008 | 62 |
|  | 1 mg/kg | 0.020 ± 0.002 | 110 |
| Example 16 | 3 mg/kg | 0.024 ± 0.003 | 90 |
| Example 27 | 3 mg/kg | 0.022 ± 0.002 | 99 |

TABLE 6b

Summary of further results from an additional study in the adoptive transfer mouse model.

| Treatment group | n | Colon weight:length |
|---|---|---|
| Non-diseased | 4 | 0.021 ± 0.001 |
| Vehicle control | 12 | 0.047 ± 0.004 |
| Example 3 (3 mg/kg) | 12 | 0.039 ± 0.003 |
| Example 16 (3 mg/kg) | 12 | 0.034 ± 0.003 |
| Example 16 (0.3 mg/kg) | 12 | 0.041 ± 0.005 |
| Example 16 (0.03 mg/kg) | 12 | 0.033 ± 0.002 |
| Example 27 (3 mg/kg) | 12 | 0.034 ± 0.003 |
| Example 27 (0.3 mg/kg) | 12 | 0.038 ± 0.004 |
| Example 27 (0.03 mg/kg) | 12 | 0.047 ± 0.005 |

As illustrated in Table 6c below, the compounds of Examples 4, 16 and 27 also significantly reduced levels of pro-inflammatory cytokines in samples of colon tissue from mice in the adoptive transfer model.

TABLE 6c

Summary of cytokine level measurements from adoptive transfer mouse model.

| Treatment group | n | IFNγ (pg/mL) | IL-8 (pg/mL) |
|---|---|---|---|
| Non-diseased | 4 | 1.3 ± 0.6 | 7.9 ± 0.9 |
| Vehicle control | 12 | 117.7 ± 36.6 | 1064.9 ± 239.6 |
| Example 4 (1 mg/kg) | 11 | 2.8 ± 0.8 | 53.3 ± 23.0 |
| Example 16 (3 mg/kg) | 12 | 10.8 ± 3.3 | 70.8 ± 22.8 |
| Example 27 (3 mg/kg) | 12 | 19.1 ± 6.5 | 131.1 ± 56.1 |

As illustrated in Tables 7a, 7b and 7c below, the compounds of Examples 4, 27, 29, 66 and 75 significantly reduced cytokine levels in both the anterior and posterior segments of the eyes of rats treated with intravitreal endotoxin LPS (see assay (vi) above).

TABLE 7a

Effect of compounds of the examples on cytokine levels in the eyes of LPS-stimulated rats.

| Treatment | Cytokine levels | | | | | |
|---|---|---|---|---|---|---|
| | IL-1β (pg/mL) | | IL-6 (pg/mL) | | MCP-1 (pg/mL) | |
| | Anterior | Posterior | Anterior | Posterior | Anterior | Posterior |
| Naïve | 395.3 ± 344.8 | 95.3 ± 69.9 | 743.2 ± 371.2 | 1219.3 ± 195.3 | 170.3 ± 133.9 | 85.6 ± 58.4 |
| Vehicle control | 1023.7 ± 388.2 | 433.8 ± 255.3 | 1324.8 ± 336.9 | 1521.3 ± 307.4 | 427.2 ± 161.9 | 190.6 ± 88.4 |
| Dexamethasone (1 mg/mL) | 553.5 ± 155.7 | 365.6 ± 178.2 | 1000.7 ± 126.2 | 1723.4 ± 224.1 | 156.3 ± 50.8 | 95.2 ± 32.5 |
| Example 4 (1 mg/mL) | 20.3 ± 18.9 | 7.6 ± 7.6 | 642.3 ± 48.9 | 897.9 ± 120.3 | 0 ± 0 | 1.0 ± 1.0 |

TABLE 7b

Effect of compounds of the examples on cytokine levels in the eyes of LPS-stimulated rats.

| | | Cytokine levels | | | | | |
|---|---|---|---|---|---|---|---|
| | | IL-1β (pg/mL) | | IL-6 (pg/mL) | | MCP-1 (pg/mL) | |
| Treatment | n | Anterior | Posterior | Anterior | Posterior | Anterior | Posterior |
| Naive | 5 | 8 ± 3 | 5 ± 3 | 67 ± 20 | 78 ± 20 | 75 ± 33 | 64 ± 29 |
| Vehicle control | 8 | 1119 ± 272 | 737 ± 162 | 1206 ± 261 | 1276 ± 255 | 579 ± 144 | 657 ± 190 |
| Ex. 27 (1 mg/mL) | 8 | 640 ± 263 | 394 ± 115 | 519 ± 196 | 424 ± 116 | 282 ± 109 | 352 ± 109 |
| Ex. 75 (1 mg/mL) | 8 | 570 ± 146 | 414 ± 97 | 393 ± 118 | 489 ± 119 | 239 ± 82 | 279 ± 83 |

TABLE 7c

Effect of compounds of the examples on cytokine levels and cell counts in the eyes of LPS-stimulated rats.

| Treatment | n | IL-1β (pg/mL) Anterior tissue | IL-1β (pg/mL) Posterior tissue | Cell counts |
|---|---|---|---|---|
| Non-diseased | 5 | 7.3 ± 4.7 | 40.5 ± 37.9 | 3.8 ± 0.8 |
| Vehicle control | 8 | 1308.5 ± 249.9 | 809.6 ± 134.7 | 68.5 ± 19.3 |
| Example 29 (1 mg/mL) | 8 | 441.3 ± 138.5 | 272.1 ± 93.8 | 33.0 ± 6.7 |
| Example 66 (1 mg/mL) | 8 | 342.7 ± 145.3 | 209.9 ± 59.0 | 28.0 ± 7.6 |

Summary of Additional Studies

Determination of Pharmacokinetic Parameters

Studies were conducted by Sai Life Sciences (Hinjewadi, Pune, India) to investigate the plasma pharmacokinetics and total colon tissue distribution of compounds of the invention. In particular, pharmacokinetic studies were carried out in:

male C57BL/6 mice, following a single oral administration; and male Wistar rats following a single intravenous or oral administration.

The data reveal that the compounds of the invention achieve substantial colonic concentrations, while plasma exposures are very low or negligible.

TABLE 8a

Median plasma concentrations (ng/mL) obtained following oral administration of compounds of the invention to mice at 5 mg/kg.

| | | Time (h) | | | | | | |
|---|---|---|---|---|---|---|---|---|
| Example | Vehicle | 1 | 2 | 4 | 6 | 8 | 12 | 24 |
| 3 | B | 0.0 | 0.0 | 0.0 | 114 | 0.0 | 0.0 | 0.0 |
| 4 | A | 5.1 | 23.2 | 2.6 | 0.7 | 0.0 | 0.0 | 0.0 |
| 16 | B | 0.0 | 0.0 | 0.0 | 0.0 | 0.0 | 0.0 | 0.0 |

TABLE 8a-continued

Median plasma concentrations (ng/mL) obtained following oral administration of compounds of the invention to mice at 5 mg/kg.

| | | Time (h) | | | | | | |
|---|---|---|---|---|---|---|---|---|
| Example | Vehicle | 1 | 2 | 4 | 6 | 8 | 12 | 24 |
| 27 | B | 1.9 | 1.2 | 0.0 | 1.3 | 0.0 | 1.1 | 0.0 |
| 75 | B | 1.8 | 1.5 | 0.0 | 0.0 | 0.0 | 0.0 | 0.0 |

Key
Vehicle A = peanut oil
Vehicle B = corn oil:transcutol:maisine:cremophor ELP (32.5:20:12.5:35)

TABLE 8b

Median total colon concentrations (ng/g) obtained following oral administration of various Compound Examples to mice at 5 mg/kg (vehicles A and B are as in respect of Table 8a).

| | | Time (h) | | | | | | |
|---|---|---|---|---|---|---|---|---|
| Example | Vehicle | 1 | 2 | 4 | 6 | 8 | 12 | 24 |
| 3 | B | 107 | 274 | 209 | 255 | 278 | 232 | 19.1 |
| 4 | A | 107 | 1718 | 2405 | 5242 | 2096 | 1188 | 118 |
| 16 | B | 0.0 | 10.4 | 420 | 3080 | 1951 | 126 | 23 |
| 27 | B | 7.0 | 52.0 | 250 | 438 | 246 | 1201 | 157 |
| 75 | B | 17.8 | 56.2 | 1338 | 5715 | 350 | 391 | 7.5 |

TABLE 9a

Pharmacokinetic data obtained following intravenous administration of various Compound Examples to rats at 0.25 mg/kg in 5% DMSO-7.5% Solutol HS15-87.5% normal saline.

| Example | $C_0$ (ng/mL) | $AUC_{last}$ (h * ng/mL) | $AUC_{INF}$ (h * ng/mL) | $T_{1/2}$ (h) | Cl (mL/min/kg) | $V_{ss}$ (L/kg) |
|---|---|---|---|---|---|---|
| 3  | 4379 | 820 | 821 | 0.2 | 5.1  | 0.1  |
| 4  | 3038 | 558 | 563 | 0.8 | 7.9  | 0.2  |
| 16 | 6536 | 869 | 871 | 0.1 | 4.8  | 0.03 |
| 27 | 3877 | 588 | 590 | 0.8 | 7.1  | 0.1  |
| 29 | 2505 | 293 | 295 | 0.7 | 14.2 | 0.3  |
| 75 | 3998 | 948 | 952 | 1.2 | 4.4  | 0.1  |

TABLE 9b

Pharmacokinetic data obtained following oral administration of various Compound Examples to rats at 5 mg/kg.

| Example | Vehicle | $T_{max}$ (h) | $C_{max}$ (ng/mL) | $AUC_{last}$ (h * ng/mL) | $AUC_{INF}$ (h * ng/mL) | $F_{po}$ (%) |
|---|---|---|---|---|---|---|
| 3  | B | NC[‡] | NC[‡] | NC[‡] | NC[‡] | 0.0 |
| 4  | C | 0.5   | 15.5  | 27.0  | 40.8  | 0.2 |
| 16 | B | NC[‡] | NC[‡] | NC[‡] | NC[‡] | 0.0 |
| 27 | B | NC[‡] | NC[‡] | NC[‡] | NC[‡] | 0.0 |
| 75 | B | 5.3   | 3.8   | 26.6  | NC[‡] | 0.1 |

Key
Vehicle B = as in respect of Table 8a.
Vehicle C = 2% hydroxypropyl methylcellulose and 0.5% Tween 80 in water.
[‡]Not calculated because no compound was detected in plasma.

TABLE 9c

Median plasma concentrations (ng/mL) obtained following oral administration of various Compound Examples to rats at 5 mg/kg

| | | Time (h) | | | | | | | | |
|---|---|---|---|---|---|---|---|---|---|---|
| Example | Vehicle | 0.25 | 0.5 | 1 | 2 | 4 | 6 | 8 | 12 | 24 |
| 3  | B | NM[‡] | 0.0  | 0.0 | 0.0 | 0.0 | 0.0 | 0.0 | 0.0 | 0.0 |
| 4  | C | NM[‡] | 13.3 | 8.6 | 3.5 | 2.1 | 0.0 | 0.0 | 0.0 | 0.0 |
| 16 | B | 0.0   | 0.0  | 0.0 | 0.0 | 0.0 | 0.0 | 0.0 | 0.0 | 0.0 |
| 27 | B | 0.0   | 0.0  | 0.0 | 0.0 | 0.0 | 0.0 | 0.0 | 0.0 | 0.0 |
| 75 | B | 0.0   | 0.0  | 0.0 | 1.2 | 3.1 | 2.0 | 3.2 | 2.3 | 0.0 |

Key
Vehicles B and C are as in respect of Table 8a
[‡]Not measured.

Determination of ADME Parameters

Assessment of certain in vitro ADME (absorption, distribution, metabolism, and excretion) parameters for certain compounds of the invention was conducted by BioFocus (Saffron Walden, UK). The results indicate that, in general, the compounds of the invention are cleared rapidly by human hepatocytes and that they have reduced liabilities for time-dependent cytochrome P450 inhibition.

TABLE 10

Data from human hepatocyte stability tests for various Compound Examples

| Example | $T_{1/2}$ (min) | Mean intrinsic clearance (μL/min/million cells) | Mean hepatic extraction ratio |
|---|---|---|---|
| 3  | 36   | 39 | 0.85  |
| 4  | 48   | 29 | 0.81  |
| 16 | 34   | 41 | 0.85  |
| 27 | 96   | 15 | 0.68  |
| 75 | >200 | <7 | <0.50 |

TABLE 11a

Summary of CYP3A4 inhibition studies for various Compound Examples (results reported are the arithmetic mean of two experiments).

| | 0 min preincubation | | 30 min preincubation | |
|---|---|---|---|---|
| Example | $IC_{50}$ (μM) | 15 μM % Inh | $IC_{50}$ (μM) | 15 μM % Inh |
| Ref Cpd A | >15 | 41     | 0.4  | 92     |
| 3  | >15 | 22     | >15  | 51     |
| 4  | >5  | 9[†]   | 2.7  | 58[†]  |
| 5  | >15 | 0      | >15  | 27     |
| 16 | >15 | 31     | 7.8  | 54     |
| 27 | >15 | 19     | 8.9  | 57     |
| 75 | >15 | 3      | >15  | 42     |

Key
Ref Cpd A: 1-(4-((2-((7-methyl-1H-indazol-5-yl)amino)pyrimidin-4- yl)oxy)-naphthalen-1-yl)-3-(3-(2-methylbut-3-yn-2-yl)-1-(p-tolyl)-1H- pyrazol-5-yl)urea (Fyfe, M. C. T., et al. WO 2014/033447).
[†]Data at 15 μM variable, therefore not used. Inhibition at 5 μM reported instead.

TABLE 11b

Summary of CYP2C9 inhibition studies for various Compound Examples (results reported are the arithmetic mean of two experiments).

| | 0 min preincubation | | 30 min preincubation | |
|---|---|---|---|---|
| Example | $IC_{50}$ (μM) | 15 μM % Inh | $IC_{50}$ (μM) | 15 μM % Inh |
| Ref Cpd A | >5  | 31[†] | 1.4 | 66[†] |
| 4  | >15 | 24 | >15 | 41 |
| 16 | >15 | 21 | >15 | 37 |
| 27 | >15 | 13 | >13 | 55 |
| 75 | >15 | 20 | >15 | 36 |

Key
Ref Cpd A: as in respect of Table 11a.
[†]Precipitation observed at 15 μM, therefore inhibition at 5 μM reported instead.

hERG Inhibition Studies

Compounds of the invention were tested for inhibition of the human ether a go-go (hERG) channel using IonWorks™ patch clamp electrophysiology at Essen Bioscience (Welwyn Garden City, England).

TABLE 12 hERG inhibition data for compounds of the invention

| Example | IC$_{50}$ (μM) | % Inhibition at 3 μM |
|---|---|---|
| 3 | >3.0 | −2 ± 2 |
| 4 | >3.0 | −4 ± 2 |
| 16 | >3.0 | −12 ± 4 |
| 27 | >3.0 | −3 ± 5 |
| 75 | >3.0 | 0 ± 6 |

Analysis of Metabolites

Studies were conducted by BioFocus (Saffron Walden, UK) to determine the metabolic fate of the compound of Example 16 following incubation with rat, Cynomolgus macaque or human hepatocytes.

Separate incubations (n=3) of the compound of Example 16 (10 μM initial concentration) or DMSO control, were performed with cryopreserved hepatocytes from each species (0.5 million cell/mL) at 37° C. for 0, 60 and 90 minutes before termination of reactions and compound extraction with acetonitrile. Sample replicates were pooled prior to analysis.

Potential metabolites were identified using time-of-flight (TOF) and triple quadruple (TQ) mass spectrometers.

The results reveal that the Compound of Example 16 forms 9 metabolites in hepatocytes, 8 of which result from oxidation on the polyethylene glycol chain of the amide moiety. The other metabolite, seen principally in cynomolgus macaque hepatocytes, arises via oxidation on the 5-(tert-butyl)-2-methoxy-3-(methylsulfonamido)phenyl fragment. Thus, no products were noted that could be connected to metabolism at the naphthalene moiety, a phenomenon that results in the hepatotoxicity associated with p38α inhibitor BIRB796 (Iwano, S., et al., *J. Appl. Toxicol.* 2011, 31, 671-677). All metabolites identified in human hepatocyte incubations were also detected in either rat or cynomolgus macaque hepatocyte incubations.

Mutagenicity Assessment (Bacterial Reverse Mutation Screen)

Studies were conducted by Sequani (Ledbury, Herefordshire, UK) to assess compounds of the invention for their ability to induce mutations in two histidine dependent auxotrophic mutants of *Salmonella typhimurium*, strains TA98 and TA100 in vitro.

The mutation screen was conducted using the plate incorporation method and was performed in both the presence and absence of S-9 mix (a liver post-mitochondrial fraction derived from the livers of Aroclor 1254 treated rats). The bacteria were exposed to test compounds dissolved in dimethylsulphoxide, which solvent was also used as the negative control. The dose levels used were 0.32, 1.6, 8, 40, 200, 1000 or 5000 μg/plate.

Analysable treatment levels of test compounds were limited by insolubility to 1000 μg/plate, as heavy precipitation observed at 5000 μg/plate affected the scoring of the colonies. Precipitation was also noted in both strains at 1000 μg/plate in the presence and absence of S-9 mix.

The compounds of Examples 4, 16, 27 and 75 produced no dose-related or statistically significant increases in revertant colonies in either *Salmonella typhimurium* strain in the presence or absence of S-9 mix.

Hydrolytic Stability Study

Chemical stability of compounds of the invention was assessed in a mixture of DMSO and water (3:1) at a test compound concentration of 1 mg/mL General HPLC Procedure
Agilent, Waters X-Select C18, 2.5 μm, 4.6×30 mm column, 4 min method, 5-95%
MeCN/water (0.1% formic acid).
Flow rate 2.5 ml/min.
Column Oven Temperature 40° C.
Detection 254 nm.
Sample Preparation A 1.0 mg sample of test compound was dissolved in 750 μL of DMSO. Water (250 μL) was added slowly, ensuring no precipitation occurred.

Recording Stability

A 50 μL aliquot of the test solution was removed and analysed in duplicate by 5 μL HPLC injections. The peak area for the test compound was recorded following manual integration of the corresponding UV trace.

The test solution was heated to 60° C., with stirring, and 50 μL aliquots removed for HPLC analysis at 5 and 24 h timepoints. In all cases, 5 μL injections were used and the samples analysed in duplicate.

The peak areas for the test compounds were recorded at both subsequent timepoints and the % decomposition calculated from the % change in peak area over time.

Reference Compound B (3-ethynyl-5-((4-((4-(3-(3-isopropyl-1-(p-tolyl)-1H-pyrazol-5-yl)ureido)naphthalen-1-yl)oxy)pyrimidin-2-yl)amino)-N-(2-morpholinoethyl)benzamide) was included in each stability study as a control to validate the study. In contrast to the compounds of the present invention, this Reference Compound underwent substantial decomposition under the conditions of the experiment.

The results of the study are reported in the table below.

| Test Compound | Time (min) | % Parent Remaining |
|---|---|---|
| Reference Compound B | 0 | 100 |
| | 300 | 82 |
| | 1440 | 36 |
| Example 4 | 0 | 100 |
| | 300 | 103 |
| | 1440 | 102 |
| Example 16 | 0 | 100 |
| | 300 | 100 |
| | 1440 | 100 |
| Example 27 | 0 | 100 |
| | 300 | 102 |
| | 1440 | 102 |
| Example 75 | 0 | 100 |
| | 300 | 101 |
| | 1440 | 99 |

Abbreviations
AcOH glacial acetic acid
aq aqueous
5-ASA 5-aminosalicylic acid
ATP adenosine-5'-triphosphate
BALF bronchioalveolar lavage fluid
BID bis in die (twice-daily)
BINAP 2,2'-bis(diphenylphosphino)-1,1'-binaphthyl
BOP (benzotriazol-1-yloxy)tris(dimethylamino)phosphonium hexafluorophosphate
br broad
BrdU 5-bromo-2'-deoxyuridine
BSA bovine serum albumin
CatCart® catalytic cartridge
CDI 1,1-carbonyl-diimidazole
COPD chronic obstructive pulmonary disease
d doublet
dba dibenzylideneacetone DBU 1,8-diazabicyclo[5.4.0]undec-7-ene
DCC dicyclohexylcarbodiimide
DCM dichloromethane
DIAD diisopropyl azodicarboxylate
DIPEA diisopropylethylamine
DMAP 4-dimethylaminopyridine
DMEM Dulbecco's modified eagle medium
DMF N,N-dimethylformamide
DMSO dim ethyl sulfoxide
DPPA diphenylphosphoryl azide
d-U937 cells PMA differentiated U-937 cells
EDTA ethylenediaminetetraacetic acid
ELISA enzyme-linked immunosorbent assay
(ES⁻) electrospray ionization, negative mode
(ES⁺) electrospray ionization, positive mode
Et ethyl
Et₃N triethylamine
EtOAc ethyl acetate
EtOH ethanol
FACS fluorescence-activated cell sorting
FBS foetal bovine serum
FCS foetal calf serum
fMLP formyl-methionyl-leucyl-phenylalanine
FRET fluorescence resonance energy transfer
GSK3α glycogen synthase kinase 3α
HBEC primary human bronchial epithelial cells
HBSS Hank's balanced salt solution
HPLC high performance liquid chromatography
HPMC hydroxypropylmethylcellulose
h or hr hour(s)
HATU 2-(1H-7-azabenzotriazol-1-yl)-1, 1,3,3-tetramethyl uronium hexafluorophosphate
HOAt 1-hydroxy-7-azabenzotriazole
HOBt hydroxybenzotriazole
HRP horseradish peroxidise
HRV human rhinovirus
ICAM-1 inter-cellular adhesion molecule 1
IFNγ interferon-γ
IL interleukin
iPrOAc isopropyl acetate
JNK c-Jun N-terminal kinase
LC liquid chromatography
Lck lymphocyte-specific protein tyrosine kinase
LPS lipopolysaccharide
m multiplet
(M+H)⁺ protonated molecular ion
MAPK mitogen-activated protein kinase
MAPKAP-K2 mitogen-activated protein kinase-activated protein kinase-2
mCPBA meta-chloroperbenzoic acid
Me methyl
MeCN acetonitrile
MeOH methanol
MHz megahertz
min or mins minute(s)
MMAD mass median aerodynamic diameter
MOI multiplicity of infection
MPO myeloperoxidase
MTT 3-(4,5-dimethylthiazol-2-yl)-2,5-diphenyltetrazolium bromide
MS mass spectrometry
m/z mass-to-charge ratio
NMP N-methyl pyrrolodinone
NMR nuclear magnetic resonance (spectroscopy)
OD optical density
PBMC peripheral blood mononuclear cell
PBS phosphate buffered saline
Ph phenyl
PHA phytohaemagglutinin
PMA phorbol myristate acetate
pTSA 4-methylbenzenesulfonic acid (para-toluenesulfonic acid)
PyBOP (benzotriazol-1-yloxy)tripyrrolidinophosphonium hexafluorophosphate
q quartet
rt or RT room temperature
RP HPLC reverse phase high performance liquid chromatography
rpm revolutions per minute
RPMI Roswell Park Memorial Institute
RSV respiratory syncytical virus
s singlet
sat or satd saturated
SCID severe combined immunodeficiency
SCX solid supported cation exchange (resin)
SDS sodium dodecyl sulfate
S$_N$Ar nucleophilic aromatic substitution
Syk Spleen tyrosine kinase
t triplet
T3P 1-propanephosphonic acid cyclic anhydride
TBAF tetrabutylammonium fluoride
TBDMS tert-butyldimethylsilyl
TCID$_{50}$ 50% tissue culture infectious dose
TEA triethylamine
THF tetrahydrofuran
TFA trifluoroacetic acid
TGFβ transforming growth factor beta
TIPS triisopropylsilyl
TMB 3,3',5,5'-tetramethylbenzidine
TMS-Cl trimethylsilyl chloride
TNFα tumor necrosis factor alpha Prefixes n-, s-, i-, t- and tert- have their usual meanings: normal, secondary, iso, and tertiary.

What is claimed is:
1. A compound of formula IIb,

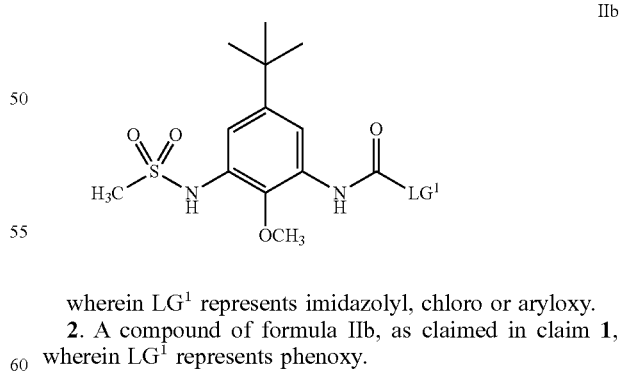

wherein LG¹ represents imidazolyl, chloro or aryloxy.

2. A compound of formula IIb, as claimed in claim 1, wherein LG¹ represents phenoxy.

* * * * *

UNITED STATES PATENT AND TRADEMARK OFFICE
CERTIFICATE OF CORRECTION

PATENT NO. : 9,790,174 B2
APPLICATION NO. : 15/261174
DATED : October 17, 2017
INVENTOR(S) : Stephen Malcolm Thom It is certified that error appears in the above-identified patent and that said Letters Patent is hereby corrected as shown below:

In the Specification

In Column 2 at Line 6, Change "2994.)." to --2994).--.

In Column 3 at Line 29, Change "-70.)." to -- -70).--.

In Column 4 at Line 16 (approx.), Change "GSK36" to --GSK3β--.

In Column 4 at Line 47, Change "-102)" to -- -102);--.

In Column 5 at Line 43, Change "$R^A$" to --$R^{A1}$--.

In Column 6 at Line 4, Change "$R^{E1}$" to --$R^{1E}$--.

In Column 6 at Line 31, Change "-$Q^1$-[—C" to -- -$Q^1$-[C--.

In Column 6 at Line 33, Change "alkylene]$R^{6a}$," to --alkylene]-$R^{6a}$,--.

In Column 6 at Line 34, After "oxo" insert --,--.

In Column 6 at Line 35, Change "-$S(O)_nR^{6b}$;" to -- -$S(O)_nR^{6b}$,--.

In Column 9 at Line 5, Change "alkylene]$R^{6a}$" to --alkylene]-$R^{6a}$--.

In Column 9 at Line 28, Change "$R^A$" to --$R^{A1}$--.

In Column 10 at Line 55, Change "$R^A$" to --$R^{A1}$--.

In Column 11 at Line 28, Delete "(m) $R^z$ represents H or halo;" and insert the same on Column 11, Line 29 as a new paragraph.

Signed and Sealed this
Twenty-eighth Day of May, 2019

Andrei Iancu
*Director of the United States Patent and Trademark Office*

CERTIFICATE OF CORRECTION (continued)
U.S. Pat. No. 9,790,174 B2

In Column 11 at Line 31, Change "-Q$^1$ -[—C(R$^{6c}$)(R$^{6d}$)—CH$_2$" to -- -Q$^1$-[C(R$^{6c}$)(R$^{6d}$)CH$_2$--.

In Column 11 at Line 32, Change "alkylene]R$^{6a}$" to --alkylene]-R$^{6a}$--.

In Column 11 at Line 34, Change "alkylene]R$^{6a}$)," to --alkylene]-R$^{6a}$),--.

In Column 11 at Line 36, Change "-S(O)nR$^{6b}$;" to -- -S(O)nR$^{6b}$,--.

In Column 11 at Line 37, Change "—COR$^{6b}$," to -- —COR$^{6b}$;--.

In Column 11 at Line 43, Change "-Q$^2$-CH$_2$[" to -- -Q$^2$-CH$_2$-[--.

In Column 13 at Line 17, Change "or)" to --or--.

In Column 15 at Line 54, Change "-Q$^1$-[—C" to -- -Q$^1$-[C--.

In Column 15 at Line 56, Change "alkylene]R$^{6a}$," to --alkylene]-R$^{6a}$,--.

In Column 16 at Line 62, Change "amino) pyrimidin" to --amino)pyrimidin--.

In Column 17 at Line 13, Change "yloxy)" to --yl)oxy--.

In Column 18 at Line 25, Change "-methoxy- ethoxy)" to -- -methoxy-ethoxy)--.

In Column 18 at Line 65, Change "yloxy)" to --yl)oxy--.

In Column 20 at Line 2, Change "-methoxy- ethoxy)" to -- -methoxy-ethoxy)--.

In Column 21 at Line 18, Change "pyridin- 4-" to --pyridin-4- --.

In Column 21 at Line 25-27, Delete "3-[[4-[(2-anilino-4-pyridyl)oxy]-2,3-difluorophenyl]carbamoylamino]-5-tert-butyl-2-methoxy-N-(oxetan-3-yl)benzamide;" and insert the same on Column 21, Line 28 as a new paragraph.

In Column 21 at Line 35, Change "[(R3)" to --[(3R)--.

In Column 27 at Line 14, Change "poly-vinylpyrollidone;" to --poly-vinylpyrrolidone;--.

In Column 27 at Line 31, Change "hydroxylpropyl" to --hydroxypropyl--.

In Column 30 at Line 37, Change "Pemulen®," to --Pemulen(R),--.

In Column 30 at Line 51-52, Change "polyquarternium-1," to --polyquaternium-1,--.

In Column 31 at Line 16, Change "daratropium," to --darotropium,--.

CERTIFICATE OF CORRECTION (continued)
U.S. Pat. No. 9,790,174 B2

In Column 31 at Line 24, Change "bisalazide);" to --balsalazide);--.

In Column 31 at Line 32, Change "ID 2/IL23" to --IL12/IL23--.

In Column 33 at Line 4, Change "II." to --II,--.

In Column 41 at Line 56, Change "XIX." to --XIX,--.

In Column 42 at Line 4, Change "($R^{6d}$)[$C_{1-5}$" to --($R^{6d}$)-[$C_{1-5}$--.

In Column 43 at Line 13, Change "XXIV." to --XXIV,--.

In Column 44 at Line 27 (approx.), Change "Fe'" to --$R^{6b}$--.

In Column 49 at Line 47, Change "45 CC" to --45 °C.--.

In Column 49 at Line 65, Change "(14" to --(1L).--.

In Column 51 at Line 53, After "purity" insert --.--.

In Column 55 at Line 22, Change "a an" to --an--.

In Column 57 at Line 4, After "3H)" insert --.--.

In Column 57 at Line 28, After "9H)" insert --.--.

In Column 57 at Line 66, After "3H)" insert --.--.

In Column 62 at Line 12-13, Change "yl)pyrimidin" to --yl)oxy)pyrimidin--.

In Column 72 at Line 52, Change "yloxy)" to --yl)oxy)--.

In Column 73 at Line 23, Change "yloxy)" to --yl)oxy)--.

In Column 74 at Line 15, Change "yloxy)" to --yl)oxy)--.

In Column 74 at Line 41, Change "yloxy)" to --yl)oxy)--.

In Column 74 at Line 43, Change "-methane sulfonamide" to -- -methanesulfonamide--.

In Column 80 at Line 42, Change "(111)" to --(III)--.

In Column 82 at Line 28, Change "40 CC" to --40 °C.--.

In Column 83-84 at Line 16-29 (approx.),

Change " 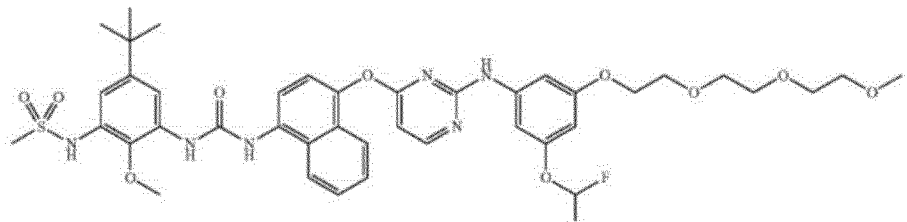 " to

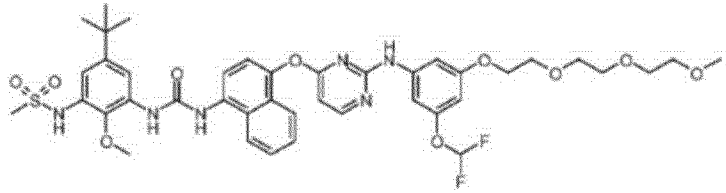

--.

In Column 92 at Line 40, Change "(M$_+$H-tBu)$^+$" to --(M+H-tBu)$^+$--.

In Column 101 at Line 61, After "present" insert --.--.

In Column 106 at Line 26, Change "3.44-0.3.38" to --3.44-3.38--.

In Column 108 at Line 57 (approx.), Change "60 CC" to --60 °C.--.

In Column 110 at Line 3, Change "-methoxy- ethoxy)" to -- -methoxy-ethoxy)--.

In Column 114 at Line 2-3, Change "phenyl) amino)" to --phenyl)amino)--.

In Column 123 at Line 2, Change "yloxy)" to --yl)oxy)--.

In Column 123-124 at Line 7-23 (approx.),

Change " 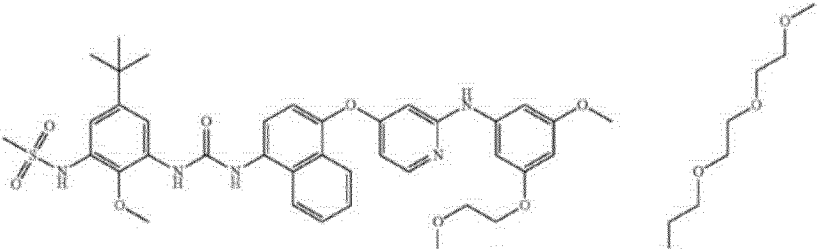 " to

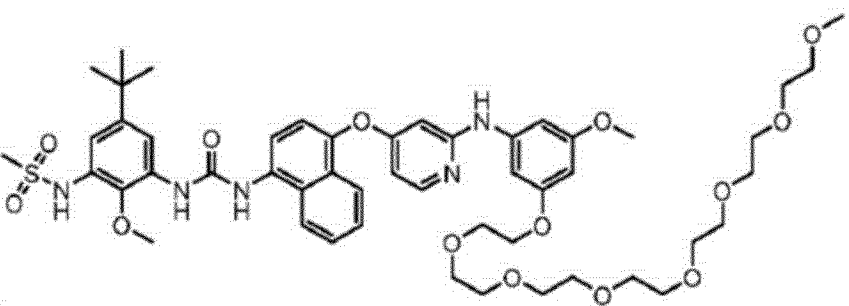

--.

CERTIFICATE OF CORRECTION (continued)
U.S. Pat. No. 9,790,174 B2

In Column 123 at Line 63, Change "yloxy)" to --yl)oxy)--.

In Column 124 at Line 25, Change "yloxy)" to --yl)oxy)--.

In Column 124 at Line 25 (approx.), Change "methoxyphenyl) amino)" to --methoxyphenyl)amino)--.

In Column 124 at Line 48, Change "yloxy)" to --yl)oxy)--.

In Column 124 at Line 56, Change "separated." to --separated,--.

In Column 125 at Line 2, Change "yloxy)" to --yl)oxy)--.

In Column 134 at Line 16, Change "90 C" to --90 °C.--.

In Column 134 at Line 30, Change "pH-4" to --pH~4--.

In Column 139 at Line 31, Change "(M+NH$_4$)+(ES$^+$);" to --(M+NH$_4$)$^+$ (ES$^+$);--.

In Column 147 at Line 16, Change "carbamoyl) phenyl)" to --carbamoyl)phenyl)--.

In Column 148 at Line 37, Change "phenyl) amino)" to --phenyl)amino)--.

In Column 151 at Line 44, Change "(M+Na)+(ES$^+$);" to --(M+Na)$^+$ (ES$^+$);--.

In Column 151 at Line 58, After "9H)" insert --.--.

In Column 152 at Line 23, Change "methoxy- ethoxy)" to --methoxy-ethoxy)--.

In Column 156 at Line 28, After "2H)" insert --.--.

In Column 156 at Line 65, After "9H)" insert --.--.

In Column 157 at Line 61, Change "(5)" to --(S)--.

In Column 158 at Line 38, Change "(M+HCO2)– (ES$^-$)" to --(M+HCO$_2$)$^-$ (ES$^-$)--.

In Column 158 at Line 40-41, Change "(m ethylsulfonamido)" to --(methylsulfonamido)--.

In Column 160 at Line 66, After "9H)" insert --.--.

In Column 162 at Line 67, Change "(M+H)2+(ES$^+$)," to --(M+H)$^{2+}$ (ES$^+$),--.

In Column 169 at Line 27 (approx.), After "CHCl$_3$" insert --.--.

In Column 170 at Line 19, Change "70 CC" to --70 °C.--.

CERTIFICATE OF CORRECTION (continued)
U.S. Pat. No. 9,790,174 B2

In Column 175 at Line 51-52, Change "amino) pyridin" to --amino)pyridin--.

In Column 176 at Line 66, After "peak)" insert --.--.

In Column 181 at Line 59, Change "(ES");" to --(ES$^+$);--.

In Column 183 at Line 17-18 (approx.), Change "amino) pyrimidin" to --amino)pyrimidin--.

In Column 185 at Line 42 (approx.), After "peak" insert --.--.

In Column 186 at Line 64, After "peak" insert --.--.

In Column 187 at Line 24, Change "methoxy- ethoxy)" to --methoxy-ethoxy)--.

In Column 188 at Line 20 (approx.), After "3H)" insert --.--.

In Column 190 at Line 42, Change "-[[2[3-" to -- -[[2-[3- --.

In Column 193 at Line 37, Change "H et al.," to --H, et al.,--.

In Column 196 at Line 54, Change "amino]5-" to --amino]-5- --.

In Column 199 at Line 34 (approx.), Change "85(i)" to --85(j)--.

In Column 199 at Line 66, After "peaks)" insert --.--.

In Column 201 at Line 31, After "signal)" insert --.--.

In Column 201 at Line 66, After "peak)" insert --.--.

In Column 209 at Line 9, Change "(M+H)+415" to --(M+H)$^+$ 415--.

In Column 213 at Line 15, Change "-3[4-" to -- -3-[4- --.

In Column 214 at Line 56, Change "-34(2-" to -- -3-((2- --.

In Column 216 at Line 58 (approx.), After "mg" insert --.--.

In Column 224 at Line 25, After "(8 µM" insert --,--.

In Column 224 at Line 64, After "0.01 µg/mL" insert --.--.

In Column 228 at Line 25, Change "Cat. No.ab43812," to --Cat. No. ab43812,--.

In Column 228 at Line 28, Change "PO447," to --P0447,--.

CERTIFICATE OF CORRECTION (continued)

In Column 229 at Line 17-18, Change "(200 pt;" to --(200 µL;--.

In Column 229 at Line 19, Change "(200 pt;" to --(200 µL;--.

In Column 229 at Line 20, Change "(200 pt)" to --(200 µL)--.

In Column 229 at Line 23, Change "(3×200 pt;" to --(3×200 µL;--.

In Column 229 at Line 43, Change "yloxy)" to --yl)oxy--.

In Column 229 at Line 60, Change "0.03 ng/mL 250 ng/mL." to --0.03 ng/mL-250 ng/mL.--.

In Column 231 at Line 51, Change "Neubaur" to --Neubauer--.

In Column 232 at Line 2, Change "bronchioalveolar" to --bronchoalveolar--.

In Column 232 at Line 59, Change "nave" to --naïve--.

In Column 232 at Line 61, Change "nave," to --naïve,--.

In Column 233 at Line 26, Change "fi-cyclodextrin," to --β-cyclodextrin,--.

In Column 233 at Line 49, Change "KINOMEscan ™" to --KINOMEscan™--.

In Column 234 at Line 1, Change "yloxy)" to --yl)oxy)--.

In Column 238 at Line 65, Change "yloxy)" to --yl)oxy)--.

In Column 242 at Line 66, Change "laminar" to --lamina--.

In Column 243 at Line 31, Change "nave," to --naïve,--.

In Column 245-246 (Table 7b) at Line 6 (approx.), Change "Naive" to --Naïve--.

In Column 249 at Line 67, After "mg/mL" insert --.--.

In Column 250 at Lines 3-4, Remove carriage return between "5-95%" and "MeCN/water".

In Column 250 at Line 55, Change "bronchioalveolar" to --bronchoalveolar--.

In Column 250 at Line 58, Change "yloxy)" to --yl)oxy--.

In Column 251 at Line 9, Change "dim ethyl" to --dimethyl--.

In Column 251 at Line 31, Change "yl)-1, 1," to --yl)-1,1,--.

CERTIFICATE OF CORRECTION (continued)
U.S. Pat. No. 9,790,174 B2

In Column 252 at Line 2, Change "pyrrolodinone" to --pyrrolidinone--.

In Column 252 at Line 12, Change "yloxy)" to --yl)oxy)--.

In Column 252 at Line 20, Change "syncytical" to --syncytial--.